US009890111B2

(12) United States Patent
Wong et al.

(10) Patent No.: US 9,890,111 B2
(45) Date of Patent: Feb. 13, 2018

(54) **CRYSTAL STRUCTURE OF BIFUNCTIONAL TRANSGLYCOSYLASE PBP1B FROM *E. COLI* AND INHIBITORS THEREOF**

(71) Applicant: Academia Sinica, Taipei (TW)

(72) Inventors: Chi-Huey Wong, Rancho Santa Fe, CA (US); Che Alex Ma, Taipei (TW); Ting-Jen Rachel Cheng, New Taipei (TW); Wei-Chieh Cheng, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/960,025

(22) Filed: Dec. 4, 2015

(65) Prior Publication Data

US 2016/0083337 A1 Mar. 24, 2016

Related U.S. Application Data

(62) Division of application No. 14/188,678, filed on Feb. 24, 2014, now abandoned, which is a division of (Continued)

(51) Int. Cl.
*C07C 235/64* (2006.01)
*C12Q 1/18* (2006.01)

(Continued)

(52) U.S. Cl.
CPC .......... *C07C 235/64* (2013.01); *C07C 235/84* (2013.01); *C12Q 1/18* (2013.01);

(Continued)

(58) Field of Classification Search
None
See application file for complete search history.

(56) References Cited

U.S. PATENT DOCUMENTS 3,577,550 A 5/1971 Moyle
3,674,850 A 7/1972 Osborne (Continued)

FOREIGN PATENT DOCUMENTS

DE 2126149 A1 7/1972
SU 697500 * 11/1979

OTHER PUBLICATIONS

Lemaire ("Synthesis and Germicidal Activity of Halogenated Salicylanilides and Related Compounds" Journal of Pharmaceutical Sciences, vol. 50, No. 10, 1961, p. 831-837).*

(Continued)

*Primary Examiner* — Jafar Parsa
*Assistant Examiner* — Amy C Bonaparte
(74) *Attorney, Agent, or Firm* — Wolf, Greenfield & Sacks, P.C.

(57) ABSTRACT

The crystal structure at 2.16 Å resolution of the full-length bacterial bifunctional transglycosylase penicillin-binding protein 1b (PBP1b) from *Escherichia coli*, in complex with its inhibitor moenomycin, is provided. The atomic coordinates of the complex as well as the moenomycin binding site are provided. Three dimensional structures of amino acid residues involved in moenomycin binding and transglycosylation activity are identified. Binding site for peptidoglycan synthesis inhibitors comprising inhibitor-binding site comprises amino acid residues from at least one of transglycosylase (TG), UvrB domain 2 homolog (UB2H) and transmembrane (TM) domains of PBP1b are identified at an atomic level of resolution. Methods for rational drug design based on the atomic coordinates are provided. Methods for screening for antibiotics based on anisotropic binding assay and transglycosylase inhibitor assays are provided. Novel antibiotics based on the screening assays of the invention are disclosed.

14 Claims, 93 Drawing Sheets

| | Native | | SeMet | |
|---|---|---|---|---|
| Data collection | | | | |
| Space group | $P2_12_12$ | | $P2_12_12$ | |
| Cell dimensions | | | | |
| a, b, c, Å | 62.9, 289.5, 62.7 | | 63.3, 297.5, 62.9 | |
| | | Peak | Inflection | Remote |
| Wavelength | 0.9000 | 0.9788 | 0.9789 | 0.9635 |
| Resolution, Å | 30.00-2.16 (2.24-2.16) | 30.0-3.1 (3.2-3.1) | 30.0-3.1 (3.2-3.1) | 30.0-3.1 (3.2-3.1) |
| $R_{sym}$, % | 7.7 (49.7) | 12.9 (46.8) | 11.5 (48.4) | 11.1 (40.0) |
| I/σ | 15.7 (2.1) | 12.5 (4.2) | 9.8 (2.7) | 10.2 (3.1) |
| Completeness, % | 96.7 (85.0) | 99.1 (100.0) | 98.5 (99.9) | 98.5 (99.6) |
| Redundancy | 4.5 (4.0) | 8.3 (8.3) | 4.3 (4.5) | 4.3 (4.3) |
| Refinement | | | | |
| Resolution, Å | 30.00-2.16 | | | 30.0-3.1 |
| No. of reflections | 59,458 | | | 21,677 |
| $R_{work}/R_{free}$ | 20.6/25.1 | | | 21.1/27.2 |
| No. of atoms | | | | |
| Protein | 5,214 | | | 5,564 |
| Ligand | 77 | | | 77 |
| Water | 235 | | | - |
| B-factors | | | | |
| Protein | 72.9 | | | 94.8 |
| Ligand | 122.7 | | | 145.5 |
| Water | 55.3 | | | - |
| R.m.s. deviations | | | | |
| Bond lengths, Å | 0.011 | | | 0.006 |
| Bond angles, ° | 1.327 | | | 1.082 |

Values in parentheses are for highest resolution shell

Related U.S. Application Data application No. 12/506,982, filed on Jul. 21, 2009, now abandoned.

(60) Provisional application No. 61/208,566, filed on Feb. 25, 2009, provisional application No. 61/135,503, filed on Jul. 21, 2008.

(51) Int. Cl.
*C12Q 1/48* (2006.01)
*C07C 235/84* (2006.01)

(52) U.S. Cl.
CPC ............ *C12Q 1/48* (2013.01); *C07K 2299/00* (2013.01); *G01N 2333/91102* (2013.01); *G01N 2500/00* (2013.01)

(56) References Cited

U.S. PATENT DOCUMENTS

| | | | | |
|---|---|---|---|---|
| 3,914,418 A * | 10/1975 | Patchett | A61K 31/60 514/166 |
| 8,916,540 B2 | 12/2014 | Wong et al. | |
| 2005/0143402 A1 | 6/2005 | Cheetham et al. | |
| 2010/0121107 A1 | 5/2010 | Wong et al. | |
| 2015/0232417 A1 | 8/2015 | Wong et al. | |

OTHER PUBLICATIONS

SID 11514056 (National Center for Biotechnology Information. PubChem Substance Database; SID=11514056, https://pubchem.ncbi.nlm.nih.gov/substance/11514056, publicly available on Jun. 5, 2006—hereafter referred to as SID).*

CID 1648676 (National Center for Biotechnology Information. PubChem Compound Database; CID=1648676, https://pubchem.ncbi.nlm.nih.gov/compound/1648676, accessed Dec. 9, 2016—hereafter referred to as CID).*

Beer ("Molluscocidal and cercaricidal properties of salicylanilides" Med. Parazitol. Parazit. Bolezni, vol. 47, issue 2, 1978, p. 16-24).*

Cheng ("High-throughput identification of antibacterials against methicillin-resistant *Staphylococcus aureus* (MRSA) and the transglycolase" Bioorganic and Medicinal Chemistry, 18, 2010, p. 8512-8529).*

Steffen ("Discovery and Structure-Activity Relationships of Modified Salicylanilides as Cell Permeable Inhibitors of Poly(ADP-ribose) Glycohydrolase (PARC)" J. Med. Chem. 54, 2011, p. 5403-5413).*

Huang ("New Continuous Fluorometric Assay for Bacterial Transglycosylase Using Forster Resonance Energy Transfer" J. Am. Chem. Soc. 2013, 135, p. 17078-17089).*

Cheng et al., Domain requirement of moenomycin binding to bifunctional transglycosylases and development of high-throughput discovery of antibiotics. Proc Natl Acad Sci U S A. Jan. 15, 2008;105(2):431-6. doi: 10.1073/pnas.0710868105. Epub Jan. 8, 2008.

Lovering et al., Structural insight into the transglycosylation step of bacterial cell-wall biosynthesis. Science. Mar. 9, 2007;315(5817):1402-5.

Wiencek, New strategies for protein crystal growth. Annu Rev Biomed Eng. 1999;1:505-34. Review.

Yuan et al., Crystal structure of a peptidoglycan glycosyltransferase suggests a model for processive glycan chain synthesis. Proc Natl Acad Sci U S A. Mar. 27, 2007;104(13):5348-53. Epub Mar. 8, 2007.

Zhao et al., Bocillin FL, a sensitive and commercially available reagent for detection of penicillin-binding proteins. Antimicrob Agents Chemother. May 1999;43(5):1124-8.

* cited by examiner

| | Native | SeMet | | |
|---|---|---|---|---|
| Data collection | | | | |
| Space group | $P2_12_12$ | $P2_12_12$ | | |
| Cell dimensions | | | | |
| *a*, *b*, *c*, Å | 62.9, 289.5, 62.7 | 63.3, 297.5, 62.9 | | |
| | | Peak | Inflection | Remote |
| Wavelength | 0.9000 | 0.9788 | 0.9789 | 0.9635 |
| Resolution, Å | 30.00–2.16 (2.24–2.16) | 30.0–3.1 (3.2–3.1) | 30.0–3.1 (3.2–3.1) | 30.0–3.1 (3.2–3.1) |
| $R_{sym}$, % | 7.7 (49.7) | 12.9 (48.6) | 11.6 (48.4) | 11.1 (40.0) |
| $I/\sigma I$ | 15.7 (2.1) | 12.5 (4.2) | 9.8 (2.7) | 10.2 (3.1) |
| Completeness, % | 96.7 (85.8) | 99.1 (100.0) | 98.5 (99.9) | 98.5 (99.6) |
| Redundancy | 4.5 (4.0) | 8.9 (9.3) | 4.3 (4.5) | 4.1 (4.3) |
| Refinement | | | | |
| Resolution, Å | 30.00–2.16 | | | 30.0–3.1 |
| No. of reflections | 59,458 | | | 21,677 |
| $R_{work}/R_{free}$ | 20.6/25.1 | | | 21.1/27.3 |
| No. of atoms | | | | |
| Protein | 5,214 | | | 5,564 |
| Ligand | 77 | | | 77 |
| Water | 235 | | | – |
| *B*-factors | | | | |
| Protein | 72.0 | | | 94.8 |
| Ligand | 122.7 | | | 145.5 |
| Water | 55.3 | | | – |
| R.m.s. deviations | | | | |
| Bond lengths, Å | 0.011 | | | 0.006 |
| Bond angles, ° | 1.327 | | | 1.082 |

Values in parentheses are for highest-resolution shell.

FIG. 1

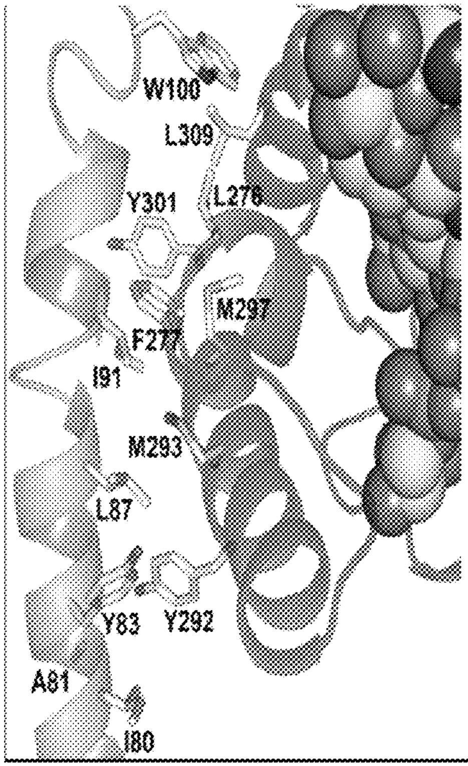

FIG. 3A

```
E. coli PBP1b   55 KGRKPRGKRGWLWLLLKLAIVFAVLIAIYGVYLDQKIRSRIDGKVWQLPAAVYG
SaPBP2          21 NSKKNRNVKRTIIKIIGFMIIAFFVVLLLGILLFAYY-------AWKAPAFTEA
AaPGT            1 -------MKKLVIGILGIVIALFVGLLVFLIPIYKNLPDPKLLESWTPPQASE-

E. coli PBP1b  109 RMVNLEPDMTISKNEMVKLLEATQYRQVSKMTRPGEFTVQANSIEMIRRPFDFP
SaPBP2          68 KLQDPIPAKIYDKN----------------------------------------
AaPGT           47 ---------VYDAK----------------------------------------

E. coli PBP1b  163 DSKEGQVRARLTFDGDHLATIVNMENNRQFGFFRLDPRLITMISSPNGEQRLFV
SaPBP2          82 --------------GELVKTL----------------------DNGQRHEHV
AaPGT           52 --------------GRLYGTI-----------------------GIQKRFYV

E. coli PBP1b  217 PRSGFPDLLVDTLLATEDRHFYEHDGISLYSIGRAVLANLTAGRTVQGASTLTQ
SaPBP2          98 NLKDVPKSMKDAVLATEDNRFYEHGALDYKRLFGAIGKNLTGGFGSEGASTLTQ
AaPGT           67 SIDKIPEHVINAFVATEDRNFWHHFGIDPVAIVRAAIVNYRAGRIVQGGSTITQ

E. coli PBP1b  271 QLVKNLFLSSERSYWRKANEAYMALIMDARYSKDRILELYMNEVYLGQSGDNEI
SaPBP2         152 QVVKDAFLSQHKSIGRKAQEAYLSYRLEQEYSKDDIFQVYLNKIYYS----DGV
AaPGT          121 QLAKNLFLTRERTLERKIKEALLAIKIERTFDKKKIMELYLNQIYLG----SGA
```

FIG. 3B

```
                     α3                α4                                 
E. coli PBP1b 217  PRSGFPDLLVDTLLATEDRHFYEHDGISLYSIGRAVLANLTAGRTVQGASTLTQ
SaPBP2         98  NLKDVPKSMKDAVLATEDNRFYEHGALDYKRLFGAIGKNLTGGFGSEGASTLTQ
AaPGT          67  SIDKIPEHVINAFVATEDRNFWHHFGIDPVAIVRAAIVNYRAGRIVQGGSTITQ

                   α5           α6                 α7          β8     β9
E. coli PBP1b 271  QLVKNLFLSSERSYWRKANEAYMALIMDARYSKDRILELYMNEVYLGQSGDNEI
SaPBP2        152  DVVKDAFLSQHKSIGRKAQEAYLSYRLEQEYSKDDIFQVYLNKIYYS----DGV
AaPGT         121  QLAKNLFLTRERTLERKIKEALLAIKIERTFDKKKIMELYLNQIYLG----SGA

                     α8                α9        α10        α11
E. coli PBP1b 325  RGFPLASLYYFGRPVEELSLDQQALLVGMVKGASIYNPWRNPKLALERRNLVLR
SaPBP2        202  TGIKAAAKYYFNKDLKDLNLAEEAYLAGLPQVPNNYNIYDHPKAAEDRKNTVLY
AaPGT         171  YGVEAAAQVYFGKHVWELSLDEAALLAALPKAPAKYNPFYHPERALQRRNLVLK
```

FIG. 4C

```
        10         20         30         40         50         60
MAGNDREPIG RKGKPTRPVK QKVSRRRYED DDDYDDYDDY EDEEPMPRKG KGKGKGRKPR
        70         80         90        100        110        120
GKRGWLWLLL KLAIVFAVLI AIYGVYLDQK IRSRIDGKVW QLPAAVYGRM VNLEPDMTIS
       130        140        150        160        170        180
KNEMVKLLEA TQYRQVSKMT RPGEFTVQAN SIEMIRRPFD FPDSKEGQVR ARLTFDGDHL
       190        200        210        220        230        240
ATIVNMENNR QFGFFRLDPR LITMISSPNG EQRLFVPRSG FPDLLVDTLL ATEDRHFYEH
       250        260        270        280        290        300
DGISLYSIGR AVLANLTAGR TVQGASTLTQ QLVKNLFLSS ERSYWRKANE AYMALIMDAR
       310        320        330        340        350        360
YSKDRILELY MNEVYLGQSG DNEIRGFPLA SLYYFGRPVE ELSLDQQALL VGMVKGASIY
       370        380        390        400        410        420
NPWRNPKLAL ERRNLVLRLL QQQQIIDQEL YDMLSARPLG VQPRGGVISP QPAFMQLVRQ
       430        440        450        460        470        480
ELQAKLGDKV KDLSGVKIFT TFDSVAQDAA EKAAVEGIPA LKKQRKLSDL ETAIVVVDRF
       490        500        510        520        530        540
SGEVRAMVGG SEPQFAGYNR AMQARRSIGS LAKPATYLTA LSQPKIYRLN TWIADAPIAL
       550        560        570        580        590        600
RQPNGQVWSP QNDDRRYSES GRVMLVDALT RSMNVPTVNL GMALGLPAVT ETWIKLGVPK
       610        620        630        640        650        660
DQLHPVPAML LGALNLTPIE VAQAFQTIAS GGNRAPLSAL RSVIAEDGKV LYQSFPQAER
       670        680        690        700        710        720
AVPAQAAYLT LWTMQQVVQR GTGRQLGAKY PNLHLAGKTG TTNNNVDTWF AGIDGSTVTI
       730        740        750        760        770        780
TWVGRDNNQP TKLYGASGAM SIYQRYLANQ TPTPLNLVPP EDIADMGVDY DGNFVCSGGM
       790        800        810        820        830        840
RILPVWTSDP QSLCQQSEMQ QQPSGNPFDQ SSQPQQQPQQ QPAQQEQKDS DGVAGWIKDM
 844
FGSN (SEQ ID NO: 1)
```

```
HEADER    TRANSFERASE, HYDROLASE                  19-JAN-09   3FWM
TITLE     CRYSTAL STRUCTURE OF THE FULL-LENGTH TRANSGLYCOSYLASE PBP1B
TITLE    2 FROM ESCHERICHIA COLI
COMPND    MOL_ID: 1;
COMPND   2 MOLECULE: PENICILLIN-BINDING PROTEIN 1B;
COMPND   3 CHAIN: A;
COMPND   4 FRAGMENT: RESIDUES 54-804;
COMPND   5 SYNONYM: PBP-1B, PBP1B, MUREIN POLYMERASE, PENICILLIN-
COMPND   6 INSENSITIVE TRANSGLYCOSYLASE, PEPTIDOGLYCAN
COMPND   7 GLYCOSYLTRANSFERASE, PEPTIDOGLYCAN TGASE, PENICILLIN-
COMPND   8 SENSITIVE TRANSPEPTIDASE, DD-TRANSPEPTIDASE;
COMPND   9 EC: 2.4.1.129, 3.4.-.-;
COMPND  10 ENGINEERED: YES
SOURCE    MOL_ID: 1;
SOURCE   2 ORGANISM_SCIENTIFIC: ESCHERICHIA COLI;
SOURCE   3 ORGANISM_TAXID: 562;
SOURCE   4 STRAIN: K-12;
SOURCE   5 GENE: B0149, JW0145, MRCB, PBPF, PONB;
SOURCE   6 EXPRESSION_SYSTEM: ESCHERICHIA COLI;
SOURCE   7 EXPRESSION_SYSTEM_TAXID: 562;
SOURCE   8 EXPRESSION_SYSTEM_STRAIN: BL21(DE3);
SOURCE   9 EXPRESSION_SYSTEM_VECTOR_TYPE: PLASMID;
SOURCE  10 EXPRESSION_SYSTEM_PLASMID: PET15B
KEYWDS    BACTERIAL CELL WALL SYNTHESIS, PENICILLIN-BINDING PROTEIN,
KEYWDS   2 ANTIBIOTICS DESIGN, TRANSFERASE, HYDROLASE
EXPDTA    X-RAY DIFFRACTION
AUTHOR    M.T.SUNG,Y.T.LAI,C.Y.HUANG,L.Y.CHOU,C.H.WONG,C.MA
REVDAT   1   02-JUN-09 3FWM    0
JRNL        AUTH   M.T.SUNG,Y.T.LAI,C.Y.HUANG,L.Y.CHOU,H.W.SHIH,
JRNL        AUTH 2 W.C.CHENG,C.H.WONG,C.MA
JRNL        TITL   CRYSTAL STRUCTURE OF THE MEMBRANE-BOUND BIFUNCTIONAL
JRNL        TITL 2 TRANSGLYCOSYLASE PBP1B FROM ESCHERICHIA COLI
JRNL        REF    PROC.NATL.ACAD.SCI.USA                    2009
JRNL        REFN                   ESSN 1091-6490
JRNL        PMID   19458048
JRNL        DOI    10.1073/PNAS.0904030106
REMARK   1
REMARK   2 RESOLUTION.    2.16 ANGSTROMS.
REMARK   3 REFINEMENT.
REMARK   3   PROGRAM     : PHENIX (PHENIX.REFINE)
REMARK   3   AUTHORS     : PAUL ADAMS,PAVEL AFONINE,VICENT CHEN,IAN
REMARK   3               : DAVIS,KRESHNA GOPAL,RALF GROSSE-
REMARK   3               : KUNSTLEVE,LI-WEI HUNG,ROBERT IMMORMINO,
REMARK   3               : TOM IOERGER,AIRLIE MCCOY,ERIK MCKEE,NIGEL
REMARK   3               : MORIARTY,REETAL PAI,RANDY READ,JANE
REMARK   3               : RICHARDSON,DAVID RICHARDSON,TOD ROMO,JIM
REMARK   3               : SACCHETTINI,NICHOLAS SAUTER,JACOB SMITH,
REMARK   3               : LAURENT STORONI,TOM TERWILLIGER,PETER
REMARK   3               : ZWART
REMARK   3
REMARK   3    REFINEMENT TARGET : ML
REMARK   3
REMARK   3  DATA USED IN REFINEMENT.
REMARK   3   RESOLUTION RANGE HIGH (ANGSTROMS) : 2.16
REMARK   3   RESOLUTION RANGE LOW  (ANGSTROMS) : 29.90
REMARK   3   MIN(FOBS/SIGMA_FOBS)              : 1.000
REMARK   3   COMPLETENESS FOR RANGE        (%) : 95.0
REMARK   3   NUMBER OF REFLECTIONS             : 59458
REMARK   3
REMARK   3  FIT TO DATA USED IN REFINEMENT.
REMARK   3   R VALUE     (WORKING + TEST SET) : 0.209
REMARK   3   R VALUE            (WORKING SET) : 0.206
REMARK   3   FREE R VALUE                     : 0.251
REMARK   3   FREE R VALUE TEST SET SIZE   (%) : 5.060
REMARK   3   FREE R VALUE TEST SET COUNT      : 3006
REMARK   3
REMARK   3  FIT TO DATA USED IN REFINEMENT (IN BINS).
REMARK   3   BIN  RESOLUTION RANGE  COMPL.    NWORK NFREE   RWORK  RFREE
REMARK   3     1 29.9050 -  5.9480    0.88     2755   141  0.2350 0.2780
REMARK   3     2  5.9480 -  4.7270    0.94     2734   156  0.2030 0.2220
REMARK   3     3  4.7270 -  4.1310    0.88     2523   132  0.1670 0.2150
REMARK   3     4  4.1310 -  3.7540    0.94     2702   135  0.1740 0.2210
REMARK   3     5  3.7540 -  3.4860    0.97     2747   130  0.1900 0.2180
REMARK   3     6  3.4860 -  3.2800    0.99     2789   173  0.2000 0.2620
REMARK   3     7  3.2800 -  3.1160    0.99     2805   149  0.1990 0.2660
REMARK   3     8  3.1160 -  2.9810    0.99     2783   132  0.2060 0.2550
REMARK   3     9  2.9810 -  2.8660    0.99     2738   169  0.2040 0.2430
```

FIG. 8-2

```
REMARK   3   10  2.8680 -  2.7670    0.98     2796   139  0.1930 0.2450
REMARK   3   11  2.7670 -  2.6810    0.98     2786   119  0.1970 0.2250
REMARK   3   12  2.6810 -  2.6040    0.97     2714   136  0.2090 0.2590
REMARK   3   13  2.6040 -  2.5360    0.97     2733   150  0.2080 0.2820
REMARK   3   14  2.5360 -  2.4740    0.97     2726   151  0.2170 0.2570
REMARK   3   15  2.4740 -  2.4180    0.97     2667   145  0.2160 0.2510
REMARK   3   16  2.4180 -  2.3660    0.97     2767   133  0.2070 0.2330
REMARK   3   17  2.3660 -  2.3190    0.96     2687   139  0.2180 0.2480
REMARK   3   18  2.3190 -  2.2750    0.96     2661   163  0.2370 0.3040
REMARK   3   19  2.2750 -  2.2350    0.95     2631   139  0.2480 0.2960
REMARK   3   20  2.2350 -  2.1970    0.96     2688   148  0.2690 0.3280
REMARK   3   21  2.1970 -  2.1610    0.76     2040   127  0.3440 0.3950
REMARK   3
REMARK   3  BULK SOLVENT MODELLING.
REMARK   3   METHOD USED        : FLAT BULK SOLVENT MODEL
REMARK   3   SOLVENT RADIUS     : 1.11
REMARK   3   SHRINKAGE RADIUS   : 0.90
REMARK   3   K_SOL              : 0.33
REMARK   3   B_SOL              : 62.32
REMARK   3
REMARK   3  ERROR ESTIMATES.
REMARK   3   COORDINATE ERROR (MAXIMUM-LIKELIHOOD BASED)     : 0.310
REMARK   3   PHASE ERROR (DEGREES, MAXIMUM-LIKELIHOOD BASED) : 26.060
REMARK   3
REMARK   3  B VALUES.
REMARK   3   FROM WILSON PLOT           (A**2) : NULL
REMARK   3   MEAN B VALUE      (OVERALL, A**2) : 72.83
REMARK   3   OVERALL ANISOTROPIC B VALUE.
REMARK   3    B11 (A**2) : -6.42700
REMARK   3    B22 (A**2) : 17.65600
REMARK   3    B33 (A**2) : -11.22900
REMARK   3    B12 (A**2) : 0.00000
REMARK   3    B13 (A**2) : -0.00000
REMARK   3    B23 (A**2) : 0.00000
REMARK   3
REMARK   3  TWINNING INFORMATION.
REMARK   3   FRACTION: NULL
REMARK   3   OPERATOR: NULL
REMARK   3
REMARK   3  DEVIATIONS FROM IDEAL VALUES.
REMARK   3                RMSD          COUNT
REMARK   3   BOND      :  0.011          5399
REMARK   3   ANGLE     :  1.327          7339
REMARK   3   CHIRALITY :  0.094           836
REMARK   3   PLANARITY :  0.006           948
REMARK   3   DIHEDRAL  : 19.157          2030
REMARK   3
REMARK   3  TLS DETAILS
REMARK   3   NUMBER OF TLS GROUPS  : 7
REMARK   3   TLS GROUP : 1
REMARK   3    SELECTION: CHAIN A AND (RESSEQ 75:98)
REMARK   3    ORIGIN FOR THE GROUP (A):  27.4588 129.9760  32.3989
REMARK   3    T TENSOR
REMARK   3      T11:   1.5299 T22:   1.3974
REMARK   3      T33:   1.1170 T12:   0.0945
REMARK   3      T13:   0.0325 T23:   0.0118
REMARK   3    L TENSOR
REMARK   3      L11:   0.4001 L22:   0.1714
REMARK   3      L33:   0.0891 L12:   0.0791
REMARK   3      L13:   0.0371 L23:  -0.0733
REMARK   3 STENSOR
REMARK   3      S11:   0.2159 S12:   0.3459 S13:  -0.1859
REMARK   3      S21:   0.0699 S22:  -0.0141 S23:   0.0987
REMARK   3      S31:  -0.3800 S32:  -0.2322 S33:  -0.2399
REMARK   3   TLS GROUP : 2
REMARK   3    SELECTION: CHAIN A AND (RESSEQ 99:109)
REMARK   3    ORIGIN FOR THE GROUP (A):  37.5252 107.0208   3.6301
REMARK   3    T TENSOR
REMARK   3      T11:   0.8526 T22:   0.3998
REMARK   3      T33:   0.4947 T12:   0.1190
REMARK   3      T13:  -0.1729 T23:  -0.1055
REMARK   3    L TENSOR
REMARK   3      L11:   1.0180 L22:  -0.2176
REMARK   3      L33:   1.5111 L12:  -0.2649
REMARK   3      L13:  -0.0375 L23:  -0.7026
REMARK   3 STENSOR
REMARK   3      S11:  -0.3710 S12:  -0.1985 S13:   0.1596
```

FIG. 8-3

```
REMARK   3      S21:   0.5875 S22:   0.1919 S23:   0.0737
REMARK   3      S31:  -1.0770 S32:  -0.1952 S33:   0.2559
REMARK   3   TLS GROUP : 3
REMARK   3    SELECTION: CHAIN A AND (RESSEQ 110:197)
REMARK   3    ORIGIN FOR THE GROUP (A):  59.4087  89.5845   7.1320
REMARK   3    T TENSOR
REMARK   3      T11:   0.6174 T22:   0.7560
REMARK   3      T33:   0.4696 T12:  -0.0048
REMARK   3      T13:  -0.0844 T23:  -0.0215
REMARK   3    L TENSOR
REMARK   3      L11:   1.4878 L22:   0.6595
REMARK   3      L33:   1.4857 L12:  -0.0939
REMARK   3      L13:  -0.2320 L23:  -0.8567
REMARK   3 STENSOR
REMARK   3      S11:  -0.4486 S12:  -0.4161 S13:   0.0120
REMARK   3      S21:   0.0967 S22:   0.0387 S23:  -0.0471
REMARK   3      S31:  -0.1191 S32:   0.6716 S33:   0.2817
REMARK   3   TLS GROUP : 4
REMARK   3    SELECTION: CHAIN A AND (RESSEQ 198:210)
REMARK   3    ORIGIN FOR THE GROUP (A):  40.3037 107.4497  -0.6748
REMARK   3    T TENSOR
REMARK   3      T11:   0.8187 T22:   0.3192
REMARK   3      T33:   0.6339 T12:   0.0774
REMARK   3      T13:  -0.2352 T23:  -0.0919
REMARK   3    L TENSOR
REMARK   3      L11:   1.5730 L22:   1.0554
REMARK   3      L33:   1.0022 L12:  -0.9001
REMARK   3      L13:   0.2877 L23:  -0.0142
REMARK   3 STENSOR
REMARK   3      S11:  -0.0601 S12:  -0.2838 S13:   0.6909
REMARK   3      S21:  -0.4824 S22:  -0.5737 S23:  -0.2392
REMARK   3      S31:  -0.3505 S32:  -0.3362 S33:   0.3778
REMARK   3   TLS GROUP : 5
REMARK   3    SELECTION: CHAIN A AND (RESSEQ 211:233)
REMARK   3    ORIGIN FOR THE GROUP (A):  48.5626 115.0851  14.2611
REMARK   3    T TENSOR
REMARK   3      T11:   1.0418 T22:   0.6242
REMARK   3      T33:   1.1177 T12:  -0.0832
REMARK   3      T13:  -0.2286 T23:  -0.1506
REMARK   3    L TENSOR
REMARK   3      L11:   0.6579 L22:   0.5122
REMARK   3      L33:   0.5440 L12:  -0.0192
REMARK   3      L13:   0.0324 L23:   0.4224
REMARK   3 STENSOR
REMARK   3      S11:   0.2318 S12:  -0.2719 S13:   0.8681
REMARK   3      S21:  -0.3815 S22:  -0.1533 S23:  -0.5806
REMARK   3      S31:   0.0221 S32:   0.2011 S33:   0.1138
REMARK   3   TLS GROUP : 6
REMARK   3    SELECTION: CHAIN A AND (RESSEQ 267:379)
REMARK   3    ORIGIN FOR THE GROUP (A):  47.8622 122.8001   9.6792
REMARK   3    T TENSOR
REMARK   3      T11:   1.3396 T22:   0.4884
REMARK   3      T33:   1.1107 T12:  -0.0786
REMARK   3      T13:  -0.1791 T23:  -0.1436
REMARK   3    L TENSOR
REMARK   3      L11:   1.0067 L22:   0.3729
REMARK   3      L33:   1.3105 L12:   0.0695
REMARK   3      L13:  -0.4048 L23:   0.0457
REMARK   3 STENSOR
REMARK   3      S11:   0.5401 S12:  -0.0577 S13:   0.8388
REMARK   3      S21:   0.6299 S22:   0.1203 S23:  -0.8353
REMARK   3      S31:  -1.2190 S32:  -0.2491 S33:  -0.5466
REMARK   3   TLS GROUP : 7
REMARK   3    SELECTION: CHAIN A AND (RESSEQ 407:800)
REMARK   3    ORIGIN FOR THE GROUP (A):  40.4012  84.0187 -24.1290
REMARK   3    T TENSOR
REMARK   3      T11:   0.2177 T22:   0.4318
REMARK   3      T33:   0.2598 T12:  -0.0158
REMARK   3      T13:  -0.0256 T23:   0.0268
REMARK   3    L TENSOR
REMARK   3      L11:   0.6287 L22:   1.6907
REMARK   3      L33:   1.7295 L12:   0.0611
REMARK   3      L13:   0.0590 L23:   0.7705
REMARK   3 STENSOR
REMARK   3      S11:  -0.0892 S12:   0.1122 S13:  -0.0269
REMARK   3      S21:  -0.1311 S22:   0.0177 S23:  -0.0672
REMARK   3      S31:  -0.1639 S32:  -0.0183 S33:   0.0678
```

FIG. 8-4

```
REMARK   3
REMARK   3  NCS DETAILS
REMARK   3   NUMBER OF NCS GROUPS : NULL
REMARK   3
REMARK   3  OTHER REFINEMENT REMARKS: NULL
REMARK   4
REMARK   4 3FWN COMPLIES WITH FORMAT V. 3.20, 01-DEC-08
REMARK 100
REMARK 100 THIS ENTRY HAS BEEN PROCESSED BY PDBJ ON 26-JAN-09.
REMARK 100 THE RCSB ID CODE IS RCSB051133.
REMARK 200
REMARK 200 EXPERIMENTAL DETAILS
REMARK 200  EXPERIMENT TYPE                : X-RAY DIFFRACTION
REMARK 200  DATE OF DATA COLLECTION        : 28-JUL-08
REMARK 200  TEMPERATURE           (KELVIN) : 100
REMARK 200  PH                             : 8.0
REMARK 200  NUMBER OF CRYSTALS USED        : 1
REMARK 200
REMARK 200  SYNCHROTRON              (Y/N) : Y
REMARK 200  RADIATION SOURCE               : SPRING-8
REMARK 200  BEAMLINE                       : BL44XU
REMARK 200  X-RAY GENERATOR MODEL          : NULL
REMARK 200  MONOCHROMATIC OR LAUE    (M/L) : M
REMARK 200  WAVELENGTH OR RANGE        (A) : 0.9
REMARK 200  MONOCHROMATOR                  : NULL
REMARK 200  OPTICS                         : NULL
REMARK 200
REMARK 200  DETECTOR TYPE                  : IMAGE PLATE
REMARK 200  DETECTOR MANUFACTURER          : BRUKER DIP-6040
REMARK 200  INTENSITY-INTEGRATION SOFTWARE : HKL-2000
REMARK 200  DATA SCALING SOFTWARE          : HKL
REMARK 200
REMARK 200  NUMBER OF UNIQUE REFLECTIONS   : 60816
REMARK 200  RESOLUTION RANGE HIGH      (A) : 2.160
REMARK 200  RESOLUTION RANGE LOW       (A) : 30.000
REMARK 200  REJECTION CRITERIA  (SIGMA(I)) : NULL
REMARK 200
REMARK 200 OVERALL.
REMARK 200  COMPLETENESS FOR RANGE     (%) : 96.7
REMARK 200  DATA REDUNDANCY                : 4.500
REMARK 200  R MERGE                    (I) : 0.07700
REMARK 200  R SYM                      (I) : NULL
REMARK 200  <I/SIGMA(I)> FOR THE DATA SET  : 15.7520
REMARK 200
REMARK 200 IN THE HIGHEST RESOLUTION SHELL.
REMARK 200  HIGHEST RESOLUTION SHELL, RANGE HIGH (A) : 2.16
REMARK 200  HIGHEST RESOLUTION SHELL, RANGE LOW  (A) : 2.24
REMARK 200  COMPLETENESS FOR SHELL     (%) : 85.8
REMARK 200  DATA REDUNDANCY IN SHELL       : 4.00
REMARK 200  R MERGE FOR SHELL          (I) : 0.43700
REMARK 200  R SYM FOR SHELL            (I) : NULL
REMARK 200  <I/SIGMA(I)> FOR SHELL         : 2.100
REMARK 200
REMARK 200 DIFFRACTION PROTOCOL: SINGLE WAVELENGTH
REMARK 200 METHOD USED TO DETERMINE THE STRUCTURE: NULL
REMARK 200 SOFTWARE USED: NULL
REMARK 200 STARTING MODEL: NULL
REMARK 200
REMARK 200 REMARK: NULL
REMARK 280
REMARK 280 CRYSTAL
REMARK 280 SOLVENT CONTENT, VS   (%): 63.98
REMARK 280 MATTHEWS COEFFICIENT, VM (ANGSTROMS**3/DA): 3.41
REMARK 280
REMARK 280 CRYSTALLIZATION CONDITIONS: 20MM TRIS, 300MM NACL, 0.28MM N-
REMARK 280  DODECYL-N,N-DIMETHYLAMINE-N-OXIDE (LDAO), 1.2M SODIUM FORMATE,
REMARK 280  3% 6-AMINOHEXANOIC ACID, PH 8.0, VAPOR DIFFUSION, SITTING
REMARK 280  DROP, TEMPERATURE 289K
REMARK 290
REMARK 290 CRYSTALLOGRAPHIC SYMMETRY
REMARK 290 SYMMETRY OPERATORS FOR SPACE GROUP: P 21 21 2
REMARK 290
REMARK 290      SYMOP   SYMMETRY
REMARK 290     NNNMMM   OPERATOR
REMARK 290       1555   X,Y,Z
REMARK 290       2555   -X,-Y,Z
REMARK 290       3555   -X+1/2,Y+1/2,-Z
```

FIG. 8-5

```
REMARK 290       4555   X+1/2,-Y+1/2,-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290   SMTRY1   1  1.000000  0.000000  0.000000        0.00000
REMARK 290   SMTRY2   1  0.000000  1.000000  0.000000        0.00000
REMARK 290   SMTRY3   1  0.000000  0.000000  1.000000        0.00000
REMARK 290   SMTRY1   2 -1.000000  0.000000  0.000000        0.00000
REMARK 290   SMTRY2   2  0.000000 -1.000000  0.000000        0.00000
REMARK 290   SMTRY3   2  0.000000  0.000000  1.000000        0.00000
REMARK 290   SMTRY1   3 -1.000000  0.000000  0.000000       31.45000
REMARK 290   SMTRY2   3  0.000000  1.000000  0.000000      144.76700
REMARK 290   SMTRY3   3  0.000000  0.000000 -1.000000        0.00000
REMARK 290   SMTRY1   4  1.000000  0.000000  0.000000       31.45000
REMARK 290   SMTRY2   4  0.000000 -1.000000  0.000000      144.76700
REMARK 290   SMTRY3   4  0.000000  0.000000 -1.000000        0.00000
REMARK 290
REMARK 290 REMARK: NULL
REMARK 300
REMARK 300 BIOMOLECULE: 1
REMARK 300 SEE REMARK 350 FOR THE AUTHOR PROVIDED AND/OR PROGRAM
REMARK 300 GENERATED ASSEMBLY INFORMATION FOR THE STRUCTURE IN
REMARK 300 THIS ENTRY. THE REMARK MAY ALSO PROVIDE INFORMATION ON
REMARK 300 BURIED SURFACE AREA.
REMARK 350
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 AUTHOR DETERMINED BIOLOGICAL UNIT: MONOMERIC
REMARK 350 SOFTWARE DETERMINED QUATERNARY STRUCTURE: MONOMERIC
REMARK 350 SOFTWARE USED: PISA
REMARK 350 APPLY THE FOLLOWING TO CHAINS: A
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 465
REMARK 465 MISSING RESIDUES
REMARK 465 THE FOLLOWING RESIDUES WERE NOT LOCATED IN THE
REMARK 465 EXPERIMENT. (M=MODEL NUMBER; RES=RESIDUE NAME; C=CHAIN
REMARK 465 IDENTIFIER; SSSEQ=SEQUENCE NUMBER; I=INSERTION CODE.)
REMARK 465
REMARK 465   M RES C SSSEQI
REMARK 465     GLY A    54
REMARK 465     SER A    55
REMARK 465     HIS A    56
REMARK 465     MET A    57
REMARK 465     LYS A    58
REMARK 465     PRO A    59
REMARK 465     ARG A    60
REMARK 465     GLY A    61
REMARK 465     LYS A    62
REMARK 465     ARG A    63
REMARK 465     GLY A    64
REMARK 465     TRP A    65
REMARK 465     LEU A    66
REMARK 465     TRP A    67
REMARK 465     LEU A    68
REMARK 465     LEU A    69
REMARK 465     LEU A    70
REMARK 465     LYS A    71
REMARK 465     LEU A    72
REMARK 465     ALA A    73
REMARK 465     ILE A    74
REMARK 465     ASP A   234
REMARK 465     ARG A   235
REMARK 465     HIS A   236
REMARK 465     PHE A   237
REMARK 465     TYR A   238
```

FIG. 8-6

```
REMARK 465     GLU A   239
REMARK 465     HIS A   240
REMARK 465     ASP A   241
REMARK 465     GLY A   242
REMARK 465     ILE A   243
REMARK 465     SER A   244
REMARK 465     LEU A   245
REMARK 465     TYR A   246
REMARK 465     SER A   247
REMARK 465     ILE A   248
REMARK 465     GLY A   249
REMARK 465     ARG A   250
REMARK 465     ALA A   251
REMARK 465     VAL A   252
REMARK 465     LEU A   253
REMARK 465     ALA A   254
REMARK 465     ASN A   255
REMARK 465     LEU A   256
REMARK 465     THR A   257
REMARK 465     ALA A   258
REMARK 465     GLY A   259
REMARK 465     ARG A   260
REMARK 465     THR A   261
REMARK 465     VAL A   262
REMARK 465     GLN A   263
REMARK 465     GLY A   264
REMARK 465     ALA A   265
REMARK 465     SER A   266
REMARK 465     LEU A   380
REMARK 465     GLN A   381
REMARK 465     GLN A   382
REMARK 465     GLN A   383
REMARK 465     GLN A   384
REMARK 465     ILE A   385
REMARK 465     ILE A   386
REMARK 465     ASP A   387
REMARK 465     GLN A   388
REMARK 465     GLU A   389
REMARK 465     LEU A   390
REMARK 465     TYR A   391
REMARK 465     ASP A   392
REMARK 465     MET A   393
REMARK 465     LEU A   394
REMARK 465     ASP A   395
REMARK 465     ALA A   396
REMARK 465     ARG A   397
REMARK 465     PRO A   398
REMARK 465     LEU A   399
REMARK 465     GLY A   400
REMARK 465     VAL A   401
REMARK 465     GLN A   402
REMARK 465     PRO A   403
REMARK 465     ARG A   404
REMARK 465     GLY A   405
REMARK 465     GLY A   406
REMARK 465     GLN A   801
REMARK 465     GLN A   802
REMARK 465     PRO A   803
REMARK 465     SER A   804
REMARK 500
REMARK 500 GEOMETRY AND STEREOCHEMISTRY
REMARK 500 SUBTOPIC: CLOSE CONTACTS IN SAME ASYMMETRIC UNIT
REMARK 500
REMARK 500 THE FOLLOWING ATOMS ARE IN CLOSE CONTACT.
REMARK 500
REMARK 500  ATM1  RES C  SSEQI   ATM2  RES C  SSEQI           DISTANCE
REMARK 500   OG   SER A   792  O    HOH A  1203              2.17
REMARK 500
REMARK 500 REMARK: NULL
REMARK 500
REMARK 500 GEOMETRY AND STEREOCHEMISTRY
REMARK 500 SUBTOPIC: TORSION ANGLES
REMARK 500
REMARK 500 TORSION ANGLES OUTSIDE THE EXPECTED RAMACHANDRAN REGIONS:
REMARK 500 (M=MODEL NUMBER; RES=RESIDUE NAME; C=CHAIN IDENTIFIER;
REMARK 500 SSEQ=SEQUENCE NUMBER; I=INSERTION CODE).
REMARK 500
```

FIG. 8-7

```
REMARK 500 STANDARD TABLE:
REMARK 500 FORMAT:(10X,I3,1X,A3,1X,A1,I4,A1,4X,F7.2,3X,F7.2)
REMARK 500
REMARK 500 EXPECTED VALUES: GJ KLEYWEGT AND TA JONES (1996). PHI/PSI-
REMARK 500 CHOLOGY: RAMACHANDRAN REVISITED. STRUCTURE 4, 1395 - 1400
REMARK 500
REMARK 500  M RES CSSEQI        PSI       PHI
REMARK 500    VAL A  76       31.73    -85.30
REMARK 500    TYR A  83       -9.18    -59.81
REMARK 500    ARG A  92      -61.38   -123.30
REMARK 500    ASP A  96       58.79    -92.33
REMARK 500    THR A 140      -25.27   -149.77
REMARK 500    SER A 164      121.48    169.32
REMARK 500    ASP A 176       63.20   -106.91
REMARK 500    ASN A 189       19.69     57.09
REMARK 500    SER A 206      128.43    -28.39
REMARK 500    ASP A 223      -60.43    -21.93
REMARK 500    GLN A 279     -163.63   -108.63
REMARK 500    GLU A 281     -176.37    -90.59
REMARK 500    TYR A 284      -55.44    -21.64
REMARK 500    LYS A 303      -92.22    -29.49
REMARK 500    ARG A 364      -78.26    -54.91
REMARK 500    ARG A 378       27.14    -72.86
REMARK 500    VAL A 430      -68.11   -133.91
REMARK 500    LEU A 470      137.84   -177.17
REMARK 500    PRO A 543      138.82    -33.63
REMARK 500    ASN A 544      116.56    -20.53
REMARK 500    GLN A 657       40.62   -154.71
REMARK 500    HIS A 694       47.75     38.94
REMARK 500    ASP A 714     -168.48   -107.89
REMARK 500    LYS A 732      -12.80     72.17
REMARK 500    ASP A 789       75.42   -159.54
REMARK 500    PRO A 790       10.33    -46.76
REMARK 500
REMARK 500 REMARK: NULL
REMARK 500
REMARK 500 GEOMETRY AND STEREOCHEMISTRY
REMARK 500 SUBTOPIC: NON-CIS, NON-TRANS
REMARK 500
REMARK 500 THE FOLLOWING PEPTIDE BONDS DEVIATE SIGNIFICANTLY FROM BOTH
REMARK 500 CIS AND TRANS CONFORMATION.  CIS BONDS, IF ANY, ARE LISTED
REMARK 500 ON CISPEP RECORDS.  TRANS IS DEFINED AS 180 +/- 30 AND
REMARK 500 CIS IS DEFINED AS 0 +/- 30 DEGREES.
REMARK 500                                  MODEL     OMEGA
REMARK 500 GLN A  791     SER A  792                   147.92
REMARK 500
REMARK 500 REMARK: NULL
REMARK 500
REMARK 500 GEOMETRY AND STEREOCHEMISTRY
REMARK 500 SUBTOPIC: CHIRAL CENTERS
REMARK 500
REMARK 500 UNEXPECTED CONFIGURATION OF THE FOLLOWING CHIRAL
REMARK 500 CENTER(S) USING IMPROPER CA--C--CB--N CHIRALITY
REMARK 500 M=MODEL NUMBER; RES=RESIDUE NAME; C=CHAIN
REMARK 500 IDENTIFIER; SSEQ=SEQUENCE NUMBER; I=INSERTION CODE
REMARK 500
REMARK 500 STANDARD TABLE:
REMARK 500 FORMAT: (11X,I3,1X,A3,1X,A1,I4,A1,6X,F5.1,6X,A1,10X,A1,3X,A16)
REMARK 500
REMARK 500   M RES CSSEQI    IMPROPER   EXPECTED   FOUND DETAILS
REMARK 500     VAL A 677        24.6      L           L   OUTSIDE RANGE
REMARK 500     TYR A 734        23.4      L           L   OUTSIDE RANGE
REMARK 500
REMARK 500 REMARK: NULL
REMARK 525
REMARK 525 SOLVENT
REMARK 525
REMARK 525 THE SOLVENT MOLECULES HAVE CHAIN IDENTIFIERS THAT
REMARK 525 INDICATE THE POLYMER CHAIN WITH WHICH THEY ARE MOST
REMARK 525 CLOSELY ASSOCIATED. THE REMARK LISTS ALL THE SOLVENT
REMARK 525 MOLECULES WHICH ARE MORE THAN 5A AWAY FROM THE
REMARK 525 NEAREST POLYMER CHAIN (M = MODEL NUMBER;
REMARK 525 RES=RESIDUE NAME; C=CHAIN IDENTIFIER; SSEQ=SEQUENCE
REMARK 525 NUMBER; I=INSERTION CODE):
REMARK 525
REMARK 525  M RES CSSEQI
REMARK 525    HOH A1196        DISTANCE =  6.10 ANGSTROMS
```

FIG. 8-8

```
REMARK 525    HOH A1138        DISTANCE =  6.01 ANGSTROMS
REMARK 610
REMARK 610 MISSING HETEROATOM
REMARK 610 THE FOLLOWING RESIDUES HAVE MISSING ATOMS (M=MODEL NUMBER;
REMARK 610 RES=RESIDUE NAME; C=CHAIN IDENTIFIER; SSEQ=SEQUENCE NUMBER;
REMARK 610 I=INSERTION CODE):
REMARK 610   M RES C SSEQI
REMARK 610     MOE A  901
REMARK 800
REMARK 800 SITE
REMARK 800 SITE_IDENTIFIER: AC1
REMARK 800 EVIDENCE_CODE: SOFTWARE
REMARK 800 SITE_DESCRIPTION: BINDING SITE FOR RESIDUE MOE A 901
REMARK 900
REMARK 900 RELATED ENTRIES
REMARK 900 RELATED ID: 3FWL   RELATED DB: PDB
DBREF  3FWM A   58   804  UNP    P02919   PBPB_ECOLI      58    804
SEQADV 3FWM GLY A   54  UNP  P02919              EXPRESSION TAG
SEQADV 3FWM SER A   55  UNP  P02919              EXPRESSION TAG
SEQADV 3FWM HIS A   56  UNP  P02919              EXPRESSION TAG
SEQADV 3FWM MET A   57  UNP  P02919              EXPRESSION TAG
SEQRES   1 A  751  GLY SER HIS MET LYS PRO ARG GLY LYS ARG GLY TRP LEU
SEQRES   2 A  751  TRP LEU LEU LEU LYS LEU ALA ILE VAL PHE ALA VAL LEU
SEQRES   3 A  751  ILE ALA ILE TYR GLY VAL TYR LEU ASP GLN LYS ILE ARG
SEQRES   4 A  751  SER ARG ILE ASP GLY LYS VAL TRP GLN LEU PRO ALA ALA
SEQRES   5 A  751  VAL TYR GLY ARG MET VAL ASN LEU GLU PRO ASP MET THR
SEQRES   6 A  751  ILE SER LYS ASN GLU MET VAL LYS LEU LEU GLU ALA THR
SEQRES   7 A  751  GLN TYR ARG GLN VAL SER LYS MET THR ARG PRO GLY GLU
SEQRES   8 A  751  PHE THR VAL GLN ALA ASN SER ILE GLU MET ILE ARG ARG
SEQRES   9 A  751  PRO PHE ASP PHE PRO ASP SER LYS GLU GLY GLN VAL ARG
SEQRES  10 A  751  ALA ARG LEU THR PHE ASP GLY ASP HIS LEU ALA THR ILE
SEQRES  11 A  751  VAL ASN MET GLU ASN ASN ARG GLN PHE GLY PHE PHE ARG
SEQRES  12 A  751  LEU ASP PRO ARG LEU ILE THR MET ILE SER SER PRO ASN
SEQRES  13 A  751  GLY GLU GLN ARG LEU PHE VAL PRO ARG SER GLY PHE PRO
SEQRES  14 A  751  ASP LEU LEU VAL ASP THR LEU LEU ALA THR GLU ASP ARG
SEQRES  15 A  751  HIS PHE TYR GLU HIS ASP GLY ILE SER LEU TYR SER ILE
SEQRES  16 A  751  GLY ARG ALA VAL LEU ALA ASN LEU THR ALA GLY ARG THR
SEQRES  17 A  751  VAL GLN GLY ALA SER THR LEU THR GLN GLN LEU VAL LYS
SEQRES  18 A  751  ASN LEU PHE LEU SER SER GLU ARG SER TYR TRP ARG LYS
SEQRES  19 A  751  ALA ASN GLU ALA TYR MET ALA LEU ILE MET ASP ALA ARG
SEQRES  20 A  751  TYR SER LYS ASP ARG ILE LEU GLU LEU TYR MET ASN GLU
SEQRES  21 A  751  VAL TYR LEU GLY GLN SER GLY ASP ASN GLU ILE ARG GLY
SEQRES  22 A  751  PHE PRO LEU ALA SER LEU TYR TYR PHE GLY ARG PRO VAL
SEQRES  23 A  751  GLU GLU LEU SER LEU ASP GLN GLN ALA LEU LEU VAL GLY
SEQRES  24 A  751  MET VAL LYS GLY ALA SER ILE TYR ASN PRO TRP ARG ASN
SEQRES  25 A  751  PRO LYS LEU ALA LEU GLU ARG ARG ASN LEU VAL LEU ARG
SEQRES  26 A  751  LEU LEU GLN GLN GLN GLN ILE ILE ASP GLN GLU LEU TYR
SEQRES  27 A  751  ASP MET LEU SER ALA ARG PRO LEU GLY VAL GLN PRO ARG
SEQRES  28 A  751  GLY GLY VAL ILE SER PRO GLN PRO ALA PHE MET GLN LEU
SEQRES  29 A  751  VAL ARG GLN GLU LEU GLN ALA LYS LEU GLY ASP LYS VAL
SEQRES  30 A  751  LYS ASP LEU SER GLY VAL LYS ILE PHE THR THR PHE ASP
SEQRES  31 A  751  SER VAL ALA GLN ASP ALA ALA GLU LYS ALA ALA VAL GLU
SEQRES  32 A  751  GLY ILE PRO ALA LEU LYS LYS GLN ARG LYS LEU SER ASP
SEQRES  33 A  751  LEU GLU THR ALA ILE VAL VAL VAL ASP ARG PHE SER GLY
SEQRES  34 A  751  GLU VAL ARG ALA MET VAL GLY GLY SER GLU PRO GLN PHE
SEQRES  35 A  751  ALA GLY TYR ASN ARG ALA MET GLN ALA ARG ARG SER ILE
SEQRES  36 A  751  GLY SER LEU ALA LYS PRO ALA THR TYR LEU THR ALA LEU
SEQRES  37 A  751  SER GLN PRO LYS ILE TYR ARG LEU ASN THR TRP ILE ALA
SEQRES  38 A  751  ASP ALA PRO ILE ALA LEU ARG GLN PRO ASN GLY GLN VAL
SEQRES  39 A  751  TRP SER PRO GLN ASN ASP ASP ARG ARG TYR SER GLU SER
SEQRES  40 A  751  GLY ARG VAL MET LEU VAL ASP ALA LEU THR ARG SER MET
SEQRES  41 A  751  ASN VAL PRO THR VAL ASN LEU GLY MET ALA LEU GLY LEU
SEQRES  42 A  751  PRO ALA VAL THR GLU THR TRP ILE LYS LEU GLY VAL PRO
SEQRES  43 A  751  LYS ASP GLN LEU HIS PRO VAL PRO ALA MET LEU LEU GLY
SEQRES  44 A  751  ALA LEU ASN LEU THR PRO ILE GLU VAL ALA GLN ALA PHE
SEQRES  45 A  751  GLN THR ILE ALA SER GLY GLY ASN ARG ALA PRO LEU SER
SEQRES  46 A  751  ALA LEU ARG SER VAL ILE ALA GLU ASP GLY LYS VAL LEU
SEQRES  47 A  751  TYR GLN SER PHE PRO GLN ALA GLU ARG ALA VAL PRO ALA
SEQRES  48 A  751  GLN ALA ALA TYR LEU THR LEU TRP THR MET GLN GLN VAL
SEQRES  49 A  751  VAL GLN ARG GLY THR GLY ARG GLN LEU GLY ALA LYS TYR
SEQRES  50 A  751  PRO ASN LEU HIS LEU ALA GLY LYS THR GLY THR THR ASN
SEQRES  51 A  751  ASN ASN VAL ASP THR TRP PHE ALA GLY ILE ASP GLY SER
SEQRES  52 A  751  THR VAL THR ILE THR TRP VAL GLY ARG ASP ASN ASN GLN
SEQRES  53 A  751  PRO THR LYS LEU TYR GLY ALA SER GLY ALA MET SER ILE
SEQRES  54 A  751  TYR GLN ARG TYR LEU ALA ASN GLN THR PRO THR PRO LEU
SEQRES  55 A  751  ASN LEU VAL PRO PRO GLU ASP ILE ALA ASP MET GLY VAL
SEQRES  56 A  751  ASP TYR ASP GLY ASN PHE VAL CYS SER GLY GLY MET ARG
```

FIG. 8-9

```
SEQRES  57 A  751  ILE LEU PRO VAL TRP THR SER ASP PRO GLN SER LEU CYS
SEQRES  58 A  751  GLN GLN SER GLU MET GLN GLN GLN PRO SER
HET    MOE  A 901      77
HETNAM     MOE MOENOMYCIN
HETSYN     MOE MOENOMYCIN
FORMUL   2  MOE    C69 H106 N5 O34 P
FORMUL   3  HOH   *235(H2 O)
HELIX    1   1 ALA A   77  ALA A   81  5                                   5
HELIX    2   2 GLN A   89  ARG A   94  1                                   6
HELIX    3   3 SER A  120  ALA A  130  1                                  11
HELIX    4   4 PRO A  222  LEU A  230  1                                   9
HELIX    5   5 THR A  267  LEU A  278  1                                  12
HELIX    6   6 ARG A  282  TYR A  301  1                                  20
HELIX    7   7 SER A  302  MET A  311  1                                  10
HELIX    8   8 GLY A  326  PHE A  335  1                                  10
HELIX    9   9 PRO A  338  LEU A  342  5                                   5
HELIX   10  10 SER A  343  VAL A  354  1                                  12
HELIX   11  11 PRO A  366  ARG A  378  1                                  13
HELIX   12  12 GLN A  411  GLY A  427  1                                  17
HELIX   13  13 ASP A  443  LYS A  466  1                                  24
HELIX   14  14 ASN A  499  ALA A  504  1                                   6
HELIX   15  15 GLY A  509  LEU A  511  5                                   3
HELIX   16  16 ALA A  512  SER A  522  1                                  11
HELIX   17  17 LEU A  565  ARG A  571  1                                   7
HELIX   18  18 MET A  573  GLY A  585  1                                  13
HELIX   19  19 GLY A  585  GLY A  597  1                                  13
HELIX   20  20 PRO A  599  LEU A  603  5                                   5
HELIX   21  21 VAL A  606  GLY A  612  5                                   7
HELIX   22  22 THR A  617  SER A  630  1                                  14
HELIX   23  23 PRO A  663  ARG A  680  1                                  18
HELIX   24  24 GLY A  683  TYR A  690  1                                   8
HELIX   25  25 PRO A  691  HIS A  694  5                                   4
HELIX   26  26 ASN A  703  ASN A  705  5                                   3
HELIX   27  27 ALA A  736  ASN A  749  1                                  14
HELIX   28  28 GLN A  791  GLU A  798  1                                   8
SHEET    1   A 5 LEU A 203  ILE A 205  0
SHEET    2   A 5 ALA A 104  TYR A 107 -1  N  VAL A 106O THR A 203
SHEET    3   A 5 LYS A 437  THR A 440  1  O  ILE A 438N ALA A 105
SHEET    4   A 5 LEU A 640  ILE A 644 -1  O  ILE A 644N LYS A 437
SHEET    5   A 5 VAL A 650  GLN A 653 -1  O  LEU A 651N VAL A 643
SHEET    1   B 2 ASN A 112  LEU A 113  0
SHEET    2   B 2 PHE A 195  ARG A 196 -1  O  PHE A 195N LEU A 113
SHEET    1C6 ARG A 134  GLN A 135  0
SHEET    2C6 GLU A 144  GLN A 148  1  O  PHE A 145N ARG A 134
SHEET    3C6 ASP A 151  ARG A 156 -1  O  GLU A 153N THR A 146
SHEET    4C6 VAL A 169  ASP A 176 -1  O  ALA A 171N MET A 154
SHEET    5C6 HIS A 179  ASN A 185 -1  O  ALA A 181N THR A 174
SHEET    6C6 ARG A 190  GLN A 191 -1  O  ARG A 190N ASN A 185
SHEET    1   D 2 PHE A 159  PHE A 161  0
SHEET    2   D 2 SER A 164  GLU A 166 -1  O  SER A 164N PHE A 161
SHEET    1   E 3 GLU A 211  GLN A 212  0
SHEET    2   E 3 ASN A 322  ARG A 325  1  O  GLU A 323N GLN A 212
SHEET    3   E 3 TYR A 315  SER A 319 -1  N  SER A 319O ASN A 322
SHEET    1   F 5 VAL A 484  VAL A 488  0
SHEET    2   F 5 GLU A 471  ASP A 478 -1  N  ILE A 474O VAL A 488
SHEET    3   F 5 THR A 717  GLY A 724 -1  O  ILE A 720N VAL A 475
SHEET    4   F 5 ASP A 707  ILE A 713 -1  N  GLY A 712O THR A 719
SHEET    5   F 5 ALA A 698  THR A 701 -1  N  ALA A 696O ILE A 713
SHEET    1   G 2 ARG A 506  SER A 507  0
SHEET    2   G 2 ASN A 615  LEU A 616 -1  O  LEU A 616N ARG A 506
SHEET    1   H 2 TRP A 532  ALA A 534  0
SHEET    2   H 2 ARG A 562  MET A 564 -1  O  VAL A 563N ILE A 533
SHEET    1   I 2 LEU A 540  ARG A 541  0
SHEET    2   I 2 VAL A 547  TRP A 548 -1  O  TRP A 548N LEU A 540
SHEET    1   J 2 ASN A 633  ARG A 634  0
SHEET    2   J 2 GLU A 659  ARG A 660 -1  O  GLU A 659N ARG A 634
SHEET    1   K 3 PHE A 774  VAL A 775  0
SHEET    2   K 3 ILE A 763  VAL A 768 -1  N  GLY A 767O VAL A 775
SHEET    3   K 3 ARG A 781  TRP A 786 -1  O  LEU A 783N MET A 766
CISPEP   1 GLU A  281    ARG A  282          0         7.61
CISPEP   2 ASN A  544    GLY A  545          0        -4.58
SITE     1 AC1 15 GLN A 271  LYS A 274  ASN A 275  GLU A 281
SITE     2 AC1 15 SER A 283  ARG A 288  TYR A 315  GLN A 318
SITE     3 AC1 15 GLU A 323  VAL A 354  LYS A 355  GLY A 356
SITE     4 AC1 15 ALA A 357  SER A 358  ILE A 359
CRYST1   62.900  288.534   62.776  90.00  90.00  90.00 P 21 21 2     4
ORIGX1      1.000000  0.000000  0.000000        0.00000
```

FIG.8-10

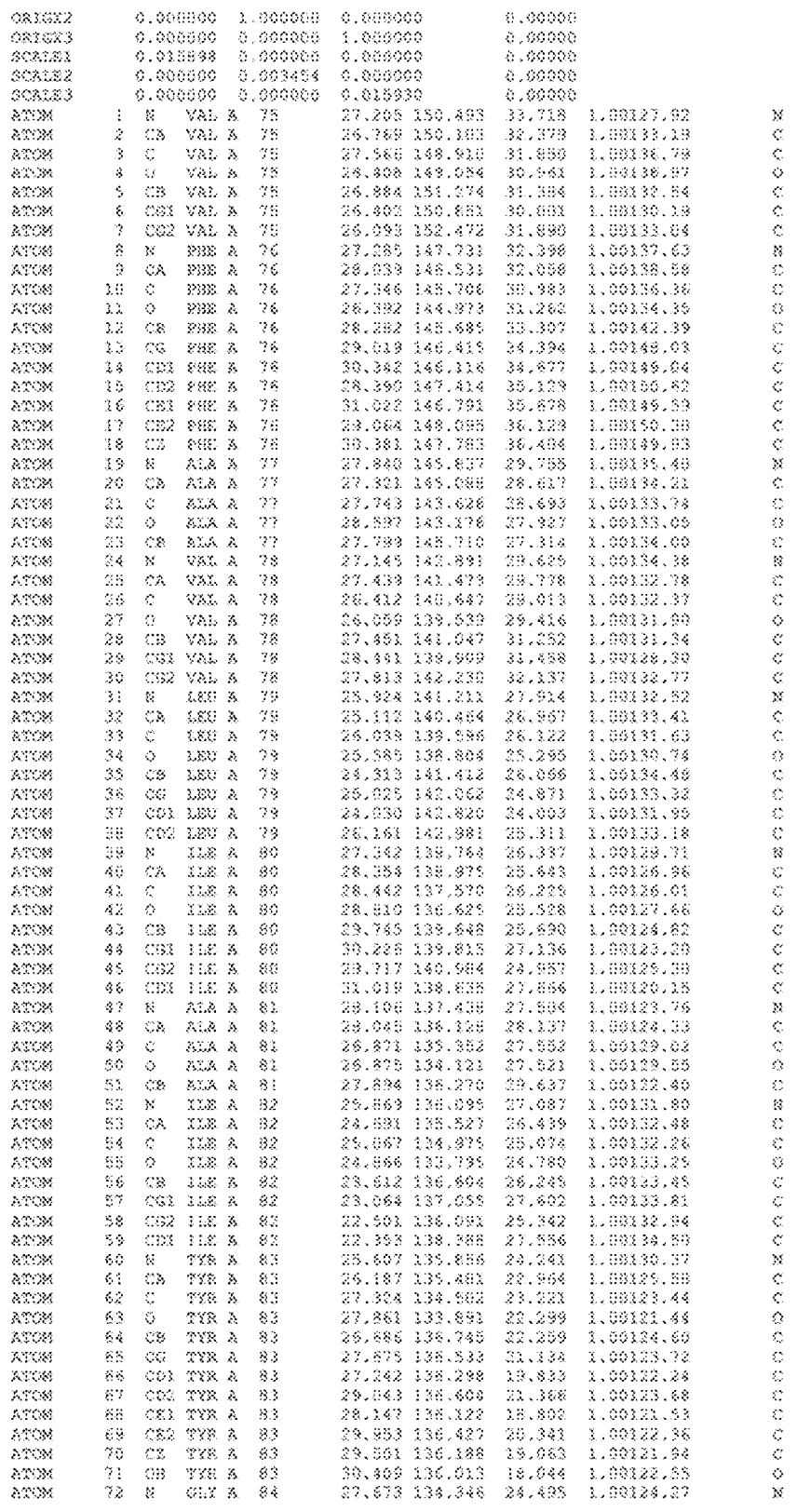

| | | | | | | | | | | |
|---|---|---|---|---|---|---|---|---|---|---|
| ORIGX2 | | 0.000000 | 1.000000 | 0.000000 | | | 0.00000 | | | |
| ORIGX3 | | 0.000000 | 0.000000 | 1.000000 | | | 0.00000 | | | |
| SCALE1 | | 0.015898 | 0.000000 | 0.000000 | | | 0.00000 | | | |
| SCALE2 | | 0.000000 | 0.003454 | 0.000000 | | | 0.00000 | | | |
| SCALE3 | | 0.000000 | 0.000000 | 0.015930 | | | 0.00000 | | | |
| ATOM | 1 | N | VAL | A | 75 | 27.205 | 150.493 | 33.718 | 1.00127.92 | N |
| ATOM | 2 | CA | VAL | A | 75 | 26.769 | 150.183 | 32.379 | 1.00133.18 | C |
| ATOM | 3 | C | VAL | A | 75 | 27.566 | 148.910 | 31.850 | 1.00136.78 | C |
| ATOM | 4 | O | VAL | A | 75 | 28.408 | 149.054 | 30.961 | 1.00138.97 | O |
| ATOM | 5 | CB | VAL | A | 75 | 26.884 | 151.374 | 31.384 | 1.00132.54 | C |
| ATOM | 6 | CG1 | VAL | A | 75 | 26.403 | 150.851 | 30.001 | 1.00130.18 | C |
| ATOM | 7 | CG2 | VAL | A | 75 | 26.093 | 152.472 | 31.890 | 1.00133.04 | C |
| ATOM | 8 | N | PHE | A | 76 | 27.285 | 147.731 | 32.398 | 1.00137.63 | N |
| ATOM | 9 | CA | PHE | A | 76 | 28.039 | 146.531 | 32.058 | 1.00138.58 | C |
| ATOM | 10 | C | PHE | A | 76 | 27.346 | 145.706 | 30.983 | 1.00136.36 | C |
| ATOM | 11 | O | PHE | A | 76 | 26.392 | 144.873 | 31.262 | 1.00134.35 | O |
| ATOM | 12 | CB | PHE | A | 76 | 28.282 | 145.685 | 33.307 | 1.00142.39 | C |
| ATOM | 13 | CG | PHE | A | 76 | 29.019 | 146.415 | 34.394 | 1.00148.03 | C |
| ATOM | 14 | CD1 | PHE | A | 76 | 30.342 | 146.116 | 34.677 | 1.00149.04 | C |
| ATOM | 15 | CD2 | PHE | A | 76 | 28.390 | 147.414 | 35.129 | 1.00150.62 | C |
| ATOM | 16 | CE1 | PHE | A | 76 | 31.022 | 146.791 | 35.678 | 1.00149.53 | C |
| ATOM | 17 | CE2 | PHE | A | 76 | 29.064 | 148.095 | 36.129 | 1.00150.38 | C |
| ATOM | 18 | CZ | PHE | A | 76 | 30.381 | 147.783 | 36.404 | 1.00149.93 | C |
| ATOM | 19 | N | ALA | A | 77 | 27.840 | 145.837 | 29.755 | 1.00135.40 | N |
| ATOM | 20 | CA | ALA | A | 77 | 27.321 | 145.088 | 28.617 | 1.00134.21 | C |
| ATOM | 21 | C | ALA | A | 77 | 27.743 | 143.628 | 28.693 | 1.00133.74 | C |
| ATOM | 22 | O | ALA | A | 77 | 28.597 | 143.176 | 27.927 | 1.00133.05 | O |
| ATOM | 23 | CB | ALA | A | 77 | 27.789 | 145.710 | 27.314 | 1.00134.00 | C |
| ATOM | 24 | N | VAL | A | 78 | 27.145 | 142.891 | 29.625 | 1.00134.38 | N |
| ATOM | 25 | CA | VAL | A | 78 | 27.439 | 141.473 | 29.778 | 1.00132.78 | C |
| ATOM | 26 | C | VAL | A | 78 | 26.412 | 140.647 | 29.013 | 1.00132.37 | C |
| ATOM | 27 | O | VAL | A | 78 | 26.059 | 139.539 | 29.416 | 1.00131.90 | O |
| ATOM | 28 | CB | VAL | A | 78 | 27.451 | 141.047 | 31.252 | 1.00131.34 | C |
| ATOM | 29 | CG1 | VAL | A | 78 | 28.441 | 139.909 | 31.458 | 1.00128.30 | C |
| ATOM | 30 | CG2 | VAL | A | 78 | 27.813 | 142.230 | 32.137 | 1.00132.77 | C |
| ATOM | 31 | N | LEU | A | 79 | 25.924 | 141.211 | 27.914 | 1.00132.52 | N |
| ATOM | 32 | CA | LEU | A | 79 | 25.112 | 140.464 | 26.967 | 1.00133.41 | C |
| ATOM | 33 | C | LEU | A | 79 | 26.039 | 139.596 | 26.122 | 1.00131.63 | C |
| ATOM | 34 | O | LEU | A | 79 | 25.585 | 138.804 | 25.295 | 1.00130.74 | O |
| ATOM | 35 | CB | LEU | A | 79 | 24.313 | 141.412 | 26.066 | 1.00134.49 | C |
| ATOM | 36 | CG | LEU | A | 79 | 25.025 | 142.062 | 24.871 | 1.00133.32 | C |
| ATOM | 37 | CD1 | LEU | A | 79 | 24.030 | 142.820 | 24.003 | 1.00131.95 | C |
| ATOM | 38 | CD2 | LEU | A | 79 | 26.161 | 142.981 | 25.311 | 1.00133.18 | C |
| ATOM | 39 | N | ILE | A | 80 | 27.342 | 139.764 | 26.337 | 1.00128.71 | N |
| ATOM | 40 | CA | ILE | A | 80 | 28.354 | 138.875 | 25.643 | 1.00126.96 | C |
| ATOM | 41 | C | ILE | A | 80 | 28.442 | 137.570 | 26.229 | 1.00126.01 | C |
| ATOM | 42 | O | ILE | A | 80 | 28.810 | 136.625 | 25.528 | 1.00127.66 | O |
| ATOM | 43 | CB | ILE | A | 80 | 29.745 | 139.648 | 25.690 | 1.00124.82 | C |
| ATOM | 44 | CG1 | ILE | A | 80 | 30.226 | 139.815 | 27.136 | 1.00123.20 | C |
| ATOM | 45 | CG2 | ILE | A | 80 | 29.717 | 140.984 | 24.957 | 1.00125.38 | C |
| ATOM | 46 | CD1 | ILE | A | 80 | 31.019 | 138.835 | 27.866 | 1.00120.15 | C |
| ATOM | 47 | N | ALA | A | 81 | 28.106 | 137.438 | 27.504 | 1.00123.76 | N |
| ATOM | 48 | CA | ALA | A | 81 | 28.045 | 136.128 | 28.137 | 1.00124.33 | C |
| ATOM | 49 | C | ALA | A | 81 | 26.871 | 135.352 | 27.552 | 1.00129.02 | C |
| ATOM | 50 | O | ALA | A | 81 | 26.875 | 134.121 | 27.521 | 1.00129.55 | O |
| ATOM | 51 | CB | ALA | A | 81 | 27.834 | 136.270 | 29.637 | 1.00122.40 | C |
| ATOM | 52 | N | ILE | A | 82 | 25.869 | 136.095 | 27.087 | 1.00131.80 | N |
| ATOM | 53 | CA | ILE | A | 82 | 24.881 | 135.527 | 26.439 | 1.00132.48 | C |
| ATOM | 54 | C | ILE | A | 82 | 25.067 | 134.875 | 25.074 | 1.00132.26 | C |
| ATOM | 55 | O | ILE | A | 82 | 24.866 | 133.795 | 24.780 | 1.00133.29 | O |
| ATOM | 56 | CB | ILE | A | 82 | 23.612 | 136.604 | 26.245 | 1.00133.45 | C |
| ATOM | 57 | CG1 | ILE | A | 82 | 23.064 | 137.055 | 27.602 | 1.00133.81 | C |
| ATOM | 58 | CG2 | ILE | A | 82 | 22.501 | 136.091 | 25.342 | 1.00132.94 | C |
| ATOM | 59 | CD1 | ILE | A | 82 | 22.393 | 138.388 | 27.556 | 1.00134.50 | C |
| ATOM | 60 | N | TYR | A | 83 | 25.607 | 135.856 | 24.241 | 1.00130.37 | N |
| ATOM | 61 | CA | TYR | A | 83 | 26.187 | 135.481 | 22.964 | 1.00125.58 | C |
| ATOM | 62 | C | TYR | A | 83 | 27.324 | 134.982 | 23.221 | 1.00123.44 | C |
| ATOM | 63 | O | TYR | A | 83 | 27.861 | 133.891 | 22.299 | 1.00121.44 | O |
| ATOM | 64 | CB | TYR | A | 83 | 26.686 | 136.745 | 22.259 | 1.00124.60 | C |
| ATOM | 65 | CG | TYR | A | 83 | 27.675 | 136.533 | 21.134 | 1.00123.72 | C |
| ATOM | 66 | CD1 | TYR | A | 83 | 27.242 | 136.298 | 19.833 | 1.00122.24 | C |
| ATOM | 67 | CD2 | TYR | A | 83 | 29.043 | 136.608 | 21.368 | 1.00123.68 | C |
| ATOM | 68 | CE1 | TYR | A | 83 | 28.147 | 136.122 | 18.802 | 1.00121.53 | C |
| ATOM | 69 | CE2 | TYR | A | 83 | 29.953 | 136.427 | 20.341 | 1.00122.36 | C |
| ATOM | 70 | CZ | TYR | A | 83 | 29.501 | 136.188 | 19.063 | 1.00121.94 | C |
| ATOM | 71 | OH | TYR | A | 83 | 30.409 | 136.013 | 18.044 | 1.00122.55 | O |
| ATOM | 72 | N | GLY | A | 84 | 27.673 | 134.346 | 24.435 | 1.00124.37 | N |

FIG. 8-11

| | | | | | | | | | | |
|---|---|---|---|---|---|---|---|---|---|---|
| ATOM | 73 | CA | GLY | A | 84 | 28.731 | 133.442 | 24.899 | 1.00125.30 | C |
| ATOM | 74 | C | GLY | A | 84 | 28.237 | 132.066 | 25.291 | 1.00127.47 | C |
| ATOM | 75 | O | GLY | A | 84 | 29.025 | 131.128 | 25.403 | 1.00127.18 | O |
| ATOM | 76 | N | VAL | A | 85 | 26.931 | 131.944 | 25.506 | 1.00130.18 | N |
| ATOM | 77 | CA | VAL | A | 85 | 26.331 | 130.651 | 25.820 | 1.00133.58 | C |
| ATOM | 78 | C | VAL | A | 85 | 25.578 | 130.086 | 24.624 | 1.00140.78 | C |
| ATOM | 79 | O | VAL | A | 85 | 25.688 | 128.897 | 24.316 | 1.00143.42 | O |
| ATOM | 80 | CB | VAL | A | 85 | 25.387 | 130.730 | 27.035 | 1.00130.18 | C |
| ATOM | 81 | CG1 | VAL | A | 85 | 24.124 | 129.915 | 26.784 | 1.00129.15 | C |
| ATOM | 82 | CG2 | VAL | A | 85 | 26.109 | 130.256 | 28.294 | 1.00127.01 | C |
| ATOM | 83 | N | TYR | A | 86 | 24.813 | 130.940 | 23.952 | 1.00143.27 | N |
| ATOM | 84 | CA | TYR | A | 86 | 24.104 | 130.534 | 22.746 | 1.00145.67 | C |
| ATOM | 85 | C | TYR | A | 86 | 25.131 | 130.198 | 21.668 | 1.00142.50 | C |
| ATOM | 86 | O | TYR | A | 86 | 24.812 | 129.578 | 20.652 | 1.00141.31 | O |
| ATOM | 87 | CB | TYR | A | 86 | 23.170 | 131.650 | 22.277 | 1.00150.99 | C |
| ATOM | 88 | CG | TYR | A | 86 | 21.974 | 131.175 | 21.476 | 1.00154.94 | C |
| ATOM | 89 | CD1 | TYR | A | 86 | 21.971 | 131.240 | 20.087 | 1.00157.26 | C |
| ATOM | 90 | CD2 | TYR | A | 86 | 20.844 | 130.672 | 22.111 | 1.00155.48 | C |
| ATOM | 91 | CE1 | TYR | A | 86 | 20.878 | 130.813 | 19.352 | 1.00158.97 | C |
| ATOM | 92 | CE2 | TYR | A | 86 | 19.747 | 130.243 | 21.386 | 1.00157.34 | C |
| ATOM | 93 | CZ | TYR | A | 86 | 19.769 | 130.315 | 20.007 | 1.00159.58 | C |
| ATOM | 94 | OH | TYR | A | 86 | 18.678 | 129.888 | 19.280 | 1.00160.77 | O |
| ATOM | 95 | N | LEU | A | 87 | 26.370 | 130.615 | 21.907 | 1.00140.00 | N |
| ATOM | 96 | CA | LEU | A | 87 | 27.486 | 130.271 | 21.036 | 1.00137.82 | C |
| ATOM | 97 | C | LEU | A | 87 | 27.874 | 128.821 | 21.296 | 1.00135.90 | C |
| ATOM | 98 | O | LEU | A | 87 | 28.134 | 128.355 | 20.367 | 1.00135.25 | O |
| ATOM | 99 | CB | LEU | A | 87 | 28.678 | 131.188 | 21.323 | 1.00136.14 | C |
| ATOM | 100 | CG | LEU | A | 87 | 29.528 | 131.648 | 20.138 | 1.00133.93 | C |
| ATOM | 101 | CD1 | LEU | A | 87 | 30.835 | 132.254 | 20.637 | 1.00131.01 | C |
| ATOM | 102 | CD2 | LEU | A | 87 | 29.792 | 130.507 | 19.169 | 1.00131.72 | C |
| ATOM | 103 | N | ASP | A | 88 | 27.910 | 128.455 | 22.573 | 1.00134.61 | N |
| ATOM | 104 | CA | ASP | A | 88 | 28.198 | 127.085 | 22.972 | 1.00133.08 | C |
| ATOM | 105 | C | ASP | A | 88 | 27.269 | 126.130 | 22.238 | 1.00129.87 | C |
| ATOM | 106 | O | ASP | A | 88 | 27.638 | 124.998 | 21.941 | 1.00127.83 | O |
| ATOM | 107 | CB | ASP | A | 88 | 28.024 | 126.927 | 24.484 | 1.00135.49 | C |
| ATOM | 108 | CG | ASP | A | 88 | 28.850 | 125.788 | 25.048 | 1.00138.41 | C |
| ATOM | 109 | OD1 | ASP | A | 88 | 29.964 | 125.550 | 24.534 | 1.00139.67 | O |
| ATOM | 110 | OD2 | ASP | A | 88 | 28.369 | 125.136 | 26.009 | 1.00138.80 | O |
| ATOM | 111 | N | GLN | A | 89 | 26.056 | 126.598 | 21.943 | 1.00137.77 | N |
| ATOM | 112 | CA | GLN | A | 89 | 25.076 | 125.793 | 21.222 | 1.00128.91 | C |
| ATOM | 113 | C | GLN | A | 89 | 25.631 | 125.276 | 19.897 | 1.00126.61 | C |
| ATOM | 114 | O | GLN | A | 89 | 25.188 | 124.248 | 19.391 | 1.00125.88 | O |
| ATOM | 115 | CB | GLN | A | 89 | 23.803 | 126.600 | 20.949 | 1.00131.92 | C |
| ATOM | 116 | CG | GLN | A | 89 | 22.761 | 125.789 | 20.270 | 1.00134.13 | C |
| ATOM | 117 | CD | GLN | A | 89 | 21.928 | 126.582 | 19.226 | 1.00135.58 | C |
| ATOM | 118 | OE1 | GLN | A | 89 | 22.513 | 127.293 | 18.404 | 1.00135.48 | O |
| ATOM | 119 | NE2 | GLN | A | 89 | 20.606 | 126.448 | 19.245 | 1.00135.74 | N |
| ATOM | 120 | N | LYS | A | 90 | 26.598 | 125.997 | 19.337 | 1.00124.73 | N |
| ATOM | 121 | CA | LYS | A | 90 | 27.130 | 125.671 | 18.015 | 1.00123.44 | C |
| ATOM | 122 | C | LYS | A | 90 | 28.419 | 124.880 | 18.090 | 1.00121.07 | C |
| ATOM | 123 | O | LYS | A | 90 | 28.713 | 124.086 | 17.200 | 1.00118.30 | O |
| ATOM | 124 | CB | LYS | A | 90 | 27.324 | 126.946 | 17.185 | 1.00121.21 | C |
| ATOM | 125 | CG | LYS | A | 90 | 26.003 | 127.561 | 16.735 | 1.00119.24 | C |
| ATOM | 126 | CD | LYS | A | 90 | 26.085 | 129.079 | 16.650 | 1.00117.99 | C |
| ATOM | 127 | CE | LYS | A | 90 | 24.659 | 129.678 | 16.620 | 1.00117.14 | C |
| ATOM | 128 | NZ | LYS | A | 90 | 24.659 | 131.170 | 16.628 | 1.00115.69 | N |
| ATOM | 129 | N | ILE | A | 91 | 29.177 | 125.047 | 19.162 | 1.00122.04 | N |
| ATOM | 130 | CA | ILE | A | 91 | 30.353 | 124.228 | 19.413 | 1.00123.66 | C |
| ATOM | 131 | C | ILE | A | 91 | 29.918 | 122.932 | 20.098 | 1.00124.92 | C |
| ATOM | 132 | O | ILE | A | 91 | 30.703 | 122.259 | 20.762 | 1.00123.18 | O |
| ATOM | 133 | CB | ILE | A | 91 | 31.387 | 124.985 | 20.265 | 1.00125.86 | C |
| ATOM | 134 | CG1 | ILE | A | 91 | 31.665 | 126.359 | 19.648 | 1.00126.60 | C |
| ATOM | 135 | CG2 | ILE | A | 91 | 32.680 | 124.192 | 20.384 | 1.00126.62 | C |
| ATOM | 136 | CD1 | ILE | A | 91 | 32.877 | 127.066 | 20.227 | 1.00125.51 | C |
| ATOM | 137 | N | ARG | A | 92 | 28.647 | 122.592 | 19.920 | 1.00125.60 | N |
| ATOM | 138 | CA | ARG | A | 92 | 28.093 | 121.362 | 20.469 | 1.00125.65 | C |
| ATOM | 139 | C | ARG | A | 92 | 27.481 | 120.500 | 19.369 | 1.00124.97 | C |
| ATOM | 140 | O | ARG | A | 92 | 27.923 | 119.376 | 19.142 | 1.00123.39 | O |
| ATOM | 141 | CB | ARG | A | 92 | 27.048 | 121.671 | 21.541 | 1.00126.36 | C |
| ATOM | 142 | CG | ARG | A | 92 | 27.835 | 122.107 | 22.865 | 1.00127.27 | C |
| ATOM | 143 | CD | ARG | A | 92 | 26.549 | 122.337 | 23.899 | 1.00130.06 | C |
| ATOM | 144 | NE | ARG | A | 92 | 27.098 | 122.411 | 25.250 | 1.00132.71 | N |
| ATOM | 145 | CZ | ARG | A | 92 | 26.364 | 122.425 | 26.357 | 1.00135.91 | C |
| ATOM | 146 | NH1 | ARG | A | 92 | 25.039 | 122.371 | 26.282 | 1.00135.27 | N |
| ATOM | 147 | NH2 | ARG | A | 92 | 26.953 | 122.491 | 27.544 | 1.00138.19 | N |
| ATOM | 148 | N | SER | A | 93 | 26.468 | 121.031 | 18.689 | 1.00129.89 | N |
| ATOM | 149 | CA | SER | A | 93 | 25.807 | 120.317 | 17.996 | 1.00127.40 | C |

FIG. 8-12

| | | | | | | | | | | | |
|---|---|---|---|---|---|---|---|---|---|---|---|
| ATOM | 150 | C | SER | A | 93 | 26.809 | 119.889 | 16.527 | 1.00 | 128.21 | C |
| ATOM | 151 | O | SER | A | 93 | 26.564 | 118.952 | 15.762 | 1.00 | 124.55 | O |
| ATOM | 152 | CB | SER | A | 93 | 24.716 | 121.186 | 16.964 | 1.00 | 130.28 | C |
| ATOM | 153 | OG | SER | A | 93 | 23.662 | 121.427 | 17.879 | 1.00 | 133.28 | O |
| ATOM | 154 | N | ARG | A | 94 | 27.839 | 120.587 | 16.488 | 1.00 | 124.68 | N |
| ATOM | 155 | CA | ARG | A | 94 | 28.993 | 120.320 | 15.522 | 1.00 | 120.89 | C |
| ATOM | 156 | C | ARG | A | 94 | 29.915 | 119.194 | 15.992 | 1.00 | 116.65 | C |
| ATOM | 157 | O | ARG | A | 94 | 30.067 | 118.179 | 15.313 | 1.00 | 115.19 | O |
| ATOM | 158 | CB | ARG | A | 94 | 29.802 | 121.599 | 15.276 | 1.00 | 119.82 | C |
| ATOM | 159 | CG | ARG | A | 94 | 30.928 | 121.441 | 14.270 | 1.00 | 119.14 | C |
| ATOM | 160 | CD | ARG | A | 94 | 30.409 | 121.169 | 12.861 | 1.00 | 116.77 | C |
| ATOM | 161 | NE | ARG | A | 94 | 31.494 | 120.814 | 11.956 | 1.00 | 113.82 | N |
| ATOM | 162 | CZ | ARG | A | 94 | 32.100 | 121.665 | 11.136 | 1.00 | 110.12 | C |
| ATOM | 163 | NH1 | ARG | A | 94 | 31.714 | 122.932 | 11.088 | 1.00 | 109.28 | N |
| ATOM | 164 | NH2 | ARG | A | 94 | 33.088 | 121.247 | 10.357 | 1.00 | 109.78 | N |
| ATOM | 165 | N | ILE | A | 95 | 30.518 | 119.377 | 17.162 | 1.00 | 114.51 | N |
| ATOM | 166 | CA | ILE | A | 95 | 31.498 | 118.424 | 17.681 | 1.00 | 113.80 | C |
| ATOM | 167 | C | ILE | A | 95 | 30.869 | 117.230 | 18.408 | 1.00 | 116.24 | C |
| ATOM | 168 | O | ILE | A | 95 | 31.528 | 116.213 | 18.654 | 1.00 | 114.93 | O |
| ATOM | 169 | CB | ILE | A | 95 | 32.518 | 119.121 | 18.589 | 1.00 | 110.85 | C |
| ATOM | 170 | CG1 | ILE | A | 95 | 33.103 | 120.336 | 17.870 | 1.00 | 112.91 | C |
| ATOM | 171 | CG2 | ILE | A | 95 | 33.622 | 118.165 | 18.991 | 1.00 | 109.50 | C |
| ATOM | 172 | CD1 | ILE | A | 95 | 34.380 | 120.871 | 18.510 | 1.00 | 114.51 | C |
| ATOM | 173 | N | ASP | A | 96 | 29.698 | 117.354 | 18.774 | 1.00 | 118.63 | N |
| ATOM | 174 | CA | ASP | A | 96 | 28.847 | 116.214 | 19.385 | 1.00 | 122.14 | C |
| ATOM | 175 | C | ASP | A | 96 | 28.123 | 115.528 | 18.132 | 1.00 | 123.29 | C |
| ATOM | 176 | O | ASP | A | 96 | 26.894 | 115.419 | 18.127 | 1.00 | 123.60 | O |
| ATOM | 177 | CB | ASP | A | 96 | 27.848 | 116.642 | 20.365 | 1.00 | 125.04 | C |
| ATOM | 178 | CG | ASP | A | 96 | 28.477 | 116.725 | 21.745 | 1.00 | 126.83 | C |
| ATOM | 179 | OD1 | ASP | A | 96 | 27.737 | 116.978 | 22.722 | 1.00 | 126.89 | O |
| ATOM | 180 | OD2 | ASP | A | 96 | 29.709 | 116.534 | 21.853 | 1.00 | 126.66 | O |
| ATOM | 181 | N | GLY | A | 97 | 28.895 | 115.081 | 17.148 | 1.00 | 121.74 | N |
| ATOM | 182 | CA | GLY | A | 97 | 28.336 | 114.421 | 15.985 | 1.00 | 120.52 | C |
| ATOM | 183 | C | GLY | A | 97 | 29.259 | 114.487 | 14.786 | 1.00 | 118.11 | C |
| ATOM | 184 | O | GLY | A | 97 | 30.476 | 114.366 | 14.919 | 1.00 | 115.04 | O |
| ATOM | 185 | N | LYS | A | 98 | 28.673 | 114.674 | 13.608 | 1.00 | 119.77 | N |
| ATOM | 186 | CA | LYS | A | 98 | 29.448 | 114.790 | 12.381 | 1.00 | 119.99 | C |
| ATOM | 187 | C | LYS | A | 98 | 30.208 | 116.107 | 12.336 | 1.00 | 119.85 | C |
| ATOM | 188 | O | LYS | A | 98 | 29.656 | 117.140 | 11.952 | 1.00 | 116.04 | O |
| ATOM | 189 | CB | LYS | A | 98 | 28.546 | 114.687 | 11.151 | 1.00 | 119.73 | C |
| ATOM | 190 | CG | LYS | A | 98 | 28.187 | 113.272 | 10.727 | 1.00 | 120.59 | C |
| ATOM | 191 | CD | LYS | A | 98 | 27.707 | 113.269 | 9.280 | 1.00 | 121.87 | C |
| ATOM | 192 | CE | LYS | A | 98 | 26.374 | 111.986 | 8.917 | 1.00 | 121.74 | C |
| ATOM | 193 | NZ | LYS | A | 98 | 26.399 | 112.059 | 7.539 | 1.00 | 120.68 | N |
| ATOM | 194 | N | VAL | A | 99 | 31.478 | 116.070 | 12.732 | 1.00 | 83.88 | N |
| ATOM | 195 | CA | VAL | A | 99 | 32.337 | 117.229 | 12.566 | 1.00 | 88.13 | C |
| ATOM | 196 | C | VAL | A | 99 | 32.553 | 117.470 | 11.079 | 1.00 | 91.35 | C |
| ATOM | 197 | O | VAL | A | 99 | 32.488 | 118.611 | 10.618 | 1.00 | 88.48 | O |
| ATOM | 198 | CB | VAL | A | 99 | 33.692 | 117.018 | 13.228 | 1.00 | 86.48 | C |
| ATOM | 199 | CG1 | VAL | A | 99 | 34.509 | 118.300 | 13.147 | 1.00 | 85.62 | C |
| ATOM | 200 | CG2 | VAL | A | 99 | 33.507 | 116.578 | 14.669 | 1.00 | 91.17 | C |
| ATOM | 201 | N | TRP | A | 100 | 32.811 | 116.397 | 10.330 | 1.00 | 95.88 | N |
| ATOM | 202 | CA | TRP | A | 100 | 32.936 | 116.495 | 8.871 | 1.00 | 95.82 | C |
| ATOM | 203 | C | TRP | A | 100 | 32.223 | 115.379 | 8.124 | 1.00 | 92.20 | C |
| ATOM | 204 | O | TRP | A | 100 | 31.899 | 114.292 | 8.657 | 1.00 | 92.82 | O |
| ATOM | 205 | CB | TRP | A | 100 | 34.398 | 116.452 | 8.422 | 1.00 | 95.03 | C |
| ATOM | 206 | CG | TRP | A | 100 | 35.319 | 117.380 | 9.119 | 1.00 | 98.20 | C |
| ATOM | 207 | CD1 | TRP | A | 100 | 35.421 | 118.729 | 8.938 | 1.00 | 101.58 | C |
| ATOM | 208 | CD2 | TRP | A | 100 | 36.310 | 117.026 | 10.084 | 1.00 | 99.44 | C |
| ATOM | 209 | NE1 | TRP | A | 100 | 36.403 | 119.241 | 9.752 | 1.00 | 104.02 | N |
| ATOM | 210 | CE2 | TRP | A | 100 | 36.966 | 118.215 | 10.465 | 1.00 | 103.56 | C |
| ATOM | 211 | CE3 | TRP | A | 100 | 36.696 | 115.821 | 10.677 | 1.00 | 100.78 | C |
| ATOM | 212 | CZ2 | TRP | A | 100 | 37.990 | 118.232 | 11.410 | 1.00 | 105.87 | C |
| ATOM | 213 | CZ3 | TRP | A | 100 | 37.713 | 115.839 | 11.617 | 1.00 | 103.36 | C |
| ATOM | 214 | CH2 | TRP | A | 100 | 38.349 | 117.037 | 11.974 | 1.00 | 106.53 | C |
| ATOM | 215 | N | GLN | A | 101 | 31.890 | 115.883 | 6.872 | 1.00 | 91.26 | N |
| ATOM | 216 | CA | GLN | A | 101 | 31.681 | 114.814 | 5.908 | 1.00 | 90.92 | C |
| ATOM | 217 | C | GLN | A | 101 | 33.006 | 114.010 | 5.567 | 1.00 | 89.18 | C |
| ATOM | 218 | O | GLN | A | 101 | 33.892 | 114.692 | 5.038 | 1.00 | 87.23 | O |
| ATOM | 219 | CB | GLN | A | 101 | 30.982 | 115.191 | 4.652 | 1.00 | 93.98 | C |
| ATOM | 220 | CG | GLN | A | 101 | 30.739 | 114.182 | 3.540 | 1.00 | 93.73 | C |
| ATOM | 221 | CD | GLN | A | 101 | 29.725 | 113.116 | 3.915 | 1.00 | 94.79 | C |
| ATOM | 222 | OE1 | GLN | A | 101 | 29.757 | 112.004 | 3.386 | 1.00 | 97.42 | O |
| ATOM | 223 | NE2 | GLN | A | 101 | 28.819 | 113.449 | 4.829 | 1.00 | 93.38 | N |
| ATOM | 224 | N | LEU | A | 102 | 33.186 | 112.740 | 5.906 | 1.00 | 83.31 | N |
| ATOM | 225 | CA | LEU | A | 102 | 34.437 | 112.059 | 5.621 | 1.00 | 76.49 | C |
| ATOM | 226 | C | LEU | A | 102 | 34.272 | 111.147 | 4.406 | 1.00 | 75.73 | C |

FIG. 8-13

| | | | | | | | | | | | |
|---|---|---|---|---|---|---|---|---|---|---|---|
| ATOM | 227 | O | LEU | A | 102 | 33.418 | 110.258 | 4.400 | 1.00 | 75.26 | O |
| ATOM | 228 | CB | LEU | A | 102 | 34.917 | 111.274 | 6.843 | 1.00 | 67.38 | C |
| ATOM | 229 | CG | LEU | A | 102 | 35.298 | 112.125 | 8.050 | 1.00 | 72.97 | C |
| ATOM | 230 | CD1 | LEU | A | 102 | 35.795 | 111.280 | 9.205 | 1.00 | 72.34 | C |
| ATOM | 231 | CD2 | LEU | A | 102 | 36.339 | 113.165 | 7.663 | 1.00 | 74.78 | C |
| ATOM | 232 | N | PRO | A | 103 | 35.083 | 111.368 | 3.365 | 1.00 | 78.85 | N |
| ATOM | 233 | CA | PRO | A | 103 | 35.018 | 110.855 | 2.039 | 1.00 | 87.69 | C |
| ATOM | 234 | C | PRO | A | 103 | 35.282 | 109.180 | 2.316 | 1.00 | 81.92 | C |
| ATOM | 235 | O | PRO | A | 103 | 35.927 | 108.807 | 3.290 | 1.00 | 63.04 | O |
| ATOM | 236 | CB | PRO | A | 103 | 36.180 | 111.279 | 1.284 | 1.00 | 69.84 | C |
| ATOM | 237 | CG | PRO | A | 103 | 37.058 | 111.904 | 2.335 | 1.00 | 72.97 | C |
| ATOM | 238 | CD | PRO | A | 103 | 36.082 | 112.463 | 3.302 | 1.00 | 73.25 | C |
| ATOM | 239 | N | ALA | A | 104 | 34.777 | 108.353 | 1.411 | 1.00 | 64.01 | N |
| ATOM | 240 | CA | ALA | A | 104 | 34.874 | 106.918 | 1.484 | 1.00 | 62.23 | C |
| ATOM | 241 | C | ALA | A | 104 | 36.426 | 106.563 | 1.167 | 1.00 | 67.78 | C |
| ATOM | 242 | O | ALA | A | 104 | 37.038 | 107.155 | 0.278 | 1.00 | 68.75 | O |
| ATOM | 243 | CB | ALA | A | 104 | 34.010 | 106.195 | 0.532 | 1.00 | 52.28 | C |
| ATOM | 244 | N | ALA | A | 105 | 36.977 | 105.612 | 1.915 | 1.00 | 65.69 | N |
| ATOM | 245 | CA | ALA | A | 105 | 38.341 | 105.163 | 1.688 | 1.00 | 57.98 | C |
| ATOM | 246 | C | ALA | A | 105 | 38.380 | 103.902 | 0.835 | 1.00 | 55.06 | C |
| ATOM | 247 | O | ALA | A | 105 | 37.635 | 102.939 | 1.110 | 1.00 | 57.25 | O |
| ATOM | 248 | CB | ALA | A | 105 | 39.048 | 104.925 | 3.007 | 1.00 | 62.39 | C |
| ATOM | 249 | N | VAL | A | 106 | 39.163 | 103.905 | -0.210 | 1.00 | 55.64 | N |
| ATOM | 250 | CA | VAL | A | 106 | 39.252 | 102.738 | -1.070 | 1.00 | 53.33 | C |
| ATOM | 251 | C | VAL | A | 106 | 40.562 | 101.999 | -0.839 | 1.00 | 50.85 | C |
| ATOM | 252 | O | VAL | A | 106 | 41.639 | 102.568 | -1.015 | 1.00 | 50.65 | O |
| ATOM | 253 | CB | VAL | A | 106 | 39.121 | 103.098 | -2.567 | 1.00 | 41.65 | C |
| ATOM | 254 | CG1 | VAL | A | 106 | 38.869 | 101.833 | -3.388 | 1.00 | 36.95 | C |
| ATOM | 255 | CG2 | VAL | A | 106 | 38.012 | 104.133 | -2.779 | 1.00 | 46.91 | C |
| ATOM | 256 | N | TYR | A | 107 | 40.444 | 100.727 | -0.474 | 1.00 | 42.19 | N |
| ATOM | 257 | CA | TYR | A | 107 | 41.591 | 99.889 | -0.166 | 1.00 | 39.61 | C |
| ATOM | 258 | C | TYR | A | 107 | 41.748 | 98.772 | -1.171 | 1.00 | 39.17 | C |
| ATOM | 259 | O | TYR | A | 107 | 40.763 | 98.250 | -1.690 | 1.00 | 42.43 | O |
| ATOM | 260 | CB | TYR | A | 107 | 41.439 | 99.267 | 1.238 | 1.00 | 37.17 | C |
| ATOM | 261 | CG | TYR | A | 107 | 41.641 | 100.281 | 2.345 | 1.00 | 41.42 | C |
| ATOM | 262 | CD1 | TYR | A | 107 | 42.916 | 100.633 | 2.727 | 1.00 | 42.30 | C |
| ATOM | 263 | CD2 | TYR | A | 107 | 40.561 | 100.800 | 3.015 | 1.00 | 49.88 | C |
| ATOM | 264 | CE1 | TYR | A | 107 | 43.109 | 101.546 | 3.755 | 1.00 | 47.58 | C |
| ATOM | 265 | CE2 | TYR | A | 107 | 40.738 | 101.718 | 4.027 | 1.00 | 51.47 | C |
| ATOM | 266 | CZ | TYR | A | 107 | 42.013 | 102.080 | 4.401 | 1.00 | 49.72 | C |
| ATOM | 267 | OH | TYR | A | 107 | 42.187 | 103.000 | 5.402 | 1.00 | 55.98 | O |
| ATOM | 268 | N | GLY | A | 108 | 42.896 | 98.378 | -1.399 | 1.00 | 40.78 | N |
| ATOM | 269 | CA | GLY | A | 108 | 43.333 | 97.267 | -2.268 | 1.00 | 36.88 | C |
| ATOM | 270 | C | GLY | A | 108 | 43.036 | 95.947 | -1.588 | 1.00 | 45.02 | C |
| ATOM | 271 | O | GLY | A | 108 | 42.299 | 95.894 | -0.595 | 1.00 | 44.39 | O |
| ATOM | 272 | N | ARG | A | 109 | 43.586 | 94.870 | -2.137 | 1.00 | 43.54 | N |
| ATOM | 273 | CA | ARG | A | 109 | 43.336 | 93.559 | -1.981 | 1.00 | 41.99 | C |
| ATOM | 274 | C | ARG | A | 109 | 44.137 | 93.325 | -0.090 | 1.00 | 34.96 | C |
| ATOM | 275 | O | ARG | A | 109 | 45.343 | 93.848 | -0.090 | 1.00 | 42.95 | O |
| ATOM | 276 | CB | ARG | A | 109 | 43.809 | 92.432 | -2.598 | 1.00 | 42.78 | C |
| ATOM | 277 | CG | ARG | A | 109 | 45.099 | 92.188 | -2.916 | 1.00 | 45.77 | C |
| ATOM | 278 | CD | ARG | A | 109 | 45.271 | 91.106 | -4.013 | 1.00 | 44.00 | C |
| ATOM | 279 | NE | ARG | A | 109 | 44.987 | 89.764 | -3.515 | 1.00 | 53.04 | N |
| ATOM | 280 | CZ | ARG | A | 109 | 45.107 | 88.647 | -4.229 | 1.00 | 58.67 | C |
| ATOM | 281 | NH1 | ARG | A | 109 | 45.494 | 88.698 | -5.498 | 1.00 | 62.78 | N |
| ATOM | 282 | NH2 | ARG | A | 109 | 44.828 | 87.475 | -3.676 | 1.00 | 56.70 | N |
| ATOM | 283 | N | MET | A | 110 | 43.928 | 92.500 | 0.556 | 1.00 | 43.58 | N |
| ATOM | 284 | CA | MET | A | 110 | 44.104 | 92.079 | 1.814 | 1.00 | 50.22 | C |
| ATOM | 285 | C | MET | A | 110 | 44.633 | 90.688 | 1.583 | 1.00 | 56.75 | C |
| ATOM | 286 | O | MET | A | 110 | 43.864 | 89.761 | 1.372 | 1.00 | 53.29 | O |
| ATOM | 287 | CB | MET | A | 110 | 43.018 | 92.052 | 2.883 | 1.00 | 44.24 | C |
| ATOM | 288 | CG | MET | A | 110 | 42.693 | 93.434 | 3.399 | 1.00 | 51.28 | C |
| ATOM | 289 | SD | MET | A | 110 | 41.283 | 93.547 | 4.509 | 1.00 | 61.95 | S |
| ATOM | 290 | CE | MET | A | 110 | 40.115 | 92.418 | 3.748 | 1.00 | 64.18 | C |
| ATOM | 291 | N | VAL | A | 111 | 45.949 | 90.534 | 1.613 | 1.00 | 58.03 | N |
| ATOM | 292 | CA | VAL | A | 111 | 46.534 | 89.236 | 1.335 | 1.00 | 46.00 | C |
| ATOM | 293 | C | VAL | A | 111 | 46.715 | 88.504 | 2.644 | 1.00 | 45.07 | C |
| ATOM | 294 | O | VAL | A | 111 | 47.149 | 89.089 | 3.621 | 1.00 | 42.87 | O |
| ATOM | 295 | CB | VAL | A | 111 | 47.904 | 89.385 | 0.668 | 1.00 | 52.01 | C |
| ATOM | 296 | CG1 | VAL | A | 111 | 48.817 | 88.058 | 0.670 | 1.00 | 50.34 | C |
| ATOM | 297 | CG2 | VAL | A | 111 | 47.731 | 89.890 | -0.769 | 1.00 | 47.09 | C |
| ATOM | 298 | N | ASN | A | 112 | 46.357 | 87.230 | 2.669 | 1.00 | 47.13 | N |
| ATOM | 299 | CA | ASN | A | 112 | 46.692 | 86.405 | 3.809 | 1.00 | 62.83 | C |
| ATOM | 300 | C | ASN | A | 112 | 47.855 | 85.506 | 3.431 | 1.00 | 60.34 | C |
| ATOM | 301 | O | ASN | A | 112 | 47.845 | 84.894 | 2.366 | 1.00 | 60.87 | O |
| ATOM | 302 | CB | ASN | A | 112 | 45.487 | 85.577 | 4.277 | 1.00 | 67.99 | C |
| ATOM | 303 | CG | ASN | A | 112 | 44.962 | 86.355 | 5.208 | 1.00 | 69.23 | C |

FIG. 8-14

| | | | | | | | | | | | |
|---|---|---|---|---|---|---|---|---|---|---|---|
| ATOM | 304 | OD1 | ASN | A | 112 | 43.898 | 85.768 | 6.084 | 1.00 | 77.14 | O |
| ATOM | 305 | ND2 | ASN | A | 112 | 44.525 | 87.682 | 5.056 | 1.00 | 63.38 | N |
| ATOM | 306 | N | LEU | A | 113 | 48.858 | 85.443 | 4.297 | 1.00 | 51.04 | N |
| ATOM | 307 | CA | LEU | A | 113 | 49.971 | 84.534 | 4.073 | 1.00 | 53.81 | C |
| ATOM | 308 | C | LEU | A | 113 | 49.756 | 83.320 | 4.932 | 1.00 | 50.76 | C |
| ATOM | 309 | O | LEU | A | 113 | 49.228 | 83.411 | 6.041 | 1.00 | 45.84 | O |
| ATOM | 310 | CB | LEU | A | 113 | 51.296 | 85.198 | 4.442 | 1.00 | 45.10 | C |
| ATOM | 311 | CG | LEU | A | 113 | 51.463 | 86.875 | 3.799 | 1.00 | 49.35 | C |
| ATOM | 312 | CD1 | LEU | A | 113 | 52.547 | 87.370 | 4.581 | 1.00 | 54.60 | C |
| ATOM | 313 | CD2 | LEU | A | 113 | 51.773 | 86.452 | 2.291 | 1.00 | 45.87 | C |
| ATOM | 314 | N | GLU | A | 114 | 50.166 | 82.176 | 4.417 | 1.00 | 45.17 | N |
| ATOM | 315 | CA | GLU | A | 114 | 50.011 | 80.914 | 5.126 | 1.00 | 46.98 | C |
| ATOM | 316 | C | GLU | A | 114 | 51.282 | 80.094 | 4.908 | 1.00 | 55.44 | C |
| ATOM | 317 | O | GLU | A | 114 | 51.940 | 80.225 | 3.881 | 1.00 | 49.07 | O |
| ATOM | 318 | CB | GLU | A | 114 | 48.807 | 80.162 | 4.589 | 1.00 | 59.24 | C |
| ATOM | 319 | CG | GLU | A | 114 | 48.739 | 78.881 | 4.920 | 1.00 | 79.19 | C |
| ATOM | 320 | CD | GLU | A | 114 | 47.522 | 77.979 | 4.307 | 1.00 | 86.55 | C |
| ATOM | 321 | OE1 | GLU | A | 114 | 46.775 | 78.841 | 3.546 | 1.00 | 83.32 | O |
| ATOM | 322 | OE2 | GLU | A | 114 | 47.325 | 76.768 | 4.588 | 1.00 | 86.40 | O |
| ATOM | 323 | N | PRO | A | 115 | 51.636 | 79.256 | 5.883 | 1.00 | 47.29 | N |
| ATOM | 324 | CA | PRO | A | 115 | 52.714 | 78.291 | 5.708 | 1.00 | 56.16 | C |
| ATOM | 325 | C | PRO | A | 115 | 52.383 | 77.383 | 4.540 | 1.00 | 63.29 | C |
| ATOM | 326 | O | PRO | A | 115 | 51.205 | 77.071 | 4.321 | 1.00 | 69.84 | O |
| ATOM | 327 | CB | PRO | A | 115 | 52.887 | 77.489 | 7.025 | 1.00 | 48.88 | C |
| ATOM | 328 | CG | PRO | A | 115 | 51.989 | 78.357 | 7.958 | 1.00 | 48.42 | C |
| ATOM | 329 | CD | PRO | A | 115 | 51.008 | 79.151 | 7.213 | 1.00 | 47.36 | C |
| ATOM | 330 | N | ASP | A | 116 | 53.420 | 76.982 | 3.809 | 1.00 | 68.50 | N |
| ATOM | 331 | CA | ASP | A | 116 | 53.322 | 76.103 | 2.639 | 1.00 | 67.73 | C |
| ATOM | 332 | C | ASP | A | 116 | 52.802 | 76.768 | 1.365 | 1.00 | 68.21 | C |
| ATOM | 333 | O | ASP | A | 116 | 52.617 | 76.090 | 0.359 | 1.00 | 73.77 | O |
| ATOM | 334 | CB | ASP | A | 116 | 52.518 | 74.835 | 2.942 | 1.00 | 72.55 | C |
| ATOM | 335 | CG | ASP | A | 116 | 53.232 | 73.912 | 3.899 | 1.00 | 79.34 | C |
| ATOM | 336 | OD1 | ASP | A | 116 | 54.450 | 73.701 | 3.727 | 1.00 | 78.88 | O |
| ATOM | 337 | OD2 | ASP | A | 116 | 52.579 | 73.405 | 4.834 | 1.00 | 80.30 | O |
| ATOM | 338 | N | MET | A | 117 | 52.590 | 78.079 | 1.382 | 1.00 | 64.18 | N |
| ATOM | 339 | CA | MET | A | 117 | 52.140 | 78.756 | 0.163 | 1.00 | 66.80 | C |
| ATOM | 340 | C | MET | A | 117 | 53.272 | 78.934 | -0.865 | 1.00 | 66.26 | C |
| ATOM | 341 | O | MET | A | 117 | 54.422 | 79.166 | -0.494 | 1.00 | 56.17 | O |
| ATOM | 342 | CB | MET | A | 117 | 51.438 | 80.083 | 0.496 | 1.00 | 88.61 | C |
| ATOM | 343 | CG | MET | A | 117 | 52.240 | 81.391 | 0.261 | 1.00 | 87.55 | C |
| ATOM | 344 | SD | MET | A | 117 | 51.513 | 82.810 | 1.079 | 1.00 | 88.54 | S |
| ATOM | 345 | CE | MET | A | 117 | 49.727 | 82.469 | 0.973 | 1.00 | 50.10 | C |
| ATOM | 346 | N | THR | A | 118 | 52.956 | 78.806 | -2.157 | 1.00 | 65.07 | N |
| ATOM | 347 | CA | THR | A | 118 | 53.986 | 78.980 | -3.197 | 1.00 | 58.32 | C |
| ATOM | 348 | C | THR | A | 118 | 54.216 | 80.459 | -3.436 | 1.00 | 56.58 | C |
| ATOM | 349 | O | THR | A | 118 | 53.518 | 81.099 | -4.210 | 1.00 | 61.80 | O |
| ATOM | 350 | CB | THR | A | 118 | 53.634 | 78.312 | -4.569 | 1.00 | 57.22 | C |
| ATOM | 351 | OG1 | THR | A | 118 | 53.219 | 76.960 | -4.354 | 1.00 | 59.04 | O |
| ATOM | 352 | CG2 | THR | A | 118 | 54.868 | 78.318 | -5.514 | 1.00 | 48.87 | C |
| ATOM | 353 | N | ILE | A | 119 | 55.180 | 81.003 | -2.720 | 1.00 | 63.25 | N |
| ATOM | 354 | CA | ILE | A | 119 | 55.674 | 82.330 | -2.989 | 1.00 | 62.54 | C |
| ATOM | 355 | C | ILE | A | 119 | 57.179 | 82.251 | -2.742 | 1.00 | 61.55 | C |
| ATOM | 356 | O | ILE | A | 119 | 57.670 | 81.328 | -2.087 | 1.00 | 66.33 | O |
| ATOM | 357 | CB | ILE | A | 119 | 54.986 | 83.399 | -2.104 | 1.00 | 60.79 | C |
| ATOM | 358 | CG1 | ILE | A | 119 | 55.680 | 84.754 | -2.251 | 1.00 | 62.59 | C |
| ATOM | 359 | CG2 | ILE | A | 119 | 55.001 | 82.954 | -0.681 | 1.00 | 60.43 | C |
| ATOM | 360 | CD1 | ILE | A | 119 | 54.889 | 85.951 | -1.730 | 1.00 | 60.56 | C |
| ATOM | 361 | N | SER | A | 120 | 57.913 | 83.194 | -3.305 | 1.00 | 51.65 | N |
| ATOM | 362 | CA | SER | A | 120 | 59.339 | 83.242 | -3.093 | 1.00 | 51.89 | C |
| ATOM | 363 | C | SER | A | 120 | 59.648 | 84.501 | -2.293 | 1.00 | 58.80 | C |
| ATOM | 364 | O | SER | A | 120 | 58.793 | 85.368 | -2.113 | 1.00 | 64.38 | O |
| ATOM | 365 | CB | SER | A | 120 | 60.073 | 83.237 | -4.442 | 1.00 | 52.16 | C |
| ATOM | 366 | OG | SER | A | 120 | 59.947 | 84.493 | -5.078 | 1.00 | 49.29 | O |
| ATOM | 367 | N | LYS | A | 121 | 60.869 | 84.593 | -1.804 | 1.00 | 50.17 | N |
| ATOM | 368 | CA | LYS | A | 121 | 61.367 | 85.716 | -0.984 | 1.00 | 54.94 | C |
| ATOM | 369 | C | LYS | A | 121 | 61.385 | 87.024 | -1.781 | 1.00 | 53.16 | C |
| ATOM | 370 | O | LYS | A | 121 | 60.777 | 88.044 | -1.304 | 1.00 | 55.25 | O |
| ATOM | 371 | CB | LYS | A | 121 | 62.644 | 85.433 | -0.395 | 1.00 | 56.80 | C |
| ATOM | 372 | CG | LYS | A | 121 | 63.108 | 86.419 | 0.671 | 1.00 | 59.69 | C |
| ATOM | 373 | CD | LYS | A | 121 | 64.641 | 86.277 | 0.903 | 1.00 | 53.68 | C |
| ATOM | 374 | CE | LYS | A | 121 | 65.394 | 86.965 | -0.211 | 1.00 | 60.28 | C |
| ATOM | 375 | NZ | LYS | A | 121 | 66.856 | 86.712 | -0.162 | 1.00 | 67.59 | N |
| ATOM | 376 | N | ASN | A | 122 | 61.833 | 86.991 | -2.984 | 1.00 | 50.98 | N |
| ATOM | 377 | CA | ASN | A | 122 | 61.821 | 88.143 | -3.887 | 1.00 | 50.38 | C |
| ATOM | 378 | C | ASN | A | 122 | 60.402 | 88.560 | -4.254 | 1.00 | 48.94 | C |
| ATOM | 379 | O | ASN | A | 122 | 60.075 | 89.749 | -4.334 | 1.00 | 49.83 | O |
| ATOM | 380 | CB | ASN | A | 122 | 62.624 | 87.833 | -5.169 | 1.00 | 56.38 | C |

FIG. 8-15

| | | | | | | | | | | | |
|---|---|---|---|---|---|---|---|---|---|---|---|
| ATOM | 381 | CG | ASN | A | 122 | 64.148 | 87.889 | -4.948 | 1.00 | 73.87 | C |
| ATOM | 382 | OD1 | ASN | A | 122 | 64.641 | 88.211 | -3.856 | 1.00 | 73.24 | O |
| ATOM | 383 | ND2 | ASN | A | 122 | 64.885 | 87.558 | -5.999 | 1.00 | 80.11 | N |
| ATOM | 384 | N | GLU | A | 123 | 59.557 | 87.571 | -4.496 | 1.00 | 54.65 | N |
| ATOM | 385 | CA | GLU | A | 123 | 58.152 | 87.837 | -4.762 | 1.00 | 52.84 | C |
| ATOM | 386 | C | GLU | A | 123 | 57.571 | 88.540 | -3.539 | 1.00 | 50.46 | C |
| ATOM | 387 | O | GLU | A | 123 | 56.835 | 89.516 | -3.658 | 1.00 | 47.68 | O |
| ATOM | 388 | CB | GLU | A | 123 | 57.433 | 86.520 | -5.043 | 1.00 | 61.85 | C |
| ATOM | 389 | CG | GLU | A | 123 | 55.990 | 86.649 | -5.511 | 1.00 | 70.70 | C |
| ATOM | 390 | CD | GLU | A | 123 | 55.344 | 85.280 | -5.769 | 1.00 | 82.78 | C |
| ATOM | 391 | OE1 | GLU | A | 123 | 56.060 | 84.248 | -5.725 | 1.00 | 86.60 | O |
| ATOM | 392 | OE2 | GLU | A | 123 | 54.117 | 85.239 | -6.010 | 1.00 | 85.46 | O |
| ATOM | 393 | N | MET | A | 124 | 57.952 | 88.087 | -2.346 | 1.00 | 57.65 | N |
| ATOM | 394 | CA | MET | A | 124 | 57.397 | 88.646 | -1.111 | 1.00 | 50.38 | C |
| ATOM | 395 | C | MET | A | 124 | 57.884 | 90.083 | -0.880 | 1.00 | 47.51 | C |
| ATOM | 396 | O | MET | A | 124 | 57.110 | 90.967 | -0.527 | 1.00 | 49.55 | O |
| ATOM | 397 | CB | MET | A | 124 | 57.740 | 87.761 | 0.070 | 1.00 | 47.64 | C |
| ATOM | 398 | CG | MET | A | 124 | 57.248 | 88.310 | 1.411 | 1.00 | 49.20 | C |
| ATOM | 399 | SD | MET | A | 124 | 55.475 | 88.038 | 1.486 | 1.00 | 61.36 | S |
| ATOM | 400 | CE | MET | A | 124 | 54.962 | 89.539 | 2.327 | 1.00 | 72.58 | C |
| ATOM | 401 | N | VAL | A | 125 | 59.164 | 90.323 | -1.108 | 1.00 | 48.42 | N |
| ATOM | 402 | CA | VAL | A | 125 | 59.679 | 91.685 | -1.104 | 1.00 | 48.93 | C |
| ATOM | 403 | C | VAL | A | 125 | 58.859 | 92.616 | -2.011 | 1.00 | 57.83 | C |
| ATOM | 404 | O | VAL | A | 125 | 58.481 | 93.722 | -1.614 | 1.00 | 59.81 | O |
| ATOM | 405 | CB | VAL | A | 125 | 61.128 | 91.720 | -1.578 | 1.00 | 52.80 | C |
| ATOM | 406 | CG1 | VAL | A | 125 | 61.607 | 93.188 | -1.788 | 1.00 | 50.57 | C |
| ATOM | 407 | CG2 | VAL | A | 125 | 62.029 | 90.923 | -0.622 | 1.00 | 50.89 | C |
| ATOM | 408 | N | LYS | A | 126 | 58.592 | 92.171 | -3.240 | 1.00 | 56.03 | N |
| ATOM | 409 | CA | LYS | A | 126 | 57.825 | 92.969 | -4.163 | 1.00 | 47.14 | C |
| ATOM | 410 | C | LYS | A | 126 | 56.427 | 93.258 | -3.589 | 1.00 | 53.07 | C |
| ATOM | 411 | O | LYS | A | 126 | 55.927 | 94.383 | -3.666 | 1.00 | 58.04 | O |
| ATOM | 412 | CB | LYS | A | 126 | 57.775 | 92.277 | -5.530 | 1.00 | 71.19 | C |
| ATOM | 413 | CG | LYS | A | 126 | 59.069 | 92.491 | -6.368 | 1.00 | 79.38 | C |
| ATOM | 414 | CD | LYS | A | 126 | 59.287 | 91.428 | -7.455 | 1.00 | 83.29 | C |
| ATOM | 415 | CE | LYS | A | 126 | 58.473 | 91.689 | -8.721 | 1.00 | 90.35 | C |
| ATOM | 416 | NZ | LYS | A | 126 | 58.869 | 92.944 | -9.435 | 1.00 | 93.75 | N |
| ATOM | 417 | N | LEU | A | 127 | 55.800 | 92.262 | -2.982 | 1.00 | 45.87 | N |
| ATOM | 418 | CA | LEU | A | 127 | 54.467 | 92.490 | -2.426 | 1.00 | 46.80 | C |
| ATOM | 419 | C | LEU | A | 127 | 54.524 | 93.481 | -1.258 | 1.00 | 53.70 | C |
| ATOM | 420 | O | LEU | A | 127 | 53.622 | 94.286 | -1.097 | 1.00 | 53.37 | O |
| ATOM | 421 | CB | LEU | A | 127 | 53.811 | 91.165 | -2.021 | 1.00 | 44.72 | C |
| ATOM | 422 | CG | LEU | A | 127 | 52.584 | 91.184 | -1.123 | 1.00 | 59.24 | C |
| ATOM | 423 | CD1 | LEU | A | 127 | 51.327 | 91.569 | -1.924 | 1.00 | 53.57 | C |
| ATOM | 424 | CD2 | LEU | A | 127 | 52.424 | 89.824 | -0.459 | 1.00 | 58.65 | C |
| ATOM | 425 | N | LEU | A | 128 | 55.605 | 93.457 | -0.469 | 1.00 | 53.74 | N |
| ATOM | 426 | CA | LEU | A | 128 | 55.738 | 94.415 | 0.617 | 1.00 | 47.72 | C |
| ATOM | 427 | C | LEU | A | 128 | 55.983 | 95.832 | 0.124 | 1.00 | 48.64 | C |
| ATOM | 428 | O | LEU | A | 128 | 55.415 | 96.780 | 0.653 | 1.00 | 59.32 | O |
| ATOM | 429 | CB | LEU | A | 128 | 56.846 | 94.021 | 1.599 | 1.00 | 52.49 | C |
| ATOM | 430 | CG | LEU | A | 128 | 56.626 | 92.737 | 2.384 | 1.00 | 58.09 | C |
| ATOM | 431 | CD1 | LEU | A | 128 | 57.853 | 92.389 | 3.169 | 1.00 | 53.78 | C |
| ATOM | 432 | CD2 | LEU | A | 128 | 55.415 | 92.875 | 3.306 | 1.00 | 66.00 | C |
| ATOM | 433 | N | GLU | A | 129 | 56.872 | 95.994 | -0.845 | 1.00 | 48.84 | N |
| ATOM | 434 | CA | GLU | A | 129 | 57.152 | 97.330 | -1.344 | 1.00 | 55.11 | C |
| ATOM | 435 | C | GLU | A | 129 | 55.906 | 97.879 | -2.050 | 1.00 | 55.83 | C |
| ATOM | 436 | O | GLU | A | 129 | 55.605 | 99.062 | -1.979 | 1.00 | 55.30 | O |
| ATOM | 437 | CB | GLU | A | 129 | 58.387 | 97.360 | -2.262 | 1.00 | 56.93 | C |
| ATOM | 438 | CG | GLU | A | 129 | 59.689 | 96.883 | -1.574 | 1.00 | 53.49 | C |
| ATOM | 439 | CD | GLU | A | 129 | 60.922 | 97.580 | -2.047 | 1.00 | 70.46 | C |
| ATOM | 440 | OE1 | GLU | A | 129 | 61.059 | 97.796 | -3.278 | 1.00 | 73.24 | O |
| ATOM | 441 | OE2 | GLU | A | 129 | 61.799 | 97.898 | -1.179 | 1.00 | 72.99 | O |
| ATOM | 442 | N | ALA | A | 130 | 55.165 | 97.000 | -2.712 | 1.00 | 59.47 | N |
| ATOM | 443 | CA | ALA | A | 130 | 53.938 | 97.415 | -3.380 | 1.00 | 55.41 | C |
| ATOM | 444 | C | ALA | A | 130 | 52.873 | 97.796 | -2.343 | 1.00 | 64.73 | C |
| ATOM | 445 | O | ALA | A | 130 | 51.875 | 98.421 | -2.689 | 1.00 | 66.80 | O |
| ATOM | 446 | CB | ALA | A | 130 | 53.439 | 96.321 | -4.274 | 1.00 | 65.04 | C |
| ATOM | 447 | N | THR | A | 131 | 53.095 | 97.429 | -1.075 | 1.00 | 66.55 | N |
| ATOM | 448 | CA | THR | A | 131 | 52.120 | 97.679 | -0.017 | 1.00 | 49.82 | C |
| ATOM | 449 | C | THR | A | 131 | 52.636 | 98.745 | 0.922 | 1.00 | 52.18 | C |
| ATOM | 450 | O | THR | A | 131 | 52.258 | 98.799 | 2.101 | 1.00 | 55.67 | O |
| ATOM | 451 | CB | THR | A | 131 | 51.774 | 96.373 | 0.762 | 1.00 | 54.84 | C |
| ATOM | 452 | OG1 | THR | A | 131 | 51.287 | 95.358 | -0.158 | 1.00 | 59.40 | O |
| ATOM | 453 | CG2 | THR | A | 131 | 50.692 | 96.612 | 1.826 | 1.00 | 54.28 | C |
| ATOM | 454 | N | GLN | A | 132 | 53.538 | 99.581 | 0.407 | 1.00 | 58.60 | N |
| ATOM | 455 | CA | GLN | A | 132 | 54.099 | 100.706 | 1.163 | 1.00 | 62.02 | C |
| ATOM | 456 | C | GLN | A | 132 | 55.144 | 100.328 | 2.202 | 1.00 | 64.10 | C |
| ATOM | 457 | O | GLN | A | 132 | 55.543 | 101.177 | 3.000 | 1.00 | 68.87 | O |

FIG. 8-16

| | | | | | | | | | | | |
|---|---|---|---|---|---|---|---|---|---|---|---|
| ATOM | 458 | CB | GLN | A | 132 | 53.000 | 101.499 | 1.876 | 1.00 | 72.84 | C |
| ATOM | 459 | CG | GLN | A | 132 | 51.845 | 101.921 | 0.891 | 1.00 | 82.40 | C |
| ATOM | 460 | CD | GLN | A | 132 | 52.276 | 102.880 | -0.080 | 1.00 | 91.90 | C |
| ATOM | 461 | OE1 | GLN | A | 132 | 53.153 | 102.574 | -0.889 | 1.00 | 94.74 | O |
| ATOM | 462 | NE2 | GLN | A | 132 | 51.660 | 104.058 | -0.099 | 1.00 | 98.97 | N |
| ATOM | 463 | N | TYR | A | 133 | 55.585 | 99.075 | 2.219 | 1.00 | 56.98 | N |
| ATOM | 464 | CA | TYR | A | 133 | 56.614 | 98.690 | 3.188 | 1.00 | 54.63 | C |
| ATOM | 465 | C | TYR | A | 133 | 57.986 | 99.152 | 2.689 | 1.00 | 57.99 | C |
| ATOM | 466 | O | TYR | A | 133 | 58.190 | 99.304 | 1.499 | 1.00 | 54.51 | O |
| ATOM | 467 | CB | TYR | A | 133 | 56.557 | 97.185 | 3.480 | 1.00 | 54.31 | C |
| ATOM | 468 | CG | TYR | A | 133 | 55.433 | 96.838 | 4.438 | 1.00 | 49.24 | C |
| ATOM | 469 | CD1 | TYR | A | 133 | 55.686 | 96.881 | 5.786 | 1.00 | 50.01 | C |
| ATOM | 470 | CD2 | TYR | A | 133 | 54.116 | 96.713 | 4.001 | 1.00 | 50.42 | C |
| ATOM | 471 | CE1 | TYR | A | 133 | 54.682 | 96.389 | 6.676 | 1.00 | 56.42 | C |
| ATOM | 472 | CE2 | TYR | A | 133 | 53.082 | 96.426 | 4.895 | 1.00 | 49.12 | C |
| ATOM | 473 | CZ | TYR | A | 133 | 53.384 | 96.262 | 6.239 | 1.00 | 51.56 | C |
| ATOM | 474 | OH | TYR | A | 133 | 52.415 | 95.981 | 7.174 | 1.00 | 52.93 | O |
| ATOM | 475 | N | ARG | A | 134 | 58.917 | 99.399 | 3.606 | 1.00 | 66.17 | N |
| ATOM | 476 | CA | ARG | A | 134 | 60.225 | 99.932 | 3.250 | 1.00 | 68.33 | C |
| ATOM | 477 | C | ARG | A | 134 | 61.325 | 99.006 | 3.743 | 1.00 | 69.62 | C |
| ATOM | 478 | O | ARG | A | 134 | 61.338 | 98.623 | 4.922 | 1.00 | 69.28 | O |
| ATOM | 479 | CB | ARG | A | 134 | 60.403 | 101.318 | 3.872 | 1.00 | 73.87 | C |
| ATOM | 480 | CG | ARG | A | 134 | 59.238 | 102.240 | 3.582 | 1.00 | 77.19 | C |
| ATOM | 481 | CD | ARG | A | 134 | 59.359 | 103.546 | 4.324 | 1.00 | 73.34 | C |
| ATOM | 482 | NE | ARG | A | 134 | 59.242 | 103.385 | 5.764 | 1.00 | 73.27 | N |
| ATOM | 483 | CZ | ARG | A | 134 | 58.098 | 103.394 | 6.446 | 1.00 | 80.66 | C |
| ATOM | 484 | NH1 | ARG | A | 134 | 56.935 | 103.507 | 5.816 | 1.00 | 79.65 | N |
| ATOM | 485 | NH2 | ARG | A | 134 | 58.116 | 103.293 | 7.771 | 1.00 | 86.19 | N |
| ATOM | 486 | N | GLN | A | 135 | 62.241 | 98.646 | 2.845 | 1.00 | 62.00 | N |
| ATOM | 487 | CA | GLN | A | 135 | 63.387 | 97.770 | 3.215 | 1.00 | 66.41 | C |
| ATOM | 488 | C | GLN | A | 135 | 64.454 | 98.557 | 3.893 | 1.00 | 69.98 | C |
| ATOM | 489 | O | GLN | A | 135 | 64.782 | 99.668 | 3.475 | 1.00 | 76.79 | O |
| ATOM | 490 | CB | GLN | A | 135 | 63.927 | 97.025 | 2.014 | 1.00 | 64.38 | C |
| ATOM | 491 | CG | GLN | A | 135 | 65.069 | 96.117 | 2.437 | 1.00 | 63.44 | C |
| ATOM | 492 | CD | GLN | A | 135 | 65.717 | 95.418 | 1.276 | 1.00 | 68.75 | C |
| ATOM | 493 | OE1 | GLN | A | 135 | 65.156 | 95.354 | 0.192 | 1.00 | 74.32 | O |
| ATOM | 494 | NE2 | GLN | A | 135 | 66.314 | 94.883 | 1.495 | 1.00 | 74.37 | N |
| ATOM | 495 | N | VAL | A | 136 | 65.024 | 97.990 | 4.942 | 1.00 | 65.27 | N |
| ATOM | 496 | CA | VAL | A | 136 | 66.003 | 98.692 | 5.749 | 1.00 | 71.83 | C |
| ATOM | 497 | C | VAL | A | 136 | 67.032 | 97.775 | 6.300 | 1.00 | 80.73 | C |
| ATOM | 498 | O | VAL | A | 136 | 67.011 | 96.548 | 6.231 | 1.00 | 79.14 | O |
| ATOM | 499 | CB | VAL | A | 136 | 65.321 | 99.434 | 6.911 | 1.00 | 69.75 | C |
| ATOM | 500 | CG1 | VAL | A | 136 | 64.130 | 100.258 | 6.392 | 1.00 | 68.96 | C |
| ATOM | 501 | CG2 | VAL | A | 136 | 64.887 | 98.443 | 7.995 | 1.00 | 62.07 | C |
| ATOM | 502 | N | SER | A | 137 | 68.115 | 98.385 | 6.906 | 1.00 | 84.03 | N |
| ATOM | 503 | CA | SER | A | 137 | 69.187 | 97.830 | 7.535 | 1.00 | 91.32 | C |
| ATOM | 504 | C | SER | A | 137 | 68.785 | 97.174 | 8.923 | 1.00 | 83.92 | C |
| ATOM | 505 | O | SER | A | 137 | 68.885 | 96.003 | 9.264 | 1.00 | 79.84 | O |
| ATOM | 506 | CB | SER | A | 137 | 70.453 | 98.480 | 7.638 | 1.00100.67 | | C |
| ATOM | 507 | OG | SER | A | 137 | 70.273 | 99.523 | 8.580 | 1.00107.20 | | O |
| ATOM | 508 | N | LYS | A | 138 | 68.240 | 98.110 | 9.716 | 1.00 | 84.64 | N |
| ATOM | 509 | CA | LYS | A | 138 | 67.756 | 97.804 | 11.057 | 1.00 | 83.00 | C |
| ATOM | 510 | C | LYS | A | 138 | 66.351 | 98.357 | 11.279 | 1.00 | 84.31 | C |
| ATOM | 511 | O | LYS | A | 138 | 66.076 | 99.519 | 10.865 | 1.00 | 81.86 | O |
| ATOM | 512 | CB | LYS | A | 138 | 68.723 | 98.333 | 12.122 | 1.00 | 83.69 | C |
| ATOM | 513 | CG | LYS | A | 138 | 69.924 | 97.428 | 12.354 | 1.00 | 85.98 | C |
| ATOM | 514 | CD | LYS | A | 138 | 70.907 | 98.044 | 13.343 | 1.00 | 85.94 | C |
| ATOM | 515 | CE | LYS | A | 138 | 71.869 | 97.001 | 13.910 | 1.00 | 83.51 | C |
| ATOM | 516 | NZ | LYS | A | 138 | 72.765 | 97.572 | 14.965 | 1.00 | 88.93 | N |
| ATOM | 517 | N | MET | A | 139 | 65.470 | 97.516 | 11.822 | 1.00 | 85.81 | N |
| ATOM | 518 | CA | MET | A | 139 | 64.056 | 97.856 | 11.965 | 1.00 | 84.88 | C |
| ATOM | 519 | C | MET | A | 139 | 63.817 | 98.887 | 13.266 | 1.00 | 86.37 | C |
| ATOM | 520 | O | MET | A | 139 | 64.477 | 98.306 | 14.251 | 1.00 | 88.63 | O |
| ATOM | 521 | CB | MET | A | 139 | 63.180 | 96.889 | 11.945 | 1.00 | 80.85 | C |
| ATOM | 522 | CG | MET | A | 139 | 63.090 | 95.887 | 10.621 | 1.00 | 58.63 | C |
| ATOM | 523 | SD | MET | A | 139 | 61.634 | 94.887 | 10.613 | 1.00 | 91.81 | S |
| ATOM | 524 | CE | MET | A | 139 | 62.213 | 93.338 | 11.370 | 1.00 | 57.75 | C |
| ATOM | 525 | N | THR | A | 140 | 62.865 | 99.316 | 13.258 | 1.00 | 78.20 | N |
| ATOM | 526 | CA | THR | A | 140 | 62.499 | 100.277 | 14.447 | 1.00 | 89.47 | C |
| ATOM | 527 | C | THR | A | 140 | 61.023 | 100.687 | 14.433 | 1.00 | 89.97 | C |
| ATOM | 528 | O | THR | A | 140 | 60.427 | 100.900 | 15.493 | 1.00 | 88.48 | O |
| ATOM | 529 | CB | THR | A | 140 | 63.359 | 101.560 | 14.604 | 1.00 | 94.42 | C |
| ATOM | 530 | OG1 | THR | A | 140 | 63.139 | 102.429 | 13.486 | 1.00 | 98.18 | O |
| ATOM | 531 | CG2 | THR | A | 140 | 64.829 | 101.216 | 14.684 | 1.00 | 92.52 | C |
| ATOM | 532 | N | ARG | A | 141 | 60.442 | 100.789 | 13.235 | 1.00 | 89.79 | N |
| ATOM | 533 | CA | ARG | A | 141 | 59.098 | 101.390 | 13.063 | 1.00 | 87.36 | C |
| ATOM | 534 | C | ARG | A | 141 | 58.158 | 100.466 | 12.243 | 1.00 | 84.30 | C |

FIG. 8-17

| | | | | | | | | | | | |
|---|---|---|---|---|---|---|---|---|---|---|---|
| ATOM | 535 | O | ARG | A | 141 | 58.595 | 99.609 | 11.473 | 1.00 | 78.92 | O |
| ATOM | 536 | CB | ARG | A | 141 | 59.178 | 102.718 | 12.386 | 1.00 | 81.44 | C |
| ATOM | 537 | CG | ARG | A | 141 | 60.095 | 103.797 | 13.068 | 1.00 | 99.78 | C |
| ATOM | 538 | CD | ARG | A | 141 | 60.520 | 104.795 | 12.100 | 1.00 | 108.31 | C |
| ATOM | 539 | NE | ARG | A | 141 | 61.190 | 105.899 | 12.780 | 1.00 | 118.33 | N |
| ATOM | 540 | CZ | ARG | A | 141 | 60.622 | 107.077 | 13.026 | 1.00 | 116.11 | C |
| ATOM | 541 | NH1 | ARG | A | 141 | 59.367 | 107.306 | 12.636 | 1.00 | 109.30 | N |
| ATOM | 542 | NH2 | ARG | A | 141 | 61.311 | 108.024 | 13.696 | 1.00 | 110.49 | N |
| ATOM | 543 | N | PRO | A | 142 | 56.848 | 100.690 | 12.390 | 1.00 | 79.03 | N |
| ATOM | 544 | CA | PRO | A | 142 | 55.899 | 99.933 | 11.581 | 1.00 | 73.97 | C |
| ATOM | 545 | C | PRO | A | 142 | 56.138 | 100.191 | 10.102 | 1.00 | 70.32 | C |
| ATOM | 546 | O | PRO | A | 142 | 56.660 | 101.250 | 9.681 | 1.00 | 64.00 | O |
| ATOM | 547 | CB | PRO | A | 142 | 54.541 | 100.504 | 12.009 | 1.00 | 75.37 | C |
| ATOM | 548 | CG | PRO | A | 142 | 54.787 | 101.112 | 13.368 | 1.00 | 78.79 | C |
| ATOM | 549 | CD | PRO | A | 142 | 56.181 | 101.629 | 13.310 | 1.00 | 81.57 | C |
| ATOM | 550 | N | GLY | A | 143 | 55.792 | 99.139 | 9.398 | 1.00 | 69.43 | N |
| ATOM | 551 | CA | GLY | A | 143 | 55.871 | 99.346 | 7.866 | 1.00 | 65.63 | C |
| ATOM | 552 | C | GLY | A | 143 | 57.292 | 99.200 | 7.378 | 1.00 | 61.88 | C |
| ATOM | 553 | O | GLY | A | 143 | 57.638 | 99.723 | 6.301 | 1.00 | 59.78 | O |
| ATOM | 554 | N | GLU | A | 144 | 58.118 | 98.530 | 8.156 | 1.00 | 65.17 | N |
| ATOM | 555 | CA | GLU | A | 144 | 59.486 | 98.273 | 7.737 | 1.00 | 68.47 | C |
| ATOM | 556 | C | GLU | A | 144 | 59.807 | 96.774 | 7.673 | 1.00 | 64.38 | C |
| ATOM | 557 | O | GLU | A | 144 | 59.116 | 95.949 | 8.270 | 1.00 | 58.57 | O |
| ATOM | 558 | CB | GLU | A | 144 | 60.449 | 99.033 | 8.642 | 1.00 | 76.80 | C |
| ATOM | 559 | CG | GLU | A | 144 | 60.110 | 100.521 | 8.724 | 1.00 | 81.83 | C |
| ATOM | 560 | CD | GLU | A | 144 | 61.203 | 101.365 | 9.378 | 1.00 | 89.32 | C |
| ATOM | 561 | OE1 | GLU | A | 144 | 62.159 | 100.772 | 9.983 | 1.00 | 90.43 | O |
| ATOM | 562 | OE2 | GLU | A | 144 | 61.097 | 102.601 | 9.324 | 1.00 | 92.25 | O |
| ATOM | 563 | N | PHE | A | 145 | 60.832 | 96.413 | 6.913 | 1.00 | 65.30 | N |
| ATOM | 564 | CA | PHE | A | 145 | 61.236 | 95.013 | 6.855 | 1.00 | 65.83 | C |
| ATOM | 565 | C | PHE | A | 145 | 62.707 | 94.825 | 6.524 | 1.00 | 64.03 | C |
| ATOM | 566 | O | PHE | A | 145 | 63.320 | 95.667 | 5.881 | 1.00 | 61.87 | O |
| ATOM | 567 | CB | PHE | A | 145 | 60.385 | 94.238 | 5.844 | 1.00 | 53.83 | C |
| ATOM | 568 | CG | PHE | A | 145 | 60.618 | 94.634 | 4.408 | 1.00 | 54.09 | C |
| ATOM | 569 | CD1 | PHE | A | 145 | 61.499 | 93.917 | 3.615 | 1.00 | 53.48 | C |
| ATOM | 570 | CD2 | PHE | A | 145 | 59.928 | 95.700 | 3.880 | 1.00 | 51.81 | C |
| ATOM | 571 | CE1 | PHE | A | 145 | 61.699 | 94.265 | 2.287 | 1.00 | 61.21 | C |
| ATOM | 572 | CE2 | PHE | A | 145 | 60.113 | 96.048 | 2.521 | 1.00 | 57.96 | C |
| ATOM | 573 | CZ | PHE | A | 145 | 60.992 | 95.328 | 1.731 | 1.00 | 62.44 | C |
| ATOM | 574 | N | THR | A | 146 | 63.272 | 93.709 | 6.897 | 1.00 | 68.03 | N |
| ATOM | 575 | CA | THR | A | 146 | 64.638 | 93.404 | 6.578 | 1.00 | 71.45 | C |
| ATOM | 576 | C | THR | A | 146 | 64.713 | 92.098 | 5.836 | 1.00 | 69.45 | C |
| ATOM | 577 | O | THR | A | 146 | 63.889 | 91.185 | 6.047 | 1.00 | 70.28 | O |
| ATOM | 578 | CB | THR | A | 146 | 65.561 | 93.383 | 7.784 | 1.00 | 74.99 | C |
| ATOM | 579 | OG1 | THR | A | 146 | 65.120 | 92.412 | 8.729 | 1.00 | 84.16 | O |
| ATOM | 580 | CG2 | THR | A | 146 | 65.625 | 94.756 | 8.428 | 1.00 | 67.83 | C |
| ATOM | 581 | N | VAL | A | 147 | 65.705 | 92.001 | 4.960 | 1.00 | 62.86 | N |
| ATOM | 582 | CA | VAL | A | 147 | 65.948 | 90.816 | 4.141 | 1.00 | 61.98 | C |
| ATOM | 583 | C | VAL | A | 147 | 67.234 | 90.084 | 4.503 | 1.00 | 68.61 | C |
| ATOM | 584 | O | VAL | A | 147 | 68.288 | 90.699 | 4.772 | 1.00 | 70.44 | O |
| ATOM | 585 | CB | VAL | A | 147 | 66.039 | 91.172 | 2.654 | 1.00 | 62.53 | C |
| ATOM | 586 | CG1 | VAL | A | 147 | 66.082 | 89.902 | 1.827 | 1.00 | 68.32 | C |
| ATOM | 587 | CG2 | VAL | A | 147 | 64.828 | 92.018 | 2.227 | 1.00 | 64.21 | C |
| ATOM | 588 | N | GLN | A | 148 | 67.117 | 88.766 | 4.677 | 1.00 | 66.47 | N |
| ATOM | 589 | CA | GLN | A | 148 | 68.248 | 87.890 | 4.897 | 1.00 | 66.29 | C |
| ATOM | 590 | C | GLN | A | 148 | 68.228 | 86.881 | 3.752 | 1.00 | 73.54 | C |
| ATOM | 591 | O | GLN | A | 148 | 67.300 | 86.886 | 2.941 | 1.00 | 79.67 | O |
| ATOM | 592 | CB | GLN | A | 148 | 68.124 | 87.201 | 6.299 | 1.00 | 55.07 | C |
| ATOM | 593 | CG | GLN | A | 148 | 67.968 | 88.180 | 7.497 | 1.00 | 86.86 | C |
| ATOM | 594 | CD | GLN | A | 148 | 66.533 | 88.817 | 7.785 | 1.00 | 83.87 | C |
| ATOM | 595 | OE1 | GLN | A | 148 | 66.261 | 89.792 | 8.022 | 1.00 | 77.94 | O |
| ATOM | 596 | NE2 | GLN | A | 148 | 65.807 | 87.685 | 7.718 | 1.00 | 80.00 | N |
| ATOM | 597 | N | ALA | A | 149 | 69.252 | 86.037 | 3.666 | 1.00 | 68.18 | N |
| ATOM | 598 | CA | ALA | A | 149 | 69.329 | 84.994 | 2.637 | 1.00 | 63.47 | C |
| ATOM | 599 | C | ALA | A | 149 | 68.014 | 84.362 | 2.324 | 1.00 | 57.75 | C |
| ATOM | 600 | O | ALA | A | 149 | 67.613 | 84.156 | 1.163 | 1.00 | 64.05 | O |
| ATOM | 601 | CB | ALA | A | 149 | 70.318 | 83.975 | 3.009 | 1.00 | 65.92 | C |
| ATOM | 602 | N | ASN | A | 150 | 67.366 | 83.755 | 3.366 | 1.00 | 59.27 | N |
| ATOM | 603 | CA | ASN | A | 150 | 66.245 | 82.825 | 3.281 | 1.00 | 59.95 | C |
| ATOM | 604 | C | ASN | A | 150 | 65.023 | 83.294 | 4.098 | 1.00 | 63.41 | C |
| ATOM | 605 | O | ASN | A | 150 | 64.147 | 82.500 | 4.390 | 1.00 | 54.85 | O |
| ATOM | 606 | CB | ASN | A | 150 | 66.650 | 81.458 | 3.830 | 1.00 | 74.71 | C |
| ATOM | 607 | CG | ASN | A | 150 | 67.577 | 80.880 | 2.910 | 1.00 | 87.94 | C |
| ATOM | 608 | OD1 | ASN | A | 150 | 68.165 | 81.231 | 1.973 | 1.00 | 90.31 | O |
| ATOM | 609 | ND2 | ASN | A | 150 | 67.711 | 79.383 | 3.178 | 1.00 | 89.87 | N |
| ATOM | 610 | N | SER | A | 151 | 64.960 | 84.574 | 4.384 | 1.00 | 61.18 | N |
| ATOM | 611 | CA | SER | A | 151 | 63.851 | 85.046 | 5.181 | 1.00 | 60.10 | C |

FIG. 8-18

| | | | | | | | | | | | |
|---|---|---|---|---|---|---|---|---|---|---|---|
| ATOM | 612 | C | SER | A | 151 | 63.740 | 88.544 | 5.152 | 1.00 | 60.92 | C |
| ATOM | 613 | O | SER | A | 151 | 64.642 | 87.255 | 4.703 | 1.00 | 54.84 | O |
| ATOM | 614 | CB | SER | A | 151 | 64.017 | 86.603 | 6.832 | 1.00 | 66.80 | C |
| ATOM | 615 | OG | SER | A | 151 | 65.066 | 85.329 | 7.249 | 1.00 | 71.33 | O |
| ATOM | 616 | N | ILE | A | 152 | 62.618 | 87.019 | 5.650 | 1.00 | 53.33 | N |
| ATOM | 617 | CA | ILE | A | 152 | 62.396 | 88.437 | 5.789 | 1.00 | 63.62 | C |
| ATOM | 618 | C | ILE | A | 152 | 61.851 | 88.615 | 7.168 | 1.00 | 55.01 | C |
| ATOM | 619 | O | ILE | A | 152 | 61.105 | 87.768 | 7.640 | 1.00 | 60.63 | O |
| ATOM | 620 | CB | ILE | A | 152 | 61.308 | 88.923 | 4.815 | 1.00 | 55.37 | C |
| ATOM | 621 | CG1 | ILE | A | 152 | 61.845 | 88.985 | 3.392 | 1.00 | 53.70 | C |
| ATOM | 622 | CG2 | ILE | A | 152 | 60.716 | 90.260 | 5.274 | 1.00 | 51.72 | C |
| ATOM | 623 | CD1 | ILE | A | 152 | 60.855 | 88.393 | 2.414 | 1.00 | 50.63 | C |
| ATOM | 624 | N | GLU | A | 153 | 62.199 | 89.723 | 7.801 | 1.00 | 54.14 | N |
| ATOM | 625 | CA | GLU | A | 153 | 61.592 | 90.083 | 9.072 | 1.00 | 57.84 | C |
| ATOM | 626 | C | GLU | A | 153 | 60.868 | 91.411 | 8.896 | 1.00 | 58.89 | C |
| ATOM | 627 | O | GLU | A | 153 | 61.426 | 92.360 | 8.366 | 1.00 | 57.52 | O |
| ATOM | 628 | CB | GLU | A | 153 | 62.643 | 90.214 | 10.175 | 1.00 | 63.04 | C |
| ATOM | 629 | CG | GLU | A | 153 | 63.323 | 88.900 | 10.580 | 1.00 | 75.34 | C |
| ATOM | 630 | CD | GLU | A | 153 | 64.655 | 89.105 | 11.327 | 1.00 | 77.09 | C |
| ATOM | 631 | OE1 | GLU | A | 153 | 64.870 | 90.211 | 11.875 | 1.00 | 78.52 | O |
| ATOM | 632 | OE2 | GLU | A | 153 | 65.489 | 88.164 | 11.355 | 1.00 | 70.02 | O |
| ATOM | 633 | N | MET | A | 154 | 59.624 | 91.497 | 9.358 | 1.00 | 57.98 | N |
| ATOM | 634 | CA | MET | A | 154 | 58.892 | 92.727 | 9.165 | 1.00 | 52.79 | C |
| ATOM | 635 | C | MET | A | 154 | 58.149 | 93.175 | 10.414 | 1.00 | 58.99 | C |
| ATOM | 636 | O | MET | A | 154 | 57.918 | 92.396 | 11.332 | 1.00 | 53.29 | O |
| ATOM | 637 | CB | MET | A | 154 | 57.920 | 92.569 | 7.988 | 1.00 | 51.33 | C |
| ATOM | 638 | CG | MET | A | 154 | 58.774 | 91.597 | 8.247 | 1.00 | 57.26 | C |
| ATOM | 639 | SD | MET | A | 154 | 55.696 | 91.368 | 6.829 | 1.00 | 57.97 | S |
| ATOM | 640 | CE | MET | A | 154 | 55.111 | 93.050 | 6.587 | 1.00 | 56.47 | C |
| ATOM | 641 | N | ILE | A | 155 | 57.798 | 94.456 | 10.442 | 1.00 | 59.64 | N |
| ATOM | 642 | CA | ILE | A | 155 | 56.807 | 94.941 | 11.371 | 1.00 | 58.30 | C |
| ATOM | 643 | C | ILE | A | 155 | 55.521 | 95.276 | 10.627 | 1.00 | 54.94 | C |
| ATOM | 644 | O | ILE | A | 155 | 55.332 | 96.396 | 10.144 | 1.00 | 52.72 | O |
| ATOM | 645 | CB | ILE | A | 155 | 57.271 | 96.176 | 12.134 | 1.00 | 66.21 | C |
| ATOM | 646 | CG1 | ILE | A | 155 | 58.681 | 95.971 | 12.693 | 1.00 | 65.18 | C |
| ATOM | 647 | CG2 | ILE | A | 155 | 56.290 | 96.465 | 13.270 | 1.00 | 63.38 | C |
| ATOM | 648 | CD1 | ILE | A | 155 | 58.978 | 96.873 | 13.881 | 1.00 | 60.47 | C |
| ATOM | 649 | N | ARG | A | 156 | 54.643 | 94.288 | 10.527 | 1.00 | 51.10 | N |
| ATOM | 650 | CA | ARG | A | 156 | 53.319 | 94.482 | 9.947 | 1.00 | 49.98 | C |
| ATOM | 651 | C | ARG | A | 156 | 52.622 | 95.592 | 10.733 | 1.00 | 61.08 | C |
| ATOM | 652 | O | ARG | A | 156 | 52.382 | 95.458 | 11.937 | 1.00 | 62.33 | O |
| ATOM | 653 | CB | ARG | A | 156 | 52.537 | 93.172 | 10.043 | 1.00 | 49.10 | C |
| ATOM | 654 | CG | ARG | A | 156 | 51.590 | 92.872 | 8.878 | 1.00 | 52.04 | C |
| ATOM | 655 | CD | ARG | A | 156 | 50.374 | 93.733 | 8.934 | 1.00 | 50.81 | C |
| ATOM | 656 | NE | ARG | A | 156 | 49.890 | 93.337 | 10.302 | 1.00 | 54.57 | N |
| ATOM | 657 | CZ | ARG | A | 156 | 49.181 | 93.044 | 10.936 | 1.00 | 59.11 | C |
| ATOM | 658 | NH1 | ARG | A | 156 | 48.913 | 91.857 | 10.484 | 1.00 | 54.00 | N |
| ATOM | 659 | NH2 | ARG | A | 156 | 48.768 | 93.523 | 12.228 | 1.00 | 61.07 | N |
| ATOM | 660 | N | ARG | A | 157 | 52.323 | 96.639 | 10.066 | 1.00 | 56.70 | N |
| ATOM | 661 | CA | ARG | A | 157 | 51.677 | 97.837 | 10.719 | 1.00 | 52.79 | C |
| ATOM | 662 | C | ARG | A | 157 | 50.250 | 97.506 | 11.175 | 1.00 | 54.78 | C |
| ATOM | 663 | O | ARG | A | 157 | 49.643 | 98.539 | 10.713 | 1.00 | 49.37 | O |
| ATOM | 664 | CB | ARG | A | 157 | 51.635 | 99.036 | 9.771 | 1.00 | 55.07 | C |
| ATOM | 665 | CG | ARG | A | 157 | 50.827 | 98.766 | 8.512 | 1.00 | 58.68 | C |
| ATOM | 666 | CD | ARG | A | 157 | 50.650 | 100.034 | 7.721 | 1.00 | 61.82 | C |
| ATOM | 667 | NE | ARG | A | 157 | 51.905 | 100.489 | 7.138 | 1.00 | 58.70 | N |
| ATOM | 668 | CZ | ARG | A | 157 | 52.260 | 100.224 | 5.888 | 1.00 | 64.98 | C |
| ATOM | 669 | NH1 | ARG | A | 157 | 51.451 | 99.507 | 5.112 | 1.00 | 58.35 | N |
| ATOM | 670 | NH2 | ARG | A | 157 | 53.415 | 100.676 | 5.411 | 1.00 | 73.07 | N |
| ATOM | 671 | N | PRO | A | 158 | 49.717 | 98.308 | 12.113 | 1.00 | 59.59 | N |
| ATOM | 672 | CA | PRO | A | 158 | 48.373 | 98.053 | 12.649 | 1.00 | 60.30 | C |
| ATOM | 673 | C | PRO | A | 158 | 47.285 | 98.346 | 11.599 | 1.00 | 64.97 | C |
| ATOM | 674 | O | PRO | A | 158 | 47.450 | 99.250 | 10.769 | 1.00 | 49.93 | O |
| ATOM | 675 | CB | PRO | A | 158 | 48.252 | 99.045 | 13.810 | 1.00 | 56.22 | C |
| ATOM | 676 | CG | PRO | A | 158 | 49.609 | 99.639 | 14.002 | 1.00 | 53.64 | C |
| ATOM | 677 | CD | PRO | A | 158 | 50.397 | 99.435 | 12.779 | 1.00 | 67.23 | C |
| ATOM | 678 | N | PHE | A | 159 | 46.184 | 97.604 | 11.631 | 1.00 | 49.07 | N |
| ATOM | 679 | CA | PHE | A | 159 | 45.092 | 97.906 | 10.716 | 1.00 | 48.23 | C |
| ATOM | 680 | C | PHE | A | 159 | 43.760 | 97.432 | 11.258 | 1.00 | 55.71 | C |
| ATOM | 681 | O | PHE | A | 159 | 43.664 | 96.367 | 11.863 | 1.00 | 57.82 | O |
| ATOM | 682 | CB | PHE | A | 159 | 45.334 | 97.260 | 9.320 | 1.00 | 55.15 | C |
| ATOM | 683 | CG | PHE | A | 159 | 44.365 | 97.719 | 8.260 | 1.00 | 49.17 | C |
| ATOM | 684 | CD1 | PHE | A | 159 | 44.562 | 98.932 | 7.611 | 1.00 | 53.00 | C |
| ATOM | 685 | CD2 | PHE | A | 159 | 43.267 | 96.946 | 7.914 | 1.00 | 49.92 | C |
| ATOM | 686 | CE1 | PHE | A | 159 | 43.679 | 99.384 | 6.623 | 1.00 | 54.45 | C |
| ATOM | 687 | CE2 | PHE | A | 159 | 42.361 | 97.382 | 6.937 | 1.00 | 53.01 | C |
| ATOM | 688 | CZ | PHE | A | 159 | 42.572 | 98.609 | 6.283 | 1.00 | 53.42 | C |

FIG. 8-19

| | | | | | | | | | | | |
|---|---|---|---|---|---|---|---|---|---|---|---|
| ATOM | 689 | N | ASP | A | 160 | 42.723 | 98.213 | 10.999 | 1.00 | 55.43 | N |
| ATOM | 690 | CA | ASP | A | 160 | 41.393 | 97.862 | 11.438 | 1.00 | 61.00 | C |
| ATOM | 691 | C | ASP | A | 160 | 40.753 | 96.800 | 10.457 | 1.00 | 57.74 | C |
| ATOM | 692 | O | ASP | A | 160 | 39.836 | 97.276 | 9.730 | 1.00 | 59.97 | O |
| ATOM | 693 | CB | ASP | A | 160 | 40.540 | 99.128 | 11.562 | 1.00 | 70.04 | C |
| ATOM | 694 | CG | ASP | A | 160 | 39.293 | 98.912 | 12.394 | 1.00 | 76.87 | C |
| ATOM | 695 | OD1 | ASP | A | 160 | 39.121 | 97.799 | 12.942 | 1.00 | 71.73 | O |
| ATOM | 696 | OD2 | ASP | A | 160 | 38.488 | 99.862 | 12.502 | 1.00 | 84.96 | O |
| ATOM | 697 | N | PHE | A | 161 | 41.233 | 95.663 | 10.410 | 1.00 | 54.61 | N |
| ATOM | 698 | CA | PHE | A | 161 | 40.641 | 94.685 | 9.489 | 1.00 | 47.23 | C |
| ATOM | 699 | C | PHE | A | 161 | 39.196 | 94.456 | 9.870 | 1.00 | 51.74 | C |
| ATOM | 700 | O | PHE | A | 161 | 38.898 | 94.233 | 11.046 | 1.00 | 50.58 | O |
| ATOM | 701 | CB | PHE | A | 161 | 41.344 | 93.341 | 9.577 | 1.00 | 44.58 | C |
| ATOM | 702 | CG | PHE | A | 161 | 42.773 | 93.361 | 9.108 | 1.00 | 52.09 | C |
| ATOM | 703 | CD1 | PHE | A | 161 | 43.077 | 93.148 | 7.776 | 1.00 | 49.80 | C |
| ATOM | 704 | CD2 | PHE | A | 161 | 43.803 | 93.559 | 10.001 | 1.00 | 47.56 | C |
| ATOM | 705 | CE1 | PHE | A | 161 | 44.378 | 93.141 | 7.356 | 1.00 | 50.29 | C |
| ATOM | 706 | CE2 | PHE | A | 161 | 45.126 | 93.566 | 9.577 | 1.00 | 51.90 | C |
| ATOM | 707 | CZ | PHE | A | 161 | 45.408 | 93.349 | 8.255 | 1.00 | 44.92 | C |
| ATOM | 708 | N | PRO | A | 162 | 38.294 | 94.475 | 8.879 | 1.00 | 63.22 | N |
| ATOM | 709 | CA | PRO | A | 162 | 36.896 | 94.163 | 9.167 | 1.00 | 58.18 | C |
| ATOM | 710 | C | PRO | A | 162 | 36.816 | 93.010 | 10.158 | 1.00 | 61.92 | C |
| ATOM | 711 | O | PRO | A | 162 | 36.142 | 93.110 | 11.192 | 1.00 | 68.29 | O |
| ATOM | 712 | CB | PRO | A | 162 | 36.362 | 93.719 | 7.805 | 1.00 | 57.97 | C |
| ATOM | 713 | CG | PRO | A | 162 | 37.134 | 94.533 | 6.841 | 1.00 | 61.22 | C |
| ATOM | 714 | CD | PRO | A | 162 | 38.522 | 94.682 | 7.435 | 1.00 | 68.05 | C |
| ATOM | 715 | N | ASP | A | 163 | 37.532 | 91.937 | 9.853 | 1.00 | 59.41 | N |
| ATOM | 716 | CA | ASP | A | 163 | 37.427 | 90.702 | 10.608 | 1.00 | 70.54 | C |
| ATOM | 717 | C | ASP | A | 163 | 37.848 | 90.798 | 12.066 | 1.00 | 78.29 | C |
| ATOM | 718 | O | ASP | A | 163 | 37.390 | 90.013 | 12.897 | 1.00 | 87.40 | O |
| ATOM | 719 | CB | ASP | A | 163 | 38.214 | 89.598 | 9.918 | 1.00 | 75.01 | C |
| ATOM | 720 | CG | ASP | A | 163 | 37.321 | 88.669 | 9.155 | 1.00 | 80.40 | C |
| ATOM | 721 | OD1 | ASP | A | 163 | 36.097 | 88.728 | 9.415 | 1.00 | 82.82 | O |
| ATOM | 722 | OD2 | ASP | A | 163 | 37.829 | 87.896 | 8.308 | 1.00 | 81.62 | O |
| ATOM | 723 | N | SER | A | 164 | 38.719 | 91.748 | 12.374 | 1.00 | 72.13 | N |
| ATOM | 724 | CA | SER | A | 164 | 39.198 | 91.924 | 13.744 | 1.00 | 70.42 | C |
| ATOM | 725 | C | SER | A | 164 | 40.356 | 92.891 | 13.724 | 1.00 | 60.01 | C |
| ATOM | 726 | O | SER | A | 164 | 41.344 | 92.652 | 13.039 | 1.00 | 66.73 | O |
| ATOM | 727 | CB | SER | A | 164 | 39.675 | 90.593 | 14.332 | 1.00 | 79.41 | C |
| ATOM | 728 | OG | SER | A | 164 | 40.169 | 90.759 | 15.654 | 1.00 | 81.41 | O |
| ATOM | 729 | N | LYS | A | 165 | 40.237 | 93.993 | 14.452 | 1.00 | 55.71 | N |
| ATOM | 730 | CA | LYS | A | 165 | 41.323 | 94.960 | 14.434 | 1.00 | 55.58 | C |
| ATOM | 731 | C | LYS | A | 165 | 42.632 | 94.320 | 15.005 | 1.00 | 62.72 | C |
| ATOM | 732 | O | LYS | A | 165 | 42.614 | 93.336 | 15.757 | 1.00 | 65.52 | O |
| ATOM | 733 | CB | LYS | A | 165 | 40.919 | 96.188 | 15.296 | 1.00 | 58.60 | C |
| ATOM | 734 | CG | LYS | A | 165 | 42.066 | 97.109 | 15.673 | 1.00 | 63.21 | C |
| ATOM | 735 | CD | LYS | A | 165 | 41.551 | 98.282 | 16.483 | 1.00 | 67.54 | C |
| ATOM | 736 | CE | LYS | A | 165 | 42.176 | 99.574 | 15.991 | 1.00 | 73.62 | C |
| ATOM | 737 | NZ | LYS | A | 165 | 41.378 | 100.779 | 16.370 | 1.00 | 76.57 | N |
| ATOM | 738 | N | GLU | A | 166 | 43.769 | 94.870 | 14.583 | 1.00 | 55.91 | N |
| ATOM | 739 | CA | GLU | A | 166 | 45.052 | 94.307 | 14.941 | 1.00 | 53.80 | C |
| ATOM | 740 | C | GLU | A | 166 | 46.077 | 95.415 | 15.124 | 1.00 | 64.39 | C |
| ATOM | 741 | O | GLU | A | 166 | 46.003 | 96.453 | 14.474 | 1.00 | 63.42 | O |
| ATOM | 742 | CB | GLU | A | 166 | 45.538 | 93.303 | 13.879 | 1.00 | 56.68 | C |
| ATOM | 743 | CG | GLU | A | 166 | 44.567 | 92.140 | 13.601 | 1.00 | 59.29 | C |
| ATOM | 744 | CD | GLU | A | 166 | 45.237 | 90.985 | 12.849 | 1.00 | 71.58 | C |
| ATOM | 745 | OE1 | GLU | A | 166 | 46.451 | 91.086 | 12.556 | 1.00 | 73.51 | O |
| ATOM | 746 | OE2 | GLU | A | 166 | 44.558 | 89.973 | 12.538 | 1.00 | 70.43 | O |
| ATOM | 747 | N | GLY | A | 167 | 47.012 | 95.199 | 16.040 | 1.00 | 67.44 | N |
| ATOM | 748 | CA | GLY | A | 167 | 48.118 | 96.116 | 16.214 | 1.00 | 73.75 | C |
| ATOM | 749 | C | GLY | A | 167 | 49.300 | 95.687 | 15.360 | 1.00 | 70.30 | C |
| ATOM | 750 | O | GLY | A | 167 | 49.144 | 94.878 | 14.451 | 1.00 | 63.66 | O |
| ATOM | 751 | N | GLN | A | 168 | 50.467 | 96.256 | 15.687 | 1.00 | 71.95 | N |
| ATOM | 752 | CA | GLN | A | 168 | 51.730 | 95.801 | 15.091 | 1.00 | 73.01 | C |
| ATOM | 753 | C | GLN | A | 168 | 51.939 | 94.347 | 15.408 | 1.00 | 73.93 | C |
| ATOM | 754 | O | GLN | A | 168 | 51.481 | 93.845 | 16.444 | 1.00 | 77.83 | O |
| ATOM | 755 | CB | GLN | A | 168 | 52.889 | 96.528 | 15.763 | 1.00 | 78.66 | C |
| ATOM | 756 | CG | GLN | A | 168 | 53.309 | 97.800 | 15.108 | 1.00 | 78.89 | C |
| ATOM | 757 | CD | GLN | A | 168 | 53.987 | 98.712 | 16.093 | 1.00 | 75.94 | C |
| ATOM | 758 | OE1 | GLN | A | 168 | 55.009 | 98.358 | 16.692 | 1.00 | 75.95 | O |
| ATOM | 759 | NE2 | GLN | A | 168 | 53.419 | 99.895 | 16.281 | 1.00 | 75.86 | N |
| ATOM | 760 | N | VAL | A | 169 | 52.688 | 93.693 | 14.531 | 1.00 | 65.95 | N |
| ATOM | 761 | CA | VAL | A | 169 | 53.165 | 92.344 | 14.748 | 1.00 | 62.93 | C |
| ATOM | 762 | C | VAL | A | 169 | 54.539 | 92.305 | 14.094 | 1.00 | 65.64 | C |
| ATOM | 763 | O | VAL | A | 169 | 54.721 | 92.792 | 12.976 | 1.00 | 70.39 | O |
| ATOM | 764 | CB | VAL | A | 169 | 52.227 | 91.312 | 14.096 | 1.00 | 63.68 | C |
| ATOM | 765 | CG1 | VAL | A | 169 | 52.588 | 89.909 | 14.538 | 1.00 | 62.55 | C |

FIG. 8-20

| | | | | | | | | | | | |
|---|---|---|---|---|---|---|---|---|---|---|---|
| ATOM | 766 | CG2 | VAL | A | 169 | 58.780 | 91.620 | 14.440 | 1.00 | 65.69 | C |
| ATOM | 767 | N | ARG | A | 170 | 55.518 | 91.770 | 13.807 | 1.00 | 66.21 | N |
| ATOM | 768 | CA | ARG | A | 170 | 56.879 | 91.681 | 13.304 | 1.00 | 66.24 | C |
| ATOM | 769 | C | ARG | A | 170 | 57.034 | 90.193 | 13.977 | 1.00 | 59.59 | C |
| ATOM | 770 | O | ARG | A | 170 | 56.977 | 89.328 | 13.849 | 1.00 | 54.23 | O |
| ATOM | 771 | CB | ARG | A | 170 | 57.874 | 92.087 | 15.381 | 1.00 | 77.35 | C |
| ATOM | 772 | CG | ARG | A | 170 | 59.152 | 92.759 | 14.878 | 1.00 | 84.61 | C |
| ATOM | 773 | CD | ARG | A | 170 | 60.177 | 92.860 | 16.016 | 1.00 | 92.54 | C |
| ATOM | 774 | NE | ARG | A | 170 | 61.156 | 93.931 | 15.840 | 1.00 | 95.88 | N |
| ATOM | 775 | CZ | ARG | A | 170 | 61.032 | 95.158 | 16.347 | 1.00 | 94.40 | C |
| ATOM | 776 | NH1 | ARG | A | 170 | 59.952 | 95.492 | 17.096 | 1.00 | 83.86 | N |
| ATOM | 777 | NH2 | ARG | A | 170 | 61.986 | 96.061 | 16.134 | 1.00 | 97.00 | N |
| ATOM | 778 | N | ALA | A | 171 | 57.188 | 89.906 | 12.703 | 1.00 | 53.40 | N |
| ATOM | 779 | CA | ALA | A | 171 | 57.103 | 88.536 | 12.250 | 1.00 | 56.45 | C |
| ATOM | 780 | C | ALA | A | 171 | 58.292 | 88.197 | 11.393 | 1.00 | 53.29 | C |
| ATOM | 781 | O | ALA | A | 171 | 58.850 | 89.074 | 10.725 | 1.00 | 55.09 | O |
| ATOM | 782 | CB | ALA | A | 171 | 55.838 | 88.343 | 11.475 | 1.00 | 50.98 | C |
| ATOM | 783 | N | ARG | A | 172 | 58.683 | 86.929 | 11.399 | 1.00 | 52.91 | N |
| ATOM | 784 | CA | ARG | A | 172 | 59.627 | 86.446 | 10.408 | 1.00 | 53.07 | C |
| ATOM | 785 | C | ARG | A | 172 | 58.987 | 85.467 | 9.442 | 1.00 | 52.05 | C |
| ATOM | 786 | O | ARG | A | 172 | 58.435 | 84.442 | 9.837 | 1.00 | 51.89 | O |
| ATOM | 787 | CB | ARG | A | 172 | 60.866 | 85.802 | 11.020 | 1.00 | 55.78 | C |
| ATOM | 788 | CG | ARG | A | 172 | 61.827 | 85.295 | 9.919 | 1.00 | 54.68 | C |
| ATOM | 789 | CD | ARG | A | 172 | 63.124 | 84.628 | 10.463 | 1.00 | 56.18 | C |
| ATOM | 790 | NE | ARG | A | 172 | 63.997 | 85.925 | 11.232 | 1.00 | 76.11 | N |
| ATOM | 791 | CZ | ARG | A | 172 | 64.102 | 85.528 | 12.565 | 1.00 | 74.30 | C |
| ATOM | 792 | NH1 | ARG | A | 172 | 64.932 | 86.375 | 13.173 | 1.00 | 63.01 | N |
| ATOM | 793 | NH2 | ARG | A | 172 | 63.379 | 84.688 | 13.296 | 1.00 | 58.11 | N |
| ATOM | 794 | N | LEU | A | 173 | 59.095 | 85.787 | 8.165 | 1.00 | 51.50 | N |
| ATOM | 795 | CA | LEU | A | 173 | 58.726 | 84.851 | 7.130 | 1.00 | 50.82 | C |
| ATOM | 796 | C | LEU | A | 173 | 60.009 | 84.128 | 6.651 | 1.00 | 51.73 | C |
| ATOM | 797 | O | LEU | A | 173 | 60.970 | 84.746 | 6.206 | 1.00 | 52.26 | O |
| ATOM | 798 | CB | LEU | A | 173 | 58.022 | 85.591 | 5.972 | 1.00 | 49.76 | C |
| ATOM | 799 | CG | LEU | A | 173 | 56.771 | 86.448 | 6.237 | 1.00 | 53.06 | C |
| ATOM | 800 | CD1 | LEU | A | 173 | 56.970 | 87.491 | 7.317 | 1.00 | 49.85 | C |
| ATOM | 801 | CD2 | LEU | A | 173 | 56.366 | 87.154 | 4.961 | 1.00 | 56.04 | C |
| ATOM | 802 | N | THR | A | 174 | 60.003 | 82.813 | 6.744 | 1.00 | 51.98 | N |
| ATOM | 803 | CA | THR | A | 174 | 61.149 | 82.028 | 6.395 | 1.00 | 52.98 | C |
| ATOM | 804 | C | THR | A | 174 | 60.789 | 81.246 | 5.126 | 1.00 | 52.45 | C |
| ATOM | 805 | O | THR | A | 174 | 59.709 | 80.634 | 5.056 | 1.00 | 51.75 | O |
| ATOM | 806 | CB | THR | A | 174 | 61.548 | 81.050 | 7.446 | 1.00 | 53.95 | C |
| ATOM | 807 | OG1 | THR | A | 174 | 62.029 | 81.778 | 8.582 | 1.00 | 65.15 | O |
| ATOM | 808 | CG2 | THR | A | 174 | 62.598 | 80.099 | 6.958 | 1.00 | 57.95 | C |
| ATOM | 809 | N | PHE | A | 175 | 61.699 | 81.267 | 4.153 | 1.00 | 52.93 | N |
| ATOM | 810 | CA | PHE | A | 175 | 61.446 | 80.677 | 2.845 | 1.00 | 60.40 | C |
| ATOM | 811 | C | PHE | A | 175 | 62.265 | 79.426 | 2.581 | 1.00 | 69.17 | C |
| ATOM | 812 | O | PHE | A | 175 | 63.470 | 79.362 | 2.857 | 1.00 | 74.22 | O |
| ATOM | 813 | CB | PHE | A | 175 | 61.677 | 81.700 | 1.725 | 1.00 | 55.08 | C |
| ATOM | 814 | CG | PHE | A | 175 | 60.754 | 82.885 | 1.795 | 1.00 | 56.64 | C |
| ATOM | 815 | CD1 | PHE | A | 175 | 59.534 | 82.886 | 1.105 | 1.00 | 49.99 | C |
| ATOM | 816 | CD2 | PHE | A | 175 | 61.107 | 83.993 | 2.545 | 1.00 | 51.30 | C |
| ATOM | 817 | CE1 | PHE | A | 175 | 58.699 | 83.974 | 1.172 | 1.00 | 61.75 | C |
| ATOM | 818 | CE2 | PHE | A | 175 | 60.272 | 85.087 | 2.630 | 1.00 | 56.45 | C |
| ATOM | 819 | CZ | PHE | A | 175 | 59.059 | 85.083 | 1.946 | 1.00 | 60.28 | C |
| ATOM | 820 | N | ASP | A | 176 | 61.581 | 78.437 | 2.030 | 1.00 | 72.31 | N |
| ATOM | 821 | CA | ASP | A | 176 | 62.203 | 77.221 | 1.553 | 1.00 | 82.40 | C |
| ATOM | 822 | C | ASP | A | 176 | 62.306 | 77.244 | 0.019 | 1.00 | 90.73 | C |
| ATOM | 823 | O | ASP | A | 176 | 61.565 | 76.414 | -0.621 | 1.00 | 98.17 | O |
| ATOM | 824 | CB | ASP | A | 176 | 61.407 | 76.028 | 2.070 | 1.00 | 84.90 | C |
| ATOM | 825 | CG | ASP | A | 176 | 62.246 | 74.778 | 2.195 | 1.00 | 84.88 | C |
| ATOM | 826 | OD1 | ASP | A | 176 | 63.184 | 74.812 | 1.382 | 1.00 | 84.14 | O |
| ATOM | 827 | OD2 | ASP | A | 176 | 61.957 | 73.965 | 3.103 | 1.00 | 75.83 | O |
| ATOM | 828 | N | GLY | A | 177 | 62.914 | 78.216 | -0.558 | 1.00 | 92.82 | N |
| ATOM | 829 | CA | GLY | A | 177 | 63.034 | 78.357 | -2.000 | 1.00 | 86.15 | C |
| ATOM | 830 | C | GLY | A | 177 | 61.714 | 78.566 | -2.726 | 1.00 | 82.41 | C |
| ATOM | 831 | O | GLY | A | 177 | 61.301 | 79.696 | -3.002 | 1.00 | 79.61 | O |
| ATOM | 832 | N | ASP | A | 178 | 61.055 | 77.461 | -3.054 | 1.00 | 82.51 | N |
| ATOM | 833 | CA | ASP | A | 178 | 59.720 | 77.494 | -3.645 | 1.00 | 85.18 | C |
| ATOM | 834 | C | ASP | A | 178 | 58.683 | 78.242 | -2.790 | 1.00 | 74.73 | C |
| ATOM | 835 | O | ASP | A | 178 | 58.013 | 79.147 | -3.276 | 1.00 | 67.88 | O |
| ATOM | 836 | CB | ASP | A | 178 | 59.238 | 76.065 | -3.937 | 1.00 | 94.30 | C |
| ATOM | 837 | CG | ASP | A | 178 | 59.895 | 75.011 | -3.124 | 1.00 | 97.73 | C |
| ATOM | 838 | OD1 | ASP | A | 178 | 59.350 | 74.221 | -2.398 | 1.00 | 92.94 | O |
| ATOM | 839 | OD2 | ASP | A | 178 | 61.241 | 74.971 | -3.217 | 1.00101.04 | | O |
| ATOM | 840 | N | HIS | A | 179 | 58.562 | 77.885 | -1.512 | 1.00 | 70.49 | N |
| ATOM | 841 | CA | HIS | A | 179 | 57.458 | 78.410 | -0.715 | 1.00 | 63.15 | C |
| ATOM | 842 | C | HIS | A | 179 | 57.822 | 79.899 | 0.613 | 1.00 | 59.37 | C |

FIG. 8-21

| | | | | | | | | | | | |
|---|---|---|---|---|---|---|---|---|---|---|---|
| ATOM | 843 | O | HIS | A | 179 | 58.990 | 79.244 | 0.945 | 1.00 | 52.46 | O |
| ATOM | 844 | CB | HIS | A | 179 | 56.426 | 77.299 | -0.482 | 1.00 | 68.70 | C |
| ATOM | 845 | CG | HIS | A | 179 | 57.097 | 76.012 | 0.009 | 1.00 | 74.41 | C |
| ATOM | 846 | ND1 | HIS | A | 179 | 56.926 | 75.611 | 1.328 | 1.00 | 78.64 | N |
| ATOM | 847 | CD2 | HIS | A | 179 | 57.683 | 75.023 | -0.644 | 1.00 | 82.99 | C |
| ATOM | 848 | CE1 | HIS | A | 179 | 57.520 | 74.437 | 1.467 | 1.00 | 82.88 | C |
| ATOM | 849 | NE2 | HIS | A | 179 | 57.978 | 74.060 | 0.284 | 1.00 | 84.15 | N |
| ATOM | 850 | N | LEU | A | 180 | 56.795 | 79.554 | 1.335 | 1.00 | 54.41 | N |
| ATOM | 851 | CA | LEU | A | 180 | 56.918 | 79.981 | 2.732 | 1.00 | 57.23 | C |
| ATOM | 852 | C | LEU | A | 180 | 57.011 | 78.714 | 3.481 | 1.00 | 58.71 | C |
| ATOM | 853 | O | LEU | A | 180 | 56.163 | 77.844 | 3.339 | 1.00 | 62.06 | O |
| ATOM | 854 | CB | LEU | A | 180 | 55.554 | 80.695 | 3.194 | 1.00 | 63.18 | C |
| ATOM | 855 | CG | LEU | A | 180 | 55.691 | 82.209 | 3.371 | 1.00 | 62.59 | C |
| ATOM | 856 | CD1 | LEU | A | 180 | 54.333 | 82.716 | 3.780 | 1.00 | 62.45 | C |
| ATOM | 857 | CD2 | LEU | A | 180 | 56.711 | 82.578 | 4.394 | 1.00 | 57.40 | C |
| ATOM | 858 | N | ALA | A | 181 | 58.049 | 78.589 | 4.286 | 1.00 | 51.08 | N |
| ATOM | 859 | CA | ALA | A | 181 | 58.092 | 77.501 | 5.234 | 1.00 | 69.10 | C |
| ATOM | 860 | C | ALA | A | 181 | 57.253 | 77.855 | 6.502 | 1.00 | 61.24 | C |
| ATOM | 861 | O | ALA | A | 181 | 56.275 | 77.154 | 6.837 | 1.00 | 51.17 | O |
| ATOM | 862 | CB | ALA | A | 181 | 59.550 | 77.168 | 5.565 | 1.00 | 53.18 | C |
| ATOM | 863 | N | THR | A | 182 | 57.605 | 78.981 | 7.162 | 1.00 | 56.40 | N |
| ATOM | 864 | CA | THR | A | 182 | 57.005 | 79.335 | 8.453 | 1.00 | 57.13 | C |
| ATOM | 865 | C | THR | A | 182 | 56.800 | 80.837 | 8.514 | 1.00 | 53.51 | C |
| ATOM | 866 | O | THR | A | 182 | 57.512 | 81.592 | 7.830 | 1.00 | 50.77 | O |
| ATOM | 867 | CB | THR | A | 182 | 57.902 | 78.934 | 9.661 | 1.00 | 52.59 | C |
| ATOM | 868 | OG1 | THR | A | 182 | 59.274 | 79.249 | 9.366 | 1.00 | 53.41 | O |
| ATOM | 869 | CG2 | THR | A | 182 | 57.799 | 77.453 | 9.952 | 1.00 | 58.48 | C |
| ATOM | 870 | N | ILE | A | 183 | 55.796 | 81.254 | 9.285 | 1.00 | 50.26 | N |
| ATOM | 871 | CA | ILE | A | 183 | 55.712 | 82.624 | 9.746 | 1.00 | 52.34 | C |
| ATOM | 872 | C | ILE | A | 183 | 55.784 | 82.598 | 11.282 | 1.00 | 53.31 | C |
| ATOM | 873 | O | ILE | A | 183 | 54.979 | 81.932 | 11.919 | 1.00 | 55.00 | O |
| ATOM | 874 | CB | ILE | A | 183 | 54.404 | 83.293 | 9.367 | 1.00 | 52.52 | C |
| ATOM | 875 | CG1 | ILE | A | 183 | 53.900 | 82.829 | 7.984 | 1.00 | 56.98 | C |
| ATOM | 876 | CG2 | ILE | A | 183 | 54.552 | 84.814 | 9.480 | 1.00 | 53.97 | C |
| ATOM | 877 | CD1 | ILE | A | 183 | 54.252 | 83.759 | 6.861 | 1.00 | 60.14 | C |
| ATOM | 878 | N | VAL | A | 184 | 56.732 | 83.322 | 11.872 | 1.00 | 53.17 | N |
| ATOM | 879 | CA | VAL | A | 184 | 56.924 | 83.265 | 13.326 | 1.00 | 52.88 | C |
| ATOM | 880 | C | VAL | A | 184 | 56.790 | 84.610 | 14.009 | 1.00 | 55.41 | C |
| ATOM | 881 | O | VAL | A | 184 | 57.445 | 85.594 | 13.627 | 1.00 | 54.91 | O |
| ATOM | 882 | CB | VAL | A | 184 | 58.278 | 82.696 | 13.734 | 1.00 | 54.12 | C |
| ATOM | 883 | CG1 | VAL | A | 184 | 58.378 | 82.630 | 15.304 | 1.00 | 55.21 | C |
| ATOM | 884 | CG2 | VAL | A | 184 | 58.444 | 81.313 | 13.155 | 1.00 | 54.11 | C |
| ATOM | 885 | N | ASN | A | 185 | 55.935 | 84.627 | 15.029 | 1.00 | 55.21 | N |
| ATOM | 886 | CA | ASN | A | 185 | 55.758 | 85.785 | 15.867 | 1.00 | 54.37 | C |
| ATOM | 887 | C | ASN | A | 185 | 57.021 | 86.027 | 16.660 | 1.00 | 58.91 | C |
| ATOM | 888 | O | ASN | A | 185 | 57.314 | 85.302 | 17.629 | 1.00 | 57.53 | O |
| ATOM | 889 | CB | ASN | A | 185 | 54.571 | 85.586 | 16.806 | 1.00 | 56.98 | C |
| ATOM | 890 | CG | ASN | A | 185 | 54.117 | 86.870 | 17.446 | 1.00 | 59.09 | C |
| ATOM | 891 | OD1 | ASN | A | 185 | 54.889 | 87.818 | 17.578 | 1.00 | 61.35 | O |
| ATOM | 892 | ND2 | ASN | A | 185 | 52.893 | 86.912 | 17.851 | 1.00 | 62.43 | N |
| ATOM | 893 | N | MET | A | 186 | 57.764 | 87.050 | 16.245 | 1.00 | 57.09 | N |
| ATOM | 894 | CA | MET | A | 186 | 58.998 | 87.449 | 16.919 | 1.00 | 59.49 | C |
| ATOM | 895 | C | MET | A | 186 | 58.802 | 87.677 | 18.409 | 1.00 | 70.20 | C |
| ATOM | 896 | O | MET | A | 186 | 59.762 | 87.621 | 19.160 | 1.00 | 65.08 | O |
| ATOM | 897 | CB | MET | A | 186 | 59.559 | 88.729 | 16.302 | 1.00 | 59.53 | C |
| ATOM | 898 | CG | MET | A | 186 | 60.024 | 88.604 | 14.857 | 1.00 | 66.56 | C |
| ATOM | 899 | SD | MET | A | 186 | 61.345 | 87.420 | 14.630 | 1.00112.98 | | S |
| ATOM | 900 | CE | MET | A | 186 | 60.374 | 85.914 | 14.571 | 1.00 | 58.28 | C |
| ATOM | 901 | N | GLU | A | 187 | 57.988 | 87.947 | 18.836 | 1.00 | 74.43 | N |
| ATOM | 902 | CA | GLU | A | 187 | 57.304 | 88.256 | 20.247 | 1.00 | 75.07 | C |
| ATOM | 903 | C | GLU | A | 187 | 57.423 | 87.040 | 21.156 | 1.00 | 68.87 | C |
| ATOM | 904 | O | GLU | A | 187 | 58.128 | 87.078 | 22.167 | 1.00 | 65.25 | O |
| ATOM | 905 | CB | GLU | A | 187 | 55.820 | 88.887 | 20.433 | 1.00 | 81.52 | C |
| ATOM | 906 | CG | GLU | A | 187 | 55.441 | 88.914 | 21.895 | 1.00 | 90.00 | C |
| ATOM | 907 | CD | GLU | A | 187 | 53.923 | 88.773 | 22.023 | 1.00 | 95.41 | C |
| ATOM | 908 | OE1 | GLU | A | 187 | 53.204 | 88.208 | 21.090 | 1.00 | 95.02 | O |
| ATOM | 909 | OE2 | GLU | A | 187 | 53.451 | 88.216 | 23.051 | 1.00 | 92.04 | O |
| ATOM | 910 | N | ASN | A | 188 | 56.706 | 85.975 | 20.810 | 1.00 | 62.54 | N |
| ATOM | 911 | CA | ASN | A | 188 | 56.709 | 84.754 | 21.611 | 1.00 | 66.20 | C |
| ATOM | 912 | C | ASN | A | 188 | 57.803 | 83.599 | 20.887 | 1.00 | 65.20 | C |
| ATOM | 913 | O | ASN | A | 188 | 57.302 | 82.456 | 21.314 | 1.00 | 59.49 | O |
| ATOM | 914 | CB | ASN | A | 188 | 55.278 | 84.358 | 21.971 | 1.00 | 58.15 | C |
| ATOM | 915 | CG | ASN | A | 188 | 54.398 | 84.138 | 20.733 | 1.00 | 60.85 | C |
| ATOM | 916 | OD1 | ASN | A | 188 | 54.902 | 83.905 | 19.620 | 1.00 | 55.63 | O |
| ATOM | 917 | ND2 | ASN | A | 188 | 53.076 | 84.239 | 20.918 | 1.00 | 55.75 | N |
| ATOM | 918 | N | ASN | A | 189 | 58.046 | 83.900 | 19.765 | 1.00 | 75.71 | N |
| ATOM | 919 | CA | ASN | A | 189 | 58.750 | 82.890 | 18.974 | 1.00 | 74.78 | C |

FIG. 8-22

| | | | | | | | | | | | |
|---|---|---|---|---|---|---|---|---|---|---|---|
| ATOM | 920 | C | ASN | A | 189 | 57.902 | 81.714 | 18.500 | 1.00 | 84.66 | C |
| ATOM | 921 | O | ASN | A | 189 | 58.448 | 80.665 | 18.162 | 1.00 | 83.59 | O |
| ATOM | 922 | CB | ASN | A | 189 | 59.961 | 82.356 | 19.750 | 1.00 | 80.97 | C |
| ATOM | 923 | CG | ASN | A | 189 | 60.982 | 83.439 | 20.052 | 1.00 | 82.12 | C |
| ATOM | 924 | OD1 | ASN | A | 189 | 61.458 | 84.135 | 19.146 | 1.00 | 79.48 | O |
| ATOM | 925 | ND2 | ASN | A | 189 | 61.330 | 83.578 | 21.332 | 1.00 | 84.05 | N |
| ATOM | 926 | N | ARG | A | 190 | 56.581 | 81.879 | 18.477 | 1.00 | 60.14 | N |
| ATOM | 927 | CA | ARG | A | 190 | 55.688 | 80.844 | 17.951 | 1.00 | 67.12 | C |
| ATOM | 928 | C | ARG | A | 190 | 55.318 | 81.088 | 16.503 | 1.00 | 61.37 | C |
| ATOM | 929 | O | ARG | A | 190 | 55.242 | 82.199 | 15.997 | 1.00 | 55.78 | O |
| ATOM | 930 | CB | ARG | A | 190 | 54.459 | 80.704 | 18.834 | 1.00 | 72.10 | C |
| ATOM | 931 | CG | ARG | A | 190 | 54.721 | 79.991 | 20.153 | 1.00 | 85.10 | C |
| ATOM | 932 | CD | ARG | A | 190 | 53.535 | 80.131 | 21.094 | 1.00 | 78.81 | C |
| ATOM | 933 | NE | ARG | A | 190 | 52.270 | 79.730 | 20.477 | 1.00 | 76.88 | N |
| ATOM | 934 | CZ | ARG | A | 190 | 51.082 | 79.845 | 21.078 | 1.00 | 82.89 | C |
| ATOM | 935 | NH1 | ARG | A | 190 | 50.998 | 80.356 | 22.306 | 1.00 | 79.29 | N |
| ATOM | 936 | NH2 | ARG | A | 190 | 49.978 | 79.449 | 20.456 | 1.00 | 81.98 | N |
| ATOM | 937 | N | GLN | A | 191 | 54.736 | 79.987 | 15.878 | 1.00 | 53.82 | N |
| ATOM | 938 | CA | GLN | A | 191 | 54.194 | 80.038 | 14.506 | 1.00 | 56.21 | C |
| ATOM | 939 | C | GLN | A | 191 | 52.784 | 80.585 | 14.367 | 1.00 | 56.93 | C |
| ATOM | 940 | O | GLN | A | 191 | 51.915 | 80.314 | 15.204 | 1.00 | 58.69 | O |
| ATOM | 941 | CB | GLN | A | 191 | 54.260 | 78.655 | 13.823 | 1.00 | 53.38 | C |
| ATOM | 942 | CG | GLN | A | 191 | 55.674 | 78.169 | 13.532 | 1.00 | 61.94 | C |
| ATOM | 943 | CD | GLN | A | 191 | 55.666 | 76.826 | 12.817 | 1.00 | 77.96 | C |
| ATOM | 944 | OE1 | GLN | A | 191 | 56.458 | 75.823 | 13.166 | 1.00 | 79.26 | O |
| ATOM | 945 | NE2 | GLN | A | 191 | 54.818 | 76.683 | 11.814 | 1.00 | 81.99 | N |
| ATOM | 946 | N | PHE | A | 192 | 52.570 | 81.343 | 13.288 | 1.00 | 57.23 | N |
| ATOM | 947 | CA | PHE | A | 192 | 51.232 | 81.735 | 12.832 | 1.00 | 59.83 | C |
| ATOM | 948 | C | PHE | A | 192 | 50.653 | 80.690 | 11.886 | 1.00 | 60.57 | C |
| ATOM | 949 | O | PHE | A | 192 | 51.381 | 80.161 | 11.103 | 1.00 | 53.76 | O |
| ATOM | 950 | CB | PHE | A | 192 | 51.264 | 83.087 | 12.103 | 1.00 | 54.87 | C |
| ATOM | 951 | CG | PHE | A | 192 | 51.465 | 84.262 | 13.011 | 1.00 | 59.80 | C |
| ATOM | 952 | CD1 | PHE | A | 192 | 52.650 | 84.879 | 12.984 | 1.00 | 52.63 | C |
| ATOM | 953 | CD2 | PHE | A | 192 | 50.464 | 84.647 | 13.903 | 1.00 | 64.55 | C |
| ATOM | 954 | CE1 | PHE | A | 192 | 52.847 | 86.058 | 13.834 | 1.00 | 61.27 | C |
| ATOM | 955 | CE2 | PHE | A | 192 | 50.654 | 85.729 | 14.763 | 1.00 | 69.31 | C |
| ATOM | 956 | CZ | PHE | A | 192 | 51.850 | 86.436 | 14.726 | 1.00 | 70.96 | C |
| ATOM | 957 | N | GLY | A | 193 | 49.339 | 80.474 | 11.941 | 1.00 | 64.94 | N |
| ATOM | 958 | CA | GLY | A | 193 | 48.689 | 79.545 | 11.027 | 1.00 | 56.14 | C |
| ATOM | 959 | C | GLY | A | 193 | 48.403 | 80.188 | 9.665 | 1.00 | 53.69 | C |
| ATOM | 960 | O | GLY | A | 193 | 48.423 | 79.531 | 8.657 | 1.00 | 58.08 | O |
| ATOM | 961 | N | PHE | A | 194 | 48.099 | 81.478 | 9.736 | 1.00 | 46.26 | N |
| ATOM | 962 | CA | PHE | A | 194 | 48.000 | 82.356 | 8.578 | 1.00 | 49.05 | C |
| ATOM | 963 | C | PHE | A | 194 | 48.284 | 83.745 | 9.113 | 1.00 | 52.05 | C |
| ATOM | 964 | O | PHE | A | 194 | 48.104 | 84.019 | 10.312 | 1.00 | 47.40 | O |
| ATOM | 965 | CB | PHE | A | 194 | 46.603 | 82.337 | 7.945 | 1.00 | 54.88 | C |
| ATOM | 966 | CG | PHE | A | 194 | 45.575 | 83.057 | 8.745 | 1.00 | 51.87 | C |
| ATOM | 967 | CD1 | PHE | A | 194 | 45.476 | 84.446 | 8.693 | 1.00 | 57.05 | C |
| ATOM | 968 | CD2 | PHE | A | 194 | 44.705 | 82.353 | 9.572 | 1.00 | 57.83 | C |
| ATOM | 969 | CE1 | PHE | A | 194 | 44.529 | 85.127 | 9.472 | 1.00 | 60.62 | C |
| ATOM | 970 | CE2 | PHE | A | 194 | 43.748 | 83.027 | 10.352 | 1.00 | 59.80 | C |
| ATOM | 971 | CZ | PHE | A | 194 | 43.659 | 84.413 | 10.302 | 1.00 | 59.51 | C |
| ATOM | 972 | N | PHE | A | 195 | 48.691 | 84.645 | 8.245 | 1.00 | 47.37 | N |
| ATOM | 973 | CA | PHE | A | 195 | 49.139 | 85.940 | 8.706 | 1.00 | 50.77 | C |
| ATOM | 974 | C | PHE | A | 195 | 48.619 | 86.998 | 7.744 | 1.00 | 44.95 | C |
| ATOM | 975 | O | PHE | A | 195 | 48.722 | 86.848 | 6.560 | 1.00 | 44.51 | O |
| ATOM | 976 | CB | PHE | A | 195 | 50.648 | 85.916 | 8.760 | 1.00 | 48.01 | C |
| ATOM | 977 | CG | PHE | A | 195 | 51.279 | 87.232 | 9.046 | 1.00 | 48.75 | C |
| ATOM | 978 | CD1 | PHE | A | 195 | 52.007 | 87.882 | 9.062 | 1.00 | 55.73 | C |
| ATOM | 979 | CD2 | PHE | A | 195 | 51.200 | 87.799 | 10.297 | 1.00 | 49.41 | C |
| ATOM | 980 | CE1 | PHE | A | 195 | 52.648 | 89.088 | 8.328 | 1.00 | 63.18 | C |
| ATOM | 981 | CE2 | PHE | A | 195 | 51.832 | 89.003 | 10.574 | 1.00 | 57.32 | C |
| ATOM | 982 | CZ | PHE | A | 195 | 52.568 | 89.647 | 9.585 | 1.00 | 61.81 | C |
| ATOM | 983 | N | ARG | A | 196 | 48.043 | 88.099 | 8.279 | 1.00 | 54.03 | N |
| ATOM | 984 | CA | ARG | A | 196 | 47.373 | 89.029 | 7.452 | 1.00 | 54.33 | C |
| ATOM | 985 | C | ARG | A | 196 | 48.325 | 90.194 | 7.129 | 1.00 | 50.83 | C |
| ATOM | 986 | O | ARG | A | 196 | 49.005 | 90.670 | 8.005 | 1.00 | 57.51 | O |
| ATOM | 987 | CB | ARG | A | 196 | 46.151 | 89.599 | 8.175 | 1.00 | 57.45 | C |
| ATOM | 988 | CG | ARG | A | 196 | 45.368 | 88.592 | 9.012 | 1.00 | 55.78 | C |
| ATOM | 989 | CD | ARG | A | 196 | 43.909 | 88.988 | 9.096 | 1.00 | 54.17 | C |
| ATOM | 990 | NE | ARG | A | 196 | 43.394 | 89.222 | 7.753 | 1.00 | 68.93 | N |
| ATOM | 991 | CZ | ARG | A | 196 | 42.345 | 89.815 | 7.473 | 1.00 | 71.11 | C |
| ATOM | 992 | NH1 | ARG | A | 196 | 41.458 | 90.248 | 8.454 | 1.00 | 71.61 | N |
| ATOM | 993 | NH2 | ARG | A | 196 | 41.896 | 89.980 | 6.201 | 1.00 | 67.47 | N |
| ATOM | 994 | N | LEU | A | 197 | 48.373 | 90.524 | 5.859 | 1.00 | 51.14 | N |
| ATOM | 995 | CA | LEU | A | 197 | 49.049 | 91.732 | 5.431 | 1.00 | 56.67 | C |
| ATOM | 996 | C | LEU | A | 197 | 47.942 | 92.785 | 5.300 | 1.00 | 55.48 | C |

FIG.8-23

| | | | | | | | | | | | |
|---|---|---|---|---|---|---|---|---|---|---|---|
| ATOM | 997 | O | LEU | A | 197 | 46.887 | 92.477 | 4.739 | 1.00 | 49.04 | O |
| ATOM | 998 | CB | LEU | A | 197 | 49.643 | 91.467 | 4.055 | 1.00 | 60.42 | C |
| ATOM | 999 | CG | LEU | A | 197 | 50.994 | 92.046 | 3.671 | 1.00 | 69.24 | C |
| ATOM | 1000 | CD1 | LEU | A | 197 | 50.968 | 92.334 | 2.175 | 1.00 | 70.50 | C |
| ATOM | 1001 | CD2 | LEU | A | 197 | 51.321 | 93.296 | 4.471 | 1.00 | 71.61 | C |
| ATOM | 1002 | N | ASP | A | 198 | 48.147 | 93.998 | 5.819 | 1.00 | 41.67 | N |
| ATOM | 1003 | CA | ASP | A | 198 | 47.171 | 95.099 | 5.682 | 1.00 | 37.07 | C |
| ATOM | 1004 | C | ASP | A | 198 | 47.038 | 95.496 | 4.175 | 1.00 | 46.90 | C |
| ATOM | 1005 | O | ASP | A | 198 | 47.973 | 95.287 | 3.381 | 1.00 | 46.14 | O |
| ATOM | 1006 | CB | ASP | A | 198 | 47.652 | 96.329 | 6.314 | 1.00 | 38.65 | C |
| ATOM | 1007 | CG | ASP | A | 198 | 49.074 | 96.709 | 6.027 | 1.00 | 49.13 | C |
| ATOM | 1008 | OD1 | ASP | A | 198 | 49.334 | 97.875 | 5.654 | 1.00 | 53.64 | O |
| ATOM | 1009 | OD2 | ASP | A | 198 | 49.925 | 95.803 | 6.094 | 1.00 | 49.12 | O |
| ATOM | 1010 | N | PRO | A | 199 | 45.897 | 96.184 | 3.768 | 1.00 | 51.14 | N |
| ATOM | 1011 | CA | PRO | A | 199 | 45.671 | 96.586 | 2.387 | 1.00 | 45.59 | C |
| ATOM | 1012 | C | PRO | A | 199 | 46.188 | 98.091 | 2.135 | 1.00 | 49.32 | C |
| ATOM | 1013 | O | PRO | A | 199 | 46.118 | 98.847 | 3.342 | 1.00 | 48.62 | O |
| ATOM | 1014 | CB | PRO | A | 199 | 44.139 | 96.588 | 2.248 | 1.00 | 46.87 | C |
| ATOM | 1015 | CG | PRO | A | 199 | 43.580 | 96.348 | 3.610 | 1.00 | 55.41 | C |
| ATOM | 1016 | CD | PRO | A | 199 | 44.714 | 96.317 | 4.612 | 1.00 | 55.67 | C |
| ATOM | 1017 | N | ARG | A | 200 | 46.652 | 98.292 | 0.920 | 1.00 | 44.01 | N |
| ATOM | 1018 | CA | ARG | A | 200 | 47.120 | 99.641 | 0.663 | 1.00 | 50.20 | C |
| ATOM | 1019 | C | ARG | A | 200 | 45.930 | 100.554 | 0.301 | 1.00 | 56.36 | C |
| ATOM | 1020 | O | ARG | A | 200 | 44.928 | 100.124 | -0.173 | 1.00 | 50.84 | O |
| ATOM | 1021 | CB | ARG | A | 200 | 48.099 | 99.674 | -0.913 | 1.00 | 60.88 | C |
| ATOM | 1022 | CG | ARG | A | 200 | 48.597 | 101.064 | -0.821 | 1.00 | 65.25 | C |
| ATOM | 1023 | CD | ARG | A | 200 | 49.670 | 101.065 | -1.889 | 1.00 | 70.15 | C |
| ATOM | 1024 | NE | ARG | A | 200 | 49.182 | 100.694 | -3.205 | 1.00 | 68.62 | N |
| ATOM | 1025 | CZ | ARG | A | 200 | 48.597 | 101.552 | -4.052 | 1.00 | 71.63 | C |
| ATOM | 1026 | NH1 | ARG | A | 200 | 48.457 | 102.828 | -3.712 | 1.00 | 69.07 | N |
| ATOM | 1027 | NH2 | ARG | A | 200 | 48.178 | 101.136 | -5.239 | 1.00 | 78.24 | N |
| ATOM | 1028 | N | LEU | A | 201 | 46.041 | 101.810 | 0.783 | 1.00 | 53.72 | N |
| ATOM | 1029 | CA | LEU | A | 201 | 45.038 | 102.782 | 0.457 | 1.00 | 51.80 | C |
| ATOM | 1030 | C | LEU | A | 201 | 45.245 | 103.242 | -0.982 | 1.00 | 69.71 | C |
| ATOM | 1031 | O | LEU | A | 201 | 46.294 | 103.785 | -1.337 | 1.00 | 67.22 | O |
| ATOM | 1032 | CB | LEU | A | 201 | 45.137 | 104.083 | 1.384 | 1.00 | 52.69 | C |
| ATOM | 1033 | CG | LEU | A | 201 | 44.080 | 105.085 | 1.093 | 1.00 | 60.56 | C |
| ATOM | 1034 | CD1 | LEU | A | 201 | 42.673 | 104.557 | 1.353 | 1.00 | 58.03 | C |
| ATOM | 1035 | CD2 | LEU | A | 201 | 44.342 | 106.337 | 1.905 | 1.00 | 64.40 | C |
| ATOM | 1036 | N | ILE | A | 202 | 44.228 | 103.033 | -1.811 | 1.00 | 60.84 | N |
| ATOM | 1037 | CA | ILE | A | 202 | 44.362 | 103.319 | -3.214 | 1.00 | 43.41 | C |
| ATOM | 1038 | C | ILE | A | 202 | 43.381 | 104.749 | -3.477 | 1.00 | 53.39 | C |
| ATOM | 1039 | O | ILE | A | 202 | 44.673 | 105.475 | -4.198 | 1.00 | 62.04 | O |
| ATOM | 1040 | CB | ILE | A | 202 | 43.449 | 102.423 | -4.035 | 1.00 | 51.90 | C |
| ATOM | 1041 | CG1 | ILE | A | 202 | 43.787 | 100.967 | -3.791 | 1.00 | 52.70 | C |
| ATOM | 1042 | CG2 | ILE | A | 202 | 43.576 | 102.755 | -5.542 | 1.00 | 60.00 | C |
| ATOM | 1043 | CD1 | ILE | A | 202 | 43.100 | 100.064 | -4.776 | 1.00 | 57.50 | C |
| ATOM | 1044 | N | THR | A | 203 | 42.864 | 105.154 | -2.891 | 1.00 | 54.67 | N |
| ATOM | 1045 | CA | THR | A | 203 | 42.363 | 106.431 | -3.119 | 1.00 | 54.31 | C |
| ATOM | 1046 | C | THR | A | 203 | 41.164 | 106.759 | -2.222 | 1.00 | 54.83 | C |
| ATOM | 1047 | O | THR | A | 203 | 40.715 | 105.879 | -1.503 | 1.00 | 56.37 | O |
| ATOM | 1048 | CB | THR | A | 203 | 41.988 | 106.638 | -4.533 | 1.00 | 62.51 | C |
| ATOM | 1049 | OG1 | THR | A | 203 | 41.609 | 108.079 | -4.820 | 1.00 | 69.49 | O |
| ATOM | 1050 | CG2 | THR | A | 203 | 40.668 | 105.852 | -4.911 | 1.00 | 60.40 | C |
| ATOM | 1051 | N | MET | A | 204 | 40.717 | 107.997 | -2.277 | 1.00 | 57.64 | N |
| ATOM | 1052 | CA | MET | A | 204 | 39.510 | 108.405 | -1.607 | 1.00 | 61.79 | C |
| ATOM | 1053 | C | MET | A | 204 | 38.460 | 108.575 | -2.694 | 1.00 | 73.13 | C |
| ATOM | 1054 | O | MET | A | 204 | 38.797 | 108.695 | -3.874 | 1.00 | 80.69 | O |
| ATOM | 1055 | CB | MET | A | 204 | 39.737 | 109.734 | -0.887 | 1.00 | 58.46 | C |
| ATOM | 1056 | CG | MET | A | 204 | 40.919 | 109.736 | 0.088 | 1.00 | 64.56 | C |
| ATOM | 1057 | SD | MET | A | 204 | 40.323 | 108.490 | 1.399 | 1.00 | 78.74 | S |
| ATOM | 1058 | CE | MET | A | 204 | 39.634 | 109.273 | 2.488 | 1.00 | 86.90 | C |
| ATOM | 1059 | N | ILE | A | 205 | 37.199 | 108.575 | -2.304 | 1.00 | 72.88 | N |
| ATOM | 1060 | CA | ILE | A | 205 | 36.122 | 108.900 | -3.222 | 1.00 | 66.39 | C |
| ATOM | 1061 | C | ILE | A | 205 | 35.840 | 110.299 | -2.889 | 1.00 | 79.82 | C |
| ATOM | 1062 | O | ILE | A | 205 | 35.013 | 110.598 | -1.853 | 1.00 | 80.36 | O |
| ATOM | 1063 | CB | ILE | A | 205 | 34.965 | 107.928 | -3.963 | 1.00 | 62.76 | C |
| ATOM | 1064 | CG1 | ILE | A | 205 | 35.385 | 106.546 | -3.549 | 1.00 | 63.56 | C |
| ATOM | 1065 | CG2 | ILE | A | 205 | 33.728 | 108.443 | -3.808 | 1.00 | 70.62 | C |
| ATOM | 1066 | CD1 | ILE | A | 205 | 34.274 | 105.539 | -3.600 | 1.00 | 67.67 | C |
| ATOM | 1067 | N | SER | A | 206 | 35.987 | 111.251 | -3.761 | 1.00 | 90.06 | N |
| ATOM | 1068 | CA | SER | A | 206 | 35.610 | 112.664 | -3.567 | 1.00 | 103.95 | C |
| ATOM | 1069 | C | SER | A | 206 | 34.346 | 112.902 | -2.729 | 1.00 | 109.11 | C |
| ATOM | 1070 | O | SER | A | 206 | 33.289 | 112.331 | -3.001 | 1.00 | 104.78 | O |
| ATOM | 1071 | CB | SER | A | 206 | 35.460 | 113.365 | -4.925 | 1.00 | 111.70 | C |
| ATOM | 1072 | OG | SER | A | 206 | 36.452 | 112.925 | -5.843 | 1.00 | 115.71 | O |
| ATOM | 1073 | N | SER | A | 207 | 34.463 | 113.746 | -1.709 | 1.00 | 107.24 | N |

FIG. 8-24

| | | | | | | | | | | |
|---|---|---|---|---|---|---|---|---|---|---|
| ATOM | 1074 | CA | SER | A | 207 | 33.297 | 114.192 | -0.931 | 1.00110.18 | C |
| ATOM | 1075 | C | SER | A | 207 | 32.809 | 115.917 | -1.415 | 1.00110.69 | C |
| ATOM | 1076 | O | SER | A | 207 | 33.606 | 116.393 | -1.844 | 1.00106.83 | O |
| ATOM | 1077 | CB | SER | A | 207 | 33.610 | 114.187 | 0.573 | 1.00110.13 | C |
| ATOM | 1078 | OG | SER | A | 207 | 34.001 | 115.481 | 0.999 | 1.00109.98 | O |
| ATOM | 1079 | N | PRO | A | 208 | 31.490 | 115.741 | -1.350 | 1.00115.20 | N |
| ATOM | 1080 | CA | PRO | A | 208 | 30.831 | 116.969 | -1.819 | 1.00120.80 | C |
| ATOM | 1081 | C | PRO | A | 208 | 31.589 | 118.247 | -1.449 | 1.00122.30 | C |
| ATOM | 1082 | O | PRO | A | 208 | 31.693 | 119.150 | -2.279 | 1.00123.06 | O |
| ATOM | 1083 | CB | PRO | A | 208 | 29.486 | 116.930 | -1.094 | 1.00123.97 | C |
| ATOM | 1084 | CG | PRO | A | 208 | 29.285 | 115.465 | -0.926 | 1.00121.48 | C |
| ATOM | 1085 | CD | PRO | A | 208 | 30.537 | 114.787 | -0.754 | 1.00115.62 | C |
| ATOM | 1086 | N | ASN | A | 209 | 32.095 | 118.311 | -0.219 | 1.00122.33 | N |
| ATOM | 1087 | CA | ASN | A | 209 | 32.854 | 119.460 | 0.283 | 1.00120.94 | C |
| ATOM | 1088 | C | ASN | A | 209 | 33.909 | 120.035 | -0.668 | 1.00116.82 | C |
| ATOM | 1089 | O | ASN | A | 209 | 34.081 | 121.241 | -0.765 | 1.00118.08 | O |
| ATOM | 1090 | CB | ASN | A | 209 | 33.557 | 119.087 | 1.594 | 1.00121.46 | C |
| ATOM | 1091 | CG | ASN | A | 209 | 32.889 | 119.689 | 2.812 | 1.00124.14 | C |
| ATOM | 1092 | OD1 | ASN | A | 209 | 31.870 | 120.375 | 2.702 | 1.00125.35 | O |
| ATOM | 1093 | ND2 | ASN | A | 209 | 33.457 | 119.442 | 3.988 | 1.00123.30 | N |
| ATOM | 1094 | N | GLY | A | 210 | 34.612 | 119.136 | -1.354 | 1.00110.84 | N |
| ATOM | 1095 | CA | GLY | A | 210 | 35.845 | 119.593 | -2.019 | 1.00106.37 | C |
| ATOM | 1096 | C | GLY | A | 210 | 36.973 | 119.387 | -1.006 | 1.00103.04 | C |
| ATOM | 1097 | O | GLY | A | 210 | 38.150 | 119.513 | -1.350 | 1.00100.86 | O |
| ATOM | 1098 | N | GLU | A | 211 | 36.602 | 119.146 | 0.253 | 1.00112.29 | N |
| ATOM | 1099 | CA | GLU | A | 211 | 37.567 | 118.974 | 1.342 | 1.00107.02 | C |
| ATOM | 1100 | C | GLU | A | 211 | 37.725 | 117.497 | 1.694 | 1.00 98.74 | C |
| ATOM | 1101 | O | GLU | A | 211 | 36.763 | 116.838 | 2.083 | 1.00 93.87 | O |
| ATOM | 1102 | CB | GLU | A | 211 | 37.140 | 119.772 | 2.579 | 1.00110.24 | C |
| ATOM | 1103 | CG | GLU | A | 211 | 37.096 | 121.282 | 2.362 | 1.00115.04 | C |
| ATOM | 1104 | CD | GLU | A | 211 | 37.040 | 122.064 | 3.664 | 1.00116.39 | C |
| ATOM | 1105 | OE1 | GLU | A | 211 | 36.533 | 121.520 | 4.667 | 1.00116.12 | O |
| ATOM | 1106 | OE2 | GLU | A | 211 | 37.583 | 123.225 | 3.682 | 1.00117.15 | O |
| ATOM | 1107 | N | GLN | A | 212 | 38.945 | 116.985 | 1.563 | 1.00 93.47 | N |
| ATOM | 1108 | CA | GLN | A | 212 | 39.192 | 115.549 | 1.681 | 1.00 94.15 | C |
| ATOM | 1109 | C | GLN | A | 212 | 40.022 | 115.280 | 2.916 | 1.00 92.95 | C |
| ATOM | 1110 | O | GLN | A | 212 | 41.108 | 115.751 | 3.120 | 1.00 93.44 | O |
| ATOM | 1111 | CB | GLN | A | 212 | 39.903 | 115.043 | 0.424 | 1.00 97.37 | C |
| ATOM | 1112 | CG | GLN | A | 212 | 39.361 | 113.733 | -0.117 | 1.00 99.66 | C |
| ATOM | 1113 | CD | GLN | A | 212 | 38.042 | 113.902 | -0.855 | 1.00 97.43 | C |
| ATOM | 1114 | OE1 | GLN | A | 212 | 37.512 | 115.010 | -0.976 | 1.00 94.31 | O |
| ATOM | 1115 | NE2 | GLN | A | 212 | 37.504 | 112.796 | -1.349 | 1.00 98.44 | N |
| ATOM | 1116 | N | ARG | A | 213 | 39.518 | 114.276 | 3.732 | 1.00 87.61 | N |
| ATOM | 1117 | CA | ARG | A | 213 | 40.194 | 113.897 | 4.970 | 1.00 78.54 | C |
| ATOM | 1118 | C | ARG | A | 213 | 40.281 | 112.392 | 5.170 | 1.00 73.27 | C |
| ATOM | 1119 | O | ARG | A | 213 | 39.461 | 111.635 | 4.628 | 1.00 67.89 | O |
| ATOM | 1120 | CB | ARG | A | 213 | 39.505 | 114.525 | 6.187 | 1.00 78.88 | C |
| ATOM | 1121 | CG | ARG | A | 213 | 39.635 | 116.029 | 6.278 | 1.00 78.17 | C |
| ATOM | 1122 | CD | ARG | A | 213 | 38.818 | 116.574 | 7.433 | 1.00 79.87 | C |
| ATOM | 1123 | NE | ARG | A | 213 | 38.641 | 118.021 | 7.343 | 1.00 82.24 | N |
| ATOM | 1124 | CZ | ARG | A | 213 | 37.772 | 118.634 | 6.532 | 1.00 85.80 | C |
| ATOM | 1125 | NH1 | ARG | A | 213 | 37.679 | 119.950 | 6.527 | 1.00 86.21 | N |
| ATOM | 1126 | NH2 | ARG | A | 213 | 36.998 | 117.908 | 5.722 | 1.00 83.87 | N |
| ATOM | 1127 | N | LEU | A | 214 | 41.234 | 111.971 | 5.965 | 1.00 71.12 | N |
| ATOM | 1128 | CA | LEU | A | 214 | 41.325 | 110.592 | 6.411 | 1.00 70.82 | C |
| ATOM | 1129 | C | LEU | A | 214 | 41.402 | 110.645 | 7.921 | 1.00 73.85 | C |
| ATOM | 1130 | O | LEU | A | 214 | 42.438 | 111.003 | 8.474 | 1.00 76.12 | O |
| ATOM | 1131 | CB | LEU | A | 214 | 42.585 | 109.939 | 5.856 | 1.00 67.37 | C |
| ATOM | 1132 | CG | LEU | A | 214 | 42.843 | 108.473 | 6.184 | 1.00 67.84 | C |
| ATOM | 1133 | CD1 | LEU | A | 214 | 41.735 | 107.547 | 5.627 | 1.00 67.01 | C |
| ATOM | 1134 | CD2 | LEU | A | 214 | 44.209 | 108.087 | 5.638 | 1.00 69.34 | C |
| ATOM | 1135 | N | PHE | A | 215 | 40.309 | 110.311 | 8.597 | 1.00 74.79 | N |
| ATOM | 1136 | CA | PHE | A | 215 | 40.300 | 110.815 | 10.050 | 1.00 77.08 | C |
| ATOM | 1137 | C | PHE | A | 215 | 41.211 | 109.807 | 10.741 | 1.00 74.81 | C |
| ATOM | 1138 | O | PHE | A | 215 | 41.077 | 108.201 | 10.550 | 1.00 72.81 | O |
| ATOM | 1139 | CB | PHE | A | 215 | 38.890 | 110.318 | 10.635 | 1.00 80.39 | C |
| ATOM | 1140 | CG | PHE | A | 215 | 38.854 | 110.928 | 12.129 | 1.00 88.61 | C |
| ATOM | 1141 | CD1 | PHE | A | 215 | 39.253 | 111.743 | 12.678 | 1.00 91.76 | C |
| ATOM | 1142 | CD2 | PHE | A | 215 | 38.453 | 109.511 | 12.964 | 1.00 86.83 | C |
| ATOM | 1143 | CE1 | PHE | A | 215 | 39.344 | 111.943 | 14.046 | 1.00 90.22 | C |
| ATOM | 1144 | CE2 | PHE | A | 215 | 38.432 | 109.711 | 14.359 | 1.00 86.47 | C |
| ATOM | 1145 | CZ | PHE | A | 215 | 38.833 | 110.828 | 14.885 | 1.00 88.62 | C |
| ATOM | 1146 | N | VAL | A | 216 | 42.122 | 109.925 | 11.556 | 1.00 73.41 | N |
| ATOM | 1147 | CA | VAL | A | 216 | 42.989 | 109.107 | 12.394 | 1.00 79.32 | C |
| ATOM | 1148 | C | VAL | A | 216 | 42.961 | 109.663 | 13.825 | 1.00 83.89 | C |
| ATOM | 1149 | O | VAL | A | 216 | 43.163 | 110.860 | 14.019 | 1.00 83.59 | O |
| ATOM | 1150 | CB | VAL | A | 216 | 44.434 | 109.101 | 11.845 | 1.00 79.38 | C |

FIG. 8-25

| | | | | | | | | | | |
|---|---|---|---|---|---|---|---|---|---|---|
| ATOM | 1151 | CG1 | VAL | A | 216 | 45.415 | 108.589 | 12.889 | 1.00 73.97 | C |
| ATOM | 1152 | CG2 | VAL | A | 216 | 44.499 | 108.288 | 10.964 | 1.00 66.81 | C |
| ATOM | 1153 | N | PRO | A | 217 | 42.788 | 108.793 | 14.828 | 1.00 86.51 | N |
| ATOM | 1154 | CA | PRO | A | 217 | 42.475 | 109.181 | 16.229 | 1.00 89.58 | C |
| ATOM | 1155 | C | PRO | A | 217 | 43.718 | 109.781 | 16.891 | 1.00 92.04 | C |
| ATOM | 1156 | O | PRO | A | 217 | 44.781 | 109.789 | 16.289 | 1.00 95.20 | O |
| ATOM | 1157 | CB | PRO | A | 217 | 42.123 | 107.882 | 16.915 | 1.00 88.71 | C |
| ATOM | 1158 | CG | PRO | A | 217 | 41.783 | 106.910 | 15.810 | 1.00 86.93 | C |
| ATOM | 1159 | CD | PRO | A | 217 | 42.816 | 107.334 | 14.848 | 1.00 88.02 | C |
| ATOM | 1160 | N | ARG | A | 218 | 43.583 | 110.285 | 18.181 | 1.00 93.38 | N |
| ATOM | 1161 | CA | ARG | A | 218 | 44.683 | 110.852 | 18.844 | 1.00 94.62 | C |
| ATOM | 1162 | C | ARG | A | 218 | 45.825 | 109.849 | 19.001 | 1.00 96.98 | C |
| ATOM | 1163 | O | ARG | A | 218 | 46.994 | 110.197 | 18.841 | 1.00 93.27 | O |
| ATOM | 1164 | CB | ARG | A | 218 | 44.237 | 111.381 | 20.217 | 1.00 95.66 | C |
| ATOM | 1165 | CG | ARG | A | 218 | 45.145 | 112.430 | 20.816 | 1.00 98.40 | C |
| ATOM | 1166 | CD | ARG | A | 218 | 46.589 | 111.975 | 20.879 | 1.00100.29 | C |
| ATOM | 1167 | NE | ARG | A | 218 | 47.495 | 113.001 | 21.382 | 1.00104.68 | N |
| ATOM | 1168 | CZ | ARG | A | 218 | 48.822 | 112.902 | 21.339 | 1.00106.77 | C |
| ATOM | 1169 | NH1 | ARG | A | 218 | 49.381 | 111.827 | 20.805 | 1.00106.20 | N |
| ATOM | 1170 | NH2 | ARG | A | 218 | 49.581 | 113.877 | 21.821 | 1.00106.82 | N |
| ATOM | 1171 | N | SER | A | 219 | 45.483 | 108.605 | 19.316 | 1.00101.25 | N |
| ATOM | 1172 | CA | SER | A | 219 | 46.480 | 107.564 | 19.486 | 1.00102.68 | C |
| ATOM | 1173 | C | SER | A | 219 | 47.335 | 107.378 | 18.226 | 1.00105.21 | C |
| ATOM | 1174 | O | SER | A | 219 | 48.549 | 107.181 | 18.309 | 1.00108.18 | O |
| ATOM | 1175 | CB | SER | A | 219 | 45.831 | 106.239 | 19.875 | 1.00104.32 | C |
| ATOM | 1176 | OG | SER | A | 219 | 45.086 | 105.702 | 18.795 | 1.00109.18 | O |
| ATOM | 1177 | N | GLY | A | 220 | 46.689 | 107.442 | 17.064 | 1.00105.35 | N |
| ATOM | 1178 | CA | GLY | A | 220 | 47.340 | 107.160 | 15.795 | 1.00103.40 | C |
| ATOM | 1179 | C | GLY | A | 220 | 48.502 | 108.060 | 15.394 | 1.00103.66 | C |
| ATOM | 1180 | O | GLY | A | 220 | 49.243 | 107.720 | 14.466 | 1.00102.19 | O |
| ATOM | 1181 | N | PHE | A | 221 | 48.670 | 109.192 | 16.077 | 1.00102.73 | N |
| ATOM | 1182 | CA | PHE | A | 221 | 49.740 | 110.132 | 15.739 | 1.00103.63 | C |
| ATOM | 1183 | C | PHE | A | 221 | 51.001 | 109.856 | 16.549 | 1.00108.43 | C |
| ATOM | 1184 | O | PHE | A | 221 | 50.924 | 109.649 | 17.758 | 1.00111.48 | O |
| ATOM | 1185 | CB | PHE | A | 221 | 49.286 | 111.577 | 15.963 | 1.00104.08 | C |
| ATOM | 1186 | CG | PHE | A | 221 | 48.006 | 111.929 | 15.261 | 1.00102.18 | C |
| ATOM | 1187 | CD1 | PHE | A | 221 | 47.971 | 112.064 | 13.884 | 1.00 99.53 | C |
| ATOM | 1188 | CD2 | PHE | A | 221 | 46.839 | 112.130 | 15.981 | 1.00101.50 | C |
| ATOM | 1189 | CE1 | PHE | A | 221 | 46.798 | 112.388 | 13.239 | 1.00 99.13 | C |
| ATOM | 1190 | CE2 | PHE | A | 221 | 45.659 | 112.453 | 15.338 | 1.00100.04 | C |
| ATOM | 1191 | CZ | PHE | A | 221 | 45.638 | 112.580 | 13.968 | 1.00 99.36 | C |
| ATOM | 1192 | N | PRO | A | 222 | 52.170 | 109.864 | 15.887 | 1.00105.04 | N |
| ATOM | 1193 | CA | PRO | A | 222 | 53.437 | 109.574 | 16.570 | 1.00107.88 | C |
| ATOM | 1194 | C | PRO | A | 222 | 53.893 | 110.739 | 17.453 | 1.00111.48 | C |
| ATOM | 1195 | O | PRO | A | 222 | 54.069 | 111.846 | 16.953 | 1.00114.33 | O |
| ATOM | 1196 | CB | PRO | A | 222 | 54.430 | 109.375 | 15.414 | 1.00105.67 | C |
| ATOM | 1197 | CG | PRO | A | 222 | 53.607 | 109.292 | 14.175 | 1.00104.74 | C |
| ATOM | 1198 | CD | PRO | A | 222 | 52.371 | 110.084 | 14.448 | 1.00104.76 | C |
| ATOM | 1199 | N | ASP | A | 223 | 54.088 | 110.472 | 18.742 | 1.00111.58 | N |
| ATOM | 1200 | CA | ASP | A | 223 | 54.549 | 111.489 | 19.697 | 1.00111.13 | C |
| ATOM | 1201 | C | ASP | A | 223 | 55.258 | 112.663 | 19.034 | 1.00106.71 | C |
| ATOM | 1202 | O | ASP | A | 223 | 54.818 | 113.808 | 19.135 | 1.00108.30 | O |
| ATOM | 1203 | CB | ASP | A | 223 | 55.468 | 110.850 | 20.745 | 1.00115.04 | C |
| ATOM | 1204 | CG | ASP | A | 223 | 54.729 | 109.918 | 21.691 | 1.00116.84 | C |
| ATOM | 1205 | OD1 | ASP | A | 223 | 55.369 | 108.979 | 22.215 | 1.00116.52 | O |
| ATOM | 1206 | OD2 | ASP | A | 223 | 53.514 | 110.131 | 21.910 | 1.00113.99 | O |
| ATOM | 1207 | N | LEU | A | 224 | 56.354 | 112.366 | 18.347 | 1.00102.27 | N |
| ATOM | 1208 | CA | LEU | A | 224 | 57.198 | 113.389 | 17.742 | 1.00102.73 | C |
| ATOM | 1209 | C | LEU | A | 224 | 56.476 | 114.429 | 16.878 | 1.00104.30 | C |
| ATOM | 1210 | O | LEU | A | 224 | 56.793 | 115.614 | 16.953 | 1.00109.38 | O |
| ATOM | 1211 | CB | LEU | A | 224 | 58.335 | 112.739 | 16.954 | 1.00102.40 | C |
| ATOM | 1212 | CG | LEU | A | 224 | 59.289 | 111.937 | 17.835 | 1.00102.60 | C |
| ATOM | 1213 | CD1 | LEU | A | 224 | 60.492 | 111.453 | 17.041 | 1.00102.38 | C |
| ATOM | 1214 | CD2 | LEU | A | 224 | 59.726 | 112.784 | 19.029 | 1.00104.99 | C |
| ATOM | 1215 | N | LEU | A | 225 | 55.520 | 114.010 | 16.056 | 1.00 99.05 | N |
| ATOM | 1216 | CA | LEU | A | 225 | 54.842 | 114.980 | 15.200 | 1.00 99.36 | C |
| ATOM | 1217 | C | LEU | A | 225 | 53.932 | 115.886 | 16.029 | 1.00101.93 | C |
| ATOM | 1218 | O | LEU | A | 225 | 53.567 | 116.980 | 15.595 | 1.00104.74 | O |
| ATOM | 1219 | CB | LEU | A | 225 | 54.056 | 114.306 | 14.069 | 1.00 94.47 | C |
| ATOM | 1220 | CG | LEU | A | 225 | 52.533 | 114.319 | 14.190 | 1.00 90.25 | C |
| ATOM | 1221 | CD1 | LEU | A | 225 | 51.868 | 114.017 | 12.847 | 1.00 94.11 | C |
| ATOM | 1222 | CD2 | LEU | A | 225 | 52.070 | 113.330 | 15.283 | 1.00 84.82 | C |
| ATOM | 1223 | N | VAL | A | 226 | 53.556 | 115.420 | 17.217 | 1.00 98.21 | N |
| ATOM | 1224 | CA | VAL | A | 226 | 52.849 | 116.267 | 18.166 | 1.00 97.86 | C |
| ATOM | 1225 | C | VAL | A | 226 | 53.844 | 117.252 | 18.763 | 1.00 96.78 | C |
| ATOM | 1226 | O | VAL | A | 226 | 53.560 | 118.443 | 18.894 | 1.00 91.74 | O |
| ATOM | 1227 | CB | VAL | A | 226 | 52.206 | 115.449 | 19.298 | 1.00 99.26 | C |

FIG. 8-26

```
ATOM   1228  CG1  VAL A 226    52.507 116.082 20.654  1.00 101.56      C
ATOM   1229  CG2  VAL A 226    50.706 115.321 19.071  1.00 98.18       C
ATOM   1230  N    ASP A 227    55.018 116.737 19.115  1.00 98.13       N
ATOM   1231  CA   ASP A 227    56.096 117.553 19.635  1.00 104.91      C
ATOM   1232  C    ASP A 227    56.512 118.356 18.576  1.00 106.79      C
ATOM   1233  O    ASP A 227    56.521 119.764 18.808  1.00 105.83      O
ATOM   1234  CB   ASP A 227    57.284 116.669 20.022  1.00 112.80      C
ATOM   1235  CG   ASP A 227    56.882 115.509 20.923  1.00 118.03      C
ATOM   1236  OD1  ASP A 227    55.855 115.633 21.626  1.00 116.96      O
ATOM   1237  OD2  ASP A 227    57.591 114.475 20.925  1.00 117.70      O
ATOM   1238  N    THR A 228    56.850 118.041 17.392  1.00 108.23      N
ATOM   1239  CA   THR A 228    57.209 118.971 16.247  1.00 111.24      C
ATOM   1240  C    THR A 228    56.135 119.825 15.988  1.00 114.45      C
ATOM   1241  O    THR A 228    56.435 121.059 15.616  1.00 116.34      O
ATOM   1242  CB   THR A 228    57.382 118.018 14.977  1.00 108.51      C
ATOM   1243  OG1  THR A 228    58.334 116.971 15.236  1.00 105.28      O
ATOM   1244  CG2  THR A 228    57.888 118.973 13.817  1.00 110.27      C
ATOM   1245  N    LEU A 229    54.889 119.342 16.195  1.00 114.10      N
ATOM   1246  CA   LEU A 229    53.771 120.474 16.059  1.00 114.40      C
ATOM   1247  C    LEU A 229    53.845 121.337 17.153  1.00 118.01      C
ATOM   1248  O    LEU A 229    53.841 122.736 16.868  1.00 128.32      O
ATOM   1249  CB   LEU A 229    52.433 119.732 16.122  1.00 108.87      C
ATOM   1250  CG   LEU A 229    51.171 120.369 15.898  1.00 106.23      C
ATOM   1251  CD1  LEU A 229    51.227 121.279 14.553  1.00 107.56      C
ATOM   1252  CD2  LEU A 229    49.925 119.705 16.005  1.00 102.13      C
ATOM   1253  N    LEU A 230    53.931 121.088 18.404  1.00 117.51      N
ATOM   1254  CA   LEU A 230    53.939 121.986 19.559  1.00 116.12      C
ATOM   1255  C    LEU A 230    55.277 122.696 19.761  1.00 113.87      C
ATOM   1256  O    LEU A 230    55.505 123.318 20.795  1.00 112.85      O
ATOM   1257  CB   LEU A 230    53.556 121.223 20.828  1.00 114.63      C
ATOM   1258  CG   LEU A 230    52.183 120.547 20.836  1.00 110.18      C
ATOM   1259  CD1  LEU A 230    51.948 119.847 22.166  1.00 110.86      O
ATOM   1260  CD2  LEU A 230    51.073 121.569 20.546  1.00 107.97      C
ATOM   1261  N    ALA A 231    56.156 122.583 18.770  1.00 111.99      N
ATOM   1262  CA   ALA A 231    57.442 123.283 18.851  1.00 110.66      C
ATOM   1263  C    ALA A 231    57.472 124.390 17.751  1.00 114.08      C
ATOM   1264  O    ALA A 231    58.400 125.198 17.707  1.00 114.00      O
ATOM   1265  CB   ALA A 231    58.583 122.352 18.576  1.00 106.70      C
ATOM   1266  N    THR A 232    56.455 124.410 16.897  1.00 117.77      N
ATOM   1267  CA   THR A 232    56.267 125.494 15.938  1.00 120.85      C
ATOM   1268  C    THR A 232    55.124 126.356 16.404  1.00 120.23      C
ATOM   1269  O    THR A 232    54.898 127.445 15.878  1.00 119.70      O
ATOM   1270  CB   THR A 232    56.020 124.968 14.517  1.00 120.32      C
ATOM   1271  OG1  THR A 232    54.703 124.403 14.449  1.00 121.30      O
ATOM   1272  CG2  THR A 232    57.051 123.911 14.144  1.00 117.17      C
ATOM   1273  N    GLU A 233    54.430 125.849 17.406  1.00 119.15      N
ATOM   1274  CA   GLU A 233    53.296 126.555 18.027  1.00 118.95      C
ATOM   1275  C    GLU A 233    53.845 126.882 19.433  1.00 113.78      C
ATOM   1276  O    GLU A 233    52.022 126.287 20.061  1.00 109.79      O
ATOM   1277  CB   GLU A 233    52.837 126.430 17.165  1.00 123.00      C
ATOM   1278  CG   GLU A 233    52.136 127.127 15.812  1.00 127.14      C
ATOM   1279  CD   GLU A 233    51.105 126.635 14.817  1.00 127.46      C
ATOM   1280  OE1  GLU A 233    50.148 125.857 15.243  1.00 127.17      O
ATOM   1281  OE2  GLU A 233    51.250 126.828 13.609  1.00 127.83      O
ATOM   1282  N    THR A 267    47.457 128.327 21.113  1.00 127.39      N
ATOM   1283  CA   THR A 267    46.711 129.406 19.956  1.00 128.42      C
ATOM   1284  C    THR A 267    46.339 128.237 19.055  1.00 125.72      C
ATOM   1285  O    THR A 267    45.877 128.426 17.933  1.00 127.65      O
ATOM   1286  CB   THR A 267    47.517 130.458 19.146  1.00 125.30      C
ATOM   1287  OG1  THR A 267    46.626 131.238 18.337  1.00 125.65      O
ATOM   1288  CG2  THR A 267    48.543 129.764 18.242  1.00 121.30      C
ATOM   1289  N    LEU A 268    46.542 127.023 19.551  1.00 120.81      N
ATOM   1290  CA   LEU A 268    46.202 125.829 18.791  1.00 113.89      C
ATOM   1291  C    LEU A 268    44.685 125.695 18.754  1.00 109.61      C
ATOM   1292  O    LEU A 268    44.105 125.303 17.739  1.00 105.88      O
ATOM   1293  CB   LEU A 268    46.839 124.588 19.437  1.00 112.48      C
ATOM   1294  CG   LEU A 268    47.492 123.561 18.523  1.00 109.57      C
ATOM   1295  CD1  LEU A 268    46.525 122.449 18.146  1.00 107.15      C
ATOM   1296  CD2  LEU A 268    48.071 124.236 17.289  1.00 111.41      C
ATOM   1297  N    THR A 269    44.049 126.027 19.873  1.00 109.65      N
ATOM   1298  CA   THR A 269    42.585 126.068 19.956  1.00 110.49      C
ATOM   1299  C    THR A 269    42.089 127.176 19.036  1.00 112.84      C
ATOM   1300  O    THR A 269    41.030 127.045 18.404  1.00 112.19      O
ATOM   1301  CB   THR A 269    42.126 126.319 21.416  1.00 108.92      C
ATOM   1302  OG1  THR A 269    40.703 126.160 21.515  1.00 105.70      O
ATOM   1303  CG2  THR A 269    42.514 127.722 21.879  1.00 113.37      C
ATOM   1304  N    GLN A 270    42.849 128.259 18.963  1.00 116.28      N
```

FIG. 8-27

| | | | | | | | | | | | |
|---|---|---|---|---|---|---|---|---|---|---|---|
| ATOM | 1305 | CA | GLN | A | 270 | 42.522 | 129.422 | 18.147 | 1.00 | 117.00 | C |
| ATOM | 1306 | C | GLN | A | 270 | 42.518 | 129.056 | 16.663 | 1.00 | 115.97 | C |
| ATOM | 1307 | O | GLN | A | 270 | 41.581 | 129.379 | 15.930 | 1.00 | 117.45 | O |
| ATOM | 1308 | CB | GLN | A | 270 | 43.550 | 130.527 | 18.408 | 1.00 | 119.34 | C |
| ATOM | 1309 | CG | GLN | A | 270 | 43.123 | 131.924 | 17.996 | 1.00 | 124.34 | C |
| ATOM | 1310 | CD | GLN | A | 270 | 42.370 | 132.660 | 19.034 | 1.00 | 127.64 | C |
| ATOM | 1311 | OE1 | GLN | A | 270 | 42.504 | 133.876 | 19.251 | 1.00 | 128.60 | O |
| ATOM | 1312 | NE2 | GLN | A | 270 | 41.575 | 131.923 | 19.862 | 1.00 | 126.27 | N |
| ATOM | 1313 | N | GLN | A | 271 | 43.577 | 128.381 | 16.225 | 1.00 | 110.87 | N |
| ATOM | 1314 | CA | GLN | A | 271 | 43.702 | 127.970 | 14.833 | 1.00 | 102.43 | C |
| ATOM | 1315 | C | GLN | A | 271 | 42.578 | 127.019 | 14.447 | 1.00 | 99.00 | C |
| ATOM | 1316 | O | GLN | A | 271 | 42.073 | 127.067 | 13.325 | 1.00 | 99.63 | O |
| ATOM | 1317 | CB | GLN | A | 271 | 45.075 | 127.335 | 14.574 | 1.00 | 97.16 | C |
| ATOM | 1318 | CG | GLN | A | 271 | 46.245 | 128.300 | 14.731 | 1.00 | 97.76 | C |
| ATOM | 1319 | CD | GLN | A | 271 | 47.605 | 127.680 | 14.580 | 1.00 | 92.71 | C |
| ATOM | 1320 | OE1 | GLN | A | 271 | 47.703 | 126.659 | 13.828 | 1.00 | 88.05 | O |
| ATOM | 1321 | NE2 | GLN | A | 271 | 48.662 | 128.308 | 15.000 | 1.00 | 95.32 | N |
| ATOM | 1322 | N | LEU | A | 272 | 42.180 | 126.157 | 15.384 | 1.00 | 94.12 | N |
| ATOM | 1323 | CA | LEU | A | 272 | 41.121 | 125.178 | 15.144 | 1.00 | 90.26 | C |
| ATOM | 1324 | C | LEU | A | 272 | 39.802 | 125.854 | 14.773 | 1.00 | 93.72 | C |
| ATOM | 1325 | O | LEU | A | 272 | 39.182 | 125.517 | 13.764 | 1.00 | 91.42 | O |
| ATOM | 1326 | CB | LEU | A | 272 | 40.932 | 124.310 | 16.386 | 1.00 | 87.49 | C |
| ATOM | 1327 | CG | LEU | A | 272 | 40.544 | 122.834 | 16.280 | 1.00 | 85.10 | C |
| ATOM | 1328 | CD1 | LEU | A | 272 | 40.025 | 122.267 | 17.518 | 1.00 | 84.54 | C |
| ATOM | 1329 | CD2 | LEU | A | 272 | 39.527 | 122.606 | 15.098 | 1.00 | 85.30 | C |
| ATOM | 1330 | N | VAL | A | 273 | 38.371 | 126.799 | 15.603 | 1.00 | 97.52 | N |
| ATOM | 1331 | CA | VAL | A | 273 | 38.121 | 127.535 | 15.367 | 1.00 | 100.18 | C |
| ATOM | 1332 | C | VAL | A | 273 | 38.167 | 128.347 | 14.082 | 1.00 | 102.56 | C |
| ATOM | 1333 | O | VAL | A | 273 | 37.200 | 128.373 | 13.320 | 1.00 | 101.69 | O |
| ATOM | 1334 | CB | VAL | A | 273 | 37.738 | 128.423 | 16.571 | 1.00 | 99.35 | C |
| ATOM | 1335 | CG1 | VAL | A | 273 | 37.240 | 127.585 | 17.748 | 1.00 | 95.80 | C |
| ATOM | 1336 | CG2 | VAL | A | 273 | 38.915 | 129.284 | 16.988 | 1.00 | 102.07 | C |
| ATOM | 1337 | N | LYS | A | 274 | 38.290 | 129.024 | 13.848 | 1.00 | 104.99 | N |
| ATOM | 1338 | CA | LYS | A | 274 | 38.479 | 129.818 | 12.631 | 1.00 | 106.31 | C |
| ATOM | 1339 | C | LYS | A | 274 | 39.213 | 129.000 | 11.363 | 1.00 | 104.89 | C |
| ATOM | 1340 | O | LYS | A | 274 | 38.615 | 128.490 | 10.403 | 1.00 | 105.77 | O |
| ATOM | 1341 | CB | LYS | A | 274 | 40.896 | 130.405 | 12.586 | 1.00 | 105.96 | C |
| ATOM | 1342 | CG | LYS | A | 274 | 41.248 | 131.098 | 11.270 | 1.00 | 104.98 | C |
| ATOM | 1343 | CD | LYS | A | 274 | 42.686 | 131.587 | 11.260 | 1.00 | 105.94 | C |
| ATOM | 1344 | CE | LYS | A | 274 | 43.690 | 130.459 | 11.268 | 1.00 | 105.76 | C |
| ATOM | 1345 | NZ | LYS | A | 274 | 45.102 | 130.841 | 11.306 | 1.00 | 109.08 | N |
| ATOM | 1346 | N | ASN | A | 275 | 38.666 | 127.751 | 11.367 | 1.00 | 103.04 | N |
| ATOM | 1347 | CA | ASN | A | 275 | 39.476 | 126.864 | 10.228 | 1.00 | 98.92 | C |
| ATOM | 1348 | C | ASN | A | 275 | 38.098 | 126.237 | 10.210 | 1.00 | 99.54 | C |
| ATOM | 1349 | O | ASN | A | 275 | 37.496 | 126.043 | 9.149 | 1.00 | 99.17 | O |
| ATOM | 1350 | CB | ASN | A | 275 | 40.547 | 125.779 | 10.223 | 1.00 | 94.37 | C |
| ATOM | 1351 | CG | ASN | A | 275 | 41.910 | 126.320 | 9.859 | 1.00 | 99.60 | C |
| ATOM | 1352 | OD1 | ASN | A | 275 | 42.482 | 127.126 | 10.592 | 1.00 | 101.86 | O |
| ATOM | 1353 | ND2 | ASN | A | 275 | 42.437 | 125.889 | 8.714 | 1.00 | 102.07 | N |
| ATOM | 1354 | N | LEU | A | 276 | 37.600 | 125.916 | 11.401 | 1.00 | 100.65 | N |
| ATOM | 1355 | CA | LEU | A | 276 | 36.378 | 125.143 | 11.557 | 1.00 | 101.51 | C |
| ATOM | 1356 | C | LEU | A | 276 | 35.100 | 125.987 | 11.483 | 1.00 | 107.27 | C |
| ATOM | 1357 | O | LEU | A | 276 | 34.062 | 125.495 | 11.041 | 1.00 | 108.62 | O |
| ATOM | 1358 | CB | LEU | A | 276 | 36.430 | 124.376 | 12.876 | 1.00 | 103.31 | C |
| ATOM | 1359 | CG | LEU | A | 276 | 35.670 | 123.054 | 12.977 | 1.00 | 104.88 | C |
| ATOM | 1360 | CD1 | LEU | A | 276 | 36.167 | 122.248 | 14.175 | 1.00 | 101.53 | C |
| ATOM | 1361 | CD2 | LEU | A | 276 | 34.171 | 123.296 | 13.072 | 1.00 | 107.39 | C |
| ATOM | 1362 | N | PHE | A | 277 | 35.169 | 127.251 | 11.894 | 1.00 | 111.88 | N |
| ATOM | 1363 | CA | PHE | A | 277 | 33.954 | 128.061 | 12.017 | 1.00 | 114.66 | C |
| ATOM | 1364 | C | PHE | A | 277 | 33.911 | 129.364 | 11.198 | 1.00 | 118.58 | C |
| ATOM | 1365 | O | PHE | A | 277 | 32.827 | 129.884 | 10.915 | 1.00 | 117.50 | O |
| ATOM | 1366 | CB | PHE | A | 277 | 33.679 | 128.387 | 13.493 | 1.00 | 115.09 | C |
| ATOM | 1367 | CG | PHE | A | 277 | 33.446 | 127.174 | 14.363 | 1.00 | 110.43 | C |
| ATOM | 1368 | CD1 | PHE | A | 277 | 32.291 | 126.419 | 14.232 | 1.00 | 107.82 | C |
| ATOM | 1369 | CD2 | PHE | A | 277 | 34.372 | 126.808 | 15.327 | 1.00 | 107.92 | C |
| ATOM | 1370 | CE1 | PHE | A | 277 | 32.075 | 125.310 | 15.036 | 1.00 | 103.14 | C |
| ATOM | 1371 | CE2 | PHE | A | 277 | 34.159 | 125.702 | 16.134 | 1.00 | 103.36 | C |
| ATOM | 1372 | CZ | PHE | A | 277 | 33.009 | 124.954 | 15.989 | 1.00 | 100.81 | C |
| ATOM | 1373 | N | LEU | A | 278 | 35.071 | 129.894 | 10.820 | 1.00 | 121.77 | N |
| ATOM | 1374 | CA | LEU | A | 278 | 35.131 | 131.255 | 10.280 | 1.00 | 124.34 | C |
| ATOM | 1375 | C | LEU | A | 278 | 35.615 | 131.360 | 8.832 | 1.00 | 128.40 | C |
| ATOM | 1376 | O | LEU | A | 278 | 36.081 | 130.384 | 8.237 | 1.00 | 126.32 | O |
| ATOM | 1377 | CB | LEU | A | 278 | 36.016 | 132.128 | 11.172 | 1.00 | 124.17 | C |
| ATOM | 1378 | CG | LEU | A | 278 | 36.021 | 131.795 | 12.666 | 1.00 | 122.82 | C |
| ATOM | 1379 | CD1 | LEU | A | 278 | 37.221 | 132.437 | 13.336 | 1.00 | 125.51 | C |
| ATOM | 1380 | CD2 | LEU | A | 278 | 34.733 | 132.233 | 13.347 | 1.00 | 121.71 | C |
| ATOM | 1381 | N | SER | A | 279 | 35.506 | 132.565 | 8.278 | 1.00 | 134.72 | N |

FIG. 8-28

| | | | | | | | | | | |
|---|---|---|---|---|---|---|---|---|---|---|
| ATOM | 1382 | CA | SER | A | 279 | 35.964 | 132.842 | 6.920 | 1.00137.59 | C |
| ATOM | 1383 | C | SER | A | 279 | 37.222 | 133.710 | 6.929 | 1.00141.06 | C |
| ATOM | 1384 | O | SER | A | 279 | 37.888 | 133.843 | 7.958 | 1.00142.74 | O |
| ATOM | 1385 | CB | SER | A | 279 | 34.861 | 133.924 | 6.107 | 1.00139.20 | C |
| ATOM | 1386 | OG | SER | A | 279 | 34.535 | 134.795 | 6.845 | 1.00141.82 | O |
| ATOM | 1387 | N | SER | A | 280 | 37.536 | 134.302 | 5.761 | 1.00141.17 | N |
| ATOM | 1388 | CA | SER | A | 280 | 38.753 | 135.094 | 5.634 | 1.00142.63 | C |
| ATOM | 1389 | C | SER | A | 280 | 38.783 | 136.341 | 6.511 | 1.00144.93 | C |
| ATOM | 1390 | O | SER | A | 280 | 37.743 | 136.818 | 6.968 | 1.00145.34 | O |
| ATOM | 1391 | CB | SER | A | 280 | 38.926 | 135.505 | 4.160 | 1.00143.77 | C |
| ATOM | 1392 | OG | SER | A | 280 | 37.957 | 136.473 | 3.787 | 1.00146.13 | O |
| ATOM | 1393 | N | GLU | A | 281 | 39.988 | 136.859 | 6.740 | 1.00146.60 | N |
| ATOM | 1394 | CA | GLU | A | 281 | 40.193 | 138.113 | 7.462 | 1.00149.09 | C |
| ATOM | 1395 | C | GLU | A | 281 | 39.300 | 139.214 | 6.866 | 1.00155.60 | C |
| ATOM | 1396 | O | GLU | A | 281 | 38.925 | 138.938 | 5.952 | 1.00153.76 | O |
| ATOM | 1397 | CB | GLU | A | 281 | 41.682 | 138.496 | 7.429 | 1.00147.91 | C |
| ATOM | 1398 | CG | GLU | A | 281 | 42.359 | 138.337 | 6.073 | 1.00146.87 | C |
| ATOM | 1399 | CD | GLU | A | 281 | 43.086 | 137.009 | 5.934 | 1.00144.47 | C |
| ATOM | 1400 | OE1 | GLU | A | 281 | 43.647 | 136.531 | 6.942 | 1.00145.20 | O |
| ATOM | 1401 | OE2 | GLU | A | 281 | 43.105 | 136.445 | 4.817 | 1.00140.95 | O |
| ATOM | 1402 | N | ARG | A | 282 | 39.399 | 140.497 | 7.346 | 1.00164.29 | N |
| ATOM | 1403 | CA | ARG | A | 282 | 40.416 | 140.895 | 8.302 | 1.00169.53 | C |
| ATOM | 1404 | C | ARG | A | 282 | 40.235 | 140.389 | 9.729 | 1.00173.24 | C |
| ATOM | 1405 | O | ARG | A | 282 | 39.183 | 139.868 | 10.099 | 1.00172.87 | O |
| ATOM | 1406 | CB | ARG | A | 282 | 40.998 | 142.418 | 8.273 | 1.00171.42 | C |
| ATOM | 1407 | CG | ARG | A | 282 | 41.602 | 142.878 | 7.235 | 1.00169.89 | C |
| ATOM | 1408 | CD | ARG | A | 282 | 42.805 | 141.938 | 7.220 | 1.00164.84 | C |
| ATOM | 1409 | NE | ARG | A | 282 | 43.832 | 142.301 | 6.243 | 1.00163.04 | N |
| ATOM | 1410 | CZ | ARG | A | 282 | 44.261 | 143.539 | 6.010 | 1.00164.33 | C |
| ATOM | 1411 | NH1 | ARG | A | 282 | 43.772 | 144.566 | 6.692 | 1.00165.48 | N |
| ATOM | 1412 | NH2 | ARG | A | 282 | 45.199 | 143.748 | 5.097 | 1.00164.79 | N |
| ATOM | 1413 | N | SER | A | 283 | 41.284 | 140.569 | 10.524 | 1.00176.97 | N |
| ATOM | 1414 | CA | SER | A | 283 | 41.435 | 139.865 | 11.791 | 1.00177.57 | C |
| ATOM | 1415 | C | SER | A | 283 | 40.674 | 140.464 | 12.977 | 1.00177.79 | C |
| ATOM | 1416 | O | SER | A | 283 | 39.720 | 139.866 | 13.458 | 1.00178.01 | O |
| ATOM | 1417 | CB | SER | A | 283 | 42.923 | 139.713 | 12.130 | 1.00179.39 | C |
| ATOM | 1418 | OG | SER | A | 283 | 43.688 | 139.019 | 11.098 | 1.00177.70 | O |
| ATOM | 1419 | N | TYR | A | 284 | 41.099 | 141.633 | 13.445 | 1.00176.41 | N |
| ATOM | 1420 | CA | TYR | A | 284 | 40.594 | 142.198 | 14.702 | 1.00173.98 | C |
| ATOM | 1421 | C | TYR | A | 284 | 39.230 | 141.685 | 15.197 | 1.00167.41 | C |
| ATOM | 1422 | O | TYR | A | 284 | 39.127 | 141.204 | 16.325 | 1.00167.08 | O |
| ATOM | 1423 | CB | TYR | A | 284 | 40.642 | 143.729 | 14.678 | 1.00178.82 | C |
| ATOM | 1424 | CG | TYR | A | 284 | 41.954 | 144.282 | 15.187 | 1.00182.11 | C |
| ATOM | 1425 | CD1 | TYR | A | 284 | 42.981 | 144.611 | 14.313 | 1.00182.93 | C |
| ATOM | 1426 | CD2 | TYR | A | 284 | 42.171 | 144.455 | 16.547 | 1.00184.67 | C |
| ATOM | 1427 | CE1 | TYR | A | 284 | 44.184 | 145.107 | 14.779 | 1.00185.76 | C |
| ATOM | 1428 | CE2 | TYR | A | 284 | 43.368 | 144.951 | 17.022 | 1.00187.87 | C |
| ATOM | 1429 | CZ | TYR | A | 284 | 44.371 | 145.275 | 16.135 | 1.00188.78 | C |
| ATOM | 1430 | OH | TYR | A | 284 | 45.563 | 145.770 | 16.611 | 1.00192.41 | O |
| ATOM | 1431 | N | TRP | A | 285 | 38.194 | 141.782 | 14.369 | 1.00161.89 | N |
| ATOM | 1432 | CA | TRP | A | 285 | 36.868 | 141.287 | 14.761 | 1.00156.90 | C |
| ATOM | 1433 | C | TRP | A | 285 | 36.763 | 139.775 | 14.670 | 1.00150.50 | C |
| ATOM | 1434 | O | TRP | A | 285 | 36.174 | 139.126 | 15.536 | 1.00147.78 | O |
| ATOM | 1435 | CB | TRP | A | 285 | 35.774 | 141.971 | 13.932 | 1.00158.55 | C |
| ATOM | 1436 | CG | TRP | A | 285 | 35.494 | 143.377 | 14.375 | 1.00164.54 | C |
| ATOM | 1437 | CD1 | TRP | A | 285 | 36.061 | 144.519 | 13.889 | 1.00167.49 | C |
| ATOM | 1438 | CD2 | TRP | A | 285 | 34.587 | 143.787 | 15.408 | 1.00166.53 | C |
| ATOM | 1439 | NE1 | TRP | A | 285 | 35.559 | 145.615 | 14.551 | 1.00170.26 | N |
| ATOM | 1440 | CE2 | TRP | A | 285 | 34.652 | 145.192 | 15.487 | 1.00169.34 | C |
| ATOM | 1441 | CE3 | TRP | A | 285 | 33.724 | 143.103 | 16.270 | 1.00165.44 | C |
| ATOM | 1442 | CZ2 | TRP | A | 285 | 33.863 | 145.925 | 16.394 | 1.00171.64 | C |
| ATOM | 1443 | CZ3 | TRP | A | 285 | 32.967 | 143.834 | 17.169 | 1.00167.07 | C |
| ATOM | 1444 | CH2 | TRP | A | 285 | 33.055 | 145.229 | 17.224 | 1.00170.05 | C |
| ATOM | 1445 | N | ARG | A | 286 | 37.331 | 139.218 | 13.607 | 1.00146.66 | N |
| ATOM | 1446 | CA | ARG | A | 286 | 37.499 | 137.778 | 13.481 | 1.00140.19 | C |
| ATOM | 1447 | C | ARG | A | 286 | 38.293 | 137.273 | 14.682 | 1.00140.44 | C |
| ATOM | 1448 | O | ARG | A | 286 | 37.803 | 136.460 | 15.467 | 1.00140.84 | O |
| ATOM | 1449 | CB | ARG | A | 286 | 38.250 | 137.461 | 12.185 | 1.00136.88 | C |
| ATOM | 1450 | CG | ARG | A | 286 | 38.501 | 135.987 | 11.908 | 1.00129.35 | C |
| ATOM | 1451 | CD | ARG | A | 286 | 39.745 | 135.832 | 11.049 | 1.00128.18 | C |
| ATOM | 1452 | NE | ARG | A | 286 | 39.688 | 134.661 | 10.182 | 1.00126.74 | N |
| ATOM | 1453 | CZ | ARG | A | 286 | 40.648 | 134.320 | 9.326 | 1.00126.19 | C |
| ATOM | 1454 | NH1 | ARG | A | 286 | 41.743 | 135.061 | 9.229 | 1.00137.92 | N |
| ATOM | 1455 | NH2 | ARG | A | 286 | 40.515 | 133.236 | 8.571 | 1.00122.70 | N |
| ATOM | 1456 | N | LYS | A | 287 | 39.519 | 137.774 | 14.816 | 1.00139.83 | N |
| ATOM | 1457 | CA | LYS | A | 287 | 40.423 | 137.404 | 15.903 | 1.00136.94 | C |
| ATOM | 1458 | C | LYS | A | 287 | 39.712 | 137.304 | 17.245 | 1.00134.88 | C |

FIG. 8-29

| | | | | | | | | | | |
|---|---|---|---|---|---|---|---|---|---|---|
| ATOM | 1459 | O | LYS | A | 287 | 39.971 | 136.390 | 18.027 | 1.00133.61 | O |
| ATOM | 1460 | CB | LYS | A | 287 | 41.564 | 138.418 | 16.006 | 1.00138.77 | C |
| ATOM | 1461 | CG | LYS | A | 287 | 42.081 | 138.408 | 17.356 | 1.00139.77 | C |
| ATOM | 1462 | CD | LYS | A | 287 | 42.952 | 139.763 | 17.614 | 1.00144.84 | C |
| ATOM | 1463 | CE | LYS | A | 287 | 43.258 | 139.988 | 19.099 | 1.00143.94 | C |
| ATOM | 1464 | NZ | LYS | A | 287 | 43.797 | 141.316 | 19.385 | 1.00145.91 | N |
| ATOM | 1465 | N | ALA | A | 288 | 38.818 | 138.252 | 17.506 | 1.00134.74 | N |
| ATOM | 1466 | CA | ALA | A | 288 | 38.094 | 138.298 | 18.771 | 1.00134.58 | C |
| ATOM | 1467 | C | ALA | A | 288 | 36.973 | 137.270 | 18.799 | 1.00131.53 | C |
| ATOM | 1468 | O | ALA | A | 288 | 36.797 | 136.992 | 19.789 | 1.00129.77 | O |
| ATOM | 1469 | CB | ALA | A | 288 | 37.939 | 139.698 | 19.013 | 1.00136.95 | C |
| ATOM | 1470 | N | ASN | A | 289 | 36.217 | 137.207 | 17.710 | 1.00130.26 | N |
| ATOM | 1471 | CA | ASN | A | 289 | 35.102 | 136.081 | 17.608 | 1.00131.13 | C |
| ATOM | 1472 | C | ASN | A | 289 | 35.951 | 134.838 | 17.832 | 1.00138.62 | C |
| ATOM | 1473 | O | ASN | A | 289 | 34.873 | 134.068 | 18.508 | 1.00125.24 | O |
| ATOM | 1474 | CB | ASN | A | 289 | 34.432 | 136.435 | 16.247 | 1.00134.83 | C |
| ATOM | 1475 | CG | ASN | A | 289 | 32.981 | 135.972 | 16.259 | 1.00136.76 | C |
| ATOM | 1476 | OD1 | ASN | A | 289 | 32.068 | 136.753 | 15.997 | 1.00138.57 | O |
| ATOM | 1477 | ND2 | ASN | A | 289 | 32.769 | 134.698 | 16.570 | 1.00135.07 | N |
| ATOM | 1478 | N | GLU | A | 290 | 36.702 | 134.483 | 17.272 | 1.00128.98 | N |
| ATOM | 1479 | CA | GLU | A | 290 | 37.268 | 133.155 | 17.478 | 1.00128.47 | C |
| ATOM | 1480 | C | GLU | A | 290 | 37.832 | 133.016 | 18.886 | 1.00129.81 | C |
| ATOM | 1481 | O | GLU | A | 290 | 37.641 | 131.992 | 19.540 | 1.00126.23 | O |
| ATOM | 1482 | CB | GLU | A | 290 | 38.358 | 132.856 | 16.446 | 1.00129.88 | C |
| ATOM | 1483 | CG | GLU | A | 290 | 39.443 | 133.951 | 16.390 | 1.00133.23 | C |
| ATOM | 1484 | CD | GLU | A | 290 | 40.671 | 133.440 | 15.596 | 1.00131.66 | C |
| ATOM | 1485 | OE1 | GLU | A | 290 | 41.301 | 134.287 | 14.890 | 1.00133.71 | O |
| ATOM | 1486 | OE2 | GLU | A | 290 | 41.004 | 132.242 | 15.711 | 1.00128.33 | O |
| ATOM | 1487 | N | ALA | A | 291 | 38.532 | 134.050 | 19.345 | 1.00134.52 | N |
| ATOM | 1488 | CA | ALA | A | 291 | 39.157 | 134.034 | 20.664 | 1.00137.21 | C |
| ATOM | 1489 | C | ALA | A | 291 | 38.143 | 133.679 | 21.745 | 1.00136.41 | C |
| ATOM | 1490 | O | ALA | A | 291 | 38.476 | 133.032 | 22.739 | 1.00132.51 | O |
| ATOM | 1491 | CB | ALA | A | 291 | 39.804 | 135.378 | 20.961 | 1.00140.85 | C |
| ATOM | 1492 | N | TYR | A | 292 | 36.904 | 134.111 | 21.539 | 1.00138.35 | N |
| ATOM | 1493 | CA | TYR | A | 292 | 35.808 | 133.803 | 22.443 | 1.00136.83 | C |
| ATOM | 1494 | C | TYR | A | 292 | 35.417 | 132.336 | 22.309 | 1.00127.52 | C |
| ATOM | 1495 | O | TYR | A | 292 | 35.189 | 131.650 | 23.307 | 1.00125.82 | O |
| ATOM | 1496 | CB | TYR | A | 292 | 34.608 | 134.705 | 22.146 | 1.00142.31 | C |
| ATOM | 1497 | CG | TYR | A | 292 | 33.576 | 134.737 | 23.247 | 1.00147.10 | C |
| ATOM | 1498 | CD1 | TYR | A | 292 | 33.944 | 134.946 | 24.570 | 1.00149.46 | C |
| ATOM | 1499 | CD2 | TYR | A | 292 | 32.239 | 134.985 | 22.967 | 1.00149.29 | C |
| ATOM | 1500 | CE1 | TYR | A | 292 | 33.010 | 134.581 | 25.583 | 1.00152.38 | C |
| ATOM | 1501 | CE2 | TYR | A | 292 | 31.296 | 135.026 | 23.976 | 1.00151.45 | C |
| ATOM | 1502 | CZ | TYR | A | 292 | 31.688 | 134.821 | 25.284 | 1.00153.37 | C |
| ATOM | 1503 | OH | TYR | A | 292 | 30.763 | 134.857 | 26.303 | 1.00155.23 | O |
| ATOM | 1504 | N | MET | A | 293 | 35.347 | 131.861 | 21.069 | 1.00120.29 | N |
| ATOM | 1505 | CA | MET | A | 293 | 35.045 | 130.459 | 20.808 | 1.00110.65 | C |
| ATOM | 1506 | C | MET | A | 293 | 36.174 | 129.548 | 21.280 | 1.00107.21 | C |
| ATOM | 1507 | O | MET | A | 293 | 35.940 | 128.389 | 21.610 | 1.00108.05 | O |
| ATOM | 1508 | CB | MET | A | 293 | 34.778 | 130.232 | 19.318 | 1.00106.54 | C |
| ATOM | 1509 | CG | MET | A | 293 | 33.507 | 130.885 | 18.804 | 1.00105.67 | C |
| ATOM | 1510 | SD | MET | A | 293 | 33.253 | 130.983 | 17.043 | 1.00134.04 | S |
| ATOM | 1511 | CE | MET | A | 293 | 31.882 | 131.684 | 16.703 | 1.00179.78 | C |
| ATOM | 1512 | N | ALA | A | 294 | 37.395 | 130.076 | 21.313 | 1.00106.87 | N |
| ATOM | 1513 | CA | ALA | A | 294 | 38.560 | 129.309 | 21.754 | 1.00104.86 | C |
| ATOM | 1514 | C | ALA | A | 294 | 38.482 | 128.924 | 23.236 | 1.00110.23 | C |
| ATOM | 1515 | O | ALA | A | 294 | 38.735 | 127.776 | 23.582 | 1.00109.83 | O |
| ATOM | 1516 | CB | ALA | A | 294 | 39.843 | 130.076 | 21.478 | 1.00105.33 | C |
| ATOM | 1517 | N | LEU | A | 295 | 38.144 | 129.887 | 24.083 | 1.00115.03 | N |
| ATOM | 1518 | CA | LEU | A | 295 | 37.958 | 129.617 | 25.510 | 1.00115.09 | C |
| ATOM | 1519 | C | LEU | A | 295 | 36.768 | 128.763 | 25.802 | 1.00116.52 | C |
| ATOM | 1520 | O | LEU | A | 295 | 36.813 | 127.864 | 26.641 | 1.00117.44 | O |
| ATOM | 1521 | CB | LEU | A | 295 | 37.939 | 130.917 | 26.311 | 1.00117.43 | C |
| ATOM | 1522 | CG | LEU | A | 295 | 39.281 | 131.586 | 26.604 | 1.00119.77 | C |
| ATOM | 1523 | CD1 | LEU | A | 295 | 39.863 | 132.187 | 25.334 | 1.00121.17 | C |
| ATOM | 1524 | CD2 | LEU | A | 295 | 39.159 | 132.648 | 27.689 | 1.00123.87 | C |
| ATOM | 1525 | N | ILE | A | 296 | 35.667 | 129.058 | 25.121 | 1.00119.98 | N |
| ATOM | 1526 | CA | ILE | A | 296 | 34.475 | 128.223 | 25.206 | 1.00124.15 | C |
| ATOM | 1527 | C | ILE | A | 296 | 34.833 | 126.791 | 24.808 | 1.00125.79 | C |
| ATOM | 1528 | O | ILE | A | 296 | 34.500 | 125.831 | 25.507 | 1.00124.56 | O |
| ATOM | 1529 | CB | ILE | A | 296 | 33.358 | 128.760 | 24.291 | 1.00125.80 | C |
| ATOM | 1530 | CG1 | ILE | A | 296 | 32.913 | 130.146 | 24.768 | 1.00130.85 | C |
| ATOM | 1531 | CG2 | ILE | A | 296 | 32.181 | 127.787 | 24.246 | 1.00121.14 | C |
| ATOM | 1532 | CD1 | ILE | A | 296 | 31.985 | 130.868 | 23.810 | 1.00133.79 | C |
| ATOM | 1533 | N | MET | A | 297 | 35.523 | 126.663 | 23.681 | 1.00126.55 | N |
| ATOM | 1534 | CA | MET | A | 297 | 36.035 | 125.380 | 23.223 | 1.00123.75 | C |
| ATOM | 1535 | C | MET | A | 297 | 36.898 | 124.732 | 24.301 | 1.00126.66 | C |

FIG. 8-30

| | | | | | | | | | |
|---|---|---|---|---|---|---|---|---|---|
| ATOM | 1536 | O | MET | A | 297 | 36.537 123.698 | 24.865 | 1.00135.54 | O |
| ATOM | 1537 | CB | MET | A | 297 | 36.858 125.573 | 21.947 | 1.00131.80 | C |
| ATOM | 1538 | CG | MET | A | 297 | 37.515 124.310 | 21.420 | 1.00138.16 | C |
| ATOM | 1539 | SD | MET | A | 297 | 36.404 123.267 | 20.451 | 1.00139.08 | S |
| ATOM | 1540 | CE | MET | A | 297 | 36.174 124.282 | 18.994 | 1.00113.65 | C |
| ATOM | 1541 | N | ASP | A | 298 | 38.033 125.359 | 24.593 | 1.00129.52 | N |
| ATOM | 1542 | CA | ASP | A | 298 | 39.028 124.784 | 25.490 | 1.00130.73 | C |
| ATOM | 1543 | C | ASP | A | 298 | 38.366 124.503 | 26.876 | 1.00134.68 | C |
| ATOM | 1544 | O | ASP | A | 298 | 39.076 123.812 | 27.687 | 1.00135.83 | O |
| ATOM | 1545 | CB | ASP | A | 298 | 40.246 125.704 | 25.591 | 1.00132.36 | C |
| ATOM | 1546 | CG | ASP | A | 298 | 41.530 124.944 | 25.866 | 1.00132.01 | C |
| ATOM | 1547 | OD1 | ASP | A | 298 | 42.614 125.548 | 25.734 | 1.00132.31 | O |
| ATOM | 1548 | OD2 | ASP | A | 298 | 41.396 123.742 | 26.205 | 1.00131.01 | O |
| ATOM | 1549 | N | ALA | A | 299 | 37.273 125.041 | 27.147 | 1.00135.94 | N |
| ATOM | 1550 | CA | ALA | A | 299 | 36.599 124.774 | 28.409 | 1.00134.38 | C |
| ATOM | 1551 | C | ALA | A | 299 | 35.891 123.424 | 28.353 | 1.00132.02 | C |
| ATOM | 1552 | O | ALA | A | 299 | 36.157 122.538 | 29.164 | 1.00132.04 | O |
| ATOM | 1553 | CB | ALA | A | 299 | 35.610 125.883 | 28.730 | 1.00133.65 | C |
| ATOM | 1554 | N | ARG | A | 300 | 35.001 123.270 | 27.380 | 1.00129.91 | N |
| ATOM | 1555 | CA | ARG | A | 300 | 34.150 122.088 | 27.298 | 1.00129.55 | C |
| ATOM | 1556 | C | ARG | A | 300 | 34.811 120.891 | 26.624 | 1.00125.23 | C |
| ATOM | 1557 | O | ARG | A | 300 | 34.211 119.821 | 26.532 | 1.00122.80 | O |
| ATOM | 1558 | CB | ARG | A | 300 | 32.840 122.429 | 26.595 | 1.00131.90 | C |
| ATOM | 1559 | CG | ARG | A | 300 | 31.822 123.298 | 27.418 | 1.00138.73 | C |
| ATOM | 1560 | CD | ARG | A | 300 | 31.612 122.623 | 28.746 | 1.00135.38 | C |
| ATOM | 1561 | NE | ARG | A | 300 | 31.138 123.582 | 29.738 | 1.00139.14 | N |
| ATOM | 1562 | CZ | ARG | A | 300 | 29.851 124.175 | 29.693 | 1.00140.18 | C |
| ATOM | 1563 | NH1 | ARG | A | 300 | 29.113 123.911 | 28.697 | 1.00137.98 | N |
| ATOM | 1564 | NH2 | ARG | A | 300 | 29.603 125.036 | 30.639 | 1.00141.84 | N |
| ATOM | 1565 | N | TYR | A | 301 | 36.039 121.068 | 26.149 | 1.00122.85 | N |
| ATOM | 1566 | CA | TYR | A | 301 | 36.750 119.970 | 25.500 | 1.00115.49 | C |
| ATOM | 1567 | C | TYR | A | 301 | 38.194 119.845 | 25.983 | 1.00119.27 | C |
| ATOM | 1568 | O | TYR | A | 301 | 38.776 120.795 | 26.480 | 1.00121.77 | O |
| ATOM | 1569 | CB | TYR | A | 301 | 36.629 120.082 | 23.975 | 1.00105.75 | C |
| ATOM | 1570 | CG | TYR | A | 301 | 35.231 119.719 | 23.521 | 1.00 97.65 | C |
| ATOM | 1571 | CD1 | TYR | A | 301 | 34.724 118.438 | 23.680 | 1.00 93.07 | C |
| ATOM | 1572 | CD2 | TYR | A | 301 | 34.404 120.688 | 22.974 | 1.00 99.90 | C |
| ATOM | 1573 | CE1 | TYR | A | 301 | 33.435 118.122 | 23.290 | 1.00 97.18 | C |
| ATOM | 1574 | CE2 | TYR | A | 301 | 33.109 120.383 | 22.576 | 1.00103.97 | C |
| ATOM | 1575 | CZ | TYR | A | 301 | 32.629 119.095 | 22.737 | 1.00103.13 | C |
| ATOM | 1576 | OH | TYR | A | 301 | 31.346 118.779 | 22.340 | 1.00104.75 | O |
| ATOM | 1577 | N | SER | A | 302 | 38.762 118.662 | 25.760 | 1.00120.35 | N |
| ATOM | 1578 | CA | SER | A | 302 | 39.961 118.247 | 26.477 | 1.00124.84 | C |
| ATOM | 1579 | C | SER | A | 302 | 41.257 118.274 | 25.674 | 1.00128.47 | C |
| ATOM | 1580 | O | SER | A | 302 | 41.256 118.460 | 24.457 | 1.00131.30 | O |
| ATOM | 1581 | CB | SER | A | 302 | 39.750 116.833 | 27.017 | 1.00125.21 | C |
| ATOM | 1582 | OG | SER | A | 302 | 39.332 115.967 | 25.970 | 1.00126.26 | O |
| ATOM | 1583 | N | LYS | A | 303 | 42.356 118.079 | 26.397 | 1.00130.44 | N |
| ATOM | 1584 | CA | LYS | A | 303 | 43.693 117.891 | 25.842 | 1.00134.97 | C |
| ATOM | 1585 | C | LYS | A | 303 | 43.688 117.251 | 24.462 | 1.00134.02 | C |
| ATOM | 1586 | O | LYS | A | 303 | 43.592 117.932 | 23.439 | 1.00133.58 | O |
| ATOM | 1587 | CB | LYS | A | 303 | 44.508 117.008 | 26.800 | 1.00139.25 | C |
| ATOM | 1588 | CG | LYS | A | 303 | 45.871 116.543 | 26.287 | 1.00141.22 | C |
| ATOM | 1589 | CD | LYS | A | 303 | 46.459 115.470 | 27.203 | 1.00141.82 | C |
| ATOM | 1590 | CE | LYS | A | 303 | 47.930 115.005 | 26.730 | 1.00141.26 | C |
| ATOM | 1591 | NZ | LYS | A | 303 | 48.275 113.773 | 27.442 | 1.00139.85 | N |
| ATOM | 1592 | N | ASP | A | 304 | 43.792 115.928 | 24.450 | 1.00131.88 | N |
| ATOM | 1593 | CA | ASP | A | 304 | 43.942 115.173 | 23.219 | 1.00125.95 | C |
| ATOM | 1594 | C | ASP | A | 304 | 42.835 115.474 | 22.213 | 1.00117.78 | C |
| ATOM | 1595 | O | ASP | A | 304 | 43.029 115.331 | 21.008 | 1.00117.34 | O |
| ATOM | 1596 | CB | ASP | A | 304 | 44.007 113.673 | 23.528 | 1.00127.95 | C |
| ATOM | 1597 | CG | ASP | A | 304 | 45.249 113.293 | 24.326 | 1.00131.97 | C |
| ATOM | 1598 | OD1 | ASP | A | 304 | 45.365 112.117 | 24.743 | 1.00131.08 | O |
| ATOM | 1599 | OD2 | ASP | A | 304 | 46.111 114.174 | 24.533 | 1.00132.88 | O |
| ATOM | 1600 | N | ARG | A | 305 | 41.679 115.908 | 22.703 | 1.00110.57 | N |
| ATOM | 1601 | CA | ARG | A | 305 | 40.530 116.107 | 21.827 | 1.00104.23 | C |
| ATOM | 1602 | C | ARG | A | 305 | 40.665 117.327 | 20.915 | 1.00103.35 | C |
| ATOM | 1603 | O | ARG | A | 305 | 40.159 117.320 | 19.799 | 1.00 99.22 | O |
| ATOM | 1604 | CB | ARG | A | 305 | 39.228 116.181 | 22.628 | 1.00103.60 | C |
| ATOM | 1605 | CG | ARG | A | 305 | 37.987 116.372 | 21.768 | 1.00102.68 | C |
| ATOM | 1606 | CD | ARG | A | 305 | 37.900 115.293 | 20.697 | 1.00100.04 | C |
| ATOM | 1607 | NE | ARG | A | 305 | 36.892 115.582 | 19.682 | 1.00101.30 | N |
| ATOM | 1608 | CZ | ARG | A | 305 | 35.676 115.049 | 19.656 | 1.00103.82 | C |
| ATOM | 1609 | NH1 | ARG | A | 305 | 35.311 114.188 | 20.601 | 1.00105.30 | N |
| ATOM | 1610 | NH2 | ARG | A | 305 | 34.829 115.356 | 18.680 | 1.00 98.33 | N |
| ATOM | 1611 | N | ILE | A | 306 | 41.337 118.373 | 21.386 | 1.00106.84 | N |
| ATOM | 1612 | CA | ILE | A | 306 | 41.494 119.578 | 20.576 | 1.00105.51 | C |

FIG.8-31

| | | | | | | | | | | |
|---|---|---|---|---|---|---|---|---|---|---|
| ATOM | 1613 | C | ILE | A | 306 | 42.411 | 119.330 | 19.384 | 1.00105.46 | C |
| ATOM | 1614 | O | ILE | A | 306 | 42.952 | 119.623 | 18.241 | 1.00104.60 | O |
| ATOM | 1615 | CB | ILE | A | 306 | 42.954 | 120.772 | 21.386 | 1.00101.78 | C |
| ATOM | 1616 | CG1 | ILE | A | 306 | 41.876 | 121.197 | 22.485 | 1.00103.08 | C |
| ATOM | 1617 | CG2 | ILE | A | 306 | 42.357 | 121.948 | 20.461 | 1.00 98.57 | C |
| ATOM | 1618 | CD1 | ILE | A | 306 | 39.841 | 121.301 | 21.375 | 1.00103.32 | C |
| ATOM | 1619 | N | LEU | A | 307 | 43.599 | 118.794 | 19.651 | 1.00104.63 | N |
| ATOM | 1620 | CA | LEU | A | 307 | 44.595 | 118.640 | 18.596 | 1.00104.64 | C |
| ATOM | 1621 | C | LEU | A | 307 | 44.321 | 117.416 | 17.718 | 1.00104.19 | C |
| ATOM | 1622 | O | LEU | A | 307 | 44.861 | 117.302 | 16.620 | 1.00104.42 | O |
| ATOM | 1623 | CB | LEU | A | 307 | 46.021 | 118.644 | 19.164 | 1.00102.76 | C |
| ATOM | 1624 | CG | LEU | A | 307 | 46.601 | 117.389 | 19.815 | 1.00102.53 | C |
| ATOM | 1625 | CD1 | LEU | A | 307 | 47.730 | 117.767 | 20.763 | 1.00 96.33 | C |
| ATOM | 1626 | CD2 | LEU | A | 307 | 45.537 | 116.627 | 20.962 | 1.00106.84 | C |
| ATOM | 1627 | N | GLU | A | 308 | 43.468 | 116.516 | 18.285 | 1.00102.97 | N |
| ATOM | 1628 | CA | GLU | A | 308 | 42.973 | 115.395 | 17.399 | 1.00 96.43 | C |
| ATOM | 1629 | C | GLU | A | 308 | 42.006 | 115.921 | 16.338 | 1.00 91.56 | C |
| ATOM | 1630 | O | GLU | A | 308 | 41.858 | 115.337 | 15.266 | 1.00 91.17 | O |
| ATOM | 1631 | CB | GLU | A | 308 | 42.234 | 114.356 | 18.290 | 1.00 98.24 | C |
| ATOM | 1632 | CG | GLU | A | 308 | 41.345 | 113.418 | 17.566 | 1.00 98.81 | C |
| ATOM | 1633 | CD | GLU | A | 308 | 40.093 | 112.413 | 18.506 | 1.00100.67 | C |
| ATOM | 1634 | OE1 | GLU | A | 308 | 41.437 | 111.700 | 19.222 | 1.00 99.31 | O |
| ATOM | 1635 | OE2 | GLU | A | 308 | 39.450 | 112.335 | 18.526 | 1.00102.21 | O |
| ATOM | 1636 | N | LEU | A | 309 | 41.344 | 117.029 | 16.643 | 1.00 89.36 | N |
| ATOM | 1637 | CA | LEU | A | 309 | 40.526 | 117.705 | 15.649 | 1.00 94.75 | C |
| ATOM | 1638 | C | LEU | A | 309 | 41.420 | 118.588 | 14.773 | 1.00 96.63 | C |
| ATOM | 1639 | O | LEU | A | 309 | 41.207 | 118.784 | 13.563 | 1.00 93.37 | O |
| ATOM | 1640 | CB | LEU | A | 309 | 39.428 | 118.508 | 16.326 | 1.00 95.84 | C |
| ATOM | 1641 | CG | LEU | A | 309 | 38.279 | 117.715 | 16.929 | 1.00 92.35 | C |
| ATOM | 1642 | CD1 | LEU | A | 309 | 37.432 | 118.576 | 17.863 | 1.00 90.06 | C |
| ATOM | 1643 | CD2 | LEU | A | 309 | 37.411 | 117.086 | 15.828 | 1.00 91.73 | C |
| ATOM | 1644 | N | TYR | A | 310 | 42.433 | 119.165 | 15.399 | 1.00 97.33 | N |
| ATOM | 1645 | CA | TYR | A | 310 | 43.484 | 120.003 | 14.702 | 1.00 98.07 | C |
| ATOM | 1646 | C | TYR | A | 310 | 44.197 | 119.212 | 13.660 | 1.00 96.99 | C |
| ATOM | 1647 | O | TYR | A | 310 | 44.242 | 119.586 | 12.488 | 1.00 86.11 | O |
| ATOM | 1648 | CB | TYR | A | 310 | 44.349 | 120.652 | 15.713 | 1.00 96.40 | C |
| ATOM | 1649 | CG | TYR | A | 310 | 45.363 | 121.588 | 15.107 | 1.00 98.76 | C |
| ATOM | 1650 | CD1 | TYR | A | 310 | 45.120 | 122.955 | 15.030 | 1.00 99.83 | C |
| ATOM | 1651 | CD2 | TYR | A | 310 | 46.571 | 121.109 | 14.624 | 1.00100.19 | C |
| ATOM | 1652 | CE1 | TYR | A | 310 | 46.055 | 123.814 | 14.481 | 1.00104.08 | C |
| ATOM | 1653 | CE2 | TYR | A | 310 | 47.511 | 121.952 | 14.070 | 1.00102.99 | C |
| ATOM | 1654 | CZ | TYR | A | 310 | 47.251 | 123.305 | 14.001 | 1.00105.73 | C |
| ATOM | 1655 | OH | TYR | A | 310 | 48.195 | 124.143 | 13.448 | 1.00106.45 | O |
| ATOM | 1656 | N | MET | A | 311 | 44.814 | 118.115 | 14.090 | 1.00 90.37 | N |
| ATOM | 1657 | CA | MET | A | 311 | 45.656 | 117.314 | 13.203 | 1.00 88.87 | C |
| ATOM | 1658 | C | MET | A | 311 | 44.852 | 116.635 | 12.103 | 1.00 81.25 | C |
| ATOM | 1659 | O | MET | A | 311 | 45.413 | 115.992 | 11.222 | 1.00 81.62 | O |
| ATOM | 1660 | CB | MET | A | 311 | 46.442 | 116.265 | 13.994 | 1.00 83.21 | C |
| ATOM | 1661 | CG | MET | A | 311 | 47.313 | 116.832 | 15.160 | 1.00 81.33 | C |
| ATOM | 1662 | SD | MET | A | 311 | 48.171 | 115.566 | 16.008 | 1.00133.23 | S |
| ATOM | 1663 | CE | MET | A | 311 | 49.783 | 115.824 | 15.275 | 1.00 81.79 | C |
| ATOM | 1664 | N | ASN | A | 312 | 43.535 | 116.771 | 12.161 | 1.00 81.66 | N |
| ATOM | 1665 | CA | ASN | A | 312 | 42.674 | 116.230 | 11.116 | 1.00 80.45 | C |
| ATOM | 1666 | C | ASN | A | 312 | 42.004 | 117.398 | 10.243 | 1.00 81.01 | C |
| ATOM | 1667 | O | ASN | A | 312 | 41.309 | 116.998 | 9.280 | 1.00 77.23 | O |
| ATOM | 1668 | CB | ASN | A | 312 | 41.630 | 115.283 | 11.725 | 1.00 80.68 | C |
| ATOM | 1669 | CG | ASN | A | 312 | 42.179 | 113.873 | 11.961 | 1.00 79.15 | C |
| ATOM | 1670 | OD1 | ASN | A | 312 | 42.087 | 113.008 | 11.091 | 1.00 79.32 | O |
| ATOM | 1671 | ND2 | ASN | A | 312 | 42.725 | 113.645 | 13.145 | 1.00 75.35 | N |
| ATOM | 1672 | N | GLU | A | 313 | 42.230 | 118.581 | 10.565 | 1.00 87.76 | N |
| ATOM | 1673 | CA | GLU | A | 313 | 41.562 | 119.684 | 9.861 | 1.00 91.75 | C |
| ATOM | 1674 | C | GLU | A | 313 | 42.496 | 120.556 | 9.011 | 1.00 93.46 | C |
| ATOM | 1675 | O | GLU | A | 313 | 42.064 | 121.097 | 7.986 | 1.00 98.55 | O |
| ATOM | 1676 | CB | GLU | A | 313 | 40.788 | 120.561 | 10.860 | 1.00 97.70 | C |
| ATOM | 1677 | CG | GLU | A | 313 | 40.804 | 121.991 | 10.393 | 1.00101.39 | C |
| ATOM | 1678 | CD | GLU | A | 313 | 39.279 | 122.100 | 9.481 | 1.00103.61 | C |
| ATOM | 1679 | OE1 | GLU | A | 313 | 39.466 | 122.650 | 8.365 | 1.00102.69 | O |
| ATOM | 1680 | OE2 | GLU | A | 313 | 38.188 | 121.645 | 9.889 | 1.00103.79 | O |
| ATOM | 1681 | N | VAL | A | 314 | 43.749 | 120.683 | 9.439 | 1.00 90.60 | N |
| ATOM | 1682 | CA | VAL | A | 314 | 44.712 | 121.608 | 8.830 | 1.00 87.36 | C |
| ATOM | 1683 | C | VAL | A | 314 | 44.938 | 121.452 | 7.320 | 1.00 85.85 | C |
| ATOM | 1684 | O | VAL | A | 314 | 45.024 | 120.333 | 6.814 | 1.00 83.42 | O |
| ATOM | 1685 | CB | VAL | A | 314 | 46.079 | 121.483 | 9.519 | 1.00 83.74 | C |
| ATOM | 1686 | CG1 | VAL | A | 314 | 46.019 | 122.044 | 10.941 | 1.00 85.56 | C |
| ATOM | 1687 | CG2 | VAL | A | 314 | 46.538 | 120.023 | 9.518 | 1.00 71.04 | C |
| ATOM | 1688 | N | TYR | A | 315 | 45.653 | 122.579 | 6.613 | 1.00 85.70 | N |
| ATOM | 1689 | CA | TYR | A | 315 | 45.300 | 122.566 | 5.166 | 1.00 88.84 | C |

FIG. 8-32

| | | | | | | | | | | | |
|---|---|---|---|---|---|---|---|---|---|---|---|
| ATOM | 1690 | C | TYR | A | 315 | 46.754 | 122.233 | 4.840 | 1.00 | 88.63 | C |
| ATOM | 1691 | O | TYR | A | 315 | 47.656 | 123.001 | 5.159 | 1.00 | 91.26 | O |
| ATOM | 1692 | CB | TYR | A | 315 | 44.921 | 123.806 | 4.518 | 1.00 | 89.19 | C |
| ATOM | 1693 | CG | TYR | A | 315 | 45.031 | 123.804 | 2.998 | 1.00 | 90.30 | C |
| ATOM | 1694 | CD1 | TYR | A | 315 | 46.125 | 124.474 | 2.352 | 1.00 | 90.73 | C |
| ATOM | 1695 | CD2 | TYR | A | 315 | 44.043 | 123.320 | 2.214 | 1.00 | 89.40 | C |
| ATOM | 1696 | CE1 | TYR | A | 315 | 46.228 | 124.466 | 0.969 | 1.00 | 90.57 | C |
| ATOM | 1697 | CE2 | TYR | A | 315 | 44.138 | 123.304 | 0.834 | 1.00 | 90.07 | C |
| ATOM | 1698 | CZ | TYR | A | 315 | 45.228 | 123.678 | 0.213 | 1.00 | 90.39 | C |
| ATOM | 1699 | OH | TYR | A | 315 | 45.313 | 123.855 | -1.164 | 1.00 | 86.77 | O |
| ATOM | 1700 | N | LEU | A | 316 | 46.982 | 121.096 | 4.191 | 1.00 | 88.47 | N |
| ATOM | 1701 | CA | LEU | A | 316 | 48.347 | 120.687 | 3.882 | 1.00 | 89.86 | C |
| ATOM | 1702 | C | LEU | A | 316 | 48.605 | 120.477 | 2.394 | 1.00 | 91.89 | C |
| ATOM | 1703 | O | LEU | A | 316 | 49.747 | 120.262 | 1.993 | 1.00 | 97.70 | O |
| ATOM | 1704 | CB | LEU | A | 316 | 48.742 | 119.433 | 4.676 | 1.00 | 87.44 | C |
| ATOM | 1705 | CG | LEU | A | 316 | 48.969 | 119.624 | 6.178 | 1.00 | 85.32 | C |
| ATOM | 1706 | CD1 | LEU | A | 316 | 49.255 | 118.296 | 6.855 | 1.00 | 80.61 | C |
| ATOM | 1707 | CD2 | LEU | A | 316 | 50.097 | 120.618 | 6.434 | 1.00 | 86.11 | C |
| ATOM | 1708 | N | GLY | A | 317 | 47.565 | 120.947 | 1.570 | 1.00 | 89.81 | N |
| ATOM | 1709 | CA | GLY | A | 317 | 47.766 | 120.358 | 0.143 | 1.00 | 91.09 | C |
| ATOM | 1710 | C | GLY | A | 317 | 46.580 | 120.598 | -0.774 | 1.00 | 93.11 | C |
| ATOM | 1711 | O | GLY | A | 317 | 45.478 | 120.936 | -0.337 | 1.00 | 94.82 | O |
| ATOM | 1712 | N | GLN | A | 318 | 46.817 | 120.811 | -2.087 | 1.00 | 93.35 | N |
| ATOM | 1713 | CA | GLN | A | 318 | 45.790 | 120.621 | -3.077 | 1.00 | 96.72 | C |
| ATOM | 1714 | C | GLN | A | 318 | 45.954 | 119.617 | -4.214 | 1.00 | 101.18 | C |
| ATOM | 1715 | O | GLN | A | 318 | 46.936 | 119.662 | -4.959 | 1.00 | 105.14 | O |
| ATOM | 1716 | CB | GLN | A | 318 | 45.871 | 122.049 | -3.623 | 1.00 | 96.91 | C |
| ATOM | 1717 | CG | GLN | A | 318 | 44.823 | 122.379 | -4.666 | 1.00 | 98.07 | C |
| ATOM | 1718 | CD | GLN | A | 318 | 43.442 | 122.595 | -4.087 | 1.00 | 100.29 | C |
| ATOM | 1719 | OE1 | GLN | A | 318 | 42.457 | 122.759 | -4.784 | 1.00 | 101.40 | O |
| ATOM | 1720 | NE2 | GLN | A | 318 | 43.361 | 122.485 | -2.744 | 1.00 | 99.31 | N |
| ATOM | 1721 | N | SER | A | 319 | 44.998 | 118.706 | -4.344 | 1.00 | 100.04 | N |
| ATOM | 1722 | CA | SER | A | 319 | 45.020 | 117.753 | -5.444 | 1.00 | 99.26 | C |
| ATOM | 1723 | C | SER | A | 319 | 44.010 | 118.169 | -6.510 | 1.00 | 100.93 | C |
| ATOM | 1724 | O | SER | A | 319 | 42.811 | 117.927 | -6.373 | 1.00 | 99.12 | O |
| ATOM | 1725 | CB | SER | A | 319 | 44.724 | 116.341 | -4.941 | 1.00 | 95.68 | C |
| ATOM | 1726 | OG | SER | A | 319 | 45.268 | 115.369 | -5.818 | 1.00 | 94.28 | O |
| ATOM | 1727 | N | GLY | A | 320 | 44.502 | 118.800 | -7.571 | 1.00 | 104.40 | N |
| ATOM | 1728 | CA | GLY | A | 320 | 43.626 | 119.336 | -8.596 | 1.00 | 107.43 | C |
| ATOM | 1729 | C | GLY | A | 320 | 42.731 | 120.411 | -8.009 | 1.00 | 109.33 | C |
| ATOM | 1730 | O | GLY | A | 320 | 43.170 | 121.545 | -7.792 | 1.00 | 112.07 | O |
| ATOM | 1731 | N | ASP | A | 321 | 41.475 | 120.062 | -7.751 | 1.00 | 106.15 | N |
| ATOM | 1732 | CA | ASP | A | 321 | 40.569 | 120.981 | -7.071 | 1.00 | 111.41 | C |
| ATOM | 1733 | C | ASP | A | 321 | 39.939 | 120.335 | -5.843 | 1.00 | 106.25 | C |
| ATOM | 1734 | O | ASP | A | 321 | 38.782 | 120.614 | -5.489 | 1.00 | 105.07 | O |
| ATOM | 1735 | CB | ASP | A | 321 | 39.511 | 121.556 | -8.023 | 1.00 | 120.65 | C |
| ATOM | 1736 | CG | ASP | A | 321 | 39.145 | 120.601 | -9.143 | 1.00 | 124.08 | C |
| ATOM | 1737 | OD1 | ASP | A | 321 | 38.440 | 119.606 | -8.869 | 1.00 | 125.11 | O |
| ATOM | 1738 | OD2 | ASP | A | 321 | 39.553 | 120.858 | -10.299 | 1.00 | 122.75 | O |
| ATOM | 1739 | N | ASN | A | 322 | 40.710 | 119.461 | -5.205 | 1.00 | 100.80 | N |
| ATOM | 1740 | CA | ASN | A | 322 | 40.359 | 118.831 | -3.896 | 1.00 | 96.36 | C |
| ATOM | 1741 | C | ASN | A | 322 | 41.367 | 119.400 | -2.850 | 1.00 | 92.74 | C |
| ATOM | 1742 | O | ASN | A | 322 | 42.578 | 119.360 | -3.073 | 1.00 | 89.62 | O |
| ATOM | 1743 | CB | ASN | A | 322 | 40.277 | 117.400 | -3.919 | 1.00 | 94.21 | C |
| ATOM | 1744 | CG | ASN | A | 322 | 39.004 | 116.891 | -4.590 | 1.00 | 93.28 | C |
| ATOM | 1745 | OD1 | ASN | A | 322 | 37.960 | 117.544 | -4.534 | 1.00 | 99.38 | O |
| ATOM | 1746 | ND2 | ASN | A | 322 | 39.086 | 115.717 | -5.194 | 1.00 | 87.29 | N |
| ATOM | 1747 | N | GLU | A | 323 | 40.859 | 119.871 | -1.718 | 1.00 | 92.45 | N |
| ATOM | 1748 | CA | GLU | A | 323 | 41.719 | 120.301 | -0.632 | 1.00 | 94.06 | C |
| ATOM | 1749 | C | GLU | A | 323 | 42.205 | 119.066 | 0.098 | 1.00 | 87.84 | C |
| ATOM | 1750 | O | GLU | A | 323 | 41.406 | 118.212 | 0.480 | 1.00 | 82.34 | O |
| ATOM | 1751 | CB | GLU | A | 323 | 40.948 | 121.188 | 0.346 | 1.00 | 102.03 | C |
| ATOM | 1752 | CG | GLU | A | 323 | 39.895 | 122.067 | -0.299 | 1.00 | 110.82 | C |
| ATOM | 1753 | CD | GLU | A | 323 | 40.461 | 123.357 | -0.851 | 1.00 | 122.02 | C |
| ATOM | 1754 | OE1 | GLU | A | 323 | 39.997 | 123.836 | -1.898 | 1.00 | 136.24 | O |
| ATOM | 1755 | OE2 | GLU | A | 323 | 41.413 | 123.891 | -0.239 | 1.00 | 135.65 | O |
| ATOM | 1756 | N | ILE | A | 324 | 43.514 | 118.958 | 0.282 | 1.00 | 88.62 | N |
| ATOM | 1757 | CA | ILE | A | 324 | 44.048 | 117.933 | 1.163 | 1.00 | 85.39 | C |
| ATOM | 1758 | C | ILE | A | 324 | 44.282 | 118.593 | 2.531 | 1.00 | 91.86 | C |
| ATOM | 1759 | O | ILE | A | 324 | 45.139 | 119.431 | 2.698 | 1.00 | 96.46 | O |
| ATOM | 1760 | CB | ILE | A | 324 | 45.370 | 117.341 | 0.648 | 1.00 | 84.50 | C |
| ATOM | 1761 | CG1 | ILE | A | 324 | 45.294 | 116.968 | -0.829 | 1.00 | 87.53 | C |
| ATOM | 1762 | CG2 | ILE | A | 324 | 45.746 | 116.128 | 1.960 | 1.00 | 79.38 | C |
| ATOM | 1763 | CD1 | ILE | A | 324 | 44.197 | 115.924 | -1.111 | 1.00 | 88.77 | C |
| ATOM | 1764 | N | ARG | A | 325 | 43.497 | 118.116 | 3.508 | 1.00 | 87.65 | N |
| ATOM | 1765 | CA | ARG | A | 325 | 43.694 | 118.565 | 4.872 | 1.00 | 84.12 | C |
| ATOM | 1766 | C | ARG | A | 325 | 43.777 | 117.387 | 5.828 | 1.00 | 80.37 | C |

FIG. 8-33

| | | | | | | | | | | | |
|---|---|---|---|---|---|---|---|---|---|---|---|
| ATOM | 1767 | O | ARG | A | 325 | 43.310 | 116.286 | 5.518 | 1.00 | 71.15 | O |
| ATOM | 1768 | CB | ARG | A | 325 | 42.621 | 119.566 | 5.291 | 1.00 | 87.38 | C |
| ATOM | 1769 | CG | ARG | A | 325 | 41.221 | 119.257 | 4.819 | 1.00 | 87.60 | C |
| ATOM | 1770 | CD | ARG | A | 325 | 40.483 | 120.567 | 4.609 | 1.00 | 92.64 | C |
| ATOM | 1771 | NE | ARG | A | 325 | 40.868 | 121.568 | 5.591 | 1.00 | 96.89 | N |
| ATOM | 1772 | CZ | ARG | A | 325 | 40.670 | 122.876 | 5.474 | 1.00 | 98.07 | C |
| ATOM | 1773 | NH1 | ARG | A | 325 | 40.054 | 123.360 | 4.403 | 1.00 | 96.83 | N |
| ATOM | 1774 | NH2 | ARG | A | 325 | 41.076 | 123.702 | 6.430 | 1.00 | 99.06 | N |
| ATOM | 1775 | N | GLY | A | 326 | 44.393 | 117.832 | 6.982 | 1.00 | 85.80 | N |
| ATOM | 1776 | CA | GLY | A | 326 | 44.724 | 116.982 | 7.925 | 1.00 | 85.13 | C |
| ATOM | 1777 | C | GLY | A | 326 | 46.108 | 116.023 | 7.652 | 1.00 | 82.84 | C |
| ATOM | 1778 | O | GLY | A | 326 | 46.517 | 115.893 | 6.494 | 1.00 | 79.46 | O |
| ATOM | 1779 | N | PHE | A | 327 | 46.832 | 115.696 | 8.719 | 1.00 | 80.40 | N |
| ATOM | 1780 | CA | PHE | A | 327 | 48.134 | 115.041 | 8.601 | 1.00 | 82.57 | C |
| ATOM | 1781 | C | PHE | A | 327 | 48.049 | 113.617 | 8.050 | 1.00 | 84.09 | C |
| ATOM | 1782 | O | PHE | A | 327 | 48.913 | 113.194 | 7.286 | 1.00 | 87.26 | O |
| ATOM | 1783 | CB | PHE | A | 327 | 48.855 | 115.030 | 9.946 | 1.00 | 81.49 | C |
| ATOM | 1784 | CG | PHE | A | 327 | 49.571 | 116.309 | 10.259 | 1.00 | 80.72 | C |
| ATOM | 1785 | CD1 | PHE | A | 327 | 50.941 | 116.318 | 10.069 | 1.00 | 81.88 | C |
| ATOM | 1786 | CD2 | PHE | A | 327 | 48.878 | 117.405 | 10.740 | 1.00 | 84.82 | C |
| ATOM | 1787 | CE1 | PHE | A | 327 | 51.612 | 117.596 | 10.364 | 1.00 | 85.56 | C |
| ATOM | 1788 | CE2 | PHE | A | 327 | 49.544 | 118.594 | 11.040 | 1.00 | 88.63 | C |
| ATOM | 1789 | CZ | PHE | A | 327 | 50.911 | 118.687 | 10.846 | 1.00 | 86.61 | C |
| ATOM | 1790 | N | PRO | A | 328 | 47.008 | 112.869 | 8.445 | 1.00 | 82.26 | N |
| ATOM | 1791 | CA | PRO | A | 328 | 46.835 | 111.489 | 7.972 | 1.00 | 84.02 | C |
| ATOM | 1792 | C | PRO | A | 328 | 46.841 | 111.348 | 6.448 | 1.00 | 85.21 | C |
| ATOM | 1793 | O | PRO | A | 328 | 47.640 | 110.581 | 5.906 | 1.00 | 88.09 | O |
| ATOM | 1794 | CB | PRO | A | 328 | 45.459 | 111.112 | 8.518 | 1.00 | 83.39 | C |
| ATOM | 1795 | CG | PRO | A | 328 | 45.289 | 111.968 | 9.725 | 1.00 | 80.69 | C |
| ATOM | 1796 | CD | PRO | A | 328 | 45.951 | 113.264 | 9.391 | 1.00 | 80.11 | C |
| ATOM | 1797 | N | LEU | A | 329 | 45.952 | 112.066 | 5.766 | 1.00 | 82.09 | N |
| ATOM | 1798 | CA | LEU | A | 329 | 45.869 | 111.899 | 4.311 | 1.00 | 79.88 | C |
| ATOM | 1799 | C | LEU | A | 329 | 47.108 | 112.652 | 3.691 | 1.00 | 79.97 | C |
| ATOM | 1800 | O | LEU | A | 329 | 47.576 | 112.181 | 2.615 | 1.00 | 79.18 | O |
| ATOM | 1801 | CB | LEU | A | 329 | 44.605 | 112.644 | 3.798 | 1.00 | 84.66 | C |
| ATOM | 1802 | CG | LEU | A | 329 | 44.273 | 112.470 | 2.318 | 1.00 | 84.88 | C |
| ATOM | 1803 | CD1 | LEU | A | 329 | 44.353 | 111.001 | 1.925 | 1.00 | 85.11 | C |
| ATOM | 1804 | CD2 | LEU | A | 329 | 42.891 | 113.039 | 2.023 | 1.00 | 82.62 | C |
| ATOM | 1805 | N | ALA | A | 330 | 47.594 | 113.735 | 4.247 | 1.00 | 80.08 | N |
| ATOM | 1806 | CA | ALA | A | 330 | 48.758 | 114.435 | 3.712 | 1.00 | 79.37 | C |
| ATOM | 1807 | C | ALA | A | 330 | 49.989 | 113.539 | 3.718 | 1.00 | 84.60 | C |
| ATOM | 1808 | O | ALA | A | 330 | 50.792 | 113.584 | 2.785 | 1.00 | 90.33 | O |
| ATOM | 1809 | CB | ALA | A | 330 | 49.025 | 115.720 | 4.484 | 1.00 | 78.60 | C |
| ATOM | 1810 | N | SER | A | 331 | 50.138 | 112.730 | 4.767 | 1.00 | 82.53 | N |
| ATOM | 1811 | CA | SER | A | 331 | 51.261 | 111.794 | 4.861 | 1.00 | 79.68 | C |
| ATOM | 1812 | C | SER | A | 331 | 51.298 | 110.891 | 3.637 | 1.00 | 75.09 | C |
| ATOM | 1813 | O | SER | A | 331 | 52.332 | 110.759 | 2.985 | 1.00 | 78.26 | O |
| ATOM | 1814 | CB | SER | A | 331 | 51.155 | 110.923 | 6.118 | 1.00 | 79.52 | C |
| ATOM | 1815 | OG | SER | A | 331 | 51.397 | 111.675 | 7.292 | 1.00 | 89.78 | O |
| ATOM | 1816 | N | LEU | A | 332 | 50.165 | 110.260 | 3.337 | 1.00 | 71.25 | N |
| ATOM | 1817 | CA | LEU | A | 332 | 50.090 | 109.360 | 2.196 | 1.00 | 71.71 | C |
| ATOM | 1818 | C | LEU | A | 332 | 50.176 | 110.127 | 0.880 | 1.00 | 73.03 | C |
| ATOM | 1819 | O | LEU | A | 332 | 50.668 | 109.608 | -0.115 | 1.00 | 79.68 | O |
| ATOM | 1820 | CB | LEU | A | 332 | 48.828 | 108.502 | 2.270 | 1.00 | 70.33 | C |
| ATOM | 1821 | CG | LEU | A | 332 | 48.877 | 107.487 | 3.423 | 1.00 | 76.91 | C |
| ATOM | 1822 | CD1 | LEU | A | 332 | 47.482 | 107.036 | 3.838 | 1.00 | 78.40 | C |
| ATOM | 1823 | CD2 | LEU | A | 332 | 49.741 | 106.283 | 3.060 | 1.00 | 75.57 | C |
| ATOM | 1824 | N | TYR | A | 333 | 49.739 | 111.376 | 0.889 | 1.00 | 72.27 | N |
| ATOM | 1825 | CA | TYR | A | 333 | 49.734 | 112.191 | -0.323 | 1.00 | 78.93 | C |
| ATOM | 1826 | C | TYR | A | 333 | 51.131 | 112.663 | -0.741 | 1.00 | 82.76 | C |
| ATOM | 1827 | O | TYR | A | 333 | 51.437 | 112.724 | -1.930 | 1.00 | 85.10 | O |
| ATOM | 1828 | CB | TYR | A | 333 | 48.801 | 113.388 | -0.142 | 1.00 | 82.58 | C |
| ATOM | 1829 | CG | TYR | A | 333 | 48.558 | 114.195 | -1.393 | 1.00 | 87.78 | C |
| ATOM | 1830 | CD1 | TYR | A | 333 | 48.966 | 115.521 | -1.475 | 1.00 | 92.71 | C |
| ATOM | 1831 | CD2 | TYR | A | 333 | 47.908 | 113.639 | -2.487 | 1.00 | 87.30 | C |
| ATOM | 1832 | CE1 | TYR | A | 333 | 48.741 | 116.268 | -2.615 | 1.00 | 92.28 | C |
| ATOM | 1833 | CE2 | TYR | A | 333 | 47.676 | 114.380 | -3.630 | 1.00 | 86.67 | C |
| ATOM | 1834 | CZ | TYR | A | 333 | 48.095 | 115.693 | -3.689 | 1.00 | 90.16 | C |
| ATOM | 1835 | OH | TYR | A | 333 | 47.869 | 116.436 | -4.828 | 1.00 | 89.70 | O |
| ATOM | 1836 | N | TYR | A | 334 | 51.972 | 112.997 | 0.232 | 1.00 | 86.17 | N |
| ATOM | 1837 | CA | TYR | A | 334 | 53.318 | 113.517 | -0.051 | 1.00 | 86.49 | C |
| ATOM | 1838 | C | TYR | A | 334 | 54.432 | 112.465 | -0.030 | 1.00 | 85.39 | C |
| ATOM | 1839 | O | TYR | A | 334 | 55.387 | 112.548 | -0.804 | 1.00 | 87.28 | O |
| ATOM | 1840 | CB | TYR | A | 334 | 53.669 | 114.660 | 0.904 | 1.00 | 85.32 | C |
| ATOM | 1841 | CG | TYR | A | 334 | 52.941 | 115.934 | 0.579 | 1.00 | 85.22 | C |
| ATOM | 1842 | CD1 | TYR | A | 334 | 53.287 | 116.685 | -0.534 | 1.00 | 86.10 | C |
| ATOM | 1843 | CD2 | TYR | A | 334 | 51.896 | 116.379 | 1.373 | 1.00 | 88.21 | C |

FIG. 8-34

| | | | | | | | | | | | |
|---|---|---|---|---|---|---|---|---|---|---|---|
| ATOM | 1844 | CE1 | TYR | A | 334 | 52.614 | 117.850 | -0.847 | 1.00 | 91.22 | C |
| ATOM | 1845 | CE2 | TYR | A | 334 | 51.218 | 117.541 | 1.071 | 1.00 | 92.24 | C |
| ATOM | 1846 | CZ | TYR | A | 334 | 51.576 | 118.274 | -0.040 | 1.00 | 95.08 | C |
| ATOM | 1847 | OH | TYR | A | 334 | 50.900 | 119.437 | -0.345 | 1.00 | 98.94 | O |
| ATOM | 1848 | N | PHE | A | 335 | 54.306 | 111.480 | 0.854 | 1.00 | 85.43 | N |
| ATOM | 1849 | CA | PHE | A | 335 | 55.340 | 110.464 | 1.018 | 1.00 | 92.78 | C |
| ATOM | 1850 | C | PHE | A | 335 | 54.822 | 109.040 | 0.842 | 1.00 | 99.82 | C |
| ATOM | 1851 | O | PHE | A | 335 | 55.603 | 108.093 | 0.809 | 1.00 | 103.56 | O |
| ATOM | 1852 | CB | PHE | A | 335 | 55.984 | 110.554 | 2.395 | 1.00 | 95.44 | C |
| ATOM | 1853 | CG | PHE | A | 335 | 56.606 | 111.934 | 2.649 | 1.00 | 99.58 | C |
| ATOM | 1854 | CD1 | PHE | A | 335 | 57.817 | 112.273 | 2.064 | 1.00 | 99.99 | C |
| ATOM | 1855 | CD2 | PHE | A | 335 | 55.988 | 112.851 | 3.483 | 1.00 | 101.82 | C |
| ATOM | 1856 | CE1 | PHE | A | 335 | 58.387 | 113.503 | 2.301 | 1.00 | 103.89 | C |
| ATOM | 1857 | CE2 | PHE | A | 335 | 56.564 | 114.086 | 3.709 | 1.00 | 104.47 | C |
| ATOM | 1858 | CZ | PHE | A | 335 | 57.770 | 114.413 | 3.137 | 1.00 | 105.63 | C |
| ATOM | 1859 | N | GLY | A | 336 | 53.507 | 108.887 | 0.737 | 1.00 | 102.03 | N |
| ATOM | 1860 | CA | GLY | A | 336 | 52.909 | 107.572 | 0.603 | 1.00 | 101.35 | C |
| ATOM | 1861 | C | GLY | A | 336 | 53.174 | 106.704 | 1.820 | 1.00 | 103.90 | C |
| ATOM | 1862 | O | GLY | A | 336 | 53.215 | 105.488 | 1.718 | 1.00 | 108.40 | O |
| ATOM | 1863 | N | ARG | A | 337 | 53.364 | 107.336 | 2.974 | 1.00 | 98.00 | N |
| ATOM | 1864 | CA | ARG | A | 337 | 53.549 | 106.606 | 4.222 | 1.00 | 90.56 | C |
| ATOM | 1865 | C | ARG | A | 337 | 52.460 | 106.993 | 5.217 | 1.00 | 83.13 | C |
| ATOM | 1866 | O | ARG | A | 337 | 52.101 | 108.165 | 5.318 | 1.00 | 79.65 | O |
| ATOM | 1867 | CB | ARG | A | 337 | 54.931 | 106.894 | 4.834 | 1.00 | 81.80 | C |
| ATOM | 1868 | CG | ARG | A | 337 | 55.953 | 107.489 | 3.868 | 1.00 | 88.62 | C |
| ATOM | 1869 | CD | ARG | A | 337 | 57.362 | 106.974 | 4.127 | 1.00 | 86.70 | C |
| ATOM | 1870 | NE | ARG | A | 337 | 57.779 | 107.131 | 5.514 | 1.00 | 92.51 | N |
| ATOM | 1871 | CZ | ARG | A | 337 | 59.045 | 107.061 | 5.924 | 1.00 | 97.75 | C |
| ATOM | 1872 | NH1 | ARG | A | 337 | 59.342 | 107.224 | 7.207 | 1.00 | 101.39 | N |
| ATOM | 1873 | NH2 | ARG | A | 337 | 60.017 | 106.835 | 5.051 | 1.00 | 97.43 | N |
| ATOM | 1874 | N | PRO | A | 338 | 51.930 | 106.007 | 5.957 | 1.00 | 81.14 | N |
| ATOM | 1875 | CA | PRO | A | 338 | 50.994 | 106.286 | 7.048 | 1.00 | 80.34 | C |
| ATOM | 1876 | C | PRO | A | 338 | 51.576 | 107.329 | 7.992 | 1.00 | 84.52 | C |
| ATOM | 1877 | O | PRO | A | 338 | 52.779 | 107.314 | 8.245 | 1.00 | 88.81 | O |
| ATOM | 1878 | CB | PRO | A | 338 | 50.886 | 104.940 | 7.763 | 1.00 | 80.36 | C |
| ATOM | 1879 | CG | PRO | A | 338 | 51.162 | 103.942 | 6.710 | 1.00 | 81.90 | C |
| ATOM | 1880 | CD | PRO | A | 338 | 52.176 | 104.564 | 5.798 | 1.00 | 83.29 | C |
| ATOM | 1881 | N | VAL | A | 339 | 50.735 | 108.229 | 8.494 | 1.00 | 82.83 | N |
| ATOM | 1882 | CA | VAL | A | 339 | 51.190 | 109.297 | 9.378 | 1.00 | 81.41 | C |
| ATOM | 1883 | C | VAL | A | 339 | 52.006 | 108.727 | 10.524 | 1.00 | 88.30 | C |
| ATOM | 1884 | O | VAL | A | 339 | 52.965 | 109.348 | 10.986 | 1.00 | 93.55 | O |
| ATOM | 1885 | CB | VAL | A | 339 | 50.005 | 110.064 | 9.979 | 1.00 | 74.60 | C |
| ATOM | 1886 | CG1 | VAL | A | 339 | 48.978 | 109.087 | 10.524 | 1.00 | 72.01 | C |
| ATOM | 1887 | CG2 | VAL | A | 339 | 50.477 | 111.025 | 11.071 | 1.00 | 72.83 | C |
| ATOM | 1888 | N | GLU | A | 340 | 51.616 | 107.540 | 10.974 | 1.00 | 91.92 | N |
| ATOM | 1889 | CA | GLU | A | 340 | 52.241 | 106.906 | 12.126 | 1.00 | 98.61 | C |
| ATOM | 1890 | C | GLU | A | 340 | 53.706 | 106.586 | 11.867 | 1.00 | 95.21 | C |
| ATOM | 1891 | O | GLU | A | 340 | 54.440 | 106.251 | 12.788 | 1.00 | 99.50 | O |
| ATOM | 1892 | CB | GLU | A | 340 | 51.492 | 105.620 | 12.493 | 1.00 | 100.83 | C |
| ATOM | 1893 | CG | GLU | A | 340 | 51.885 | 105.046 | 13.844 | 1.00 | 103.67 | C |
| ATOM | 1894 | CD | GLU | A | 340 | 51.429 | 103.612 | 14.044 | 1.00 | 102.99 | C |
| ATOM | 1895 | OE1 | GLU | A | 340 | 51.118 | 103.245 | 15.200 | 1.00 | 107.82 | O |
| ATOM | 1896 | OE2 | GLU | A | 340 | 51.363 | 102.851 | 13.054 | 1.00 | 95.41 | O |
| ATOM | 1897 | N | GLU | A | 341 | 54.133 | 106.696 | 10.614 | 1.00 | 91.20 | N |
| ATOM | 1898 | CA | GLU | A | 341 | 55.447 | 106.197 | 10.228 | 1.00 | 87.39 | C |
| ATOM | 1899 | C | GLU | A | 341 | 56.397 | 107.250 | 9.613 | 1.00 | 91.42 | C |
| ATOM | 1900 | O | GLU | A | 341 | 57.421 | 106.931 | 9.097 | 1.00 | 93.13 | O |
| ATOM | 1901 | CB | GLU | A | 341 | 55.281 | 105.028 | 9.273 | 1.00 | 81.83 | C |
| ATOM | 1902 | CG | GLU | A | 341 | 54.219 | 104.064 | 9.730 | 1.00 | 82.34 | C |
| ATOM | 1903 | CD | GLU | A | 341 | 54.126 | 102.872 | 8.836 | 1.00 | 93.38 | C |
| ATOM | 1904 | OE1 | GLU | A | 341 | 53.238 | 102.029 | 9.068 | 1.00 | 99.59 | O |
| ATOM | 1905 | OE2 | GLU | A | 341 | 54.941 | 102.788 | 7.893 | 1.00 | 99.19 | O |
| ATOM | 1906 | N | LEU | A | 342 | 55.837 | 108.504 | 9.681 | 1.00 | 90.57 | N |
| ATOM | 1907 | CA | LEU | A | 342 | 56.757 | 109.590 | 9.196 | 1.00 | 94.30 | C |
| ATOM | 1908 | C | LEU | A | 342 | 58.105 | 109.615 | 9.914 | 1.00 | 106.22 | C |
| ATOM | 1909 | O | LEU | A | 342 | 58.189 | 109.355 | 11.116 | 1.00 | 111.16 | O |
| ATOM | 1910 | CB | LEU | A | 342 | 56.039 | 110.916 | 9.416 | 1.00 | 93.38 | C |
| ATOM | 1911 | CG | LEU | A | 342 | 54.940 | 111.207 | 8.407 | 1.00 | 94.33 | C |
| ATOM | 1912 | CD1 | LEU | A | 342 | 54.840 | 112.656 | 8.566 | 1.00 | 96.52 | C |
| ATOM | 1913 | CD2 | LEU | A | 342 | 55.480 | 110.969 | 7.009 | 1.00 | 94.53 | C |
| ATOM | 1914 | N | SER | A | 343 | 59.163 | 109.917 | 9.170 | 1.00 | 108.25 | N |
| ATOM | 1915 | CA | SER | A | 343 | 60.437 | 110.259 | 9.784 | 1.00 | 108.76 | C |
| ATOM | 1916 | C | SER | A | 343 | 60.341 | 111.697 | 10.289 | 1.00 | 109.39 | C |
| ATOM | 1917 | O | SER | A | 343 | 59.420 | 112.427 | 9.920 | 1.00 | 109.33 | O |
| ATOM | 1918 | CB | SER | A | 343 | 61.582 | 110.101 | 8.782 | 1.00 | 109.22 | C |
| ATOM | 1919 | OG | SER | A | 343 | 61.248 | 110.638 | 7.513 | 1.00 | 104.42 | O |
| ATOM | 1920 | N | LEU | A | 344 | 61.279 | 112.105 | 11.137 | 1.00 | 109.83 | N |

FIG. 8-35

| | | | | | | | | | | |
|---|---|---|---|---|---|---|---|---|---|---|
| ATOM | 1921 | CA | LEU | A | 344 | 61.185 | 113.415 | 11.772 | 1.00109.84 | C |
| ATOM | 1922 | C | LEU | A | 344 | 61.313 | 114.944 | 10.750 | 1.00114.01 | C |
| ATOM | 1923 | O | LEU | A | 344 | 60.688 | 115.697 | 10.889 | 1.00114.63 | O |
| ATOM | 1924 | CB | LEU | A | 344 | 62.234 | 113.555 | 12.872 | 1.00112.28 | C |
| ATOM | 1925 | CG | LEU | A | 344 | 61.986 | 114.599 | 13.967 | 1.00110.64 | C |
| ATOM | 1926 | CD1 | LEU | A | 344 | 60.936 | 114.112 | 14.952 | 1.00110.38 | C |
| ATOM | 1927 | CD2 | LEU | A | 344 | 63.277 | 114.909 | 14.686 | 1.00107.91 | C |
| ATOM | 1928 | N | ASP | A | 345 | 62.121 | 114.311 | 9.723 | 1.00117.13 | N |
| ATOM | 1929 | CA | ASP | A | 345 | 62.234 | 115.263 | 8.629 | 1.00116.70 | C |
| ATOM | 1930 | C | ASP | A | 345 | 60.989 | 115.460 | 7.868 | 1.00113.33 | C |
| ATOM | 1931 | O | ASP | A | 345 | 60.657 | 116.573 | 7.483 | 1.00115.63 | O |
| ATOM | 1932 | CB | ASP | A | 345 | 63.363 | 114.757 | 7.663 | 1.00117.84 | C |
| ATOM | 1933 | CG | ASP | A | 345 | 63.133 | 113.316 | 7.250 | 1.00117.50 | C |
| ATOM | 1934 | OD1 | ASP | A | 345 | 63.604 | 112.406 | 7.968 | 1.00116.54 | O |
| ATOM | 1935 | OD2 | ASP | A | 345 | 62.479 | 113.096 | 6.206 | 1.00117.84 | O |
| ATOM | 1936 | N | GLN | A | 346 | 60.260 | 114.368 | 7.666 | 1.00105.45 | N |
| ATOM | 1937 | CA | GLN | A | 346 | 58.965 | 114.429 | 6.999 | 1.00103.08 | C |
| ATOM | 1938 | C | GLN | A | 346 | 57.930 | 115.092 | 7.901 | 1.00105.50 | C |
| ATOM | 1939 | O | GLN | A | 346 | 57.014 | 115.760 | 7.420 | 1.00107.99 | O |
| ATOM | 1940 | CB | GLN | A | 346 | 58.509 | 113.029 | 6.587 | 1.00 97.39 | C |
| ATOM | 1941 | CG | GLN | A | 346 | 59.418 | 112.379 | 5.551 | 1.00 97.33 | C |
| ATOM | 1942 | CD | GLN | A | 346 | 59.183 | 110.879 | 5.429 | 1.00 97.87 | C |
| ATOM | 1943 | OE1 | GLN | A | 346 | 58.793 | 110.215 | 6.383 | 1.00 97.05 | O |
| ATOM | 1944 | NE2 | GLN | A | 346 | 59.459 | 110.340 | 4.241 | 1.00 97.76 | N |
| ATOM | 1945 | N | GLN | A | 347 | 58.086 | 114.908 | 9.211 | 1.00104.95 | N |
| ATOM | 1946 | CA | GLN | A | 347 | 57.201 | 115.531 | 10.192 | 1.00106.57 | C |
| ATOM | 1947 | C | GLN | A | 347 | 57.409 | 117.042 | 10.235 | 1.00105.77 | C |
| ATOM | 1948 | O | GLN | A | 347 | 56.453 | 117.810 | 10.344 | 1.00108.43 | O |
| ATOM | 1949 | CB | GLN | A | 347 | 57.431 | 114.929 | 11.590 | 1.00110.93 | C |
| ATOM | 1950 | CG | GLN | A | 347 | 56.739 | 113.592 | 11.801 | 1.00112.57 | C |
| ATOM | 1951 | CD | GLN | A | 347 | 57.429 | 112.757 | 12.860 | 1.00115.40 | C |
| ATOM | 1952 | OE1 | GLN | A | 347 | 58.645 | 112.781 | 12.980 | 1.00118.18 | O |
| ATOM | 1953 | NE2 | GLN | A | 347 | 56.644 | 112.005 | 13.629 | 1.00115.40 | N |
| ATOM | 1954 | N | ALA | A | 348 | 58.665 | 117.462 | 10.146 | 1.00100.16 | N |
| ATOM | 1955 | CA | ALA | A | 348 | 59.001 | 118.879 | 10.128 | 1.00103.39 | C |
| ATOM | 1956 | C | ALA | A | 348 | 58.411 | 119.550 | 8.897 | 1.00103.66 | C |
| ATOM | 1957 | O | ALA | A | 348 | 57.976 | 120.701 | 8.946 | 1.00104.18 | O |
| ATOM | 1958 | CB | ALA | A | 348 | 60.508 | 119.058 | 10.150 | 1.00104.60 | C |
| ATOM | 1959 | N | LEU | A | 349 | 58.406 | 118.817 | 7.789 | 1.00101.89 | N |
| ATOM | 1960 | CA | LEU | A | 349 | 57.899 | 119.337 | 6.530 | 1.00102.90 | C |
| ATOM | 1961 | C | LEU | A | 349 | 56.408 | 119.633 | 6.631 | 1.00102.96 | C |
| ATOM | 1962 | O | LEU | A | 349 | 55.988 | 120.787 | 6.525 | 1.00105.23 | O |
| ATOM | 1963 | CB | LEU | A | 349 | 58.163 | 118.344 | 5.402 | 1.00101.25 | C |
| ATOM | 1964 | CG | LEU | A | 349 | 57.761 | 118.836 | 4.019 | 1.00103.59 | C |
| ATOM | 1965 | CD1 | LEU | A | 349 | 58.470 | 120.142 | 3.698 | 1.00107.68 | C |
| ATOM | 1966 | CD2 | LEU | A | 349 | 58.083 | 117.782 | 2.997 | 1.00101.89 | C |
| ATOM | 1967 | N | LEU | A | 350 | 55.613 | 118.586 | 6.836 | 1.00 99.31 | N |
| ATOM | 1968 | CA | LEU | A | 350 | 54.179 | 118.750 | 7.019 | 1.00 94.20 | C |
| ATOM | 1969 | C | LEU | A | 350 | 53.895 | 119.876 | 7.994 | 1.00 96.94 | C |
| ATOM | 1970 | O | LEU | A | 350 | 53.239 | 120.855 | 7.649 | 1.00101.59 | O |
| ATOM | 1971 | CB | LEU | A | 350 | 53.527 | 117.481 | 7.880 | 1.00 90.37 | C |
| ATOM | 1972 | CG | LEU | A | 350 | 53.045 | 116.535 | 6.371 | 1.00 85.93 | C |
| ATOM | 1973 | CD1 | LEU | A | 350 | 54.229 | 116.108 | 5.513 | 1.00 88.16 | C |
| ATOM | 1974 | CD2 | LEU | A | 350 | 52.309 | 115.321 | 6.906 | 1.00 81.61 | C |
| ATOM | 1975 | N | VAL | A | 351 | 54.407 | 119.740 | 9.211 | 1.00 95.72 | N |
| ATOM | 1976 | CA | VAL | A | 351 | 54.188 | 120.754 | 10.229 | 1.00 97.43 | C |
| ATOM | 1977 | C | VAL | A | 351 | 54.551 | 122.125 | 9.688 | 1.00 99.87 | C |
| ATOM | 1978 | O | VAL | A | 351 | 53.802 | 123.082 | 9.853 | 1.00102.00 | O |
| ATOM | 1979 | CB | VAL | A | 351 | 54.998 | 120.469 | 11.501 | 1.00 95.10 | C |
| ATOM | 1980 | CG1 | VAL | A | 351 | 55.148 | 121.727 | 12.311 | 1.00 96.48 | C |
| ATOM | 1981 | CG2 | VAL | A | 351 | 54.322 | 119.374 | 12.319 | 1.00 91.71 | C |
| ATOM | 1982 | N | GLY | A | 352 | 55.760 | 122.213 | 9.029 | 1.00 99.73 | N |
| ATOM | 1983 | CA | GLY | A | 352 | 56.122 | 123.459 | 8.420 | 1.00103.27 | C |
| ATOM | 1984 | C | GLY | A | 352 | 55.091 | 123.977 | 7.435 | 1.00104.08 | C |
| ATOM | 1985 | O | GLY | A | 352 | 54.785 | 125.165 | 7.415 | 1.00103.91 | O |
| ATOM | 1986 | N | MET | A | 353 | 54.540 | 123.080 | 6.622 | 1.00102.84 | N |
| ATOM | 1987 | CA | MET | A | 353 | 53.584 | 123.485 | 5.604 | 1.00103.70 | C |
| ATOM | 1988 | C | MET | A | 353 | 52.311 | 124.056 | 6.207 | 1.00105.66 | C |
| ATOM | 1989 | O | MET | A | 353 | 51.482 | 124.609 | 5.486 | 1.00108.28 | O |
| ATOM | 1990 | CB | MET | A | 353 | 53.212 | 122.319 | 4.704 | 1.00102.98 | C |
| ATOM | 1991 | CG | MET | A | 353 | 54.372 | 121.623 | 4.041 | 1.00104.78 | C |
| ATOM | 1992 | SD | MET | A | 353 | 53.767 | 120.655 | 2.693 | 1.00115.66 | S |
| ATOM | 1993 | CE | MET | A | 353 | 54.781 | 119.189 | 2.777 | 1.00171.08 | C |
| ATOM | 1994 | N | VAL | A | 354 | 52.144 | 123.916 | 7.519 | 1.00105.44 | N |
| ATOM | 1995 | CA | VAL | A | 354 | 50.916 | 124.371 | 8.168 | 1.00110.18 | C |
| ATOM | 1996 | C | VAL | A | 354 | 50.718 | 125.884 | 8.040 | 1.00113.63 | C |
| ATOM | 1997 | O | VAL | A | 354 | 49.587 | 126.361 | 7.923 | 1.00113.01 | O |

FIG. 8-36

| | | | | | | | | | | |
|---|---|---|---|---|---|---|---|---|---|---|
| ATOM | 1998 | CB | VAL | A | 354 | 50.856 | 123.967 | 9.660 | 1.00113.86 | C |
| ATOM | 1999 | CG1 | VAL | A | 354 | 51.713 | 124.802 | 10.586 | 1.00119.76 | C |
| ATOM | 2000 | CG2 | VAL | A | 354 | 49.417 | 123.986 | 10.154 | 1.00113.08 | C |
| ATOM | 2001 | N | LYS | A | 355 | 51.818 | 126.633 | 8.053 | 1.00116.17 | N |
| ATOM | 2002 | CA | LYS | A | 355 | 51.752 | 128.087 | 7.964 | 1.00119.06 | C |
| ATOM | 2003 | C | LYS | A | 355 | 51.342 | 128.571 | 6.582 | 1.00119.66 | C |
| ATOM | 2004 | O | LYS | A | 355 | 51.126 | 129.766 | 6.382 | 1.00123.44 | O |
| ATOM | 2005 | CB | LYS | A | 355 | 53.088 | 128.719 | 8.350 | 1.00122.82 | C |
| ATOM | 2006 | CG | LYS | A | 355 | 53.138 | 129.067 | 9.822 | 1.00126.97 | C |
| ATOM | 2007 | CD | LYS | A | 355 | 54.181 | 130.210 | 10.035 | 1.00130.43 | C |
| ATOM | 2008 | CE | LYS | A | 355 | 54.050 | 130.813 | 11.426 | 1.00130.67 | C |
| ATOM | 2009 | NZ | LYS | A | 355 | 54.879 | 132.041 | 11.568 | 1.00133.17 | N |
| ATOM | 2010 | N | GLY | A | 356 | 51.240 | 127.642 | 5.634 | 1.00115.39 | N |
| ATOM | 2011 | CA | GLY | A | 356 | 50.882 | 127.971 | 4.264 | 1.00114.69 | C |
| ATOM | 2012 | C | GLY | A | 356 | 51.296 | 126.882 | 3.292 | 1.00112.88 | C |
| ATOM | 2013 | O | GLY | A | 356 | 52.344 | 126.967 | 2.651 | 1.00111.42 | O |
| ATOM | 2014 | N | ALA | A | 357 | 50.456 | 125.858 | 3.176 | 1.00112.71 | N |
| ATOM | 2015 | CA | ALA | A | 357 | 50.788 | 124.662 | 2.410 | 1.00112.81 | C |
| ATOM | 2016 | C | ALA | A | 357 | 50.990 | 124.912 | 0.916 | 1.00118.56 | C |
| ATOM | 2017 | O | ALA | A | 357 | 51.770 | 124.211 | 0.272 | 1.00117.83 | O |
| ATOM | 2018 | CB | ALA | A | 357 | 49.734 | 123.591 | 2.628 | 1.00110.41 | C |
| ATOM | 2019 | N | SER | A | 358 | 50.287 | 125.898 | 0.365 | 1.00118.29 | N |
| ATOM | 2020 | CA | SER | A | 358 | 50.394 | 126.194 | -1.064 | 1.00118.76 | C |
| ATOM | 2021 | C | SER | A | 358 | 51.749 | 126.792 | -1.453 | 1.00120.97 | C |
| ATOM | 2022 | O | SER | A | 358 | 52.288 | 126.472 | -2.515 | 1.00120.32 | O |
| ATOM | 2023 | CB | SER | A | 358 | 49.250 | 127.098 | -1.532 | 1.00120.32 | C |
| ATOM | 2024 | OG | SER | A | 358 | 48.108 | 126.334 | -1.887 | 1.00120.17 | O |
| ATOM | 2025 | N | ILE | A | 359 | 52.237 | 127.653 | -0.597 | 1.00122.33 | N |
| ATOM | 2026 | CA | ILE | A | 359 | 53.595 | 128.269 | -0.874 | 1.00124.32 | C |
| ATOM | 2027 | C | ILE | A | 359 | 54.769 | 127.417 | -0.388 | 1.00122.26 | C |
| ATOM | 2028 | O | ILE | A | 359 | 55.908 | 127.615 | -0.811 | 1.00122.93 | O |
| ATOM | 2029 | CB | ILE | A | 359 | 53.781 | 129.707 | -0.309 | 1.00129.78 | C |
| ATOM | 2030 | CG1 | ILE | A | 359 | 53.875 | 129.782 | 1.084 | 1.00131.96 | C |
| ATOM | 2031 | CG2 | ILE | A | 359 | 53.839 | 130.706 | -1.252 | 1.00130.09 | C |
| ATOM | 2032 | CD1 | ILE | A | 359 | 54.015 | 129.409 | 2.198 | 1.00133.19 | C |
| ATOM | 2033 | N | TYR | A | 360 | 54.487 | 126.465 | 0.492 | 1.00120.43 | N |
| ATOM | 2034 | CA | TYR | A | 360 | 55.511 | 125.525 | 0.930 | 1.00119.16 | C |
| ATOM | 2035 | C | TYR | A | 360 | 55.398 | 124.208 | 0.168 | 1.00111.94 | C |
| ATOM | 2036 | O | TYR | A | 360 | 56.130 | 123.255 | 0.437 | 1.00108.88 | O |
| ATOM | 2037 | CB | TYR | A | 360 | 55.428 | 125.280 | 2.440 | 1.00121.21 | C |
| ATOM | 2038 | CG | TYR | A | 360 | 55.718 | 126.530 | 3.251 | 1.00123.78 | C |
| ATOM | 2039 | CD1 | TYR | A | 360 | 56.688 | 127.445 | 2.838 | 1.00125.18 | C |
| ATOM | 2040 | CD2 | TYR | A | 360 | 55.029 | 126.781 | 4.433 | 1.00128.07 | C |
| ATOM | 2041 | CE1 | TYR | A | 360 | 56.932 | 128.584 | 3.576 | 1.00130.37 | C |
| ATOM | 2042 | CE2 | TYR | A | 360 | 55.287 | 127.917 | 5.181 | 1.00129.57 | C |
| ATOM | 2043 | CZ | TYR | A | 360 | 56.240 | 128.816 | 4.747 | 1.00131.56 | C |
| ATOM | 2044 | OH | TYR | A | 360 | 56.903 | 129.949 | 5.486 | 1.00133.21 | O |
| ATOM | 2045 | N | ASN | A | 361 | 54.481 | 124.174 | -0.791 | 1.00111.38 | N |
| ATOM | 2046 | CA | ASN | A | 361 | 54.274 | 123.002 | -1.627 | 1.00112.89 | C |
| ATOM | 2047 | C | ASN | A | 361 | 55.588 | 122.466 | -2.191 | 1.00117.96 | C |
| ATOM | 2048 | O | ASN | A | 361 | 56.234 | 123.130 | -3.003 | 1.00121.73 | O |
| ATOM | 2049 | CB | ASN | A | 361 | 53.303 | 123.337 | -2.758 | 1.00110.87 | C |
| ATOM | 2050 | CG | ASN | A | 361 | 52.881 | 122.115 | -3.546 | 1.00108.45 | C |
| ATOM | 2051 | OD1 | ASN | A | 361 | 53.720 | 121.395 | -4.093 | 1.00109.00 | O |
| ATOM | 2052 | ND2 | ASN | A | 361 | 51.573 | 121.877 | -3.618 | 1.00108.83 | N |
| ATOM | 2053 | N | PRO | A | 362 | 55.984 | 121.258 | -1.753 | 1.00118.16 | N |
| ATOM | 2054 | CA | PRO | A | 362 | 57.259 | 120.611 | -2.087 | 1.00118.11 | C |
| ATOM | 2055 | C | PRO | A | 362 | 57.404 | 120.280 | -3.580 | 1.00118.31 | C |
| ATOM | 2056 | O | PRO | A | 362 | 58.527 | 120.261 | -4.084 | 1.00120.07 | O |
| ATOM | 2057 | CB | PRO | A | 362 | 57.230 | 119.315 | -1.278 | 1.00116.54 | C |
| ATOM | 2058 | CG | PRO | A | 362 | 56.254 | 119.569 | -0.180 | 1.00117.54 | C |
| ATOM | 2059 | CD | PRO | A | 362 | 55.210 | 120.456 | -0.782 | 1.00117.59 | C |
| ATOM | 2060 | N | TRP | A | 363 | 56.300 | 120.006 | -4.266 | 1.00118.76 | N |
| ATOM | 2061 | CA | TRP | A | 363 | 56.376 | 119.741 | -5.688 | 1.00115.81 | C |
| ATOM | 2062 | C | TRP | A | 363 | 56.606 | 121.047 | -6.470 | 1.00111.16 | C |
| ATOM | 2063 | O | TRP | A | 363 | 57.577 | 121.164 | -7.219 | 1.00106.83 | O |
| ATOM | 2064 | CB | TRP | A | 363 | 55.126 | 119.085 | -6.204 | 1.00119.07 | C |
| ATOM | 2065 | CG | TRP | A | 363 | 54.815 | 117.693 | -5.493 | 1.00122.17 | C |
| ATOM | 2066 | CD1 | TRP | A | 363 | 53.838 | 117.481 | -4.560 | 1.00122.02 | C |
| ATOM | 2067 | CD2 | TRP | A | 363 | 55.472 | 116.425 | -5.676 | 1.00124.37 | C |
| ATOM | 2068 | NE1 | TRP | A | 363 | 53.849 | 116.169 | -4.148 | 1.00121.83 | N |
| ATOM | 2069 | CE2 | TRP | A | 363 | 54.840 | 115.499 | -4.816 | 1.00123.96 | C |
| ATOM | 2070 | CE3 | TRP | A | 363 | 56.530 | 115.984 | -6.479 | 1.00126.88 | C |
| ATOM | 2071 | CZ2 | TRP | A | 363 | 55.234 | 114.157 | -4.736 | 1.00124.83 | C |
| ATOM | 2072 | CZ3 | TRP | A | 363 | 56.921 | 114.646 | -6.399 | 1.00126.83 | C |
| ATOM | 2073 | CH2 | TRP | A | 363 | 56.272 | 113.751 | -5.533 | 1.00129.14 | C |
| ATOM | 2074 | N | ARG | A | 364 | 55.726 | 122.029 | -6.266 | 1.00110.32 | N |

FIG. 8-37

| | | | | | | | | | | |
|---|---|---|---|---|---|---|---|---|---|---|
| ATOM | 2075 | CA | ARG | A | 364 | 55.815 | 123.381 | -6.956 | 1.00111.87 | C |
| ATOM | 2076 | C | ARG | A | 364 | 57.166 | 124.019 | -6.782 | 1.00115.44 | C |
| ATOM | 2077 | O | ARG | A | 364 | 57.898 | 124.009 | -7.690 | 1.00116.39 | O |
| ATOM | 2078 | CB | ARG | A | 364 | 54.687 | 124.258 | -6.516 | 1.00113.62 | C |
| ATOM | 2079 | CG | ARG | A | 364 | 53.503 | 124.235 | -7.465 | 1.00115.45 | C |
| ATOM | 2080 | CD | ARG | A | 364 | 52.754 | 122.977 | -7.464 | 1.00117.26 | C |
| ATOM | 2081 | NE | ARG | A | 364 | 51.707 | 122.940 | -8.482 | 1.00121.65 | N |
| ATOM | 2082 | CZ | ARG | A | 364 | 51.838 | 122.392 | -9.668 | 1.00124.72 | C |
| ATOM | 2083 | NH1 | ARG | A | 364 | 52.975 | 121.747 | -9.989 | 1.00125.17 | N |
| ATOM | 2084 | NH2 | ARG | A | 364 | 50.830 | 122.368 | -10.535 | 1.00124.24 | N |
| ATOM | 2085 | N | ASN | A | 365 | 57.378 | 124.644 | -5.627 | 1.00116.55 | N |
| ATOM | 2086 | CA | ASN | A | 365 | 58.674 | 125.233 | -5.313 | 1.00121.18 | C |
| ATOM | 2087 | C | ASN | A | 365 | 59.336 | 124.610 | -4.084 | 1.00120.86 | C |
| ATOM | 2088 | O | ASN | A | 365 | 59.016 | 124.958 | -2.950 | 1.00120.77 | O |
| ATOM | 2089 | CB | ASN | A | 365 | 58.603 | 126.765 | -5.202 | 1.00126.07 | C |
| ATOM | 2090 | CG | ASN | A | 365 | 57.376 | 127.249 | -4.453 | 1.00127.88 | C |
| ATOM | 2091 | OD1 | ASN | A | 365 | 56.612 | 126.456 | -3.839 | 1.00126.85 | O |
| ATOM | 2092 | ND2 | ASN | A | 365 | 57.182 | 128.566 | -4.434 | 1.00130.23 | N |
| ATOM | 2093 | N | PRO | A | 366 | 60.272 | 123.680 | -4.328 | 1.00121.23 | N |
| ATOM | 2094 | CA | PRO | A | 366 | 60.986 | 122.866 | -3.335 | 1.00122.35 | C |
| ATOM | 2095 | C | PRO | A | 366 | 62.006 | 123.645 | -2.509 | 1.00125.76 | C |
| ATOM | 2096 | O | PRO | A | 366 | 62.587 | 123.080 | -1.578 | 1.00124.43 | O |
| ATOM | 2097 | CB | PRO | A | 366 | 61.730 | 121.838 | -4.200 | 1.00120.89 | C |
| ATOM | 2098 | CG | PRO | A | 366 | 61.031 | 121.907 | -5.551 | 1.00119.72 | C |
| ATOM | 2099 | CD | PRO | A | 366 | 60.655 | 123.319 | -5.700 | 1.00120.79 | C |
| ATOM | 2100 | N | LYS | A | 367 | 62.230 | 124.912 | -2.848 | 1.00128.74 | N |
| ATOM | 2101 | CA | LYS | A | 367 | 63.263 | 125.696 | -2.178 | 1.00130.57 | C |
| ATOM | 2102 | C | LYS | A | 367 | 62.782 | 126.374 | -0.903 | 1.00131.73 | C |
| ATOM | 2103 | O | LYS | A | 367 | 63.327 | 126.171 | 0.171 | 1.00132.10 | O |
| ATOM | 2104 | CB | LYS | A | 367 | 63.897 | 126.700 | -3.140 | 1.00133.47 | C |
| ATOM | 2105 | CG | LYS | A | 367 | 64.829 | 126.047 | -4.152 | 1.00133.16 | C |
| ATOM | 2106 | CD | LYS | A | 367 | 65.418 | 127.062 | -5.117 | 1.00136.33 | C |
| ATOM | 2107 | CE | LYS | A | 367 | 66.289 | 126.378 | -6.160 | 1.00135.65 | C |
| ATOM | 2108 | NZ | LYS | A | 367 | 66.700 | 127.313 | -7.243 | 1.00137.86 | N |
| ATOM | 2109 | N | LEU | A | 368 | 61.703 | 127.171 | -1.013 | 1.00132.86 | N |
| ATOM | 2110 | CA | LEU | A | 368 | 61.087 | 127.743 | 0.181 | 1.00134.76 | C |
| ATOM | 2111 | C | LEU | A | 368 | 60.360 | 126.652 | 0.964 | 1.00135.06 | C |
| ATOM | 2112 | O | LEU | A | 368 | 59.831 | 126.934 | 1.918 | 1.00135.90 | O |
| ATOM | 2113 | CB | LEU | A | 368 | 60.142 | 128.895 | -0.165 | 1.00133.55 | C |
| ATOM | 2114 | CG | LEU | A | 368 | 60.845 | 130.190 | -0.563 | 1.00136.17 | C |
| ATOM | 2115 | CD1 | LEU | A | 368 | 59.980 | 131.400 | -0.247 | 1.00138.41 | C |
| ATOM | 2116 | CD2 | LEU | A | 368 | 62.186 | 130.293 | 0.138 | 1.00137.88 | C |
| ATOM | 2117 | N | ALA | A | 369 | 60.567 | 125.405 | 0.545 | 1.00131.88 | N |
| ATOM | 2118 | CA | ALA | A | 369 | 60.046 | 124.243 | 1.257 | 1.00132.25 | C |
| ATOM | 2119 | C | ALA | A | 369 | 61.152 | 123.568 | 2.070 | 1.00133.48 | C |
| ATOM | 2120 | O | ALA | A | 369 | 60.941 | 123.187 | 3.223 | 1.00133.70 | O |
| ATOM | 2121 | CB | ALA | A | 369 | 59.409 | 123.293 | 0.282 | 1.00128.54 | C |
| ATOM | 2122 | N | LEU | A | 370 | 62.331 | 123.425 | 1.469 | 1.00133.49 | N |
| ATOM | 2123 | CA | LEU | A | 370 | 63.466 | 122.829 | 2.168 | 1.00132.34 | C |
| ATOM | 2124 | C | LEU | A | 370 | 64.087 | 123.834 | 3.134 | 1.00138.18 | C |
| ATOM | 2125 | O | LEU | A | 370 | 64.764 | 123.453 | 4.088 | 1.00141.40 | O |
| ATOM | 2126 | CB | LEU | A | 370 | 64.510 | 122.303 | 1.176 | 1.00128.12 | C |
| ATOM | 2127 | CG | LEU | A | 370 | 65.471 | 121.228 | 1.702 | 1.00125.27 | C |
| ATOM | 2128 | CD1 | LEU | A | 370 | 65.934 | 120.305 | 0.582 | 1.00123.60 | C |
| ATOM | 2129 | CD2 | LEU | A | 370 | 66.663 | 121.838 | 2.422 | 1.00125.95 | C |
| ATOM | 2130 | N | GLU | A | 371 | 63.846 | 125.119 | 2.885 | 1.00139.34 | N |
| ATOM | 2131 | CA | GLU | A | 371 | 64.339 | 126.173 | 3.768 | 1.00141.73 | C |
| ATOM | 2132 | C | GLU | A | 371 | 63.384 | 126.384 | 4.940 | 1.00141.81 | C |
| ATOM | 2133 | O | GLU | A | 371 | 63.767 | 126.841 | 5.970 | 1.00144.56 | O |
| ATOM | 2134 | CB | GLU | A | 371 | 64.544 | 127.482 | 2.991 | 1.00143.74 | C |
| ATOM | 2135 | CG | GLU | A | 371 | 65.245 | 128.585 | 3.785 | 1.00146.98 | C |
| ATOM | 2136 | CD | GLU | A | 371 | 65.690 | 129.794 | 2.930 | 1.00150.30 | C |
| ATOM | 2137 | OE1 | GLU | A | 371 | 65.238 | 129.805 | 1.734 | 1.00151.30 | O |
| ATOM | 2138 | OE2 | GLU | A | 371 | 66.240 | 130.733 | 3.452 | 1.00151.32 | O |
| ATOM | 2139 | N | ARG | A | 372 | 62.142 | 125.834 | 4.778 | 1.00138.74 | N |
| ATOM | 2140 | CA | ARG | A | 372 | 61.142 | 126.020 | 5.841 | 1.00138.28 | C |
| ATOM | 2141 | C | ARG | A | 372 | 61.082 | 124.698 | 6.603 | 1.00133.43 | C |
| ATOM | 2142 | O | ARG | A | 372 | 60.718 | 124.657 | 7.779 | 1.00132.58 | O |
| ATOM | 2143 | CB | ARG | A | 372 | 59.766 | 126.380 | 5.265 | 1.00138.42 | C |
| ATOM | 2144 | CG | ARG | A | 372 | 58.811 | 127.061 | 6.249 | 1.00140.32 | C |
| ATOM | 2145 | CD | ARG | A | 372 | 58.055 | 126.093 | 7.106 | 1.00138.62 | C |
| ATOM | 2146 | NE | ARG | A | 372 | 56.973 | 126.671 | 7.874 | 1.00138.26 | N |
| ATOM | 2147 | CZ | ARG | A | 372 | 57.094 | 126.984 | 9.161 | 1.00137.34 | C |
| ATOM | 2148 | NH1 | ARG | A | 372 | 58.169 | 126.762 | 9.838 | 1.00137.20 | N |
| ATOM | 2149 | NH2 | ARG | A | 372 | 56.017 | 127.547 | 9.774 | 1.00137.55 | N |
| ATOM | 2150 | N | ARG | A | 373 | 61.441 | 123.617 | 5.920 | 1.00130.64 | N |
| ATOM | 2151 | CA | ARG | A | 373 | 61.578 | 122.315 | 6.557 | 1.00127.11 | C |

FIG.8-38

| | | | | | | | | | | |
|---|---|---|---|---|---|---|---|---|---|---|
| ATOM | 2152 | C | ARG | A | 373 | 62.728 | 122.404 | 7.864 | 1.00131.18 | C |
| ATOM | 2153 | O | ARG | A | 373 | 62.588 | 122.040 | 8.734 | 1.00134.73 | O |
| ATOM | 2154 | CB | ARG | A | 373 | 61.956 | 121.248 | 5.496 | 1.00119.03 | C |
| ATOM | 2155 | CG | ARG | A | 373 | 61.646 | 119.804 | 5.905 | 1.00118.79 | C |
| ATOM | 2156 | CD | ARG | A | 373 | 62.302 | 119.212 | 6.968 | 1.00122.00 | C |
| ATOM | 2157 | NE | ARG | A | 373 | 64.097 | 118.488 | 5.731 | 1.00123.59 | N |
| ATOM | 2158 | CZ | ARG | A | 373 | 64.647 | 118.631 | 4.914 | 1.00116.98 | C |
| ATOM | 2159 | NH1 | ARG | A | 373 | 64.116 | 117.428 | 4.739 | 1.00105.67 | N |
| ATOM | 2160 | NH2 | ARG | A | 373 | 65.731 | 118.980 | 4.236 | 1.00118.80 | N |
| ATOM | 2161 | N | ASN | A | 374 | 63.063 | 122.916 | 7.103 | 1.00127.56 | N |
| ATOM | 2162 | CA | ASN | A | 374 | 63.839 | 123.055 | 7.949 | 1.00126.99 | C |
| ATOM | 2163 | C | ASN | A | 374 | 64.826 | 124.044 | 9.102 | 1.00129.52 | C |
| ATOM | 2164 | O | ASN | A | 374 | 65.313 | 123.818 | 10.206 | 1.00132.90 | O |
| ATOM | 2165 | CB | ASN | A | 374 | 66.265 | 123.425 | 7.109 | 1.00126.13 | C |
| ATOM | 2166 | CG | ASN | A | 374 | 66.626 | 122.345 | 6.081 | 1.00122.11 | C |
| ATOM | 2167 | OD1 | ASN | A | 374 | 65.818 | 121.463 | 5.774 | 1.00113.83 | O |
| ATOM | 2168 | ND2 | ASN | A | 374 | 67.845 | 122.415 | 5.563 | 1.00128.84 | N |
| ATOM | 2169 | N | LEU | A | 375 | 64.098 | 125.131 | 8.843 | 1.00127.80 | N |
| ATOM | 2170 | CA | LEU | A | 375 | 63.627 | 126.025 | 9.907 | 1.00125.55 | C |
| ATOM | 2171 | C | LEU | A | 375 | 63.049 | 125.241 | 11.081 | 1.00127.30 | C |
| ATOM | 2172 | O | LEU | A | 375 | 63.497 | 125.380 | 12.218 | 1.00126.92 | O |
| ATOM | 2173 | CB | LEU | A | 375 | 62.528 | 126.954 | 9.384 | 1.00122.79 | C |
| ATOM | 2174 | CG | LEU | A | 375 | 62.799 | 128.426 | 9.084 | 1.00125.10 | C |
| ATOM | 2175 | CD1 | LEU | A | 375 | 61.496 | 129.111 | 8.669 | 1.00122.93 | C |
| ATOM | 2176 | CD2 | LEU | A | 375 | 63.398 | 129.120 | 10.298 | 1.00128.20 | C |
| ATOM | 2177 | N | VAL | A | 376 | 62.636 | 124.427 | 10.791 | 1.00130.63 | N |
| ATOM | 2178 | CA | VAL | A | 376 | 61.345 | 123.653 | 11.815 | 1.00132.27 | C |
| ATOM | 2179 | C | VAL | A | 376 | 62.327 | 122.783 | 12.596 | 1.00134.81 | C |
| ATOM | 2180 | O | VAL | A | 376 | 62.308 | 122.770 | 13.826 | 1.00139.27 | O |
| ATOM | 2181 | CB | VAL | A | 376 | 60.244 | 122.783 | 11.208 | 1.00129.94 | C |
| ATOM | 2182 | CG1 | VAL | A | 376 | 59.656 | 121.845 | 12.270 | 1.00121.65 | C |
| ATOM | 2183 | CG2 | VAL | A | 376 | 59.154 | 123.623 | 10.578 | 1.00130.72 | C |
| ATOM | 2184 | N | LEU | A | 377 | 63.180 | 122.082 | 11.872 | 1.00130.78 | N |
| ATOM | 2185 | CA | LEU | A | 377 | 64.226 | 121.272 | 12.484 | 1.00130.15 | C |
| ATOM | 2186 | C | LEU | A | 377 | 65.058 | 122.104 | 13.482 | 1.00139.65 | C |
| ATOM | 2187 | O | LEU | A | 377 | 65.387 | 121.644 | 14.578 | 1.00142.93 | O |
| ATOM | 2188 | CB | LEU | A | 377 | 65.127 | 120.664 | 11.416 | 1.00123.75 | C |
| ATOM | 2189 | CG | LEU | A | 377 | 64.490 | 119.738 | 10.374 | 1.00115.97 | C |
| ATOM | 2190 | CD1 | LEU | A | 377 | 65.283 | 119.768 | 9.079 | 1.00116.35 | C |
| ATOM | 2191 | CD2 | LEU | A | 377 | 64.360 | 118.302 | 10.884 | 1.00107.63 | C |
| ATOM | 2192 | N | ARG | A | 378 | 65.378 | 123.339 | 13.091 | 1.00143.01 | N |
| ATOM | 2193 | CA | ARG | A | 378 | 66.209 | 124.219 | 13.908 | 1.00148.38 | C |
| ATOM | 2194 | C | ARG | A | 378 | 65.469 | 124.748 | 15.127 | 1.00148.20 | C |
| ATOM | 2195 | O | ARG | A | 378 | 65.790 | 125.826 | 15.620 | 1.00150.20 | O |
| ATOM | 2196 | CB | ARG | A | 378 | 66.711 | 125.402 | 13.078 | 1.00154.24 | C |
| ATOM | 2197 | CG | ARG | A | 378 | 67.352 | 125.016 | 11.797 | 1.00156.91 | C |
| ATOM | 2198 | CD | ARG | A | 378 | 67.621 | 126.235 | 10.880 | 1.00161.86 | C |
| ATOM | 2199 | NE | ARG | A | 378 | 67.624 | 125.882 | 9.461 | 1.00161.79 | N |
| ATOM | 2200 | CZ | ARG | A | 378 | 67.954 | 126.714 | 8.476 | 1.00162.48 | C |
| ATOM | 2201 | NH1 | ARG | A | 378 | 68.323 | 127.960 | 8.748 | 1.00163.86 | N |
| ATOM | 2202 | NH2 | ARG | A | 378 | 67.938 | 126.294 | 7.218 | 1.00159.93 | N |
| ATOM | 2203 | N | LEU | A | 379 | 64.483 | 124.004 | 15.613 | 1.00146.98 | N |
| ATOM | 2204 | CA | LEU | A | 379 | 63.679 | 124.463 | 16.732 | 1.00149.24 | C |
| ATOM | 2205 | C | LEU | A | 379 | 63.762 | 123.561 | 17.944 | 1.00149.87 | C |
| ATOM | 2206 | O | LEU | A | 379 | 64.138 | 123.997 | 19.035 | 1.00152.30 | O |
| ATOM | 2207 | CB | LEU | A | 379 | 62.222 | 124.687 | 16.308 | 1.00148.01 | C |
| ATOM | 2208 | CG | LEU | A | 379 | 61.979 | 125.589 | 15.090 | 1.00147.46 | C |
| ATOM | 2209 | CD1 | LEU | A | 379 | 60.498 | 125.873 | 14.914 | 1.00145.50 | C |
| ATOM | 2210 | CD2 | LEU | A | 379 | 62.756 | 126.888 | 15.203 | 1.00150.77 | C |
| ATOM | 2211 | N | VAL | A | 407 | 49.396 | 113.507 | -7.455 | 1.00168.50 | N |
| ATOM | 2212 | CA | VAL | A | 407 | 48.490 | 112.512 | -8.029 | 1.00168.61 | C |
| ATOM | 2213 | C | VAL | A | 407 | 47.035 | 112.857 | -7.718 | 1.00106.67 | C |
| ATOM | 2214 | O | VAL | A | 407 | 46.571 | 112.674 | -6.591 | 1.00106.31 | O |
| ATOM | 2215 | CB | VAL | A | 407 | 48.800 | 111.098 | -7.485 | 1.00111.98 | C |
| ATOM | 2216 | CG1 | VAL | A | 407 | 47.970 | 110.060 | -8.233 | 1.00109.28 | C |
| ATOM | 2217 | CG2 | VAL | A | 407 | 50.250 | 110.786 | -7.624 | 1.00113.57 | C |
| ATOM | 2218 | N | ILE | A | 408 | 46.319 | 113.354 | -8.724 | 1.00108.37 | N |
| ATOM | 2219 | CA | ILE | A | 408 | 44.935 | 113.808 | -8.533 | 1.00103.81 | C |
| ATOM | 2220 | C | ILE | A | 408 | 43.897 | 112.682 | -8.624 | 1.00 96.57 | C |
| ATOM | 2221 | O | ILE | A | 408 | 42.891 | 112.734 | -7.872 | 1.00 96.90 | O |
| ATOM | 2222 | CB | ILE | A | 408 | 44.583 | 114.961 | -9.480 | 1.00119.71 | C |
| ATOM | 2223 | CG1 | ILE | A | 408 | 43.062 | 115.137 | -9.632 | 1.00119.19 | C |
| ATOM | 2224 | CG2 | ILE | A | 408 | 45.248 | 114.781 | -10.848 | 1.00119.73 | C |
| ATOM | 2225 | CD1 | ILE | A | 408 | 43.370 | 115.717 | -8.401 | 1.00118.09 | C |
| ATOM | 2226 | N | SER | A | 409 | 44.193 | 111.659 | -8.413 | 1.00 90.52 | N |
| ATOM | 2227 | CA | SER | A | 409 | 43.278 | 110.529 | -8.580 | 1.00 88.89 | C |
| ATOM | 2228 | C | SER | A | 409 | 44.018 | 109.209 | -8.742 | 1.00 78.91 | C |

FIG. 8-39

| | | | | | | | | | | | |
|---|---|---|---|---|---|---|---|---|---|---|---|
| ATOM | 2229 | O | SER | A | 409 | 44.393 | 108.882 | -10.858 | 1.00 | 76.79 | O |
| ATOM | 2230 | CB | SER | A | 409 | 42.309 | 110.771 | -10.696 | 1.00 | 94.30 | C |
| ATOM | 2231 | OG | SER | A | 409 | 41.396 | 109.698 | -10.815 | 1.00 | 99.58 | O |
| ATOM | 2232 | N | PRO | A | 410 | 44.226 | 108.448 | -8.656 | 1.00 | 73.66 | N |
| ATOM | 2233 | CA | PRO | A | 410 | 44.913 | 107.154 | -8.764 | 1.00 | 87.58 | C |
| ATOM | 2234 | C | PRO | A | 410 | 44.016 | 106.059 | -9.345 | 1.00 | 83.01 | C |
| ATOM | 2235 | O | PRO | A | 410 | 42.822 | 105.994 | -9.043 | 1.00 | 59.16 | O |
| ATOM | 2236 | CB | PRO | A | 410 | 45.279 | 106.828 | -7.313 | 1.00 | 66.34 | C |
| ATOM | 2237 | CG | PRO | A | 410 | 45.160 | 108.137 | -6.579 | 1.00 | 70.39 | C |
| ATOM | 2238 | CD | PRO | A | 410 | 44.031 | 108.839 | -7.255 | 1.00 | 71.01 | C |
| ATOM | 2239 | N | GLN | A | 411 | 44.603 | 105.227 | -10.195 | 1.00 | 80.18 | N |
| ATOM | 2240 | CA | GLN | A | 411 | 43.823 | 104.068 | -10.762 | 1.00 | 53.74 | C |
| ATOM | 2241 | C | GLN | A | 411 | 42.603 | 104.420 | -11.450 | 1.00 | 51.36 | C |
| ATOM | 2242 | O | GLN | A | 411 | 41.580 | 103.787 | -11.206 | 1.00 | 55.70 | O |
| ATOM | 2243 | CB | GLN | A | 411 | 43.729 | 103.006 | -9.674 | 1.00 | 48.64 | C |
| ATOM | 2244 | CG | GLN | A | 411 | 45.048 | 102.582 | -9.060 | 1.00 | 48.22 | C |
| ATOM | 2245 | CD | GLN | A | 411 | 46.088 | 102.207 | -10.121 | 1.00 | 56.81 | C |
| ATOM | 2246 | OE1 | GLN | A | 411 | 47.277 | 102.555 | -10.034 | 1.00 | 61.25 | O |
| ATOM | 2247 | NE2 | GLN | A | 411 | 45.634 | 101.488 | -11.123 | 1.00 | 48.39 | N |
| ATOM | 2248 | N | PRO | A | 412 | 42.635 | 105.428 | -12.341 | 1.00 | 57.23 | N |
| ATOM | 2249 | CA | PRO | A | 412 | 41.397 | 105.698 | -12.957 | 1.00 | 55.77 | C |
| ATOM | 2250 | C | PRO | A | 412 | 40.644 | 104.751 | -13.609 | 1.00 | 58.28 | C |
| ATOM | 2251 | O | PRO | A | 412 | 39.419 | 104.685 | -13.518 | 1.00 | 60.75 | O |
| ATOM | 2252 | CB | PRO | A | 412 | 41.888 | 106.853 | -14.065 | 1.00 | 57.23 | C |
| ATOM | 2253 | CG | PRO | A | 412 | 43.323 | 107.092 | -13.810 | 1.00 | 58.37 | C |
| ATOM | 2254 | CD | PRO | A | 412 | 43.836 | 105.918 | -13.037 | 1.00 | 58.43 | C |
| ATOM | 2255 | N | ALA | A | 413 | 41.359 | 103.848 | -14.274 | 1.00 | 45.55 | N |
| ATOM | 2256 | CA | ALA | A | 413 | 40.649 | 102.789 | -14.991 | 1.00 | 52.48 | C |
| ATOM | 2257 | C | ALA | A | 413 | 39.931 | 101.843 | -14.027 | 1.00 | 50.27 | C |
| ATOM | 2258 | O | ALA | A | 413 | 38.763 | 101.549 | -14.195 | 1.00 | 50.60 | O |
| ATOM | 2259 | CB | ALA | A | 413 | 41.589 | 102.027 | -15.907 | 1.00 | 48.03 | C |
| ATOM | 2260 | N | PHE | A | 414 | 40.642 | 101.373 | -13.010 | 1.00 | 47.68 | N |
| ATOM | 2261 | CA | PHE | A | 414 | 40.060 | 100.452 | -12.049 | 1.00 | 44.69 | C |
| ATOM | 2262 | C | PHE | A | 414 | 38.873 | 101.144 | -11.232 | 1.00 | 50.42 | C |
| ATOM | 2263 | O | PHE | A | 414 | 37.851 | 100.541 | -10.933 | 1.00 | 54.83 | O |
| ATOM | 2264 | CB | PHE | A | 414 | 41.149 | 99.877 | -11.127 | 1.00 | 43.58 | C |
| ATOM | 2265 | CG | PHE | A | 414 | 40.643 | 98.821 | -10.190 | 1.00 | 41.53 | C |
| ATOM | 2266 | CD1 | PHE | A | 414 | 40.296 | 99.140 | -8.890 | 1.00 | 42.68 | C |
| ATOM | 2267 | CD2 | PHE | A | 414 | 40.533 | 97.511 | -10.604 | 1.00 | 45.46 | C |
| ATOM | 2268 | CE1 | PHE | A | 414 | 39.834 | 98.193 | -8.017 | 1.00 | 42.89 | C |
| ATOM | 2269 | CE2 | PHE | A | 414 | 40.072 | 96.522 | -9.748 | 1.00 | 42.60 | C |
| ATOM | 2270 | CZ | PHE | A | 414 | 39.713 | 96.843 | -8.460 | 1.00 | 45.11 | C |
| ATOM | 2271 | N | MET | A | 415 | 39.179 | 102.407 | -10.875 | 1.00 | 45.91 | N |
| ATOM | 2272 | CA | MET | A | 415 | 38.148 | 103.125 | -10.128 | 1.00 | 50.13 | C |
| ATOM | 2273 | C | MET | A | 415 | 36.885 | 103.273 | -10.879 | 1.00 | 56.08 | C |
| ATOM | 2274 | O | MET | A | 415 | 35.741 | 103.358 | -10.256 | 1.00 | 55.24 | O |
| ATOM | 2275 | CB | MET | A | 415 | 38.671 | 104.477 | -9.633 | 1.00 | 54.17 | C |
| ATOM | 2276 | CG | MET | A | 415 | 39.984 | 104.383 | -8.402 | 1.00 | 56.37 | C |
| ATOM | 2277 | SD | MET | A | 415 | 38.860 | 103.428 | -7.060 | 1.00 | 61.13 | S |
| ATOM | 2278 | CE | MET | A | 415 | 37.332 | 104.322 | -6.797 | 1.00 | 56.15 | C |
| ATOM | 2279 | N | GLN | A | 416 | 36.840 | 103.275 | -12.208 | 1.00 | 56.28 | N |
| ATOM | 2280 | CA | GLN | A | 416 | 35.602 | 103.267 | -12.992 | 1.00 | 55.27 | C |
| ATOM | 2281 | C | GLN | A | 416 | 34.779 | 102.021 | -12.684 | 1.00 | 49.49 | C |
| ATOM | 2282 | O | GLN | A | 416 | 33.961 | 102.084 | -12.552 | 1.00 | 51.39 | O |
| ATOM | 2283 | CB | GLN | A | 416 | 35.880 | 103.317 | -14.507 | 1.00 | 62.20 | C |
| ATOM | 2284 | CG | GLN | A | 416 | 36.367 | 104.650 | -15.038 | 1.00 | 64.54 | C |
| ATOM | 2285 | CD | GLN | A | 416 | 36.193 | 104.782 | -16.551 | 1.00 | 68.47 | C |
| ATOM | 2286 | OE1 | GLN | A | 416 | 35.787 | 103.836 | -17.236 | 1.00 | 59.84 | O |
| ATOM | 2287 | NE2 | GLN | A | 416 | 36.488 | 105.968 | -17.073 | 1.00 | 72.10 | N |
| ATOM | 2288 | N | LEU | A | 417 | 35.446 | 100.878 | -12.615 | 1.00 | 45.52 | N |
| ATOM | 2289 | CA | LEU | A | 417 | 34.777 | 99.641 | -12.289 | 1.00 | 46.50 | C |
| ATOM | 2290 | C | LEU | A | 417 | 34.268 | 99.779 | -10.866 | 1.00 | 51.00 | C |
| ATOM | 2291 | O | LEU | A | 417 | 33.111 | 99.455 | -10.575 | 1.00 | 52.62 | O |
| ATOM | 2292 | CB | LEU | A | 417 | 35.749 | 98.450 | -12.363 | 1.00 | 46.30 | C |
| ATOM | 2293 | CG | LEU | A | 417 | 35.084 | 97.103 | -12.044 | 1.00 | 53.08 | C |
| ATOM | 2294 | CD1 | LEU | A | 417 | 33.783 | 96.909 | -12.855 | 1.00 | 50.01 | C |
| ATOM | 2295 | CD2 | LEU | A | 417 | 36.049 | 95.973 | -12.331 | 1.00 | 63.82 | C |
| ATOM | 2296 | N | VAL | A | 418 | 35.127 | 100.239 | -9.966 | 1.00 | 48.56 | N |
| ATOM | 2297 | CA | VAL | A | 418 | 34.676 | 100.393 | -8.590 | 1.00 | 53.72 | C |
| ATOM | 2298 | C | VAL | A | 418 | 33.408 | 101.268 | -8.507 | 1.00 | 52.60 | C |
| ATOM | 2299 | O | VAL | A | 418 | 32.406 | 100.812 | -7.969 | 1.00 | 51.66 | O |
| ATOM | 2300 | CB | VAL | A | 418 | 35.798 | 100.803 | -7.832 | 1.00 | 51.05 | C |
| ATOM | 2301 | CG1 | VAL | A | 418 | 35.272 | 100.962 | -6.187 | 1.00 | 48.32 | C |
| ATOM | 2302 | CG2 | VAL | A | 418 | 36.882 | 99.745 | -7.870 | 1.00 | 50.09 | C |
| ATOM | 2303 | N | ARG | A | 419 | 33.426 | 102.467 | -9.098 | 1.00 | 52.43 | N |
| ATOM | 2304 | CA | ARG | A | 419 | 32.266 | 103.383 | -9.016 | 1.00 | 62.32 | C |
| ATOM | 2305 | C | ARG | A | 419 | 30.992 | 102.742 | -9.547 | 1.00 | 61.41 | C |

FIG. 8-40

| | | | | | | | | | | | |
|---|---|---|---|---|---|---|---|---|---|---|---|
| ATOM | 2306 | O | ARG | A | 419 | 29.918 | 102.839 | -8.941 | 1.00 | 82.67 | O |
| ATOM | 2307 | CB | ARG | A | 419 | 32.519 | 104.690 | -9.785 | 1.00 | 67.94 | C |
| ATOM | 2308 | CG | ARG | A | 419 | 33.462 | 105.681 | -9.108 | 1.00 | 78.19 | C |
| ATOM | 2309 | CD | ARG | A | 419 | 33.607 | 106.997 | -9.948 | 1.00 | 88.55 | C |
| ATOM | 2310 | NE | ARG | A | 419 | 33.898 | 106.673 | -11.357 | 1.00 | 96.19 | N |
| ATOM | 2311 | CZ | ARG | A | 419 | 33.062 | 106.911 | -12.370 | 1.00 | 100.49 | C |
| ATOM | 2312 | NH1 | ARG | A | 419 | 31.869 | 107.455 | -12.147 | 1.00 | 103.22 | N |
| ATOM | 2313 | NH2 | ARG | A | 419 | 33.422 | 106.609 | -13.612 | 1.00 | 96.75 | N |
| ATOM | 2314 | N | GLN | A | 420 | 31.128 | 102.090 | -10.694 | 1.00 | 56.00 | N |
| ATOM | 2315 | CA | GLN | A | 420 | 30.037 | 101.369 | -11.308 | 1.00 | 53.17 | C |
| ATOM | 2316 | C | GLN | A | 420 | 29.494 | 100.221 | -10.470 | 1.00 | 49.84 | C |
| ATOM | 2317 | O | GLN | A | 420 | 28.284 | 100.067 | -10.307 | 1.00 | 53.16 | O |
| ATOM | 2318 | CB | GLN | A | 420 | 30.529 | 100.852 | -12.673 | 1.00 | 61.20 | C |
| ATOM | 2319 | CG | GLN | A | 420 | 29.587 | 99.964 | -13.423 | 1.00 | 69.30 | C |
| ATOM | 2320 | CD | GLN | A | 420 | 30.207 | 99.510 | -14.735 | 1.00 | 72.30 | C |
| ATOM | 2321 | OE1 | GLN | A | 420 | 30.758 | 98.410 | -14.819 | 1.00 | 74.52 | O |
| ATOM | 2322 | NE2 | GLN | A | 420 | 30.161 | 100.375 | -15.749 | 1.00 | 66.84 | N |
| ATOM | 2323 | N | GLU | A | 421 | 30.373 | 99.408 | -9.906 | 1.00 | 43.66 | N |
| ATOM | 2324 | CA | GLU | A | 421 | 29.898 | 98.368 | -8.997 | 1.00 | 53.46 | C |
| ATOM | 2325 | C | GLU | A | 421 | 29.213 | 98.881 | -7.724 | 1.00 | 56.64 | C |
| ATOM | 2326 | O | GLU | A | 421 | 28.297 | 98.243 | -7.220 | 1.00 | 59.73 | O |
| ATOM | 2327 | CB | GLU | A | 421 | 31.016 | 97.411 | -8.618 | 1.00 | 50.81 | C |
| ATOM | 2328 | CG | GLU | A | 421 | 30.510 | 96.030 | -8.351 | 1.00 | 59.01 | C |
| ATOM | 2329 | CD | GLU | A | 421 | 31.602 | 95.003 | -8.405 | 1.00 | 63.66 | C |
| ATOM | 2330 | OE1 | GLU | A | 421 | 32.580 | 95.232 | -9.148 | 1.00 | 76.19 | O |
| ATOM | 2331 | OE2 | GLU | A | 421 | 31.488 | 93.978 | -7.697 | 1.00 | 73.57 | O |
| ATOM | 2332 | N | LEU | A | 422 | 29.652 | 100.016 | -7.198 | 1.00 | 56.66 | N |
| ATOM | 2333 | CA | LEU | A | 422 | 29.016 | 100.571 | -6.001 | 1.00 | 62.08 | C |
| ATOM | 2334 | C | LEU | A | 422 | 27.579 | 100.989 | -6.280 | 1.00 | 66.74 | C |
| ATOM | 2335 | O | LEU | A | 422 | 26.679 | 100.709 | -5.499 | 1.00 | 70.35 | O |
| ATOM | 2336 | CB | LEU | A | 422 | 29.807 | 101.766 | -5.464 | 1.00 | 59.13 | C |
| ATOM | 2337 | CG | LEU | A | 422 | 31.075 | 101.373 | -4.734 | 1.00 | 60.57 | C |
| ATOM | 2338 | CD1 | LEU | A | 422 | 31.863 | 102.604 | -4.339 | 1.00 | 65.83 | C |
| ATOM | 2339 | CD2 | LEU | A | 422 | 30.721 | 100.881 | -3.476 | 1.00 | 62.85 | C |
| ATOM | 2340 | N | GLN | A | 423 | 27.373 | 101.867 | -7.339 | 1.00 | 67.22 | N |
| ATOM | 2341 | CA | GLN | A | 423 | 26.031 | 102.052 | -7.812 | 1.00 | 67.52 | C |
| ATOM | 2342 | C | GLN | A | 423 | 25.148 | 100.820 | -7.932 | 1.00 | 65.87 | C |
| ATOM | 2343 | O | GLN | A | 423 | 24.067 | 100.761 | -7.365 | 1.00 | 68.89 | O |
| ATOM | 2344 | CB | GLN | A | 423 | 26.067 | 102.777 | -9.152 | 1.00 | 62.66 | C |
| ATOM | 2345 | CG | GLN | A | 423 | 24.801 | 103.561 | -9.421 | 1.00 | 68.24 | C |
| ATOM | 2346 | CD | GLN | A | 423 | 24.730 | 104.799 | -8.568 | 1.00 | 72.00 | C |
| ATOM | 2347 | OE1 | GLN | A | 423 | 23.649 | 105.234 | -8.179 | 1.00 | 78.23 | O |
| ATOM | 2348 | NE2 | GLN | A | 423 | 25.893 | 105.373 | -8.298 | 1.00 | 71.32 | N |
| ATOM | 2349 | N | ALA | A | 424 | 25.628 | 99.827 | -8.667 | 1.00 | 56.10 | N |
| ATOM | 2350 | CA | ALA | A | 424 | 24.863 | 98.598 | -8.828 | 1.00 | 59.98 | C |
| ATOM | 2351 | C | ALA | A | 424 | 24.527 | 97.914 | -7.499 | 1.00 | 67.63 | C |
| ATOM | 2352 | O | ALA | A | 424 | 23.399 | 97.472 | -7.310 | 1.00 | 71.65 | O |
| ATOM | 2353 | CB | ALA | A | 424 | 25.578 | 97.630 | -9.778 | 1.00 | 51.19 | C |
| ATOM | 2354 | N | LYS | A | 425 | 25.493 | 97.834 | -6.581 | 1.00 | 68.64 | N |
| ATOM | 2355 | CA | LYS | A | 425 | 25.294 | 97.074 | -5.340 | 1.00 | 73.54 | C |
| ATOM | 2356 | C | LYS | A | 425 | 24.509 | 97.813 | -4.257 | 1.00 | 79.13 | C |
| ATOM | 2357 | O | LYS | A | 425 | 23.525 | 97.294 | -3.733 | 1.00 | 83.30 | O |
| ATOM | 2358 | CB | LYS | A | 425 | 26.626 | 96.595 | -4.761 | 1.00 | 73.50 | C |
| ATOM | 2359 | CG | LYS | A | 425 | 27.373 | 95.629 | -5.655 | 1.00 | 79.98 | C |
| ATOM | 2360 | CD | LYS | A | 425 | 26.420 | 94.626 | -6.266 | 1.00 | 79.81 | C |
| ATOM | 2361 | CE | LYS | A | 425 | 27.080 | 93.897 | -7.429 | 1.00 | 76.06 | C |
| ATOM | 2362 | NZ | LYS | A | 425 | 28.324 | 93.195 | -7.022 | 1.00 | 72.98 | N |
| ATOM | 2363 | N | LEU | A | 426 | 24.958 | 99.014 | -3.917 | 1.00 | 75.50 | N |
| ATOM | 2364 | CA | LEU | A | 426 | 24.390 | 99.769 | -2.808 | 1.00 | 70.25 | C |
| ATOM | 2365 | C | LEU | A | 426 | 23.465 | 100.872 | -3.284 | 1.00 | 76.41 | C |
| ATOM | 2366 | O | LEU | A | 426 | 22.624 | 101.365 | -2.525 | 1.00 | 82.45 | O |
| ATOM | 2367 | CB | LEU | A | 426 | 25.507 | 100.393 | -1.993 | 1.00 | 66.85 | C |
| ATOM | 2368 | CG | LEU | A | 426 | 26.477 | 99.384 | -1.382 | 1.00 | 65.37 | C |
| ATOM | 2369 | CD1 | LEU | A | 426 | 27.794 | 100.085 | -1.107 | 1.00 | 61.53 | C |
| ATOM | 2370 | CD2 | LEU | A | 426 | 25.876 | 98.786 | -0.115 | 1.00 | 61.86 | C |
| ATOM | 2371 | N | GLY | A | 427 | 23.627 | 101.261 | -4.543 | 1.00 | 73.60 | N |
| ATOM | 2372 | CA | GLY | A | 427 | 22.876 | 102.368 | -5.094 | 1.00 | 75.58 | C |
| ATOM | 2373 | C | GLY | A | 427 | 23.455 | 103.688 | -4.642 | 1.00 | 81.43 | C |
| ATOM | 2374 | O | GLY | A | 427 | 24.623 | 103.775 | -4.265 | 1.00 | 80.08 | O |
| ATOM | 2375 | N | ASP | A | 428 | 22.626 | 104.723 | -4.674 | 1.00 | 91.31 | N |
| ATOM | 2376 | CA | ASP | A | 428 | 23.063 | 106.067 | -4.330 | 1.00 | 104.95 | C |
| ATOM | 2377 | C | ASP | A | 428 | 23.045 | 106.285 | -2.815 | 1.00 | 109.42 | C |
| ATOM | 2378 | O | ASP | A | 428 | 23.607 | 107.258 | -2.313 | 1.00 | 109.22 | O |
| ATOM | 2379 | CB | ASP | A | 428 | 22.172 | 107.106 | -5.022 | 1.00 | 114.31 | C |
| ATOM | 2380 | CG | ASP | A | 428 | 21.805 | 106.711 | -6.451 | 1.00 | 119.73 | C |
| ATOM | 2381 | OD1 | ASP | A | 428 | 22.308 | 107.357 | -7.397 | 1.00 | 121.33 | O |
| ATOM | 2382 | OD2 | ASP | A | 428 | 21.014 | 105.756 | -6.629 | 1.00 | 119.28 | O |

FIG. 8-41

| | | | | | | | | | | |
|---|---|---|---|---|---|---|---|---|---|---|
| ATOM | 2383 | N | LYS | A | 429 | 22.391 | 105.379 | -2.093 | 1.00112.37 | N |
| ATOM | 2384 | CA | LYS | A | 429 | 22.295 | 105.495 | -0.642 | 1.00115.36 | C |
| ATOM | 2385 | C | LYS | A | 429 | 23.576 | 104.999 | 0.014 | 1.00114.60 | C |
| ATOM | 2386 | O | LYS | A | 429 | 23.567 | 104.027 | 0.768 | 1.00114.53 | O |
| ATOM | 2387 | CB | LYS | A | 429 | 21.084 | 104.723 | -0.103 | 1.00116.91 | C |
| ATOM | 2388 | CG | LYS | A | 429 | 20.830 | 104.933 | 1.384 | 1.00116.49 | C |
| ATOM | 2389 | CD | LYS | A | 429 | 20.539 | 106.396 | 1.696 | 1.00116.23 | C |
| ATOM | 2390 | CE | LYS | A | 429 | 20.808 | 106.715 | 3.155 | 1.00113.73 | C |
| ATOM | 2391 | NZ | LYS | A | 429 | 22.285 | 106.503 | 3.487 | 1.00110.71 | N |
| ATOM | 2392 | N | VAL | A | 430 | 24.679 | 105.672 | -0.287 | 1.00113.34 | N |
| ATOM | 2393 | CA | VAL | A | 430 | 25.971 | 105.278 | 0.249 | 1.00112.25 | C |
| ATOM | 2394 | C | VAL | A | 430 | 26.739 | 106.477 | 0.780 | 1.00112.55 | C |
| ATOM | 2395 | O | VAL | A | 430 | 26.930 | 106.587 | 1.985 | 1.00116.10 | O |
| ATOM | 2396 | CB | VAL | A | 430 | 26.821 | 104.516 | -0.792 | 1.00111.39 | C |
| ATOM | 2397 | CG1 | VAL | A | 430 | 26.770 | 105.216 | -2.152 | 1.00109.71 | C |
| ATOM | 2398 | CG2 | VAL | A | 430 | 28.257 | 104.349 | -0.293 | 1.00107.65 | C |
| ATOM | 2399 | N | LYS | A | 431 | 27.172 | 107.374 | -0.099 | 1.00111.34 | N |
| ATOM | 2400 | CA | LYS | A | 431 | 27.993 | 108.487 | 0.366 | 1.00112.24 | C |
| ATOM | 2401 | C | LYS | A | 431 | 27.159 | 109.616 | 0.962 | 1.00111.99 | C |
| ATOM | 2402 | O | LYS | A | 431 | 27.598 | 110.767 | 1.040 | 1.00110.45 | O |
| ATOM | 2403 | CB | LYS | A | 431 | 28.868 | 108.988 | -0.781 | 1.00114.25 | C |
| ATOM | 2404 | CG | LYS | A | 431 | 30.305 | 109.418 | -0.180 | 1.00114.37 | C |
| ATOM | 2405 | CD | LYS | A | 431 | 30.755 | 108.422 | 0.979 | 1.00109.31 | C |
| ATOM | 2406 | CE | LYS | A | 431 | 31.749 | 109.042 | 1.963 | 1.00103.41 | C |
| ATOM | 2407 | NZ | LYS | A | 431 | 31.990 | 108.179 | 3.170 | 1.00 91.29 | N |
| ATOM | 2408 | N | ASP | A | 432 | 25.946 | 109.261 | 1.369 | 1.00110.53 | N |
| ATOM | 2409 | CA | ASP | A | 432 | 25.233 | 110.016 | 2.377 | 1.00113.61 | C |
| ATOM | 2410 | C | ASP | A | 432 | 26.005 | 109.783 | 3.677 | 1.00108.76 | C |
| ATOM | 2411 | O | ASP | A | 432 | 26.000 | 110.619 | 4.586 | 1.00113.79 | O |
| ATOM | 2412 | CB | ASP | A | 432 | 23.799 | 109.493 | 2.498 | 1.00123.51 | C |
| ATOM | 2413 | CG | ASP | A | 432 | 23.009 | 110.177 | 3.608 | 1.00135.60 | C |
| ATOM | 2414 | OD1 | ASP | A | 432 | 21.839 | 109.691 | 3.979 | 1.00139.15 | O |
| ATOM | 2415 | OD2 | ASP | A | 432 | 23.450 | 111.238 | 4.109 | 1.00139.49 | O |
| ATOM | 2416 | N | LEU | A | 433 | 26.693 | 108.644 | 3.743 | 1.00 96.85 | N |
| ATOM | 2417 | CA | LEU | A | 433 | 27.426 | 108.238 | 4.943 | 1.00 88.97 | C |
| ATOM | 2418 | C | LEU | A | 433 | 28.832 | 108.830 | 5.022 | 1.00 88.84 | C |
| ATOM | 2419 | O | LEU | A | 433 | 29.431 | 109.188 | 4.013 | 1.00 85.52 | O |
| ATOM | 2420 | CB | LEU | A | 433 | 27.512 | 106.715 | 5.015 | 1.00 81.12 | C |
| ATOM | 2421 | CG | LEU | A | 433 | 26.203 | 105.980 | 4.759 | 1.00 77.38 | C |
| ATOM | 2422 | CD1 | LEU | A | 433 | 26.436 | 104.483 | 4.801 | 1.00 78.63 | C |
| ATOM | 2423 | CD2 | LEU | A | 433 | 25.164 | 106.406 | 5.783 | 1.00 80.58 | C |
| ATOM | 2424 | N | SER | A | 434 | 29.356 | 108.921 | 6.237 | 1.00 84.30 | N |
| ATOM | 2425 | CA | SER | A | 434 | 30.694 | 109.446 | 6.460 | 1.00 79.61 | C |
| ATOM | 2426 | C | SER | A | 434 | 31.608 | 108.301 | 6.895 | 1.00 76.72 | C |
| ATOM | 2427 | O | SER | A | 434 | 31.158 | 107.363 | 7.561 | 1.00 75.02 | O |
| ATOM | 2428 | CB | SER | A | 434 | 30.643 | 110.526 | 7.548 | 1.00 77.35 | C |
| ATOM | 2429 | OG | SER | A | 434 | 31.716 | 111.448 | 7.448 | 1.00 71.23 | O |
| ATOM | 2430 | N | GLY | A | 435 | 32.885 | 108.381 | 6.920 | 1.00 76.32 | N |
| ATOM | 2431 | CA | GLY | A | 435 | 33.887 | 107.405 | 6.939 | 1.00 71.91 | C |
| ATOM | 2432 | C | GLY | A | 435 | 33.560 | 105.966 | 6.562 | 1.00 64.90 | C |
| ATOM | 2433 | O | GLY | A | 435 | 33.671 | 105.062 | 7.382 | 1.00 62.69 | O |
| ATOM | 2434 | N | VAL | A | 436 | 33.136 | 105.759 | 5.319 | 1.00 66.06 | N |
| ATOM | 2435 | CA | VAL | A | 436 | 32.849 | 104.420 | 4.808 | 1.00 64.60 | C |
| ATOM | 2436 | C | VAL | A | 436 | 34.144 | 103.783 | 4.274 | 1.00 59.73 | C |
| ATOM | 2437 | O | VAL | A | 436 | 34.976 | 104.481 | 3.694 | 1.00 57.71 | O |
| ATOM | 2438 | CB | VAL | A | 436 | 31.770 | 104.480 | 3.700 | 1.00 70.19 | C |
| ATOM | 2439 | CG1 | VAL | A | 436 | 31.992 | 103.134 | 3.008 | 1.00 70.66 | C |
| ATOM | 2440 | CG2 | VAL | A | 436 | 30.447 | 104.969 | 4.277 | 1.00 71.46 | C |
| ATOM | 2441 | N | LYS | A | 437 | 34.329 | 102.491 | 4.490 | 1.00 53.71 | N |
| ATOM | 2442 | CA | LYS | A | 437 | 35.501 | 101.802 | 3.987 | 1.00 46.63 | C |
| ATOM | 2443 | C | LYS | A | 437 | 35.161 | 100.773 | 2.868 | 1.00 54.23 | C |
| ATOM | 2444 | O | LYS | A | 437 | 34.363 | 99.897 | 3.074 | 1.00 61.27 | O |
| ATOM | 2445 | CB | LYS | A | 437 | 36.319 | 101.196 | 5.181 | 1.00 53.54 | C |
| ATOM | 2446 | CG | LYS | A | 437 | 36.695 | 102.291 | 6.178 | 1.00 57.30 | C |
| ATOM | 2447 | CD | LYS | A | 437 | 36.700 | 101.695 | 7.616 | 1.00 65.52 | C |
| ATOM | 2448 | CE | LYS | A | 437 | 38.120 | 101.521 | 8.171 | 1.00 81.37 | C |
| ATOM | 2449 | NZ | LYS | A | 437 | 38.765 | 100.199 | 7.863 | 1.00 86.08 | N |
| ATOM | 2450 | N | ILE | A | 438 | 35.761 | 100.957 | 1.693 | 1.00 53.58 | N |
| ATOM | 2451 | CA | ILE | A | 438 | 35.934 | 100.089 | 0.537 | 1.00 48.18 | C |
| ATOM | 2452 | C | ILE | A | 438 | 36.707 | 99.199 | 0.353 | 1.00 50.67 | C |
| ATOM | 2453 | O | ILE | A | 438 | 37.871 | 99.708 | 0.146 | 1.00 50.14 | O |
| ATOM | 2454 | CB | ILE | A | 438 | 35.277 | 100.935 | -0.711 | 1.00 51.43 | C |
| ATOM | 2455 | CG1 | ILE | A | 438 | 33.964 | 101.702 | -0.565 | 1.00 50.09 | C |
| ATOM | 2456 | CG2 | ILE | A | 438 | 35.245 | 100.082 | -2.012 | 1.00 43.73 | C |
| ATOM | 2457 | CD1 | ILE | A | 438 | 33.944 | 102.987 | -1.350 | 1.00 59.08 | C |
| ATOM | 2458 | N | PHE | A | 439 | 36.586 | 97.885 | 0.983 | 1.00 42.81 | N |
| ATOM | 2459 | CA | PHE | A | 439 | 37.666 | 96.926 | 0.305 | 1.00 39.55 | C |

FIG. 8-42

| | | | | | | | | | | | |
|---|---|---|---|---|---|---|---|---|---|---|---|
| ATOM | 2460 | C | PHE | A | 439 | 37.469 | 96.286 | -1.055 | 1.00 | 45.67 | C |
| ATOM | 2461 | O | PHE | A | 439 | 36.459 | 95.636 | -1.299 | 1.00 | 51.71 | O |
| ATOM | 2462 | CB | PHE | A | 439 | 37.716 | 95.903 | 1.453 | 1.00 | 40.37 | C |
| ATOM | 2463 | CG | PHE | A | 439 | 37.941 | 96.549 | 2.830 | 1.00 | 43.69 | C |
| ATOM | 2464 | CD1 | PHE | A | 439 | 39.223 | 96.793 | 3.299 | 1.00 | 47.89 | C |
| ATOM | 2465 | CD2 | PHE | A | 439 | 36.876 | 96.948 | 3.612 | 1.00 | 48.61 | C |
| ATOM | 2466 | CE1 | PHE | A | 439 | 39.434 | 97.409 | 4.498 | 1.00 | 47.92 | C |
| ATOM | 2467 | CE2 | PHE | A | 439 | 37.097 | 97.588 | 4.852 | 1.00 | 51.30 | C |
| ATOM | 2468 | CZ | PHE | A | 439 | 38.370 | 97.788 | 5.277 | 1.00 | 49.02 | C |
| ATOM | 2469 | N | THR | A | 440 | 38.411 | 96.536 | -1.963 | 1.00 | 48.39 | N |
| ATOM | 2470 | CA | THR | A | 440 | 38.337 | 96.076 | -3.356 | 1.00 | 41.23 | C |
| ATOM | 2471 | C | THR | A | 440 | 39.223 | 94.841 | -3.603 | 1.00 | 42.63 | C |
| ATOM | 2472 | O | THR | A | 440 | 39.787 | 94.277 | -2.692 | 1.00 | 41.74 | O |
| ATOM | 2473 | CB | THR | A | 440 | 38.747 | 97.201 | -4.320 | 1.00 | 41.82 | C |
| ATOM | 2474 | OG1 | THR | A | 440 | 40.153 | 97.402 | -4.232 | 1.00 | 43.90 | O |
| ATOM | 2475 | CG2 | THR | A | 440 | 38.104 | 98.497 | -3.923 | 1.00 | 48.14 | C |
| ATOM | 2476 | N | THR | A | 441 | 39.336 | 94.425 | -4.858 | 1.00 | 46.67 | N |
| ATOM | 2477 | CA | THR | A | 441 | 40.084 | 93.173 | -5.202 | 1.00 | 45.46 | C |
| ATOM | 2478 | C | THR | A | 441 | 41.350 | 93.515 | -5.828 | 1.00 | 43.75 | C |
| ATOM | 2479 | O | THR | A | 441 | 42.075 | 92.643 | -6.289 | 1.00 | 44.90 | O |
| ATOM | 2480 | CB | THR | A | 441 | 39.214 | 92.463 | -6.327 | 1.00 | 39.78 | C |
| ATOM | 2481 | OG1 | THR | A | 441 | 38.923 | 93.420 | -7.344 | 1.00 | 44.98 | O |
| ATOM | 2482 | CG2 | THR | A | 441 | 37.904 | 91.838 | -5.818 | 1.00 | 37.92 | C |
| ATOM | 2483 | N | PHE | A | 442 | 41.617 | 94.812 | -5.900 | 1.00 | 39.04 | N |
| ATOM | 2484 | CA | PHE | A | 442 | 42.741 | 95.389 | -6.621 | 1.00 | 42.41 | C |
| ATOM | 2485 | C | PHE | A | 442 | 44.039 | 94.798 | -6.132 | 1.00 | 42.33 | C |
| ATOM | 2486 | O | PHE | A | 442 | 44.290 | 94.743 | -4.926 | 1.00 | 44.81 | O |
| ATOM | 2487 | CB | PHE | A | 442 | 42.730 | 96.899 | -6.388 | 1.00 | 45.08 | C |
| ATOM | 2488 | CG | PHE | A | 442 | 43.867 | 97.643 | -7.032 | 1.00 | 43.55 | C |
| ATOM | 2489 | CD1 | PHE | A | 442 | 43.841 | 97.943 | -8.385 | 1.00 | 44.42 | C |
| ATOM | 2490 | CD2 | PHE | A | 442 | 44.929 | 98.102 | -6.269 | 1.00 | 46.85 | C |
| ATOM | 2491 | CE1 | PHE | A | 442 | 44.892 | 98.656 | -8.975 | 1.00 | 47.30 | C |
| ATOM | 2492 | CE2 | PHE | A | 442 | 45.983 | 98.816 | -6.850 | 1.00 | 43.66 | C |
| ATOM | 2493 | CZ | PHE | A | 442 | 45.954 | 99.098 | -8.197 | 1.00 | 42.13 | C |
| ATOM | 2494 | N | ASP | A | 443 | 44.832 | 94.307 | -7.066 | 1.00 | 45.71 | N |
| ATOM | 2495 | CA | ASP | A | 443 | 46.159 | 93.782 | -6.748 | 1.00 | 48.74 | C |
| ATOM | 2496 | C | ASP | A | 443 | 47.231 | 94.789 | -7.168 | 1.00 | 46.07 | C |
| ATOM | 2497 | O | ASP | A | 443 | 47.455 | 95.088 | -8.377 | 1.00 | 40.93 | O |
| ATOM | 2498 | CB | ASP | A | 443 | 46.368 | 92.465 | -7.494 | 1.00 | 53.73 | C |
| ATOM | 2499 | CG | ASP | A | 443 | 47.655 | 91.780 | -7.113 | 1.00 | 60.83 | C |
| ATOM | 2500 | OD1 | ASP | A | 443 | 47.596 | 90.959 | -6.846 | 1.00 | 65.18 | O |
| ATOM | 2501 | OD2 | ASP | A | 443 | 48.717 | 92.461 | -7.073 | 1.00 | 57.04 | O |
| ATOM | 2502 | N | SER | A | 444 | 47.891 | 95.392 | -6.187 | 1.00 | 40.37 | N |
| ATOM | 2503 | CA | SER | A | 444 | 48.950 | 96.404 | -6.415 | 1.00 | 46.75 | C |
| ATOM | 2504 | C | SER | A | 444 | 50.158 | 95.836 | -7.224 | 1.00 | 43.96 | C |
| ATOM | 2505 | O | SER | A | 444 | 50.736 | 96.685 | -8.025 | 1.00 | 55.10 | O |
| ATOM | 2506 | CB | SER | A | 444 | 49.452 | 96.874 | -5.087 | 1.00 | 57.41 | C |
| ATOM | 2507 | OG | SER | A | 444 | 48.517 | 98.021 | -4.630 | 1.00 | 61.43 | O |
| ATOM | 2508 | N | VAL | A | 445 | 50.591 | 94.707 | -6.990 | 1.00 | 48.44 | N |
| ATOM | 2509 | CA | VAL | A | 445 | 51.709 | 94.135 | -7.731 | 1.00 | 42.57 | C |
| ATOM | 2510 | C | VAL | A | 445 | 51.344 | 93.886 | -9.183 | 1.00 | 47.02 | C |
| ATOM | 2511 | O | VAL | A | 445 | 52.119 | 94.179 | -10.082 | 1.00 | 53.83 | O |
| ATOM | 2512 | CB | VAL | A | 445 | 52.070 | 92.783 | -7.162 | 1.00 | 44.23 | C |
| ATOM | 2513 | CG1 | VAL | A | 445 | 53.227 | 92.154 | -7.876 | 1.00 | 45.63 | C |
| ATOM | 2514 | CG2 | VAL | A | 445 | 52.399 | 92.938 | -5.697 | 1.00 | 36.52 | C |
| ATOM | 2515 | N | ALA | A | 446 | 50.150 | 93.347 | -9.413 | 1.00 | 49.73 | N |
| ATOM | 2516 | CA | ALA | A | 446 | 49.706 | 93.082 | -10.779 | 1.00 | 43.46 | C |
| ATOM | 2517 | C | ALA | A | 446 | 49.507 | 94.385 | -11.565 | 1.00 | 36.69 | C |
| ATOM | 2518 | O | ALA | A | 446 | 49.830 | 94.489 | -12.698 | 1.00 | 40.48 | O |
| ATOM | 2519 | CB | ALA | A | 446 | 48.436 | 92.237 | -10.774 | 1.00 | 35.50 | C |
| ATOM | 2520 | N | GLN | A | 447 | 48.938 | 95.389 | -10.891 | 1.00 | 38.72 | N |
| ATOM | 2521 | CA | GLN | A | 447 | 48.739 | 96.681 | -11.528 | 1.00 | 38.41 | C |
| ATOM | 2522 | C | GLN | A | 447 | 50.073 | 97.264 | -11.914 | 1.00 | 37.24 | C |
| ATOM | 2523 | O | GLN | A | 447 | 50.271 | 97.651 | -13.081 | 1.00 | 45.23 | O |
| ATOM | 2524 | CB | GLN | A | 447 | 47.903 | 97.656 | -10.685 | 1.00 | 42.93 | C |
| ATOM | 2525 | CG | GLN | A | 447 | 47.527 | 98.961 | -11.411 | 1.00 | 41.34 | C |
| ATOM | 2526 | CD | GLN | A | 447 | 46.466 | 98.777 | -12.534 | 1.00 | 43.87 | C |
| ATOM | 2527 | OE1 | GLN | A | 447 | 45.721 | 97.791 | -12.571 | 1.00 | 42.80 | O |
| ATOM | 2528 | NE2 | GLN | A | 447 | 46.367 | 99.768 | -13.406 | 1.00 | 40.34 | N |
| ATOM | 2529 | N | ASP | A | 448 | 51.023 | 97.267 | -10.983 | 1.00 | 47.13 | N |
| ATOM | 2530 | CA | ASP | A | 448 | 52.370 | 97.761 | -11.286 | 1.00 | 43.58 | C |
| ATOM | 2531 | C | ASP | A | 448 | 52.932 | 97.069 | -12.532 | 1.00 | 43.44 | C |
| ATOM | 2532 | O | ASP | A | 448 | 53.497 | 97.710 | -13.426 | 1.00 | 44.58 | O |
| ATOM | 2533 | CB | ASP | A | 448 | 53.321 | 97.566 | -10.112 | 1.00 | 45.12 | C |
| ATOM | 2534 | CG | ASP | A | 448 | 53.070 | 98.567 | -8.971 | 1.00 | 58.19 | C |
| ATOM | 2535 | OD1 | ASP | A | 448 | 52.235 | 99.485 | -9.164 | 1.00 | 79.52 | O |
| ATOM | 2536 | OD2 | ASP | A | 448 | 53.789 | 98.436 | -7.885 | 1.00 | 62.87 | O |

FIG. 8-43

| | | | | | | | | | | | |
|---|---|---|---|---|---|---|---|---|---|---|---|
| ATOM | 2537 | N | ALA | A | 449 | 52.795 | 95.750 | -12.584 | 1.00 | 43.68 | N |
| ATOM | 2538 | CA | ALA | A | 449 | 53.363 | 95.010 | -13.710 | 1.00 | 42.84 | C |
| ATOM | 2539 | C | ALA | A | 449 | 52.829 | 95.295 | -15.039 | 1.00 | 41.35 | C |
| ATOM | 2540 | O | ALA | A | 449 | 53.273 | 95.368 | -16.089 | 1.00 | 45.59 | O |
| ATOM | 2541 | CB | ALA | A | 449 | 53.430 | 93.498 | -13.407 | 1.00 | 38.48 | C |
| ATOM | 2542 | N | ALA | A | 450 | 51.305 | 95.463 | -15.008 | 1.00 | 44.75 | N |
| ATOM | 2543 | CA | ALA | A | 450 | 50.583 | 95.748 | -16.258 | 1.00 | 44.45 | C |
| ATOM | 2544 | C | ALA | A | 450 | 50.893 | 97.144 | -16.742 | 1.00 | 44.59 | C |
| ATOM | 2545 | O | ALA | A | 450 | 51.112 | 97.351 | -17.933 | 1.00 | 43.78 | O |
| ATOM | 2546 | CB | ALA | A | 450 | 49.080 | 95.552 | -16.134 | 1.00 | 38.37 | C |
| ATOM | 2547 | N | GLU | A | 451 | 50.810 | 98.100 | -15.821 | 1.00 | 40.73 | N |
| ATOM | 2548 | CA | GLU | A | 451 | 51.202 | 99.474 | -16.183 | 1.00 | 47.56 | C |
| ATOM | 2549 | C | GLU | A | 451 | 52.589 | 99.566 | -16.807 | 1.00 | 50.78 | C |
| ATOM | 2550 | O | GLU | A | 451 | 52.785 | 100.256 | -17.797 | 1.00 | 49.73 | O |
| ATOM | 2551 | CB | GLU | A | 451 | 51.090 | 100.392 | -14.960 | 1.00 | 51.31 | C |
| ATOM | 2552 | CG | GLU | A | 451 | 49.640 | 100.648 | -14.548 | 1.00 | 58.55 | C |
| ATOM | 2553 | CD | GLU | A | 451 | 49.527 | 101.605 | -13.369 | 1.00 | 64.83 | C |
| ATOM | 2554 | OE1 | GLU | A | 451 | 50.582 | 102.122 | -12.935 | 1.00 | 72.92 | O |
| ATOM | 2555 | OE2 | GLU | A | 451 | 48.389 | 101.843 | -12.888 | 1.00 | 57.09 | O |
| ATOM | 2556 | N | LYS | A | 452 | 53.551 | 98.860 | -16.224 | 1.00 | 44.75 | N |
| ATOM | 2557 | CA | LYS | A | 452 | 54.903 | 98.878 | -16.749 | 1.00 | 45.12 | C |
| ATOM | 2558 | C | LYS | A | 452 | 54.982 | 98.230 | -18.132 | 1.00 | 47.25 | C |
| ATOM | 2559 | O | LYS | A | 452 | 55.734 | 98.685 | -19.002 | 1.00 | 52.50 | O |
| ATOM | 2560 | CB | LYS | A | 452 | 55.868 | 98.221 | -15.758 | 1.00 | 46.69 | C |
| ATOM | 2561 | CG | LYS | A | 452 | 57.251 | 97.877 | -16.291 | 1.00 | 57.80 | C |
| ATOM | 2562 | CD | LYS | A | 452 | 58.190 | 97.523 | -15.178 | 1.00 | 62.07 | C |
| ATOM | 2563 | CE | LYS | A | 452 | 59.218 | 98.601 | -14.868 | 1.00 | 77.28 | C |
| ATOM | 2564 | NZ | LYS | A | 452 | 58.629 | 99.886 | -14.364 | 1.00 | 82.71 | N |
| ATOM | 2565 | N | ALA | A | 453 | 54.205 | 97.177 | -18.349 | 1.00 | 42.04 | N |
| ATOM | 2566 | CA | ALA | A | 453 | 54.197 | 96.535 | -19.653 | 1.00 | 41.66 | C |
| ATOM | 2567 | C | ALA | A | 453 | 53.583 | 97.445 | -20.704 | 1.00 | 50.33 | C |
| ATOM | 2568 | O | ALA | A | 453 | 54.098 | 97.544 | -21.831 | 1.00 | 49.59 | O |
| ATOM | 2569 | CB | ALA | A | 453 | 53.465 | 95.188 | -19.603 | 1.00 | 40.03 | C |
| ATOM | 2570 | N | ALA | A | 454 | 52.467 | 98.081 | -20.349 | 1.00 | 49.10 | N |
| ATOM | 2571 | CA | ALA | A | 454 | 51.845 | 99.112 | -21.197 | 1.00 | 45.65 | C |
| ATOM | 2572 | C | ALA | A | 454 | 52.769 | 100.307 | -21.484 | 1.00 | 51.87 | C |
| ATOM | 2573 | O | ALA | A | 454 | 52.936 | 100.711 | -22.637 | 1.00 | 55.68 | O |
| ATOM | 2574 | CB | ALA | A | 454 | 50.567 | 99.610 | -20.558 | 1.00 | 44.77 | C |
| ATOM | 2575 | N | VAL | A | 455 | 53.362 | 100.877 | -20.438 | 1.00 | 46.27 | N |
| ATOM | 2576 | CA | VAL | A | 455 | 54.144 | 102.097 | -20.595 | 1.00 | 47.83 | C |
| ATOM | 2577 | C | VAL | A | 455 | 55.402 | 101.834 | -21.436 | 1.00 | 53.96 | C |
| ATOM | 2578 | O | VAL | A | 455 | 55.730 | 102.615 | -22.335 | 1.00 | 55.58 | O |
| ATOM | 2579 | CB | VAL | A | 455 | 54.537 | 102.751 | -19.235 | 1.00 | 54.85 | C |
| ATOM | 2580 | CG1 | VAL | A | 455 | 55.199 | 104.083 | -19.460 | 1.00 | 60.40 | C |
| ATOM | 2581 | CG2 | VAL | A | 455 | 53.314 | 102.978 | -18.355 | 1.00 | 46.65 | C |
| ATOM | 2582 | N | GLU | A | 456 | 56.077 | 100.717 | -21.176 | 1.00 | 54.99 | N |
| ATOM | 2583 | CA | GLU | A | 456 | 57.308 | 100.413 | -21.903 | 1.00 | 58.83 | C |
| ATOM | 2584 | C | GLU | A | 456 | 57.068 | 99.632 | -23.194 | 1.00 | 61.65 | C |
| ATOM | 2585 | O | GLU | A | 456 | 57.708 | 99.890 | -24.203 | 1.00 | 60.94 | O |
| ATOM | 2586 | CB | GLU | A | 456 | 58.313 | 99.699 | -20.997 | 1.00 | 57.23 | C |
| ATOM | 2587 | CG | GLU | A | 456 | 58.665 | 100.511 | -19.751 | 1.00 | 62.14 | C |
| ATOM | 2588 | CD | GLU | A | 456 | 59.457 | 99.715 | -18.732 | 1.00 | 74.70 | C |
| ATOM | 2589 | OE1 | GLU | A | 456 | 59.733 | 98.516 | -18.979 | 1.00 | 78.70 | O |
| ATOM | 2590 | OE2 | GLU | A | 456 | 59.808 | 100.290 | -17.679 | 1.00 | 89.32 | O |
| ATOM | 2591 | N | GLY | A | 457 | 56.130 | 98.694 | -23.178 | 1.00 | 62.44 | N |
| ATOM | 2592 | CA | GLY | A | 457 | 55.873 | 97.803 | -24.365 | 1.00 | 58.36 | C |
| ATOM | 2593 | C | GLY | A | 457 | 55.431 | 98.696 | -25.592 | 1.00 | 59.13 | C |
| ATOM | 2594 | O | GLY | A | 457 | 55.867 | 98.424 | -26.703 | 1.00 | 61.83 | O |
| ATOM | 2595 | N | ILE | A | 458 | 54.561 | 99.677 | -25.394 | 1.00 | 52.98 | N |
| ATOM | 2596 | CA | ILE | A | 458 | 53.906 | 100.345 | -26.511 | 1.00 | 47.84 | C |
| ATOM | 2597 | C | ILE | A | 458 | 54.849 | 101.203 | -27.339 | 1.00 | 57.17 | C |
| ATOM | 2598 | O | ILE | A | 458 | 54.852 | 101.109 | -28.577 | 1.00 | 61.31 | O |
| ATOM | 2599 | CB | ILE | A | 458 | 52.679 | 101.147 | -26.050 | 1.00 | 47.85 | C |
| ATOM | 2600 | CG1 | ILE | A | 458 | 51.513 | 100.186 | -25.765 | 1.00 | 48.52 | C |
| ATOM | 2601 | CG2 | ILE | A | 458 | 52.287 | 102.178 | -27.084 | 1.00 | 52.36 | C |
| ATOM | 2602 | CD1 | ILE | A | 458 | 51.129 | 99.365 | -27.027 | 1.00 | 49.28 | C |
| ATOM | 2603 | N | PRO | A | 459 | 55.659 | 102.041 | -26.670 | 1.00 | 59.06 | N |
| ATOM | 2604 | CA | PRO | A | 459 | 56.719 | 102.799 | -27.355 | 1.00 | 61.22 | C |
| ATOM | 2605 | C | PRO | A | 459 | 57.732 | 101.889 | -28.044 | 1.00 | 62.83 | C |
| ATOM | 2606 | O | PRO | A | 459 | 58.301 | 103.275 | -29.063 | 1.00 | 72.38 | O |
| ATOM | 2607 | CB | PRO | A | 459 | 57.410 | 103.551 | -26.210 | 1.00 | 61.23 | C |
| ATOM | 2608 | CG | PRO | A | 459 | 56.376 | 103.678 | -25.159 | 1.00 | 57.74 | C |
| ATOM | 2609 | CD | PRO | A | 459 | 55.466 | 103.479 | -25.280 | 1.00 | 53.42 | C |
| ATOM | 2610 | N | ALA | A | 460 | 57.972 | 100.705 | -27.487 | 1.00 | 54.71 | N |
| ATOM | 2611 | CA | ALA | A | 460 | 58.879 | 99.757 | -28.113 | 1.00 | 53.15 | C |
| ATOM | 2612 | C | ALA | A | 460 | 58.273 | 99.233 | -29.408 | 1.00 | 64.38 | C |
| ATOM | 2613 | O | ALA | A | 460 | 58.973 | 99.087 | -30.403 | 1.00 | 74.35 | O |

FIG. 8-44

| | | | | | | | | | | | |
|---|---|---|---|---|---|---|---|---|---|---|---|
| ATOM | 2614 | CB | ALA | A | 460 | 59.194 | 98.623 | -27.179 | 1.00 | 53.96 | C |
| ATOM | 2615 | N | LEU | A | 461 | 56.972 | 98.997 | -29.401 | 1.00 | 63.43 | N |
| ATOM | 2616 | CA | LEU | A | 461 | 56.296 | 98.482 | -30.615 | 1.00 | 61.45 | C |
| ATOM | 2617 | C | LEU | A | 461 | 56.261 | 99.538 | -31.714 | 1.00 | 63.20 | C |
| ATOM | 2618 | O | LEU | A | 461 | 56.339 | 99.215 | -32.904 | 1.00 | 58.30 | O |
| ATOM | 2619 | CB | LEU | A | 461 | 54.880 | 97.990 | -30.304 | 1.00 | 51.82 | C |
| ATOM | 2620 | CG | LEU | A | 461 | 54.824 | 96.728 | -29.427 | 1.00 | 59.77 | C |
| ATOM | 2621 | CD1 | LEU | A | 461 | 53.365 | 96.321 | -29.071 | 1.00 | 55.32 | C |
| ATOM | 2622 | CD2 | LEU | A | 461 | 55.573 | 95.570 | -30.082 | 1.00 | 54.61 | C |
| ATOM | 2623 | N | LYS | A | 462 | 56.150 | 100.801 | -31.313 | 1.00 | 66.90 | N |
| ATOM | 2624 | CA | LYS | A | 462 | 56.115 | 101.908 | -32.264 | 1.00 | 69.17 | C |
| ATOM | 2625 | C | LYS | A | 462 | 57.479 | 102.180 | -32.876 | 1.00 | 75.12 | C |
| ATOM | 2626 | O | LYS | A | 462 | 57.578 | 102.525 | -34.044 | 1.00 | 80.05 | O |
| ATOM | 2627 | CB | LYS | A | 462 | 55.670 | 103.187 | -31.531 | 1.00 | 66.87 | C |
| ATOM | 2628 | CG | LYS | A | 462 | 54.045 | 103.180 | -31.332 | 1.00 | 65.77 | C |
| ATOM | 2629 | CD | LYS | A | 462 | 53.656 | 103.872 | -30.298 | 1.00 | 60.34 | C |
| ATOM | 2630 | CE | LYS | A | 462 | 53.960 | 105.333 | -30.265 | 1.00 | 67.06 | C |
| ATOM | 2631 | NZ | LYS | A | 462 | 53.997 | 105.920 | -28.931 | 1.00 | 68.97 | N |
| ATOM | 2632 | N | LYS | A | 463 | 58.529 | 102.042 | -32.074 | 1.00 | 77.82 | N |
| ATOM | 2633 | CA | LYS | A | 463 | 59.889 | 102.198 | -32.566 | 1.00 | 78.63 | C |
| ATOM | 2634 | C | LYS | A | 463 | 60.217 | 101.064 | -33.525 | 1.00 | 83.57 | C |
| ATOM | 2635 | O | LYS | A | 463 | 60.786 | 101.284 | -34.595 | 1.00 | 84.05 | O |
| ATOM | 2636 | CB | LYS | A | 463 | 60.892 | 102.214 | -31.406 | 1.00 | 76.15 | C |
| ATOM | 2637 | CG | LYS | A | 463 | 61.328 | 103.608 | -30.989 | 1.00 | 80.22 | C |
| ATOM | 2638 | CD | LYS | A | 463 | 62.182 | 104.243 | -32.075 | 1.00 | 89.86 | C |
| ATOM | 2639 | CE | LYS | A | 463 | 62.052 | 105.764 | -32.096 | 1.00 | 93.44 | C |
| ATOM | 2640 | NZ | LYS | A | 463 | 62.666 | 106.349 | -33.331 | 1.00 | 96.66 | N |
| ATOM | 2641 | N | GLN | A | 464 | 59.828 | 99.851 | -33.143 | 1.00 | 80.58 | N |
| ATOM | 2642 | CA | GLN | A | 464 | 60.187 | 98.664 | -33.902 | 1.00 | 83.53 | C |
| ATOM | 2643 | C | GLN | A | 464 | 59.425 | 98.528 | -35.223 | 1.00 | 90.24 | C |
| ATOM | 2644 | O | GLN | A | 464 | 59.824 | 97.747 | -36.084 | 1.00 | 92.80 | O |
| ATOM | 2645 | CB | GLN | A | 464 | 60.003 | 97.414 | -33.047 | 1.00 | 84.74 | C |
| ATOM | 2646 | CG | GLN | A | 464 | 60.564 | 96.149 | -33.664 | 1.00 | 88.75 | C |
| ATOM | 2647 | CD | GLN | A | 464 | 60.557 | 94.978 | -32.694 | 1.00 | 95.28 | C |
| ATOM | 2648 | OE1 | GLN | A | 464 | 59.846 | 94.985 | -31.678 | 1.00 | 93.51 | O |
| ATOM | 2649 | NE2 | GLN | A | 464 | 61.355 | 93.961 | -33.002 | 1.00 | 96.75 | N |
| ATOM | 2650 | N | ARG | A | 465 | 58.333 | 99.272 | -35.388 | 1.00 | 91.28 | N |
| ATOM | 2651 | CA | ARG | A | 465 | 57.651 | 99.318 | -36.688 | 1.00 | 95.25 | C |
| ATOM | 2652 | C | ARG | A | 465 | 57.160 | 100.705 | -37.129 | 1.00 | 92.64 | C |
| ATOM | 2653 | O | ARG | A | 465 | 58.356 | 100.819 | -38.048 | 1.00 | 86.39 | O |
| ATOM | 2654 | CB | ARG | A | 465 | 56.557 | 98.246 | -36.815 | 1.00 | 97.84 | C |
| ATOM | 2655 | CG | ARG | A | 465 | 56.094 | 97.630 | -35.511 | 1.00 | 100.98 | C |
| ATOM | 2656 | CD | ARG | A | 465 | 55.744 | 96.159 | -35.711 | 1.00 | 104.74 | C |
| ATOM | 2657 | NE | ARG | A | 465 | 56.921 | 95.293 | -35.615 | 1.00 | 108.44 | N |
| ATOM | 2658 | CZ | ARG | A | 465 | 57.002 | 94.060 | -36.114 | 1.00 | 108.59 | C |
| ATOM | 2659 | NH1 | ARG | A | 465 | 55.979 | 93.531 | -36.770 | 1.00 | 108.40 | N |
| ATOM | 2660 | NH2 | ARG | A | 465 | 58.120 | 93.359 | -35.964 | 1.00 | 107.08 | N |
| ATOM | 2661 | N | LYS | A | 466 | 57.662 | 101.747 | -36.473 | 1.00 | 99.34 | N |
| ATOM | 2662 | CA | LYS | A | 466 | 57.565 | 103.122 | -36.974 | 1.00 | 103.73 | C |
| ATOM | 2663 | C | LYS | A | 466 | 56.169 | 103.752 | -36.887 | 1.00 | 102.41 | C |
| ATOM | 2664 | O | LYS | A | 466 | 55.867 | 104.708 | -37.604 | 1.00 | 106.12 | O |
| ATOM | 2665 | CB | LYS | A | 466 | 58.091 | 103.197 | -38.416 | 1.00 | 108.73 | C |
| ATOM | 2666 | CG | LYS | A | 466 | 59.359 | 102.380 | -38.665 | 1.00 | 111.55 | C |
| ATOM | 2667 | CD | LYS | A | 466 | 60.596 | 103.060 | -38.093 | 1.00 | 117.15 | C |
| ATOM | 2668 | CE | LYS | A | 466 | 61.347 | 103.835 | -39.176 | 1.00 | 123.44 | C |
| ATOM | 2669 | NZ | LYS | A | 466 | 60.464 | 104.749 | -39.955 | 1.00 | 129.59 | N |
| ATOM | 2670 | N | LEU | A | 467 | 55.335 | 103.233 | -35.992 | 1.00 | 99.39 | N |
| ATOM | 2671 | CA | LEU | A | 467 | 53.948 | 103.681 | -35.876 | 1.00 | 86.96 | C |
| ATOM | 2672 | C | LEU | A | 467 | 53.832 | 105.056 | -35.221 | 1.00 | 91.26 | C |
| ATOM | 2673 | O | LEU | A | 467 | 54.643 | 105.416 | -34.370 | 1.00 | 93.05 | O |
| ATOM | 2674 | CB | LEU | A | 467 | 53.133 | 102.653 | -35.080 | 1.00 | 78.21 | C |
| ATOM | 2675 | CG | LEU | A | 467 | 53.963 | 101.201 | -35.315 | 1.00 | 70.50 | C |
| ATOM | 2676 | CD1 | LEU | A | 467 | 52.522 | 100.278 | -34.763 | 1.00 | 62.96 | C |
| ATOM | 2677 | CD2 | LEU | A | 467 | 53.819 | 100.900 | -36.812 | 1.00 | 64.18 | C |
| ATOM | 2678 | N | SER | A | 468 | 52.816 | 105.818 | -35.618 | 1.00 | 94.36 | N |
| ATOM | 2679 | CA | SER | A | 468 | 52.621 | 107.169 | -35.089 | 1.00 | 95.38 | C |
| ATOM | 2680 | C | SER | A | 468 | 51.787 | 107.193 | -33.818 | 1.00 | 91.59 | C |
| ATOM | 2681 | O | SER | A | 468 | 51.941 | 107.998 | -32.934 | 1.00 | 92.72 | O |
| ATOM | 2682 | CB | SER | A | 468 | 51.944 | 108.054 | -36.136 | 1.00 | 101.11 | C |
| ATOM | 2683 | OG | SER | A | 468 | 50.708 | 107.499 | -36.550 | 1.00 | 101.55 | O |
| ATOM | 2684 | N | ASP | A | 469 | 50.882 | 106.191 | -33.736 | 1.00 | 85.34 | N |
| ATOM | 2685 | CA | ASP | A | 469 | 50.045 | 106.069 | -32.561 | 1.00 | 83.76 | C |
| ATOM | 2686 | C | ASP | A | 469 | 49.729 | 104.604 | -32.353 | 1.00 | 74.58 | C |
| ATOM | 2687 | O | ASP | A | 469 | 49.833 | 103.798 | -33.280 | 1.00 | 73.76 | O |
| ATOM | 2688 | CB | ASP | A | 469 | 48.767 | 106.903 | -32.697 | 1.00 | 88.17 | C |
| ATOM | 2689 | CG | ASP | A | 469 | 47.832 | 106.385 | -33.779 | 1.00 | 90.62 | C |
| ATOM | 2690 | OD1 | ASP | A | 469 | 47.716 | 107.061 | -34.831 | 1.00 | 91.74 | O |

FIG. 8-45

| | | | | | | | | | | | |
|---|---|---|---|---|---|---|---|---|---|---|---|
| ATOM | 2691 | OD2 | ASP | A | 469 | 47.203 | 105.333 | -33.576 | 1.00 | 91.43 | O |
| ATOM | 2692 | N | LEU | A | 470 | 49.363 | 104.258 | -31.131 | 1.00 | 62.63 | N |
| ATOM | 2693 | CA | LEU | A | 470 | 49.106 | 102.889 | -30.797 | 1.00 | 60.03 | C |
| ATOM | 2694 | C | LEU | A | 470 | 48.650 | 102.842 | -29.368 | 1.00 | 59.95 | C |
| ATOM | 2695 | O | LEU | A | 470 | 49.193 | 103.584 | -28.531 | 1.00 | 62.49 | O |
| ATOM | 2696 | CB | LEU | A | 470 | 50.373 | 102.029 | -30.964 | 1.00 | 56.51 | C |
| ATOM | 2697 | CG | LEU | A | 470 | 50.191 | 100.514 | -30.915 | 1.00 | 54.59 | C |
| ATOM | 2698 | CD1 | LEU | A | 470 | 49.205 | 100.042 | -31.988 | 1.00 | 49.75 | C |
| ATOM | 2699 | CD2 | LEU | A | 470 | 51.522 | 99.817 | -31.090 | 1.00 | 55.40 | C |
| ATOM | 2700 | N | GLU | A | 471 | 47.831 | 102.036 | -29.089 | 1.00 | 60.99 | N |
| ATOM | 2701 | CA | GLU | A | 471 | 47.090 | 101.955 | -27.781 | 1.00 | 58.60 | C |
| ATOM | 2702 | C | GLU | A | 471 | 46.919 | 100.520 | -27.291 | 1.00 | 53.11 | C |
| ATOM | 2703 | O | GLU | A | 471 | 47.136 | 99.578 | -28.060 | 1.00 | 51.88 | O |
| ATOM | 2704 | CB | GLU | A | 471 | 45.768 | 102.711 | -27.636 | 1.00 | 64.87 | C |
| ATOM | 2705 | CG | GLU | A | 471 | 45.938 | 104.211 | -27.587 | 1.00 | 71.19 | C |
| ATOM | 2706 | CD | GLU | A | 471 | 46.810 | 104.647 | -26.423 | 1.00 | 81.70 | C |
| ATOM | 2707 | OE1 | GLU | A | 471 | 46.962 | 103.853 | -25.457 | 1.00 | 86.87 | O |
| ATOM | 2708 | OE2 | GLU | A | 471 | 47.341 | 105.777 | -26.477 | 1.00 | 88.89 | O |
| ATOM | 2709 | N | THR | A | 472 | 46.528 | 100.368 | -26.033 | 1.00 | 55.45 | N |
| ATOM | 2710 | CA | THR | A | 472 | 46.491 | 99.065 | -25.390 | 1.00 | 51.45 | C |
| ATOM | 2711 | C | THR | A | 472 | 45.603 | 99.106 | -24.177 | 1.00 | 48.69 | C |
| ATOM | 2712 | O | THR | A | 472 | 45.330 | 100.164 | -23.607 | 1.00 | 52.54 | O |
| ATOM | 2713 | CB | THR | A | 472 | 47.895 | 98.581 | -24.932 | 1.00 | 67.95 | C |
| ATOM | 2714 | OG1 | THR | A | 472 | 47.852 | 97.165 | -24.719 | 1.00 | 65.73 | O |
| ATOM | 2715 | CG2 | THR | A | 472 | 48.368 | 99.295 | -23.618 | 1.00 | 42.39 | C |
| ATOM | 2716 | N | ALA | A | 473 | 45.136 | 97.831 | -23.795 | 1.00 | 43.09 | N |
| ATOM | 2717 | CA | ALA | A | 473 | 44.312 | 97.753 | -22.621 | 1.00 | 37.32 | C |
| ATOM | 2718 | C | ALA | A | 473 | 44.688 | 96.385 | -22.105 | 1.00 | 46.83 | C |
| ATOM | 2719 | O | ALA | A | 473 | 45.017 | 95.477 | -22.886 | 1.00 | 48.86 | O |
| ATOM | 2720 | CB | ALA | A | 473 | 42.826 | 97.796 | -22.965 | 1.00 | 42.14 | C |
| ATOM | 2721 | N | ILE | A | 474 | 44.659 | 96.244 | -20.788 | 1.00 | 37.82 | N |
| ATOM | 2722 | CA | ILE | A | 474 | 45.011 | 94.993 | -20.163 | 1.00 | 40.25 | C |
| ATOM | 2723 | C | ILE | A | 474 | 44.067 | 94.812 | -19.005 | 1.00 | 40.03 | C |
| ATOM | 2724 | O | ILE | A | 474 | 43.896 | 95.738 | -18.221 | 1.00 | 43.21 | O |
| ATOM | 2725 | CB | ILE | A | 474 | 46.431 | 95.047 | -19.574 | 1.00 | 39.83 | C |
| ATOM | 2726 | CG1 | ILE | A | 474 | 47.464 | 95.405 | -20.646 | 1.00 | 41.77 | C |
| ATOM | 2727 | CG2 | ILE | A | 474 | 46.770 | 93.739 | -18.813 | 1.00 | 38.79 | C |
| ATOM | 2728 | CD1 | ILE | A | 474 | 48.938 | 95.548 | -20.032 | 1.00 | 38.89 | C |
| ATOM | 2729 | N | VAL | A | 475 | 43.514 | 93.616 | -18.890 | 1.00 | 37.74 | N |
| ATOM | 2730 | CA | VAL | A | 475 | 42.696 | 93.270 | -17.793 | 1.00 | 41.28 | C |
| ATOM | 2731 | C | VAL | A | 475 | 43.153 | 91.941 | -17.210 | 1.00 | 38.38 | C |
| ATOM | 2732 | O | VAL | A | 475 | 43.296 | 90.971 | -17.964 | 1.00 | 39.34 | O |
| ATOM | 2733 | CB | VAL | A | 475 | 41.212 | 93.110 | -18.119 | 1.00 | 39.06 | C |
| ATOM | 2734 | CG1 | VAL | A | 475 | 40.812 | 92.916 | -18.841 | 1.00 | 39.04 | C |
| ATOM | 2735 | CG2 | VAL | A | 475 | 40.734 | 94.302 | -18.862 | 1.00 | 43.33 | C |
| ATOM | 2736 | N | VAL | A | 476 | 43.367 | 91.905 | -15.900 | 1.00 | 33.88 | N |
| ATOM | 2737 | CA | VAL | A | 476 | 43.783 | 90.700 | -15.130 | 1.00 | 33.78 | C |
| ATOM | 2738 | C | VAL | A | 476 | 42.700 | 90.354 | -14.165 | 1.00 | 39.34 | C |
| ATOM | 2739 | O | VAL | A | 476 | 42.345 | 91.206 | -13.374 | 1.00 | 41.05 | O |
| ATOM | 2740 | CB | VAL | A | 476 | 45.025 | 90.962 | -14.353 | 1.00 | 30.56 | C |
| ATOM | 2741 | CG1 | VAL | A | 476 | 45.395 | 89.697 | -13.568 | 1.00 | 36.67 | C |
| ATOM | 2742 | CG2 | VAL | A | 476 | 46.157 | 91.433 | -15.227 | 1.00 | 31.28 | C |
| ATOM | 2743 | N | VAL | A | 477 | 42.227 | 89.103 | -14.178 | 1.00 | 38.15 | N |
| ATOM | 2744 | CA | VAL | A | 477 | 41.225 | 88.604 | -13.250 | 1.00 | 35.30 | C |
| ATOM | 2745 | C | VAL | A | 477 | 41.592 | 87.238 | -12.683 | 1.00 | 36.27 | C |
| ATOM | 2746 | O | VAL | A | 477 | 42.232 | 86.388 | -13.320 | 1.00 | 38.46 | O |
| ATOM | 2747 | CB | VAL | A | 477 | 39.787 | 88.480 | -13.883 | 1.00 | 44.70 | C |
| ATOM | 2748 | CG1 | VAL | A | 477 | 39.462 | 89.653 | -14.799 | 1.00 | 43.59 | C |
| ATOM | 2749 | CG2 | VAL | A | 477 | 39.645 | 87.174 | -14.629 | 1.00 | 46.45 | C |
| ATOM | 2750 | N | ASP | A | 478 | 41.123 | 87.014 | -11.481 | 1.00 | 31.04 | N |
| ATOM | 2751 | CA | ASP | A | 478 | 41.337 | 85.753 | -10.809 | 1.00 | 34.16 | C |
| ATOM | 2752 | C | ASP | A | 478 | 40.664 | 84.597 | -11.540 | 1.00 | 38.32 | C |
| ATOM | 2753 | O | ASP | A | 478 | 39.498 | 84.663 | -11.900 | 1.00 | 40.14 | O |
| ATOM | 2754 | CB | ASP | A | 478 | 40.830 | 85.849 | -9.374 | 1.00 | 44.82 | C |
| ATOM | 2755 | CG | ASP | A | 478 | 41.122 | 84.601 | -8.581 | 1.00 | 55.25 | C |
| ATOM | 2756 | OD1 | ASP | A | 478 | 42.112 | 84.619 | -7.815 | 1.00 | 61.51 | O |
| ATOM | 2757 | OD2 | ASP | A | 478 | 40.378 | 83.600 | -8.736 | 1.00 | 52.26 | O |
| ATOM | 2758 | N | ARG | A | 479 | 41.410 | 83.529 | -11.731 | 1.00 | 40.74 | N |
| ATOM | 2759 | CA | ARG | A | 479 | 40.963 | 82.401 | -12.599 | 1.00 | 39.49 | C |
| ATOM | 2760 | C | ARG | A | 479 | 39.636 | 81.811 | -12.099 | 1.00 | 37.72 | C |
| ATOM | 2761 | O | ARG | A | 479 | 38.718 | 81.511 | -12.892 | 1.00 | 39.19 | O |
| ATOM | 2762 | CB | ARG | A | 479 | 42.107 | 81.359 | -12.580 | 1.00 | 40.22 | C |
| ATOM | 2763 | CG | ARG | A | 479 | 41.825 | 80.088 | -13.316 | 1.00 | 38.55 | C |
| ATOM | 2764 | CD | ARG | A | 479 | 43.092 | 79.210 | -13.350 | 1.00 | 34.15 | C |
| ATOM | 2765 | NE | ARG | A | 479 | 42.738 | 77.858 | -13.797 | 1.00 | 33.15 | N |
| ATOM | 2766 | CZ | ARG | A | 479 | 43.355 | 76.752 | -13.396 | 1.00 | 38.26 | C |
| ATOM | 2767 | NH1 | ARG | A | 479 | 44.356 | 76.820 | -12.529 | 1.00 | 32.05 | N |

FIG. 8-46

| | | | | | | | | | | | |
|---|---|---|---|---|---|---|---|---|---|---|---|
| ATOM | 2768 | NH2 | ARG | A | 479 | 42.975 | 75.570 | -13.856 | 1.00 | 38.18 | N |
| ATOM | 2769 | N | PHE | A | 480 | 39.515 | 81.695 | -10.740 | 1.00 | 39.20 | N |
| ATOM | 2770 | CA | PHE | A | 480 | 38.443 | 80.934 | -10.133 | 1.00 | 42.10 | C |
| ATOM | 2771 | C | PHE | A | 480 | 37.322 | 81.815 | -9.566 | 1.00 | 50.46 | C |
| ATOM | 2772 | O | PHE | A | 480 | 36.126 | 81.478 | -9.682 | 1.00 | 45.90 | O |
| ATOM | 2773 | CB | PHE | A | 480 | 39.018 | 80.007 | -9.043 | 1.00 | 46.61 | C |
| ATOM | 2774 | CG | PHE | A | 480 | 39.909 | 78.830 | -9.585 | 1.00 | 47.34 | C |
| ATOM | 2775 | CD1 | PHE | A | 480 | 41.284 | 78.885 | -9.401 | 1.00 | 47.36 | C |
| ATOM | 2776 | CD2 | PHE | A | 480 | 39.375 | 77.881 | -10.528 | 1.00 | 48.95 | C |
| ATOM | 2777 | CE1 | PHE | A | 480 | 42.126 | 77.887 | -9.910 | 1.00 | 45.54 | C |
| ATOM | 2778 | CE2 | PHE | A | 480 | 40.198 | 76.887 | -10.862 | 1.00 | 43.07 | C |
| ATOM | 2779 | CZ | PHE | A | 480 | 41.580 | 76.938 | -10.639 | 1.00 | 49.86 | C |
| ATOM | 2780 | N | SER | A | 481 | 37.702 | 82.961 | -9.007 | 1.00 | 43.28 | N |
| ATOM | 2781 | CA | SER | A | 481 | 36.763 | 83.787 | -8.261 | 1.00 | 46.78 | C |
| ATOM | 2782 | C | SER | A | 481 | 36.215 | 84.945 | -9.079 | 1.00 | 46.79 | C |
| ATOM | 2783 | O | SER | A | 481 | 35.230 | 85.592 | -8.671 | 1.00 | 43.21 | O |
| ATOM | 2784 | CB | SER | A | 481 | 37.436 | 84.329 | -6.983 | 1.00 | 48.85 | C |
| ATOM | 2785 | OG | SER | A | 481 | 38.219 | 85.476 | -7.281 | 1.00 | 44.87 | O |
| ATOM | 2786 | N | GLY | A | 482 | 36.858 | 85.215 | -10.221 | 1.00 | 41.25 | N |
| ATOM | 2787 | CA | GLY | A | 482 | 36.431 | 86.284 | -11.107 | 1.00 | 38.48 | C |
| ATOM | 2788 | C | GLY | A | 482 | 36.784 | 87.675 | -10.608 | 1.00 | 41.06 | C |
| ATOM | 2789 | O | GLY | A | 482 | 36.359 | 88.683 | -11.166 | 1.00 | 45.33 | O |
| ATOM | 2790 | N | GLU | A | 483 | 37.587 | 87.732 | -9.558 | 1.00 | 43.50 | N |
| ATOM | 2791 | CA | GLU | A | 483 | 37.965 | 89.004 | -8.975 | 1.00 | 41.57 | C |
| ATOM | 2792 | C | GLU | A | 483 | 38.956 | 89.718 | -9.845 | 1.00 | 43.06 | C |
| ATOM | 2793 | O | GLU | A | 483 | 39.968 | 89.146 | -10.257 | 1.00 | 37.56 | O |
| ATOM | 2794 | CB | GLU | A | 483 | 38.562 | 88.791 | -7.608 | 1.00 | 40.00 | C |
| ATOM | 2795 | CG | GLU | A | 483 | 37.548 | 88.321 | -6.588 | 1.00 | 52.34 | C |
| ATOM | 2796 | CD | GLU | A | 483 | 38.210 | 87.888 | -5.302 | 1.00 | 68.84 | C |
| ATOM | 2797 | OE1 | GLU | A | 483 | 39.019 | 86.823 | -5.330 | 1.00 | 72.87 | O |
| ATOM | 2798 | OE2 | GLU | A | 483 | 37.926 | 88.525 | -4.266 | 1.00 | 72.52 | O |
| ATOM | 2799 | N | VAL | A | 484 | 38.667 | 90.984 | -10.104 | 1.00 | 41.09 | N |
| ATOM | 2800 | CA | VAL | A | 484 | 39.489 | 91.779 | -10.992 | 1.00 | 36.16 | C |
| ATOM | 2801 | C | VAL | A | 484 | 40.682 | 92.320 | -10.241 | 1.00 | 43.39 | C |
| ATOM | 2802 | O | VAL | A | 484 | 40.520 | 93.116 | -9.318 | 1.00 | 45.77 | O |
| ATOM | 2803 | CB | VAL | A | 484 | 38.709 | 92.949 | -11.544 | 1.00 | 36.45 | C |
| ATOM | 2804 | CG1 | VAL | A | 484 | 39.595 | 93.803 | -12.461 | 1.00 | 37.74 | C |
| ATOM | 2805 | CG2 | VAL | A | 484 | 37.460 | 92.435 | -12.278 | 1.00 | 33.92 | C |
| ATOM | 2806 | N | ARG | A | 485 | 41.876 | 91.906 | -10.667 | 1.00 | 42.40 | N |
| ATOM | 2807 | CA | ARG | A | 485 | 43.118 | 92.216 | -9.957 | 1.00 | 38.09 | C |
| ATOM | 2808 | C | ARG | A | 485 | 43.734 | 93.490 | -10.515 | 1.00 | 43.11 | C |
| ATOM | 2809 | O | ARG | A | 485 | 44.334 | 94.255 | -9.765 | 1.00 | 40.88 | O |
| ATOM | 2810 | CB | ARG | A | 485 | 44.127 | 91.048 | -10.067 | 1.00 | 29.75 | C |
| ATOM | 2811 | CG | ARG | A | 485 | 43.530 | 89.618 | -9.978 | 1.00 | 40.39 | C |
| ATOM | 2812 | CD | ARG | A | 485 | 43.458 | 88.881 | -8.591 | 1.00 | 55.54 | C |
| ATOM | 2813 | NE | ARG | A | 485 | 42.898 | 89.642 | -7.488 | 1.00 | 49.61 | N |
| ATOM | 2814 | CZ | ARG | A | 485 | 42.271 | 89.129 | -6.411 | 1.00 | 50.71 | C |
| ATOM | 2815 | NH1 | ARG | A | 485 | 42.054 | 87.816 | -6.250 | 1.00 | 40.80 | N |
| ATOM | 2816 | NH2 | ARG | A | 485 | 41.832 | 89.961 | -5.468 | 1.00 | 40.81 | N |
| ATOM | 2817 | N | ALA | A | 486 | 43.560 | 93.736 | -11.826 | 1.00 | 39.27 | N |
| ATOM | 2818 | CA | ALA | A | 486 | 44.243 | 94.844 | -12.478 | 1.00 | 35.79 | C |
| ATOM | 2819 | C | ALA | A | 486 | 43.515 | 95.286 | -13.724 | 1.00 | 45.68 | C |
| ATOM | 2820 | O | ALA | A | 486 | 42.865 | 94.474 | -14.399 | 1.00 | 37.31 | O |
| ATOM | 2821 | CB | ALA | A | 486 | 45.664 | 94.452 | -12.843 | 1.00 | 43.35 | C |
| ATOM | 2822 | N | MET | A | 487 | 43.646 | 96.570 | -14.039 | 1.00 | 44.36 | N |
| ATOM | 2823 | CA | MET | A | 487 | 43.087 | 97.121 | -15.223 | 1.00 | 40.39 | C |
| ATOM | 2824 | C | MET | A | 487 | 43.825 | 98.283 | -15.758 | 1.00 | 45.63 | C |
| ATOM | 2825 | O | MET | A | 487 | 44.069 | 99.271 | -15.055 | 1.00 | 46.76 | O |
| ATOM | 2826 | CB | MET | A | 487 | 41.597 | 97.590 | -14.914 | 1.00 | 46.30 | C |
| ATOM | 2827 | CG | MET | A | 487 | 40.871 | 98.169 | -16.125 | 1.00 | 45.86 | C |
| ATOM | 2828 | SD | MET | A | 487 | 39.131 | 98.532 | -15.793 | 1.00 | 54.45 | S |
| ATOM | 2829 | CE | MET | A | 487 | 38.557 | 96.866 | -15.510 | 1.00 | 55.71 | C |
| ATOM | 2830 | N | VAL | A | 488 | 44.243 | 98.163 | -17.015 | 1.00 | 33.27 | N |
| ATOM | 2831 | CA | VAL | A | 488 | 45.042 | 99.182 | -17.643 | 1.00 | 34.49 | C |
| ATOM | 2832 | C | VAL | A | 488 | 44.241 | 99.989 | -18.646 | 1.00 | 43.94 | C |
| ATOM | 2833 | O | VAL | A | 488 | 43.938 | 98.756 | -19.717 | 1.00 | 33.21 | O |
| ATOM | 2834 | CB | VAL | A | 488 | 46.423 | 98.636 | -18.065 | 1.00 | 34.29 | C |
| ATOM | 2835 | CG1 | VAL | A | 488 | 47.011 | 99.458 | -19.234 | 1.00 | 34.16 | C |
| ATOM | 2836 | CG2 | VAL | A | 488 | 47.377 | 98.618 | -16.873 | 1.00 | 34.68 | C |
| ATOM | 2837 | N | GLY | A | 489 | 43.882 | 100.864 | -18.890 | 1.00 | 50.60 | N |
| ATOM | 2838 | CA | GLY | A | 489 | 42.981 | 101.335 | -19.920 | 1.00 | 53.36 | C |
| ATOM | 2839 | C | GLY | A | 489 | 43.628 | 102.155 | -21.015 | 1.00 | 50.83 | C |
| ATOM | 2840 | O | GLY | A | 489 | 42.926 | 102.781 | -21.810 | 1.00 | 52.74 | O |
| ATOM | 2841 | N | GLY | A | 490 | 44.957 | 102.168 | -21.056 | 1.00 | 48.58 | N |
| ATOM | 2842 | CA | GLY | A | 490 | 45.666 | 103.873 | -22.035 | 1.00 | 45.35 | C |
| ATOM | 2843 | C | GLY | A | 490 | 47.165 | 102.854 | -21.834 | 1.00 | 57.81 | C |
| ATOM | 2844 | O | GLY | A | 490 | 47.665 | 103.616 | -20.753 | 1.00 | 58.39 | O |

FIG. 8-47

| | | | | | | | | | | | |
|---|---|---|---|---|---|---|---|---|---|---|---|
| ATOM | 2845 | N | SER | A | 491 | 47.881 | 103.320 | -22.889 | 1.00 | 87.77 | N |
| ATOM | 2846 | CA | SER | A | 491 | 49.339 | 103.280 | -22.909 | 1.00 | 74.86 | C |
| ATOM | 2847 | C | SER | A | 491 | 49.868 | 104.239 | -21.914 | 1.00 | 77.03 | C |
| ATOM | 2848 | O | SER | A | 491 | 51.147 | 104.120 | -21.611 | 1.00 | 81.74 | O |
| ATOM | 2849 | CB | SER | A | 491 | 49.850 | 103.602 | -24.314 | 1.00 | 78.98 | C |
| ATOM | 2850 | OG | SER | A | 491 | 49.375 | 104.868 | -24.747 | 1.00 | 76.81 | O |
| ATOM | 2851 | N | GLU | A | 492 | 49.181 | 105.193 | -21.435 | 1.00 | 78.13 | N |
| ATOM | 2852 | CA | GLU | A | 492 | 49.604 | 106.117 | -20.382 | 1.00 | 84.11 | C |
| ATOM | 2853 | C | GLU | A | 492 | 48.673 | 105.982 | -19.169 | 1.00 | 85.94 | C |
| ATOM | 2854 | O | GLU | A | 492 | 47.830 | 106.843 | -18.928 | 1.00 | 78.99 | O |
| ATOM | 2855 | CB | GLU | A | 492 | 49.621 | 107.550 | -20.908 | 1.00 | 90.73 | C |
| ATOM | 2856 | CG | GLU | A | 492 | 50.823 | 107.839 | -21.801 | 1.00 | 104.04 | C |
| ATOM | 2857 | CD | GLU | A | 492 | 50.842 | 109.261 | -22.349 | 1.00 | 113.88 | C |
| ATOM | 2858 | OE1 | GLU | A | 492 | 51.865 | 109.944 | -22.209 | 1.00 | 114.19 | O |
| ATOM | 2859 | OE2 | GLU | A | 492 | 49.815 | 109.693 | -22.919 | 1.00 | 115.73 | O |
| ATOM | 2860 | N | PRO | A | 493 | 48.847 | 104.895 | -18.392 | 1.00 | 90.32 | N |
| ATOM | 2861 | CA | PRO | A | 493 | 47.867 | 104.462 | -17.391 | 1.00 | 94.15 | C |
| ATOM | 2862 | C | PRO | A | 493 | 47.878 | 105.380 | -16.169 | 1.00 | 104.14 | C |
| ATOM | 2863 | O | PRO | A | 493 | 48.917 | 105.417 | -15.395 | 1.00 | 98.75 | O |
| ATOM | 2864 | CB | PRO | A | 493 | 48.353 | 103.054 | -17.004 | 1.00 | 86.59 | C |
| ATOM | 2865 | CG | PRO | A | 493 | 49.592 | 102.787 | -17.842 | 1.00 | 86.79 | C |
| ATOM | 2866 | CD | PRO | A | 493 | 50.093 | 104.124 | -18.278 | 1.00 | 89.97 | C |
| ATOM | 2867 | N | GLN | A | 494 | 46.972 | 106.116 | -16.009 | 1.00 | 115.36 | N |
| ATOM | 2868 | CA | GLN | A | 494 | 49.067 | 107.102 | -14.942 | 1.00 | 126.50 | C |
| ATOM | 2869 | C | GLN | A | 494 | 47.858 | 108.134 | -15.090 | 1.00 | 132.74 | C |
| ATOM | 2870 | O | GLN | A | 494 | 47.167 | 108.384 | -14.187 | 1.00 | 130.49 | O |
| ATOM | 2871 | CB | GLN | A | 494 | 50.434 | 107.784 | -14.980 | 1.00 | 129.81 | C |
| ATOM | 2872 | CG | GLN | A | 494 | 51.982 | 106.824 | -14.732 | 1.00 | 129.90 | C |
| ATOM | 2873 | CD | GLN | A | 494 | 51.372 | 105.987 | -13.480 | 1.00 | 126.38 | C |
| ATOM | 2874 | OE1 | GLN | A | 494 | 51.369 | 104.755 | -13.531 | 1.00 | 121.75 | O |
| ATOM | 2875 | NE2 | GLN | A | 494 | 51.163 | 106.686 | -12.349 | 1.00 | 126.94 | N |
| ATOM | 2876 | N | PHE | A | 495 | 47.903 | 108.747 | -16.270 | 1.00 | 137.92 | N |
| ATOM | 2877 | CA | PHE | A | 495 | 46.935 | 109.794 | -16.566 | 1.00 | 139.45 | C |
| ATOM | 2878 | C | PHE | A | 495 | 45.897 | 109.284 | -17.563 | 1.00 | 134.08 | C |
| ATOM | 2879 | O | PHE | A | 495 | 46.130 | 109.307 | -18.772 | 1.00 | 134.14 | O |
| ATOM | 2880 | CB | PHE | A | 495 | 47.656 | 111.015 | -17.140 | 1.00 | 145.35 | C |
| ATOM | 2881 | CG | PHE | A | 495 | 49.100 | 111.110 | -16.731 | 1.00 | 149.67 | C |
| ATOM | 2882 | CD1 | PHE | A | 495 | 49.448 | 111.303 | -15.403 | 1.00 | 150.87 | C |
| ATOM | 2883 | CD2 | PHE | A | 495 | 50.108 | 111.009 | -17.679 | 1.00 | 152.09 | C |
| ATOM | 2884 | CE1 | PHE | A | 495 | 50.779 | 111.388 | -15.023 | 1.00 | 152.49 | C |
| ATOM | 2885 | CE2 | PHE | A | 495 | 51.436 | 111.091 | -17.302 | 1.00 | 154.75 | C |
| ATOM | 2886 | CZ | PHE | A | 495 | 51.771 | 111.283 | -15.973 | 1.00 | 154.52 | C |
| ATOM | 2887 | N | ALA | A | 496 | 44.751 | 108.843 | -17.059 | 1.00 | 128.59 | N |
| ATOM | 2888 | CA | ALA | A | 496 | 43.727 | 108.264 | -17.922 | 1.00 | 126.48 | C |
| ATOM | 2889 | C | ALA | A | 496 | 42.401 | 109.028 | -17.917 | 1.00 | 125.50 | C |
| ATOM | 2890 | O | ALA | A | 496 | 41.929 | 109.484 | -16.871 | 1.00 | 124.88 | O |
| ATOM | 2891 | CB | ALA | A | 496 | 43.498 | 106.794 | -17.571 | 1.00 | 123.64 | C |
| ATOM | 2892 | N | GLY | A | 497 | 41.818 | 109.162 | -19.107 | 1.00 | 121.80 | N |
| ATOM | 2893 | CA | GLY | A | 497 | 40.472 | 109.686 | -19.289 | 1.00 | 115.78 | C |
| ATOM | 2894 | C | GLY | A | 497 | 39.996 | 108.848 | -19.951 | 1.00 | 105.85 | C |
| ATOM | 2895 | O | GLY | A | 497 | 38.991 | 108.197 | -19.394 | 1.00 | 105.17 | O |
| ATOM | 2896 | N | TYR | A | 498 | 39.965 | 108.268 | -21.165 | 1.00 | 93.98 | N |
| ATOM | 2897 | CA | TYR | A | 498 | 39.327 | 107.183 | -21.887 | 1.00 | 77.08 | C |
| ATOM | 2898 | C | TYR | A | 498 | 39.856 | 105.846 | -21.360 | 1.00 | 67.93 | C |
| ATOM | 2899 | O | TYR | A | 498 | 41.054 | 105.558 | -21.459 | 1.00 | 58.67 | O |
| ATOM | 2900 | CB | TYR | A | 498 | 39.603 | 107.309 | -23.387 | 1.00 | 70.53 | C |
| ATOM | 2901 | CG | TYR | A | 498 | 38.764 | 106.405 | -24.262 | 1.00 | 67.74 | C |
| ATOM | 2902 | CD1 | TYR | A | 498 | 37.384 | 106.381 | -24.144 | 1.00 | 68.81 | C |
| ATOM | 2903 | CD2 | TYR | A | 498 | 39.353 | 105.604 | -25.230 | 1.00 | 75.26 | C |
| ATOM | 2904 | CE1 | TYR | A | 498 | 36.610 | 105.568 | -24.949 | 1.00 | 76.78 | C |
| ATOM | 2905 | CE2 | TYR | A | 498 | 38.588 | 104.782 | -26.050 | 1.00 | 78.00 | C |
| ATOM | 2906 | CZ | TYR | A | 498 | 37.217 | 104.764 | -25.901 | 1.00 | 81.93 | C |
| ATOM | 2907 | OH | TYR | A | 498 | 36.446 | 103.951 | -26.707 | 1.00 | 86.60 | O |
| ATOM | 2908 | N | ASN | A | 499 | 38.964 | 105.046 | -20.779 | 1.00 | 59.55 | N |
| ATOM | 2909 | CA | ASN | A | 499 | 39.339 | 103.742 | -20.244 | 1.00 | 52.33 | C |
| ATOM | 2910 | C | ASN | A | 499 | 39.050 | 102.613 | -21.240 | 1.00 | 54.60 | C |
| ATOM | 2911 | O | ASN | A | 499 | 37.909 | 102.167 | -21.397 | 1.00 | 53.80 | O |
| ATOM | 2912 | CB | ASN | A | 499 | 38.626 | 103.498 | -18.924 | 1.00 | 47.52 | C |
| ATOM | 2913 | CG | ASN | A | 499 | 38.868 | 102.118 | -18.372 | 1.00 | 49.18 | C |
| ATOM | 2914 | OD1 | ASN | A | 499 | 38.248 | 101.698 | -17.407 | 1.00 | 51.31 | O |
| ATOM | 2915 | ND2 | ASN | A | 499 | 39.839 | 101.396 | -18.978 | 1.00 | 46.82 | N |
| ATOM | 2916 | N | ARG | A | 500 | 40.087 | 102.155 | -21.926 | 1.00 | 50.41 | N |
| ATOM | 2917 | CA | ARG | A | 500 | 39.870 | 101.222 | -23.038 | 1.00 | 46.37 | C |
| ATOM | 2918 | C | ARG | A | 500 | 39.521 | 99.814 | -22.549 | 1.00 | 45.43 | C |
| ATOM | 2919 | O | ARG | A | 500 | 38.911 | 99.050 | -23.275 | 1.00 | 45.60 | O |
| ATOM | 2920 | CB | ARG | A | 500 | 41.088 | 101.198 | -23.936 | 1.00 | 43.15 | C |
| ATOM | 2921 | CG | ARG | A | 500 | 41.362 | 102.549 | -24.578 | 1.00 | 48.68 | C |

FIG. 8-48

| | | | | | | | | | | | |
|---|---|---|---|---|---|---|---|---|---|---|---|
| ATOM | 2922 | CD | ARG | A | 500 | 42.713 | 102.568 | -25.277 | 1.00 | 48.85 | C |
| ATOM | 2923 | NE | ARG | A | 500 | 42.979 | 103.861 | -25.898 | 1.00 | 54.03 | N |
| ATOM | 2924 | CZ | ARG | A | 500 | 43.325 | 104.958 | -25.223 | 1.00 | 52.18 | C |
| ATOM | 2925 | NH1 | ARG | A | 500 | 43.552 | 106.090 | -25.871 | 1.00 | 51.44 | N |
| ATOM | 2926 | NH2 | ARG | A | 500 | 43.430 | 104.916 | -23.899 | 1.00 | 43.95 | N |
| ATOM | 2927 | N | ALA | A | 501 | 39.889 | 99.479 | -21.317 | 1.00 | 39.84 | N |
| ATOM | 2928 | CA | ALA | A | 501 | 39.541 | 98.174 | -20.766 | 1.00 | 37.53 | C |
| ATOM | 2929 | C | ALA | A | 501 | 38.003 | 97.994 | -20.642 | 1.00 | 43.42 | C |
| ATOM | 2930 | O | ALA | A | 501 | 37.482 | 96.878 | -20.670 | 1.00 | 47.73 | O |
| ATOM | 2931 | CB | ALA | A | 501 | 40.231 | 97.971 | -19.405 | 1.00 | 31.14 | C |
| ATOM | 2932 | N | MET | A | 502 | 37.287 | 99.098 | -20.501 | 1.00 | 42.63 | N |
| ATOM | 2933 | CA | MET | A | 502 | 35.850 | 99.043 | -20.246 | 1.00 | 49.43 | C |
| ATOM | 2934 | C | MET | A | 502 | 34.993 | 99.682 | -21.334 | 1.00 | 52.53 | C |
| ATOM | 2935 | O | MET | A | 502 | 33.815 | 99.362 | -21.461 | 1.00 | 59.23 | O |
| ATOM | 2936 | CB | MET | A | 502 | 35.524 | 99.711 | -18.908 | 1.00 | 47.85 | C |
| ATOM | 2937 | CG | MET | A | 502 | 35.835 | 98.864 | -17.698 | 1.00 | 54.16 | C |
| ATOM | 2938 | SD | MET | A | 502 | 35.649 | 99.851 | -16.225 | 1.00 | 58.53 | S |
| ATOM | 2939 | CE | MET | A | 502 | 33.841 | 99.840 | -16.143 | 1.00 | 47.72 | C |
| ATOM | 2940 | N | GLN | A | 503 | 35.580 | 100.588 | -22.107 | 1.00 | 56.20 | N |
| ATOM | 2941 | CA | GLN | A | 503 | 34.818 | 101.363 | -23.087 | 1.00 | 59.57 | C |
| ATOM | 2942 | C | GLN | A | 503 | 35.162 | 101.075 | -24.547 | 1.00 | 59.59 | C |
| ATOM | 2943 | O | GLN | A | 503 | 34.356 | 101.337 | -25.430 | 1.00 | 58.36 | O |
| ATOM | 2944 | CB | GLN | A | 503 | 34.983 | 102.852 | -22.814 | 1.00 | 65.48 | C |
| ATOM | 2945 | CG | GLN | A | 503 | 34.817 | 103.215 | -21.350 | 1.00 | 75.55 | C |
| ATOM | 2946 | CD | GLN | A | 503 | 34.810 | 104.709 | -21.138 | 1.00 | 82.49 | C |
| ATOM | 2947 | OE1 | GLN | A | 503 | 33.998 | 105.424 | -21.725 | 1.00 | 84.55 | O |
| ATOM | 2948 | NE2 | GLN | A | 503 | 35.718 | 105.195 | -20.298 | 1.00 | 84.70 | N |
| ATOM | 2949 | N | ALA | A | 504 | 36.355 | 100.556 | -24.816 | 1.00 | 58.04 | N |
| ATOM | 2950 | CA | ALA | A | 504 | 36.731 | 100.269 | -26.208 | 1.00 | 58.89 | C |
| ATOM | 2951 | C | ALA | A | 504 | 36.191 | 98.911 | -26.635 | 1.00 | 58.81 | C |
| ATOM | 2952 | O | ALA | A | 504 | 36.764 | 97.870 | -26.301 | 1.00 | 61.28 | O |
| ATOM | 2953 | CB | ALA | A | 504 | 38.257 | 100.330 | -26.401 | 1.00 | 54.20 | C |
| ATOM | 2954 | N | ARG | A | 505 | 35.080 | 98.835 | -27.364 | 1.00 | 53.86 | N |
| ATOM | 2955 | CA | ARG | A | 505 | 34.463 | 97.734 | -27.831 | 1.00 | 48.15 | C |
| ATOM | 2956 | C | ARG | A | 505 | 35.135 | 97.390 | -29.223 | 1.00 | 49.46 | C |
| ATOM | 2957 | O | ARG | A | 505 | 35.176 | 98.212 | -30.117 | 1.00 | 46.33 | O |
| ATOM | 2958 | CB | ARG | A | 505 | 32.974 | 98.005 | -28.106 | 1.00 | 53.20 | C |
| ATOM | 2959 | CG | ARG | A | 505 | 32.191 | 96.876 | -28.755 | 1.00 | 55.08 | C |
| ATOM | 2960 | CD | ARG | A | 505 | 30.670 | 97.035 | -28.442 | 1.00 | 58.70 | C |
| ATOM | 2961 | NE | ARG | A | 505 | 30.466 | 97.316 | -27.024 | 1.00 | 45.69 | N |
| ATOM | 2962 | CZ | ARG | A | 505 | 30.273 | 96.385 | -26.086 | 1.00 | 55.80 | C |
| ATOM | 2963 | NH1 | ARG | A | 505 | 30.241 | 95.108 | -26.420 | 1.00 | 55.06 | N |
| ATOM | 2964 | NH2 | ARG | A | 505 | 30.123 | 96.730 | -24.804 | 1.00 | 55.67 | N |
| ATOM | 2965 | N | ARG | A | 506 | 35.683 | 96.174 | -29.388 | 1.00 | 46.83 | N |
| ATOM | 2966 | CA | ARG | A | 506 | 36.503 | 95.847 | -30.506 | 1.00 | 44.10 | C |
| ATOM | 2967 | C | ARG | A | 506 | 36.303 | 94.814 | -30.933 | 1.00 | 40.08 | C |
| ATOM | 2968 | O | ARG | A | 506 | 36.299 | 93.905 | -30.100 | 1.00 | 39.49 | O |
| ATOM | 2969 | CB | ARG | A | 506 | 37.989 | 95.995 | -30.108 | 1.00 | 51.47 | C |
| ATOM | 2970 | CG | ARG | A | 506 | 38.461 | 97.425 | -29.923 | 1.00 | 50.82 | C |
| ATOM | 2971 | CD | ARG | A | 506 | 38.451 | 98.098 | -31.277 | 1.00 | 56.73 | C |
| ATOM | 2972 | NE | ARG | A | 506 | 38.805 | 99.498 | -31.194 | 1.00 | 58.45 | N |
| ATOM | 2973 | CZ | ARG | A | 506 | 39.810 | 100.067 | -31.843 | 1.00 | 53.86 | C |
| ATOM | 2974 | NH1 | ARG | A | 506 | 40.530 | 99.366 | -32.679 | 1.00 | 46.92 | N |
| ATOM | 2975 | NH2 | ARG | A | 506 | 40.007 | 101.364 | -31.671 | 1.00 | 53.50 | N |
| ATOM | 2976 | N | SER | A | 507 | 36.238 | 94.218 | -32.239 | 1.00 | 37.73 | N |
| ATOM | 2977 | CA | SER | A | 507 | 36.227 | 92.899 | -32.850 | 1.00 | 41.20 | C |
| ATOM | 2978 | C | SER | A | 507 | 37.300 | 91.885 | -32.263 | 1.00 | 46.38 | C |
| ATOM | 2979 | O | SER | A | 507 | 38.475 | 92.343 | -32.183 | 1.00 | 37.78 | O |
| ATOM | 2980 | CB | SER | A | 507 | 36.386 | 93.068 | -34.372 | 1.00 | 47.25 | C |
| ATOM | 2981 | OG | SER | A | 507 | 36.444 | 91.812 | -35.016 | 1.00 | 60.81 | O |
| ATOM | 2982 | N | ILE | A | 508 | 36.859 | 90.817 | -31.799 | 1.00 | 45.35 | N |
| ATOM | 2983 | CA | ILE | A | 508 | 37.834 | 89.917 | -31.161 | 1.00 | 47.26 | C |
| ATOM | 2984 | C | ILE | A | 508 | 38.579 | 88.996 | -32.137 | 1.00 | 45.10 | C |
| ATOM | 2985 | O | ILE | A | 508 | 39.590 | 88.342 | -31.748 | 1.00 | 40.20 | O |
| ATOM | 2986 | CB | ILE | A | 508 | 37.177 | 89.098 | -30.069 | 1.00 | 37.47 | C |
| ATOM | 2987 | CG1 | ILE | A | 508 | 36.213 | 88.039 | -30.684 | 1.00 | 37.37 | C |
| ATOM | 2988 | CG2 | ILE | A | 508 | 36.523 | 89.935 | -29.015 | 1.00 | 39.93 | C |
| ATOM | 2989 | CD1 | ILE | A | 508 | 35.519 | 87.173 | -29.575 | 1.00 | 43.45 | C |
| ATOM | 2990 | N | GLY | A | 509 | 38.134 | 88.922 | -33.387 | 1.00 | 36.37 | N |
| ATOM | 2991 | CA | GLY | A | 509 | 38.889 | 88.144 | -34.360 | 1.00 | 42.54 | C |
| ATOM | 2992 | C | GLY | A | 509 | 39.022 | 86.681 | -33.945 | 1.00 | 44.36 | C |
| ATOM | 2993 | O | GLY | A | 509 | 38.085 | 86.067 | -33.448 | 1.00 | 40.40 | O |
| ATOM | 2994 | N | SER | A | 510 | 40.190 | 86.102 | -34.152 | 1.00 | 37.26 | N |
| ATOM | 2995 | CA | SER | A | 510 | 40.357 | 84.668 | -33.935 | 1.00 | 33.04 | C |
| ATOM | 2996 | C | SER | A | 510 | 40.357 | 84.227 | -32.473 | 1.00 | 35.32 | C |
| ATOM | 2997 | O | SER | A | 510 | 40.455 | 83.030 | -32.165 | 1.00 | 43.24 | O |
| ATOM | 2998 | CB | SER | A | 510 | 41.660 | 84.200 | -34.639 | 1.00 | 43.41 | C |

FIG.8-49

| | | | | | | | | | | | |
|---|---|---|---|---|---|---|---|---|---|---|---|
| ATOM | 2999 | OG | SER | A | 510 | 42.758 | 85.009 | -34.249 | 1.00 | 43.80 | O |
| ATOM | 3000 | N | LEU | A | 511 | 40.251 | 85.189 | -31.572 | 1.00 | 30.67 | N |
| ATOM | 3001 | CA | LEU | A | 511 | 39.987 | 84.803 | -30.154 | 1.00 | 36.20 | C |
| ATOM | 3002 | C | LEU | A | 511 | 38.588 | 84.277 | -29.959 | 1.00 | 39.67 | C |
| ATOM | 3003 | O | LEU | A | 511 | 38.299 | 83.639 | -28.943 | 1.00 | 45.66 | O |
| ATOM | 3004 | CB | LEU | A | 511 | 40.112 | 86.214 | -29.353 | 1.00 | 36.06 | C |
| ATOM | 3005 | CG | LEU | A | 511 | 40.596 | 86.237 | -27.932 | 1.00 | 41.70 | C |
| ATOM | 3006 | CD1 | LEU | A | 511 | 42.006 | 85.685 | -27.938 | 1.00 | 42.51 | C |
| ATOM | 3007 | CD2 | LEU | A | 511 | 40.580 | 87.637 | -27.363 | 1.00 | 40.23 | C |
| ATOM | 3008 | N | ALA | A | 512 | 37.708 | 84.441 | -30.928 | 1.00 | 34.70 | N |
| ATOM | 3009 | CA | ALA | A | 512 | 36.423 | 83.795 | -30.851 | 1.00 | 39.27 | C |
| ATOM | 3010 | C | ALA | A | 512 | 36.504 | 82.218 | -31.016 | 1.00 | 44.58 | C |
| ATOM | 3011 | O | ALA | A | 512 | 35.552 | 81.535 | -30.685 | 1.00 | 47.37 | O |
| ATOM | 3012 | CB | ALA | A | 512 | 35.445 | 84.344 | -31.883 | 1.00 | 33.26 | C |
| ATOM | 3013 | N | LYS | A | 513 | 37.616 | 81.663 | -31.513 | 1.00 | 37.95 | N |
| ATOM | 3014 | CA | LYS | A | 513 | 37.608 | 80.243 | -31.922 | 1.00 | 34.75 | C |
| ATOM | 3015 | C | LYS | A | 513 | 37.368 | 79.205 | -30.826 | 1.00 | 38.00 | C |
| ATOM | 3016 | O | LYS | A | 513 | 36.640 | 78.231 | -31.054 | 1.00 | 40.80 | O |
| ATOM | 3017 | CB | LYS | A | 513 | 38.851 | 79.833 | -32.727 | 1.00 | 37.58 | C |
| ATOM | 3018 | CG | LYS | A | 513 | 39.123 | 80.678 | -34.004 | 1.00 | 46.35 | C |
| ATOM | 3019 | CD | LYS | A | 513 | 40.281 | 80.057 | -34.757 | 1.00 | 43.33 | C |
| ATOM | 3020 | CE | LYS | A | 513 | 40.284 | 80.332 | -36.270 | 1.00 | 45.38 | C |
| ATOM | 3021 | NZ | LYS | A | 513 | 40.544 | 81.749 | -36.617 | 1.00 | 41.91 | N |
| ATOM | 3022 | N | PRO | A | 514 | 37.999 | 79.377 | -29.648 | 1.00 | 35.99 | N |
| ATOM | 3023 | CA | PRO | A | 514 | 37.783 | 78.336 | -28.643 | 1.00 | 34.40 | C |
| ATOM | 3024 | C | PRO | A | 514 | 36.235 | 78.161 | -28.354 | 1.00 | 42.83 | C |
| ATOM | 3025 | O | PRO | A | 514 | 35.805 | 77.057 | -28.035 | 1.00 | 43.07 | O |
| ATOM | 3026 | CB | PRO | A | 514 | 38.483 | 78.866 | -27.403 | 1.00 | 44.61 | C |
| ATOM | 3027 | CG | PRO | A | 514 | 39.370 | 79.985 | -27.856 | 1.00 | 41.43 | C |
| ATOM | 3028 | CD | PRO | A | 514 | 38.641 | 80.560 | -29.060 | 1.00 | 39.44 | C |
| ATOM | 3029 | N | ALA | A | 515 | 35.436 | 79.216 | -28.493 | 1.00 | 45.79 | N |
| ATOM | 3030 | CA | ALA | A | 515 | 33.980 | 79.094 | -28.268 | 1.00 | 42.06 | C |
| ATOM | 3031 | C | ALA | A | 515 | 33.421 | 77.963 | -29.124 | 1.00 | 45.26 | C |
| ATOM | 3032 | O | ALA | A | 515 | 32.618 | 77.155 | -28.655 | 1.00 | 34.86 | O |
| ATOM | 3033 | CB | ALA | A | 515 | 33.274 | 80.399 | -28.560 | 1.00 | 37.18 | C |
| ATOM | 3034 | N | THR | A | 516 | 33.919 | 77.854 | -30.360 | 1.00 | 26.30 | N |
| ATOM | 3035 | CA | THR | A | 516 | 33.432 | 76.815 | -31.258 | 1.00 | 32.51 | C |
| ATOM | 3036 | C | THR | A | 516 | 33.900 | 75.415 | -30.876 | 1.00 | 37.13 | C |
| ATOM | 3037 | O | THR | A | 516 | 33.168 | 74.423 | -30.978 | 1.00 | 35.83 | O |
| ATOM | 3038 | CB | THR | A | 516 | 33.888 | 77.109 | -32.678 | 1.00 | 36.34 | C |
| ATOM | 3039 | OG1 | THR | A | 516 | 33.208 | 78.284 | -33.128 | 1.00 | 45.09 | O |
| ATOM | 3040 | CG2 | THR | A | 516 | 33.601 | 75.940 | -33.596 | 1.00 | 40.95 | C |
| ATOM | 3041 | N | TYR | A | 517 | 35.137 | 75.340 | -30.449 | 1.00 | 31.28 | N |
| ATOM | 3042 | CA | TYR | A | 517 | 35.730 | 74.067 | -30.091 | 1.00 | 35.44 | C |
| ATOM | 3043 | C | TYR | A | 517 | 35.171 | 73.597 | -28.758 | 1.00 | 36.34 | C |
| ATOM | 3044 | O | TYR | A | 517 | 35.014 | 72.395 | -28.529 | 1.00 | 39.16 | O |
| ATOM | 3045 | CB | TYR | A | 517 | 37.251 | 74.269 | -30.020 | 1.00 | 34.71 | C |
| ATOM | 3046 | CG | TYR | A | 517 | 37.772 | 74.486 | -31.416 | 1.00 | 33.31 | C |
| ATOM | 3047 | CD1 | TYR | A | 517 | 38.098 | 73.389 | -32.223 | 1.00 | 39.31 | C |
| ATOM | 3048 | CD2 | TYR | A | 517 | 37.821 | 75.761 | -31.980 | 1.00 | 33.72 | C |
| ATOM | 3049 | CE1 | TYR | A | 517 | 38.510 | 73.551 | -33.526 | 1.00 | 40.01 | C |
| ATOM | 3050 | CE2 | TYR | A | 517 | 38.281 | 75.936 | -33.312 | 1.00 | 36.58 | C |
| ATOM | 3051 | CZ | TYR | A | 517 | 38.619 | 74.817 | -34.066 | 1.00 | 37.86 | C |
| ATOM | 3052 | OH | TYR | A | 517 | 39.042 | 74.916 | -35.381 | 1.00 | 40.49 | O |
| ATOM | 3053 | N | LEU | A | 518 | 34.867 | 74.551 | -27.883 | 1.00 | 31.55 | N |
| ATOM | 3054 | CA | LEU | A | 518 | 34.278 | 74.240 | -26.571 | 1.00 | 33.74 | C |
| ATOM | 3055 | C | LEU | A | 518 | 32.853 | 73.722 | -26.833 | 1.00 | 33.57 | C |
| ATOM | 3056 | O | LEU | A | 518 | 32.392 | 72.800 | -26.192 | 1.00 | 35.14 | O |
| ATOM | 3057 | CB | LEU | A | 518 | 34.205 | 75.503 | -25.721 | 1.00 | 39.57 | C |
| ATOM | 3058 | CG | LEU | A | 518 | 33.690 | 75.448 | -24.293 | 1.00 | 41.93 | C |
| ATOM | 3059 | CD1 | LEU | A | 518 | 34.522 | 74.494 | -23.461 | 1.00 | 46.12 | C |
| ATOM | 3060 | CD2 | LEU | A | 518 | 33.718 | 76.867 | -23.704 | 1.00 | 48.82 | C |
| ATOM | 3061 | N | THR | A | 519 | 32.193 | 74.290 | -27.826 | 1.00 | 36.48 | N |
| ATOM | 3062 | CA | THR | A | 519 | 30.840 | 73.801 | -28.205 | 1.00 | 44.79 | C |
| ATOM | 3063 | C | THR | A | 519 | 30.939 | 72.351 | -28.656 | 1.00 | 44.49 | C |
| ATOM | 3064 | O | THR | A | 519 | 30.190 | 71.517 | -28.179 | 1.00 | 50.59 | O |
| ATOM | 3065 | CB | THR | A | 519 | 30.224 | 74.675 | -29.275 | 1.00 | 36.12 | C |
| ATOM | 3066 | OG1 | THR | A | 519 | 30.227 | 76.030 | -28.823 | 1.00 | 38.08 | O |
| ATOM | 3067 | CG2 | THR | A | 519 | 28.798 | 74.255 | -29.532 | 1.00 | 42.68 | C |
| ATOM | 3068 | N | ALA | A | 520 | 31.891 | 72.047 | -29.530 | 1.00 | 38.26 | N |
| ATOM | 3069 | CA | ALA | A | 520 | 32.075 | 70.680 | -30.031 | 1.00 | 29.15 | C |
| ATOM | 3070 | C | ALA | A | 520 | 32.423 | 69.661 | -28.924 | 1.00 | 38.06 | C |
| ATOM | 3071 | O | ALA | A | 520 | 31.770 | 68.612 | -28.793 | 1.00 | 29.73 | O |
| ATOM | 3072 | CB | ALA | A | 520 | 33.122 | 70.675 | -31.085 | 1.00 | 34.18 | C |
| ATOM | 3073 | N | LEU | A | 521 | 33.461 | 69.986 | -28.146 | 1.00 | 33.44 | N |
| ATOM | 3074 | CA | LEU | A | 521 | 34.015 | 69.132 | -27.089 | 1.00 | 33.73 | C |
| ATOM | 3075 | C | LEU | A | 521 | 33.055 | 68.875 | -25.926 | 1.00 | 40.09 | C |

FIG. 8-50

| | | | | | | | | | | | |
|---|---|---|---|---|---|---|---|---|---|---|---|
| ATOM | 3076 | O | LEU | A | 521 | 33.279 | 67.964 | -25.131 | 1.00 | 40.78 | O |
| ATOM | 3077 | CB | LEU | A | 521 | 35.336 | 69.786 | -26.951 | 1.00 | 36.15 | C |
| ATOM | 3078 | CG | LEU | A | 521 | 36.387 | 69.783 | -27.688 | 1.00 | 36.62 | C |
| ATOM | 3079 | CD1 | LEU | A | 521 | 37.706 | 70.810 | -27.333 | 1.00 | 35.69 | C |
| ATOM | 3080 | CD2 | LEU | A | 521 | 36.677 | 68.373 | -28.119 | 1.00 | 33.27 | C |
| ATOM | 3081 | N | SER | A | 522 | 31.989 | 69.672 | -25.830 | 1.00 | 34.57 | N |
| ATOM | 3082 | CA | SER | A | 522 | 30.936 | 69.402 | -24.870 | 1.00 | 38.57 | C |
| ATOM | 3083 | C | SER | A | 522 | 30.101 | 68.231 | -25.328 | 1.00 | 44.81 | C |
| ATOM | 3084 | O | SER | A | 522 | 29.133 | 67.896 | -24.804 | 1.00 | 44.31 | O |
| ATOM | 3085 | CB | SER | A | 522 | 30.038 | 70.832 | -24.668 | 1.00 | 41.80 | C |
| ATOM | 3086 | OG | SER | A | 522 | 30.823 | 71.789 | -24.298 | 1.00 | 44.77 | O |
| ATOM | 3087 | N | GLN | A | 523 | 30.431 | 67.831 | -26.481 | 1.00 | 40.03 | N |
| ATOM | 3088 | CA | GLN | A | 523 | 29.717 | 66.408 | -26.920 | 1.00 | 41.67 | C |
| ATOM | 3089 | C | GLN | A | 523 | 30.683 | 65.222 | -27.131 | 1.00 | 38.90 | C |
| ATOM | 3090 | O | GLN | A | 523 | 31.022 | 64.865 | -28.242 | 1.00 | 38.36 | O |
| ATOM | 3091 | CB | GLN | A | 523 | 28.861 | 66.688 | -28.164 | 1.00 | 43.88 | C |
| ATOM | 3092 | CG | GLN | A | 523 | 28.202 | 68.010 | -28.223 | 1.00 | 60.63 | C |
| ATOM | 3093 | CD | GLN | A | 523 | 28.162 | 68.561 | -29.645 | 1.00 | 76.71 | C |
| ATOM | 3094 | OE1 | GLN | A | 523 | 27.111 | 68.609 | -30.290 | 1.00 | 82.27 | O |
| ATOM | 3095 | NE2 | GLN | A | 523 | 29.321 | 68.965 | -30.144 | 1.00 | 84.98 | N |
| ATOM | 3096 | N | PRO | A | 524 | 31.120 | 64.590 | -26.039 | 1.00 | 39.00 | N |
| ATOM | 3097 | CA | PRO | A | 524 | 32.217 | 63.608 | -26.021 | 1.00 | 33.57 | C |
| ATOM | 3098 | C | PRO | A | 524 | 31.958 | 62.339 | -26.858 | 1.00 | 31.75 | C |
| ATOM | 3099 | O | PRO | A | 524 | 32.889 | 61.987 | -27.166 | 1.00 | 34.45 | O |
| ATOM | 3100 | CB | PRO | A | 524 | 32.329 | 63.247 | -24.515 | 1.00 | 30.71 | C |
| ATOM | 3101 | CG | PRO | A | 524 | 30.825 | 63.478 | -23.992 | 1.00 | 36.02 | C |
| ATOM | 3102 | CD | PRO | A | 524 | 30.450 | 64.743 | -24.722 | 1.00 | 38.16 | C |
| ATOM | 3103 | N | LYS | A | 525 | 30.709 | 62.070 | -27.197 | 1.00 | 37.78 | N |
| ATOM | 3104 | CA | LYS | A | 525 | 30.399 | 60.886 | -27.977 | 1.00 | 39.83 | C |
| ATOM | 3105 | C | LYS | A | 525 | 30.576 | 61.226 | -29.435 | 1.00 | 40.64 | C |
| ATOM | 3106 | O | LYS | A | 525 | 30.693 | 60.337 | -30.272 | 1.00 | 40.83 | O |
| ATOM | 3107 | CB | LYS | A | 525 | 28.947 | 60.439 | -27.755 | 1.00 | 53.15 | C |
| ATOM | 3108 | CG | LYS | A | 525 | 28.600 | 60.179 | -26.310 | 1.00 | 57.83 | C |
| ATOM | 3109 | CD | LYS | A | 525 | 29.489 | 59.090 | -25.725 | 1.00 | 64.39 | C |
| ATOM | 3110 | CE | LYS | A | 525 | 28.791 | 57.746 | -25.757 | 1.00 | 72.39 | C |
| ATOM | 3111 | NZ | LYS | A | 525 | 27.590 | 57.748 | -24.866 | 1.00 | 72.31 | N |
| ATOM | 3112 | N | ILE | A | 526 | 30.558 | 62.513 | -29.758 | 1.00 | 39.30 | N |
| ATOM | 3113 | CA | ILE | A | 526 | 30.596 | 62.889 | -31.184 | 1.00 | 41.59 | C |
| ATOM | 3114 | C | ILE | A | 526 | 31.898 | 63.646 | -31.550 | 1.00 | 47.83 | C |
| ATOM | 3115 | O | ILE | A | 526 | 32.586 | 63.290 | -32.508 | 1.00 | 47.84 | O |
| ATOM | 3116 | CB | ILE | A | 526 | 29.264 | 63.579 | -31.697 | 1.00 | 71.82 | C |
| ATOM | 3117 | CG1 | ILE | A | 526 | 29.266 | 65.076 | -31.444 | 1.00 | 74.31 | C |
| ATOM | 3118 | CG2 | ILE | A | 526 | 27.985 | 62.966 | -31.058 | 1.00 | 37.27 | C |
| ATOM | 3119 | CD1 | ILE | A | 526 | 27.896 | 65.710 | -31.592 | 1.00 | 69.15 | C |
| ATOM | 3120 | N | TYR | A | 527 | 32.285 | 64.631 | -30.747 | 1.00 | 36.44 | N |
| ATOM | 3121 | CA | TYR | A | 527 | 33.510 | 65.357 | -31.040 | 1.00 | 45.29 | C |
| ATOM | 3122 | C | TYR | A | 527 | 34.598 | 65.123 | -29.988 | 1.00 | 39.78 | C |
| ATOM | 3123 | O | TYR | A | 527 | 34.347 | 65.255 | -28.788 | 1.00 | 37.34 | O |
| ATOM | 3124 | CB | TYR | A | 527 | 33.229 | 66.856 | -31.167 | 1.00 | 42.25 | C |
| ATOM | 3125 | CG | TYR | A | 527 | 32.437 | 67.235 | -32.384 | 1.00 | 37.75 | C |
| ATOM | 3126 | CD1 | TYR | A | 527 | 33.034 | 67.254 | -33.629 | 1.00 | 32.88 | C |
| ATOM | 3127 | CD2 | TYR | A | 527 | 31.080 | 67.570 | -32.291 | 1.00 | 35.92 | C |
| ATOM | 3128 | CE1 | TYR | A | 527 | 32.331 | 67.606 | -34.760 | 1.00 | 41.88 | C |
| ATOM | 3129 | CE2 | TYR | A | 527 | 30.371 | 67.947 | -33.422 | 1.00 | 34.70 | C |
| ATOM | 3130 | CZ | TYR | A | 527 | 31.002 | 67.954 | -34.648 | 1.00 | 30.86 | C |
| ATOM | 3131 | OH | TYR | A | 527 | 30.332 | 68.300 | -35.765 | 1.00 | 42.52 | O |
| ATOM | 3132 | N | ARG | A | 528 | 35.804 | 64.815 | -30.460 | 1.00 | 34.84 | N |
| ATOM | 3133 | CA | ARG | A | 528 | 36.987 | 64.726 | -29.604 | 1.00 | 29.95 | C |
| ATOM | 3134 | C | ARG | A | 528 | 38.147 | 65.468 | -30.226 | 1.00 | 34.80 | C |
| ATOM | 3135 | O | ARG | A | 528 | 38.101 | 65.881 | -31.399 | 1.00 | 41.56 | O |
| ATOM | 3136 | CB | ARG | A | 528 | 37.398 | 63.265 | -29.425 | 1.00 | 30.74 | C |
| ATOM | 3137 | CG | ARG | A | 528 | 36.246 | 62.381 | -28.996 | 1.00 | 34.73 | C |
| ATOM | 3138 | CD | ARG | A | 528 | 36.676 | 60.938 | -28.944 | 1.00 | 35.21 | C |
| ATOM | 3139 | NE | ARG | A | 528 | 35.621 | 60.137 | -28.340 | 1.00 | 33.28 | N |
| ATOM | 3140 | CZ | ARG | A | 528 | 34.808 | 59.348 | -29.030 | 1.00 | 46.10 | C |
| ATOM | 3141 | NH1 | ARG | A | 528 | 33.843 | 58.677 | -28.404 | 1.00 | 50.74 | N |
| ATOM | 3142 | NH2 | ARG | A | 528 | 34.947 | 59.253 | -30.349 | 1.00 | 41.21 | N |
| ATOM | 3143 | N | LEU | A | 529 | 39.229 | 65.562 | -29.478 | 1.00 | 31.52 | N |
| ATOM | 3144 | CA | LEU | A | 529 | 40.464 | 66.149 | -30.020 | 1.00 | 32.03 | C |
| ATOM | 3145 | C | LEU | A | 529 | 40.937 | 65.482 | -31.318 | 1.00 | 29.04 | C |
| ATOM | 3146 | O | LEU | A | 529 | 41.387 | 66.171 | -32.226 | 1.00 | 40.82 | O |
| ATOM | 3147 | CB | LEU | A | 529 | 41.526 | 66.197 | -28.932 | 1.00 | 28.23 | C |
| ATOM | 3148 | CG | LEU | A | 529 | 41.141 | 67.047 | -27.721 | 1.00 | 30.15 | C |
| ATOM | 3149 | CD1 | LEU | A | 529 | 42.215 | 66.925 | -26.706 | 1.00 | 32.09 | C |
| ATOM | 3150 | CD2 | LEU | A | 529 | 40.983 | 68.520 | -28.157 | 1.00 | 30.82 | C |
| ATOM | 3151 | N | ASN | A | 530 | 40.779 | 64.185 | -31.449 | 1.00 | 42.55 | N |
| ATOM | 3152 | CA | ASN | A | 530 | 41.202 | 63.476 | -32.685 | 1.00 | 36.20 | C |

FIG. 8-51

| | | | | | | | | | | | |
|---|---|---|---|---|---|---|---|---|---|---|---|
| ATOM | 3153 | C | ASN | A | 530 | 40.147 | 63.466 | -33.785 | 1.00 | 41.20 | C |
| ATOM | 3154 | O | ASN | A | 530 | 40.307 | 63.809 | -34.823 | 1.00 | 45.25 | O |
| ATOM | 3155 | CB | ASN | A | 530 | 41.659 | 63.028 | -33.439 | 1.00 | 35.40 | C |
| ATOM | 3156 | CG | ASN | A | 530 | 40.496 | 61.120 | -32.817 | 1.00 | 43.60 | C |
| ATOM | 3157 | OD1 | ASN | A | 530 | 40.524 | 59.896 | -32.187 | 1.00 | 44.82 | O |
| ATOM | 3158 | ND2 | ASN | A | 530 | 39.457 | 61.740 | -31.483 | 1.00 | 34.10 | N |
| ATOM | 3159 | N | THR | A | 531 | 39.058 | 64.188 | -33.594 | 1.00 | 42.81 | N |
| ATOM | 3160 | CA | THR | A | 531 | 38.048 | 64.181 | -34.647 | 1.00 | 31.32 | C |
| ATOM | 3161 | C | THR | A | 531 | 38.564 | 64.835 | -35.694 | 1.00 | 38.72 | C |
| ATOM | 3162 | O | THR | A | 531 | 39.098 | 66.026 | -35.774 | 1.00 | 45.43 | O |
| ATOM | 3163 | CB | THR | A | 531 | 36.712 | 64.770 | -34.156 | 1.00 | 34.42 | C |
| ATOM | 3164 | OG1 | THR | A | 531 | 36.209 | 63.981 | -33.052 | 1.00 | 32.59 | O |
| ATOM | 3165 | CG2 | THR | A | 531 | 35.685 | 64.739 | -35.335 | 1.00 | 49.74 | C |
| ATOM | 3166 | N | TRP | A | 532 | 38.405 | 64.357 | -37.080 | 1.00 | 36.11 | N |
| ATOM | 3167 | CA | TRP | A | 532 | 38.865 | 64.989 | -38.323 | 1.00 | 36.67 | C |
| ATOM | 3168 | C | TRP | A | 532 | 37.864 | 66.024 | -38.832 | 1.00 | 42.59 | C |
| ATOM | 3169 | O | TRP | A | 532 | 36.676 | 65.731 | -38.883 | 1.00 | 35.55 | O |
| ATOM | 3170 | CB | TRP | A | 532 | 39.059 | 63.942 | -39.432 | 1.00 | 34.84 | C |
| ATOM | 3171 | CG | TRP | A | 532 | 40.193 | 62.989 | -39.227 | 1.00 | 40.53 | C |
| ATOM | 3172 | CD1 | TRP | A | 532 | 40.081 | 61.649 | -38.890 | 1.00 | 44.30 | C |
| ATOM | 3173 | CD2 | TRP | A | 532 | 41.606 | 63.233 | -39.349 | 1.00 | 38.25 | C |
| ATOM | 3174 | NE1 | TRP | A | 532 | 41.334 | 61.073 | -38.805 | 1.00 | 41.54 | N |
| ATOM | 3175 | CE2 | TRP | A | 532 | 42.281 | 62.021 | -39.084 | 1.00 | 40.75 | C |
| ATOM | 3176 | CE3 | TRP | A | 532 | 42.388 | 64.370 | -39.666 | 1.00 | 35.24 | C |
| ATOM | 3177 | CZ2 | TRP | A | 532 | 43.670 | 61.912 | -39.127 | 1.00 | 39.53 | C |
| ATOM | 3178 | CZ3 | TRP | A | 532 | 43.736 | 64.259 | -39.732 | 1.00 | 48.72 | C |
| ATOM | 3179 | CH2 | TRP | A | 532 | 44.384 | 63.040 | -39.445 | 1.00 | 46.45 | C |
| ATOM | 3180 | N | ILE | A | 533 | 38.349 | 67.216 | -39.187 | 1.00 | 41.29 | N |
| ATOM | 3181 | CA | ILE | A | 533 | 37.532 | 68.303 | -39.719 | 1.00 | 42.25 | C |
| ATOM | 3182 | C | ILE | A | 533 | 37.943 | 68.594 | -41.182 | 1.00 | 48.13 | C |
| ATOM | 3183 | O | ILE | A | 533 | 39.131 | 68.770 | -41.469 | 1.00 | 46.59 | O |
| ATOM | 3184 | CB | ILE | A | 533 | 37.762 | 69.631 | -38.940 | 1.00 | 37.07 | C |
| ATOM | 3185 | CG1 | ILE | A | 533 | 37.325 | 69.493 | -37.441 | 1.00 | 36.10 | C |
| ATOM | 3186 | CG2 | ILE | A | 533 | 36.855 | 70.738 | -39.528 | 1.00 | 42.93 | C |
| ATOM | 3187 | CD1 | ILE | A | 533 | 36.119 | 68.946 | -37.105 | 1.00 | 52.41 | C |
| ATOM | 3188 | N | ALA | A | 534 | 36.997 | 68.643 | -42.115 | 1.00 | 41.75 | N |
| ATOM | 3189 | CA | ALA | A | 534 | 37.337 | 69.002 | -43.486 | 1.00 | 46.29 | C |
| ATOM | 3190 | C | ALA | A | 534 | 38.091 | 70.351 | -43.560 | 1.00 | 50.99 | C |
| ATOM | 3191 | O | ALA | A | 534 | 37.719 | 71.321 | -42.885 | 1.00 | 50.53 | O |
| ATOM | 3192 | CB | ALA | A | 534 | 36.122 | 69.020 | -44.411 | 1.00 | 46.22 | C |
| ATOM | 3193 | N | ASP | A | 535 | 39.146 | 70.382 | -44.370 | 1.00 | 49.12 | N |
| ATOM | 3194 | CA | ASP | A | 535 | 39.893 | 71.590 | -44.643 | 1.00 | 47.23 | C |
| ATOM | 3195 | C | ASP | A | 535 | 39.992 | 71.717 | -46.162 | 1.00 | 59.33 | C |
| ATOM | 3196 | O | ASP | A | 535 | 40.954 | 71.228 | -46.777 | 1.00 | 60.83 | O |
| ATOM | 3197 | CB | ASP | A | 535 | 41.292 | 71.513 | -44.052 | 1.00 | 62.78 | C |
| ATOM | 3198 | CG | ASP | A | 535 | 42.046 | 72.832 | -44.172 | 1.00 | 56.54 | C |
| ATOM | 3199 | OD1 | ASP | A | 535 | 41.360 | 73.871 | -44.281 | 1.00 | 48.52 | O |
| ATOM | 3200 | OD2 | ASP | A | 535 | 43.314 | 72.847 | -44.154 | 1.00 | 62.50 | O |
| ATOM | 3201 | N | ALA | A | 536 | 38.384 | 72.349 | -46.761 | 1.00 | 55.87 | N |
| ATOM | 3202 | CA | ALA | A | 536 | 38.900 | 72.489 | -48.225 | 1.00 | 54.91 | C |
| ATOM | 3203 | C | ALA | A | 536 | 38.142 | 73.764 | -48.592 | 1.00 | 47.21 | C |
| ATOM | 3204 | O | ALA | A | 536 | 37.591 | 74.364 | -47.744 | 1.00 | 50.87 | O |
| ATOM | 3205 | CB | ALA | A | 536 | 38.232 | 71.254 | -48.857 | 1.00 | 51.93 | C |
| ATOM | 3206 | N | PRO | A | 537 | 38.223 | 74.193 | -49.858 | 1.00 | 53.42 | N |
| ATOM | 3207 | CA | PRO | A | 537 | 37.529 | 75.440 | -50.180 | 1.00 | 61.19 | C |
| ATOM | 3208 | C | PRO | A | 537 | 36.135 | 75.515 | -49.568 | 1.00 | 66.57 | C |
| ATOM | 3209 | O | PRO | A | 537 | 35.435 | 74.510 | -49.472 | 1.00 | 68.90 | O |
| ATOM | 3210 | CB | PRO | A | 537 | 37.461 | 75.408 | -51.715 | 1.00 | 57.90 | C |
| ATOM | 3211 | CG | PRO | A | 537 | 38.739 | 74.713 | -52.098 | 1.00 | 54.14 | C |
| ATOM | 3212 | CD | PRO | A | 537 | 38.986 | 73.670 | -51.009 | 1.00 | 53.92 | C |
| ATOM | 3213 | N | ILE | A | 538 | 35.759 | 76.710 | -49.134 | 1.00 | 71.34 | N |
| ATOM | 3214 | CA | ILE | A | 538 | 34.431 | 76.976 | -48.593 | 1.00 | 71.83 | C |
| ATOM | 3215 | C | ILE | A | 538 | 33.792 | 78.050 | -49.485 | 1.00 | 64.57 | C |
| ATOM | 3216 | O | ILE | A | 538 | 34.501 | 78.908 | -50.004 | 1.00 | 57.29 | O |
| ATOM | 3217 | CB | ILE | A | 538 | 34.922 | 77.473 | -47.110 | 1.00 | 59.40 | C |
| ATOM | 3218 | CG1 | ILE | A | 538 | 34.858 | 76.323 | -46.165 | 1.00 | 53.97 | C |
| ATOM | 3219 | CG2 | ILE | A | 538 | 33.233 | 78.138 | -46.665 | 1.00 | 60.26 | C |
| ATOM | 3220 | CD1 | ILE | A | 538 | 35.033 | 76.762 | -44.715 | 1.00 | 50.01 | C |
| ATOM | 3221 | N | ALA | A | 539 | 32.470 | 77.981 | -49.684 | 1.00 | 63.74 | N |
| ATOM | 3222 | CA | ALA | A | 539 | 31.693 | 79.001 | -50.365 | 1.00 | 65.60 | C |
| ATOM | 3223 | C | ALA | A | 539 | 30.251 | 79.027 | -49.820 | 1.00 | 70.52 | C |
| ATOM | 3224 | O | ALA | A | 539 | 29.419 | 78.195 | -50.177 | 1.00 | 73.24 | O |
| ATOM | 3225 | CB | ALA | A | 539 | 31.697 | 78.751 | -51.897 | 1.00 | 62.28 | C |
| ATOM | 3226 | N | LEU | A | 540 | 29.962 | 79.995 | -48.961 | 1.00 | 67.62 | N |
| ATOM | 3227 | CA | LEU | A | 540 | 28.692 | 80.039 | -48.254 | 1.00 | 69.52 | C |
| ATOM | 3228 | C | LEU | A | 540 | 27.794 | 81.122 | -48.797 | 1.00 | 74.87 | C |
| ATOM | 3229 | O | LEU | A | 540 | 27.981 | 82.318 | -48.610 | 1.00 | 77.86 | O |

FIG. 8-52

| | | | | | | | | | | |
|---|---|---|---|---|---|---|---|---|---|---|
| ATOM | 3230 | CB | LEU | A | 540 | 28.941 | 80.269 | -46.760 | 1.00 66.78 | C |
| ATOM | 3231 | CG | LEU | A | 540 | 29.306 | 79.045 | -45.908 | 1.00 74.47 | C |
| ATOM | 3232 | CD1 | LEU | A | 540 | 30.083 | 79.398 | -44.603 | 1.00 51.58 | C |
| ATOM | 3233 | CD2 | LEU | A | 540 | 28.045 | 78.266 | -45.594 | 1.00 72.01 | C |
| ATOM | 3234 | N | ARG | A | 541 | 26.690 | 80.709 | -49.467 | 1.00 80.11 | N |
| ATOM | 3235 | CA | ARG | A | 541 | 25.703 | 81.674 | -49.911 | 1.00 84.01 | C |
| ATOM | 3236 | C | ARG | A | 541 | 25.010 | 82.349 | -48.685 | 1.00 83.20 | C |
| ATOM | 3237 | O | ARG | A | 541 | 24.571 | 81.505 | -47.800 | 1.00 77.58 | O |
| ATOM | 3238 | CB | ARG | A | 541 | 24.707 | 81.028 | -50.868 | 1.00 89.91 | C |
| ATOM | 3239 | CG | ARG | A | 541 | 25.183 | 81.019 | -52.317 | 1.00100.61 | C |
| ATOM | 3240 | CD | ARG | A | 541 | 24.287 | 81.865 | -53.226 | 1.00105.38 | C |
| ATOM | 3241 | NE | ARG | A | 541 | 25.037 | 82.568 | -54.265 | 1.00104.66 | N |
| ATOM | 3242 | CZ | ARG | A | 541 | 25.851 | 81.978 | -55.135 | 1.00105.93 | C |
| ATOM | 3243 | NH1 | ARG | A | 541 | 26.041 | 80.665 | -55.088 | 1.00105.46 | N |
| ATOM | 3244 | NH2 | ARG | A | 541 | 26.487 | 82.706 | -56.048 | 1.00105.74 | N |
| ATOM | 3245 | N | GLN | A | 542 | 24.949 | 83.574 | -48.612 | 1.00 99.34 | N |
| ATOM | 3246 | CA | GLN | A | 542 | 24.217 | 84.241 | -47.539 | 1.00100.60 | C |
| ATOM | 3247 | C | GLN | A | 542 | 23.112 | 85.159 | -48.081 | 1.00110.09 | C |
| ATOM | 3248 | O | GLN | A | 542 | 23.014 | 85.366 | -49.314 | 1.00111.51 | O |
| ATOM | 3249 | CB | GLN | A | 542 | 25.180 | 85.020 | -46.632 | 1.00105.05 | C |
| ATOM | 3250 | CG | GLN | A | 542 | 25.937 | 86.136 | -47.333 | 1.00107.58 | C |
| ATOM | 3251 | CD | GLN | A | 542 | 26.903 | 86.854 | -46.413 | 1.00105.24 | C |
| ATOM | 3252 | OE1 | GLN | A | 542 | 26.683 | 86.934 | -45.205 | 1.00105.28 | O |
| ATOM | 3253 | NE2 | GLN | A | 542 | 27.983 | 87.382 | -46.983 | 1.00103.67 | N |
| ATOM | 3254 | N | PRO | A | 543 | 22.263 | 85.687 | -47.189 | 1.00112.24 | N |
| ATOM | 3255 | CA | PRO | A | 543 | 21.263 | 86.704 | -47.509 | 1.00115.44 | C |
| ATOM | 3256 | C | PRO | A | 543 | 21.745 | 87.656 | -48.594 | 1.00120.12 | C |
| ATOM | 3257 | O | PRO | A | 543 | 22.889 | 88.117 | -48.562 | 1.00118.65 | O |
| ATOM | 3258 | CB | PRO | A | 543 | 21.108 | 87.435 | -46.184 | 1.00116.44 | C |
| ATOM | 3259 | CG | PRO | A | 543 | 21.268 | 86.335 | -45.163 | 1.00114.95 | C |
| ATOM | 3260 | CD | PRO | A | 543 | 22.178 | 85.385 | -45.773 | 1.00113.49 | C |
| ATOM | 3261 | N | ASN | A | 544 | 20.851 | 87.951 | -49.531 | 1.00126.88 | N |
| ATOM | 3262 | CA | ASN | A | 544 | 21.204 | 88.619 | -50.783 | 1.00133.27 | C |
| ATOM | 3263 | C | ASN | A | 544 | 22.523 | 89.383 | -50.752 | 1.00131.22 | C |
| ATOM | 3264 | O | ASN | A | 544 | 22.706 | 90.324 | -49.978 | 1.00132.54 | O |
| ATOM | 3265 | CB | ASN | A | 544 | 20.048 | 89.484 | -51.327 | 1.00136.94 | C |
| ATOM | 3266 | CG | ASN | A | 544 | 19.795 | 90.734 | -50.498 | 1.00136.98 | C |
| ATOM | 3267 | OD1 | ASN | A | 544 | 19.316 | 91.744 | -51.017 | 1.00136.20 | O |
| ATOM | 3268 | ND2 | ASN | A | 544 | 20.110 | 90.671 | -49.207 | 1.00135.59 | N |
| ATOM | 3269 | N | GLY | A | 545 | 23.454 | 88.923 | -51.580 | 1.00126.53 | N |
| ATOM | 3270 | CA | GLY | A | 545 | 23.230 | 87.718 | -52.361 | 1.00117.20 | C |
| ATOM | 3271 | C | GLY | A | 545 | 24.524 | 86.958 | -52.554 | 1.00105.97 | C |
| ATOM | 3272 | O | GLY | A | 545 | 24.565 | 85.906 | -53.191 | 1.00 91.97 | O |
| ATOM | 3273 | N | GLN | A | 546 | 25.587 | 87.490 | -51.963 | 1.00108.55 | N |
| ATOM | 3274 | CA | GLN | A | 546 | 26.934 | 87.051 | -52.287 | 1.00106.15 | C |
| ATOM | 3275 | C | GLN | A | 546 | 27.497 | 85.941 | -51.405 | 1.00 95.70 | C |
| ATOM | 3276 | O | GLN | A | 546 | 27.009 | 85.668 | -50.299 | 1.00 91.50 | O |
| ATOM | 3277 | CB | GLN | A | 546 | 27.879 | 88.253 | -52.340 | 1.00109.64 | C |
| ATOM | 3278 | CG | GLN | A | 546 | 27.578 | 89.164 | -53.510 | 1.00115.33 | C |
| ATOM | 3279 | CD | GLN | A | 546 | 27.703 | 90.631 | -53.176 | 1.00118.11 | C |
| ATOM | 3280 | OE1 | GLN | A | 546 | 26.861 | 91.445 | -53.569 | 1.00120.15 | O |
| ATOM | 3281 | NE2 | GLN | A | 546 | 28.751 | 90.981 | -52.434 | 1.00116.02 | N |
| ATOM | 3282 | N | VAL | A | 547 | 28.544 | 85.321 | -51.936 | 1.00 86.08 | N |
| ATOM | 3283 | CA | VAL | A | 547 | 29.127 | 84.108 | -51.403 | 1.00 79.07 | C |
| ATOM | 3284 | C | VAL | A | 547 | 30.284 | 84.417 | -50.448 | 1.00 80.21 | C |
| ATOM | 3285 | O | VAL | A | 547 | 31.226 | 85.127 | -50.880 | 1.00 83.61 | O |
| ATOM | 3286 | CB | VAL | A | 547 | 29.610 | 83.219 | -52.565 | 1.00 72.92 | C |
| ATOM | 3287 | CG1 | VAL | A | 547 | 30.013 | 81.841 | -52.090 | 1.00 74.45 | C |
| ATOM | 3288 | CG2 | VAL | A | 547 | 28.522 | 83.092 | -53.585 | 1.00 80.56 | C |
| ATOM | 3289 | N | TRP | A | 548 | 30.189 | 83.885 | -49.232 | 1.00 70.38 | N |
| ATOM | 3290 | CA | TRP | A | 548 | 31.226 | 84.029 | -48.217 | 1.00 65.80 | C |
| ATOM | 3291 | C | TRP | A | 548 | 32.267 | 82.949 | -48.498 | 1.00 63.23 | C |
| ATOM | 3292 | O | TRP | A | 548 | 31.971 | 81.754 | -48.361 | 1.00 66.32 | O |
| ATOM | 3293 | CB | TRP | A | 548 | 30.591 | 83.870 | -46.829 | 1.00 70.04 | C |
| ATOM | 3294 | CG | TRP | A | 548 | 31.431 | 84.341 | -45.686 | 1.00 71.15 | C |
| ATOM | 3295 | CD1 | TRP | A | 548 | 31.952 | 85.589 | -45.512 | 1.00 71.94 | C |
| ATOM | 3296 | CD2 | TRP | A | 548 | 31.824 | 83.578 | -44.541 | 1.00 65.03 | C |
| ATOM | 3297 | NE1 | TRP | A | 548 | 32.657 | 85.651 | -44.341 | 1.00 71.71 | N |
| ATOM | 3298 | CE2 | TRP | A | 548 | 32.599 | 84.431 | -43.720 | 1.00 70.06 | C |
| ATOM | 3299 | CE3 | TRP | A | 548 | 31.610 | 82.255 | -44.135 | 1.00 59.58 | C |
| ATOM | 3300 | CZ2 | TRP | A | 548 | 33.174 | 84.003 | -42.513 | 1.00 63.04 | C |
| ATOM | 3301 | CZ3 | TRP | A | 548 | 32.172 | 81.828 | -42.923 | 1.00 59.68 | C |
| ATOM | 3302 | CH2 | TRP | A | 548 | 32.938 | 82.708 | -42.125 | 1.00 61.60 | C |
| ATOM | 3303 | N | SER | A | 549 | 33.484 | 83.338 | -48.806 | 1.00 63.24 | N |
| ATOM | 3304 | CA | SER | A | 549 | 34.515 | 82.346 | -49.102 | 1.00 62.81 | C |
| ATOM | 3305 | C | SER | A | 549 | 35.747 | 82.543 | -48.217 | 1.00 63.10 | C |
| ATOM | 3306 | O | SER | A | 549 | 36.754 | 83.103 | -48.658 | 1.00 71.80 | O |

FIG. 8-53

| | | | | | | | | | | | |
|---|---|---|---|---|---|---|---|---|---|---|---|
| ATOM | 3307 | CB | SER | A | 549 | 34.892 | 82.383 | -50.587 | 1.00 | 67.22 | C |
| ATOM | 3308 | OG | SER | A | 549 | 35.558 | 81.191 | -50.969 | 1.00 | 72.16 | O |
| ATOM | 3309 | N | PRO | A | 550 | 35.661 | 82.086 | -46.955 | 1.00 | 56.34 | N |
| ATOM | 3310 | CA | PRO | A | 550 | 36.746 | 82.270 | -45.984 | 1.00 | 53.07 | C |
| ATOM | 3311 | C | PRO | A | 550 | 37.976 | 81.487 | -46.383 | 1.00 | 53.87 | C |
| ATOM | 3312 | O | PRO | A | 550 | 37.854 | 80.357 | -46.845 | 1.00 | 55.96 | O |
| ATOM | 3313 | CB | PRO | A | 550 | 36.171 | 81.677 | -44.681 | 1.00 | 48.69 | C |
| ATOM | 3314 | CG | PRO | A | 550 | 34.706 | 81.710 | -44.881 | 1.00 | 52.37 | C |
| ATOM | 3315 | CD | PRO | A | 550 | 34.487 | 81.434 | -46.351 | 1.00 | 42.67 | C |
| ATOM | 3316 | N | GLN | A | 551 | 39.147 | 82.078 | -46.200 | 1.00 | 50.95 | N |
| ATOM | 3317 | CA | GLN | A | 551 | 40.396 | 81.402 | -46.513 | 1.00 | 53.16 | C |
| ATOM | 3318 | C | GLN | A | 551 | 41.226 | 81.236 | -45.254 | 1.00 | 52.53 | C |
| ATOM | 3319 | O | GLN | A | 551 | 41.128 | 82.033 | -44.314 | 1.00 | 43.49 | O |
| ATOM | 3320 | CB | GLN | A | 551 | 41.194 | 82.225 | -47.515 | 1.00 | 56.58 | C |
| ATOM | 3321 | CG | GLN | A | 551 | 40.482 | 82.442 | -48.844 | 1.00 | 71.91 | C |
| ATOM | 3322 | CD | GLN | A | 551 | 40.805 | 81.359 | -49.846 | 1.00 | 82.18 | C |
| ATOM | 3323 | OE1 | GLN | A | 551 | 41.894 | 80.774 | -49.813 | 1.00 | 86.03 | O |
| ATOM | 3324 | NE2 | GLN | A | 551 | 39.865 | 81.084 | -50.740 | 1.00 | 87.73 | N |
| ATOM | 3325 | N | ASN | A | 552 | 42.040 | 80.188 | -45.348 | 1.00 | 49.38 | N |
| ATOM | 3326 | CA | ASN | A | 552 | 43.130 | 80.058 | -44.295 | 1.00 | 43.63 | C |
| ATOM | 3327 | C | ASN | A | 552 | 44.101 | 81.249 | -44.316 | 1.00 | 44.49 | C |
| ATOM | 3328 | O | ASN | A | 552 | 44.192 | 82.000 | -45.302 | 1.00 | 42.86 | O |
| ATOM | 3329 | CB | ASN | A | 552 | 43.846 | 78.723 | -44.523 | 1.00 | 42.06 | C |
| ATOM | 3330 | CG | ASN | A | 552 | 43.003 | 77.543 | -44.046 | 1.00 | 52.08 | C |
| ATOM | 3331 | OD1 | ASN | A | 552 | 42.892 | 76.435 | -44.718 | 1.00 | 48.26 | O |
| ATOM | 3332 | ND2 | ASN | A | 552 | 42.355 | 77.736 | -42.894 | 1.00 | 33.39 | N |
| ATOM | 3333 | N | ASP | A | 553 | 44.802 | 81.397 | -43.201 | 1.00 | 48.92 | N |
| ATOM | 3334 | CA | ASP | A | 553 | 45.797 | 82.425 | -42.982 | 1.00 | 53.38 | C |
| ATOM | 3335 | C | ASP | A | 553 | 46.736 | 82.557 | -44.161 | 1.00 | 51.61 | C |
| ATOM | 3336 | O | ASP | A | 553 | 46.993 | 83.668 | -44.637 | 1.00 | 56.03 | O |
| ATOM | 3337 | CB | ASP | A | 553 | 46.574 | 82.013 | -41.710 | 1.00 | 67.45 | C |
| ATOM | 3338 | CG | ASP | A | 553 | 47.845 | 82.836 | -41.482 | 1.00 | 86.43 | C |
| ATOM | 3339 | OD1 | ASP | A | 553 | 48.499 | 83.297 | -42.476 | 1.00 | 91.37 | O |
| ATOM | 3340 | OD2 | ASP | A | 553 | 48.201 | 83.036 | -40.286 | 1.00 | 79.99 | O |
| ATOM | 3341 | N | ASP | A | 554 | 47.224 | 81.414 | -44.651 | 1.00 | 40.95 | N |
| ATOM | 3342 | CA | ASP | A | 554 | 48.197 | 81.362 | -45.742 | 1.00 | 55.30 | C |
| ATOM | 3343 | C | ASP | A | 554 | 47.554 | 80.967 | -47.053 | 1.00 | 51.93 | C |
| ATOM | 3344 | O | ASP | A | 554 | 48.238 | 80.598 | -47.972 | 1.00 | 53.24 | O |
| ATOM | 3345 | CB | ASP | A | 554 | 49.279 | 80.332 | -45.415 | 1.00 | 62.96 | C |
| ATOM | 3346 | CG | ASP | A | 554 | 48.696 | 78.965 | -45.086 | 1.00 | 70.75 | C |
| ATOM | 3347 | OD1 | ASP | A | 554 | 49.485 | 78.030 | -44.822 | 1.00 | 74.93 | O |
| ATOM | 3348 | OD2 | ASP | A | 554 | 47.447 | 78.822 | -45.095 | 1.00 | 82.73 | O |
| ATOM | 3349 | N | ARG | A | 555 | 46.229 | 80.978 | -47.123 | 1.00 | 50.70 | N |
| ATOM | 3350 | CA | ARG | A | 555 | 45.561 | 80.659 | -48.391 | 1.00 | 42.82 | C |
| ATOM | 3351 | C | ARG | A | 555 | 45.917 | 79.278 | -48.933 | 1.00 | 43.54 | C |
| ATOM | 3352 | O | ARG | A | 555 | 45.850 | 79.021 | -50.147 | 1.00 | 53.90 | O |
| ATOM | 3353 | CB | ARG | A | 555 | 45.789 | 81.790 | -49.371 | 1.00 | 51.15 | C |
| ATOM | 3354 | CG | ARG | A | 555 | 44.844 | 82.943 | -49.026 | 1.00 | 59.88 | C |
| ATOM | 3355 | CD | ARG | A | 555 | 45.501 | 84.318 | -48.874 | 1.00 | 55.69 | C |
| ATOM | 3356 | NE | ARG | A | 555 | 46.249 | 84.788 | -50.042 | 1.00 | 68.53 | N |
| ATOM | 3357 | CZ | ARG | A | 555 | 46.226 | 86.047 | -50.481 | 1.00 | 73.53 | C |
| ATOM | 3358 | NH1 | ARG | A | 555 | 45.442 | 86.946 | -49.894 | 1.00 | 72.43 | N |
| ATOM | 3359 | NH2 | ARG | A | 555 | 46.957 | 86.404 | -51.529 | 1.00 | 78.65 | N |
| ATOM | 3360 | N | ARG | A | 556 | 45.252 | 78.382 | -48.002 | 1.00 | 50.04 | N |
| ATOM | 3361 | CA | ARG | A | 556 | 45.528 | 76.977 | -48.311 | 1.00 | 58.47 | C |
| ATOM | 3362 | C | ARG | A | 556 | 45.517 | 76.048 | -47.636 | 1.00 | 53.08 | C |
| ATOM | 3363 | O | ARG | A | 556 | 44.914 | 76.417 | -46.641 | 1.00 | 50.81 | O |
| ATOM | 3364 | CB | ARG | A | 556 | 47.942 | 76.602 | -47.873 | 1.00 | 62.66 | C |
| ATOM | 3365 | CG | ARG | A | 556 | 49.010 | 77.276 | -48.728 | 1.00 | 68.89 | C |
| ATOM | 3366 | CD | ARG | A | 556 | 50.189 | 76.383 | -48.970 | 1.00 | 77.49 | C |
| ATOM | 3367 | NE | ARG | A | 556 | 51.015 | 76.235 | -47.776 | 1.00 | 78.87 | N |
| ATOM | 3368 | CZ | ARG | A | 556 | 51.973 | 75.332 | -47.614 | 1.00 | 78.64 | C |
| ATOM | 3369 | NH1 | ARG | A | 556 | 52.231 | 74.452 | -48.576 | 1.00 | 80.78 | N |
| ATOM | 3370 | NH2 | ARG | A | 556 | 52.670 | 75.312 | -46.485 | 1.00 | 77.49 | N |
| ATOM | 3371 | N | TYR | A | 557 | 45.351 | 74.851 | -48.200 | 1.00 | 46.38 | N |
| ATOM | 3372 | CA | TYR | A | 557 | 44.501 | 73.802 | -47.662 | 1.00 | 48.23 | C |
| ATOM | 3373 | C | TYR | A | 557 | 45.370 | 72.815 | -47.293 | 1.00 | 52.31 | C |
| ATOM | 3374 | O | TYR | A | 557 | 46.376 | 72.384 | -47.951 | 1.00 | 55.32 | O |
| ATOM | 3375 | CB | TYR | A | 557 | 43.467 | 73.410 | -48.708 | 1.00 | 57.19 | C |
| ATOM | 3376 | CG | TYR | A | 557 | 42.529 | 74.557 | -48.997 | 1.00 | 59.41 | C |
| ATOM | 3377 | CD1 | TYR | A | 557 | 42.646 | 75.221 | -50.229 | 1.00 | 54.96 | C |
| ATOM | 3378 | CD2 | TYR | A | 557 | 41.665 | 75.017 | -48.005 | 1.00 | 46.41 | C |
| ATOM | 3379 | CE1 | TYR | A | 557 | 41.695 | 76.299 | -50.477 | 1.00 | 55.24 | C |
| ATOM | 3380 | CE2 | TYR | A | 557 | 40.826 | 76.075 | -48.235 | 1.00 | 54.99 | C |
| ATOM | 3381 | CZ | TYR | A | 557 | 40.832 | 76.715 | -49.469 | 1.00 | 55.42 | C |
| ATOM | 3382 | OH | TYR | A | 557 | 39.968 | 77.777 | -49.653 | 1.00 | 56.79 | O |
| ATOM | 3383 | N | SER | A | 558 | 45.002 | 71.880 | -46.253 | 1.00 | 48.59 | N |

FIG. 8-54

| | | | | | | | | | | | |
|---|---|---|---|---|---|---|---|---|---|---|---|
| ATOM | 3384 | CA | SER | A | 558 | 43.786 | 70.717 | -45.835 | 1.00 | 54.28 | C |
| ATOM | 3385 | C | SER | A | 558 | 45.796 | 69.732 | -46.998 | 1.00 | 54.37 | C |
| ATOM | 3386 | O | SER | A | 558 | 44.740 | 69.455 | -47.591 | 1.00 | 53.29 | O |
| ATOM | 3387 | CB | SER | A | 558 | 45.189 | 70.091 | -44.577 | 1.00 | 59.99 | C |
| ATOM | 3388 | OG | SER | A | 558 | 44.854 | 70.989 | -43.934 | 1.00 | 58.15 | O |
| ATOM | 3389 | N | GLU | A | 559 | 46.969 | 69.197 | -47.328 | 1.00 | 50.95 | N |
| ATOM | 3390 | CA | GLU | A | 559 | 47.079 | 68.401 | -48.557 | 1.00 | 60.50 | C |
| ATOM | 3391 | C | GLU | A | 559 | 46.123 | 67.217 | -48.510 | 1.00 | 59.85 | C |
| ATOM | 3392 | O | GLU | A | 559 | 45.499 | 66.864 | -49.517 | 1.00 | 63.36 | O |
| ATOM | 3393 | CB | GLU | A | 559 | 48.505 | 67.919 | -48.805 | 1.00 | 67.83 | C |
| ATOM | 3394 | CG | GLU | A | 559 | 48.686 | 66.417 | -48.638 | 1.00 | 81.64 | C |
| ATOM | 3395 | CD | GLU | A | 559 | 48.065 | 65.598 | -49.776 | 1.00 | 89.50 | C |
| ATOM | 3396 | OE1 | GLU | A | 559 | 48.567 | 65.666 | -50.825 | 1.00 | 92.54 | O |
| ATOM | 3397 | OE2 | GLU | A | 559 | 47.066 | 64.864 | -49.511 | 1.00 | 88.24 | O |
| ATOM | 3398 | N | SER | A | 560 | 45.996 | 66.606 | -47.338 | 1.00 | 48.38 | N |
| ATOM | 3399 | CA | SER | A | 560 | 45.040 | 65.556 | -47.178 | 1.00 | 60.08 | C |
| ATOM | 3400 | C | SER | A | 560 | 43.573 | 65.981 | -47.241 | 1.00 | 55.29 | C |
| ATOM | 3401 | O | SER | A | 560 | 42.661 | 65.134 | -47.201 | 1.00 | 59.95 | O |
| ATOM | 3402 | CB | SER | A | 560 | 45.295 | 64.774 | -45.846 | 1.00 | 64.90 | C |
| ATOM | 3403 | OG | SER | A | 560 | 44.932 | 65.597 | -44.755 | 1.00 | 63.22 | O |
| ATOM | 3404 | N | GLY | A | 561 | 43.326 | 67.269 | -47.315 | 1.00 | 48.79 | N |
| ATOM | 3405 | CA | GLY | A | 561 | 41.942 | 67.757 | -47.246 | 1.00 | 45.23 | C |
| ATOM | 3406 | C | GLY | A | 561 | 41.337 | 67.761 | -45.845 | 1.00 | 45.17 | C |
| ATOM | 3407 | O | GLY | A | 561 | 40.174 | 68.102 | -45.662 | 1.00 | 47.97 | O |
| ATOM | 3408 | N | ARG | A | 562 | 42.163 | 67.370 | -44.828 | 1.00 | 47.39 | N |
| ATOM | 3409 | CA | ARG | A | 562 | 41.921 | 67.282 | -43.463 | 1.00 | 47.71 | C |
| ATOM | 3410 | C | ARG | A | 562 | 42.947 | 67.535 | -42.369 | 1.00 | 43.04 | C |
| ATOM | 3411 | O | ARG | A | 562 | 43.767 | 67.450 | -42.600 | 1.00 | 48.57 | O |
| ATOM | 3412 | CB | ARG | A | 562 | 40.891 | 65.912 | -43.228 | 1.00 | 48.95 | C |
| ATOM | 3413 | CG | ARG | A | 562 | 41.930 | 64.840 | -42.937 | 1.00 | 46.15 | C |
| ATOM | 3414 | CD | ARG | A | 562 | 41.374 | 63.425 | -43.062 | 1.00 | 46.54 | C |
| ATOM | 3415 | NE | ARG | A | 562 | 42.429 | 62.473 | -42.751 | 1.00 | 56.09 | N |
| ATOM | 3416 | CZ | ARG | A | 562 | 42.226 | 61.210 | -42.388 | 1.00 | 60.12 | C |
| ATOM | 3417 | NH1 | ARG | A | 562 | 40.994 | 60.726 | -42.322 | 1.00 | 52.44 | N |
| ATOM | 3418 | NH2 | ARG | A | 562 | 43.267 | 60.435 | -42.090 | 1.00 | 64.41 | N |
| ATOM | 3419 | N | VAL | A | 563 | 42.057 | 67.874 | -41.179 | 1.00 | 40.03 | N |
| ATOM | 3420 | CA | VAL | A | 563 | 42.926 | 68.149 | -40.042 | 1.00 | 45.72 | C |
| ATOM | 3421 | C | VAL | A | 563 | 42.188 | 67.772 | -38.770 | 1.00 | 42.48 | C |
| ATOM | 3422 | O | VAL | A | 563 | 40.954 | 67.837 | -38.718 | 1.00 | 40.48 | O |
| ATOM | 3423 | CB | VAL | A | 563 | 43.283 | 69.637 | -39.986 | 1.00 | 49.32 | C |
| ATOM | 3424 | CG1 | VAL | A | 563 | 43.908 | 70.036 | -41.276 | 1.00 | 50.92 | C |
| ATOM | 3425 | CG2 | VAL | A | 563 | 41.968 | 70.450 | -39.780 | 1.00 | 57.41 | C |
| ATOM | 3426 | N | MET | A | 564 | 42.876 | 67.293 | -37.750 | 1.00 | 39.23 | N |
| ATOM | 3427 | CA | MET | A | 564 | 42.220 | 66.914 | -36.493 | 1.00 | 34.75 | C |
| ATOM | 3428 | C | MET | A | 564 | 41.878 | 68.163 | -35.733 | 1.00 | 39.33 | C |
| ATOM | 3429 | O | MET | A | 564 | 42.588 | 69.198 | -35.844 | 1.00 | 37.27 | O |
| ATOM | 3430 | CB | MET | A | 564 | 43.096 | 65.985 | -35.664 | 1.00 | 42.15 | C |
| ATOM | 3431 | CG | MET | A | 564 | 43.008 | 64.531 | -36.092 | 1.00 | 45.87 | C |
| ATOM | 3432 | SD | MET | A | 564 | 44.069 | 63.467 | -35.088 | 1.00 | 54.04 | S |
| ATOM | 3433 | CE | MET | A | 564 | 45.292 | 64.674 | -34.639 | 1.00 | 44.92 | C |
| ATOM | 3434 | N | LEU | A | 565 | 40.773 | 68.068 | -34.966 | 1.00 | 34.02 | N |
| ATOM | 3435 | CA | LEU | A | 565 | 40.227 | 69.188 | -34.249 | 1.00 | 31.18 | C |
| ATOM | 3436 | C | LEU | A | 565 | 41.307 | 69.737 | -33.392 | 1.00 | 36.60 | C |
| ATOM | 3437 | O | LEU | A | 565 | 41.435 | 71.031 | -33.314 | 1.00 | 36.74 | O |
| ATOM | 3438 | CB | LEU | A | 565 | 39.034 | 68.749 | -33.412 | 1.00 | 33.50 | C |
| ATOM | 3439 | CG | LEU | A | 565 | 38.293 | 69.757 | -32.562 | 1.00 | 32.84 | C |
| ATOM | 3440 | CD1 | LEU | A | 565 | 36.912 | 69.222 | -32.367 | 1.00 | 30.40 | C |
| ATOM | 3441 | CD2 | LEU | A | 565 | 38.997 | 69.953 | -31.153 | 1.00 | 33.15 | C |
| ATOM | 3442 | N | VAL | A | 566 | 42.113 | 68.939 | -32.766 | 1.00 | 33.81 | N |
| ATOM | 3443 | CA | VAL | A | 566 | 43.131 | 69.459 | -31.875 | 1.00 | 31.41 | C |
| ATOM | 3444 | C | VAL | A | 566 | 43.876 | 70.489 | -32.599 | 1.00 | 32.43 | C |
| ATOM | 3445 | O | VAL | A | 566 | 44.199 | 71.598 | -32.087 | 1.00 | 44.58 | O |
| ATOM | 3446 | CB | VAL | A | 566 | 43.982 | 69.320 | -31.203 | 1.00 | 48.83 | C |
| ATOM | 3447 | CG1 | VAL | A | 566 | 44.838 | 67.607 | -32.197 | 1.00 | 43.15 | C |
| ATOM | 3448 | CG2 | VAL | A | 566 | 44.820 | 68.879 | -30.068 | 1.00 | 43.16 | C |
| ATOM | 3449 | N | ASP | A | 567 | 44.398 | 70.141 | -33.809 | 1.00 | 38.79 | N |
| ATOM | 3450 | CA | ASP | A | 567 | 45.354 | 70.958 | -34.573 | 1.00 | 41.37 | C |
| ATOM | 3451 | C | ASP | A | 567 | 44.769 | 72.182 | -35.218 | 1.00 | 36.76 | C |
| ATOM | 3452 | O | ASP | A | 567 | 45.346 | 73.234 | -35.372 | 1.00 | 38.69 | O |
| ATOM | 3453 | CB | ASP | A | 567 | 46.078 | 70.098 | -35.596 | 1.00 | 39.85 | C |
| ATOM | 3454 | CG | ASP | A | 567 | 46.843 | 68.926 | -34.942 | 1.00 | 51.89 | C |
| ATOM | 3455 | OD1 | ASP | A | 567 | 46.885 | 67.799 | -35.502 | 1.00 | 50.21 | O |
| ATOM | 3456 | OD2 | ASP | A | 567 | 47.421 | 69.142 | -33.861 | 1.00 | 48.05 | O |
| ATOM | 3457 | N | ALA | A | 568 | 43.437 | 72.091 | -35.565 | 1.00 | 34.36 | N |
| ATOM | 3458 | CA | ALA | A | 568 | 43.735 | 73.293 | -36.073 | 1.00 | 34.11 | C |
| ATOM | 3459 | C | ALA | A | 568 | 42.754 | 74.404 | -35.074 | 1.00 | 36.43 | C |
| ATOM | 3460 | O | ALA | A | 568 | 42.982 | 75.551 | -35.442 | 1.00 | 39.64 | O |

FIG. 8-55

| | | | | | | | | | | | |
|---|---|---|---|---|---|---|---|---|---|---|---|
| ATOM | 3461 | CB | ALA | A | 568 | 41.299 | 72.894 | -36.462 | 1.00 | 28.83 | C |
| ATOM | 3462 | N | LEU | A | 569 | 42.495 | 74.106 | -33.805 | 1.00 | 39.89 | N |
| ATOM | 3463 | CA | LEU | A | 569 | 42.531 | 75.149 | -32.782 | 1.00 | 33.65 | C |
| ATOM | 3464 | C | LEU | A | 569 | 43.843 | 75.614 | -32.526 | 1.00 | 30.70 | C |
| ATOM | 3465 | O | LEU | A | 569 | 44.178 | 76.808 | -32.404 | 1.00 | 36.63 | O |
| ATOM | 3466 | CB | LEU | A | 569 | 41.910 | 74.679 | -31.445 | 1.00 | 34.39 | C |
| ATOM | 3467 | CG | LEU | A | 569 | 41.790 | 75.754 | -30.343 | 1.00 | 37.24 | C |
| ATOM | 3468 | CD1 | LEU | A | 569 | 41.361 | 77.124 | -30.850 | 1.00 | 38.43 | C |
| ATOM | 3469 | CD2 | LEU | A | 569 | 40.805 | 75.357 | -29.216 | 1.00 | 35.30 | C |
| ATOM | 3470 | N | THR | A | 570 | 44.868 | 74.662 | -32.379 | 1.00 | 31.01 | N |
| ATOM | 3471 | CA | THR | A | 570 | 46.282 | 74.979 | -32.097 | 1.00 | 32.18 | C |
| ATOM | 3472 | C | THR | A | 570 | 46.819 | 76.013 | -33.073 | 1.00 | 42.81 | C |
| ATOM | 3473 | O | THR | A | 570 | 47.467 | 76.992 | -32.676 | 1.00 | 43.45 | O |
| ATOM | 3474 | CB | THR | A | 570 | 47.141 | 73.692 | -32.087 | 1.00 | 34.31 | C |
| ATOM | 3475 | OG1 | THR | A | 570 | 46.631 | 72.820 | -31.064 | 1.00 | 43.34 | O |
| ATOM | 3476 | CG2 | THR | A | 570 | 48.661 | 73.978 | -31.789 | 1.00 | 31.45 | C |
| ATOM | 3477 | N | ARG | A | 571 | 46.487 | 75.809 | -34.346 | 1.00 | 47.84 | N |
| ATOM | 3478 | CA | ARG | A | 571 | 47.007 | 76.602 | -35.445 | 1.00 | 47.50 | C |
| ATOM | 3479 | C | ARG | A | 571 | 46.034 | 77.703 | -35.867 | 1.00 | 43.01 | C |
| ATOM | 3480 | O | ARG | A | 571 | 46.288 | 78.436 | -36.819 | 1.00 | 45.51 | O |
| ATOM | 3481 | CB | ARG | A | 571 | 47.315 | 75.667 | -36.629 | 1.00 | 38.06 | C |
| ATOM | 3482 | CG | ARG | A | 571 | 48.575 | 74.828 | -36.303 | 1.00 | 50.26 | C |
| ATOM | 3483 | CD | ARG | A | 571 | 48.707 | 73.594 | -37.158 | 1.00 | 46.04 | C |
| ATOM | 3484 | NE | ARG | A | 571 | 48.705 | 73.937 | -38.582 | 1.00 | 59.18 | N |
| ATOM | 3485 | CZ | ARG | A | 571 | 48.358 | 73.084 | -39.542 | 1.00 | 64.87 | C |
| ATOM | 3486 | NH1 | ARG | A | 571 | 48.013 | 71.844 | -39.205 | 1.00 | 68.41 | N |
| ATOM | 3487 | NH2 | ARG | A | 571 | 48.375 | 73.459 | -40.828 | 1.00 | 59.79 | N |
| ATOM | 3488 | N | SER | A | 572 | 44.923 | 77.820 | -35.163 | 1.00 | 35.90 | N |
| ATOM | 3489 | CA | SER | A | 572 | 43.926 | 78.847 | -35.477 | 1.00 | 43.92 | C |
| ATOM | 3490 | C | SER | A | 572 | 43.591 | 78.846 | -37.008 | 1.00 | 44.53 | C |
| ATOM | 3491 | O | SER | A | 572 | 43.597 | 79.884 | -37.692 | 1.00 | 36.47 | O |
| ATOM | 3492 | CB | SER | A | 572 | 44.449 | 80.211 | -35.005 | 1.00 | 44.34 | C |
| ATOM | 3493 | OG | SER | A | 572 | 43.387 | 81.081 | -34.662 | 1.00 | 38.68 | O |
| ATOM | 3494 | N | MET | A | 573 | 43.312 | 77.653 | -37.513 | 1.00 | 38.92 | N |
| ATOM | 3495 | CA | MET | A | 573 | 42.933 | 77.429 | -38.903 | 1.00 | 39.33 | C |
| ATOM | 3496 | C | MET | A | 573 | 41.510 | 77.947 | -39.185 | 1.00 | 42.80 | C |
| ATOM | 3497 | O | MET | A | 573 | 40.552 | 77.452 | -38.823 | 1.00 | 37.08 | O |
| ATOM | 3498 | CB | MET | A | 573 | 43.025 | 75.932 | -39.154 | 1.00 | 31.42 | C |
| ATOM | 3499 | CG | MET | A | 573 | 44.470 | 75.424 | -38.895 | 1.00 | 30.74 | C |
| ATOM | 3500 | SD | MET | A | 573 | 44.743 | 73.744 | -39.473 | 1.00 | 44.42 | S |
| ATOM | 3501 | CE | MET | A | 573 | 45.026 | 74.100 | -41.196 | 1.00 | 56.41 | C |
| ATOM | 3502 | N | ASN | A | 574 | 41.386 | 78.981 | -40.000 | 1.00 | 43.61 | N |
| ATOM | 3503 | CA | ASN | A | 574 | 40.085 | 79.576 | -40.306 | 1.00 | 36.76 | C |
| ATOM | 3504 | C | ASN | A | 574 | 39.091 | 78.587 | -40.903 | 1.00 | 44.77 | C |
| ATOM | 3505 | O | ASN | A | 574 | 37.917 | 78.543 | -40.502 | 1.00 | 39.11 | O |
| ATOM | 3506 | CB | ASN | A | 574 | 40.268 | 80.730 | -41.305 | 1.00 | 39.40 | C |
| ATOM | 3507 | CG | ASN | A | 574 | 41.068 | 81.879 | -40.705 | 1.00 | 46.22 | C |
| ATOM | 3508 | OD1 | ASN | A | 574 | 40.985 | 82.121 | -39.498 | 1.00 | 39.41 | O |
| ATOM | 3509 | ND2 | ASN | A | 574 | 41.864 | 82.571 | -41.533 | 1.00 | 50.69 | N |
| ATOM | 3510 | N | VAL | A | 575 | 39.555 | 77.794 | -41.861 | 1.00 | 42.78 | N |
| ATOM | 3511 | CA | VAL | A | 575 | 38.628 | 76.995 | -42.647 | 1.00 | 49.05 | C |
| ATOM | 3512 | C | VAL | A | 575 | 38.043 | 75.807 | -41.888 | 1.00 | 44.03 | C |
| ATOM | 3513 | O | VAL | A | 575 | 36.885 | 75.557 | -41.986 | 1.00 | 40.47 | O |
| ATOM | 3514 | CB | VAL | A | 575 | 39.243 | 76.553 | -44.008 | 1.00 | 47.03 | C |
| ATOM | 3515 | CG1 | VAL | A | 575 | 38.497 | 75.335 | -44.571 | 1.00 | 36.91 | C |
| ATOM | 3516 | CG2 | VAL | A | 575 | 39.188 | 77.718 | -45.006 | 1.00 | 44.50 | C |
| ATOM | 3517 | N | PRO | A | 576 | 38.867 | 75.037 | -41.176 | 1.00 | 41.23 | N |
| ATOM | 3518 | CA | PRO | A | 576 | 38.255 | 73.987 | -40.363 | 1.00 | 41.67 | C |
| ATOM | 3519 | C | PRO | A | 576 | 37.331 | 74.525 | -39.277 | 1.00 | 41.52 | C |
| ATOM | 3520 | O | PRO | A | 576 | 36.434 | 73.799 | -38.840 | 1.00 | 34.70 | O |
| ATOM | 3521 | CB | PRO | A | 576 | 39.467 | 73.332 | -39.686 | 1.00 | 35.60 | C |
| ATOM | 3522 | CG | PRO | A | 576 | 40.552 | 73.477 | -40.756 | 1.00 | 39.13 | C |
| ATOM | 3523 | CD | PRO | A | 576 | 40.323 | 74.856 | -41.313 | 1.00 | 43.64 | C |
| ATOM | 3524 | N | THR | A | 577 | 37.596 | 75.734 | -38.789 | 1.00 | 32.57 | N |
| ATOM | 3525 | CA | THR | A | 577 | 36.761 | 76.318 | -37.748 | 1.00 | 33.50 | C |
| ATOM | 3526 | C | THR | A | 577 | 35.350 | 76.580 | -38.236 | 1.00 | 40.88 | C |
| ATOM | 3527 | O | THR | A | 577 | 34.400 | 76.399 | -37.524 | 1.00 | 44.04 | O |
| ATOM | 3528 | CB | THR | A | 577 | 37.360 | 77.649 | -37.260 | 1.00 | 45.55 | C |
| ATOM | 3529 | OG1 | THR | A | 577 | 38.678 | 77.398 | -36.780 | 1.00 | 43.33 | O |
| ATOM | 3530 | CG2 | THR | A | 577 | 36.486 | 78.278 | -36.110 | 1.00 | 43.65 | C |
| ATOM | 3531 | N | VAL | A | 578 | 35.225 | 77.087 | -39.473 | 1.00 | 44.55 | N |
| ATOM | 3532 | CA | VAL | A | 578 | 33.935 | 77.376 | -40.082 | 1.00 | 40.24 | C |
| ATOM | 3533 | C | VAL | A | 578 | 33.237 | 76.049 | -40.406 | 1.00 | 41.50 | C |
| ATOM | 3534 | O | VAL | A | 578 | 32.059 | 75.929 | -40.250 | 1.00 | 47.40 | O |
| ATOM | 3535 | CB | VAL | A | 578 | 34.115 | 78.233 | -41.388 | 1.00 | 44.79 | C |
| ATOM | 3536 | CG1 | VAL | A | 578 | 32.792 | 78.377 | -42.150 | 1.00 | 39.39 | C |
| ATOM | 3537 | CG2 | VAL | A | 578 | 34.691 | 79.601 | -41.085 | 1.00 | 34.33 | C |

FIG. 8-56

| | | | | | | | | | | | |
|---|---|---|---|---|---|---|---|---|---|---|---|
| ATOM | 3538 | N | ASN | A | 579 | 33.968 | 75.047 | -40.875 | 1.00 | 42.83 | N |
| ATOM | 3539 | CA | ASN | A | 579 | 33.338 | 73.766 | -41.134 | 1.00 | 34.58 | C |
| ATOM | 3540 | C | ASN | A | 579 | 32.895 | 73.140 | -39.848 | 1.00 | 42.73 | C |
| ATOM | 3541 | O | ASN | A | 579 | 31.788 | 72.613 | -39.766 | 1.00 | 39.80 | O |
| ATOM | 3542 | CB | ASN | A | 579 | 34.275 | 72.817 | -41.879 | 1.00 | 43.30 | C |
| ATOM | 3543 | CG | ASN | A | 579 | 34.351 | 73.127 | -43.354 | 1.00 | 45.15 | C |
| ATOM | 3544 | OD1 | ASN | A | 579 | 33.423 | 73.684 | -43.923 | 1.00 | 48.52 | O |
| ATOM | 3545 | ND2 | ASN | A | 579 | 35.456 | 72.782 | -43.981 | 1.00 | 48.76 | N |
| ATOM | 3546 | N | LEU | A | 580 | 33.729 | 73.221 | -38.806 | 1.00 | 33.11 | N |
| ATOM | 3547 | CA | LEU | A | 580 | 33.274 | 72.742 | -37.485 | 1.00 | 30.25 | C |
| ATOM | 3548 | C | LEU | A | 580 | 32.023 | 73.520 | -36.984 | 1.00 | 40.34 | C |
| ATOM | 3549 | O | LEU | A | 580 | 31.006 | 72.833 | -36.671 | 1.00 | 47.07 | O |
| ATOM | 3550 | CB | LEU | A | 580 | 34.397 | 72.826 | -36.421 | 1.00 | 30.75 | C |
| ATOM | 3551 | CG | LEU | A | 580 | 33.972 | 72.384 | -35.008 | 1.00 | 31.45 | C |
| ATOM | 3552 | CD1 | LEU | A | 580 | 33.448 | 70.938 | -35.014 | 1.00 | 32.48 | C |
| ATOM | 3553 | CD2 | LEU | A | 580 | 35.069 | 72.542 | -34.020 | 1.00 | 30.04 | C |
| ATOM | 3554 | N | GLY | A | 581 | 32.139 | 74.838 | -36.903 | 1.00 | 36.97 | N |
| ATOM | 3555 | CA | GLY | A | 581 | 31.107 | 75.695 | -36.371 | 1.00 | 33.71 | C |
| ATOM | 3556 | C | GLY | A | 581 | 29.812 | 75.616 | -37.157 | 1.00 | 40.08 | C |
| ATOM | 3557 | O | GLY | A | 581 | 28.743 | 75.604 | -36.550 | 1.00 | 32.47 | O |
| ATOM | 3558 | N | MET | A | 582 | 29.913 | 75.560 | -38.493 | 1.00 | 39.78 | N |
| ATOM | 3559 | CA | MET | A | 582 | 28.741 | 75.423 | -39.348 | 1.00 | 39.35 | C |
| ATOM | 3560 | C | MET | A | 582 | 28.050 | 74.075 | -39.105 | 1.00 | 49.06 | C |
| ATOM | 3561 | O | MET | A | 582 | 26.832 | 73.991 | -39.175 | 1.00 | 54.26 | O |
| ATOM | 3562 | CB | MET | A | 582 | 29.102 | 75.571 | -40.861 | 1.00 | 34.13 | C |
| ATOM | 3563 | CG | MET | A | 582 | 29.174 | 77.029 | -41.359 | 1.00 | 48.51 | C |
| ATOM | 3564 | SD | MET | A | 582 | 28.002 | 78.219 | -40.507 | 1.00 | 51.39 | S |
| ATOM | 3565 | CE | MET | A | 582 | 26.827 | 78.445 | -41.761 | 1.00 | 50.53 | C |
| ATOM | 3566 | N | ALA | A | 583 | 28.835 | 73.025 | -38.857 | 1.00 | 47.16 | N |
| ATOM | 3567 | CA | ALA | A | 583 | 28.315 | 71.683 | -38.573 | 1.00 | 46.92 | C |
| ATOM | 3568 | C | ALA | A | 583 | 27.559 | 71.643 | -37.230 | 1.00 | 42.64 | C |
| ATOM | 3569 | O | ALA | A | 583 | 26.502 | 71.028 | -37.134 | 1.00 | 49.88 | O |
| ATOM | 3570 | CB | ALA | A | 583 | 29.464 | 70.638 | -38.577 | 1.00 | 42.44 | C |
| ATOM | 3571 | N | LEU | A | 584 | 28.109 | 72.296 | -36.209 | 1.00 | 46.69 | N |
| ATOM | 3572 | CA | LEU | A | 584 | 27.477 | 72.429 | -34.870 | 1.00 | 36.06 | C |
| ATOM | 3573 | C | LEU | A | 584 | 26.272 | 73.364 | -34.953 | 1.00 | 42.02 | C |
| ATOM | 3574 | O | LEU | A | 584 | 25.331 | 73.294 | -34.179 | 1.00 | 40.07 | O |
| ATOM | 3575 | CB | LEU | A | 584 | 28.477 | 73.072 | -33.870 | 1.00 | 34.65 | C |
| ATOM | 3576 | CG | LEU | A | 584 | 29.751 | 72.324 | -33.467 | 1.00 | 36.51 | C |
| ATOM | 3577 | CD1 | LEU | A | 584 | 30.763 | 73.231 | -32.692 | 1.00 | 35.26 | C |
| ATOM | 3578 | CD2 | LEU | A | 584 | 29.333 | 71.123 | -32.620 | 1.00 | 35.85 | C |
| ATOM | 3579 | N | GLY | A | 585 | 26.326 | 74.314 | -35.879 | 1.00 | 37.61 | N |
| ATOM | 3580 | CA | GLY | A | 585 | 25.273 | 75.300 | -35.988 | 1.00 | 46.29 | C |
| ATOM | 3581 | C | GLY | A | 585 | 25.602 | 76.535 | -35.135 | 1.00 | 42.02 | C |
| ATOM | 3582 | O | GLY | A | 585 | 26.118 | 76.442 | -34.079 | 1.00 | 40.96 | O |
| ATOM | 3583 | N | LEU | A | 586 | 25.305 | 77.693 | -35.777 | 1.00 | 35.03 | N |
| ATOM | 3584 | CA | LEU | A | 586 | 25.502 | 78.980 | -35.108 | 1.00 | 39.75 | C |
| ATOM | 3585 | C | LEU | A | 586 | 24.639 | 79.166 | -33.844 | 1.00 | 41.56 | C |
| ATOM | 3586 | O | LEU | A | 586 | 25.017 | 79.870 | -32.930 | 1.00 | 45.48 | O |
| ATOM | 3587 | CB | LEU | A | 586 | 25.219 | 80.120 | -36.089 | 1.00 | 47.77 | C |
| ATOM | 3588 | CG | LEU | A | 586 | 26.070 | 80.157 | -37.371 | 1.00 | 53.75 | C |
| ATOM | 3589 | CD1 | LEU | A | 586 | 25.499 | 81.164 | -38.348 | 1.00 | 56.36 | C |
| ATOM | 3590 | CD2 | LEU | A | 586 | 27.474 | 80.522 | -37.004 | 1.00 | 52.41 | C |
| ATOM | 3591 | N | PRO | A | 587 | 23.448 | 78.552 | -33.793 | 1.00 | 39.41 | N |
| ATOM | 3592 | CA | PRO | A | 587 | 22.714 | 78.704 | -32.505 | 1.00 | 33.98 | C |
| ATOM | 3593 | C | PRO | A | 587 | 23.494 | 78.091 | -31.341 | 1.00 | 41.94 | C |
| ATOM | 3594 | O | PRO | A | 587 | 23.631 | 78.629 | -30.263 | 1.00 | 42.42 | O |
| ATOM | 3595 | CB | PRO | A | 587 | 21.399 | 77.965 | -32.743 | 1.00 | 35.31 | C |
| ATOM | 3596 | CG | PRO | A | 587 | 21.240 | 77.911 | -34.335 | 1.00 | 44.70 | C |
| ATOM | 3597 | CD | PRO | A | 587 | 22.731 | 77.736 | -34.781 | 1.00 | 35.04 | C |
| ATOM | 3598 | N | ALA | A | 588 | 23.968 | 76.831 | -31.552 | 1.00 | 41.66 | N |
| ATOM | 3599 | CA | ALA | A | 588 | 24.668 | 76.112 | -30.490 | 1.00 | 43.23 | C |
| ATOM | 3600 | C | ALA | A | 588 | 25.831 | 76.931 | -30.101 | 1.00 | 40.22 | C |
| ATOM | 3601 | O | ALA | A | 588 | 26.176 | 77.125 | -28.930 | 1.00 | 45.87 | O |
| ATOM | 3602 | CB | ALA | A | 588 | 25.083 | 74.728 | -30.978 | 1.00 | 50.03 | C |
| ATOM | 3603 | N | VAL | A | 589 | 26.619 | 77.433 | -31.031 | 1.00 | 38.27 | N |
| ATOM | 3604 | CA | VAL | A | 589 | 27.731 | 78.231 | -30.761 | 1.00 | 42.52 | C |
| ATOM | 3605 | C | VAL | A | 589 | 27.362 | 79.488 | -30.010 | 1.00 | 39.34 | C |
| ATOM | 3606 | O | VAL | A | 589 | 28.000 | 79.886 | -29.058 | 1.00 | 37.88 | O |
| ATOM | 3607 | CB | VAL | A | 589 | 28.613 | 78.678 | -31.986 | 1.00 | 40.21 | C |
| ATOM | 3608 | CG1 | VAL | A | 589 | 29.688 | 79.652 | -31.485 | 1.00 | 37.22 | C |
| ATOM | 3609 | CG2 | VAL | A | 589 | 29.235 | 77.469 | -32.753 | 1.00 | 32.15 | C |
| ATOM | 3610 | N | THR | A | 590 | 26.309 | 80.142 | -30.481 | 1.00 | 37.18 | N |
| ATOM | 3611 | CA | THR | A | 590 | 25.823 | 81.375 | -29.834 | 1.00 | 36.76 | C |
| ATOM | 3612 | C | THR | A | 590 | 25.447 | 81.163 | -28.357 | 1.00 | 39.91 | C |
| ATOM | 3613 | O | THR | A | 590 | 25.691 | 82.016 | -27.487 | 1.00 | 43.01 | O |
| ATOM | 3614 | CB | THR | A | 590 | 24.678 | 81.947 | -30.658 | 1.00 | 44.22 | C |

FIG. 8-57

| | | | | | | | | | | | |
|---|---|---|---|---|---|---|---|---|---|---|---|
| ATOM | 3615 | OG1 | THR | A | 590 | 25.215 | 82.384 | -31.308 | 1.00 | 42.38 | O |
| ATOM | 3616 | CG2 | THR | A | 590 | 24.003 | 83.122 | -29.945 | 1.00 | 43.13 | C |
| ATOM | 3617 | N | GLU | A | 591 | 24.878 | 80.082 | -28.070 | 1.00 | 44.55 | N |
| ATOM | 3618 | CA | GLU | A | 591 | 24.466 | 79.647 | -26.709 | 1.00 | 42.30 | C |
| ATOM | 3619 | C | GLU | A | 591 | 25.720 | 79.456 | -25.817 | 1.00 | 45.19 | C |
| ATOM | 3620 | O | GLU | A | 591 | 25.740 | 79.766 | -24.601 | 1.00 | 41.69 | O |
| ATOM | 3621 | CB | GLU | A | 591 | 23.650 | 78.359 | -26.776 | 1.00 | 44.60 | C |
| ATOM | 3622 | CG | GLU | A | 591 | 23.039 | 77.870 | -25.469 | 1.00 | 68.01 | C |
| ATOM | 3623 | CD | GLU | A | 591 | 22.402 | 76.474 | -25.891 | 1.00 | 85.45 | C |
| ATOM | 3624 | OE1 | GLU | A | 591 | 22.359 | 75.939 | -26.734 | 1.00 | 88.75 | O |
| ATOM | 3625 | OE2 | GLU | A | 591 | 21.853 | 75.908 | -24.974 | 1.00 | 92.31 | O |
| ATOM | 3626 | N | THR | A | 592 | 26.782 | 78.960 | -26.432 | 1.00 | 42.98 | N |
| ATOM | 3627 | CA | THR | A | 592 | 28.044 | 78.800 | -25.708 | 1.00 | 40.48 | C |
| ATOM | 3628 | C | THR | A | 592 | 28.581 | 80.162 | -25.282 | 1.00 | 37.35 | C |
| ATOM | 3629 | O | THR | A | 592 | 28.946 | 80.354 | -24.145 | 1.00 | 38.36 | O |
| ATOM | 3630 | CB | THR | A | 592 | 29.038 | 78.039 | -26.551 | 1.00 | 43.26 | C |
| ATOM | 3631 | OG1 | THR | A | 592 | 28.512 | 76.713 | -26.717 | 1.00 | 39.73 | O |
| ATOM | 3632 | CG2 | THR | A | 592 | 30.405 | 77.977 | -25.875 | 1.00 | 48.06 | C |
| ATOM | 3633 | N | TRP | A | 593 | 28.486 | 81.121 | -26.198 | 1.00 | 42.65 | N |
| ATOM | 3634 | CA | TRP | A | 593 | 28.886 | 82.491 | -25.907 | 1.00 | 43.90 | C |
| ATOM | 3635 | C | TRP | A | 593 | 28.117 | 83.075 | -24.701 | 1.00 | 44.80 | C |
| ATOM | 3636 | O | TRP | A | 593 | 28.678 | 83.804 | -23.898 | 1.00 | 41.37 | O |
| ATOM | 3637 | CB | TRP | A | 593 | 28.700 | 83.361 | -27.156 | 1.00 | 37.87 | C |
| ATOM | 3638 | CG | TRP | A | 593 | 29.891 | 83.308 | -28.072 | 1.00 | 47.35 | C |
| ATOM | 3639 | CD1 | TRP | A | 593 | 29.917 | 82.908 | -29.385 | 1.00 | 44.89 | C |
| ATOM | 3640 | CD2 | TRP | A | 593 | 31.247 | 83.606 | -27.712 | 1.00 | 37.55 | C |
| ATOM | 3641 | NE1 | TRP | A | 593 | 31.210 | 82.996 | -29.871 | 1.00 | 39.72 | N |
| ATOM | 3642 | CE2 | TRP | A | 593 | 32.037 | 83.421 | -28.863 | 1.00 | 42.52 | C |
| ATOM | 3643 | CE3 | TRP | A | 593 | 31.859 | 84.061 | -26.536 | 1.00 | 39.03 | C |
| ATOM | 3644 | CZ2 | TRP | A | 593 | 33.413 | 83.647 | -28.863 | 1.00 | 36.44 | C |
| ATOM | 3645 | CZ3 | TRP | A | 593 | 33.228 | 84.280 | -26.539 | 1.00 | 41.75 | C |
| ATOM | 3646 | CH2 | TRP | A | 593 | 33.981 | 84.088 | -27.701 | 1.00 | 35.88 | C |
| ATOM | 3647 | N | ILE | A | 594 | 26.836 | 82.760 | -24.581 | 1.00 | 40.29 | N |
| ATOM | 3648 | CA | ILE | A | 594 | 26.024 | 83.357 | -23.523 | 1.00 | 34.69 | C |
| ATOM | 3649 | C | ILE | A | 594 | 26.374 | 82.753 | -22.181 | 1.00 | 38.68 | C |
| ATOM | 3650 | O | ILE | A | 594 | 26.460 | 83.444 | -21.185 | 1.00 | 38.09 | O |
| ATOM | 3651 | CB | ILE | A | 594 | 24.518 | 83.171 | -23.798 | 1.00 | 38.98 | C |
| ATOM | 3652 | CG1 | ILE | A | 594 | 24.075 | 84.007 | -24.996 | 1.00 | 43.94 | C |
| ATOM | 3653 | CG2 | ILE | A | 594 | 23.703 | 83.596 | -22.609 | 1.00 | 46.03 | C |
| ATOM | 3654 | CD1 | ILE | A | 594 | 22.872 | 83.407 | -25.727 | 1.00 | 47.11 | C |
| ATOM | 3655 | N | LYS | A | 595 | 26.541 | 81.438 | -22.173 | 1.00 | 39.62 | N |
| ATOM | 3656 | CA | LYS | A | 595 | 26.936 | 80.711 | -21.006 | 1.00 | 34.11 | C |
| ATOM | 3657 | C | LYS | A | 595 | 28.311 | 81.172 | -20.517 | 1.00 | 40.40 | C |
| ATOM | 3658 | O | LYS | A | 595 | 28.570 | 81.167 | -19.318 | 1.00 | 46.36 | O |
| ATOM | 3659 | CB | LYS | A | 595 | 27.056 | 79.232 | -21.351 | 1.00 | 47.64 | C |
| ATOM | 3660 | CG | LYS | A | 595 | 25.748 | 78.515 | -21.536 | 1.00 | 48.86 | C |
| ATOM | 3661 | CD | LYS | A | 595 | 26.010 | 77.119 | -22.073 | 1.00 | 59.93 | C |
| ATOM | 3662 | CE | LYS | A | 595 | 24.762 | 76.512 | -22.697 | 1.00 | 66.40 | C |
| ATOM | 3663 | NZ | LYS | A | 595 | 25.046 | 75.208 | -23.351 | 1.00 | 73.01 | N |
| ATOM | 3664 | N | LEU | A | 596 | 29.192 | 81.591 | -21.436 | 1.00 | 33.09 | N |
| ATOM | 3665 | CA | LEU | A | 596 | 30.559 | 81.968 | -21.076 | 1.00 | 33.69 | C |
| ATOM | 3666 | C | LEU | A | 596 | 30.468 | 83.355 | -20.501 | 1.00 | 42.19 | C |
| ATOM | 3667 | O | LEU | A | 596 | 31.411 | 83.840 | -19.895 | 1.00 | 51.93 | O |
| ATOM | 3668 | CB | LEU | A | 596 | 31.452 | 82.024 | -22.310 | 1.00 | 36.89 | C |
| ATOM | 3669 | CG | LEU | A | 596 | 31.965 | 80.727 | -22.921 | 1.00 | 45.93 | C |
| ATOM | 3670 | CD1 | LEU | A | 596 | 32.980 | 81.009 | -24.059 | 1.00 | 39.31 | C |
| ATOM | 3671 | CD2 | LEU | A | 596 | 32.686 | 79.895 | -21.838 | 1.00 | 49.10 | C |
| ATOM | 3672 | N | GLY | A | 597 | 29.356 | 84.032 | -20.763 | 1.00 | 43.46 | N |
| ATOM | 3673 | CA | GLY | A | 597 | 29.102 | 85.284 | -20.081 | 1.00 | 50.22 | C |
| ATOM | 3674 | C | GLY | A | 597 | 29.161 | 86.566 | -20.893 | 1.00 | 54.60 | C |
| ATOM | 3675 | O | GLY | A | 597 | 29.190 | 87.643 | -20.303 | 1.00 | 54.86 | O |
| ATOM | 3676 | N | VAL | A | 598 | 29.154 | 86.486 | -22.223 | 1.00 | 51.72 | N |
| ATOM | 3677 | CA | VAL | A | 598 | 29.244 | 87.718 | -23.014 | 1.00 | 46.51 | C |
| ATOM | 3678 | C | VAL | A | 598 | 27.895 | 88.443 | -23.154 | 1.00 | 53.23 | C |
| ATOM | 3679 | O | VAL | A | 598 | 26.834 | 87.815 | -23.061 | 1.00 | 60.12 | O |
| ATOM | 3680 | CB | VAL | A | 598 | 29.847 | 87.485 | -24.372 | 1.00 | 52.40 | C |
| ATOM | 3681 | CG1 | VAL | A | 598 | 31.210 | 86.694 | -24.148 | 1.00 | 62.10 | C |
| ATOM | 3682 | CG2 | VAL | A | 598 | 29.068 | 86.752 | -25.331 | 1.00 | 51.70 | C |
| ATOM | 3683 | N | PRO | A | 599 | 27.930 | 89.775 | -23.362 | 1.00 | 51.87 | N |
| ATOM | 3684 | CA | PRO | A | 599 | 26.680 | 90.528 | -23.510 | 1.00 | 45.80 | C |
| ATOM | 3685 | C | PRO | A | 599 | 25.839 | 89.853 | -24.639 | 1.00 | 56.48 | C |
| ATOM | 3686 | O | PRO | A | 599 | 26.343 | 89.788 | -25.758 | 1.00 | 58.12 | O |
| ATOM | 3687 | CB | PRO | A | 599 | 27.140 | 91.822 | -23.814 | 1.00 | 48.28 | C |
| ATOM | 3688 | CG | PRO | A | 599 | 28.577 | 92.005 | -23.530 | 1.00 | 52.57 | C |
| ATOM | 3689 | CD | PRO | A | 599 | 29.126 | 90.618 | -23.546 | 1.00 | 55.73 | C |
| ATOM | 3690 | N | LYS | A | 600 | 24.564 | 89.685 | -24.362 | 1.00 | 49.66 | N |
| ATOM | 3691 | CA | LYS | A | 600 | 23.713 | 89.007 | -25.311 | 1.00 | 50.23 | C |

FIG. 8-58

| | | | | | | | | | | | |
|---|---|---|---|---|---|---|---|---|---|---|---|
| ATOM | 3692 | C | LYS | A | 600 | 23.466 | 89.832 | -26.575 | 1.00 | 64.39 | C |
| ATOM | 3693 | O | LYS | A | 600 | 23.249 | 89.274 | -27.666 | 1.00 | 62.08 | O |
| ATOM | 3694 | CB | LYS | A | 600 | 22.366 | 88.674 | -24.655 | 1.00 | 47.90 | C |
| ATOM | 3695 | CG | LYS | A | 600 | 22.449 | 87.487 | -23.713 | 1.00 | 56.68 | C |
| ATOM | 3696 | CD | LYS | A | 600 | 21.686 | 87.737 | -22.411 | 1.00 | 56.28 | C |
| ATOM | 3697 | CE | LYS | A | 600 | 21.630 | 86.461 | -21.583 | 1.00 | 61.36 | C |
| ATOM | 3698 | NZ | LYS | A | 600 | 21.728 | 86.687 | -20.120 | 1.00 | 69.95 | N |
| ATOM | 3699 | N | ASP | A | 601 | 23.459 | 91.156 | -26.436 | 1.00 | 58.30 | N |
| ATOM | 3700 | CA | ASP | A | 601 | 23.079 | 91.976 | -27.879 | 1.00 | 60.48 | C |
| ATOM | 3701 | C | ASP | A | 601 | 24.259 | 92.303 | -28.501 | 1.00 | 53.18 | C |
| ATOM | 3702 | O | ASP | A | 601 | 24.129 | 93.090 | -29.431 | 1.00 | 57.27 | O |
| ATOM | 3703 | CB | ASP | A | 601 | 22.283 | 93.222 | -27.167 | 1.00 | 57.61 | C |
| ATOM | 3704 | CG | ASP | A | 601 | 23.197 | 94.231 | -26.414 | 1.00 | 70.89 | C |
| ATOM | 3705 | OD1 | ASP | A | 601 | 24.262 | 93.918 | -26.056 | 1.00 | 74.64 | O |
| ATOM | 3706 | OD2 | ASP | A | 601 | 22.589 | 95.347 | -26.173 | 1.00 | 76.53 | O |
| ATOM | 3707 | N | GLN | A | 602 | 25.389 | 91.669 | -28.242 | 1.00 | 45.64 | N |
| ATOM | 3708 | CA | GLN | A | 602 | 26.555 | 91.785 | -29.111 | 1.00 | 44.35 | C |
| ATOM | 3709 | C | GLN | A | 602 | 26.611 | 90.597 | -30.094 | 1.00 | 45.17 | C |
| ATOM | 3710 | O | GLN | A | 602 | 27.425 | 90.423 | -30.910 | 1.00 | 61.73 | O |
| ATOM | 3711 | CB | GLN | A | 602 | 27.839 | 91.837 | -28.263 | 1.00 | 45.12 | C |
| ATOM | 3712 | CG | GLN | A | 602 | 28.098 | 93.210 | -27.620 | 1.00 | 39.83 | C |
| ATOM | 3713 | CD | GLN | A | 602 | 27.947 | 94.377 | -28.583 | 1.00 | 56.21 | C |
| ATOM | 3714 | OE1 | GLN | A | 602 | 28.258 | 94.273 | -29.781 | 1.00 | 57.93 | O |
| ATOM | 3715 | NE2 | GLN | A | 602 | 27.451 | 95.501 | -28.066 | 1.00 | 60.98 | N |
| ATOM | 3716 | N | LEU | A | 603 | 25.745 | 89.935 | -29.748 | 1.00 | 47.85 | N |
| ATOM | 3717 | CA | LEU | A | 603 | 25.742 | 88.300 | -30.537 | 1.00 | 50.18 | C |
| ATOM | 3718 | C | LEU | A | 603 | 24.860 | 88.380 | -31.767 | 1.00 | 50.86 | C |
| ATOM | 3719 | O | LEU | A | 603 | 23.638 | 88.512 | -31.659 | 1.00 | 51.22 | O |
| ATOM | 3720 | CB | LEU | A | 603 | 25.339 | 87.091 | -29.677 | 1.00 | 45.94 | C |
| ATOM | 3721 | CG | LEU | A | 603 | 26.373 | 86.780 | -28.608 | 1.00 | 51.88 | C |
| ATOM | 3722 | CD1 | LEU | A | 603 | 25.762 | 86.033 | -27.415 | 1.00 | 55.65 | C |
| ATOM | 3723 | CD2 | LEU | A | 603 | 27.490 | 86.007 | -29.261 | 1.00 | 51.19 | C |
| ATOM | 3724 | N | HIS | A | 604 | 25.482 | 88.277 | -32.940 | 1.00 | 52.00 | N |
| ATOM | 3725 | CA | HIS | A | 604 | 24.742 | 88.206 | -34.206 | 1.00 | 51.79 | C |
| ATOM | 3726 | C | HIS | A | 604 | 25.132 | 86.936 | -34.923 | 1.00 | 49.43 | C |
| ATOM | 3727 | O | HIS | A | 604 | 26.251 | 86.792 | -35.378 | 1.00 | 51.52 | O |
| ATOM | 3728 | CB | HIS | A | 604 | 25.022 | 89.440 | -35.040 | 1.00 | 54.61 | C |
| ATOM | 3729 | CG | HIS | A | 604 | 24.920 | 90.702 | -34.245 | 1.00 | 59.02 | C |
| ATOM | 3730 | ND1 | HIS | A | 604 | 26.017 | 91.313 | -33.677 | 1.00 | 61.60 | N |
| ATOM | 3731 | CD2 | HIS | A | 604 | 23.845 | 91.435 | -33.874 | 1.00 | 59.78 | C |
| ATOM | 3732 | CE1 | HIS | A | 604 | 25.626 | 92.392 | -33.019 | 1.00 | 63.15 | C |
| ATOM | 3733 | NE2 | HIS | A | 604 | 24.312 | 92.482 | -33.114 | 1.00 | 63.14 | N |
| ATOM | 3734 | N | PRO | A | 605 | 24.214 | 85.979 | -34.963 | 1.00 | 46.52 | N |
| ATOM | 3735 | CA | PRO | A | 605 | 24.475 | 84.604 | -35.408 | 1.00 | 45.43 | C |
| ATOM | 3736 | C | PRO | A | 605 | 24.469 | 84.434 | -36.939 | 1.00 | 51.46 | C |
| ATOM | 3737 | O | PRO | A | 605 | 23.465 | 83.974 | -37.503 | 1.00 | 62.97 | O |
| ATOM | 3738 | CB | PRO | A | 605 | 23.319 | 83.850 | -34.770 | 1.00 | 52.15 | C |
| ATOM | 3739 | CG | PRO | A | 605 | 22.144 | 84.850 | -34.973 | 1.00 | 42.91 | C |
| ATOM | 3740 | CD | PRO | A | 605 | 22.785 | 86.202 | -34.632 | 1.00 | 46.03 | C |
| ATOM | 3741 | N | VAL | A | 606 | 25.579 | 84.812 | -37.577 | 1.00 | 46.64 | N |
| ATOM | 3742 | CA | VAL | A | 606 | 25.854 | 84.602 | -39.002 | 1.00 | 51.10 | C |
| ATOM | 3743 | C | VAL | A | 606 | 27.262 | 83.987 | -39.089 | 1.00 | 46.54 | C |
| ATOM | 3744 | O | VAL | A | 606 | 28.002 | 84.044 | -38.142 | 1.00 | 39.48 | O |
| ATOM | 3745 | CB | VAL | A | 606 | 25.788 | 85.931 | -39.816 | 1.00 | 56.47 | C |
| ATOM | 3746 | CG1 | VAL | A | 606 | 24.404 | 86.553 | -39.686 | 1.00 | 54.69 | C |
| ATOM | 3747 | CG2 | VAL | A | 606 | 26.847 | 86.931 | -39.322 | 1.00 | 54.99 | C |
| ATOM | 3748 | N | PRO | A | 607 | 27.602 | 83.354 | -40.215 | 1.00 | 52.80 | N |
| ATOM | 3749 | CA | PRO | A | 607 | 28.869 | 82.608 | -40.342 | 1.00 | 45.02 | C |
| ATOM | 3750 | C | PRO | A | 607 | 30.123 | 83.344 | -39.746 | 1.00 | 45.37 | C |
| ATOM | 3751 | O | PRO | A | 607 | 30.998 | 82.690 | -39.178 | 1.00 | 48.25 | O |
| ATOM | 3752 | CB | PRO | A | 607 | 29.021 | 82.238 | -41.722 | 1.00 | 35.89 | C |
| ATOM | 3753 | CG | PRO | A | 607 | 27.492 | 82.097 | -42.211 | 1.00 | 41.99 | C |
| ATOM | 3754 | CD | PRO | A | 607 | 26.765 | 83.162 | -41.437 | 1.00 | 47.30 | C |
| ATOM | 3755 | N | ALA | A | 608 | 30.225 | 84.653 | -39.367 | 1.00 | 44.75 | N |
| ATOM | 3756 | CA | ALA | A | 608 | 31.445 | 85.395 | -39.631 | 1.00 | 43.92 | C |
| ATOM | 3757 | C | ALA | A | 608 | 31.678 | 85.473 | -38.117 | 1.00 | 53.78 | C |
| ATOM | 3758 | O | ALA | A | 608 | 32.813 | 85.677 | -37.647 | 1.00 | 53.11 | O |
| ATOM | 3759 | CB | ALA | A | 608 | 31.380 | 86.777 | -40.213 | 1.00 | 49.03 | C |
| ATOM | 3760 | N | MET | A | 609 | 30.604 | 85.329 | -37.343 | 1.00 | 49.99 | N |
| ATOM | 3761 | CA | MET | A | 609 | 30.722 | 85.242 | -35.894 | 1.00 | 51.55 | C |
| ATOM | 3762 | C | MET | A | 609 | 31.729 | 84.176 | -35.507 | 1.00 | 44.66 | C |
| ATOM | 3763 | O | MET | A | 609 | 32.534 | 84.382 | -34.588 | 1.00 | 46.34 | O |
| ATOM | 3764 | CB | MET | A | 609 | 29.367 | 84.894 | -35.282 | 1.00 | 58.76 | C |
| ATOM | 3765 | CG | MET | A | 609 | 29.427 | 83.791 | -34.216 | 1.00 | 71.75 | C |
| ATOM | 3766 | SD | MET | A | 609 | 28.009 | 83.812 | -33.084 | 1.00 | 61.03 | S |
| ATOM | 3767 | CE | MET | A | 609 | 28.064 | 85.562 | -32.707 | 1.00 | 46.76 | C |
| ATOM | 3768 | N | LEU | A | 610 | 31.677 | 83.047 | -36.211 | 1.00 | 45.81 | N |

FIG. 8-59

| | | | | | | | | | | | |
|---|---|---|---|---|---|---|---|---|---|---|---|
| ATOM | 3769 | CA | LEU | A | 610 | 32.577 | 81.924 | -35.937 | 1.00 | 48.17 | C |
| ATOM | 3770 | C | LEU | A | 610 | 34.056 | 82.359 | -36.011 | 1.00 | 51.00 | C |
| ATOM | 3771 | O | LEU | A | 610 | 34.910 | 81.809 | -35.306 | 1.00 | 49.34 | O |
| ATOM | 3772 | CB | LEU | A | 610 | 32.323 | 80.805 | -36.963 | 1.00 | 48.61 | C |
| ATOM | 3773 | CG | LEU | A | 610 | 30.907 | 80.239 | -37.033 | 1.00 | 39.87 | C |
| ATOM | 3774 | CD1 | LEU | A | 610 | 30.666 | 79.428 | -38.335 | 1.00 | 41.88 | C |
| ATOM | 3775 | CD2 | LEU | A | 610 | 30.679 | 79.382 | -35.797 | 1.00 | 50.04 | C |
| ATOM | 3776 | N | LEU | A | 611 | 34.357 | 83.326 | -36.885 | 1.00 | 45.79 | N |
| ATOM | 3777 | CA | LEU | A | 611 | 35.730 | 83.834 | -37.027 | 1.00 | 42.81 | C |
| ATOM | 3778 | C | LEU | A | 611 | 35.983 | 85.181 | -36.341 | 1.00 | 42.37 | C |
| ATOM | 3779 | O | LEU | A | 611 | 37.002 | 85.816 | -36.578 | 1.00 | 43.83 | O |
| ATOM | 3780 | CB | LEU | A | 611 | 36.133 | 83.952 | -38.801 | 1.00 | 35.36 | C |
| ATOM | 3781 | CG | LEU | A | 611 | 35.955 | 82.724 | -39.397 | 1.00 | 39.70 | C |
| ATOM | 3782 | CD1 | LEU | A | 611 | 35.569 | 83.042 | -40.773 | 1.00 | 47.78 | C |
| ATOM | 3783 | CD2 | LEU | A | 611 | 36.626 | 81.493 | -38.769 | 1.00 | 32.31 | C |
| ATOM | 3784 | N | GLY | A | 612 | 35.040 | 85.626 | -35.526 | 1.00 | 43.42 | N |
| ATOM | 3785 | CA | GLY | A | 612 | 35.273 | 86.743 | -34.626 | 1.00 | 41.97 | C |
| ATOM | 3786 | C | GLY | A | 612 | 34.630 | 88.063 | -34.995 | 1.00 | 47.21 | C |
| ATOM | 3787 | O | GLY | A | 612 | 35.118 | 89.113 | -34.578 | 1.00 | 49.20 | O |
| ATOM | 3788 | N | ALA | A | 613 | 33.558 | 88.013 | -35.791 | 1.00 | 48.50 | N |
| ATOM | 3789 | CA | ALA | A | 613 | 32.666 | 89.160 | -35.974 | 1.00 | 43.83 | C |
| ATOM | 3790 | C | ALA | A | 613 | 31.860 | 89.335 | -34.689 | 1.00 | 49.49 | C |
| ATOM | 3791 | O | ALA | A | 613 | 30.682 | 89.030 | -34.612 | 1.00 | 48.66 | O |
| ATOM | 3792 | CB | ALA | A | 613 | 31.733 | 88.974 | -37.227 | 1.00 | 33.54 | C |
| ATOM | 3793 | N | LEU | A | 614 | 32.535 | 89.783 | -33.649 | 1.00 | 46.28 | N |
| ATOM | 3794 | CA | LEU | A | 614 | 31.921 | 89.882 | -32.348 | 1.00 | 42.36 | C |
| ATOM | 3795 | C | LEU | A | 614 | 32.701 | 90.947 | -31.634 | 1.00 | 39.90 | C |
| ATOM | 3796 | O | LEU | A | 614 | 33.894 | 90.787 | -31.369 | 1.00 | 40.98 | O |
| ATOM | 3797 | CB | LEU | A | 614 | 31.995 | 88.536 | -31.635 | 1.00 | 38.83 | C |
| ATOM | 3798 | CG | LEU | A | 614 | 31.552 | 88.566 | -30.177 | 1.00 | 43.98 | C |
| ATOM | 3799 | CD1 | LEU | A | 614 | 30.259 | 89.349 | -30.008 | 1.00 | 47.36 | C |
| ATOM | 3800 | CD2 | LEU | A | 614 | 31.418 | 87.193 | -29.578 | 1.00 | 46.38 | C |
| ATOM | 3801 | N | ASN | A | 615 | 32.039 | 92.055 | -31.337 | 1.00 | 40.38 | N |
| ATOM | 3802 | CA | ASN | A | 615 | 32.695 | 93.219 | -30.748 | 1.00 | 42.71 | C |
| ATOM | 3803 | C | ASN | A | 615 | 32.505 | 93.303 | -29.240 | 1.00 | 49.45 | C |
| ATOM | 3804 | O | ASN | A | 615 | 31.381 | 93.437 | -28.758 | 1.00 | 44.89 | O |
| ATOM | 3805 | CB | ASN | A | 615 | 32.203 | 94.499 | -31.430 | 1.00 | 40.75 | C |
| ATOM | 3806 | CG | ASN | A | 615 | 32.330 | 94.455 | -32.942 | 1.00 | 52.49 | C |
| ATOM | 3807 | OD1 | ASN | A | 615 | 31.535 | 94.901 | -33.703 | 1.00 | 56.30 | O |
| ATOM | 3808 | ND2 | ASN | A | 615 | 33.497 | 93.870 | -33.387 | 1.00 | 44.19 | N |
| ATOM | 3809 | N | LEU | A | 616 | 33.609 | 93.228 | -28.499 | 1.00 | 39.58 | N |
| ATOM | 3810 | CA | LEU | A | 616 | 33.551 | 93.159 | -27.050 | 1.00 | 30.96 | C |
| ATOM | 3811 | C | LEU | A | 616 | 34.567 | 94.117 | -26.461 | 1.00 | 42.22 | C |
| ATOM | 3812 | O | LEU | A | 616 | 35.493 | 94.529 | -27.140 | 1.00 | 46.14 | O |
| ATOM | 3813 | CB | LEU | A | 616 | 33.889 | 91.749 | -26.603 | 1.00 | 28.46 | C |
| ATOM | 3814 | CG | LEU | A | 616 | 32.939 | 90.661 | -27.048 | 1.00 | 33.05 | C |
| ATOM | 3815 | CD1 | LEU | A | 616 | 33.414 | 89.366 | -26.484 | 1.00 | 34.32 | C |
| ATOM | 3816 | CD2 | LEU | A | 616 | 31.528 | 91.017 | -26.509 | 1.00 | 38.98 | C |
| ATOM | 3817 | N | THR | A | 617 | 34.368 | 94.500 | -25.210 | 1.00 | 35.50 | N |
| ATOM | 3818 | CA | THR | A | 617 | 35.378 | 95.240 | -24.487 | 1.00 | 39.53 | C |
| ATOM | 3819 | C | THR | A | 617 | 36.352 | 94.222 | -23.873 | 1.00 | 38.51 | C |
| ATOM | 3820 | O | THR | A | 617 | 36.042 | 93.038 | -23.777 | 1.00 | 46.72 | O |
| ATOM | 3821 | CB | THR | A | 617 | 34.769 | 96.080 | -23.352 | 1.00 | 40.71 | C |
| ATOM | 3822 | OG1 | THR | A | 617 | 34.138 | 95.206 | -22.411 | 1.00 | 42.64 | O |
| ATOM | 3823 | CG2 | THR | A | 617 | 33.760 | 97.078 | -23.888 | 1.00 | 40.95 | C |
| ATOM | 3824 | N | PRO | A | 618 | 37.546 | 94.676 | -23.472 | 1.00 | 38.74 | N |
| ATOM | 3825 | CA | PRO | A | 618 | 38.469 | 93.735 | -22.829 | 1.00 | 38.45 | C |
| ATOM | 3826 | C | PRO | A | 618 | 37.887 | 93.091 | -21.580 | 1.00 | 42.76 | C |
| ATOM | 3827 | O | PRO | A | 618 | 38.048 | 91.884 | -21.374 | 1.00 | 47.21 | O |
| ATOM | 3828 | CB | PRO | A | 618 | 39.674 | 94.629 | -22.468 | 1.00 | 42.33 | C |
| ATOM | 3829 | CG | PRO | A | 618 | 39.698 | 95.681 | -23.646 | 1.00 | 35.32 | C |
| ATOM | 3830 | CD | PRO | A | 618 | 38.194 | 95.963 | -23.813 | 1.00 | 38.05 | C |
| ATOM | 3831 | N | ILE | A | 619 | 37.193 | 93.869 | -20.758 | 1.00 | 41.45 | N |
| ATOM | 3832 | CA | ILE | A | 619 | 36.602 | 93.289 | -19.544 | 1.00 | 44.56 | C |
| ATOM | 3833 | C | ILE | A | 619 | 35.548 | 92.213 | -19.803 | 1.00 | 38.54 | C |
| ATOM | 3834 | O | ILE | A | 619 | 35.438 | 91.277 | -19.026 | 1.00 | 39.17 | O |
| ATOM | 3835 | CB | ILE | A | 619 | 36.059 | 94.337 | -18.584 | 1.00 | 47.21 | C |
| ATOM | 3836 | CG1 | ILE | A | 619 | 35.748 | 93.680 | -17.243 | 1.00 | 56.18 | C |
| ATOM | 3837 | CG2 | ILE | A | 619 | 34.857 | 95.026 | -19.197 | 1.00 | 47.99 | C |
| ATOM | 3838 | CD1 | ILE | A | 619 | 35.958 | 94.527 | -16.021 | 1.00 | 53.48 | C |
| ATOM | 3839 | N | GLU | A | 620 | 34.834 | 92.320 | -20.928 | 1.00 | 37.23 | N |
| ATOM | 3840 | CA | GLU | A | 620 | 33.863 | 91.308 | -21.357 | 1.00 | 40.09 | C |
| ATOM | 3841 | C | GLU | A | 620 | 34.595 | 90.062 | -21.869 | 1.00 | 43.34 | C |
| ATOM | 3842 | O | GLU | A | 620 | 34.222 | 88.934 | -21.554 | 1.00 | 36.41 | O |
| ATOM | 3843 | CB | GLU | A | 620 | 32.965 | 91.888 | -22.449 | 1.00 | 40.58 | C |
| ATOM | 3844 | CG | GLU | A | 620 | 31.938 | 92.933 | -21.937 | 1.00 | 47.25 | C |
| ATOM | 3845 | CD | GLU | A | 620 | 31.337 | 93.843 | -23.011 | 1.00 | 50.23 | C |

FIG.8-60

| | | | | | | | | | | | |
|---|---|---|---|---|---|---|---|---|---|---|---|
| ATOM | 3846 | OE1 | GLU | A | 620 | 30.612 | 94.801 | -22.670 | 1.00 | 55.87 | O |
| ATOM | 3847 | OE2 | GLU | A | 620 | 31.589 | 93.623 | -24.209 | 1.00 | 46.88 | O |
| ATOM | 3848 | N | VAL | A | 621 | 35.665 | 90.255 | -22.641 | 1.00 | 38.16 | N |
| ATOM | 3849 | CA | VAL | A | 621 | 36.467 | 89.108 | -23.041 | 1.00 | 32.37 | C |
| ATOM | 3850 | C | VAL | A | 621 | 36.981 | 88.362 | -21.818 | 1.00 | 33.13 | C |
| ATOM | 3851 | O | VAL | A | 621 | 36.900 | 87.130 | -21.761 | 1.00 | 38.70 | O |
| ATOM | 3852 | CB | VAL | A | 621 | 37.652 | 89.624 | -23.913 | 1.00 | 41.95 | C |
| ATOM | 3853 | CG1 | VAL | A | 621 | 38.521 | 88.328 | -24.207 | 1.00 | 35.13 | C |
| ATOM | 3854 | CG2 | VAL | A | 621 | 37.141 | 90.148 | -25.300 | 1.00 | 38.33 | C |
| ATOM | 3855 | N | ALA | A | 622 | 37.532 | 89.088 | -20.641 | 1.00 | 36.58 | N |
| ATOM | 3856 | CA | ALA | A | 622 | 37.983 | 88.487 | -19.568 | 1.00 | 36.71 | C |
| ATOM | 3857 | C | ALA | A | 622 | 36.949 | 87.384 | -18.923 | 1.00 | 36.79 | C |
| ATOM | 3858 | O | ALA | A | 622 | 37.257 | 86.456 | -18.544 | 1.00 | 37.76 | O |
| ATOM | 3859 | CB | ALA | A | 622 | 38.436 | 89.590 | -18.583 | 1.00 | 33.19 | C |
| ATOM | 3860 | N | GLN | A | 623 | 35.717 | 88.069 | -18.805 | 1.00 | 42.54 | N |
| ATOM | 3861 | CA | GLN | A | 623 | 34.621 | 87.225 | -18.305 | 1.00 | 36.58 | C |
| ATOM | 3862 | C | GLN | A | 623 | 34.577 | 85.883 | -19.048 | 1.00 | 42.19 | C |
| ATOM | 3863 | O | GLN | A | 623 | 34.516 | 84.832 | -18.428 | 1.00 | 37.45 | O |
| ATOM | 3864 | CB | GLN | A | 623 | 33.273 | 87.933 | -18.441 | 1.00 | 34.30 | C |
| ATOM | 3865 | CG | GLN | A | 623 | 32.109 | 87.111 | -17.905 | 1.00 | 35.75 | C |
| ATOM | 3866 | CD | GLN | A | 623 | 32.266 | 86.790 | -16.414 | 1.00 | 46.52 | C |
| ATOM | 3867 | OE1 | GLN | A | 623 | 31.792 | 87.590 | -15.574 | 1.00 | 48.05 | O |
| ATOM | 3868 | NE2 | GLN | A | 623 | 32.933 | 85.676 | -16.088 | 1.00 | 40.36 | N |
| ATOM | 3869 | N | ALA | A | 624 | 34.683 | 85.953 | -20.389 | 1.00 | 39.77 | N |
| ATOM | 3870 | CA | ALA | A | 624 | 34.477 | 84.758 | -21.216 | 1.00 | 33.52 | C |
| ATOM | 3871 | C | ALA | A | 624 | 35.588 | 83.794 | -20.983 | 1.00 | 34.88 | C |
| ATOM | 3872 | O | ALA | A | 624 | 35.369 | 82.589 | -20.820 | 1.00 | 38.15 | O |
| ATOM | 3873 | CB | ALA | A | 624 | 34.383 | 85.127 | -22.737 | 1.00 | 32.14 | C |
| ATOM | 3874 | N | PHE | A | 625 | 36.813 | 84.242 | -20.987 | 1.00 | 30.18 | N |
| ATOM | 3875 | CA | PHE | A | 625 | 37.921 | 83.331 | -20.726 | 1.00 | 30.65 | C |
| ATOM | 3876 | C | PHE | A | 625 | 38.024 | 82.879 | -19.257 | 1.00 | 36.78 | C |
| ATOM | 3877 | O | PHE | A | 625 | 38.591 | 81.778 | -18.978 | 1.00 | 35.88 | O |
| ATOM | 3878 | CB | PHE | A | 625 | 39.210 | 83.959 | -21.258 | 1.00 | 28.14 | C |
| ATOM | 3879 | CG | PHE | A | 625 | 39.356 | 83.825 | -22.784 | 1.00 | 35.52 | C |
| ATOM | 3880 | CD1 | PHE | A | 625 | 40.023 | 82.738 | -23.293 | 1.00 | 35.87 | C |
| ATOM | 3881 | CD2 | PHE | A | 625 | 38.790 | 84.779 | -23.606 | 1.00 | 45.42 | C |
| ATOM | 3882 | CE1 | PHE | A | 625 | 40.192 | 82.628 | -24.683 | 1.00 | 37.38 | C |
| ATOM | 3883 | CE2 | PHE | A | 625 | 38.916 | 84.658 | -24.993 | 1.00 | 50.51 | C |
| ATOM | 3884 | CZ | PHE | A | 625 | 39.601 | 83.577 | -25.533 | 1.00 | 44.06 | C |
| ATOM | 3885 | N | GLN | A | 626 | 37.530 | 83.698 | -18.320 | 1.00 | 27.58 | N |
| ATOM | 3886 | CA | GLN | A | 626 | 37.435 | 83.258 | -16.909 | 1.00 | 32.51 | C |
| ATOM | 3887 | C | GLN | A | 626 | 36.573 | 82.031 | -16.771 | 1.00 | 37.88 | C |
| ATOM | 3888 | O | GLN | A | 626 | 36.836 | 81.140 | -15.967 | 1.00 | 33.78 | O |
| ATOM | 3889 | CB | GLN | A | 626 | 36.996 | 84.374 | -15.975 | 1.00 | 38.01 | C |
| ATOM | 3890 | CG | GLN | A | 626 | 36.886 | 83.971 | -14.474 | 1.00 | 36.10 | C |
| ATOM | 3891 | CD | GLN | A | 626 | 35.659 | 83.102 | -14.167 | 1.00 | 39.43 | C |
| ATOM | 3892 | OE1 | GLN | A | 626 | 34.559 | 83.350 | -14.668 | 1.00 | 33.10 | O |
| ATOM | 3893 | NE2 | GLN | A | 626 | 35.860 | 82.063 | -13.351 | 1.00 | 38.48 | N |
| ATOM | 3894 | N | THR | A | 627 | 35.494 | 82.015 | -17.553 | 1.00 | 36.46 | N |
| ATOM | 3895 | CA | THR | A | 627 | 34.561 | 80.899 | -17.462 | 1.00 | 35.88 | C |
| ATOM | 3896 | C | THR | A | 627 | 35.211 | 79.600 | -17.888 | 1.00 | 36.32 | C |
| ATOM | 3897 | O | THR | A | 627 | 34.939 | 78.547 | -17.339 | 1.00 | 39.18 | O |
| ATOM | 3898 | CB | THR | A | 627 | 33.327 | 81.171 | -18.310 | 1.00 | 30.83 | C |
| ATOM | 3899 | OG1 | THR | A | 627 | 32.692 | 82.329 | -17.841 | 1.00 | 36.47 | O |
| ATOM | 3900 | CG2 | THR | A | 627 | 32.366 | 79.911 | -18.117 | 1.00 | 32.33 | C |
| ATOM | 3901 | N | ILE | A | 628 | 36.098 | 79.668 | -18.862 | 1.00 | 41.29 | N |
| ATOM | 3902 | CA | ILE | A | 628 | 36.716 | 78.440 | -19.293 | 1.00 | 38.57 | C |
| ATOM | 3903 | C | ILE | A | 628 | 37.923 | 78.094 | -18.433 | 1.00 | 36.57 | C |
| ATOM | 3904 | O | ILE | A | 628 | 38.125 | 76.918 | -18.100 | 1.00 | 38.26 | O |
| ATOM | 3905 | CB | ILE | A | 628 | 36.947 | 78.407 | -20.854 | 1.00 | 53.85 | C |
| ATOM | 3906 | CG1 | ILE | A | 628 | 38.350 | 77.929 | -21.206 | 1.00 | 58.79 | C |
| ATOM | 3907 | CG2 | ILE | A | 628 | 36.646 | 79.752 | -21.473 | 1.00 | 59.49 | C |
| ATOM | 3908 | CD1 | ILE | A | 628 | 38.401 | 76.454 | -21.534 | 1.00 | 62.39 | C |
| ATOM | 3909 | N | ALA | A | 629 | 38.715 | 79.111 | -18.063 | 1.00 | 33.56 | N |
| ATOM | 3910 | CA | ALA | A | 629 | 39.900 | 78.936 | -17.186 | 1.00 | 35.32 | C |
| ATOM | 3911 | C | ALA | A | 629 | 39.553 | 78.342 | -15.815 | 1.00 | 33.19 | C |
| ATOM | 3912 | O | ALA | A | 629 | 40.332 | 77.583 | -15.240 | 1.00 | 35.34 | O |
| ATOM | 3913 | CB | ALA | A | 629 | 40.597 | 80.257 | -16.983 | 1.00 | 38.01 | C |
| ATOM | 3914 | N | SER | A | 630 | 38.363 | 78.664 | -15.288 | 1.00 | 32.87 | N |
| ATOM | 3915 | CA | SER | A | 630 | 37.983 | 78.182 | -13.965 | 1.00 | 36.48 | C |
| ATOM | 3916 | C | SER | A | 630 | 37.808 | 76.713 | -14.099 | 1.00 | 47.94 | C |
| ATOM | 3917 | O | SER | A | 630 | 37.303 | 76.073 | -13.180 | 1.00 | 53.32 | O |
| ATOM | 3918 | CB | SER | A | 630 | 36.795 | 78.952 | -13.426 | 1.00 | 34.12 | C |
| ATOM | 3919 | OG | SER | A | 630 | 35.857 | 78.664 | -14.245 | 1.00 | 40.08 | O |
| ATOM | 3920 | N | GLY | A | 631 | 37.613 | 76.185 | -15.317 | 1.00 | 46.71 | N |
| ATOM | 3921 | CA | GLY | A | 631 | 37.113 | 74.838 | -15.548 | 1.00 | 41.03 | C |
| ATOM | 3922 | C | GLY | A | 631 | 35.613 | 74.789 | -15.148 | 1.00 | 36.09 | C |

FIG. 8-61

| | | | | | | | | | | | |
|---|---|---|---|---|---|---|---|---|---|---|---|
| ATOM | 3923 | O | GLY | A | 631 | 34.970 | 73.732 | -15.656 | 1.00 | 42.54 | O |
| ATOM | 3924 | N | GLY | A | 632 | 35.039 | 75.892 | -16.301 | 1.00 | 27.74 | N |
| ATOM | 3925 | CA | GLY | A | 632 | 33.646 | 75.901 | -16.740 | 1.00 | 39.44 | C |
| ATOM | 3926 | C | GLY | A | 632 | 32.635 | 76.526 | -15.784 | 1.00 | 45.78 | C |
| ATOM | 3927 | O | GLY | A | 632 | 31.420 | 76.458 | -16.008 | 1.00 | 41.03 | O |
| ATOM | 3928 | N | ASN | A | 633 | 33.133 | 77.147 | -14.722 | 1.00 | 35.50 | N |
| ATOM | 3929 | CA | ASN | A | 633 | 32.283 | 77.870 | -13.783 | 1.00 | 40.18 | C |
| ATOM | 3930 | C | ASN | A | 633 | 32.376 | 79.376 | -14.055 | 1.00 | 43.48 | C |
| ATOM | 3931 | O | ASN | A | 633 | 33.460 | 79.950 | -14.035 | 1.00 | 47.87 | O |
| ATOM | 3932 | CB | ASN | A | 633 | 32.710 | 77.565 | -12.351 | 1.00 | 39.65 | C |
| ATOM | 3933 | CG | ASN | A | 633 | 32.359 | 76.135 | -11.897 | 1.00 | 43.49 | C |
| ATOM | 3934 | OD1 | ASN | A | 633 | 33.173 | 75.466 | -11.254 | 1.00 | 48.04 | O |
| ATOM | 3935 | ND2 | ASN | A | 633 | 31.164 | 75.662 | -12.242 | 1.00 | 37.73 | N |
| ATOM | 3936 | N | ARG | A | 634 | 31.250 | 80.003 | -14.351 | 1.00 | 39.97 | N |
| ATOM | 3937 | CA | ARG | A | 634 | 31.197 | 81.436 | -14.636 | 1.00 | 43.48 | C |
| ATOM | 3938 | C | ARG | A | 634 | 31.133 | 82.201 | -13.300 | 1.00 | 45.85 | C |
| ATOM | 3939 | O | ARG | A | 634 | 30.116 | 82.200 | -12.624 | 1.00 | 48.40 | O |
| ATOM | 3940 | CB | ARG | A | 634 | 29.952 | 81.759 | -15.514 | 1.00 | 47.77 | C |
| ATOM | 3941 | CG | ARG | A | 634 | 29.879 | 83.197 | -16.063 | 1.00 | 41.26 | C |
| ATOM | 3942 | CD | ARG | A | 634 | 28.720 | 83.423 | -17.010 | 1.00 | 47.45 | C |
| ATOM | 3943 | NE | ARG | A | 634 | 27.428 | 83.227 | -16.348 | 1.00 | 42.88 | N |
| ATOM | 3944 | CZ | ARG | A | 634 | 26.630 | 82.173 | -16.524 | 1.00 | 52.09 | C |
| ATOM | 3945 | NH1 | ARG | A | 634 | 26.981 | 81.216 | -17.381 | 1.00 | 44.83 | N |
| ATOM | 3946 | NH2 | ARG | A | 634 | 25.462 | 82.082 | -15.852 | 1.00 | 49.24 | N |
| ATOM | 3947 | N | ALA | A | 635 | 32.230 | 82.826 | -12.915 | 1.00 | 41.54 | N |
| ATOM | 3948 | CA | ALA | A | 635 | 32.240 | 83.701 | -11.758 | 1.00 | 49.77 | C |
| ATOM | 3949 | C | ALA | A | 635 | 32.141 | 85.137 | -12.225 | 1.00 | 48.56 | C |
| ATOM | 3950 | O | ALA | A | 635 | 33.110 | 85.677 | -12.767 | 1.00 | 45.17 | O |
| ATOM | 3951 | CB | ALA | A | 635 | 33.531 | 83.493 | -10.958 | 1.00 | 34.09 | C |
| ATOM | 3952 | N | PRO | A | 636 | 30.981 | 85.771 | -12.013 | 1.00 | 43.08 | N |
| ATOM | 3953 | CA | PRO | A | 636 | 30.747 | 87.141 | -12.517 | 1.00 | 49.08 | C |
| ATOM | 3954 | C | PRO | A | 636 | 31.848 | 88.060 | -12.032 | 1.00 | 50.38 | C |
| ATOM | 3955 | O | PRO | A | 636 | 32.113 | 88.024 | -10.848 | 1.00 | 43.39 | O |
| ATOM | 3956 | CB | PRO | A | 636 | 29.432 | 87.539 | -11.848 | 1.00 | 54.31 | C |
| ATOM | 3957 | CG | PRO | A | 636 | 28.736 | 86.237 | -11.620 | 1.00 | 56.51 | C |
| ATOM | 3958 | CD | PRO | A | 636 | 29.818 | 85.238 | -11.292 | 1.00 | 50.36 | C |
| ATOM | 3959 | N | LEU | A | 637 | 32.493 | 88.830 | -12.906 | 1.00 | 38.96 | N |
| ATOM | 3960 | CA | LEU | A | 637 | 33.640 | 89.622 | -12.497 | 1.00 | 38.71 | C |
| ATOM | 3961 | C | LEU | A | 637 | 33.258 | 90.682 | -11.475 | 1.00 | 42.07 | C |
| ATOM | 3962 | O | LEU | A | 637 | 32.265 | 91.353 | -11.644 | 1.00 | 42.11 | O |
| ATOM | 3963 | CB | LEU | A | 637 | 34.308 | 90.283 | -13.695 | 1.00 | 41.67 | C |
| ATOM | 3964 | CG | LEU | A | 637 | 34.824 | 89.346 | -14.793 | 1.00 | 42.86 | C |
| ATOM | 3965 | CD1 | LEU | A | 637 | 35.617 | 90.135 | -15.823 | 1.00 | 38.82 | C |
| ATOM | 3966 | CD2 | LEU | A | 637 | 35.640 | 88.188 | -14.213 | 1.00 | 33.40 | C |
| ATOM | 3967 | N | SER | A | 638 | 34.048 | 90.833 | -10.411 | 1.00 | 40.91 | N |
| ATOM | 3968 | CA | SER | A | 638 | 33.785 | 91.895 | -9.460 | 1.00 | 44.24 | C |
| ATOM | 3969 | C | SER | A | 638 | 35.042 | 92.614 | -8.990 | 1.00 | 44.23 | C |
| ATOM | 3970 | O | SER | A | 638 | 36.127 | 92.040 | -8.971 | 1.00 | 41.60 | O |
| ATOM | 3971 | CB | SER | A | 638 | 33.026 | 91.328 | -8.253 | 1.00 | 53.38 | C |
| ATOM | 3972 | OG | SER | A | 638 | 33.892 | 90.543 | -7.438 | 1.00 | 69.10 | O |
| ATOM | 3973 | N | ALA | A | 639 | 34.873 | 93.864 | -8.562 | 1.00 | 43.21 | N |
| ATOM | 3974 | CA | ALA | A | 639 | 35.972 | 94.640 | -8.017 | 1.00 | 45.35 | C |
| ATOM | 3975 | C | ALA | A | 639 | 35.827 | 94.920 | -6.498 | 1.00 | 57.96 | C |
| ATOM | 3976 | O | ALA | A | 639 | 36.718 | 95.504 | -5.892 | 1.00 | 52.01 | O |
| ATOM | 3977 | CB | ALA | A | 639 | 36.122 | 95.935 | -8.799 | 1.00 | 46.38 | C |
| ATOM | 3978 | N | LEU | A | 640 | 34.708 | 94.492 | -5.907 | 1.00 | 50.75 | N |
| ATOM | 3979 | CA | LEU | A | 640 | 34.405 | 94.723 | -4.498 | 1.00 | 51.20 | C |
| ATOM | 3980 | C | LEU | A | 640 | 34.464 | 93.453 | -3.673 | 1.00 | 47.49 | C |
| ATOM | 3981 | O | LEU | A | 640 | 34.050 | 92.375 | -4.104 | 1.00 | 50.94 | O |
| ATOM | 3982 | CB | LEU | A | 640 | 33.006 | 95.305 | -4.309 | 1.00 | 54.72 | C |
| ATOM | 3983 | CG | LEU | A | 640 | 32.643 | 96.658 | -4.902 | 1.00 | 58.63 | C |
| ATOM | 3984 | CD1 | LEU | A | 640 | 31.129 | 96.853 | -4.776 | 1.00 | 55.91 | C |
| ATOM | 3985 | CD2 | LEU | A | 640 | 33.389 | 97.732 | -4.161 | 1.00 | 57.64 | C |
| ATOM | 3986 | N | ARG | A | 641 | 34.983 | 93.598 | -2.469 | 1.00 | 46.90 | N |
| ATOM | 3987 | CA | ARG | A | 641 | 35.063 | 92.492 | -1.548 | 1.00 | 54.29 | C |
| ATOM | 3988 | C | ARG | A | 641 | 34.138 | 92.820 | -0.386 | 1.00 | 54.09 | C |
| ATOM | 3989 | O | ARG | A | 641 | 33.345 | 91.974 | 0.027 | 1.00 | 49.75 | O |
| ATOM | 3990 | CB | ARG | A | 641 | 36.501 | 92.283 | -1.088 | 1.00 | 62.41 | C |
| ATOM | 3991 | CG | ARG | A | 641 | 36.965 | 90.844 | -1.208 | 1.00 | 73.31 | C |
| ATOM | 3992 | CD | ARG | A | 641 | 36.176 | 89.960 | -0.254 | 1.00 | 83.82 | C |
| ATOM | 3993 | NE | ARG | A | 641 | 36.574 | 88.556 | -0.336 | 1.00 | 92.00 | N |
| ATOM | 3994 | CZ | ARG | A | 641 | 36.316 | 87.763 | -1.373 | 1.00 | 99.78 | C |
| ATOM | 3995 | NH1 | ARG | A | 641 | 35.667 | 88.236 | -2.428 | 1.00 | 102.60 | N |
| ATOM | 3996 | NH2 | ARG | A | 641 | 36.712 | 86.496 | -1.359 | 1.00 | 103.23 | N |
| ATOM | 3997 | N | SER | A | 642 | 34.216 | 94.052 | 0.122 | 1.00 | 50.80 | N |
| ATOM | 3998 | CA | SER | A | 642 | 33.232 | 94.511 | 1.116 | 1.00 | 55.42 | C |
| ATOM | 3999 | C | SER | A | 642 | 33.091 | 96.037 | 1.200 | 1.00 | 54.49 | C |

FIG. 8-62

| | | | | | | | | | | | |
|---|---|---|---|---|---|---|---|---|---|---|---|
| ATOM | 4000 | O | SER | A | 642 | 33.930 | 96.782 | 0.669 | 1.00 | 54.38 | O |
| ATOM | 4001 | CB | SER | A | 642 | 33.491 | 93.895 | 2.489 | 1.00 | 52.46 | C |
| ATOM | 4002 | OG | SER | A | 642 | 34.732 | 94.325 | 3.016 | 1.00 | 63.19 | O |
| ATOM | 4003 | N | VAL | A | 643 | 31.989 | 96.485 | 1.804 | 1.00 | 44.80 | N |
| ATOM | 4004 | CA | VAL | A | 643 | 31.790 | 97.900 | 2.134 | 1.00 | 50.92 | C |
| ATOM | 4005 | C | VAL | A | 643 | 31.347 | 97.993 | 3.587 | 1.00 | 53.72 | C |
| ATOM | 4006 | O | VAL | A | 643 | 30.339 | 97.405 | 3.962 | 1.00 | 56.56 | O |
| ATOM | 4007 | CB | VAL | A | 643 | 30.728 | 98.605 | 1.267 | 1.00 | 53.00 | C |
| ATOM | 4008 | CG1 | VAL | A | 643 | 30.782 | 100.107 | 1.508 | 1.00 | 51.63 | C |
| ATOM | 4009 | CG2 | VAL | A | 643 | 30.939 | 98.339 | -0.199 | 1.00 | 55.03 | C |
| ATOM | 4010 | N | ILE | A | 644 | 32.107 | 98.733 | 4.391 | 1.00 | 49.38 | N |
| ATOM | 4011 | CA | ILE | A | 644 | 31.910 | 98.797 | 5.841 | 1.00 | 53.68 | C |
| ATOM | 4012 | C | ILE | A | 644 | 31.651 | 100.243 | 6.228 | 1.00 | 54.08 | C |
| ATOM | 4013 | O | ILE | A | 644 | 32.190 | 101.155 | 5.602 | 1.00 | 60.87 | O |
| ATOM | 4014 | CB | ILE | A | 644 | 33.175 | 98.302 | 6.591 | 1.00 | 58.04 | C |
| ATOM | 4015 | CG1 | ILE | A | 644 | 33.747 | 97.047 | 5.919 | 1.00 | 58.48 | C |
| ATOM | 4016 | CG2 | ILE | A | 644 | 32.868 | 98.015 | 8.040 | 1.00 | 56.65 | C |
| ATOM | 4017 | CD1 | ILE | A | 644 | 33.027 | 95.761 | 6.279 | 1.00 | 53.89 | C |
| ATOM | 4018 | N | ALA | A | 645 | 30.803 | 100.450 | 7.231 | 1.00 | 53.13 | N |
| ATOM | 4019 | CA | ALA | A | 645 | 30.525 | 101.788 | 7.763 | 1.00 | 61.20 | C |
| ATOM | 4020 | C | ALA | A | 645 | 31.610 | 102.189 | 8.765 | 1.00 | 64.04 | C |
| ATOM | 4021 | O | ALA | A | 645 | 32.371 | 101.333 | 9.221 | 1.00 | 64.67 | O |
| ATOM | 4022 | CB | ALA | A | 645 | 29.134 | 101.822 | 8.438 | 1.00 | 54.93 | C |
| ATOM | 4023 | N | GLU | A | 646 | 31.680 | 103.474 | 9.119 | 1.00 | 65.15 | N |
| ATOM | 4024 | CA | GLU | A | 646 | 32.664 | 103.929 | 10.115 | 1.00 | 65.72 | C |
| ATOM | 4025 | C | GLU | A | 646 | 32.628 | 103.108 | 11.395 | 1.00 | 70.35 | C |
| ATOM | 4026 | O | GLU | A | 646 | 33.649 | 102.935 | 12.065 | 1.00 | 74.98 | O |
| ATOM | 4027 | CB | GLU | A | 646 | 32.522 | 105.427 | 10.449 | 1.00 | 69.47 | C |
| ATOM | 4028 | CG | GLU | A | 646 | 31.101 | 105.972 | 10.422 | 1.00 | 86.32 | C |
| ATOM | 4029 | CD | GLU | A | 646 | 30.970 | 107.338 | 11.101 | 1.00 | 96.20 | C |
| ATOM | 4030 | OE1 | GLU | A | 646 | 31.514 | 107.499 | 12.218 | 1.00 | 97.60 | O |
| ATOM | 4031 | OE2 | GLU | A | 646 | 30.317 | 108.242 | 10.525 | 1.00 | 96.60 | O |
| ATOM | 4032 | N | ASP | A | 647 | 31.456 | 102.588 | 11.725 | 1.00 | 71.94 | N |
| ATOM | 4033 | CA | ASP | A | 647 | 31.264 | 101.882 | 12.987 | 1.00 | 82.60 | C |
| ATOM | 4034 | C | ASP | A | 647 | 31.483 | 100.377 | 12.849 | 1.00 | 80.14 | C |
| ATOM | 4035 | O | ASP | A | 647 | 31.369 | 99.632 | 13.825 | 1.00 | 84.03 | O |
| ATOM | 4036 | CB | ASP | A | 647 | 29.862 | 102.160 | 13.527 | 1.00 | 91.28 | C |
| ATOM | 4037 | CG | ASP | A | 647 | 28.792 | 102.029 | 12.452 | 1.00 | 99.55 | C |
| ATOM | 4038 | OD1 | ASP | A | 647 | 29.153 | 101.788 | 11.278 | 1.00 | 94.69 | O |
| ATOM | 4039 | OD2 | ASP | A | 647 | 27.594 | 102.168 | 12.782 | 1.00 | 106.32 | O |
| ATOM | 4040 | N | GLY | A | 648 | 31.798 | 99.933 | 11.638 | 1.00 | 69.86 | N |
| ATOM | 4041 | CA | GLY | A | 648 | 32.051 | 98.527 | 11.391 | 1.00 | 68.22 | C |
| ATOM | 4042 | C | GLY | A | 648 | 30.857 | 97.734 | 10.880 | 1.00 | 70.36 | C |
| ATOM | 4043 | O | GLY | A | 648 | 30.961 | 96.519 | 10.693 | 1.00 | 71.20 | O |
| ATOM | 4044 | N | LYS | A | 649 | 29.731 | 98.408 | 10.646 | 1.00 | 68.48 | N |
| ATOM | 4045 | CA | LYS | A | 649 | 28.553 | 97.753 | 10.069 | 1.00 | 67.13 | C |
| ATOM | 4046 | C | LYS | A | 649 | 28.801 | 97.399 | 8.601 | 1.00 | 60.76 | C |
| ATOM | 4047 | O | LYS | A | 649 | 29.271 | 98.230 | 7.823 | 1.00 | 59.87 | O |
| ATOM | 4048 | CB | LYS | A | 649 | 27.310 | 98.638 | 10.192 | 1.00 | 70.97 | C |
| ATOM | 4049 | CG | LYS | A | 649 | 26.062 | 97.999 | 9.603 | 1.00 | 79.28 | C |
| ATOM | 4050 | CD | LYS | A | 649 | 24.925 | 98.998 | 9.444 | 1.00 | 84.12 | C |
| ATOM | 4051 | CE | LYS | A | 649 | 23.819 | 98.432 | 8.567 | 1.00 | 87.33 | C |
| ATOM | 4052 | NZ | LYS | A | 649 | 23.061 | 99.515 | 7.877 | 1.00 | 88.72 | N |
| ATOM | 4053 | N | VAL | A | 650 | 28.507 | 96.161 | 8.228 | 1.00 | 54.11 | N |
| ATOM | 4054 | CA | VAL | A | 650 | 28.736 | 95.731 | 6.860 | 1.00 | 61.38 | C |
| ATOM | 4055 | C | VAL | A | 650 | 27.633 | 96.223 | 5.949 | 1.00 | 61.41 | C |
| ATOM | 4056 | O | VAL | A | 650 | 26.510 | 95.731 | 6.013 | 1.00 | 62.86 | O |
| ATOM | 4057 | CB | VAL | A | 650 | 28.792 | 94.206 | 6.739 | 1.00 | 65.92 | C |
| ATOM | 4058 | CG1 | VAL | A | 650 | 28.955 | 93.810 | 5.272 | 1.00 | 62.20 | C |
| ATOM | 4059 | CG2 | VAL | A | 650 | 29.931 | 93.649 | 7.577 | 1.00 | 55.21 | C |
| ATOM | 4060 | N | LEU | A | 651 | 27.945 | 97.198 | 5.107 | 1.00 | 57.37 | N |
| ATOM | 4061 | CA | LEU | A | 651 | 26.973 | 97.667 | 4.122 | 1.00 | 60.89 | C |
| ATOM | 4062 | C | LEU | A | 651 | 26.877 | 96.721 | 2.922 | 1.00 | 64.11 | C |
| ATOM | 4063 | O | LEU | A | 651 | 25.840 | 96.649 | 2.259 | 1.00 | 70.24 | O |
| ATOM | 4064 | CB | LEU | A | 651 | 27.321 | 99.078 | 3.673 | 1.00 | 55.19 | C |
| ATOM | 4065 | CG | LEU | A | 651 | 27.632 | 99.931 | 4.898 | 1.00 | 55.59 | C |
| ATOM | 4066 | CD1 | LEU | A | 651 | 28.260 | 101.245 | 4.490 | 1.00 | 56.55 | C |
| ATOM | 4067 | CD2 | LEU | A | 651 | 26.360 | 100.165 | 5.752 | 1.00 | 50.57 | C |
| ATOM | 4068 | N | TYR | A | 652 | 27.958 | 95.992 | 2.653 | 1.00 | 58.52 | N |
| ATOM | 4069 | CA | TYR | A | 652 | 27.981 | 95.003 | 1.574 | 1.00 | 50.45 | C |
| ATOM | 4070 | C | TYR | A | 652 | 29.067 | 93.944 | 1.767 | 1.00 | 49.75 | C |
| ATOM | 4071 | O | TYR | A | 652 | 30.193 | 94.253 | 2.137 | 1.00 | 55.05 | O |
| ATOM | 4072 | CB | TYR | A | 652 | 28.191 | 95.679 | 0.235 | 1.00 | 50.57 | C |
| ATOM | 4073 | CG | TYR | A | 652 | 28.462 | 94.685 | -0.861 | 1.00 | 55.28 | C |
| ATOM | 4074 | CD1 | TYR | A | 652 | 27.419 | 94.107 | -1.571 | 1.00 | 59.18 | C |
| ATOM | 4075 | CD2 | TYR | A | 652 | 29.757 | 94.318 | -1.182 | 1.00 | 61.80 | C |
| ATOM | 4076 | CE1 | TYR | A | 652 | 27.649 | 93.187 | -2.567 | 1.00 | 51.33 | C |

FIG. 8-63

| | | | | | | | | | | | |
|---|---|---|---|---|---|---|---|---|---|---|---|
| ATOM | 4077 | CE2 | TYR | A | 652 | 30.010 | 93.401 | -2.189 | 1.00 | 61.90 | C |
| ATOM | 4078 | CZ | TYR | A | 652 | 28.948 | 92.837 | -2.877 | 1.00 | 53.79 | C |
| ATOM | 4079 | OH | TYR | A | 652 | 29.195 | 91.917 | -3.872 | 1.00 | 49.46 | O |
| ATOM | 4080 | N | GLN | A | 653 | 28.716 | 92.692 | 1.520 | 1.00 | 53.00 | N |
| ATOM | 4081 | CA | GLN | A | 653 | 29.679 | 91.605 | 1.559 | 1.00 | 59.64 | C |
| ATOM | 4082 | C | GLN | A | 653 | 29.546 | 90.714 | 0.324 | 1.00 | 67.93 | C |
| ATOM | 4083 | O | GLN | A | 653 | 28.482 | 90.166 | 0.050 | 1.00 | 74.80 | O |
| ATOM | 4084 | CB | GLN | A | 653 | 29.494 | 90.755 | 2.814 | 1.00 | 60.31 | C |
| ATOM | 4085 | CG | GLN | A | 653 | 30.531 | 89.660 | 2.961 | 1.00 | 56.78 | C |
| ATOM | 4086 | CD | GLN | A | 653 | 31.833 | 90.186 | 3.546 | 1.00 | 62.47 | C |
| ATOM | 4087 | OE1 | GLN | A | 653 | 32.861 | 90.291 | 2.856 | 1.00 | 62.73 | O |
| ATOM | 4088 | NE2 | GLN | A | 653 | 31.787 | 90.546 | 4.825 | 1.00 | 63.01 | N |
| ATOM | 4089 | N | SER | A | 654 | 30.639 | 90.576 | -0.413 | 1.00 | 65.73 | N |
| ATOM | 4090 | CA | SER | A | 654 | 30.706 | 89.652 | -1.527 | 1.00 | 61.63 | C |
| ATOM | 4091 | C | SER | A | 654 | 30.699 | 88.206 | -1.056 | 1.00 | 59.52 | C |
| ATOM | 4092 | O | SER | A | 654 | 31.446 | 87.829 | -0.158 | 1.00 | 63.96 | O |
| ATOM | 4093 | CB | SER | A | 654 | 31.983 | 89.902 | -2.316 | 1.00 | 67.37 | C |
| ATOM | 4094 | OG | SER | A | 654 | 32.363 | 88.743 | -3.041 | 1.00 | 75.48 | O |
| ATOM | 4095 | N | PHE | A | 655 | 29.849 | 87.392 | -1.660 | 1.00 | 59.73 | N |
| ATOM | 4096 | CA | PHE | A | 655 | 29.943 | 85.950 | -1.476 | 1.00 | 66.48 | C |
| ATOM | 4097 | C | PHE | A | 655 | 30.167 | 85.274 | -2.841 | 1.00 | 66.92 | C |
| ATOM | 4098 | O | PHE | A | 655 | 29.675 | 85.765 | -3.863 | 1.00 | 63.98 | O |
| ATOM | 4099 | CB | PHE | A | 655 | 28.690 | 85.401 | -0.771 | 1.00 | 71.50 | C |
| ATOM | 4100 | CG | PHE | A | 655 | 27.482 | 85.312 | -1.656 | 1.00 | 84.81 | C |
| ATOM | 4101 | CD1 | PHE | A | 655 | 27.112 | 84.102 | -2.229 | 1.00 | 91.38 | C |
| ATOM | 4102 | CD2 | PHE | A | 655 | 26.710 | 86.439 | -1.920 | 1.00 | 91.52 | C |
| ATOM | 4103 | CE1 | PHE | A | 655 | 25.996 | 84.017 | -3.062 | 1.00 | 91.76 | C |
| ATOM | 4104 | CE2 | PHE | A | 655 | 25.592 | 86.362 | -2.744 | 1.00 | 92.89 | C |
| ATOM | 4105 | CZ | PHE | A | 655 | 25.238 | 85.150 | -3.317 | 1.00 | 92.67 | C |
| ATOM | 4106 | N | PRO | A | 656 | 30.921 | 84.161 | -2.850 | 1.00 | 66.99 | N |
| ATOM | 4107 | CA | PRO | A | 656 | 31.144 | 83.290 | -4.005 | 1.00 | 68.83 | C |
| ATOM | 4108 | C | PRO | A | 656 | 29.828 | 82.937 | -4.657 | 1.00 | 79.28 | C |
| ATOM | 4109 | O | PRO | A | 656 | 28.880 | 82.601 | -3.954 | 1.00 | 88.29 | O |
| ATOM | 4110 | CB | PRO | A | 656 | 31.728 | 82.024 | -3.375 | 1.00 | 69.06 | C |
| ATOM | 4111 | CG | PRO | A | 656 | 32.446 | 82.510 | -2.169 | 1.00 | 76.11 | C |
| ATOM | 4112 | CD | PRO | A | 656 | 31.598 | 83.649 | -1.642 | 1.00 | 79.41 | C |
| ATOM | 4113 | N | GLN | A | 657 | 29.759 | 83.006 | -5.977 | 1.00 | 78.78 | N |
| ATOM | 4114 | CA | GLN | A | 657 | 28.530 | 82.640 | -6.665 | 1.00 | 79.55 | C |
| ATOM | 4115 | C | GLN | A | 657 | 28.810 | 82.193 | -8.093 | 1.00 | 72.31 | C |
| ATOM | 4116 | O | GLN | A | 657 | 28.071 | 82.544 | -9.022 | 1.00 | 75.44 | O |
| ATOM | 4117 | CB | GLN | A | 657 | 27.541 | 83.804 | -6.645 | 1.00 | 84.28 | C |
| ATOM | 4118 | CG | GLN | A | 657 | 28.073 | 85.070 | -7.285 | 1.00 | 90.58 | C |
| ATOM | 4119 | CD | GLN | A | 657 | 27.466 | 86.322 | -6.690 | 1.00 | 95.04 | C |
| ATOM | 4120 | OE1 | GLN | A | 657 | 27.936 | 87.434 | -6.945 | 1.00 | 94.84 | O |
| ATOM | 4121 | NE2 | GLN | A | 657 | 26.419 | 86.150 | -5.883 | 1.00 | 96.12 | N |
| ATOM | 4122 | N | ALA | A | 658 | 29.886 | 81.429 | -8.262 | 1.00 | 57.30 | N |
| ATOM | 4123 | CA | ALA | A | 658 | 30.153 | 80.748 | -9.527 | 1.00 | 58.93 | C |
| ATOM | 4124 | C | ALA | A | 658 | 28.973 | 79.881 | -10.003 | 1.00 | 58.94 | C |
| ATOM | 4125 | O | ALA | A | 658 | 28.377 | 79.150 | -9.227 | 1.00 | 61.33 | O |
| ATOM | 4126 | CB | ALA | A | 658 | 31.414 | 79.898 | -9.411 | 1.00 | 66.59 | C |
| ATOM | 4127 | N | GLU | A | 659 | 28.655 | 79.956 | -11.290 | 1.00 | 49.10 | N |
| ATOM | 4128 | CA | GLU | A | 659 | 27.616 | 79.123 | -11.876 | 1.00 | 52.95 | C |
| ATOM | 4129 | C | GLU | A | 659 | 28.249 | 78.153 | -12.871 | 1.00 | 47.90 | C |
| ATOM | 4130 | O | GLU | A | 659 | 28.976 | 78.591 | -13.768 | 1.00 | 38.25 | O |
| ATOM | 4131 | CB | GLU | A | 659 | 26.604 | 79.999 | -12.629 | 1.00 | 44.86 | C |
| ATOM | 4132 | CG | GLU | A | 659 | 25.153 | 79.526 | -12.527 | 1.00 | 71.38 | C |
| ATOM | 4133 | CD | GLU | A | 659 | 24.407 | 80.144 | -11.338 | 1.00 | 84.63 | C |
| ATOM | 4134 | OE1 | GLU | A | 659 | 24.664 | 81.330 | -11.029 | 1.00 | 87.56 | O |
| ATOM | 4135 | OE2 | GLU | A | 659 | 23.561 | 79.450 | -10.722 | 1.00 | 86.16 | O |
| ATOM | 4136 | N | ARG | A | 660 | 27.953 | 76.860 | -12.727 | 1.00 | 49.03 | N |
| ATOM | 4137 | CA | ARG | A | 660 | 28.271 | 75.847 | -13.748 | 1.00 | 47.61 | C |
| ATOM | 4138 | C | ARG | A | 660 | 27.770 | 76.271 | -15.111 | 1.00 | 45.54 | C |
| ATOM | 4139 | O | ARG | A | 660 | 26.562 | 76.302 | -15.346 | 1.00 | 49.97 | O |
| ATOM | 4140 | CB | ARG | A | 660 | 27.642 | 74.490 | -13.388 | 1.00 | 46.41 | C |
| ATOM | 4141 | CG | ARG | A | 660 | 27.704 | 73.434 | -14.516 | 1.00 | 35.74 | C |
| ATOM | 4142 | CD | ARG | A | 660 | 29.150 | 73.172 | -14.941 | 1.00 | 38.40 | C |
| ATOM | 4143 | NE | ARG | A | 660 | 30.001 | 72.887 | -13.794 | 1.00 | 39.83 | N |
| ATOM | 4144 | CZ | ARG | A | 660 | 31.320 | 72.847 | -13.842 | 1.00 | 46.78 | C |
| ATOM | 4145 | NH1 | ARG | A | 660 | 31.953 | 73.089 | -15.003 | 1.00 | 31.16 | N |
| ATOM | 4146 | NH2 | ARG | A | 660 | 31.996 | 72.605 | -12.722 | 1.00 | 42.87 | N |
| ATOM | 4147 | N | ALA | A | 661 | 28.689 | 76.562 | -16.038 | 1.00 | 44.55 | N |
| ATOM | 4148 | CA | ALA | A | 661 | 28.293 | 77.048 | -17.366 | 1.00 | 40.28 | C |
| ATOM | 4149 | C | ALA | A | 661 | 28.515 | 76.032 | -18.474 | 1.00 | 40.56 | C |
| ATOM | 4150 | O | ALA | A | 661 | 27.592 | 75.757 | -19.262 | 1.00 | 42.47 | O |
| ATOM | 4151 | CB | ALA | A | 661 | 29.001 | 78.350 | -17.681 | 1.00 | 36.99 | C |
| ATOM | 4152 | N | VAL | A | 662 | 29.748 | 75.502 | -18.561 | 1.00 | 44.20 | N |
| ATOM | 4153 | CA | VAL | A | 662 | 30.068 | 74.407 | -19.491 | 1.00 | 34.07 | C |

FIG. 8-64

| | | | | | | | | | | | |
|---|---|---|---|---|---|---|---|---|---|---|---|
| ATOM | 4154 | C | VAL | A | 662 | 30.588 | 73.168 | -18.752 | 1.00 | 32.68 | C |
| ATOM | 4155 | O | VAL | A | 662 | 31.034 | 73.286 | -17.636 | 1.00 | 37.05 | O |
| ATOM | 4156 | CB | VAL | A | 662 | 30.961 | 74.880 | -20.644 | 1.00 | 47.46 | C |
| ATOM | 4157 | CG1 | VAL | A | 662 | 30.170 | 75.879 | -21.498 | 1.00 | 41.47 | C |
| ATOM | 4158 | CG2 | VAL | A | 662 | 32.291 | 75.517 | -20.117 | 1.00 | 33.26 | C |
| ATOM | 4159 | N | PRO | A | 663 | 30.461 | 71.962 | -19.339 | 1.00 | 36.64 | N |
| ATOM | 4160 | CA | PRO | A | 663 | 31.019 | 70.766 | -18.678 | 1.00 | 33.42 | C |
| ATOM | 4161 | C | PRO | A | 663 | 32.512 | 71.014 | -18.310 | 1.00 | 37.17 | C |
| ATOM | 4162 | O | PRO | A | 663 | 33.193 | 71.684 | -19.070 | 1.00 | 39.61 | O |
| ATOM | 4163 | CB | PRO | A | 663 | 30.952 | 69.691 | -19.788 | 1.00 | 40.53 | C |
| ATOM | 4164 | CG | PRO | A | 663 | 29.853 | 70.137 | -20.707 | 1.00 | 42.10 | C |
| ATOM | 4165 | CD | PRO | A | 663 | 29.835 | 71.651 | -20.642 | 1.00 | 45.87 | C |
| ATOM | 4166 | N | ALA | A | 664 | 32.970 | 70.495 | -17.167 | 1.00 | 32.41 | N |
| ATOM | 4167 | CA | ALA | A | 664 | 34.306 | 70.671 | -16.670 | 1.00 | 37.97 | C |
| ATOM | 4168 | C | ALA | A | 664 | 35.290 | 69.947 | -17.595 | 1.00 | 34.61 | C |
| ATOM | 4169 | O | ALA | A | 664 | 36.370 | 70.455 | -17.848 | 1.00 | 39.25 | O |
| ATOM | 4170 | CB | ALA | A | 664 | 34.399 | 70.141 | -15.183 | 1.00 | 32.62 | C |
| ATOM | 4171 | N | GLN | A | 665 | 34.889 | 68.783 | -18.120 | 1.00 | 34.86 | N |
| ATOM | 4172 | CA | GLN | A | 665 | 35.672 | 68.037 | -19.106 | 1.00 | 37.56 | C |
| ATOM | 4173 | C | GLN | A | 665 | 35.838 | 68.747 | -20.469 | 1.00 | 44.69 | C |
| ATOM | 4174 | O | GLN | A | 665 | 36.909 | 68.648 | -21.099 | 1.00 | 36.43 | O |
| ATOM | 4175 | CB | GLN | A | 665 | 35.102 | 66.633 | -19.314 | 1.00 | 32.60 | C |
| ATOM | 4176 | CG | GLN | A | 665 | 35.066 | 65.748 | -18.056 | 1.00 | 29.11 | C |
| ATOM | 4177 | CD | GLN | A | 665 | 33.926 | 66.038 | -17.127 | 1.00 | 38.48 | C |
| ATOM | 4178 | OE1 | GLN | A | 665 | 33.739 | 65.329 | -16.139 | 1.00 | 45.45 | O |
| ATOM | 4179 | NE2 | GLN | A | 665 | 33.149 | 67.081 | -17.425 | 1.00 | 33.89 | N |
| ATOM | 4180 | N | ALA | A | 666 | 34.799 | 69.442 | -20.946 | 1.00 | 33.23 | N |
| ATOM | 4181 | CA | ALA | A | 666 | 34.959 | 70.233 | -22.178 | 1.00 | 26.25 | C |
| ATOM | 4182 | C | ALA | A | 666 | 35.839 | 71.455 | -21.918 | 1.00 | 44.72 | C |
| ATOM | 4183 | O | ALA | A | 666 | 36.716 | 71.766 | -22.737 | 1.00 | 38.03 | O |
| ATOM | 4184 | CB | ALA | A | 666 | 33.638 | 70.677 | -22.772 | 1.00 | 29.50 | C |
| ATOM | 4185 | N | ALA | A | 667 | 35.585 | 72.168 | -20.810 | 1.00 | 36.85 | N |
| ATOM | 4186 | CA | ALA | A | 667 | 36.468 | 73.276 | -20.404 | 1.00 | 36.17 | C |
| ATOM | 4187 | C | ALA | A | 667 | 37.921 | 72.777 | -20.314 | 1.00 | 41.07 | C |
| ATOM | 4188 | O | ALA | A | 667 | 38.872 | 73.405 | -20.833 | 1.00 | 37.62 | O |
| ATOM | 4189 | CB | ALA | A | 667 | 36.046 | 73.854 | -19.074 | 1.00 | 45.73 | C |
| ATOM | 4190 | N | TYR | A | 668 | 38.095 | 71.619 | -19.703 | 1.00 | 31.58 | N |
| ATOM | 4191 | CA | TYR | A | 668 | 39.449 | 71.066 | -19.600 | 1.00 | 32.64 | C |
| ATOM | 4192 | C | TYR | A | 668 | 40.115 | 70.742 | -20.966 | 1.00 | 38.21 | C |
| ATOM | 4193 | O | TYR | A | 668 | 41.279 | 71.057 | -21.158 | 1.00 | 33.37 | O |
| ATOM | 4194 | CB | TYR | A | 668 | 39.525 | 69.869 | -18.640 | 1.00 | 27.32 | C |
| ATOM | 4195 | CG | TYR | A | 668 | 40.828 | 69.092 | -18.742 | 1.00 | 37.80 | C |
| ATOM | 4196 | CD1 | TYR | A | 668 | 41.699 | 69.354 | -17.882 | 1.00 | 38.45 | C |
| ATOM | 4197 | CD2 | TYR | A | 668 | 40.999 | 68.122 | -19.725 | 1.00 | 39.21 | C |
| ATOM | 4198 | CE1 | TYR | A | 668 | 43.103 | 68.622 | -17.982 | 1.00 | 38.01 | C |
| ATOM | 4199 | CE2 | TYR | A | 668 | 42.158 | 67.398 | -19.832 | 1.00 | 27.50 | C |
| ATOM | 4200 | CZ | TYR | A | 668 | 43.228 | 67.653 | -18.969 | 1.00 | 40.38 | C |
| ATOM | 4201 | OH | TYR | A | 668 | 44.414 | 66.942 | -19.111 | 1.00 | 46.98 | O |
| ATOM | 4202 | N | LEU | A | 669 | 39.397 | 70.130 | -21.900 | 1.00 | 38.76 | N |
| ATOM | 4203 | CA | LEU | A | 669 | 39.988 | 69.792 | -23.206 | 1.00 | 37.38 | C |
| ATOM | 4204 | C | LEU | A | 669 | 40.318 | 71.070 | -23.944 | 1.00 | 35.29 | C |
| ATOM | 4205 | O | LEU | A | 669 | 41.280 | 71.144 | -24.688 | 1.00 | 36.54 | O |
| ATOM | 4206 | CB | LEU | A | 669 | 39.023 | 68.957 | -24.052 | 1.00 | 26.28 | C |
| ATOM | 4207 | CG | LEU | A | 669 | 38.683 | 67.636 | -23.397 | 1.00 | 36.08 | C |
| ATOM | 4208 | CD1 | LEU | A | 669 | 37.574 | 66.943 | -24.140 | 1.00 | 39.14 | C |
| ATOM | 4209 | CD2 | LEU | A | 669 | 39.906 | 66.791 | -23.370 | 1.00 | 38.15 | C |
| ATOM | 4210 | N | THR | A | 670 | 39.504 | 72.094 | -23.740 | 1.00 | 34.37 | N |
| ATOM | 4211 | CA | THR | A | 670 | 39.755 | 73.344 | -24.433 | 1.00 | 37.81 | C |
| ATOM | 4212 | C | THR | A | 670 | 41.015 | 74.012 | -23.906 | 1.00 | 32.21 | C |
| ATOM | 4213 | O | THR | A | 670 | 41.781 | 74.543 | -24.692 | 1.00 | 36.23 | O |
| ATOM | 4214 | CB | THR | A | 670 | 38.545 | 74.287 | -24.390 | 1.00 | 36.56 | C |
| ATOM | 4215 | OG1 | THR | A | 670 | 37.425 | 73.602 | -24.941 | 1.00 | 38.74 | O |
| ATOM | 4216 | CG2 | THR | A | 670 | 38.800 | 75.522 | -25.207 | 1.00 | 34.11 | C |
| ATOM | 4217 | N | LEU | A | 671 | 41.228 | 73.982 | -22.584 | 1.00 | 32.08 | N |
| ATOM | 4218 | CA | LEU | A | 671 | 42.435 | 74.551 | -21.946 | 1.00 | 25.64 | C |
| ATOM | 4219 | C | LEU | A | 671 | 43.724 | 73.819 | -22.325 | 1.00 | 35.15 | C |
| ATOM | 4220 | O | LEU | A | 671 | 44.776 | 74.433 | -22.501 | 1.00 | 36.69 | O |
| ATOM | 4221 | CB | LEU | A | 671 | 42.313 | 74.444 | -20.425 | 1.00 | 28.74 | C |
| ATOM | 4222 | CG | LEU | A | 671 | 41.901 | 75.694 | -19.653 | 1.00 | 49.16 | C |
| ATOM | 4223 | CD1 | LEU | A | 671 | 41.642 | 76.893 | -20.542 | 1.00 | 53.78 | C |
| ATOM | 4224 | CD2 | LEU | A | 671 | 40.677 | 75.377 | -18.747 | 1.00 | 56.62 | C |
| ATOM | 4225 | N | TRP | A | 672 | 43.639 | 72.489 | -22.319 | 1.00 | 31.28 | N |
| ATOM | 4226 | CA | TRP | A | 672 | 44.712 | 71.625 | -22.738 | 1.00 | 36.44 | C |
| ATOM | 4227 | C | TRP | A | 672 | 45.110 | 72.000 | -24.181 | 1.00 | 42.08 | C |
| ATOM | 4228 | O | TRP | A | 672 | 46.292 | 72.074 | -24.526 | 1.00 | 39.92 | O |
| ATOM | 4229 | CB | TRP | A | 672 | 44.215 | 70.179 | -22.713 | 1.00 | 33.70 | C |
| ATOM | 4230 | CG | TRP | A | 672 | 45.308 | 69.186 | -22.889 | 1.00 | 36.54 | C |

FIG. 8-65

| | | | | | | | | | | | |
|---|---|---|---|---|---|---|---|---|---|---|---|
| ATOM | 4231 | CD1 | TRP | A | 672 | 46.114 | 68.648 | -21.888 | 1.00 | 36.53 | C |
| ATOM | 4232 | CD2 | TRP | A | 672 | 45.778 | 68.635 | -24.115 | 1.00 | 36.60 | C |
| ATOM | 4233 | NE1 | TRP | A | 672 | 46.996 | 67.757 | -22.433 | 1.00 | 38.23 | N |
| ATOM | 4234 | CE2 | TRP | A | 672 | 46.843 | 67.753 | -23.798 | 1.00 | 42.40 | C |
| ATOM | 4235 | CE3 | TRP | A | 672 | 45.438 | 68.824 | -25.460 | 1.00 | 31.73 | C |
| ATOM | 4236 | CZ2 | TRP | A | 672 | 47.519 | 67.025 | -24.772 | 1.00 | 36.73 | C |
| ATOM | 4237 | CZ3 | TRP | A | 672 | 46.122 | 68.099 | -26.426 | 1.00 | 38.20 | C |
| ATOM | 4238 | CH2 | TRP | A | 672 | 47.150 | 67.225 | -26.087 | 1.00 | 34.42 | C |
| ATOM | 4239 | N | THR | A | 673 | 44.122 | 72.251 | -25.026 | 1.00 | 33.15 | N |
| ATOM | 4240 | CA | THR | A | 673 | 44.452 | 72.630 | -26.413 | 1.00 | 33.57 | C |
| ATOM | 4241 | C | THR | A | 673 | 45.044 | 74.027 | -26.477 | 1.00 | 27.72 | C |
| ATOM | 4242 | O | THR | A | 673 | 45.949 | 74.286 | -27.267 | 1.00 | 35.92 | O |
| ATOM | 4243 | CB | THR | A | 673 | 43.249 | 72.529 | -27.369 | 1.00 | 32.40 | C |
| ATOM | 4244 | OG1 | THR | A | 673 | 42.622 | 71.251 | -27.182 | 1.00 | 32.08 | O |
| ATOM | 4245 | CG2 | THR | A | 673 | 43.764 | 72.637 | -28.856 | 1.00 | 35.01 | C |
| ATOM | 4246 | N | MET | A | 674 | 44.575 | 74.906 | -25.601 | 1.00 | 27.16 | N |
| ATOM | 4247 | CA | MET | A | 674 | 45.154 | 76.238 | -25.486 | 1.00 | 34.04 | C |
| ATOM | 4248 | C | MET | A | 674 | 46.580 | 76.198 | -24.929 | 1.00 | 38.70 | C |
| ATOM | 4249 | O | MET | A | 674 | 47.367 | 77.141 | -25.164 | 1.00 | 36.72 | O |
| ATOM | 4250 | CB | MET | A | 674 | 44.268 | 77.150 | -24.644 | 1.00 | 35.70 | C |
| ATOM | 4251 | CG | MET | A | 674 | 43.033 | 77.641 | -25.422 | 1.00 | 43.76 | C |
| ATOM | 4252 | SD | MET | A | 674 | 41.960 | 78.588 | -24.346 | 1.00 | 45.26 | S |
| ATOM | 4253 | CE | MET | A | 674 | 40.833 | 77.326 | -23.796 | 1.00 | 99.40 | C |
| ATOM | 4254 | N | GLN | A | 675 | 46.926 | 75.118 | -24.218 | 1.00 | 33.25 | N |
| ATOM | 4255 | CA | GLN | A | 675 | 48.322 | 74.962 | -23.768 | 1.00 | 31.44 | C |
| ATOM | 4256 | C | GLN | A | 675 | 49.156 | 74.585 | -25.007 | 1.00 | 35.56 | C |
| ATOM | 4257 | O | GLN | A | 675 | 50.329 | 74.962 | -25.098 | 1.00 | 39.13 | O |
| ATOM | 4258 | CB | GLN | A | 675 | 48.486 | 73.905 | -22.666 | 1.00 | 35.25 | C |
| ATOM | 4259 | CG | GLN | A | 675 | 47.769 | 74.204 | -21.319 | 1.00 | 28.98 | C |
| ATOM | 4260 | CD | GLN | A | 675 | 48.166 | 73.194 | -20.275 | 1.00 | 38.36 | C |
| ATOM | 4261 | OE1 | GLN | A | 675 | 47.983 | 71.997 | -20.471 | 1.00 | 43.39 | O |
| ATOM | 4262 | NE2 | GLN | A | 675 | 48.818 | 73.658 | -19.207 | 1.00 | 30.24 | N |
| ATOM | 4263 | N | GLN | A | 676 | 48.537 | 73.851 | -25.948 | 1.00 | 29.94 | N |
| ATOM | 4264 | CA | GLN | A | 676 | 49.151 | 73.536 | -27.250 | 1.00 | 34.47 | C |
| ATOM | 4265 | C | GLN | A | 676 | 49.291 | 74.798 | -28.040 | 1.00 | 31.88 | C |
| ATOM | 4266 | O | GLN | A | 676 | 50.303 | 74.998 | -28.687 | 1.00 | 35.94 | O |
| ATOM | 4267 | CB | GLN | A | 676 | 48.344 | 72.557 | -28.109 | 1.00 | 38.36 | C |
| ATOM | 4268 | CG | GLN | A | 676 | 48.005 | 71.260 | -27.452 | 1.00 | 45.67 | C |
| ATOM | 4269 | CD | GLN | A | 676 | 49.230 | 70.617 | -26.832 | 1.00 | 50.83 | C |
| ATOM | 4270 | OE1 | GLN | A | 676 | 50.067 | 70.079 | -27.528 | 1.00 | 45.95 | O |
| ATOM | 4271 | NE2 | GLN | A | 676 | 49.328 | 70.670 | -25.513 | 1.00 | 51.28 | N |
| ATOM | 4272 | N | VAL | A | 677 | 48.294 | 75.674 | -28.030 | 1.00 | 29.31 | N |
| ATOM | 4273 | CA | VAL | A | 677 | 48.530 | 76.875 | -28.807 | 1.00 | 32.24 | C |
| ATOM | 4274 | C | VAL | A | 677 | 49.772 | 77.639 | -28.370 | 1.00 | 32.93 | C |
| ATOM | 4275 | O | VAL | A | 677 | 50.454 | 78.225 | -29.209 | 1.00 | 40.85 | O |
| ATOM | 4276 | CB | VAL | A | 677 | 47.290 | 77.777 | -29.120 | 1.00 | 34.21 | C |
| ATOM | 4277 | CG1 | VAL | A | 677 | 46.014 | 77.210 | -28.589 | 1.00 | 37.77 | C |
| ATOM | 4278 | CG2 | VAL | A | 677 | 47.538 | 79.212 | -28.763 | 1.00 | 29.39 | C |
| ATOM | 4279 | N | VAL | A | 678 | 50.109 | 77.568 | -27.084 | 1.00 | 35.26 | N |
| ATOM | 4280 | CA | VAL | A | 678 | 51.195 | 78.373 | -26.537 | 1.00 | 33.31 | C |
| ATOM | 4281 | C | VAL | A | 678 | 52.520 | 77.616 | -26.659 | 1.00 | 32.61 | C |
| ATOM | 4282 | O | VAL | A | 678 | 53.574 | 78.203 | -26.814 | 1.00 | 29.82 | O |
| ATOM | 4283 | CB | VAL | A | 678 | 50.894 | 78.800 | -25.077 | 1.00 | 43.57 | C |
| ATOM | 4284 | CG1 | VAL | A | 678 | 52.157 | 79.151 | -24.345 | 1.00 | 39.87 | C |
| ATOM | 4285 | CG2 | VAL | A | 678 | 49.959 | 80.003 | -25.076 | 1.00 | 37.38 | C |
| ATOM | 4286 | N | GLN | A | 679 | 52.451 | 76.298 | -26.670 | 1.00 | 30.95 | N |
| ATOM | 4287 | CA | GLN | A | 679 | 53.671 | 75.510 | -26.865 | 1.00 | 30.24 | C |
| ATOM | 4288 | C | GLN | A | 679 | 54.009 | 75.305 | -28.347 | 1.00 | 41.34 | C |
| ATOM | 4289 | O | GLN | A | 679 | 55.126 | 75.487 | -28.727 | 1.00 | 37.02 | O |
| ATOM | 4290 | CB | GLN | A | 679 | 53.548 | 74.170 | -26.141 | 1.00 | 38.26 | C |
| ATOM | 4291 | CG | GLN | A | 679 | 54.822 | 73.401 | -25.962 | 1.00 | 43.59 | C |
| ATOM | 4292 | CD | GLN | A | 679 | 54.619 | 72.126 | -25.166 | 1.00 | 41.96 | C |
| ATOM | 4293 | OE1 | GLN | A | 679 | 53.632 | 71.437 | -25.363 | 1.00 | 41.53 | O |
| ATOM | 4294 | NE2 | GLN | A | 679 | 55.565 | 71.802 | -24.262 | 1.00 | 45.72 | N |
| ATOM | 4295 | N | ARG | A | 680 | 53.061 | 74.919 | -29.196 | 1.00 | 40.37 | N |
| ATOM | 4296 | CA | ARG | A | 680 | 53.447 | 74.633 | -30.561 | 1.00 | 37.94 | C |
| ATOM | 4297 | C | ARG | A | 680 | 52.587 | 75.364 | -31.595 | 1.00 | 33.47 | C |
| ATOM | 4298 | O | ARG | A | 680 | 52.918 | 75.340 | -32.734 | 1.00 | 34.47 | O |
| ATOM | 4299 | CB | ARG | A | 680 | 53.393 | 73.137 | -30.852 | 1.00 | 36.42 | C |
| ATOM | 4300 | CG | ARG | A | 680 | 51.973 | 72.649 | -30.876 | 1.00 | 38.07 | C |
| ATOM | 4301 | CD | ARG | A | 680 | 51.834 | 71.154 | -31.073 | 1.00 | 46.28 | C |
| ATOM | 4302 | NE | ARG | A | 680 | 52.504 | 70.698 | -32.290 | 1.00 | 45.81 | N |
| ATOM | 4303 | CZ | ARG | A | 680 | 52.176 | 69.589 | -32.946 | 1.00 | 49.52 | C |
| ATOM | 4304 | NH1 | ARG | A | 680 | 51.178 | 68.822 | -32.519 | 1.00 | 45.52 | N |
| ATOM | 4305 | NH2 | ARG | A | 680 | 52.834 | 69.256 | -34.044 | 1.00 | 53.99 | N |
| ATOM | 4306 | N | GLY | A | 681 | 51.511 | 76.022 | -31.195 | 1.00 | 40.96 | N |
| ATOM | 4307 | CA | GLY | A | 681 | 50.701 | 76.764 | -32.146 | 1.00 | 39.17 | C |

FIG. 8-66

| | | | | | | | | | | | |
|---|---|---|---|---|---|---|---|---|---|---|---|
| ATOM | 4308 | C | GLY | A | 681 | 51.087 | 78.221 | -32.261 | 1.00 | 39.01 | C |
| ATOM | 4309 | O | GLY | A | 681 | 52.252 | 78.578 | -32.176 | 1.00 | 40.64 | O |
| ATOM | 4310 | N | THR | A | 682 | 50.089 | 79.059 | -32.472 | 1.00 | 42.21 | N |
| ATOM | 4311 | CA | THR | A | 682 | 50.270 | 80.461 | -32.827 | 1.00 | 41.52 | C |
| ATOM | 4312 | C | THR | A | 682 | 50.844 | 81.274 | -31.681 | 1.00 | 35.96 | C |
| ATOM | 4313 | O | THR | A | 682 | 51.399 | 82.357 | -31.882 | 1.00 | 37.81 | O |
| ATOM | 4314 | CB | THR | A | 682 | 48.915 | 81.106 | -33.234 | 1.00 | 43.84 | C |
| ATOM | 4315 | OG1 | THR | A | 682 | 47.994 | 80.975 | -32.156 | 1.00 | 42.01 | O |
| ATOM | 4316 | CG2 | THR | A | 682 | 48.305 | 80.412 | -34.462 | 1.00 | 43.56 | C |
| ATOM | 4317 | N | GLY | A | 683 | 50.739 | 80.750 | -30.472 | 1.00 | 33.78 | N |
| ATOM | 4318 | CA | GLY | A | 683 | 51.232 | 81.483 | -29.331 | 1.00 | 32.61 | C |
| ATOM | 4319 | C | GLY | A | 683 | 52.631 | 81.011 | -28.941 | 1.00 | 42.71 | C |
| ATOM | 4320 | O | GLY | A | 683 | 53.144 | 81.321 | -27.825 | 1.00 | 32.80 | O |
| ATOM | 4321 | N | ARG | A | 684 | 53.256 | 80.271 | -29.851 | 1.00 | 33.02 | N |
| ATOM | 4322 | CA | ARG | A | 684 | 54.470 | 79.521 | -29.497 | 1.00 | 38.11 | C |
| ATOM | 4323 | C | ARG | A | 684 | 55.659 | 80.366 | -29.056 | 1.00 | 36.57 | C |
| ATOM | 4324 | O | ARG | A | 684 | 56.554 | 79.850 | -28.395 | 1.00 | 36.52 | O |
| ATOM | 4325 | CB | ARG | A | 684 | 54.887 | 78.538 | -30.608 | 1.00 | 35.47 | C |
| ATOM | 4326 | CG | ARG | A | 684 | 55.306 | 79.233 | -31.825 | 1.00 | 34.81 | C |
| ATOM | 4327 | CD | ARG | A | 684 | 55.569 | 78.281 | -33.000 | 1.00 | 46.06 | C |
| ATOM | 4328 | NE | ARG | A | 684 | 55.436 | 79.058 | -34.223 | 1.00 | 59.94 | N |
| ATOM | 4329 | CZ | ARG | A | 684 | 54.354 | 79.068 | -35.007 | 1.00 | 61.99 | C |
| ATOM | 4330 | NH1 | ARG | A | 684 | 53.317 | 78.279 | -34.760 | 1.00 | 47.14 | N |
| ATOM | 4331 | NH2 | ARG | A | 684 | 54.338 | 79.836 | -36.085 | 1.00 | 76.69 | N |
| ATOM | 4332 | N | GLN | A | 685 | 55.687 | 81.657 | -29.379 | 1.00 | 39.51 | N |
| ATOM | 4333 | CA | GLN | A | 685 | 56.802 | 82.473 | -28.875 | 1.00 | 40.69 | C |
| ATOM | 4334 | C | GLN | A | 685 | 56.764 | 82.633 | -27.348 | 1.00 | 46.78 | C |
| ATOM | 4335 | O | GLN | A | 685 | 57.791 | 82.914 | -26.694 | 1.00 | 37.17 | O |
| ATOM | 4336 | CB | GLN | A | 685 | 56.889 | 83.849 | -29.548 | 1.00 | 48.34 | C |
| ATOM | 4337 | CG | GLN | A | 685 | 55.793 | 84.818 | -29.139 | 1.00 | 71.96 | C |
| ATOM | 4338 | CD | GLN | A | 685 | 56.326 | 86.223 | -28.892 | 1.00 | 78.63 | C |
| ATOM | 4339 | OE1 | GLN | A | 685 | 56.062 | 87.156 | -29.658 | 1.00 | 75.40 | O |
| ATOM | 4340 | NE2 | GLN | A | 685 | 57.086 | 86.377 | -27.810 | 1.00 | 86.44 | N |
| ATOM | 4341 | N | LEU | A | 686 | 55.576 | 82.485 | -26.785 | 1.00 | 37.55 | N |
| ATOM | 4342 | CA | LEU | A | 686 | 55.411 | 82.590 | -25.330 | 1.00 | 38.62 | C |
| ATOM | 4343 | C | LEU | A | 686 | 55.773 | 81.276 | -24.649 | 1.00 | 37.90 | C |
| ATOM | 4344 | O | LEU | A | 686 | 56.217 | 81.276 | -23.524 | 1.00 | 50.13 | O |
| ATOM | 4345 | CB | LEU | A | 686 | 53.959 | 82.969 | -24.976 | 1.00 | 41.05 | C |
| ATOM | 4346 | CG | LEU | A | 686 | 53.649 | 84.467 | -24.850 | 1.00 | 53.92 | C |
| ATOM | 4347 | CD1 | LEU | A | 686 | 52.165 | 84.723 | -24.594 | 1.00 | 54.64 | C |
| ATOM | 4348 | CD2 | LEU | A | 686 | 54.451 | 85.081 | -23.720 | 1.00 | 54.38 | C |
| ATOM | 4349 | N | GLY | A | 687 | 55.586 | 80.154 | -25.349 | 1.00 | 43.35 | N |
| ATOM | 4350 | CA | GLY | A | 687 | 55.888 | 78.843 | -24.801 | 1.00 | 32.54 | C |
| ATOM | 4351 | C | GLY | A | 687 | 57.372 | 78.586 | -24.679 | 1.00 | 46.98 | C |
| ATOM | 4352 | O | GLY | A | 687 | 57.803 | 77.670 | -23.991 | 1.00 | 52.51 | O |
| ATOM | 4353 | N | ALA | A | 688 | 58.158 | 79.388 | -25.379 | 1.00 | 41.16 | N |
| ATOM | 4354 | CA | ALA | A | 688 | 59.550 | 79.066 | -25.563 | 1.00 | 45.23 | C |
| ATOM | 4355 | C | ALA | A | 688 | 60.281 | 79.887 | -24.516 | 1.00 | 43.88 | C |
| ATOM | 4356 | O | ALA | A | 688 | 61.229 | 79.443 | -23.946 | 1.00 | 43.10 | O |
| ATOM | 4357 | CB | ALA | A | 688 | 60.008 | 79.433 | -26.959 | 1.00 | 39.70 | C |
| ATOM | 4358 | N | LYS | A | 689 | 59.785 | 81.088 | -24.282 | 1.00 | 43.70 | N |
| ATOM | 4359 | CA | LYS | A | 689 | 60.259 | 81.961 | -23.249 | 1.00 | 50.46 | C |
| ATOM | 4360 | C | LYS | A | 689 | 59.799 | 81.513 | -21.850 | 1.00 | 54.74 | C |
| ATOM | 4361 | O | LYS | A | 689 | 60.535 | 81.622 | -20.909 | 1.00 | 52.56 | O |
| ATOM | 4362 | CB | LYS | A | 689 | 59.794 | 83.387 | -23.577 | 1.00 | 51.52 | C |
| ATOM | 4363 | CG | LYS | A | 689 | 60.606 | 84.004 | -24.734 | 1.00 | 55.12 | C |
| ATOM | 4364 | CD | LYS | A | 689 | 60.595 | 85.543 | -24.764 | 1.00 | 62.13 | C |
| ATOM | 4365 | CE | LYS | A | 689 | 59.627 | 86.100 | -25.833 | 1.00 | 72.75 | C |
| ATOM | 4366 | NZ | LYS | A | 689 | 58.175 | 86.069 | -25.412 | 1.00 | 61.32 | N |
| ATOM | 4367 | N | TYR | A | 690 | 58.576 | 81.023 | -21.694 | 1.00 | 50.85 | N |
| ATOM | 4368 | CA | TYR | A | 690 | 58.192 | 80.579 | -20.371 | 1.00 | 46.03 | C |
| ATOM | 4369 | C | TYR | A | 690 | 57.778 | 79.128 | -20.344 | 1.00 | 32.47 | C |
| ATOM | 4370 | O | TYR | A | 690 | 56.691 | 78.833 | -19.994 | 1.00 | 34.12 | O |
| ATOM | 4371 | CB | TYR | A | 690 | 57.062 | 81.472 | -19.854 | 1.00 | 36.80 | C |
| ATOM | 4372 | CG | TYR | A | 690 | 57.485 | 82.917 | -19.782 | 1.00 | 46.06 | C |
| ATOM | 4373 | CD1 | TYR | A | 690 | 58.370 | 83.343 | -18.809 | 1.00 | 51.77 | C |
| ATOM | 4374 | CD2 | TYR | A | 690 | 57.018 | 83.851 | -20.694 | 1.00 | 51.39 | C |
| ATOM | 4375 | CE1 | TYR | A | 690 | 58.783 | 84.657 | -18.746 | 1.00 | 59.84 | C |
| ATOM | 4376 | CE2 | TYR | A | 690 | 57.428 | 85.175 | -20.638 | 1.00 | 54.89 | C |
| ATOM | 4377 | CZ | TYR | A | 690 | 58.309 | 85.570 | -19.663 | 1.00 | 59.12 | C |
| ATOM | 4378 | OH | TYR | A | 690 | 58.730 | 86.883 | -19.590 | 1.00 | 61.51 | O |
| ATOM | 4379 | N | PRO | A | 691 | 58.654 | 78.212 | -20.714 | 1.00 | 33.51 | N |
| ATOM | 4380 | CA | PRO | A | 691 | 58.221 | 76.815 | -20.837 | 1.00 | 36.34 | C |
| ATOM | 4381 | C | PRO | A | 691 | 57.691 | 76.222 | -19.530 | 1.00 | 46.03 | C |
| ATOM | 4382 | O | PRO | A | 691 | 56.812 | 75.357 | -19.551 | 1.00 | 42.30 | O |
| ATOM | 4383 | CB | PRO | A | 691 | 59.511 | 76.084 | -21.231 | 1.00 | 38.91 | C |
| ATOM | 4384 | CG | PRO | A | 691 | 60.652 | 77.062 | -20.891 | 1.00 | 39.04 | C |

FIG. 8-67

| | | | | | | | | | | | |
|---|---|---|---|---|---|---|---|---|---|---|---|
| ATOM | 4385 | CD | PRO | A | 691 | 60.041 | 78.406 | -21.175 | 1.00 | 35.01 | C |
| ATOM | 4386 | N | ASN | A | 692 | 58.226 | 76.666 | -18.399 | 1.00 | 45.88 | N |
| ATOM | 4387 | CA | ASN | A | 692 | 57.846 | 76.073 | -17.124 | 1.00 | 44.99 | C |
| ATOM | 4388 | C | ASN | A | 692 | 56.518 | 76.565 | -16.547 | 1.00 | 46.35 | C |
| ATOM | 4389 | O | ASN | A | 692 | 56.078 | 76.066 | -15.513 | 1.00 | 47.24 | O |
| ATOM | 4390 | CB | ASN | A | 692 | 58.989 | 76.241 | -16.108 | 1.00 | 42.69 | C |
| ATOM | 4391 | CG | ASN | A | 692 | 60.247 | 75.502 | -16.556 | 1.00 | 58.37 | C |
| ATOM | 4392 | OD1 | ASN | A | 692 | 60.147 | 74.396 | -17.101 | 1.00 | 62.11 | O |
| ATOM | 4393 | ND2 | ASN | A | 692 | 61.429 | 76.103 | -16.339 | 1.00 | 56.13 | N |
| ATOM | 4394 | N | LEU | A | 693 | 55.984 | 77.558 | -17.194 | 1.00 | 37.14 | N |
| ATOM | 4395 | CA | LEU | A | 693 | 54.602 | 78.043 | -16.774 | 1.00 | 38.37 | C |
| ATOM | 4396 | C | LEU | A | 693 | 53.464 | 77.259 | -17.404 | 1.00 | 45.00 | C |
| ATOM | 4397 | O | LEU | A | 693 | 52.326 | 77.396 | -16.976 | 1.00 | 42.00 | O |
| ATOM | 4398 | CB | LEU | A | 693 | 54.415 | 79.522 | -17.120 | 1.00 | 37.61 | C |
| ATOM | 4399 | CG | LEU | A | 693 | 55.477 | 80.544 | -16.728 | 1.00 | 57.93 | C |
| ATOM | 4400 | CD1 | LEU | A | 693 | 54.900 | 81.910 | -17.111 | 1.00 | 57.45 | C |
| ATOM | 4401 | CD2 | LEU | A | 693 | 55.897 | 80.460 | -15.206 | 1.00 | 46.74 | C |
| ATOM | 4402 | N | HIS | A | 694 | 53.760 | 76.467 | -18.438 | 1.00 | 49.68 | N |
| ATOM | 4403 | CA | HIS | A | 694 | 52.712 | 75.772 | -19.205 | 1.00 | 39.02 | C |
| ATOM | 4404 | C | HIS | A | 694 | 51.481 | 76.636 | -19.407 | 1.00 | 33.06 | C |
| ATOM | 4405 | O | HIS | A | 694 | 50.372 | 76.149 | -19.211 | 1.00 | 34.16 | O |
| ATOM | 4406 | CB | HIS | A | 694 | 52.288 | 74.471 | -18.487 | 1.00 | 31.33 | C |
| ATOM | 4407 | CG | HIS | A | 694 | 53.445 | 73.638 | -18.034 | 1.00 | 45.24 | C |
| ATOM | 4408 | ND1 | HIS | A | 694 | 53.839 | 73.557 | -16.712 | 1.00 | 52.47 | N |
| ATOM | 4409 | CD2 | HIS | A | 694 | 54.325 | 72.880 | -18.732 | 1.00 | 49.11 | C |
| ATOM | 4410 | CE1 | HIS | A | 694 | 54.891 | 72.765 | -16.614 | 1.00 | 51.87 | C |
| ATOM | 4411 | NE2 | HIS | A | 694 | 55.203 | 72.335 | -17.827 | 1.00 | 46.89 | N |
| ATOM | 4412 | N | LEU | A | 695 | 51.644 | 77.892 | -19.830 | 1.00 | 37.70 | N |
| ATOM | 4413 | CA | LEU | A | 695 | 50.466 | 78.744 | -20.057 | 1.00 | 40.74 | C |
| ATOM | 4414 | C | LEU | A | 695 | 49.477 | 78.159 | -21.058 | 1.00 | 39.63 | C |
| ATOM | 4415 | O | LEU | A | 695 | 49.864 | 77.411 | -21.928 | 1.00 | 40.09 | O |
| ATOM | 4416 | CB | LEU | A | 695 | 50.822 | 80.154 | -20.533 | 1.00 | 47.23 | C |
| ATOM | 4417 | CG | LEU | A | 695 | 51.641 | 81.137 | -19.698 | 1.00 | 49.40 | C |
| ATOM | 4418 | CD1 | LEU | A | 695 | 51.576 | 80.845 | -18.222 | 1.00 | 42.09 | C |
| ATOM | 4419 | CD2 | LEU | A | 695 | 52.984 | 81.000 | -20.167 | 1.00 | 44.12 | C |
| ATOM | 4420 | N | ALA | A | 696 | 48.197 | 78.482 | -20.870 | 1.00 | 30.06 | N |
| ATOM | 4421 | CA | ALA | A | 696 | 47.154 | 78.234 | -21.853 | 1.00 | 38.83 | C |
| ATOM | 4422 | C | ALA | A | 696 | 46.765 | 79.598 | -22.417 | 1.00 | 33.84 | C |
| ATOM | 4423 | O | ALA | A | 696 | 46.764 | 80.594 | -21.712 | 1.00 | 44.38 | O |
| ATOM | 4424 | CB | ALA | A | 696 | 45.953 | 77.511 | -21.227 | 1.00 | 31.24 | C |
| ATOM | 4425 | N | GLY | A | 697 | 46.545 | 79.673 | -23.714 | 1.00 | 41.44 | N |
| ATOM | 4426 | CA | GLY | A | 697 | 46.335 | 80.971 | -24.308 | 1.00 | 38.82 | C |
| ATOM | 4427 | C | GLY | A | 697 | 45.745 | 80.880 | -25.675 | 1.00 | 36.18 | C |
| ATOM | 4428 | O | GLY | A | 697 | 45.630 | 79.800 | -26.271 | 1.00 | 39.60 | O |
| ATOM | 4429 | N | LYS | A | 698 | 45.305 | 82.034 | -26.145 | 1.00 | 29.63 | N |
| ATOM | 4430 | CA | LYS | A | 698 | 44.751 | 82.167 | -27.455 | 1.00 | 29.51 | C |
| ATOM | 4431 | C | LYS | A | 698 | 45.115 | 83.545 | -28.015 | 1.00 | 33.91 | C |
| ATOM | 4432 | O | LYS | A | 698 | 44.871 | 84.573 | -27.380 | 1.00 | 34.42 | O |
| ATOM | 4433 | CB | LYS | A | 698 | 43.230 | 81.961 | -27.437 | 1.00 | 30.25 | C |
| ATOM | 4434 | CG | LYS | A | 698 | 42.619 | 81.950 | -28.881 | 1.00 | 41.40 | C |
| ATOM | 4435 | CD | LYS | A | 698 | 42.937 | 80.633 | -29.620 | 1.00 | 29.85 | C |
| ATOM | 4436 | CE | LYS | A | 698 | 42.771 | 80.666 | -31.175 | 1.00 | 33.64 | C |
| ATOM | 4437 | NZ | LYS | A | 698 | 43.436 | 81.749 | -31.909 | 1.00 | 29.74 | N |
| ATOM | 4438 | N | THR | A | 699 | 45.735 | 83.550 | -29.190 | 1.00 | 32.66 | N |
| ATOM | 4439 | CA | THR | A | 699 | 45.918 | 84.757 | -29.966 | 1.00 | 37.46 | C |
| ATOM | 4440 | C | THR | A | 699 | 44.649 | 85.215 | -30.690 | 1.00 | 42.07 | C |
| ATOM | 4441 | O | THR | A | 699 | 43.852 | 84.397 | -31.166 | 1.00 | 35.61 | O |
| ATOM | 4442 | CB | THR | A | 699 | 46.950 | 84.521 | -31.070 | 1.00 | 39.73 | C |
| ATOM | 4443 | OG1 | THR | A | 699 | 46.584 | 83.346 | -31.809 | 1.00 | 35.66 | O |
| ATOM | 4444 | CG2 | THR | A | 699 | 48.345 | 84.344 | -30.458 | 1.00 | 45.58 | C |
| ATOM | 4445 | N | GLY | A | 700 | 44.505 | 86.534 | -30.814 | 1.00 | 36.47 | N |
| ATOM | 4446 | CA | GLY | A | 700 | 43.433 | 87.118 | -31.579 | 1.00 | 36.57 | C |
| ATOM | 4447 | C | GLY | A | 700 | 43.981 | 88.065 | -32.620 | 1.00 | 42.49 | C |
| ATOM | 4448 | O | GLY | A | 700 | 44.742 | 88.977 | -32.295 | 1.00 | 43.17 | O |
| ATOM | 4449 | N | THR | A | 701 | 43.663 | 87.797 | -33.885 | 1.00 | 45.97 | N |
| ATOM | 4450 | CA | THR | A | 701 | 43.981 | 88.726 | -34.954 | 1.00 | 48.30 | C |
| ATOM | 4451 | C | THR | A | 701 | 42.714 | 88.959 | -35.764 | 1.00 | 44.73 | C |
| ATOM | 4452 | O | THR | A | 701 | 41.797 | 88.144 | -35.715 | 1.00 | 45.03 | O |
| ATOM | 4453 | CB | THR | A | 701 | 45.134 | 88.235 | -35.900 | 1.00 | 56.07 | C |
| ATOM | 4454 | OG1 | THR | A | 701 | 44.724 | 87.051 | -36.595 | 1.00 | 51.70 | O |
| ATOM | 4455 | CG2 | THR | A | 701 | 46.443 | 87.956 | -35.102 | 1.00 | 47.07 | C |
| ATOM | 4456 | N | THR | A | 702 | 42.705 | 90.063 | -36.508 | 1.00 | 43.81 | N |
| ATOM | 4457 | CA | THR | A | 702 | 41.609 | 90.486 | -37.359 | 1.00 | 48.00 | C |
| ATOM | 4458 | C | THR | A | 702 | 42.223 | 90.839 | -38.723 | 1.00 | 52.89 | C |
| ATOM | 4459 | O | THR | A | 702 | 43.445 | 91.035 | -38.842 | 1.00 | 47.61 | O |
| ATOM | 4460 | CB | THR | A | 702 | 40.973 | 91.768 | -36.791 | 1.00 | 46.67 | C |
| ATOM | 4461 | OG1 | THR | A | 702 | 42.012 | 92.721 | -36.539 | 1.00 | 52.35 | O |

FIG. 8-68

| | | | | | | | | | | | |
|---|---|---|---|---|---|---|---|---|---|---|---|
| ATOM | 4462 | CG2 | THR | A | 702 | 40.226 | 91.504 | -35.477 | 1.00 | 40.08 | C |
| ATOM | 4463 | N | ASN | A | 703 | 41.403 | 90.927 | -39.763 | 1.00 | 57.39 | N |
| ATOM | 4464 | CA | ASN | A | 703 | 41.943 | 91.302 | -41.082 | 1.00 | 53.91 | C |
| ATOM | 4465 | C | ASN | A | 703 | 42.822 | 92.560 | -41.047 | 1.00 | 57.56 | C |
| ATOM | 4466 | O | ASN | A | 703 | 42.435 | 93.596 | -40.509 | 1.00 | 65.43 | O |
| ATOM | 4467 | CB | ASN | A | 703 | 40.818 | 91.482 | -42.066 | 1.00 | 63.31 | C |
| ATOM | 4468 | CG | ASN | A | 703 | 41.246 | 91.194 | -43.491 | 1.00 | 69.61 | C |
| ATOM | 4469 | OD1 | ASN | A | 703 | 40.728 | 91.794 | -44.435 | 1.00 | 68.79 | O |
| ATOM | 4470 | ND2 | ASN | A | 703 | 42.200 | 90.271 | -43.653 | 1.00 | 69.70 | N |
| ATOM | 4471 | N | ASN | A | 704 | 44.028 | 92.460 | -41.584 | 1.00 | 60.92 | N |
| ATOM | 4472 | CA | ASN | A | 704 | 44.962 | 93.592 | -41.576 | 1.00 | 64.48 | C |
| ATOM | 4473 | C | ASN | A | 704 | 45.446 | 94.041 | -40.201 | 1.00 | 60.95 | C |
| ATOM | 4474 | O | ASN | A | 704 | 46.015 | 95.122 | -40.060 | 1.00 | 60.28 | O |
| ATOM | 4475 | CB | ASN | A | 704 | 44.347 | 94.787 | -42.294 | 1.00 | 72.26 | C |
| ATOM | 4476 | CG | ASN | A | 704 | 44.705 | 94.827 | -43.762 | 1.00 | 72.11 | C |
| ATOM | 4477 | OD1 | ASN | A | 704 | 44.749 | 93.790 | -44.441 | 1.00 | 68.82 | O |
| ATOM | 4478 | ND2 | ASN | A | 704 | 44.962 | 96.029 | -44.265 | 1.00 | 73.44 | N |
| ATOM | 4479 | N | ASN | A | 705 | 45.197 | 93.226 | -39.188 | 1.00 | 60.16 | N |
| ATOM | 4480 | CA | ASN | A | 705 | 45.563 | 93.589 | -37.822 | 1.00 | 62.85 | C |
| ATOM | 4481 | C | ASN | A | 705 | 45.025 | 94.960 | -37.371 | 1.00 | 60.26 | C |
| ATOM | 4482 | O | ASN | A | 705 | 45.784 | 95.795 | -36.860 | 1.00 | 57.54 | O |
| ATOM | 4483 | CB | ASN | A | 705 | 47.084 | 93.532 | -37.653 | 1.00 | 64.38 | C |
| ATOM | 4484 | CG | ASN | A | 705 | 47.692 | 92.287 | -38.275 | 1.00 | 69.49 | C |
| ATOM | 4485 | OD1 | ASN | A | 705 | 48.503 | 92.372 | -39.210 | 1.00 | 80.28 | O |
| ATOM | 4486 | ND2 | ASN | A | 705 | 47.294 | 91.121 | -37.774 | 1.00 | 59.85 | N |
| ATOM | 4487 | N | VAL | A | 706 | 43.722 | 95.192 | -37.558 | 1.00 | 48.04 | N |
| ATOM | 4488 | CA | VAL | A | 706 | 43.059 | 96.340 | -36.930 | 1.00 | 41.28 | C |
| ATOM | 4489 | C | VAL | A | 706 | 43.061 | 96.193 | -35.386 | 1.00 | 43.95 | C |
| ATOM | 4490 | O | VAL | A | 706 | 43.372 | 97.148 | -34.666 | 1.00 | 45.01 | O |
| ATOM | 4491 | CB | VAL | A | 706 | 41.627 | 96.534 | -37.476 | 1.00 | 49.41 | C |
| ATOM | 4492 | CG1 | VAL | A | 706 | 40.857 | 97.541 | -36.642 | 1.00 | 49.48 | C |
| ATOM | 4493 | CG2 | VAL | A | 706 | 41.671 | 96.985 | -38.948 | 1.00 | 54.34 | C |
| ATOM | 4494 | N | ASP | A | 707 | 42.729 | 94.990 | -34.899 | 1.00 | 44.94 | N |
| ATOM | 4495 | CA | ASP | A | 707 | 42.755 | 94.644 | -33.468 | 1.00 | 47.05 | C |
| ATOM | 4496 | C | ASP | A | 707 | 43.584 | 93.401 | -33.273 | 1.00 | 40.74 | C |
| ATOM | 4497 | O | ASP | A | 707 | 43.503 | 92.473 | -34.079 | 1.00 | 40.78 | O |
| ATOM | 4498 | CB | ASP | A | 707 | 41.332 | 94.309 | -32.961 | 1.00 | 45.39 | C |
| ATOM | 4499 | CG | ASP | A | 707 | 40.386 | 95.491 | -33.052 | 1.00 | 54.05 | C |
| ATOM | 4500 | OD1 | ASP | A | 707 | 40.606 | 96.472 | -32.299 | 1.00 | 55.64 | O |
| ATOM | 4501 | OD2 | ASP | A | 707 | 39.414 | 95.426 | -33.855 | 1.00 | 49.55 | O |
| ATOM | 4502 | N | THR | A | 708 | 44.353 | 93.356 | -32.193 | 1.00 | 42.20 | N |
| ATOM | 4503 | CA | THR | A | 708 | 45.156 | 92.176 | -31.867 | 1.00 | 42.58 | C |
| ATOM | 4504 | C | THR | A | 708 | 45.002 | 91.942 | -30.383 | 1.00 | 40.41 | C |
| ATOM | 4505 | O | THR | A | 708 | 44.830 | 92.885 | -29.602 | 1.00 | 36.76 | O |
| ATOM | 4506 | CB | THR | A | 708 | 46.660 | 92.344 | -32.148 | 1.00 | 46.97 | C |
| ATOM | 4507 | OG1 | THR | A | 708 | 47.173 | 93.390 | -31.325 | 1.00 | 55.25 | O |
| ATOM | 4508 | CG2 | THR | A | 708 | 46.945 | 92.670 | -33.621 | 1.00 | 55.91 | C |
| ATOM | 4509 | N | TRP | A | 709 | 45.072 | 90.687 | -29.986 | 1.00 | 31.70 | N |
| ATOM | 4510 | CA | TRP | A | 709 | 44.631 | 90.354 | -28.653 | 1.00 | 36.11 | C |
| ATOM | 4511 | C | TRP | A | 709 | 45.451 | 89.182 | -28.266 | 1.00 | 37.41 | C |
| ATOM | 4512 | O | TRP | A | 709 | 45.884 | 88.407 | -29.143 | 1.00 | 33.86 | O |
| ATOM | 4513 | CB | TRP | A | 709 | 43.174 | 89.849 | -28.609 | 1.00 | 38.46 | C |
| ATOM | 4514 | CG | TRP | A | 709 | 41.997 | 90.762 | -28.944 | 1.00 | 38.42 | C |
| ATOM | 4515 | CD1 | TRP | A | 709 | 41.503 | 91.012 | -30.174 | 1.00 | 43.24 | C |
| ATOM | 4516 | CD2 | TRP | A | 709 | 41.106 | 91.430 | -28.017 | 1.00 | 36.38 | C |
| ATOM | 4517 | NE1 | TRP | A | 709 | 40.384 | 91.830 | -30.098 | 1.00 | 41.54 | N |
| ATOM | 4518 | CE2 | TRP | A | 709 | 40.126 | 92.112 | -28.792 | 1.00 | 39.46 | C |
| ATOM | 4519 | CE3 | TRP | A | 709 | 41.079 | 91.571 | -26.630 | 1.00 | 31.70 | C |
| ATOM | 4520 | CZ2 | TRP | A | 709 | 39.106 | 92.891 | -28.217 | 1.00 | 47.51 | C |
| ATOM | 4521 | CZ3 | TRP | A | 709 | 40.055 | 92.337 | -26.047 | 1.00 | 47.93 | C |
| ATOM | 4522 | CH2 | TRP | A | 709 | 39.080 | 92.991 | -26.845 | 1.00 | 43.83 | C |
| ATOM | 4523 | N | PHE | A | 710 | 45.625 | 89.042 | -26.952 | 1.00 | 33.16 | N |
| ATOM | 4524 | CA | PHE | A | 710 | 46.060 | 87.790 | -26.385 | 1.00 | 42.33 | C |
| ATOM | 4525 | C | PHE | A | 710 | 45.342 | 87.497 | -25.079 | 1.00 | 41.86 | C |
| ATOM | 4526 | O | PHE | A | 710 | 45.129 | 88.382 | -24.234 | 1.00 | 36.56 | O |
| ATOM | 4527 | CB | PHE | A | 710 | 47.574 | 87.748 | -26.183 | 1.00 | 46.10 | C |
| ATOM | 4528 | CG | PHE | A | 710 | 48.088 | 86.377 | -25.874 | 1.00 | 47.37 | C |
| ATOM | 4529 | CD1 | PHE | A | 710 | 48.348 | 85.992 | -24.569 | 1.00 | 42.25 | C |
| ATOM | 4530 | CD2 | PHE | A | 710 | 48.261 | 85.450 | -26.887 | 1.00 | 41.23 | C |
| ATOM | 4531 | CE1 | PHE | A | 710 | 48.814 | 84.706 | -24.293 | 1.00 | 44.05 | C |
| ATOM | 4532 | CE2 | PHE | A | 710 | 48.712 | 84.173 | -26.615 | 1.00 | 41.00 | C |
| ATOM | 4533 | CZ | PHE | A | 710 | 49.001 | 83.792 | -25.326 | 1.00 | 40.35 | C |
| ATOM | 4534 | N | ALA | A | 711 | 44.956 | 86.235 | -24.924 | 1.00 | 41.17 | N |
| ATOM | 4535 | CA | ALA | A | 711 | 44.341 | 85.788 | -23.689 | 1.00 | 35.36 | C |
| ATOM | 4536 | C | ALA | A | 711 | 45.187 | 84.698 | -23.104 | 1.00 | 41.05 | C |
| ATOM | 4537 | O | ALA | A | 711 | 45.389 | 83.613 | -23.700 | 1.00 | 39.44 | O |
| ATOM | 4538 | CB | ALA | A | 711 | 42.903 | 85.307 | -23.912 | 1.00 | 32.78 | C |

FIG. 8-69

| | | | | | | | | | | | |
|---|---|---|---|---|---|---|---|---|---|---|---|
| ATOM | 4539 | N | GLY | A | 712 | 45.708 | 85.011 | -21.931 | 1.00 | 39.25 | N |
| ATOM | 4540 | CA | GLY | A | 712 | 46.701 | 84.178 | -21.305 | 1.00 | 34.79 | C |
| ATOM | 4541 | C | GLY | A | 712 | 46.177 | 83.714 | -19.976 | 1.00 | 36.32 | C |
| ATOM | 4542 | O | GLY | A | 712 | 45.806 | 84.511 | -19.123 | 1.00 | 40.20 | O |
| ATOM | 4543 | N | ILE | A | 713 | 46.165 | 82.406 | -19.805 | 1.00 | 36.27 | N |
| ATOM | 4544 | CA | ILE | A | 713 | 45.732 | 81.802 | -18.571 | 1.00 | 34.89 | C |
| ATOM | 4545 | C | ILE | A | 713 | 46.908 | 81.139 | -17.880 | 1.00 | 39.11 | C |
| ATOM | 4546 | O | ILE | A | 713 | 47.509 | 80.186 | -18.410 | 1.00 | 30.77 | O |
| ATOM | 4547 | CB | ILE | A | 713 | 44.698 | 80.729 | -18.859 | 1.00 | 35.24 | C |
| ATOM | 4548 | CG1 | ILE | A | 713 | 43.517 | 81.359 | -19.638 | 1.00 | 37.94 | C |
| ATOM | 4549 | CG2 | ILE | A | 713 | 44.342 | 79.979 | -17.547 | 1.00 | 31.40 | C |
| ATOM | 4550 | CD1 | ILE | A | 713 | 42.652 | 80.373 | -20.345 | 1.00 | 41.75 | C |
| ATOM | 4551 | N | ASP | A | 714 | 47.234 | 81.626 | -16.687 | 1.00 | 39.92 | N |
| ATOM | 4552 | CA | ASP | A | 714 | 48.221 | 80.948 | -15.874 | 1.00 | 36.92 | C |
| ATOM | 4553 | C | ASP | A | 714 | 47.547 | 80.244 | -14.667 | 1.00 | 45.06 | C |
| ATOM | 4554 | O | ASP | A | 714 | 46.317 | 80.127 | -14.596 | 1.00 | 37.09 | O |
| ATOM | 4555 | CB | ASP | A | 714 | 49.347 | 81.915 | -15.472 | 1.00 | 41.18 | C |
| ATOM | 4556 | CG | ASP | A | 714 | 49.041 | 82.721 | -14.213 | 1.00 | 55.57 | C |
| ATOM | 4557 | OD1 | ASP | A | 714 | 49.857 | 83.619 | -13.883 | 1.00 | 67.90 | O |
| ATOM | 4558 | OD2 | ASP | A | 714 | 48.028 | 82.466 | -13.528 | 1.00 | 57.12 | O |
| ATOM | 4559 | N | GLY | A | 715 | 48.357 | 79.793 | -13.728 | 1.00 | 36.54 | N |
| ATOM | 4560 | CA | GLY | A | 715 | 47.878 | 79.077 | -12.562 | 1.00 | 44.91 | C |
| ATOM | 4561 | C | GLY | A | 715 | 46.782 | 79.794 | -11.802 | 1.00 | 43.36 | C |
| ATOM | 4562 | O | GLY | A | 715 | 45.850 | 79.154 | -11.334 | 1.00 | 46.26 | O |
| ATOM | 4563 | N | SER | A | 716 | 46.844 | 81.117 | -11.729 | 1.00 | 38.47 | N |
| ATOM | 4564 | CA | SER | A | 716 | 45.984 | 81.843 | -10.795 | 1.00 | 47.02 | C |
| ATOM | 4565 | C | SER | A | 716 | 45.149 | 82.923 | -11.470 | 1.00 | 46.32 | C |
| ATOM | 4566 | O | SER | A | 716 | 44.168 | 83.392 | -10.916 | 1.00 | 43.20 | O |
| ATOM | 4567 | CB | SER | A | 716 | 46.836 | 82.506 | -9.688 | 1.00 | 50.58 | C |
| ATOM | 4568 | OG | SER | A | 716 | 47.743 | 81.598 | -9.090 | 1.00 | 62.19 | O |
| ATOM | 4569 | N | THR | A | 717 | 45.539 | 83.350 | -12.660 | 1.00 | 40.95 | N |
| ATOM | 4570 | CA | THR | A | 717 | 44.823 | 84.468 | -13.255 | 1.00 | 38.70 | C |
| ATOM | 4571 | C | THR | A | 717 | 44.632 | 84.296 | -14.761 | 1.00 | 39.08 | C |
| ATOM | 4572 | O | THR | A | 717 | 45.205 | 83.393 | -15.370 | 1.00 | 36.96 | O |
| ATOM | 4573 | CB | THR | A | 717 | 45.493 | 85.820 | -12.929 | 1.00 | 45.91 | C |
| ATOM | 4574 | OG1 | THR | A | 717 | 46.713 | 85.940 | -13.671 | 1.00 | 44.74 | O |
| ATOM | 4575 | CG2 | THR | A | 717 | 45.811 | 85.940 | -11.354 | 1.00 | 31.83 | C |
| ATOM | 4576 | N | VAL | A | 718 | 43.784 | 85.148 | -15.298 | 1.00 | 35.18 | N |
| ATOM | 4577 | CA | VAL | A | 718 | 43.476 | 85.294 | -16.704 | 1.00 | 35.71 | C |
| ATOM | 4578 | C | VAL | A | 718 | 43.806 | 86.737 | -17.030 | 1.00 | 39.68 | C |
| ATOM | 4579 | O | VAL | A | 718 | 43.384 | 87.658 | -16.347 | 1.00 | 42.04 | O |
| ATOM | 4580 | CB | VAL | A | 718 | 42.005 | 85.035 | -17.021 | 1.00 | 38.10 | C |
| ATOM | 4581 | CG1 | VAL | A | 718 | 41.721 | 85.302 | -18.528 | 1.00 | 36.72 | C |
| ATOM | 4582 | CG2 | VAL | A | 718 | 41.627 | 83.612 | -16.642 | 1.00 | 36.30 | C |
| ATOM | 4583 | N | THR | A | 719 | 44.619 | 86.929 | -18.058 | 1.00 | 37.64 | N |
| ATOM | 4584 | CA | THR | A | 719 | 45.012 | 88.265 | -18.446 | 1.00 | 38.26 | C |
| ATOM | 4585 | C | THR | A | 719 | 44.561 | 88.457 | -19.886 | 1.00 | 42.49 | C |
| ATOM | 4586 | O | THR | A | 719 | 44.906 | 87.677 | -20.752 | 1.00 | 42.40 | O |
| ATOM | 4587 | CB | THR | A | 719 | 46.546 | 88.446 | -18.318 | 1.00 | 39.41 | C |
| ATOM | 4588 | OG1 | THR | A | 719 | 46.967 | 88.120 | -16.969 | 1.00 | 44.82 | O |
| ATOM | 4589 | CG2 | THR | A | 719 | 46.951 | 89.887 | -18.628 | 1.00 | 40.53 | C |
| ATOM | 4590 | N | ILE | A | 720 | 43.764 | 89.483 | -20.127 | 1.00 | 44.03 | N |
| ATOM | 4591 | CA | ILE | A | 720 | 43.403 | 89.859 | -21.476 | 1.00 | 40.10 | C |
| ATOM | 4592 | C | ILE | A | 720 | 44.191 | 91.093 | -21.874 | 1.00 | 42.76 | C |
| ATOM | 4593 | O | ILE | A | 720 | 44.260 | 92.060 | -21.128 | 1.00 | 46.84 | O |
| ATOM | 4594 | CB | ILE | A | 720 | 41.882 | 90.124 | -21.655 | 1.00 | 44.70 | C |
| ATOM | 4595 | CG1 | ILE | A | 720 | 41.059 | 88.909 | -21.221 | 1.00 | 41.30 | C |
| ATOM | 4596 | CG2 | ILE | A | 720 | 41.576 | 90.449 | -23.103 | 1.00 | 43.63 | C |
| ATOM | 4597 | CD1 | ILE | A | 720 | 41.537 | 87.592 | -21.847 | 1.00 | 39.33 | C |
| ATOM | 4598 | N | THR | A | 721 | 44.778 | 91.047 | -23.067 | 1.00 | 35.89 | N |
| ATOM | 4599 | CA | THR | A | 721 | 45.559 | 92.142 | -23.582 | 1.00 | 30.47 | C |
| ATOM | 4600 | C | THR | A | 721 | 44.995 | 92.456 | -24.986 | 1.00 | 36.60 | C |
| ATOM | 4601 | O | THR | A | 721 | 44.836 | 91.555 | -25.799 | 1.00 | 36.76 | O |
| ATOM | 4602 | CB | THR | A | 721 | 47.036 | 91.715 | -23.704 | 1.00 | 43.32 | C |
| ATOM | 4603 | OG1 | THR | A | 721 | 47.581 | 91.429 | -22.408 | 1.00 | 44.08 | O |
| ATOM | 4604 | CG2 | THR | A | 721 | 47.867 | 92.788 | -24.370 | 1.00 | 42.53 | C |
| ATOM | 4605 | N | TRP | A | 722 | 44.676 | 93.727 | -25.232 | 1.00 | 31.55 | N |
| ATOM | 4606 | CA | TRP | A | 722 | 44.339 | 94.246 | -26.541 | 1.00 | 37.16 | C |
| ATOM | 4607 | C | TRP | A | 722 | 45.351 | 95.298 | -26.946 | 1.00 | 41.59 | C |
| ATOM | 4608 | O | TRP | A | 722 | 45.710 | 96.132 | -26.129 | 1.00 | 38.30 | O |
| ATOM | 4609 | CB | TRP | A | 722 | 42.986 | 94.932 | -26.472 | 1.00 | 41.16 | C |
| ATOM | 4610 | CG | TRP | A | 722 | 42.654 | 95.720 | -27.663 | 1.00 | 48.84 | C |
| ATOM | 4611 | CD1 | TRP | A | 722 | 42.108 | 95.253 | -28.824 | 1.00 | 45.36 | C |
| ATOM | 4612 | CD2 | TRP | A | 722 | 42.838 | 97.133 | -27.845 | 1.00 | 50.02 | C |
| ATOM | 4613 | NE1 | TRP | A | 722 | 41.938 | 96.273 | -29.696 | 1.00 | 39.40 | N |
| ATOM | 4614 | CE2 | TRP | A | 722 | 42.382 | 97.441 | -29.136 | 1.00 | 47.43 | C |
| ATOM | 4615 | CE3 | TRP | A | 722 | 43.333 | 98.161 | -27.039 | 1.00 | 43.50 | C |

FIG. 8-70

| | | | | | | | | | | | |
|---|---|---|---|---|---|---|---|---|---|---|---|
| ATOM | 4616 | CZ2 | TRP | A | 722 | 42.405 | 98.742 | -29.651 | 1.00 | 49.78 | C |
| ATOM | 4617 | CZ3 | TRP | A | 722 | 43.366 | 99.444 | -27.542 | 1.00 | 44.92 | C |
| ATOM | 4618 | CH2 | TRP | A | 722 | 42.904 | 99.728 | -28.844 | 1.00 | 50.23 | C |
| ATOM | 4619 | N | VAL | A | 723 | 45.759 | 95.272 | -28.218 | 1.00 | 42.23 | N |
| ATOM | 4620 | CA | VAL | A | 723 | 46.586 | 96.300 | -28.850 | 1.00 | 42.05 | C |
| ATOM | 4621 | C | VAL | A | 723 | 45.985 | 96.699 | -30.192 | 1.00 | 41.45 | C |
| ATOM | 4622 | O | VAL | A | 723 | 45.654 | 95.839 | -31.006 | 1.00 | 41.10 | O |
| ATOM | 4623 | CB | VAL | A | 723 | 47.990 | 95.784 | -29.164 | 1.00 | 41.90 | C |
| ATOM | 4624 | CG1 | VAL | A | 723 | 48.773 | 96.840 | -29.893 | 1.00 | 44.24 | C |
| ATOM | 4625 | CG2 | VAL | A | 723 | 48.710 | 95.448 | -27.898 | 1.00 | 44.66 | C |
| ATOM | 4626 | N | GLY | A | 724 | 45.829 | 97.997 | -30.416 | 1.00 | 39.48 | N |
| ATOM | 4627 | CA | GLY | A | 724 | 45.299 | 98.492 | -31.669 | 1.00 | 40.59 | C |
| ATOM | 4628 | C | GLY | A | 724 | 45.299 | 100.005 | -31.621 | 1.00 | 48.38 | C |
| ATOM | 4629 | O | GLY | A | 724 | 45.898 | 100.587 | -30.728 | 1.00 | 49.32 | O |
| ATOM | 4630 | N | ARG | A | 725 | 44.597 | 100.649 | -32.549 | 1.00 | 50.67 | N |
| ATOM | 4631 | CA | ARG | A | 725 | 44.592 | 102.111 | -32.606 | 1.00 | 52.94 | C |
| ATOM | 4632 | C | ARG | A | 725 | 43.199 | 102.679 | -32.392 | 1.00 | 58.29 | C |
| ATOM | 4633 | O | ARG | A | 725 | 42.216 | 102.106 | -32.848 | 1.00 | 53.66 | O |
| ATOM | 4634 | CB | ARG | A | 725 | 45.127 | 102.572 | -33.951 | 1.00 | 51.51 | C |
| ATOM | 4635 | CG | ARG | A | 725 | 46.403 | 101.863 | -34.375 | 1.00 | 54.62 | C |
| ATOM | 4636 | CD | ARG | A | 725 | 46.760 | 102.234 | -35.815 | 1.00 | 65.15 | C |
| ATOM | 4637 | NE | ARG | A | 725 | 47.424 | 103.526 | -35.893 | 1.00 | 69.21 | N |
| ATOM | 4638 | CZ | ARG | A | 725 | 47.679 | 104.161 | -37.028 | 1.00 | 74.53 | C |
| ATOM | 4639 | NH1 | ARG | A | 725 | 47.310 | 103.629 | -38.187 | 1.00 | 73.40 | N |
| ATOM | 4640 | NH2 | ARG | A | 725 | 48.295 | 105.332 | -36.999 | 1.00 | 80.77 | N |
| ATOM | 4641 | N | ASP | A | 726 | 43.108 | 103.809 | -31.698 | 1.00 | 63.03 | N |
| ATOM | 4642 | CA | ASP | A | 726 | 41.801 | 104.384 | -31.387 | 1.00 | 59.41 | C |
| ATOM | 4643 | C | ASP | A | 726 | 40.987 | 104.679 | -32.655 | 1.00 | 66.00 | C |
| ATOM | 4644 | O | ASP | A | 726 | 39.759 | 104.541 | -32.658 | 1.00 | 70.95 | O |
| ATOM | 4645 | CB | ASP | A | 726 | 41.952 | 105.660 | -30.561 | 1.00 | 59.01 | C |
| ATOM | 4646 | CG | ASP | A | 726 | 42.443 | 105.396 | -29.142 | 1.00 | 58.71 | C |
| ATOM | 4647 | OD1 | ASP | A | 726 | 42.377 | 104.240 | -28.671 | 1.00 | 52.10 | O |
| ATOM | 4648 | OD2 | ASP | A | 726 | 42.904 | 106.361 | -28.495 | 1.00 | 61.73 | O |
| ATOM | 4649 | N | ASN | A | 727 | 41.662 | 105.082 | -33.731 | 1.00 | 63.66 | N |
| ATOM | 4650 | CA | ASN | A | 727 | 40.954 | 105.418 | -34.968 | 1.00 | 64.15 | C |
| ATOM | 4651 | C | ASN | A | 727 | 40.569 | 104.196 | -35.801 | 1.00 | 63.77 | C |
| ATOM | 4652 | O | ASN | A | 727 | 39.959 | 104.331 | -36.857 | 1.00 | 63.55 | O |
| ATOM | 4653 | CB | ASN | A | 727 | 41.751 | 106.413 | -35.816 | 1.00 | 64.31 | C |
| ATOM | 4654 | CG | ASN | A | 727 | 43.068 | 105.832 | -36.323 | 1.00 | 70.08 | C |
| ATOM | 4655 | OD1 | ASN | A | 727 | 43.293 | 104.622 | -36.258 | 1.00 | 66.75 | O |
| ATOM | 4656 | ND2 | ASN | A | 727 | 43.943 | 106.696 | -36.837 | 1.00 | 72.48 | N |
| ATOM | 4657 | N | ASN | A | 728 | 40.923 | 103.006 | -35.328 | 1.00 | 57.70 | N |
| ATOM | 4658 | CA | ASN | A | 728 | 40.446 | 101.774 | -35.956 | 1.00 | 63.21 | C |
| ATOM | 4659 | C | ASN | A | 728 | 41.097 | 101.439 | -37.289 | 1.00 | 66.90 | C |
| ATOM | 4660 | O | ASN | A | 728 | 40.504 | 100.736 | -38.103 | 1.00 | 73.92 | O |
| ATOM | 4661 | CB | ASN | A | 728 | 38.928 | 101.824 | -36.159 | 1.00 | 62.95 | C |
| ATOM | 4662 | CG | ASN | A | 728 | 38.164 | 101.292 | -34.970 | 1.00 | 68.88 | C |
| ATOM | 4663 | OD1 | ASN | A | 728 | 38.245 | 100.099 | -34.630 | 1.00 | 69.52 | O |
| ATOM | 4664 | ND2 | ASN | A | 728 | 37.399 | 102.171 | -34.333 | 1.00 | 66.56 | N |
| ATOM | 4665 | N | GLN | A | 729 | 42.306 | 101.941 | -37.514 | 1.00 | 63.92 | N |
| ATOM | 4666 | CA | GLN | A | 729 | 43.051 | 101.640 | -38.731 | 1.00 | 69.09 | C |
| ATOM | 4667 | C | GLN | A | 729 | 44.076 | 100.530 | -38.495 | 1.00 | 62.41 | C |
| ATOM | 4668 | O | GLN | A | 729 | 44.396 | 100.213 | -37.357 | 1.00 | 63.37 | O |
| ATOM | 4669 | CB | GLN | A | 729 | 43.750 | 102.896 | -39.226 | 1.00 | 78.44 | C |
| ATOM | 4670 | CG | GLN | A | 729 | 42.798 | 104.007 | -39.604 | 1.00 | 89.95 | C |
| ATOM | 4671 | CD | GLN | A | 729 | 43.509 | 105.334 | -39.727 | 1.00 | 102.64 | C |
| ATOM | 4672 | OE1 | GLN | A | 729 | 44.449 | 105.616 | -38.978 | 1.00 | 103.05 | O |
| ATOM | 4673 | NE2 | GLN | A | 729 | 43.072 | 106.160 | -40.679 | 1.00 | 107.97 | N |
| ATOM | 4674 | N | PRO | A | 730 | 44.602 | 99.936 | -39.575 | 1.00 | 59.41 | N |
| ATOM | 4675 | CA | PRO | A | 730 | 45.536 | 98.824 | -39.384 | 1.00 | 57.99 | C |
| ATOM | 4676 | C | PRO | A | 730 | 46.799 | 99.249 | -38.623 | 1.00 | 67.75 | C |
| ATOM | 4677 | O | PRO | A | 730 | 47.284 | 100.379 | -38.765 | 1.00 | 72.71 | O |
| ATOM | 4678 | CB | PRO | A | 730 | 45.876 | 98.386 | -40.804 | 1.00 | 58.46 | C |
| ATOM | 4679 | CG | PRO | A | 730 | 44.754 | 98.948 | -41.667 | 1.00 | 66.02 | C |
| ATOM | 4680 | CD | PRO | A | 730 | 44.367 | 100.236 | -40.996 | 1.00 | 65.19 | C |
| ATOM | 4681 | N | THR | A | 731 | 47.316 | 98.326 | -37.817 | 1.00 | 63.93 | N |
| ATOM | 4682 | CA | THR | A | 731 | 48.388 | 98.610 | -36.881 | 1.00 | 69.38 | C |
| ATOM | 4683 | C | THR | A | 731 | 49.777 | 98.414 | -37.462 | 1.00 | 77.90 | C |
| ATOM | 4684 | O | THR | A | 731 | 50.750 | 98.940 | -36.916 | 1.00 | 79.43 | O |
| ATOM | 4685 | CB | THR | A | 731 | 48.287 | 97.687 | -35.689 | 1.00 | 65.57 | C |
| ATOM | 4686 | OG1 | THR | A | 731 | 48.261 | 96.336 | -36.169 | 1.00 | 67.37 | O |
| ATOM | 4687 | CG2 | THR | A | 731 | 47.015 | 97.975 | -34.917 | 1.00 | 62.30 | C |
| ATOM | 4688 | N | LYS | A | 732 | 49.866 | 97.656 | -38.556 | 1.00 | 78.93 | N |
| ATOM | 4689 | CA | LYS | A | 732 | 51.151 | 97.263 | -39.143 | 1.00 | 78.67 | C |
| ATOM | 4690 | C | LYS | A | 732 | 51.888 | 96.208 | -38.288 | 1.00 | 78.98 | C |
| ATOM | 4691 | O | LYS | A | 732 | 52.857 | 95.603 | -38.737 | 1.00 | 80.82 | O |
| ATOM | 4692 | CB | LYS | A | 732 | 52.055 | 98.480 | -39.390 | 1.00 | 80.61 | C |

FIG. 8-71

| | | | | | | | | | | | |
|---|---|---|---|---|---|---|---|---|---|---|---|
| ATOM | 4693 | CG | LYS | A | 732 | 51.338 | 99.762 | -39.814 | 1.00 | 84.97 | C |
| ATOM | 4694 | CD | LYS | A | 732 | 50.647 | 99.622 | -41.168 | 1.00 | 91.05 | C |
| ATOM | 4695 | CE | LYS | A | 732 | 50.207 | 100.982 | -41.720 | 1.00 | 94.45 | C |
| ATOM | 4696 | NZ | LYS | A | 732 | 49.236 | 101.707 | -40.836 | 1.00 | 93.76 | N |
| ATOM | 4697 | N | LEU | A | 733 | 51.433 | 95.992 | -37.055 | 1.00 | 78.57 | N |
| ATOM | 4698 | CA | LEU | A | 733 | 51.956 | 94.895 | -36.241 | 1.00 | 75.79 | C |
| ATOM | 4699 | C | LEU | A | 733 | 51.746 | 93.605 | -37.007 | 1.00 | 77.47 | C |
| ATOM | 4700 | O | LEU | A | 733 | 50.811 | 93.517 | -37.809 | 1.00 | 85.44 | O |
| ATOM | 4701 | CB | LEU | A | 733 | 51.193 | 94.815 | -34.927 | 1.00 | 75.86 | C |
| ATOM | 4702 | CG | LEU | A | 733 | 51.174 | 96.140 | -34.170 | 1.00 | 78.88 | C |
| ATOM | 4703 | CD1 | LEU | A | 733 | 50.294 | 96.042 | -32.930 | 1.00 | 76.40 | C |
| ATOM | 4704 | CD2 | LEU | A | 733 | 52.600 | 96.564 | -33.816 | 1.00 | 76.94 | C |
| ATOM | 4705 | N | TYR | A | 734 | 52.574 | 92.590 | -36.788 | 1.00 | 68.81 | N |
| ATOM | 4706 | CA | TYR | A | 734 | 52.249 | 91.337 | -37.463 | 1.00 | 79.78 | C |
| ATOM | 4707 | C | TYR | A | 734 | 51.833 | 90.138 | -36.617 | 1.00 | 74.70 | C |
| ATOM | 4708 | O | TYR | A | 734 | 52.462 | 89.784 | -35.623 | 1.00 | 70.05 | O |
| ATOM | 4709 | CB | TYR | A | 734 | 53.211 | 91.004 | -38.603 | 1.00 | 98.72 | C |
| ATOM | 4710 | CG | TYR | A | 734 | 52.607 | 91.389 | -39.948 | 1.00 | 109.73 | C |
| ATOM | 4711 | CD1 | TYR | A | 734 | 51.330 | 90.943 | -40.307 | 1.00 | 113.99 | C |
| ATOM | 4712 | CD2 | TYR | A | 734 | 53.290 | 92.206 | -40.843 | 1.00 | 113.44 | C |
| ATOM | 4713 | CE1 | TYR | A | 734 | 50.758 | 91.290 | -41.522 | 1.00 | 117.24 | C |
| ATOM | 4714 | CE2 | TYR | A | 734 | 52.726 | 92.557 | -42.067 | 1.00 | 118.88 | C |
| ATOM | 4715 | CZ | TYR | A | 734 | 51.461 | 92.096 | -42.402 | 1.00 | 119.52 | C |
| ATOM | 4716 | OH | TYR | A | 734 | 50.898 | 92.442 | -43.614 | 1.00 | 117.41 | O |
| ATOM | 4717 | N | GLY | A | 735 | 50.711 | 89.550 | -37.011 | 1.00 | 76.46 | N |
| ATOM | 4718 | CA | GLY | A | 735 | 50.048 | 88.558 | -36.186 | 1.00 | 77.83 | C |
| ATOM | 4719 | C | GLY | A | 735 | 49.739 | 89.070 | -34.780 | 1.00 | 68.82 | C |
| ATOM | 4720 | O | GLY | A | 735 | 49.795 | 90.281 | -34.512 | 1.00 | 60.29 | O |
| ATOM | 4721 | N | ALA | A | 736 | 49.611 | 88.148 | -33.854 | 1.00 | 69.52 | N |
| ATOM | 4722 | CA | ALA | A | 736 | 49.281 | 88.558 | -32.495 | 1.00 | 60.97 | C |
| ATOM | 4723 | C | ALA | A | 736 | 50.557 | 88.940 | -31.703 | 1.00 | 60.85 | C |
| ATOM | 4724 | O | ALA | A | 736 | 50.566 | 89.022 | -30.465 | 1.00 | 53.61 | O |
| ATOM | 4725 | CB | ALA | A | 736 | 48.494 | 87.484 | -31.804 | 1.00 | 48.51 | C |
| ATOM | 4726 | N | SER | A | 737 | 51.624 | 89.211 | -32.432 | 1.00 | 58.12 | N |
| ATOM | 4727 | CA | SER | A | 737 | 52.899 | 89.528 | -31.794 | 1.00 | 68.04 | C |
| ATOM | 4728 | C | SER | A | 737 | 52.902 | 90.826 | -30.961 | 1.00 | 62.92 | C |
| ATOM | 4729 | O | SER | A | 737 | 53.730 | 90.983 | -30.074 | 1.00 | 63.04 | O |
| ATOM | 4730 | CB | SER | A | 737 | 54.026 | 89.534 | -32.832 | 1.00 | 75.98 | C |
| ATOM | 4731 | OG | SER | A | 737 | 54.307 | 88.207 | -33.262 | 1.00 | 79.49 | O |
| ATOM | 4732 | N | GLY | A | 738 | 51.989 | 91.750 | -31.246 | 1.00 | 63.57 | N |
| ATOM | 4733 | CA | GLY | A | 738 | 51.883 | 92.970 | -30.465 | 1.00 | 57.91 | C |
| ATOM | 4734 | C | GLY | A | 738 | 51.316 | 92.713 | -29.069 | 1.00 | 54.03 | C |
| ATOM | 4735 | O | GLY | A | 738 | 51.908 | 93.079 | -28.039 | 1.00 | 55.28 | O |
| ATOM | 4736 | N | ALA | A | 739 | 50.156 | 92.073 | -29.033 | 1.00 | 52.51 | N |
| ATOM | 4737 | CA | ALA | A | 739 | 49.499 | 91.753 | -27.769 | 1.00 | 46.08 | C |
| ATOM | 4738 | C | ALA | A | 739 | 50.320 | 90.708 | -27.003 | 1.00 | 44.94 | C |
| ATOM | 4739 | O | ALA | A | 739 | 50.350 | 90.717 | -25.785 | 1.00 | 44.84 | O |
| ATOM | 4740 | CB | ALA | A | 739 | 48.092 | 91.256 | -28.021 | 1.00 | 43.04 | C |
| ATOM | 4741 | N | MET | A | 740 | 50.996 | 89.815 | -27.716 | 1.00 | 41.29 | N |
| ATOM | 4742 | CA | MET | A | 740 | 51.855 | 88.850 | -27.047 | 1.00 | 46.60 | C |
| ATOM | 4743 | C | MET | A | 740 | 53.116 | 89.491 | -26.476 | 1.00 | 53.82 | C |
| ATOM | 4744 | O | MET | A | 740 | 53.623 | 89.032 | -25.464 | 1.00 | 55.84 | O |
| ATOM | 4745 | CB | MET | A | 740 | 52.247 | 87.702 | -27.972 | 1.00 | 47.15 | C |
| ATOM | 4746 | CG | MET | A | 740 | 51.180 | 86.633 | -28.091 | 1.00 | 46.97 | C |
| ATOM | 4747 | SD | MET | A | 740 | 51.809 | 85.143 | -28.876 | 1.00 | 54.81 | S |
| ATOM | 4748 | CE | MET | A | 740 | 51.823 | 85.672 | -30.608 | 1.00 | 40.75 | C |
| ATOM | 4749 | N | SER | A | 741 | 53.651 | 90.526 | -27.119 | 1.00 | 48.86 | N |
| ATOM | 4750 | CA | SER | A | 741 | 54.844 | 91.170 | -26.552 | 1.00 | 52.97 | C |
| ATOM | 4751 | C | SER | A | 741 | 54.539 | 91.989 | -25.282 | 1.00 | 47.66 | C |
| ATOM | 4752 | O | SER | A | 741 | 55.390 | 92.132 | -24.410 | 1.00 | 57.67 | O |
| ATOM | 4753 | CB | SER | A | 741 | 55.522 | 92.065 | -27.583 | 1.00 | 59.74 | C |
| ATOM | 4754 | OG | SER | A | 741 | 54.670 | 93.165 | -27.840 | 1.00 | 70.60 | O |
| ATOM | 4755 | N | ILE | A | 742 | 53.334 | 92.547 | -25.195 | 1.00 | 44.25 | N |
| ATOM | 4756 | CA | ILE | A | 742 | 52.901 | 93.290 | -24.010 | 1.00 | 44.51 | C |
| ATOM | 4757 | C | ILE | A | 742 | 52.659 | 92.304 | -22.867 | 1.00 | 46.49 | C |
| ATOM | 4758 | O | ILE | A | 742 | 53.141 | 92.490 | -21.757 | 1.00 | 44.38 | O |
| ATOM | 4759 | CB | ILE | A | 742 | 51.622 | 94.113 | -24.288 | 1.00 | 43.91 | C |
| ATOM | 4760 | CG1 | ILE | A | 742 | 51.896 | 95.290 | -25.243 | 1.00 | 47.12 | C |
| ATOM | 4761 | CG2 | ILE | A | 742 | 50.955 | 94.561 | -23.011 | 1.00 | 38.34 | C |
| ATOM | 4762 | CD1 | ILE | A | 742 | 53.238 | 95.957 | -25.131 | 1.00 | 52.43 | C |
| ATOM | 4763 | N | TYR | A | 743 | 51.935 | 91.231 | -23.156 | 1.00 | 43.15 | N |
| ATOM | 4764 | CA | TYR | A | 743 | 51.663 | 90.235 | -22.135 | 1.00 | 46.14 | C |
| ATOM | 4765 | C | TYR | A | 743 | 52.973 | 89.657 | -21.688 | 1.00 | 44.57 | C |
| ATOM | 4766 | O | TYR | A | 743 | 53.189 | 89.394 | -20.511 | 1.00 | 45.81 | O |
| ATOM | 4767 | CB | TYR | A | 743 | 50.822 | 89.109 | -22.701 | 1.00 | 42.83 | C |
| ATOM | 4768 | CG | TYR | A | 743 | 50.541 | 87.976 | -21.729 | 1.00 | 50.81 | C |
| ATOM | 4769 | CD1 | TYR | A | 743 | 49.870 | 88.201 | -20.529 | 1.00 | 43.86 | C |

FIG. 8-72

| | | | | | | | | | | | |
|---|---|---|---|---|---|---|---|---|---|---|---|
| ATOM | 4770 | CD2 | TYR | A | 743 | 50.888 | 86.674 | -22.046 | 1.00 | 58.26 | C |
| ATOM | 4771 | CE1 | TYR | A | 743 | 49.580 | 87.160 | -19.666 | 1.00 | 44.00 | C |
| ATOM | 4772 | CE2 | TYR | A | 743 | 50.599 | 85.632 | -21.199 | 1.00 | 57.65 | C |
| ATOM | 4773 | CZ | TYR | A | 743 | 49.944 | 85.876 | -20.017 | 1.00 | 50.82 | C |
| ATOM | 4774 | OH | TYR | A | 743 | 49.681 | 84.823 | -19.190 | 1.00 | 52.12 | O |
| ATOM | 4775 | N | GLN | A | 744 | 53.858 | 89.418 | -22.635 | 1.00 | 53.16 | N |
| ATOM | 4776 | CA | GLN | A | 744 | 55.102 | 88.779 | -22.270 | 1.00 | 51.17 | C |
| ATOM | 4777 | C | GLN | A | 744 | 55.915 | 89.664 | -21.335 | 1.00 | 50.45 | C |
| ATOM | 4778 | O | GLN | A | 744 | 56.516 | 89.144 | -20.406 | 1.00 | 54.25 | O |
| ATOM | 4779 | CB | GLN | A | 744 | 55.891 | 88.317 | -23.481 | 1.00 | 61.30 | C |
| ATOM | 4780 | CG | GLN | A | 744 | 56.850 | 89.323 | -24.047 | 1.00 | 85.12 | C |
| ATOM | 4781 | CD | GLN | A | 744 | 57.087 | 89.078 | -25.526 | 1.00 | 100.56 | C |
| ATOM | 4782 | OE1 | GLN | A | 744 | 56.245 | 88.469 | -26.203 | 1.00 | 100.01 | O |
| ATOM | 4783 | NE2 | GLN | A | 744 | 58.226 | 89.554 | -26.041 | 1.00 | 103.36 | N |
| ATOM | 4784 | N | ARG | A | 745 | 55.927 | 90.981 | -21.561 | 1.00 | 46.25 | N |
| ATOM | 4785 | CA | ARG | A | 745 | 56.540 | 91.912 | -20.590 | 1.00 | 45.17 | C |
| ATOM | 4786 | C | ARG | A | 745 | 55.743 | 91.881 | -19.269 | 1.00 | 53.23 | C |
| ATOM | 4787 | O | ARG | A | 745 | 56.313 | 91.979 | -18.178 | 1.00 | 50.40 | O |
| ATOM | 4788 | CB | ARG | A | 745 | 56.528 | 93.343 | -21.109 | 1.00 | 42.35 | C |
| ATOM | 4789 | CG | ARG | A | 745 | 57.379 | 93.609 | -22.300 | 1.00 | 46.10 | C |
| ATOM | 4790 | CD | ARG | A | 745 | 57.062 | 94.974 | -22.910 | 1.00 | 49.88 | C |
| ATOM | 4791 | NE | ARG | A | 745 | 58.080 | 95.338 | -23.907 | 1.00 | 56.91 | N |
| ATOM | 4792 | CZ | ARG | A | 745 | 59.082 | 96.152 | -23.618 | 1.00 | 60.73 | C |
| ATOM | 4793 | NH1 | ARG | A | 745 | 59.179 | 96.662 | -22.393 | 1.00 | 60.71 | N |
| ATOM | 4794 | NH2 | ARG | A | 745 | 59.996 | 96.462 | -24.529 | 1.00 | 55.34 | N |
| ATOM | 4795 | N | TYR | A | 746 | 54.424 | 91.752 | -19.363 | 1.00 | 49.84 | N |
| ATOM | 4796 | CA | TYR | A | 746 | 53.650 | 91.590 | -18.142 | 1.00 | 46.47 | C |
| ATOM | 4797 | C | TYR | A | 746 | 54.164 | 90.394 | -17.344 | 1.00 | 43.55 | C |
| ATOM | 4798 | O | TYR | A | 746 | 54.398 | 90.510 | -16.155 | 1.00 | 43.78 | O |
| ATOM | 4799 | CB | TYR | A | 746 | 52.147 | 91.483 | -18.416 | 1.00 | 46.13 | C |
| ATOM | 4800 | CG | TYR | A | 746 | 51.323 | 91.126 | -17.200 | 1.00 | 47.04 | C |
| ATOM | 4801 | CD1 | TYR | A | 746 | 50.993 | 92.092 | -16.257 | 1.00 | 46.45 | C |
| ATOM | 4802 | CD2 | TYR | A | 746 | 50.907 | 89.816 | -16.975 | 1.00 | 48.78 | C |
| ATOM | 4803 | CE1 | TYR | A | 746 | 50.278 | 91.774 | -15.135 | 1.00 | 44.60 | C |
| ATOM | 4804 | CE2 | TYR | A | 746 | 50.141 | 89.485 | -15.857 | 1.00 | 42.56 | C |
| ATOM | 4805 | CZ | TYR | A | 746 | 49.849 | 90.473 | -14.936 | 1.00 | 49.86 | C |
| ATOM | 4806 | OH | TYR | A | 746 | 49.108 | 90.173 | -13.813 | 1.00 | 57.12 | O |
| ATOM | 4807 | N | LEU | A | 747 | 54.325 | 89.242 | -17.985 | 1.00 | 47.21 | N |
| ATOM | 4808 | CA | LEU | A | 747 | 54.823 | 88.053 | -17.289 | 1.00 | 45.08 | C |
| ATOM | 4809 | C | LEU | A | 747 | 56.208 | 88.247 | -16.695 | 1.00 | 50.92 | C |
| ATOM | 4810 | O | LEU | A | 747 | 56.552 | 87.606 | -15.689 | 1.00 | 47.06 | O |
| ATOM | 4811 | CB | LEU | A | 747 | 54.879 | 86.838 | -18.220 | 1.00 | 44.45 | C |
| ATOM | 4812 | CG | LEU | A | 747 | 53.568 | 86.316 | -18.820 | 1.00 | 44.48 | C |
| ATOM | 4813 | CD1 | LEU | A | 747 | 53.889 | 85.387 | -20.009 | 1.00 | 50.90 | C |
| ATOM | 4814 | CD2 | LEU | A | 747 | 52.764 | 85.578 | -17.799 | 1.00 | 41.63 | C |
| ATOM | 4815 | N | ALA | A | 748 | 57.023 | 89.093 | -17.319 | 1.00 | 42.47 | N |
| ATOM | 4816 | CA | ALA | A | 748 | 58.391 | 89.289 | -16.820 | 1.00 | 52.73 | C |
| ATOM | 4817 | C | ALA | A | 748 | 58.421 | 90.239 | -15.625 | 1.00 | 50.95 | C |
| ATOM | 4818 | O | ALA | A | 748 | 59.322 | 90.204 | -14.817 | 1.00 | 54.94 | O |
| ATOM | 4819 | CB | ALA | A | 748 | 59.307 | 89.809 | -17.924 | 1.00 | 48.94 | C |
| ATOM | 4820 | N | ASN | A | 749 | 57.432 | 91.106 | -15.538 | 1.00 | 48.04 | N |
| ATOM | 4821 | CA | ASN | A | 749 | 57.420 | 92.145 | -14.525 | 1.00 | 53.47 | C |
| ATOM | 4822 | C | ASN | A | 749 | 56.889 | 91.681 | -13.168 | 1.00 | 56.83 | C |
| ATOM | 4823 | O | ASN | A | 749 | 56.900 | 92.444 | -12.215 | 1.00 | 56.15 | O |
| ATOM | 4824 | CB | ASN | A | 749 | 56.571 | 93.312 | -15.006 | 1.00 | 60.02 | C |
| ATOM | 4825 | CG | ASN | A | 749 | 57.301 | 94.189 | -15.970 | 1.00 | 59.59 | C |
| ATOM | 4826 | OD1 | ASN | A | 749 | 58.532 | 94.221 | -15.979 | 1.00 | 61.09 | O |
| ATOM | 4827 | ND2 | ASN | A | 749 | 56.547 | 94.926 | -16.787 | 1.00 | 60.30 | N |
| ATOM | 4828 | N | GLN | A | 750 | 56.388 | 90.452 | -13.107 | 1.00 | 57.25 | N |
| ATOM | 4829 | CA | GLN | A | 750 | 55.941 | 89.862 | -11.856 | 1.00 | 65.63 | C |
| ATOM | 4830 | C | GLN | A | 750 | 56.278 | 88.381 | -11.832 | 1.00 | 67.54 | C |
| ATOM | 4831 | O | GLN | A | 750 | 57.004 | 87.898 | -12.693 | 1.00 | 68.70 | O |
| ATOM | 4832 | CB | GLN | A | 750 | 54.446 | 90.105 | -11.623 | 1.00 | 65.60 | C |
| ATOM | 4833 | CG | GLN | A | 750 | 53.570 | 90.080 | -12.880 | 1.00 | 67.52 | C |
| ATOM | 4834 | CD | GLN | A | 750 | 52.729 | 88.822 | -12.977 | 1.00 | 72.15 | C |
| ATOM | 4835 | OE1 | GLN | A | 750 | 52.410 | 88.197 | -11.964 | 1.00 | 73.72 | O |
| ATOM | 4836 | NE2 | GLN | A | 750 | 52.357 | 88.448 | -14.192 | 1.00 | 69.21 | N |
| ATOM | 4837 | N | THR | A | 751 | 55.776 | 87.665 | -10.831 | 1.00 | 64.51 | N |
| ATOM | 4838 | CA | THR | A | 751 | 56.087 | 86.248 | -10.713 | 1.00 | 62.80 | C |
| ATOM | 4839 | C | THR | A | 751 | 54.817 | 85.475 | -11.014 | 1.00 | 62.13 | C |
| ATOM | 4840 | O | THR | A | 751 | 53.916 | 85.381 | -10.183 | 1.00 | 60.45 | O |
| ATOM | 4841 | CB | THR | A | 751 | 56.677 | 85.876 | -9.338 | 1.00 | 66.19 | C |
| ATOM | 4842 | OG1 | THR | A | 751 | 57.724 | 86.800 | -8.991 | 1.00 | 72.47 | O |
| ATOM | 4843 | CG2 | THR | A | 751 | 57.248 | 84.465 | -9.372 | 1.00 | 63.05 | C |
| ATOM | 4844 | N | PRO | A | 752 | 54.721 | 84.964 | -12.245 | 1.00 | 56.18 | N |
| ATOM | 4845 | CA | PRO | A | 752 | 53.499 | 84.278 | -12.676 | 1.00 | 40.91 | C |
| ATOM | 4846 | C | PRO | A | 752 | 53.432 | 82.874 | -12.070 | 1.00 | 40.71 | C |

FIG. 8-73

| | | | | | | | | | | | |
|---|---|---|---|---|---|---|---|---|---|---|---|
| ATOM | 4847 | O | PRO | A | 752 | 54.450 | 82.299 | -11.718 | 1.00 | 40.65 | O |
| ATOM | 4848 | CB | PRO | A | 752 | 53.644 | 84.198 | -14.205 | 1.00 | 49.90 | C |
| ATOM | 4849 | CG | PRO | A | 752 | 54.841 | 85.049 | -14.566 | 1.00 | 57.54 | C |
| ATOM | 4850 | CD | PRO | A | 752 | 55.715 | 85.108 | -13.328 | 1.00 | 48.08 | C |
| ATOM | 4851 | N | THR | A | 753 | 52.231 | 82.330 | -11.939 | 1.00 | 44.41 | N |
| ATOM | 4852 | CA | THR | A | 753 | 52.055 | 81.034 | -11.307 | 1.00 | 46.71 | C |
| ATOM | 4853 | C | THR | A | 753 | 51.978 | 79.949 | -12.370 | 1.00 | 38.00 | C |
| ATOM | 4854 | O | THR | A | 753 | 51.187 | 80.067 | -13.294 | 1.00 | 39.23 | O |
| ATOM | 4855 | CB | THR | A | 753 | 50.710 | 81.002 | -10.552 | 1.00 | 49.89 | C |
| ATOM | 4856 | OG1 | THR | A | 753 | 50.695 | 82.033 | -9.552 | 1.00 | 47.50 | O |
| ATOM | 4857 | CG2 | THR | A | 753 | 50.451 | 79.616 | -9.950 | 1.00 | 41.63 | C |
| ATOM | 4858 | N | PRO | A | 754 | 52.762 | 78.870 | -12.228 | 1.00 | 37.18 | N |
| ATOM | 4859 | CA | PRO | A | 754 | 52.562 | 77.833 | -13.247 | 1.00 | 34.04 | C |
| ATOM | 4860 | C | PRO | A | 754 | 51.126 | 77.301 | -13.277 | 1.00 | 46.13 | C |
| ATOM | 4861 | O | PRO | A | 754 | 50.420 | 77.163 | -12.279 | 1.00 | 46.83 | O |
| ATOM | 4862 | CB | PRO | A | 754 | 53.556 | 76.738 | -12.849 | 1.00 | 40.14 | C |
| ATOM | 4863 | CG | PRO | A | 754 | 54.709 | 77.513 | -12.169 | 1.00 | 34.38 | C |
| ATOM | 4864 | CD | PRO | A | 754 | 53.967 | 78.629 | -11.403 | 1.00 | 37.56 | C |
| ATOM | 4865 | N | LEU | A | 755 | 50.691 | 77.038 | -14.493 | 1.00 | 37.17 | N |
| ATOM | 4866 | CA | LEU | A | 755 | 49.481 | 76.341 | -14.729 | 1.00 | 30.28 | C |
| ATOM | 4867 | C | LEU | A | 755 | 49.726 | 74.837 | -14.716 | 1.00 | 38.67 | C |
| ATOM | 4868 | O | LEU | A | 755 | 50.306 | 74.269 | -15.657 | 1.00 | 46.10 | O |
| ATOM | 4869 | CB | LEU | A | 755 | 48.950 | 76.783 | -16.106 | 1.00 | 33.95 | C |
| ATOM | 4870 | CG | LEU | A | 755 | 47.613 | 76.148 | -16.456 | 1.00 | 35.91 | C |
| ATOM | 4871 | CD1 | LEU | A | 755 | 46.762 | 76.421 | -15.284 | 1.00 | 40.23 | C |
| ATOM | 4872 | CD2 | LEU | A | 755 | 47.025 | 76.731 | -17.719 | 1.00 | 28.07 | C |
| ATOM | 4873 | N | ASN | A | 756 | 49.281 | 74.187 | -13.651 | 1.00 | 41.15 | N |
| ATOM | 4874 | CA | ASN | A | 756 | 49.236 | 72.737 | -13.610 | 1.00 | 41.90 | C |
| ATOM | 4875 | C | ASN | A | 756 | 47.782 | 72.254 | -13.677 | 1.00 | 45.16 | C |
| ATOM | 4876 | O | ASN | A | 756 | 47.107 | 72.170 | -12.665 | 1.00 | 51.30 | O |
| ATOM | 4877 | CB | ASN | A | 756 | 49.961 | 72.210 | -12.373 | 1.00 | 46.69 | C |
| ATOM | 4878 | CG | ASN | A | 756 | 51.452 | 72.609 | -12.363 | 1.00 | 57.14 | C |
| ATOM | 4879 | OD1 | ASN | A | 756 | 51.900 | 73.318 | -11.473 | 1.00 | 62.74 | O |
| ATOM | 4880 | ND2 | ASN | A | 756 | 52.203 | 72.175 | -13.373 | 1.00 | 56.39 | N |
| ATOM | 4881 | N | LEU | A | 757 | 47.321 | 71.980 | -14.896 | 1.00 | 42.99 | N |
| ATOM | 4882 | CA | LEU | A | 757 | 45.969 | 71.558 | -15.192 | 1.00 | 43.43 | C |
| ATOM | 4883 | C | LEU | A | 757 | 45.664 | 70.195 | -14.611 | 1.00 | 53.69 | C |
| ATOM | 4884 | O | LEU | A | 757 | 46.166 | 69.192 | -15.096 | 1.00 | 63.93 | O |
| ATOM | 4885 | CB | LEU | A | 757 | 45.783 | 71.465 | -16.712 | 1.00 | 50.79 | C |
| ATOM | 4886 | CG | LEU | A | 757 | 45.150 | 72.577 | -17.538 | 1.00 | 50.51 | C |
| ATOM | 4887 | CD1 | LEU | A | 757 | 44.751 | 72.028 | -18.923 | 1.00 | 45.22 | C |
| ATOM | 4888 | CD2 | LEU | A | 757 | 43.908 | 73.172 | -16.814 | 1.00 | 42.07 | C |
| ATOM | 4889 | N | VAL | A | 758 | 44.824 | 70.166 | -13.584 | 1.00 | 49.47 | N |
| ATOM | 4890 | CA | VAL | A | 758 | 44.347 | 68.929 | -12.989 | 1.00 | 45.43 | C |
| ATOM | 4891 | C | VAL | A | 758 | 43.119 | 68.459 | -13.762 | 1.00 | 48.41 | C |
| ATOM | 4892 | O | VAL | A | 758 | 42.155 | 69.209 | -13.926 | 1.00 | 40.04 | O |
| ATOM | 4893 | CB | VAL | A | 758 | 43.939 | 69.186 | -11.571 | 1.00 | 47.10 | C |
| ATOM | 4894 | CG1 | VAL | A | 758 | 43.476 | 67.889 | -10.895 | 1.00 | 51.69 | C |
| ATOM | 4895 | CG2 | VAL | A | 758 | 45.099 | 69.826 | -10.827 | 1.00 | 54.85 | C |
| ATOM | 4896 | N | PRO | A | 759 | 43.169 | 67.230 | -14.286 | 1.00 | 48.06 | N |
| ATOM | 4897 | CA | PRO | A | 759 | 42.046 | 66.747 | -15.096 | 1.00 | 51.04 | C |
| ATOM | 4898 | C | PRO | A | 759 | 40.836 | 66.447 | -14.219 | 1.00 | 46.15 | C |
| ATOM | 4899 | O | PRO | A | 759 | 40.998 | 65.846 | -13.167 | 1.00 | 46.79 | O |
| ATOM | 4900 | CB | PRO | A | 759 | 42.594 | 65.455 | -15.724 | 1.00 | 50.27 | C |
| ATOM | 4901 | CG | PRO | A | 759 | 44.071 | 65.549 | -15.602 | 1.00 | 49.71 | C |
| ATOM | 4902 | CD | PRO | A | 759 | 44.317 | 66.311 | -14.322 | 1.00 | 40.75 | C |
| ATOM | 4903 | N | PRO | A | 760 | 39.633 | 66.877 | -14.632 | 1.00 | 48.21 | N |
| ATOM | 4904 | CA | PRO | A | 760 | 38.429 | 66.506 | -13.851 | 1.00 | 43.44 | C |
| ATOM | 4905 | C | PRO | A | 760 | 38.102 | 65.024 | -14.071 | 1.00 | 46.01 | C |
| ATOM | 4906 | O | PRO | A | 760 | 38.855 | 64.314 | -14.737 | 1.00 | 45.96 | O |
| ATOM | 4907 | CB | PRO | A | 760 | 37.352 | 67.427 | -14.402 | 1.00 | 34.00 | C |
| ATOM | 4908 | CG | PRO | A | 760 | 37.851 | 67.684 | -15.873 | 1.00 | 33.08 | C |
| ATOM | 4909 | CD | PRO | A | 760 | 39.338 | 67.825 | -15.714 | 1.00 | 40.88 | C |
| ATOM | 4910 | N | GLU | A | 761 | 37.019 | 64.544 | -13.489 | 1.00 | 47.17 | N |
| ATOM | 4911 | CA | GLU | A | 761 | 36.657 | 63.134 | -13.605 | 1.00 | 44.05 | C |
| ATOM | 4912 | C | GLU | A | 761 | 36.418 | 62.709 | -15.058 | 1.00 | 41.23 | C |
| ATOM | 4913 | O | GLU | A | 761 | 36.024 | 63.520 | -15.910 | 1.00 | 38.21 | O |
| ATOM | 4914 | CB | GLU | A | 761 | 35.383 | 62.870 | -12.738 | 1.00 | 57.73 | C |
| ATOM | 4915 | CG | GLU | A | 761 | 35.564 | 62.973 | -11.230 | 1.00 | 73.59 | C |
| ATOM | 4916 | CD | GLU | A | 761 | 35.772 | 64.408 | -10.769 | 1.00 | 81.66 | C |
| ATOM | 4917 | OE1 | GLU | A | 761 | 35.605 | 65.391 | -11.546 | 1.00 | 70.88 | O |
| ATOM | 4918 | OE2 | GLU | A | 761 | 36.104 | 64.538 | -9.564 | 1.00 | 90.36 | O |
| ATOM | 4919 | N | ASP | A | 762 | 36.645 | 61.433 | -15.348 | 1.00 | 33.70 | N |
| ATOM | 4920 | CA | ASP | A | 762 | 36.311 | 60.927 | -16.665 | 1.00 | 38.78 | C |
| ATOM | 4921 | C | ASP | A | 762 | 37.159 | 61.497 | -17.811 | 1.00 | 41.41 | C |
| ATOM | 4922 | O | ASP | A | 762 | 36.710 | 61.533 | -18.978 | 1.00 | 38.75 | O |
| ATOM | 4923 | CB | ASP | A | 762 | 34.837 | 61.192 | -16.938 | 1.00 | 43.91 | C |

FIG. 8-74

| | | | | | | | | | | | |
|---|---|---|---|---|---|---|---|---|---|---|---|
| ATOM | 4924 | CG | ASP | A | 762 | 33.927 | 60.276 | -16.133 | 1.00 | 57.70 | C |
| ATOM | 4925 | OD1 | ASP | A | 762 | 32.755 | 60.638 | -15.921 | 1.00 | 63.66 | O |
| ATOM | 4926 | OD2 | ASP | A | 762 | 34.381 | 59.195 | -15.714 | 1.00 | 59.53 | O |
| ATOM | 4927 | N | ILE | A | 763 | 38.369 | 61.961 | -17.485 | 1.00 | 36.76 | N |
| ATOM | 4928 | CA | ILE | A | 763 | 39.337 | 62.313 | -18.523 | 1.00 | 41.43 | C |
| ATOM | 4929 | C | ILE | A | 763 | 40.393 | 61.223 | -18.544 | 1.00 | 41.69 | C |
| ATOM | 4930 | O | ILE | A | 763 | 40.938 | 60.887 | -17.508 | 1.00 | 39.82 | O |
| ATOM | 4931 | CB | ILE | A | 763 | 40.013 | 63.640 | -18.229 | 1.00 | 41.66 | C |
| ATOM | 4932 | CG1 | ILE | A | 763 | 38.978 | 64.757 | -18.200 | 1.00 | 35.74 | C |
| ATOM | 4933 | CG2 | ILE | A | 763 | 41.073 | 63.927 | -19.305 | 1.00 | 41.04 | C |
| ATOM | 4934 | CD1 | ILE | A | 763 | 38.358 | 65.000 | -19.569 | 1.00 | 37.48 | C |
| ATOM | 4935 | N | ALA | A | 764 | 40.663 | 60.653 | -19.712 | 1.00 | 34.33 | N |
| ATOM | 4936 | CA | ALA | A | 764 | 41.673 | 59.595 | -19.845 | 1.00 | 40.34 | C |
| ATOM | 4937 | C | ALA | A | 764 | 42.600 | 59.930 | -21.009 | 1.00 | 41.99 | C |
| ATOM | 4938 | O | ALA | A | 764 | 42.130 | 60.358 | -22.044 | 1.00 | 39.40 | O |
| ATOM | 4939 | CB | ALA | A | 764 | 41.021 | 58.268 | -20.142 | 1.00 | 38.33 | C |
| ATOM | 4940 | N | ASP | A | 765 | 43.898 | 59.682 | -20.850 | 1.00 | 35.25 | N |
| ATOM | 4941 | CA | ASP | A | 765 | 44.887 | 59.937 | -21.917 | 1.00 | 41.09 | C |
| ATOM | 4942 | C | ASP | A | 765 | 44.915 | 58.736 | -22.799 | 1.00 | 43.18 | C |
| ATOM | 4943 | O | ASP | A | 765 | 45.143 | 57.627 | -22.317 | 1.00 | 46.05 | O |
| ATOM | 4944 | CB | ASP | A | 765 | 46.282 | 60.114 | -21.310 | 1.00 | 55.25 | C |
| ATOM | 4945 | CG | ASP | A | 765 | 46.462 | 61.466 | -20.636 | 1.00 | 67.99 | C |
| ATOM | 4946 | OD1 | ASP | A | 765 | 45.678 | 62.402 | -20.937 | 1.00 | 69.92 | O |
| ATOM | 4947 | OD2 | ASP | A | 765 | 47.398 | 61.592 | -19.813 | 1.00 | 74.64 | O |
| ATOM | 4948 | N | MET | A | 766 | 44.652 | 58.937 | -24.087 | 1.00 | 38.63 | N |
| ATOM | 4949 | CA | MET | A | 766 | 44.556 | 57.824 | -25.011 | 1.00 | 41.53 | C |
| ATOM | 4950 | C | MET | A | 766 | 45.476 | 58.017 | -26.201 | 1.00 | 36.85 | C |
| ATOM | 4951 | O | MET | A | 766 | 45.729 | 59.149 | -26.624 | 1.00 | 47.36 | O |
| ATOM | 4952 | CB | MET | A | 766 | 43.090 | 57.664 | -25.498 | 1.00 | 39.59 | C |
| ATOM | 4953 | CG | MET | A | 766 | 42.152 | 57.401 | -24.370 | 1.00 | 43.54 | C |
| ATOM | 4954 | SD | MET | A | 766 | 40.500 | 57.099 | -24.956 | 1.00 | 54.79 | S |
| ATOM | 4955 | CE | MET | A | 766 | 40.745 | 55.507 | -25.728 | 1.00 | 51.18 | C |
| ATOM | 4956 | N | GLY | A | 767 | 45.969 | 56.904 | -26.732 | 1.00 | 36.28 | N |
| ATOM | 4957 | CA | GLY | A | 767 | 46.849 | 56.926 | -27.885 | 1.00 | 35.83 | C |
| ATOM | 4958 | C | GLY | A | 767 | 46.045 | 56.862 | -29.171 | 1.00 | 40.44 | C |
| ATOM | 4959 | O | GLY | A | 767 | 45.004 | 56.198 | -29.244 | 1.00 | 44.36 | O |
| ATOM | 4960 | N | VAL | A | 768 | 46.526 | 57.556 | -30.198 | 1.00 | 37.39 | N |
| ATOM | 4961 | CA | VAL | A | 768 | 45.958 | 57.443 | -31.532 | 1.00 | 35.43 | C |
| ATOM | 4962 | C | VAL | A | 768 | 47.073 | 57.131 | -32.497 | 1.00 | 45.95 | C |
| ATOM | 4963 | O | VAL | A | 768 | 48.225 | 57.558 | -32.278 | 1.00 | 46.74 | O |
| ATOM | 4964 | CB | VAL | A | 768 | 45.289 | 58.777 | -31.953 | 1.00 | 59.50 | C |
| ATOM | 4965 | CG1 | VAL | A | 768 | 43.962 | 59.006 | -31.199 | 1.00 | 53.45 | C |
| ATOM | 4966 | CG2 | VAL | A | 768 | 46.227 | 59.932 | -31.699 | 1.00 | 58.54 | C |
| ATOM | 4967 | N | ASP | A | 769 | 46.758 | 56.412 | -33.580 | 1.00 | 37.00 | N |
| ATOM | 4968 | CA | ASP | A | 769 | 47.773 | 56.196 | -34.619 | 1.00 | 37.90 | C |
| ATOM | 4969 | C | ASP | A | 769 | 47.799 | 57.391 | -35.577 | 1.00 | 38.75 | C |
| ATOM | 4970 | O | ASP | A | 769 | 47.110 | 58.373 | -35.352 | 1.00 | 38.99 | O |
| ATOM | 4971 | CB | ASP | A | 769 | 47.563 | 54.860 | -35.305 | 1.00 | 39.10 | C |
| ATOM | 4972 | CG | ASP | A | 769 | 46.191 | 54.747 | -35.985 | 1.00 | 57.42 | C |
| ATOM | 4973 | OD1 | ASP | A | 769 | 45.815 | 53.618 | -36.368 | 1.00 | 61.90 | O |
| ATOM | 4974 | OD2 | ASP | A | 769 | 45.498 | 55.773 | -36.158 | 1.00 | 49.43 | O |
| ATOM | 4975 | N | TYR | A | 770 | 48.628 | 57.345 | -36.613 | 1.00 | 51.93 | N |
| ATOM | 4976 | CA | TYR | A | 770 | 48.716 | 58.456 | -37.564 | 1.00 | 55.44 | C |
| ATOM | 4977 | C | TYR | A | 770 | 47.380 | 58.717 | -38.303 | 1.00 | 55.11 | C |
| ATOM | 4978 | O | TYR | A | 770 | 47.042 | 59.866 | -38.602 | 1.00 | 60.25 | O |
| ATOM | 4979 | CB | TYR | A | 770 | 49.849 | 58.211 | -38.569 | 1.00 | 52.96 | C |
| ATOM | 4980 | CG | TYR | A | 770 | 50.222 | 59.431 | -39.392 | 1.00 | 63.26 | C |
| ATOM | 4981 | CD1 | TYR | A | 770 | 50.139 | 59.415 | -40.782 | 1.00 | 70.22 | C |
| ATOM | 4982 | CD2 | TYR | A | 770 | 50.629 | 60.605 | -38.776 | 1.00 | 66.74 | C |
| ATOM | 4983 | CE1 | TYR | A | 770 | 50.473 | 60.530 | -41.525 | 1.00 | 73.35 | C |
| ATOM | 4984 | CE2 | TYR | A | 770 | 50.973 | 61.723 | -39.510 | 1.00 | 69.81 | C |
| ATOM | 4985 | CZ | TYR | A | 770 | 50.899 | 61.682 | -40.883 | 1.00 | 76.27 | C |
| ATOM | 4986 | OH | TYR | A | 770 | 51.247 | 62.808 | -41.612 | 1.00 | 81.97 | O |
| ATOM | 4987 | N | ASP | A | 771 | 46.637 | 57.651 | -38.601 | 1.00 | 46.52 | N |
| ATOM | 4988 | CA | ASP | A | 771 | 45.287 | 57.774 | -39.140 | 1.00 | 48.38 | C |
| ATOM | 4989 | C | ASP | A | 771 | 44.279 | 58.441 | -38.191 | 1.00 | 52.74 | C |
| ATOM | 4990 | O | ASP | A | 771 | 43.159 | 58.727 | -38.597 | 1.00 | 54.67 | O |
| ATOM | 4991 | CB | ASP | A | 771 | 44.750 | 56.405 | -39.573 | 1.00 | 61.09 | C |
| ATOM | 4992 | CG | ASP | A | 771 | 43.535 | 56.520 | -40.500 | 1.00 | 76.39 | C |
| ATOM | 4993 | OD1 | ASP | A | 771 | 42.603 | 55.681 | -40.404 | 1.00 | 80.72 | O |
| ATOM | 4994 | OD2 | ASP | A | 771 | 43.508 | 57.463 | -41.327 | 1.00 | 79.16 | O |
| ATOM | 4995 | N | GLY | A | 772 | 44.661 | 58.668 | -36.928 | 1.00 | 53.40 | N |
| ATOM | 4996 | CA | GLY | A | 772 | 43.799 | 59.346 | -35.962 | 1.00 | 39.90 | C |
| ATOM | 4997 | C | GLY | A | 772 | 42.917 | 58.415 | -35.150 | 1.00 | 36.79 | C |
| ATOM | 4998 | O | GLY | A | 772 | 42.075 | 58.847 | -34.366 | 1.00 | 53.01 | O |
| ATOM | 4999 | N | ASN | A | 773 | 43.076 | 57.121 | -35.346 | 1.00 | 38.88 | N |
| ATOM | 5000 | CA | ASN | A | 773 | 42.199 | 56.147 | -34.696 | 1.00 | 39.44 | C |

FIG.8-75

| | | | | | | | | | | | |
|---|---|---|---|---|---|---|---|---|---|---|---|
| ATOM | 5001 | C | ASN | A | 773 | 42.743 | 55.788 | -33.307 | 1.00 | 42.68 | C |
| ATOM | 5002 | O | ASN | A | 773 | 43.950 | 55.666 | -33.150 | 1.00 | 37.82 | O |
| ATOM | 5003 | CB | ASN | A | 773 | 42.187 | 54.871 | -35.541 | 1.00 | 41.05 | C |
| ATOM | 5004 | CG | ASN | A | 773 | 41.724 | 55.115 | -36.965 | 1.00 | 52.25 | C |
| ATOM | 5005 | OD1 | ASN | A | 773 | 40.706 | 55.775 | -37.193 | 1.00 | 58.37 | O |
| ATOM | 5006 | ND2 | ASN | A | 773 | 42.461 | 54.567 | -37.931 | 1.00 | 50.08 | N |
| ATOM | 5007 | N | PHE | A | 774 | 41.891 | 55.557 | -32.310 | 1.00 | 41.46 | N |
| ATOM | 5008 | CA | PHE | A | 774 | 42.427 | 55.114 | -31.020 | 1.00 | 44.29 | C |
| ATOM | 5009 | C | PHE | A | 774 | 43.086 | 53.745 | -31.114 | 1.00 | 44.43 | C |
| ATOM | 5010 | O | PHE | A | 774 | 42.734 | 52.911 | -31.945 | 1.00 | 49.37 | O |
| ATOM | 5011 | CB | PHE | A | 774 | 41.383 | 55.135 | -29.891 | 1.00 | 35.99 | C |
| ATOM | 5012 | CG | PHE | A | 774 | 40.832 | 56.500 | -29.610 | 1.00 | 39.21 | C |
| ATOM | 5013 | CD1 | PHE | A | 774 | 41.638 | 57.477 | -29.043 | 1.00 | 33.95 | C |
| ATOM | 5014 | CD2 | PHE | A | 774 | 39.503 | 56.803 | -29.907 | 1.00 | 43.45 | C |
| ATOM | 5015 | CE1 | PHE | A | 774 | 41.164 | 58.737 | -28.826 | 1.00 | 38.21 | C |
| ATOM | 5016 | CE2 | PHE | A | 774 | 38.992 | 58.053 | -29.651 | 1.00 | 43.02 | C |
| ATOM | 5017 | CZ | PHE | A | 774 | 39.820 | 59.032 | -29.119 | 1.00 | 40.70 | C |
| ATOM | 5018 | N | VAL | A | 775 | 44.040 | 53.521 | -30.231 | 1.00 | 47.00 | N |
| ATOM | 5019 | CA | VAL | A | 775 | 44.829 | 52.305 | -30.241 | 1.00 | 45.34 | C |
| ATOM | 5020 | C | VAL | A | 775 | 44.898 | 51.835 | -28.771 | 1.00 | 53.99 | C |
| ATOM | 5021 | O | VAL | A | 775 | 44.676 | 52.659 | -27.851 | 1.00 | 48.61 | O |
| ATOM | 5022 | CB | VAL | A | 775 | 46.204 | 52.600 | -30.943 | 1.00 | 46.86 | C |
| ATOM | 5023 | CG1 | VAL | A | 775 | 47.360 | 52.137 | -30.143 | 1.00 | 56.18 | C |
| ATOM | 5024 | CG2 | VAL | A | 775 | 46.226 | 52.053 | -32.408 | 1.00 | 44.75 | C |
| ATOM | 5025 | N | CYS | A | 776 | 44.901 | 50.525 | -28.537 | 1.00 | 57.49 | N |
| ATOM | 5026 | CA | CYS | A | 776 | 44.869 | 50.021 | -27.162 | 1.00 | 65.71 | C |
| ATOM | 5027 | C | CYS | A | 776 | 46.130 | 50.378 | -26.388 | 1.00 | 67.09 | C |
| ATOM | 5028 | O | CYS | A | 776 | 46.065 | 50.867 | -25.263 | 1.00 | 69.08 | O |
| ATOM | 5029 | CB | CYS | A | 776 | 44.650 | 48.503 | -27.142 | 1.00 | 74.44 | C |
| ATOM | 5030 | SG | CYS | A | 776 | 42.914 | 48.009 | -27.348 | 1.00 | 106.35 | S |
| ATOM | 5031 | N | SER | A | 777 | 47.282 | 50.118 | -26.999 | 1.00 | 70.08 | N |
| ATOM | 5032 | CA | SER | A | 777 | 48.572 | 50.493 | -26.429 | 1.00 | 62.46 | C |
| ATOM | 5033 | C | SER | A | 777 | 49.455 | 51.010 | -27.547 | 1.00 | 62.64 | C |
| ATOM | 5034 | O | SER | A | 777 | 49.281 | 50.647 | -28.727 | 1.00 | 59.08 | O |
| ATOM | 5035 | CB | SER | A | 777 | 49.247 | 49.299 | -25.768 | 1.00 | 62.42 | C |
| ATOM | 5036 | OG | SER | A | 777 | 50.088 | 48.639 | -26.695 | 1.00 | 71.39 | O |
| ATOM | 5037 | N | GLY | A | 778 | 50.417 | 51.844 | -27.183 | 1.00 | 60.40 | N |
| ATOM | 5038 | CA | GLY | A | 778 | 51.214 | 52.516 | -28.188 | 1.00 | 66.13 | C |
| ATOM | 5039 | C | GLY | A | 778 | 50.434 | 53.723 | -28.675 | 1.00 | 66.57 | C |
| ATOM | 5040 | O | GLY | A | 778 | 49.601 | 54.288 | -27.942 | 1.00 | 71.56 | O |
| ATOM | 5041 | N | GLY | A | 779 | 50.680 | 54.105 | -29.910 | 1.00 | 56.41 | N |
| ATOM | 5042 | CA | GLY | A | 779 | 50.139 | 55.339 | -30.458 | 1.00 | 56.26 | C |
| ATOM | 5043 | C | GLY | A | 779 | 51.276 | 56.339 | -30.581 | 1.00 | 52.95 | C |
| ATOM | 5044 | O | GLY | A | 779 | 52.123 | 56.393 | -29.723 | 1.00 | 47.07 | O |
| ATOM | 5045 | N | MET | A | 780 | 51.297 | 57.128 | -31.641 | 1.00 | 41.19 | N |
| ATOM | 5046 | CA | MET | A | 780 | 52.392 | 58.045 | -31.832 | 1.00 | 48.94 | C |
| ATOM | 5047 | C | MET | A | 780 | 52.059 | 59.396 | -31.238 | 1.00 | 44.36 | C |
| ATOM | 5048 | O | MET | A | 780 | 52.903 | 60.306 | -31.172 | 1.00 | 44.69 | O |
| ATOM | 5049 | CB | MET | A | 780 | 52.784 | 58.144 | -33.315 | 1.00 | 51.69 | C |
| ATOM | 5050 | CG | MET | A | 780 | 51.650 | 58.162 | -34.323 | 1.00 | 49.98 | C |
| ATOM | 5051 | SD | MET | A | 780 | 50.802 | 59.756 | -34.375 | 1.00 | 84.01 | S |
| ATOM | 5052 | CE | MET | A | 780 | 52.145 | 60.939 | -34.397 | 1.00 | 82.23 | C |
| ATOM | 5053 | N | ARG | A | 781 | 50.821 | 59.505 | -30.795 | 1.00 | 37.80 | N |
| ATOM | 5054 | CA | ARG | A | 781 | 50.319 | 60.725 | -30.183 | 1.00 | 39.32 | C |
| ATOM | 5055 | C | ARG | A | 781 | 49.268 | 60.422 | -29.118 | 1.00 | 39.72 | C |
| ATOM | 5056 | O | ARG | A | 781 | 48.454 | 59.534 | -29.289 | 1.00 | 34.61 | O |
| ATOM | 5057 | CB | ARG | A | 781 | 49.695 | 61.603 | -31.225 | 1.00 | 34.91 | C |
| ATOM | 5058 | CG | ARG | A | 781 | 49.453 | 62.997 | -30.724 | 1.00 | 36.24 | C |
| ATOM | 5059 | CD | ARG | A | 781 | 48.770 | 63.751 | -31.830 | 1.00 | 44.13 | C |
| ATOM | 5060 | NE | ARG | A | 781 | 48.733 | 65.184 | -31.584 | 1.00 | 45.98 | N |
| ATOM | 5061 | CZ | ARG | A | 781 | 48.371 | 66.056 | -32.516 | 1.00 | 42.86 | C |
| ATOM | 5062 | NH1 | ARG | A | 781 | 48.050 | 65.619 | -33.738 | 1.00 | 39.70 | N |
| ATOM | 5063 | NH2 | ARG | A | 781 | 48.344 | 67.350 | -32.235 | 1.00 | 36.32 | N |
| ATOM | 5064 | N | ILE | A | 782 | 49.331 | 61.146 | -28.011 | 1.00 | 34.30 | N |
| ATOM | 5065 | CA | ILE | A | 782 | 48.544 | 60.841 | -26.830 | 1.00 | 33.50 | C |
| ATOM | 5066 | C | ILE | A | 782 | 47.644 | 62.024 | -26.591 | 1.00 | 40.05 | C |
| ATOM | 5067 | O | ILE | A | 782 | 48.126 | 63.137 | -26.469 | 1.00 | 37.07 | O |
| ATOM | 5068 | CB | ILE | A | 782 | 49.447 | 60.610 | -25.595 | 1.00 | 43.74 | C |
| ATOM | 5069 | CG1 | ILE | A | 782 | 50.472 | 59.498 | -25.883 | 1.00 | 45.69 | C |
| ATOM | 5070 | CG2 | ILE | A | 782 | 48.603 | 60.210 | -24.378 | 1.00 | 38.83 | C |
| ATOM | 5071 | CD1 | ILE | A | 782 | 51.318 | 59.131 | -24.651 | 1.00 | 51.27 | C |
| ATOM | 5072 | N | LEU | A | 783 | 46.332 | 61.795 | -26.560 | 1.00 | 37.92 | N |
| ATOM | 5073 | CA | LEU | A | 783 | 45.367 | 62.885 | -26.382 | 1.00 | 40.30 | C |
| ATOM | 5074 | C | LEU | A | 783 | 44.453 | 62.552 | -25.209 | 1.00 | 35.33 | C |
| ATOM | 5075 | O | LEU | A | 783 | 44.015 | 61.394 | -25.121 | 1.00 | 32.44 | O |
| ATOM | 5076 | CB | LEU | A | 783 | 44.499 | 63.026 | -27.643 | 1.00 | 35.57 | C |
| ATOM | 5077 | CG | LEU | A | 783 | 45.233 | 63.368 | -28.924 | 1.00 | 43.79 | C |

FIG. 8-76

| | | | | | | | | | | | |
|---|---|---|---|---|---|---|---|---|---|---|---|
| ATOM | 5078 | CD1 | LEU | A | 783 | 44.289 | 63.341 | -30.158 | 1.00 | 35.47 | C |
| ATOM | 5079 | CD2 | LEU | A | 783 | 46.009 | 64.713 | -28.779 | 1.00 | 30.10 | C |
| ATOM | 5080 | N | PRO | A | 784 | 44.154 | 63.547 | -24.335 | 1.00 | 32.39 | N |
| ATOM | 5081 | CA | PRO | A | 784 | 43.114 | 63.358 | -23.307 | 1.00 | 40.47 | C |
| ATOM | 5082 | C | PRO | A | 784 | 41.722 | 63.261 | -23.946 | 1.00 | 35.03 | C |
| ATOM | 5083 | O | PRO | A | 784 | 41.407 | 63.989 | -24.901 | 1.00 | 36.86 | O |
| ATOM | 5084 | CB | PRO | A | 784 | 43.167 | 64.643 | -22.456 | 1.00 | 29.03 | C |
| ATOM | 5085 | CG | PRO | A | 784 | 43.880 | 65.656 | -23.305 | 1.00 | 29.54 | C |
| ATOM | 5086 | CD | PRO | A | 784 | 44.597 | 64.954 | -24.431 | 1.00 | 30.87 | C |
| ATOM | 5087 | N | VAL | A | 785 | 40.891 | 62.402 | -23.374 | 1.00 | 33.48 | N |
| ATOM | 5088 | CA | VAL | A | 785 | 39.586 | 62.077 | -23.912 | 1.00 | 30.23 | C |
| ATOM | 5089 | C | VAL | A | 785 | 38.552 | 61.980 | -22.758 | 1.00 | 44.07 | C |
| ATOM | 5090 | O | VAL | A | 785 | 38.789 | 61.296 | -21.781 | 1.00 | 42.72 | O |
| ATOM | 5091 | CB | VAL | A | 785 | 39.643 | 60.718 | -24.626 | 1.00 | 31.18 | C |
| ATOM | 5092 | CG1 | VAL | A | 785 | 38.231 | 60.221 | -24.922 | 1.00 | 34.22 | C |
| ATOM | 5093 | CG2 | VAL | A | 785 | 40.451 | 60.813 | -25.911 | 1.00 | 34.37 | C |
| ATOM | 5094 | N | TRP | A | 786 | 37.423 | 62.673 | -22.899 | 1.00 | 36.62 | N |
| ATOM | 5095 | CA | TRP | A | 786 | 36.305 | 62.605 | -21.997 | 1.00 | 34.22 | C |
| ATOM | 5096 | C | TRP | A | 786 | 35.640 | 61.234 | -22.165 | 1.00 | 37.43 | C |
| ATOM | 5097 | O | TRP | A | 786 | 34.926 | 60.982 | -23.142 | 1.00 | 39.63 | O |
| ATOM | 5098 | CB | TRP | A | 786 | 35.338 | 63.780 | -22.282 | 1.00 | 31.13 | C |
| ATOM | 5099 | CG | TRP | A | 786 | 34.109 | 63.907 | -21.340 | 1.00 | 40.96 | C |
| ATOM | 5100 | CD1 | TRP | A | 786 | 33.773 | 63.075 | -20.318 | 1.00 | 46.17 | C |
| ATOM | 5101 | CD2 | TRP | A | 786 | 33.088 | 64.934 | -21.374 | 1.00 | 39.88 | C |
| ATOM | 5102 | NE1 | TRP | A | 786 | 32.608 | 63.501 | -19.723 | 1.00 | 44.35 | N |
| ATOM | 5103 | CE2 | TRP | A | 786 | 32.173 | 64.646 | -20.343 | 1.00 | 43.09 | C |
| ATOM | 5104 | CE3 | TRP | A | 786 | 32.857 | 66.060 | -22.192 | 1.00 | 34.67 | C |
| ATOM | 5105 | CZ2 | TRP | A | 786 | 31.035 | 65.444 | -20.094 | 1.00 | 39.34 | C |
| ATOM | 5106 | CZ3 | TRP | A | 786 | 31.773 | 66.864 | -21.931 | 1.00 | 37.36 | C |
| ATOM | 5107 | CH2 | TRP | A | 786 | 30.861 | 66.556 | -20.879 | 1.00 | 40.31 | C |
| ATOM | 5108 | N | THR | A | 787 | 35.883 | 60.338 | -21.217 | 1.00 | 34.29 | N |
| ATOM | 5109 | CA | THR | A | 787 | 35.389 | 58.968 | -21.325 | 1.00 | 43.97 | C |
| ATOM | 5110 | C | THR | A | 787 | 35.430 | 58.411 | -19.941 | 1.00 | 47.22 | C |
| ATOM | 5111 | O | THR | A | 787 | 36.396 | 58.651 | -19.245 | 1.00 | 46.26 | O |
| ATOM | 5112 | CB | THR | A | 787 | 36.381 | 57.984 | -21.941 | 1.00 | 56.07 | C |
| ATOM | 5113 | OG1 | THR | A | 787 | 37.298 | 58.632 | -22.816 | 1.00 | 61.10 | O |
| ATOM | 5114 | CG2 | THR | A | 787 | 35.645 | 56.875 | -22.594 | 1.00 | 34.92 | C |
| ATOM | 5115 | N | SER | A | 788 | 34.441 | 57.593 | -19.590 | 1.00 | 53.55 | N |
| ATOM | 5116 | CA | SER | A | 788 | 34.459 | 56.853 | -18.337 | 1.00 | 60.92 | C |
| ATOM | 5117 | C | SER | A | 788 | 34.933 | 55.418 | -18.584 | 1.00 | 58.84 | C |
| ATOM | 5118 | O | SER | A | 788 | 34.954 | 54.593 | -17.677 | 1.00 | 63.18 | O |
| ATOM | 5119 | CB | SER | A | 788 | 33.066 | 56.844 | -17.711 | 1.00 | 54.60 | C |
| ATOM | 5120 | OG | SER | A | 788 | 32.104 | 56.324 | -18.616 | 1.00 | 56.63 | O |
| ATOM | 5121 | N | ASP | A | 789 | 35.309 | 55.123 | -19.820 | 1.00 | 51.74 | N |
| ATOM | 5122 | CA | ASP | A | 789 | 35.700 | 53.774 | -20.169 | 1.00 | 53.55 | C |
| ATOM | 5123 | C | ASP | A | 789 | 36.542 | 53.760 | -21.432 | 1.00 | 51.03 | C |
| ATOM | 5124 | O | ASP | A | 789 | 36.053 | 53.360 | -22.481 | 1.00 | 47.34 | O |
| ATOM | 5125 | CB | ASP | A | 789 | 34.448 | 52.917 | -20.391 | 1.00 | 64.55 | C |
| ATOM | 5126 | CG | ASP | A | 789 | 34.776 | 51.486 | -20.804 | 1.00 | 81.52 | C |
| ATOM | 5127 | OD1 | ASP | A | 789 | 33.826 | 50.722 | -21.083 | 1.00 | 91.31 | O |
| ATOM | 5128 | OD2 | ASP | A | 789 | 35.971 | 51.120 | -20.856 | 1.00 | 84.39 | O |
| ATOM | 5129 | N | PRO | A | 790 | 37.822 | 54.166 | -21.332 | 1.00 | 51.05 | N |
| ATOM | 5130 | CA | PRO | A | 790 | 38.642 | 54.257 | -22.547 | 1.00 | 48.59 | C |
| ATOM | 5131 | C | PRO | A | 790 | 38.565 | 53.045 | -23.484 | 1.00 | 56.06 | C |
| ATOM | 5132 | O | PRO | A | 790 | 39.343 | 53.007 | -24.414 | 1.00 | 54.16 | O |
| ATOM | 5133 | CB | PRO | A | 790 | 40.067 | 54.400 | -22.013 | 1.00 | 46.41 | C |
| ATOM | 5134 | CG | PRO | A | 790 | 39.913 | 54.945 | -20.596 | 1.00 | 49.24 | C |
| ATOM | 5135 | CD | PRO | A | 790 | 38.538 | 54.605 | -20.110 | 1.00 | 40.43 | C |
| ATOM | 5136 | N | GLN | A | 791 | 37.653 | 52.090 | -23.294 | 1.00 | 77.95 | N |
| ATOM | 5137 | CA | GLN | A | 791 | 37.505 | 50.992 | -24.284 | 1.00 | 75.99 | C |
| ATOM | 5138 | C | GLN | A | 791 | 36.619 | 51.365 | -25.477 | 1.00 | 62.38 | C |
| ATOM | 5139 | O | GLN | A | 791 | 36.063 | 50.553 | -26.238 | 1.00 | 51.67 | O |
| ATOM | 5140 | CB | GLN | A | 791 | 37.197 | 49.669 | -23.625 | 1.00 | 74.59 | C |
| ATOM | 5141 | CG | GLN | A | 791 | 38.496 | 48.941 | -23.287 | 1.00 | 74.31 | C |
| ATOM | 5142 | CD | GLN | A | 791 | 39.475 | 49.741 | -22.421 | 1.00 | 68.09 | C |
| ATOM | 5143 | OE1 | GLN | A | 791 | 40.266 | 49.151 | -21.689 | 1.00 | 76.36 | O |
| ATOM | 5144 | NE2 | GLN | A | 791 | 39.436 | 51.071 | -22.501 | 1.00 | 51.89 | N |
| ATOM | 5145 | N | SER | A | 792 | 36.548 | 52.671 | -25.604 | 1.00 | 59.17 | N |
| ATOM | 5146 | CA | SER | A | 792 | 36.410 | 53.334 | -26.856 | 1.00 | 53.48 | C |
| ATOM | 5147 | C | SER | A | 792 | 37.517 | 52.859 | -27.823 | 1.00 | 60.41 | C |
| ATOM | 5148 | O | SER | A | 792 | 37.389 | 53.020 | -29.045 | 1.00 | 64.83 | O |
| ATOM | 5149 | CB | SER | A | 792 | 36.498 | 54.828 | -26.566 | 1.00 | 46.95 | C |
| ATOM | 5150 | OG | SER | A | 792 | 37.252 | 55.505 | -27.539 | 1.00 | 61.48 | O |
| ATOM | 5151 | N | LEU | A | 793 | 38.581 | 52.244 | -27.300 | 1.00 | 59.51 | N |
| ATOM | 5152 | CA | LEU | A | 793 | 39.659 | 51.773 | -28.187 | 1.00 | 60.18 | C |
| ATOM | 5153 | C | LEU | A | 793 | 39.573 | 50.330 | -28.682 | 1.00 | 58.54 | C |
| ATOM | 5154 | O | LEU | A | 793 | 40.016 | 50.044 | -29.784 | 1.00 | 60.39 | O |

FIG. 8-77

| | | | | | | | | | | |
|---|---|---|---|---|---|---|---|---|---|---|
| ATOM | 5155 | CB | LEU | A | 793 | 41.049 | 52.048 | -27.619 | 1.00 55.85 | C |
| ATOM | 5156 | CG | LEU | A | 793 | 41.248 | 51.822 | -26.134 | 1.00 54.21 | C |
| ATOM | 5157 | CD1 | LEU | A | 793 | 41.535 | 50.372 | -25.850 | 1.00 45.85 | C |
| ATOM | 5158 | CD2 | LEU | A | 793 | 42.356 | 52.720 | -25.659 | 1.00 65.72 | C |
| ATOM | 5159 | N | CYS | A | 794 | 39.018 | 49.417 | -27.894 | 1.00 59.77 | N |
| ATOM | 5160 | CA | CYS | A | 794 | 38.885 | 48.036 | -28.371 | 1.00 60.53 | C |
| ATOM | 5161 | C | CYS | A | 794 | 37.986 | 48.069 | -29.598 | 1.00 67.14 | C |
| ATOM | 5162 | O | CYS | A | 794 | 38.081 | 47.247 | -30.513 | 1.00 69.97 | O |
| ATOM | 5163 | CB | CYS | A | 794 | 38.289 | 47.137 | -27.284 | 1.00 59.81 | C |
| ATOM | 5164 | SG | CYS | A | 794 | 39.272 | 47.053 | -25.770 | 1.00148.69 | S |
| ATOM | 5165 | N | GLN | A | 795 | 37.118 | 49.068 | -29.598 | 1.00 73.66 | N |
| ATOM | 5166 | CA | GLN | A | 795 | 36.169 | 49.285 | -30.656 | 1.00 67.25 | C |
| ATOM | 5167 | C | GLN | A | 795 | 36.885 | 49.865 | -31.858 | 1.00 65.13 | C |
| ATOM | 5168 | O | GLN | A | 795 | 36.716 | 49.374 | -32.976 | 1.00 64.06 | O |
| ATOM | 5169 | CB | GLN | A | 795 | 35.084 | 50.237 | -30.167 | 1.00 76.54 | C |
| ATOM | 5170 | CG | GLN | A | 795 | 34.154 | 50.738 | -31.247 | 1.00 88.98 | C |
| ATOM | 5171 | CD | GLN | A | 795 | 33.280 | 51.878 | -30.761 | 1.00 99.49 | C |
| ATOM | 5172 | OE1 | GLN | A | 795 | 33.437 | 52.365 | -29.634 | 1.00100.52 | O |
| ATOM | 5173 | NE2 | GLN | A | 795 | 32.353 | 52.314 | -31.610 | 1.00102.92 | N |
| ATOM | 5174 | N | GLN | A | 796 | 37.679 | 50.913 | -31.642 | 1.00 61.56 | N |
| ATOM | 5175 | CA | GLN | A | 796 | 38.410 | 51.530 | -32.752 | 1.00 62.46 | C |
| ATOM | 5176 | C | GLN | A | 796 | 39.297 | 50.446 | -33.420 | 1.00 63.23 | C |
| ATOM | 5177 | O | GLN | A | 796 | 39.184 | 50.181 | -34.642 | 1.00 53.87 | O |
| ATOM | 5178 | CB | GLN | A | 796 | 39.203 | 52.776 | -32.279 | 1.00 66.22 | C |
| ATOM | 5179 | CG | GLN | A | 796 | 39.879 | 53.622 | -33.397 | 1.00135.73 | C |
| ATOM | 5180 | CD | GLN | A | 796 | 39.186 | 54.978 | -33.741 | 1.00 74.19 | C |
| ATOM | 5181 | OE1 | GLN | A | 796 | 39.115 | 55.900 | -32.914 | 1.00 61.21 | O |
| ATOM | 5182 | NE2 | GLN | A | 796 | 38.743 | 55.109 | -34.994 | 1.00 71.77 | N |
| ATOM | 5183 | N | SER | A | 797 | 40.117 | 49.781 | -32.599 | 1.00 62.06 | N |
| ATOM | 5184 | CA | SER | A | 797 | 40.994 | 48.687 | -33.035 | 1.00 71.31 | C |
| ATOM | 5185 | C | SER | A | 797 | 40.324 | 47.643 | -33.938 | 1.00 84.10 | C |
| ATOM | 5186 | O | SER | A | 797 | 40.979 | 47.048 | -34.792 | 1.00 83.71 | O |
| ATOM | 5187 | CB | SER | A | 797 | 41.574 | 47.952 | -31.817 | 1.00 77.21 | C |
| ATOM | 5188 | OG | SER | A | 797 | 42.475 | 48.761 | -31.076 | 1.00 81.58 | O |
| ATOM | 5189 | N | GLU | A | 798 | 39.033 | 47.395 | -33.734 | 1.00 94.90 | N |
| ATOM | 5190 | CA | GLU | A | 798 | 38.385 | 46.250 | -34.373 | 1.00102.80 | C |
| ATOM | 5191 | C | GLU | A | 798 | 37.985 | 46.492 | -35.833 | 1.00105.22 | C |
| ATOM | 5192 | O | GLU | A | 798 | 37.257 | 45.694 | -36.422 | 1.00108.54 | O |
| ATOM | 5193 | CB | GLU | A | 798 | 37.195 | 45.750 | -33.542 | 1.00106.70 | C |
| ATOM | 5194 | CG | GLU | A | 798 | 35.890 | 46.480 | -33.785 | 1.00111.02 | C |
| ATOM | 5195 | CD | GLU | A | 798 | 34.713 | 45.784 | -33.127 | 1.00117.15 | C |
| ATOM | 5196 | OE1 | GLU | A | 798 | 33.891 | 45.182 | -33.853 | 1.00119.54 | O |
| ATOM | 5197 | OE2 | GLU | A | 798 | 34.617 | 45.823 | -31.883 | 1.00118.29 | O |
| ATOM | 5198 | N | MET | A | 799 | 38.479 | 47.583 | -36.412 | 1.00104.95 | N |
| ATOM | 5199 | CA | MET | A | 799 | 38.307 | 47.858 | -37.839 | 1.00103.57 | C |
| ATOM | 5200 | C | MET | A | 799 | 38.858 | 46.722 | -38.700 | 1.00112.38 | C |
| ATOM | 5201 | O | MET | A | 799 | 38.114 | 46.082 | -39.454 | 1.00113.77 | O |
| ATOM | 5202 | CB | MET | A | 799 | 38.995 | 49.171 | -38.217 | 1.00 95.15 | C |
| ATOM | 5203 | CG | MET | A | 799 | 40.503 | 49.177 | -37.982 | 1.00 92.45 | C |
| ATOM | 5204 | SD | MET | A | 799 | 41.270 | 50.796 | -38.202 | 1.00136.24 | S |
| ATOM | 5205 | CE | MET | A | 799 | 43.006 | 50.367 | -38.085 | 1.00128.50 | C |
| ATOM | 5206 | N | GLN | A | 800 | 40.163 | 46.482 | -38.580 | 1.00117.78 | N |
| ATOM | 5207 | CA | GLN | A | 800 | 40.853 | 45.424 | -39.322 | 1.00123.45 | C |
| ATOM | 5208 | C | GLN | A | 800 | 40.339 | 45.277 | -40.756 | 1.00124.02 | C |
| ATOM | 5209 | O | GLN | A | 800 | 41.088 | 45.445 | -41.721 | 1.00123.21 | O |
| ATOM | 5210 | CB | GLN | A | 800 | 40.735 | 44.091 | -38.578 | 1.00126.70 | C |
| ATOM | 5211 | CG | GLN | A | 800 | 40.881 | 44.212 | -37.068 | 1.00128.60 | C |
| ATOM | 5212 | CD | GLN | A | 800 | 40.590 | 42.910 | -36.348 | 1.00132.85 | C |
| ATOM | 5213 | OE1 | GLN | A | 800 | 39.565 | 42.774 | -35.675 | 1.00134.53 | O |
| ATOM | 5214 | NE2 | GLN | A | 800 | 41.486 | 41.939 | -36.496 | 1.00133.48 | N |
| TER | 5215 | | GLN | A | 800 | | | | | |
| HETATM | 5216 | ODF | MOE | A | 901 | 45.927 | 137.485 | 12.818 | 1.00145.84 | O |
| HETATM | 5217 | CDG | MOE | A | 901 | 46.456 | 136.532 | 11.890 | 1.00146.04 | C |
| HETATM | 5218 | CDH | MOE | A | 901 | 46.789 | 135.252 | 12.604 | 1.00143.89 | C |
| HETATM | 5219 | ODI | MOE | A | 901 | 47.716 | 135.261 | 13.439 | 1.00143.44 | O |
| HETATM | 5220 | ODJ | MOE | A | 901 | 46.132 | 134.221 | 12.338 | 1.00143.52 | O |
| HETATM | 5221 | CDK | MOE | A | 901 | 45.443 | 136.260 | 10.782 | 1.00148.88 | C |
| HETATM | 5222 | OBF | MOE | A | 901 | 46.164 | 135.721 | 9.677 | 1.00150.34 | O |
| HETATM | 5223 | PBI | MOE | A | 901 | 45.638 | 134.441 | 8.857 | 1.00116.65 | P |
| HETATM | 5224 | OBB | MOE | A | 901 | 45.908 | 134.658 | 7.386 | 1.00119.80 | O |
| HETATM | 5225 | OAZ | MOE | A | 901 | 44.243 | 134.098 | 9.326 | 1.00114.14 | O |
| HETATM | 5226 | OBG | MOE | A | 901 | 46.658 | 133.336 | 9.425 | 1.00132.65 | O |
| HETATM | 5227 | CAX | MOE | A | 901 | 47.933 | 133.102 | 8.833 | 1.00133.05 | C |
| HETATM | 5228 | OBE | MOE | A | 901 | 48.861 | 134.120 | 9.229 | 1.00134.48 | O |
| HETATM | 5229 | CAQ | MOE | A | 901 | 49.157 | 134.122 | 10.628 | 1.00134.51 | C |
| HETATM | 5230 | CAW | MOE | A | 901 | 50.132 | 135.215 | 10.960 | 1.00133.74 | C |
| HETATM | 5231 | OBD | MOE | A | 901 | 50.201 | 135.653 | 12.097 | 1.00133.17 | O |

FIG. 8-78

| | | | | | | | | | |
|---|---|---|---|---|---|---|---|---|---|
| HETATM | 5232 | NAU | MOE | A 901 | 50.901 | 135.655 | 9.969 | 1.00133.00 | N |
| HETATM | 5233 | CAO | MOE | A 901 | 49.763 | 132.788 | 11.033 | 1.00133.95 | C |
| HETATM | 5234 | OBA | MOE | A 901 | 50.040 | 132.800 | 12.440 | 1.00132.87 | O |
| HETATM | 5235 | CAS | MOE | A 901 | 51.060 | 132.542 | 10.267 | 1.00133.06 | C |
| HETATM | 5236 | CAP | MOE | A 901 | 48.764 | 131.679 | 10.741 | 1.00132.58 | C |
| HETATM | 5237 | OBH | MOE | A 901 | 49.388 | 130.443 | 11.077 | 1.00131.07 | O |
| HETATM | 5238 | CAV | MOE | A 901 | 48.423 | 129.407 | 11.396 | 1.00127.58 | C |
| HETATM | 5239 | OBC | MOE | A 901 | 47.516 | 129.662 | 12.173 | 1.00123.84 | O |
| HETATM | 5240 | NAT | MOE | A 901 | 48.592 | 128.208 | 10.854 | 1.00128.30 | N |
| HETATM | 5241 | CAR | MOE | A 901 | 48.384 | 131.712 | 9.269 | 1.00131.03 | C |
| HETATM | 5242 | O1 | MOE | A 901 | 47.281 | 130.837 | 9.057 | 1.00126.61 | O |
| HETATM | 5243 | C1 | MOE | A 901 | 47.624 | 129.867 | 8.079 | 1.00124.20 | C |
| HETATM | 5244 | C2 | MOE | A 901 | 46.447 | 128.910 | 7.937 | 1.00121.13 | C |
| HETATM | 5245 | C3 | MOE | A 901 | 46.284 | 128.255 | 6.564 | 1.00121.72 | C |
| HETATM | 5246 | O3 | MOE | A 901 | 44.893 | 127.951 | 6.395 | 1.00122.86 | O |
| HETATM | 5247 | N2 | MOE | A 901 | 46.815 | 127.810 | 8.818 | 1.00118.63 | N |
| HETATM | 5248 | CAG | MOE | A 901 | 45.956 | 127.278 | 9.684 | 1.00115.06 | C |
| HETATM | 5249 | CAH | MOE | A 901 | 46.487 | 126.151 | 10.521 | 1.00111.39 | C |
| HETATM | 5250 | OAN | MOE | A 901 | 44.812 | 127.685 | 9.790 | 1.00115.15 | O |
| HETATM | 5251 | O5 | MOE | A 901 | 47.833 | 130.615 | 6.897 | 1.00123.86 | O |
| HETATM | 5252 | C5 | MOE | A 901 | 48.034 | 129.830 | 5.742 | 1.00124.49 | C |
| HETATM | 5253 | C6 | MOE | A 901 | 48.404 | 130.833 | 4.676 | 1.00130.12 | C |
| HETATM | 5254 | O6 | MOE | A 901 | 47.504 | 131.928 | 4.812 | 1.00134.25 | O |
| HETATM | 5255 | CBJ | MOE | A 901 | 47.903 | 133.011 | 3.981 | 1.00137.61 | C |
| HETATM | 5256 | OBS | MOE | A 901 | 48.770 | 133.875 | 4.714 | 1.00137.34 | O |
| HETATM | 5257 | CBN | MOE | A 901 | 49.256 | 134.946 | 3.906 | 1.00137.89 | C |
| HETATM | 5258 | CBO | MOE | A 901 | 50.241 | 135.778 | 4.717 | 1.00137.91 | C |
| HETATM | 5259 | OBT | MOE | A 901 | 51.215 | 134.910 | 5.305 | 1.00138.96 | O |
| HETATM | 5260 | CBM | MOE | A 901 | 48.108 | 135.812 | 3.393 | 1.00138.80 | C |
| HETATM | 5261 | OBR | MOE | A 901 | 48.620 | 136.781 | 2.472 | 1.00138.12 | O |
| HETATM | 5262 | CBL | MOE | A 901 | 47.026 | 134.982 | 2.706 | 1.00139.89 | C |
| HETATM | 5263 | OBQ | MOE | A 901 | 45.859 | 135.784 | 2.488 | 1.00140.63 | O |
| HETATM | 5264 | CBK | MOE | A 901 | 46.655 | 133.770 | 3.548 | 1.00139.08 | C |
| HETATM | 5265 | OBP | MOE | A 901 | 45.800 | 132.905 | 2.787 | 1.00138.20 | O |
| HETATM | 5266 | C4 | MOE | A 901 | 46.737 | 129.129 | 5.397 | 1.00120.15 | C |
| HETATM | 5267 | O4 | MOE | A 901 | 46.933 | 128.322 | 4.231 | 1.00114.64 | O |
| HETATM | 5268 | CBU | MOE | A 901 | 46.070 | 128.692 | 3.153 | 1.00109.26 | C |
| HETATM | 5269 | CBV | MOE | A 901 | 46.866 | 128.691 | 1.848 | 1.00108.50 | C |
| HETATM | 5270 | CBW | MOE | A 901 | 45.961 | 128.970 | 0.647 | 1.00107.31 | C |
| HETATM | 5271 | OCD | MOE | A 901 | 46.689 | 128.780 | -0.573 | 1.00105.93 | O |
| HETATM | 5272 | NCC | MOE | A 901 | 47.787 | 129.822 | 1.919 | 1.00107.54 | N |
| HETATM | 5273 | CCA | MOE | A 901 | 49.073 | 129.732 | 1.565 | 1.00105.05 | C |
| HETATM | 5274 | CCB | MOE | A 901 | 49.877 | 130.994 | 1.696 | 1.00102.66 | C |
| HETATM | 5275 | OCG | MOE | A 901 | 49.576 | 128.693 | 1.168 | 1.00104.22 | O |
| HETATM | 5276 | OCF | MOE | A 901 | 45.009 | 127.741 | 3.049 | 1.00105.39 | O |
| HETATM | 5277 | CBY | MOE | A 901 | 44.074 | 128.035 | 2.007 | 1.00103.70 | C |
| HETATM | 5278 | CBZ | MOE | A 901 | 42.923 | 127.034 | 2.060 | 1.00101.55 | C |
| HETATM | 5279 | CBX | MOE | A 901 | 44.760 | 128.032 | 0.645 | 1.00106.45 | C |
| HETATM | 5280 | OCE | MOE | A 901 | 43.824 | 128.434 | -0.359 | 1.00107.19 | O |
| HETATM | 5281 | CCH | MOE | A 901 | 43.446 | 127.354 | -1.218 | 1.00105.25 | C |
| HETATM | 5282 | OCP | MOE | A 901 | 44.283 | 127.357 | -2.377 | 1.00105.87 | O |
| HETATM | 5283 | CCI | MOE | A 901 | 41.989 | 127.523 | -1.639 | 1.00100.78 | C |
| HETATM | 5284 | OCN | MOE | A 901 | 41.138 | 127.415 | -0.493 | 1.00 96.75 | O |
| HETATM | 5285 | CCJ | MOE | A 901 | 41.564 | 126.469 | -2.657 | 1.00103.43 | C |
| HETATM | 5286 | OCO | MOE | A 901 | 40.274 | 126.806 | -3.186 | 1.00103.47 | O |
| HETATM | 5287 | CCK | MOE | A 901 | 42.578 | 126.331 | -3.789 | 1.00104.96 | C |
| HETATM | 5288 | OCR | MOE | A 901 | 42.445 | 127.440 | -4.687 | 1.00107.69 | O |
| HETATM | 5289 | CCL | MOE | A 901 | 44.002 | 126.256 | -3.239 | 1.00104.51 | C |
| HETATM | 5290 | CCM | MOE | A 901 | 45.003 | 126.241 | -4.353 | 1.00104.31 | C |
| HETATM | 5291 | OCQ | MOE | A 901 | 46.280 | 126.543 | -4.114 | 1.00105.36 | O |
| HETATM | 5292 | NCS | MOE | A 901 | 44.590 | 125.925 | -5.504 | 1.00102.02 | N |
| HETATM | 5293 | O | HOH | A1001 | 27.796 | 68.940 | -35.444 | 1.00 35.49 | O |
| HETATM | 5294 | O | HOH | A1002 | 35.027 | 61.681 | -25.721 | 1.00 34.47 | O |
| HETATM | 5295 | O | HOH | A1003 | 45.869 | 66.992 | -37.887 | 1.00 34.18 | O |
| HETATM | 5296 | O | HOH | A1004 | 34.787 | 65.703 | -26.135 | 1.00 35.00 | O |
| HETATM | 5297 | O | HOH | A1005 | 29.375 | 92.649 | -31.605 | 1.00 40.05 | O |
| HETATM | 5298 | O | HOH | A1006 | 36.660 | 63.983 | -25.749 | 1.00 26.19 | O |
| HETATM | 5299 | O | HOH | A1007 | 47.197 | 88.610 | -22.355 | 1.00 39.10 | O |
| HETATM | 5300 | O | HOH | A1008 | 51.749 | 75.605 | -22.871 | 1.00 29.09 | O |
| HETATM | 5301 | O | HOH | A1009 | 23.157 | 75.018 | -33.645 | 1.00 38.60 | O |
| HETATM | 5302 | O | HOH | A1010 | 40.245 | 94.484 | 0.062 | 1.00 39.61 | O |
| HETATM | 5303 | O | HOH | A1011 | 39.292 | 64.388 | -26.813 | 1.00 32.53 | O |
| HETATM | 5304 | O | HOH | A1012 | 48.420 | 69.777 | -19.340 | 1.00 36.69 | O |
| HETATM | 5305 | O | HOH | A1013 | 56.611 | 75.199 | -23.972 | 1.00 33.51 | O |
| HETATM | 5306 | O | HOH | A1014 | 54.203 | 78.450 | -21.271 | 1.00 39.76 | O |
| HETATM | 5307 | O | HOH | A1015 | 52.402 | 70.560 | -27.866 | 1.00 43.17 | O |
| HETATM | 5308 | O | HOH | A1016 | 47.638 | 85.281 | -16.971 | 1.00 44.51 | O |

FIG. 8-79

| | | | | | | | | | | |
|---|---|---|---|---|---|---|---|---|---|---|
| HETATM | 5309 | O | HOH | A1017 | 62.743 | 82.087 | -1.599 | 1.00 | 50.03 | O |
| HETATM | 5310 | O | HOH | A1018 | 27.288 | 71.634 | -27.552 | 1.00 | 44.27 | O |
| HETATM | 5311 | O | HOH | A1019 | 28.333 | 88.656 | -32.951 | 1.00 | 35.37 | O |
| HETATM | 5312 | O | HOH | A1020 | 48.765 | 90.883 | -4.247 | 1.00 | 57.66 | O |
| HETATM | 5313 | O | HOH | A1021 | 51.658 | 63.117 | -28.051 | 1.00 | 37.40 | O |
| HETATM | 5314 | O | HOH | A1022 | 42.413 | 78.673 | -47.654 | 1.00 | 58.60 | O |
| HETATM | 5315 | O | HOH | A1023 | 21.586 | 80.713 | -29.923 | 1.00 | 47.61 | O |
| HETATM | 5316 | O | HOH | A1024 | 37.918 | 71.729 | -15.896 | 1.00 | 41.13 | O |
| HETATM | 5317 | O | HOH | A1025 | 37.864 | 57.590 | -17.574 | 1.00 | 51.65 | O |
| HETATM | 5318 | O | HOH | A1026 | 38.755 | 91.372 | 7.336 | 1.00 | 54.87 | O |
| HETATM | 5319 | O | HOH | A1027 | 34.057 | 87.939 | -8.770 | 1.00 | 44.69 | O |
| HETATM | 5320 | O | HOH | A1028 | 46.526 | 77.134 | -43.247 | 1.00 | 47.77 | O |
| HETATM | 5321 | O | HOH | A1029 | 57.340 | 77.088 | -28.597 | 1.00 | 44.20 | O |
| HETATM | 5322 | O | HOH | A1030 | 46.431 | 96.200 | -3.661 | 1.00 | 43.41 | O |
| HETATM | 5323 | O | HOH | A1031 | 36.811 | 60.662 | -32.176 | 1.00 | 48.16 | O |
| HETATM | 5324 | O | HOH | A1032 | 40.442 | 75.062 | -14.946 | 1.00 | 38.57 | O |
| HETATM | 5325 | O | HOH | A1033 | 62.585 | 77.028 | -24.502 | 1.00 | 47.18 | O |
| HETATM | 5326 | O | HOH | A1034 | 21.757 | 89.987 | -30.191 | 1.00 | 49.16 | O |
| HETATM | 5327 | O | HOH | A1035 | 53.013 | 63.057 | -30.487 | 1.00 | 53.50 | O |
| HETATM | 5328 | O | HOH | A1036 | 34.714 | 89.799 | -4.600 | 1.00 | 53.04 | O |
| HETATM | 5329 | O | HOH | A1037 | 48.209 | 70.565 | -31.477 | 1.00 | 40.23 | O |
| HETATM | 5330 | O | HOH | A1038 | 24.610 | 75.415 | -39.730 | 1.00 | 44.14 | O |
| HETATM | 5331 | O | HOH | A1039 | 50.341 | 85.897 | -14.363 | 1.00 | 57.62 | O |
| HETATM | 5332 | O | HOH | A1040 | 49.801 | 65.116 | -27.006 | 1.00 | 55.45 | O |
| HETATM | 5333 | O | HOH | A1041 | 59.986 | 78.955 | -17.610 | 1.00 | 46.14 | O |
| HETATM | 5334 | O | HOH | A1042 | 54.168 | 76.327 | -22.573 | 1.00 | 33.25 | O |
| HETATM | 5335 | O | HOH | A1043 | 59.471 | 82.146 | 10.286 | 1.00 | 50.83 | O |
| HETATM | 5336 | O | HOH | A1044 | 54.084 | 83.018 | -31.248 | 1.00 | 50.39 | O |
| HETATM | 5337 | O | HOH | A1045 | 33.281 | 84.597 | -6.900 | 1.00 | 55.80 | O |
| HETATM | 5338 | O | HOH | A1046 | 35.250 | 61.821 | -33.763 | 1.00 | 55.58 | O |
| HETATM | 5339 | O | HOH | A1047 | 43.815 | 73.078 | -12.546 | 1.00 | 57.07 | O |
| HETATM | 5340 | O | HOH | A1048 | 44.681 | 54.570 | -25.388 | 1.00 | 66.83 | O |
| HETATM | 5341 | O | HOH | A1049 | 25.660 | 71.183 | -32.265 | 1.00 | 42.24 | O |
| HETATM | 5342 | O | HOH | A1050 | 32.333 | 57.433 | -21.378 | 1.00 | 44.08 | O |
| HETATM | 5343 | O | HOH | A1051 | 47.401 | 93.070 | 1.381 | 1.00 | 51.35 | O |
| HETATM | 5344 | O | HOH | A1052 | 60.167 | 83.439 | -27.742 | 1.00 | 61.06 | O |
| HETATM | 5345 | O | HOH | A1053 | 43.302 | 99.763 | -34.905 | 1.00 | 51.88 | O |
| HETATM | 5346 | O | HOH | A1054 | 60.383 | 91.865 | -20.980 | 1.00 | 52.84 | O |
| HETATM | 5347 | O | HOH | A1055 | 47.079 | 65.016 | -38.073 | 1.00 | 55.41 | O |
| HETATM | 5348 | O | HOH | A1056 | 47.659 | 99.884 | 4.868 | 1.00 | 59.43 | O |
| HETATM | 5349 | O | HOH | A1057 | 40.388 | 72.715 | -16.095 | 1.00 | 41.99 | O |
| HETATM | 5350 | O | HOH | A1058 | 39.182 | 73.424 | -12.679 | 1.00 | 53.29 | O |
| HETATM | 5351 | O | HOH | A1059 | 49.317 | 66.766 | -29.226 | 1.00 | 41.02 | O |
| HETATM | 5352 | O | HOH | A1060 | 23.977 | 77.426 | -38.545 | 1.00 | 42.79 | O |
| HETATM | 5353 | O | HOH | A1061 | 37.804 | 109.858 | 5.314 | 1.00 | 65.32 | O |
| HETATM | 5354 | O | HOH | A1062 | 40.031 | 82.167 | -6.242 | 1.00 | 59.06 | O |
| HETATM | 5355 | O | HOH | A1063 | 52.298 | 73.175 | -21.807 | 1.00 | 47.48 | O |
| HETATM | 5356 | O | HOH | A1064 | 43.807 | 80.396 | -41.092 | 1.00 | 37.36 | O |
| HETATM | 5357 | O | HOH | A1065 | 34.224 | 80.525 | -33.038 | 1.00 | 46.52 | O |
| HETATM | 5358 | O | HOH | A1066 | 32.105 | 82.491 | -32.578 | 1.00 | 39.91 | O |
| HETATM | 5359 | O | HOH | A1067 | 54.988 | 101.218 | -3.415 | 1.00 | 60.68 | O |
| HETATM | 5360 | O | HOH | A1068 | 30.515 | 57.592 | -29.683 | 1.00 | 54.68 | O |
| HETATM | 5361 | O | HOH | A1069 | 31.210 | 91.419 | -5.485 | 1.00 | 52.43 | O |
| HETATM | 5362 | O | HOH | A1070 | 25.733 | 86.086 | -21.243 | 1.00 | 52.53 | O |
| HETATM | 5363 | O | HOH | A1071 | 45.110 | 63.076 | -42.749 | 1.00 | 50.60 | O |
| HETATM | 5364 | O | HOH | A1072 | 37.572 | 78.433 | -48.680 | 1.00 | 50.35 | O |
| HETATM | 5365 | O | HOH | A1073 | 44.926 | 48.563 | -30.590 | 1.00 | 66.80 | O |
| HETATM | 5366 | O | HOH | A1074 | 45.259 | 64.253 | -19.136 | 1.00 | 54.71 | O |
| HETATM | 5367 | O | HOH | A1075 | 40.340 | 58.456 | -37.691 | 1.00 | 68.69 | O |
| HETATM | 5368 | O | HOH | A1076 | 56.701 | 96.358 | -5.644 | 1.00 | 46.40 | O |
| HETATM | 5369 | O | HOH | A1077 | 49.120 | 68.687 | -15.178 | 1.00 | 66.06 | O |
| HETATM | 5370 | O | HOH | A1078 | 19.526 | 90.161 | -29.233 | 1.00 | 56.65 | O |
| HETATM | 5371 | O | HOH | A1079 | 25.267 | 74.893 | -27.048 | 1.00 | 47.86 | O |
| HETATM | 5372 | O | HOH | A1080 | 37.258 | 96.715 | -34.073 | 1.00 | 46.73 | O |
| HETATM | 5373 | O | HOH | A1081 | 58.971 | 86.218 | -14.830 | 1.00 | 53.05 | O |
| HETATM | 5374 | O | HOH | A1082 | 67.343 | 94.362 | 4.710 | 1.00 | 62.87 | O |
| HETATM | 5375 | O | HOH | A1083 | 30.602 | 67.101 | -16.722 | 1.00 | 48.66 | O |
| HETATM | 5376 | O | HOH | A1084 | 47.407 | 66.974 | -44.730 | 1.00 | 57.99 | O |
| HETATM | 5377 | O | HOH | A1085 | 39.204 | 60.181 | -35.652 | 1.00 | 45.15 | O |
| HETATM | 5378 | O | HOH | A1086 | 47.370 | 72.120 | -9.802 | 1.00 | 47.70 | O |
| HETATM | 5379 | O | HOH | A1087 | 46.731 | 68.053 | -18.050 | 1.00 | 46.46 | O |
| HETATM | 5380 | O | HOH | A1088 | 48.390 | 70.425 | -23.297 | 1.00 | 42.96 | O |
| HETATM | 5381 | O | HOH | A1089 | 28.729 | 88.297 | -36.445 | 1.00 | 54.68 | O |
| HETATM | 5382 | O | HOH | A1090 | 48.718 | 94.360 | -0.861 | 1.00 | 55.36 | O |
| HETATM | 5383 | O | HOH | A1091 | 26.274 | 95.403 | -25.206 | 1.00 | 64.62 | O |
| HETATM | 5384 | O | HOH | A1092 | 55.089 | 89.685 | -5.799 | 1.00 | 43.39 | O |
| HETATM | 5385 | O | HOH | A1093 | 51.388 | 75.963 | -9.785 | 1.00 | 45.98 | O |

FIG. 8-80

| | | | | | | | | | | |
|---|---|---|---|---|---|---|---|---|---|---|
| HETATM | 5386 | O | HOH | A1094 | 34.142 | 68.949 | -41.521 | 1.00 | 45.96 | O |
| HETATM | 5387 | O | HOH | A1095 | 38.027 | 58.789 | -34.103 | 1.00 | 55.68 | O |
| HETATM | 5388 | O | HOH | A1096 | 54.553 | 100.251 | -13.032 | 1.00 | 54.30 | O |
| HETATM | 5389 | O | HOH | A1097 | 46.360 | 105.269 | -30.702 | 1.00 | 71.57 | O |
| HETATM | 5390 | O | HOH | A1098 | 48.070 | 62.674 | -38.053 | 1.00 | 54.00 | O |
| HETATM | 5391 | O | HOH | A1099 | 49.360 | 88.059 | -7.099 | 1.00 | 54.47 | O |
| HETATM | 5392 | O | HOH | A1100 | 40.406 | 91.852 | 0.341 | 1.00 | 48.69 | O |
| HETATM | 5393 | O | HOH | A1101 | 47.618 | 105.239 | -5.056 | 1.00 | 65.04 | O |
| HETATM | 5394 | O | HOH | A1102 | 33.135 | 86.142 | 1.416 | 1.00 | 82.53 | O |
| HETATM | 5395 | O | HOH | A1103 | 45.557 | 74.849 | -44.232 | 1.00 | 50.82 | O |
| HETATM | 5396 | O | HOH | A1104 | 36.185 | 57.190 | -15.265 | 1.00 | 51.32 | O |
| HETATM | 5397 | O | HOH | A1105 | 34.186 | 86.316 | -4.246 | 1.00 | 69.94 | O |
| HETATM | 5398 | O | HOH | A1106 | 27.249 | 76.840 | -8.541 | 1.00 | 67.44 | O |
| HETATM | 5399 | O | HOH | A1107 | 53.566 | 54.943 | -27.502 | 1.00 | 51.57 | O |
| HETATM | 5400 | O | HOH | A1108 | 30.809 | 69.222 | -15.629 | 1.00 | 50.27 | O |
| HETATM | 5401 | O | HOH | A1109 | 28.565 | 86.201 | -42.091 | 1.00 | 48.91 | O |
| HETATM | 5402 | O | HOH | A1110 | 48.180 | 93.795 | -3.486 | 1.00 | 48.48 | O |
| HETATM | 5403 | O | HOH | A1111 | 34.940 | 72.764 | -12.473 | 1.00 | 59.92 | O |
| HETATM | 5404 | O | HOH | A1112 | 59.258 | 93.599 | -19.089 | 1.00 | 53.68 | O |
| HETATM | 5405 | O | HOH | A1113 | 43.898 | 113.583 | 6.579 | 1.00 | 64.66 | O |
| HETATM | 5406 | O | HOH | A1114 | 48.985 | 63.629 | -35.343 | 1.00 | 47.52 | O |
| HETATM | 5407 | O | HOH | A1115 | 45.864 | 107.466 | -29.433 | 1.00 | 54.45 | O |
| HETATM | 5408 | O | HOH | A1116 | 50.049 | 99.500 | -7.967 | 1.00 | 55.41 | O |
| HETATM | 5409 | O | HOH | A1117 | 43.523 | 51.581 | -34.569 | 1.00 | 66.55 | O |
| HETATM | 5410 | O | HOH | A1118 | 27.507 | 95.813 | -33.823 | 1.00 | 61.87 | O |
| HETATM | 5411 | O | HOH | A1119 | 37.503 | 95.890 | 12.510 | 1.00 | 63.43 | O |
| HETATM | 5412 | O | HOH | A1120 | 55.499 | 96.469 | -7.851 | 1.00 | 59.91 | O |
| HETATM | 5413 | O | HOH | A1121 | 43.760 | 84.876 | -46.211 | 1.00 | 60.07 | O |
| HETATM | 5414 | O | HOH | A1122 | 38.113 | 51.252 | -19.304 | 1.00 | 61.23 | O |
| HETATM | 5415 | O | HOH | A1123 | 32.734 | 69.585 | -39.466 | 1.00 | 62.31 | O |
| HETATM | 5416 | O | HOH | A1124 | 54.879 | 85.440 | -31.749 | 1.00 | 51.62 | O |
| HETATM | 5417 | O | HOH | A1125 | 37.206 | 61.696 | -37.170 | 1.00 | 47.67 | O |
| HETATM | 5418 | O | HOH | A1126 | 21.756 | 76.388 | -38.007 | 1.00 | 50.77 | O |
| HETATM | 5419 | O | HOH | A1127 | 42.100 | 71.713 | -13.962 | 1.00 | 73.04 | O |
| HETATM | 5420 | O | HOH | A1128 | 19.749 | 78.050 | -37.545 | 1.00 | 45.11 | O |
| HETATM | 5421 | O | HOH | A1129 | 56.058 | 103.819 | 2.926 | 1.00 | 55.00 | O |
| HETATM | 5422 | O | HOH | A1130 | 44.778 | 102.945 | -17.247 | 1.00 | 49.22 | O |
| HETATM | 5423 | O | HOH | A1131 | 50.331 | 106.240 | -28.494 | 1.00 | 68.88 | O |
| HETATM | 5424 | O | HOH | A1132 | 21.643 | 75.529 | -40.470 | 1.00 | 53.94 | O |
| HETATM | 5425 | O | HOH | A1133 | 49.134 | 72.973 | -47.586 | 1.00 | 59.15 | O |
| HETATM | 5426 | O | HOH | A1134 | 54.878 | 94.364 | -9.725 | 1.00 | 55.48 | O |
| HETATM | 5427 | O | HOH | A1135 | 26.683 | 72.786 | -42.128 | 1.00 | 53.19 | O |
| HETATM | 5428 | O | HOH | A1136 | 56.545 | 73.640 | -21.680 | 1.00 | 52.96 | O |
| HETATM | 5429 | O | HOH | A1137 | 62.377 | 91.342 | -5.394 | 1.00 | 63.43 | O |
| HETATM | 5430 | O | HOH | A1138 | 39.280 | 84.395 | -36.908 | 1.00 | 46.17 | O |
| HETATM | 5431 | O | HOH | A1139 | 47.518 | 75.508 | -11.748 | 1.00 | 46.08 | O |
| HETATM | 5432 | O | HOH | A1140 | 30.001 | 71.755 | -42.013 | 1.00 | 54.12 | O |
| HETATM | 5433 | O | HOH | A1141 | 31.539 | 62.194 | -17.430 | 1.00 | 52.67 | O |
| HETATM | 5434 | O | HOH | A1142 | 56.366 | 99.175 | -4.863 | 1.00 | 57.43 | O |
| HETATM | 5435 | O | HOH | A1143 | 56.550 | 95.448 | -11.935 | 1.00 | 50.73 | O |
| HETATM | 5436 | O | HOH | A1144 | 41.535 | 70.304 | -49.610 | 1.00 | 59.72 | O |
| HETATM | 5437 | O | HOH | A1145 | 24.795 | 84.000 | -19.188 | 1.00 | 68.52 | O |
| HETATM | 5438 | O | HOH | A1146 | 32.518 | 96.683 | -20.555 | 1.00 | 56.57 | O |
| HETATM | 5439 | O | HOH | A1147 | 47.176 | 54.132 | -24.480 | 1.00 | 66.02 | O |
| HETATM | 5440 | O | HOH | A1148 | 22.710 | 82.608 | -18.901 | 1.00 | 70.03 | O |
| HETATM | 5441 | O | HOH | A1149 | 37.523 | 59.400 | -13.378 | 1.00 | 58.73 | O |
| HETATM | 5442 | O | HOH | A1150 | 50.925 | 72.248 | -40.671 | 1.00 | 62.73 | O |
| HETATM | 5443 | O | HOH | A1151 | 21.297 | 77.568 | -42.082 | 1.00 | 53.51 | O |
| HETATM | 5444 | O | HOH | A1152 | 22.873 | 73.464 | -27.980 | 1.00 | 56.00 | O |
| HETATM | 5445 | O | HOH | A1153 | 44.608 | 106.157 | -33.520 | 1.00 | 65.17 | O |
| HETATM | 5446 | O | HOH | A1154 | 43.948 | 101.190 | -13.062 | 1.00 | 58.40 | O |
| HETATM | 5447 | O | HOH | A1155 | 18.804 | 92.518 | -28.965 | 1.00 | 48.91 | O |
| HETATM | 5448 | O | HOH | A1156 | 59.161 | 94.863 | -12.154 | 1.00 | 68.60 | O |
| HETATM | 5449 | O | HOH | A1157 | 60.356 | 85.192 | -30.029 | 1.00 | 62.50 | O |
| HETATM | 5450 | O | HOH | A1158 | 49.189 | 85.131 | -34.425 | 1.00 | 52.56 | O |
| HETATM | 5451 | O | HOH | A1159 | 40.129 | 94.081 | -39.577 | 1.00 | 59.19 | O |
| HETATM | 5452 | O | HOH | A1160 | 64.798 | 82.122 | -0.004 | 1.00 | 52.10 | O |
| HETATM | 5453 | O | HOH | A1161 | 24.383 | 69.225 | -29.391 | 1.00 | 59.62 | O |
| HETATM | 5454 | O | HOH | A1162 | 32.159 | 87.831 | -5.937 | 1.00 | 68.54 | O |
| HETATM | 5455 | O | HOH | A1163 | 45.466 | 77.497 | -52.302 | 1.00 | 53.17 | O |
| HETATM | 5456 | O | HOH | A1164 | 50.476 | 77.389 | -2.679 | 1.00 | 68.20 | O |
| HETATM | 5457 | O | HOH | A1165 | 50.873 | 102.384 | 10.665 | 1.00 | 70.61 | O |
| HETATM | 5458 | O | HOH | A1166 | 33.023 | 58.528 | -25.811 | 1.00 | 58.44 | O |
| HETATM | 5459 | O | HOH | A1167 | 55.368 | 81.792 | -34.075 | 1.00 | 44.68 | O |
| HETATM | 5460 | O | HOH | A1168 | 45.614 | 79.584 | -32.024 | 1.00 | 42.57 | O |
| HETATM | 5461 | O | HOH | A1169 | 44.101 | 69.271 | -50.207 | 1.00 | 67.46 | O |
| HETATM | 5462 | O | HOH | A1170 | 46.101 | 67.307 | -52.464 | 1.00 | 57.43 | O |

FIG. 8-81

```
HETATM 5463  O   HOH A1171      48.262  63.476 -18.438  1.00 66.32           O
HETATM 5464  O   HOH A1172      51.648  83.698 -34.156  1.00 47.21           O
HETATM 5465  O   HOH A1173      48.094  88.840 -51.581  1.00 56.02           O
HETATM 5466  O   HOH A1174      46.055  60.810 -41.624  1.00 46.76           O
HETATM 5467  O   HOH A1175      29.797 105.055   7.548  1.00 61.28           O
HETATM 5468  O   HOH A1176      48.702  63.820 -42.765  1.00 68.10           O
HETATM 5469  O   HOH A1177      51.845  85.229 -38.366  1.00 89.02           O
HETATM 5470  O   HOH A1178      38.054  80.611  -5.600  1.00 54.61           O
HETATM 5471  O   HOH A1179      48.435  96.051 -40.233  1.00 63.09           O
HETATM 5472  O   HOH A1180      55.972  90.000  -8.227  1.00 51.01           O
HETATM 5473  O   HOH A1181      54.818  71.772 -21.323  1.00 49.22           O
HETATM 5474  O   HOH A1182      57.852  95.939 -19.444  1.00 56.83           O
HETATM 5475  O   HOH A1183      38.794  89.445   6.026  1.00 51.45           O
HETATM 5476  O   HOH A1184      44.375 102.876   6.515  1.00 64.66           O
HETATM 5477  O   HOH A1185      47.329  68.350 -39.508  1.00 84.61           O
HETATM 5478  O   HOH A1186      48.796  89.367  16.825  1.00 75.07           O
HETATM 5479  O   HOH A1187      38.694  52.645 -35.861  1.00 66.98           O
HETATM 5480  O   HOH A1188      49.868  65.962 -41.136  1.00 65.89           O
HETATM 5481  O   HOH A1189      36.546 106.779   5.094  1.00 62.00           O
HETATM 5482  O   HOH A1190      52.884  86.892 -36.837  1.00 68.93           O
HETATM 5483  O   HOH A1191      47.770  61.250 -34.856  1.00 70.78           O
HETATM 5484  O   HOH A1192      49.748  68.655 -40.239  1.00 78.38           O
HETATM 5485  O   HOH A1193      51.564  90.387 -10.362  1.00 58.46           O
HETATM 5486  O   HOH A1194      33.743  91.902 -35.802  1.00 69.89           O
HETATM 5487  O   HOH A1195      27.460  74.156 -25.481  1.00 62.23           O
HETATM 5488  O   HOH A1196      39.539  56.191 -13.879  1.00 49.24           O
HETATM 5489  O   HOH A1197      57.081  83.241 -34.690  1.00 43.80           O
HETATM 5490  O   HOH A1198      38.888  53.870 -13.197  1.00 78.06           O
HETATM 5491  O   HOH A1199      46.611  96.057  -0.946  1.00 49.36           O
HETATM 5492  O   HOH A1200      44.317  91.330  17.255  1.00 75.78           O
HETATM 5493  O   HOH A1201      25.006  79.093 -16.716  1.00 69.12           O
HETATM 5494  O   HOH A1202      40.756  58.099 -40.657  1.00 61.04           O
HETATM 5495  O   HOH A1203      36.772  57.218 -26.301  1.00 49.32           O
HETATM 5496  O   HOH A1204      47.106  91.186  15.906  1.00 61.65           O
HETATM 5497  O   HOH A1205      24.046  94.894  -2.761  1.00 72.02           O
HETATM 5498  O   HOH A1206      27.864  63.463 -26.842  1.00 43.52           O
HETATM 5499  O   HOH A1207      25.965  95.173 -31.640  1.00 69.85           O
HETATM 5500  O   HOH A1208      37.325  71.609 -13.151  1.00 50.56           O
HETATM 5501  O   HOH A1209      35.735  76.522 -10.794  1.00 49.24           O
HETATM 5502  O   HOH A1210      35.182  79.139 -10.183  1.00 49.36           O
HETATM 5503  O   HOH A1211      53.247  86.085 -34.510  1.00 78.58           O
HETATM 5504  O   HOH A1212      56.263  87.338 -34.839  1.00 63.63           O
HETATM 5505  O   HOH A1213      53.690  88.265  -8.709  1.00 53.94           O
HETATM 5506  O   HOH A1214      48.583  87.653 -13.596  1.00 57.26           O
HETATM 5507  O   HOH A1215      50.007  66.928 -17.635  1.00 57.91           O
HETATM 5508  O   HOH A1216      49.461  67.277 -20.152  1.00 66.75           O
HETATM 5509  O   HOH A1217      39.684  65.344 -10.868  1.00 54.20           O
HETATM 5510  O   HOH A1218      32.400  59.617 -23.614  1.00 56.94           O
HETATM 5511  O   HOH A1219      36.508  49.413 -36.073  1.00 54.64           O
HETATM 5512  O   HOH A1220      35.875  45.805 -29.132  1.00 62.14           O
HETATM 5513  O   HOH A1221      55.472  77.352  16.354  1.00 78.76           O
HETATM 5514  O   HOH A1222      48.771  74.637  -9.235  1.00 60.02           O
HETATM 5515  O   HOH A1223      65.881  90.076  -7.201  1.00 75.47           O
HETATM 5516  O   HOH A1224      50.724  99.500  17.020  1.00 71.54           O
HETATM 5517  O   HOH A1225      60.843  80.166  -0.638  1.00 64.67           O
HETATM 5518  O   HOH A1226      54.326 103.227  -5.586  1.00 67.51           O
HETATM 5519  O   HOH A1227      46.997 103.903 -13.385  1.00 60.08           O
HETATM 5520  O   HOH A1228      48.667 109.500 -35.232  1.00 70.17           O
HETATM 5521  O   HOH A1229      51.626  77.941 -45.688  1.00 52.72           O
HETATM 5522  O   HOH A1230      49.257  75.315 -44.134  1.00 85.66           O
HETATM 5523  O   HOH A1231      45.647  78.594 -41.240  1.00 73.79           O
HETATM 5524  O   HOH A1232      49.029  70.309 -37.254  1.00 78.22           O
HETATM 5525  O   HOH A1233      63.936  80.339 -25.446  1.00 59.89           O
HETATM 5526  O   HOH A1234      48.450  96.314 -42.984  1.00 58.32           O
HETATM 5527  O   HOH A1235      49.853  71.594 -16.874  1.00 54.19           O
CONECT 5216 5217
CONECT 5217 5216 5218 5221
CONECT 5218 5217 5219 5220
CONECT 5219 5218
CONECT 5220 5218
CONECT 5221 5217 5222
CONECT 5222 5221 5223
CONECT 5223 5222 5224 5225 5226
CONECT 5224 5223
CONECT 5225 5223
CONECT 5226 5223 5227
CONECT 5227 5226 5228 5241
```

FIG. 8-82

```
CONECT 5228 5227 5229
CONECT 5229 5228 5230 5233
CONECT 5230 5229 5231 5232
CONECT 5231 5230
CONECT 5232 5230
CONECT 5233 5229 5234 5235 5236
CONECT 5234 5233
CONECT 5235 5233
CONECT 5236 5233 5237 5241
CONECT 5237 5236 5238
CONECT 5238 5237 5239 5240
CONECT 5239 5238
CONECT 5240 5238
CONECT 5241 5227 5236 5242
CONECT 5242 5241 5243
CONECT 5243 5242 5244 5251
CONECT 5244 5243 5245 5247
CONECT 5245 5244 5246 5266
CONECT 5246 5245
CONECT 5247 5244 5248
CONECT 5248 5247 5249 5250
CONECT 5249 5248
CONECT 5250 5248
CONECT 5251 5243 5252
CONECT 5252 5251 5253 5266
CONECT 5253 5252 5254
CONECT 5254 5253 5255
CONECT 5255 5254 5256 5264
CONECT 5256 5255 5257
CONECT 5257 5256 5258 5260
CONECT 5258 5257 5259
CONECT 5259 5258
CONECT 5260 5257 5261 5262
CONECT 5261 5260
CONECT 5262 5260 5263 5264
CONECT 5263 5262
CONECT 5264 5255 5262 5265
CONECT 5265 5264
CONECT 5266 5245 5252 5267
CONECT 5267 5266 5268
CONECT 5268 5267 5269 5276
CONECT 5269 5268 5270 5272
CONECT 5270 5269 5271 5279
CONECT 5271 5270
CONECT 5272 5269 5273
CONECT 5273 5272 5274 5275
CONECT 5274 5273
CONECT 5275 5273
CONECT 5276 5268 5277
CONECT 5277 5276 5278 5279
CONECT 5278 5277
CONECT 5279 5270 5277 5280
CONECT 5280 5279 5281
CONECT 5281 5280 5282 5283
CONECT 5282 5281 5289
CONECT 5283 5281 5284 5285
CONECT 5284 5283
CONECT 5285 5283 5286 5287
CONECT 5286 5285
CONECT 5287 5285 5288 5289
CONECT 5288 5287
CONECT 5289 5282 5287 5290
CONECT 5290 5289 5291 5292
CONECT 5291 5290
CONECT 5292 5290
MASTER        521    0    1   28   34    0    4    6 5526    1   77   58
END
```

CRYSTAL STRUCTURE OF BIFUNCTIONAL TRANSGLYCOSYLASE PBP1B FROM *E. COLI* AND INHIBITORS THEREOF

CROSS-REFERENCE TO RELATED APPLICATIONS

This application is a divisional application of U.S. Ser. No. 14/188,678 filed Feb. 24, 2014, which is a divisional application of U.S. Ser. No. 12/506,982 filed Jul. 21, 2009 which claims priority of provisional patent application U.S. Ser. No. 61/208,566, titled "Structure and Functional Aspects of the Bacterial Bifunctional Transglycosylase PBP1b From *E. coli* And Binding Interactions With Moenomycin" filed Feb. 25, 2009, and U.S. Ser. No. 61/135,503, titled "Structure and Functional Aspects of the Bacterial Bifunctional Transglycosylase PBP1b From *E. coli* And Binding Interactions With Moenomycin" filed Jul. 21, 2008, the contents of each of which are incorporated herein by reference in their entirety.

TECHNICAL FIELD OF THE INVENTION

The present invention relates to a bacterial bifunctional Transglycosylase PBP1b from E. *Coli*, that can be co-crystallized with an inhibitory ligand such as moenomycin, and more particularly, to the detailed crystallographic data obtained from said co-crystallization which is disclosed herein. The invention also relates to methods of using the crystal structure and x-ray crystallographic coordinates of the moenomycin-bound bacterial bifunctional Transglycosylase PBP1b to design, isolate and screen compounds which bind to and inhibit the active site of *E. coli* Transglycosylase PBP1b and related proteins.

BACKGROUND OF THE INVENTION

Bacterial cell wall biosynthesis is one of the major targets where many antibiotics are designed and acted upon. The cell walls of both Gram-positive and -negative bacteria consist of layers of peptidoglycan, which has a mesh-like structure scaffolding the cytoplasmic membrane. Cell wall maintains the shape and integrity of bacteria. It can protect bacterial cells against osmotic pressure, and its disruption can lead to cell lysis and death. (Holtje, J. V. (1998). Growth of the stress-bearing and shape-maintaining murein sacculus of *Escherichia coli*. Microbiol Mol Biol Rev 62, 181-203.)

The discovery and clinical development of penicillin ushered in the modern antibiotic era and stimulated the discovery of the antibiotics in current clinical use. Some 80 years after their discovery, penicillins and related antibiotics (collectively called β-lactams) remain clinically useful. Nevertheless, the remarkable ability of bacteria to develop resistance to β-lactam and other antibiotics means that there is a continued need for new antibiotic targets and new antimicrobial agents. (Wright G D. Science (2007) 315 (5817):1373-1374.)

Penicillin and other β-lactam antibiotics target several bacterial enzymes, collectively termed penicillin-binding proteins (PBPs). PBPs are necessary for the growth and maintenance of the peptidoglycan layer, which forms part of the bacterial cell wall and protects the cell from osmotic stress. Inhibition of peptidoglycan biosynthesis and of its controlled breakdown (for example, to enable partition of the cell wall during cell division) therefore inhibits cell growth. Because the peptidoglycan polymer is ubiquitous and essential to bacterial life, its assembly and maintenance are targets for many antibiotics.

Bacteria use a peptidoglycan layer to protect themselves from osmotic stress. Synthesis of this layer proceeds in several steps. First, lipid II is synthesized in the cell. It is then transferred to the outside, where it is added to the peptidoglycan polymer by membrane-associated transglycosylase enzymes. Finally, the polymer is cross-linked via interstrand peptide bonds catalyzed by transpeptidase enzymes.

The peptidoglycan consists of a backbone chain of repeating two-sugar units (called NAG and NAM) and a pentapeptide chain bound to each NAM. The NAG-NAM-pentapeptide core (called lipid II) is synthesized in the cell and tethered to the cell membrane by a lipid linker. Lipid II is then transferred from the inside of the cell to the outside, where membrane-associated glycosyltransferases assist in grafting it onto the polymer. Transpeptidases catalyze the formation of peptide bonds between polymer strands, thereby making the wall more rigid. These tasks are performed by bifunctional enzymes that contain glycosyltransferase and transpeptidase domains; the latter are sensitive to β-lactams.

The peptidoglycan glycosyltransferase activity of the bifunctional enzymes is an excellent target for the development of new antibiotics. The bifunctional enzymes include PBP1b from *Escherichia coli*. Despite their importance to bacterial physiology and drug discovery, they have resisted detailed study, mainly because these large membrane proteins are difficult to purify, assay, and crystallize.

The high-molecular-weight penicillin-binding proteins (PBPs) are responsible for the enlargement of the essential bacterial murein (peptidoglycan) sacculus by transpeptidation and transglycosylation of the murein precursors (Park, J. T. 1996. The murein sacculus, p. 48-57. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (ed.), *Escherichia coli* and *Salmonella*: cellular and molecular biology. ASM Press, Washington, D.C.). In *E. coli* there are three bifunctional enzymes catalyzing both reactions, PBP1A, PBP1B, and PBP1C, and two monofunctional transpeptidases, PBP2 and PBP3. (Höltje, J.-V. 1998. Growth of the stress-bearing and shape-maintaining murein sacculus of *Escherichia coli*. Microbiol. Mol. Biol. Rev. 62:181-203). PBP1a and PBP 1b are the major bifunctional enzymes (Ishino, F., K. Mitsui, S. Tamaki, and M. Matsuhashi. 1980. Biochem. Biophys. Res. Commun. 97:287-293; Terrak, M., et al., 1999. Mol. Microbiol. 34:350-364.), and a deletion of both is lethal for the cell (Suzuki, H., Y. Nishimura, and Y. Hirota. 1978. On the process of cellular division in *E. coli*: a series of mutants of *E. coli* altered in the penicillin-binding proteins. Proc. Natl. Acad. Sci. USA 75:664-668). Encoded by a single gene (ponB or mrcB), PBP1b was shown to exist in three forms (α, β, and γ) which differ in the length of the short cytoplasmic part of the protein. (Nakagawa, J., and M. Matsuhashi. 1982. Molecular divergence of a major peptidoglycan synthetase with transglycosylase-transpeptidase activities in *Escherichia coli*-penicillin-binding protein 1Bs. Biochem. Biophys. Res. Commun. 105:1546-1553).

PBP1a and PBP1b are not essential for cell growth, but cells lacking both enzymes are not viable, indicating that both have a similar, essential function that cannot be taken over by other murein synthases (Suzuki, H., Nishimura, Y., and Hirota, Y. (1978) *Proc. Natl. Acad. Sci. U.S.A* 75, 664-668; Yousif, S. Y., Broome-Smith, J. K., and Spratt, B. G. (1985) J. Gen. Microbiol. 131, 2839-2845). Yet, mutants lacking either PBP1a or PBP1b show particular phenotypes, indicating that these synthases may play distinct roles during cell growth and division. For example, mutants without PBP1b are more sensitive to β-lactam antibiotics than mutants without PBP1a (Yousif, S. Y., Broome-Smith, J. K., and Spratt, B. G. (1985) *J. Gen. Microbiol.* 131, 2839-2845).

*Escherichia coli* PBP1b is a bifunctional transglycosylase, also known as peptidoglycan glycosyltransferase or murein synthase. It contains a transmembrane (TM) helix, two enzymatic domains—transglycosylase (TG) and transpeptidase (TP) (Goffin C, Ghuysen J M (1998). Microbiol Mol Biol Rev 62:1079-1093), and a domain composed of about 100 amino acid residues between TM and TG with unknown structure and functionality (FIG. 2B). For over 50 years, TP has been the main target for 2 most important classes of antibiotics: β-lactams (e.g., penicillin and methicillin) and glycopeptides (e.g., vancomycin). Not too long after they were introduced, resistant bacteria had emerged rapidly and caused serious medical problems. In contrast, resistant strains against moenomycin, the only natural inhibitor to TG from *Streptomyces*, have rarely been found. The development of new antibiotics against TG domains has been highly anticipated (Halliday J, McKeveney D, Muldoon C, Rajaratnam P, Meutermans W (2006) Biochem Pharmacol 71:957-967), and not until recently have the molecular structures of TG domain been available, even with the TM structure undefined.

During the years, resistance bacteria strains against two of the most important antibiotics, β-lactam (such as penicillin) and glycopeptide (such as vancomycin), have become a very serious medical problem in the treatment of bacterial infections. (Fisher, J. F., Merouch, S. O. & Mobashery, S. (2005). Chem Rev 105, 395-424.; Pootoolal, J., Thomas, M. G., Marshall, C. G., Neu, J. M., Hubbard, B. K., Walsh, C. T. & Wright, G. D. (2002). Proc Natl Acad Sci USA 99, 8962-7.) β-lactam and glycopeptide antibiotics target against the transpeptidation process, i.e. the action of transpeptidase.

Unlike the prevalence of antibiotic resistant bacterial strains against transpeptidase, resistance phenotype against transglycosylase has not been reported. There is only one reported inhibitor against transglycosylase, Moenomycin. Therefore, there is a need for new antibiotics against the transglycosylase domain of PBP1b.

SUMMARY OF THE INVENTION

In order to facilitate the new antibiotic discovery, the atomic-resolution three-dimensional structure of this membrane-bound enzyme is determined by X-ray crystallography. The crystal structure of the full-length bacterial bifunctional transglycosylase PBP1b from *Escherichia coli*, in complex with its inhibitor Moenomycin, is provided herein at 2.16 angstrom resolution. New findings from this structure, the comparison with previous available data and the implication for drug discovery are discussed.

The invention relates to a method for identifying a potential inhibitor compound for bacterial transglycosylase (peptidoglycan glycosyltransferase or murein synthase), the method comprising the steps of: (a) using a three-dimensional structure of PBP1b as defined by atomic coordinates according to FIGS. 8-1 through 8-82; (b) employing said three-dimensional structure to design or select said potential inhibitor such that said potential inhibitor is capable of binding to at least one amino acid in the active site of PBP1b transglycosylase; (c) synthesizing the potential inhibitor; (d) in an assay, contacting the potential inhibitor with the PBP1b transglycosylase in the presence of lipid II, or derivative thereof; and (e) determining the transglycosylase inhibitory activity of the potential inhibitor.

The invention relates to a method of using a co-crystal of an *E. coli* PBP1b transglycosylase enzyme with moenomycin A for screening for a novel drug capable of inhibiting a bacterial transglycosylase, wherein said crystal effectively diffracts X-rays for the determination of the atomic coordinates of said PBP1b-moenomycin complex to a resolution of greater than 2.16 Å, and according to FIGS. 8-1 through 8-82, and wherein said method comprises: (a) selecting a potential ligand by performing rational drug design with the three-dimensional structure of the moenomycin binding site determined for the crystal; (b) in an assay, contacting the potential ligand with the ligand binding domain of the enzyme; and (c) detecting the binding potential of the potential ligand for the ligand binding domain, wherein the potential ligand is selected as a novel drug based on the potential ligand having a greater affinity for the ligand binding domain than that of a known drug.

In some aspects, the potential transglycosylase inhibitor is designed or selected using computer modeling. In some aspects, the potential transglycosylase inhibitor is designed de novo. In some aspects, the potential transglycosylase inhibitor is designed based on a known inhibitor. In some embodiments, the known inhibitor is moenomycin A.

In some aspects, the transglycosylase active site comprises one or more of the amino acid residues E114, E171, E233, E290, S398, and S510.

In some aspects, the inhibitor-binding site comprises one or more of moenomycin-binding residues Thr269, Va1273, Phe277, Tyr315, Gln318, Lys355, Gly356, and Ser 358 residues of PBP1b. In some embodiments, the inhibitor binding comprises a hydrogen-bonding interaction with one or more of Glu233, Gln271, Asn275, Lys355, Arg286, Glu290 and Ser358 residues of *E. Coli* PBP1b. Some inhibitor-binding site residues comprise hydrophobic interactions with the inhibitor compound. In one aspect the inhibitor binding site comprises the transmembrane (TM) domain of PBP1b. In some aspects the binding is mediated by at least some portion of the TM domain of PBP1b.

In some aspects, the inhibitor prevents peptidoglycan elongation by structurally mimicking lipid IV at the binding site of transglycosylase.

The invention further relates to a method of evaluating the binding properties of a potential PBP1b transglycosylase inhibitor compound comprising the steps of: (a) co-crystallizing said compound with PBP1b; (b) determining the three-dimensional structure of said PBP1b-potential inhibitor complex co-crystal by molecular replacement using the three-dimensional structure of PBP1b as defined by atomic coordinates according to FIGS. 8-1 through 8-82; and (c) analyzing said three-dimensional structure of said PBP1b bound to said potential inhibitor compound to evaluate the binding characteristics of said potential inhibitor compound.

The invention relates to method for identifying a potential inhibitor compound for *E. coli* Penicillin binding protein 1b (PBP1b) transglycosylase, the method comprising the steps of: (a) providing a candidate agent; (b) in an anisotropy measurement assay, determining an effectiveness of the candidate agent to bind PBP1b; and (c) in a transglycosylation assay, contacting the candidate agent with the PBP1b transglycosylase in the presence of lipid II and determining a PBP1b transglycosylase inhibitory activity of the candidate agent.

In some embodiments the method further comprises: (d) co-crystallizing said candidate agent with PBP1b; (e) determining the three-dimensional structure of said PBP1b— candidate agent complex co-crystal by comparing the three-dimensional structure of PBP1b—moenomycin as defined by atomic coordinates according to FIGS. 8-1 through 8-82; and (f) analyzing said three-dimensional structure of said PBP1b bound to said candidate agent to evaluate the binding characteristics of said potential inhibitor compound.

The invention relates to a candidate PBP1b inhibitory agent which is a compound of the formula:

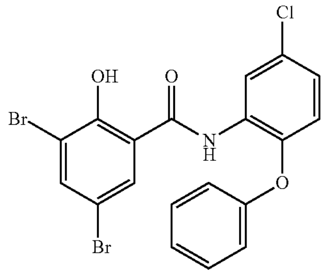 [SMILES: O=C(Nc1cc(Cl)ccc1Oc1ccccc1)c1cc(Br)cc(Br)c1O]

In some aspects, the candidate PBP1b inhibitory agent is a compound of the formula (WCKTS-A1N1):

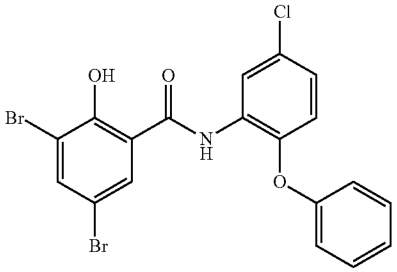 [SMILES: O=C(Nc1cc(Cl)ccc1Oc1ccccc1)c1cc(Br)cc(Br)c1O]

or the formula (WCKTS-A1N3):

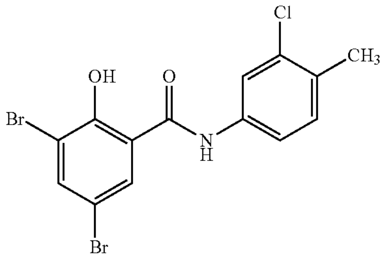 [SMILES: Cc1ccc(NC(=O)c2cc(Br)cc(Br)c2O)cc1Cl]

In one aspect the candidate inhibitory agent is a compound of the formula:

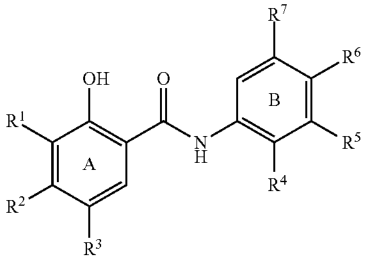

wherein $R^1$=Br, Cl, I, H or OH;

$R^2$=H, OH or Cl;

$R^3$=Br, Cl, I, H, or

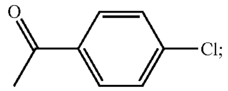

$R^4$=H, OH, Cl,

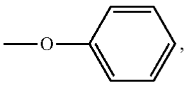, 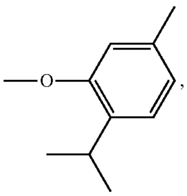,

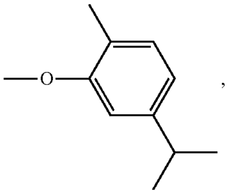, or 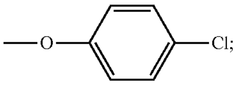

$R^5$=H, Cl,

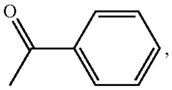, 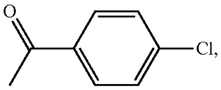 or

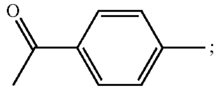

$R^6$=H, $CH_3$, OH, $OCH_3$, Cl, $NO_2$, or

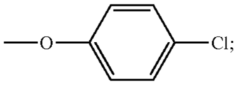

and $R^7$=H, Cl,

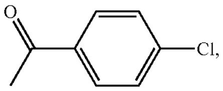 or 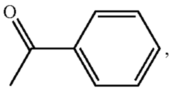, wherein the compound (a) binds PBP1b, and (b) exhibits transglycosylase activity.

In one aspect, the binding of the candidate inhibitory agent to PBP1b requires at least a portion of the transmembrane (TM) domain.

The invention relates to anti-bacterial compounds comprising the general formula:

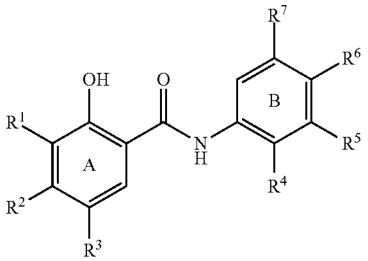

wherein $R^1$=Br, Cl, I, H or OH;

$R^2$=H, OH or Cl;

$R^3$=Br, Cl, I, H, or

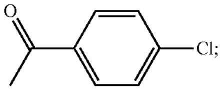
;

$R^4$=H, OH, Cl,

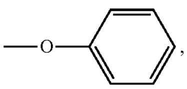
,
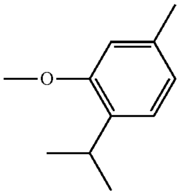
,
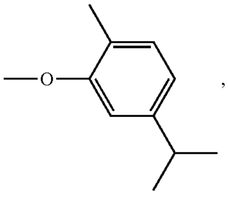
, or
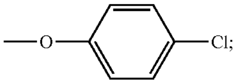
;

$R^5$=H, Cl,

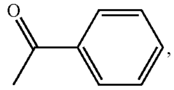
,
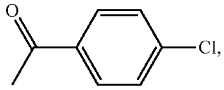
, or
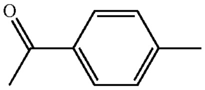
;

$R^6$=H, $CH_3$, OH, $OCH_3$, Cl, $NO_2$, or

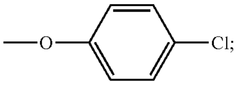
;

and $R^7$=H, Cl,

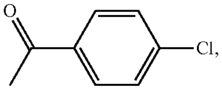
, or
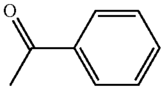

wherein the compound (a) binds PBP1b, and (b) exhibits transglycosylase activity.

The invention relates to anti-bacterial compounds comprising the general formula:

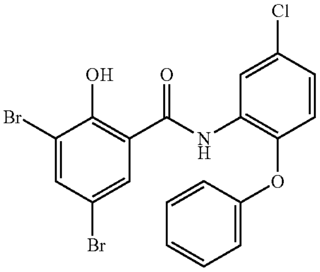

wherein the compound (a) binds PBP1b and (b) exhibits transglycosylase activity.

In some aspects, the anti-bacterial compound has the formula (WCKTS-A1N1):

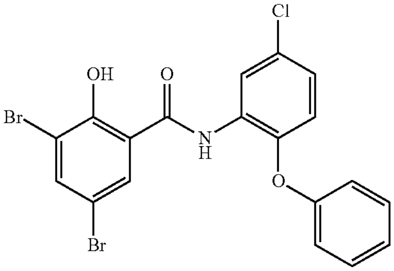 [SMILES: O=C(Nc1cc(Cl)ccc1Oc1ccccc1)c1cc(Br)cc(Br)c1O]

In some aspects, the anti-bacterial compound has the formula (WCKTS-A1N3):

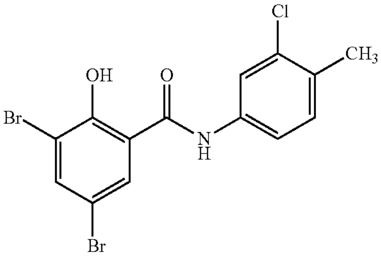 [SMILES: Cc1ccc(NC(=O)c2cc(Br)cc(Br)c2O)cc1Cl]

In some embodiment. the anti-bacterial compound is effective in inhibiting the growth of at least one of *Staphylococcus aureus* (ATCC29213, SA), methicillin-resistant *Staphylococcus aureus* (ATCC33592, MRSA), *Mycobacterium smegmatis* (ATCC11565, MS), and *Escherichia coli* (ATCC 25922, EC), *Streptococcus pneumonia, Bacillus subtilis, Enterococcus faecalis, Acinetobacter baumannii, Pseudomonas aeruginosa, Stenotrophomonas maltophilia*, and *Mycobacterium smegmatis*.

In some aspects, the anti-bacterial compound, in a co-crystal of the compound with PBP1b, the compound contacts the moneomycin-binding site of PBP1b as defined by atomic coordinates according to FIGS. 8-1 through 8-82.

In one aspect the anti-bacterial compound binds PBP1b in a binding interaction mediated by one or more residues of the transmembrane (TM) domain, UvrB domain 2 homolog (UB2H) domain, or transglycosylase (TG) domain of PBP1b.

In one aspect the anti-bacterial compound binds *E. coli* PBP1b by binding to at least one portion of the UvrB domain 2 homolog (UB2H) domain of PBP1b. In some embodiments, the UB2H binding further inhibits cell wall synthesis. In some embodiments, the UB2H binding further inhibits DNA repair.

In one aspect the anti-bacterial compound prevents peptidoglycan elongation by structurally mimicking lipid IV at the binding site of transglycosylase. In some embodiments, the compound inhibits a peptidoglycan glucosyltransferase. In some embodiments, the peptidoglycan glucosyltransferase is PBP1b, SaPBP2 or AaPGT.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 1 shows the statistics of data collection and structure determination for the structure determination of *E. coli* PBP1b at 2.63 Å resolution.

(FIG. 2A) The crystal structure of PBP1b is represented as a ribbon diagram. The TM, UB2H, TG, and TP domains are color coded in cyan, yellow, red, and blue, respectively. Moenomycin is represented as van der Waals spheres. Tryptophan and tyrosine residues located near the water-membrane interfaces are shown in black sticks. The proposed membrane location is indicated by a gray rectangle. All figures of 3D structural representations were made with PyMOL (www.pymol.org). (FIG. 2B) The 1D and 2D topology of *E. coli* PBP1b are color-coded as in A. The numbering (1-5) at the N terminus of UB2H domain and the alphabet (A-E) at the C terminus of UB2H domain are markers for the locations used in the combinatorial domain deletion experiments.

FIGS. 3A-3B show contact interface between the TM and TG domains of PBP1b. (FIG. 3A) The TM and TG domains are shown in cyan and red, respectively. Contact residues are shown as sticks. (FIG. 3B) Sequence alignment of the three transglycosylases PBP1b (SEQ ID NO: 2), PBP2 (SEQ ID NO: 3) and AaPGT (SEQ ID NO: 4) from *E. coli, S. aureus*, and *A. aeolicus*, respectively. The numbering indicates the sequential position of residues. Contact residues with moderate conservation are shaded in red.

FIGS. 4A-4C show the amino acid residues in PBP1b interacting with moenomycin and structure-based sequence alignment of transglycosylases. (FIG. 4A) The potential hydrogen-bonding interactions (distance cutoff 3.2 Å) between *E. coli* PBP1b and moenomycin are shown as dashed lines in black. The interactions between the putative active sites (*E*233 and *E*290) and moenomycin proposed in ref. 6 are shown as dashed lines in red. (FIG. 4B) Comparison of moenomycin-binding modes between *E. coli* PBP1b and SaPBP2 (Left); between *E. coli* PBP1b and AaPGT (Right). TG and residues of *E. coli* PBP1b, SaPBP2, and AaPGT are shown in red, cyan, and green, respectively. Moenomycin are shown in light gray (for *E. coli* PBP1b) and dark gray (for SaPBP2 and AaPGT). (FIG. 4C) Sequences of TG from *E. coli* PBP1b (SEQ ID NO: 5), SaPBP2 (SEQ ID NO: 6), and AaPGT (SEQ ID NO: 7) are aligned according to their secondary structure elements. Residues forming the potential interaction with moenomycin are shaded in red.

(FIG. 5A) The structurally homologous domains from PBP1b, UvrB (PDB ID code 2NMV), and TRCF (PDB ID code 2EYQ) are shown in yellow, cyan, and magenta, respectively. The nonhomologous parts of these proteins are colored in gray. (FIG. 5B) Morphological differences and DNA segregation between the wild type and UB2H-truncated (PBP1b ΔUB2H) strains are shown in differential interference contrast microscopy combined with DAPI staining images. (Scale bar, 1 μm.) (FIG. 5C) Wild-type PBP1b, deletion mutant PBP1bΔUB2H, and UB2H domain only were coupled to CNBr-activated Sepharose, and their binding abilities to MltA, PBP3, and FtsN respectively, were examined.

(FIG. 6A) *E. coli* PBP1b and 2 SaPBP2 conformers (Lovering A L, et al., (2007) Science 315:1402-1405; Lovering A L, et al. (2008) J Mol Biol 383:167-177) were indicated by colored, light gray (PDB ID code 3DWK), and dark gray (PDB ID code 2OLV), respectively. The TG domain of SaPBP2 was superimposed onto the TG of *E. coli* PBP1b. Side view (Left) and top view (Right) of the comparison reveals possible flexibility of a hinge region between TG and TP domains. (FIG. 6B) Active sites of TG and TP were shown by van der Waals spheres. The disaccharide, pentapeptide, and lipid tail of lipid II and peptidoglycan were shown in orange surface, green surface, and blue line, respectively. A single strand of the proposed peptidoglycan model (Meroueh S O, et al. (2006) Proc Natl Acad Sci USA 103:4404-4409) was docked onto the structure of *E. coli* PBP1b, with lipid IV portion replacing moenomycin. The incoming lipid II, of which the chemical structure is shown on top, diffuses in the plane of the membrane. After the TG reaction, the lipid moiety of this lipid II is kept as the membrane anchor, whereas the original lipid tail (shown as dotted line) is recycled. The polymerized peptidoglycan grows perpendicularly to the membrane and toward the TP domain, where the crosslinking reaction of the pentapeptides takes place.

FIG. 7 shows the amino acid sequence of *E. coli* PBP1b (SEQ ID NO: 1; amino acids 1-844; Swiss Prot Database accession number P02919).

FIGS. 8-1 through 8-82 list the atomic structure coordinates for PBP1b as derived by X-ray diffraction from a crystal of PBP1b-moenomycin A complex at 2.16 Å resolution. The amino acid sequence shown on FIG. 8-8: SEQ ID NO:8.

Figure 2A:
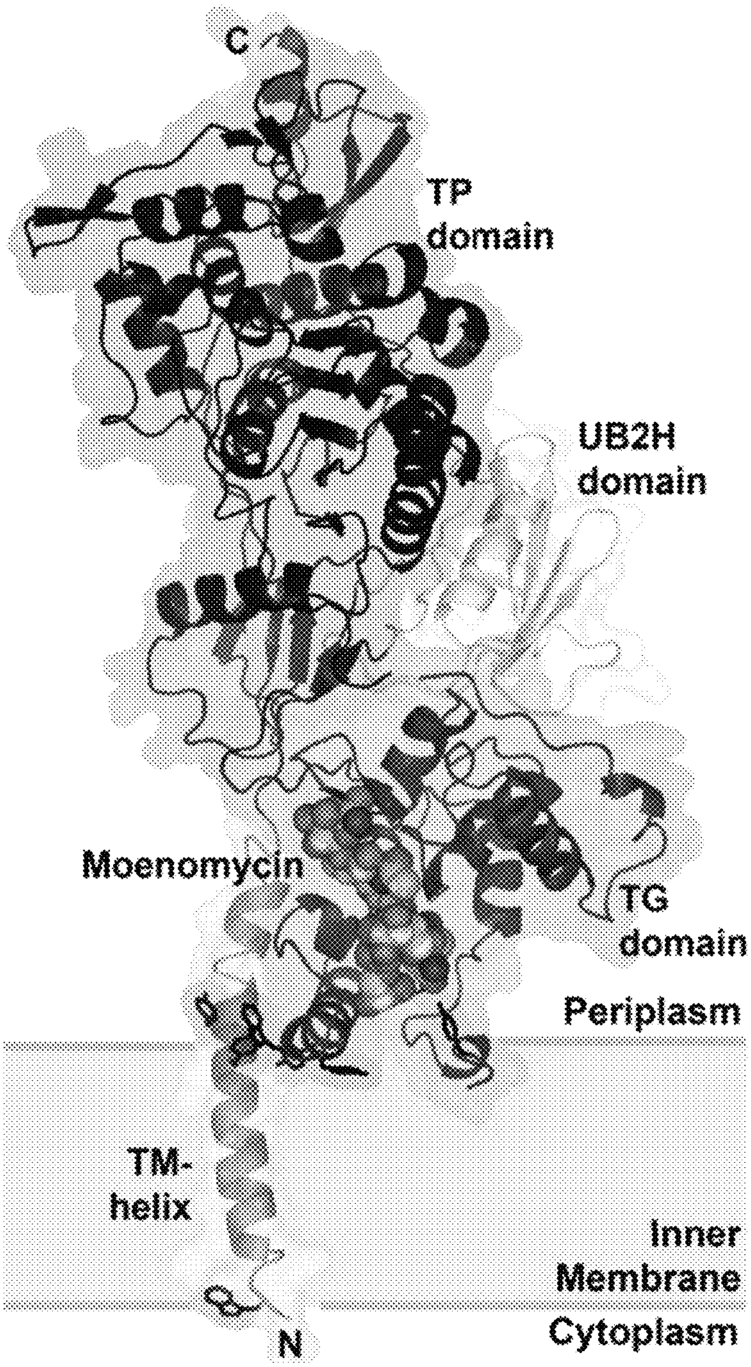
FIGS. 2A-2B show the overall structure and topology of *E. coli* PBP1b.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The transglycosylase domain of *E. coli* PBP1b, a multi-domain membrane protein essential for cell wall synthesis, is an excellent target for the development of new antibiotics. The X-ray crystal structure of the bifunctional transglycosylase penicillin-binding protein 1b (PBP1b) from *Escherichia coli* in complex with its inhibitor moenomycin resolved to 2.16 Å resolution is provided. In addition to the transglycosylase and transpeptidase domains, the structure provides a complete visualization of this important target for designing antibacterial agents. A domain for protein-protein interaction and a transmembrane helix domain essential for substrate binding, enzymatic activity, and membrane orientation is disclosed.

The only known potent inhibitors for transglycosylase (TG) are moenomycin complexes (flavomycin), including moenomycin A (Moe A), A12, C1, C3, and C4. (Adachi M, et al. Degradation and reconstruction of moenomycin A derivatives: Dissecting the function of the isoprenoid chain. J Am Chem Soc. 2006; 128:14012-14013). Assays for binding of moenomycin to various truncated PBPs concluded that the transmembrane (TM) domain is critical for moenomycin binding. (Cheng et al., *Proc Natl Acad Sci USA*. 2008 Jan. 15; 105(2): 431-436.)

To grow the crystals of the present invention, the *E. coli* PBP1b and an inhibitory compound complex are purified to greater than 80% total protein and more preferably purified to greater than 90% total protein. For expression and purification purposes, the full-length PBP1b may be subcloned from *E. coli* chromosomal DNA preparation by the polymerase chain reaction (PCR) and inserted into an expression vector.

A large number of vector-host systems known in the art may be used. Possible vectors include, but are not limited to, plasmids or modified viruses, but the vector system must be compatible with the host cell used. Examples of vectors include *E. coli* bacteriophages such as lambda derivatives, or plasmids such as pBR322 derivatives or pUC plasmid derivatives, e.g., pGEX vectors (Amersham-Pharmacia, Piscataway, N.J.), pET vectors (Novagen, Madison, Wis.), pmal-c vectors (Amersham-Pharmacia, Piscataway, N.J.), pFLAG vectors (Chiang and Roeder, 1993, Pept. Res. 6:62 64), baculovirus vectors (Invitrogen, Carlsbad, Calif.; Pharmingen, San Diego, Calif.), etc. The insertion into a cloning vector can, for example, be accomplished by ligating the DNA fragment into a cloning vector which has complementary cohesive termini, by blunt end ligation if no complementary cohesive termini are available or by through nucleotide linkers using techniques standard in the art. E.g., Ausubel et al. (eds.), Current Protocols in Molecular Biology, (1992). Recombinant vectors comprising the nucleic acid of interest may then be introduced into a host cell compatible with-the vector (e.g. *E. coli*, insect cells, mammalian cells, etc.) via transformation, transfection, infection, electroporation, etc. The nucleic acid may also be placed in a shuttle vector which may be cloned and propagated to large quantities in bacteria and then introduced into a eukaryotic cell host for expression. The vector systems of the present invention may provide expression control sequences and may allow for the expression of proteins in vitro.

In a preferred embodiment, the full length PBP1b is subcloned from *E. coli* chromosomal DNA preparation into pET15b (Novagen). In order, to construct PBP1b mutants PCR site directed mutagenesis may be employed with verification by DNA sequencing by methods known to those skilled in the art. The mutants of the present invention may be subcloned into a suitable expression vector and introduced into a host cell for protein production, as described above.

The PBP1b nucleic acids of the present invention may be subcloned into an expression vector to create an expression construct such that the resultant PBP1b molecule which is produced comprises a fusion protein wherein said fusion protein comprises a tag for ease of purification. As referred to herein, a "tag" is any additional amino acids which are provided in a protein either C-terminally, N-terminally or internally for the ease of purification, for the improvement of production or for any other purpose which may facilitate the goals of the present invention (e.g. to achieve higher levels of production and/or purification). Such tags include tags known to those skilled in the art to be useful in purification such as, but not limited to, His tag, glutathione-s-transferase tag, flag tag, mbp (maltose binding protein) tag, etc. In a preferred embodiment, the wild-type and mutant PBP1bs of the present invention are tagged with $His_6$ (see Example 1 below). Such tagged proteins may also be engineered to comprise a cleavage site, such as a thrombin, enterokinase or factor X cleavage site, for ease of removal of the tag before, during or after purification. Vector systems which provide a tag and a cleavage site for removal of the tag are particularly useful to make the expression constructs of the present invention.

The tagged PBP1b of the present invention may be purified by immuno-affinity or conventional chromatography, including but not limited to, chromatography employing the following: nickel or cobalt-purification resins, anion exchange chromatography, cation exchange chromatography, hydrophobic resins, gel filtration, antiflag epitope resin, reverse phase chromatography, etc. After purification, the PBP1b and PBP1b-inhibitor compound complex may be concentrated to greater than 1 mg/ml for crystallization purposes. In a preferred embodiment PBP1b and PBP1b-inhibitor complexes are concentrated to greater than 10 mg/ml for crystallization and in a particularly preferred embodiment, PBP1b and PBP1b-inhibitor complexes are concentrated to greater than 20 mg/ml.

In order to determine whether the purified PBP1b of the present invention demonstrate transglycosylase activity, the purified PBP1b and also any PBP1b-related protein may be assayed by any method known to those skilled in the art for the determination of said activity.

In another embodiment, the crystals of the present invention comprise purified wild-type PBP1b (SEQ ID NO:1) and are grown at or below room temperature, preferably at 16° C. by the hanging-drop vapor-diffusion method from a crystallization solution comprising one or more precipitants such as sodium formate. Any crystallization technique known to those skilled in the art may be employed to obtain the crystals of the present invention, including, but not limited to, batch crystallization, vapor diffusion (either by sitting drop or hanging drop) and micro dialysis. Seeding of the crystals in some instances may be required to obtain X-ray quality crystals. Standard micro and/or macro seeding of crystals may therefore be used.

The crystals of the present invention may form in the space group $P2_12_12$ in native form with unit dimensions of a=63.1 Å, b=288.5 Å, c=62.4 Å and α, β, γ=90, 90, 90 degrees. The crystals diffract to a resolution greater than 3.6 Å, preferably greater than 2.16 Å.

The determination of the structure of PBP1b and PBP1b bound to an inhibitory compound has enabled, for the first time, the identification of the active site of PBP1b.

The three-dimensional structural information and the atomic coordinates associated with said structural information of PBP1b bound to an inhibitory compound is useful in rational drug design providing for a method of identifying inhibitory compounds which bind to and inhibit the enzymatic activity of PBP1b and related proteins. Said method for identifying said potential inhibitor for an enzyme comprising transglycosylase activity comprises the steps of (a) using a three-dimensional structure of PBP1b as defined by its atomic coordinates listed in FIGS. 8-1 through 8-82; (b) employing said three-dimensional structure to design or select said potential inhibitor; (c) synthesizing said potential inhibitor; (d) contacting said potential inhibitor with said enzyme in the presence of an acetylated substrate; and (e) determining the ability of said inhibitor to inhibit said deacetylase activity.

The present invention permits the use of molecular design techniques to design, identify and synthesize chemical entities and compounds, including inhibitory compounds, capable of binding to the active site of PBP1b and PBP1b-related proteins. The atomic coordinates of inhibitor-bound PBP1b may be used in conjunction with computer modeling using a docking program such as GRAM, DOCK, HOOK or AUTODOCK (Dunbrack et al., 1997, Folding & Design 2:27 42) to identify potential inhibitors of PBP1b. This procedure can include computer fitting of potential inhibitors to the active site of PBP1b to ascertain how well the shape and the chemical structure of the potential inhibitor will complement the active site or to compare the potential inhibitors with-the binding of Moenomycin A in the active site. (See Bugg et al, 1998, Scientific American December: 92 98; West et-al., 1995, TIPS 16:67 74.) The potential inhibitors designed by modeling with a docking program may conform to the general formula related to Moenomycin. Computer programs may also be-employed to estimate the attraction, repulsion and steric hindrance of the PBP1b and potential inhibitor compound. Generally, the tighter the fit, the lower the steric hindrances, the greater the attractive forces, and the greater the specificity which are important features for a specific inhibitory compound which is more likely to interact with PBP1b and related proteins rather than other classes of proteins. These features are desired particularly where the inhibitory compound is a potential transglycosylase drug.

The compounds of the present invention may also be designed by visually inspecting the three-dimensional structure to determine more effective transglycosylase inhibitors. This type of modeling may be referred to as "manual" drug design. Manual drug design may employ visual inspection and analysis using a graphics visualization program such as "O" (Jones, T. A., Zhou, J. Y., Cowan, S. W., and Kjeldgaard, M., Improved method for building protein models in electron density maps and the location of errors in these models, Acta Crystallog., A47, 110 119.)

Initially potential inhibitor compounds can be selected for their structural similarity to Moenomycin by manual drug design. The structural analog thus designed can then be modified by computer modeling programs to better define the most likely effective candidates. Reduction of the number of potential candidates is useful as it may not be possible to synthesize and screen a countless number of variations compounds that may have some similarity to known inhibitory molecules. Such analysis has been shown effective in the development of HIV protease inhibitors (Lam et al., 1994, Science 263:380 384; Wlodawer et al., 1993, Ann. Rev. Biochem. 62:543 585; Appelt, 1993 Perspectives in Drug Discovery and Design 1:23 48; Erickson, 1993, Perspectives in Drug Discovery and Design 1:109 128. Alternatively, random screening of an small molecule library could lead to potential inhibitors whose inhibitory activity may then be analyzed by computer modeling as described above to better determine their effectiveness as inhibitors.

Copending U.S. patent application Ser. No. 12/354,717 discloses a method for initial screening, the method comprising obtaining a candidate for screening; carrying out an anisotropy measurement assay, such as fluorescent anisotropy, with a class A penicillin-binding protein comprising at least a transmembrane and a transglycosylase domains; and determining the effectiveness of the candidate as a transglycosylase inhibitor. U.S. patent application Ser. No. 12/354,717 is incorporated herein by reference in its entirety.

Definitions

Position specific iterative BLAST (PSI-BLAST) refers to a feature of BLAST 2.0 in which a profile (or position specific scoring matrix, PSSM) is constructed (automatically) from a multiple alignment of the highest scoring hits in an initial BLAST search. The PSSM is generated by calculating position-specific scores for each position in the alignment. Highly conserved positions receive high scores and weakly conserved positions receive scores near zero. The profile is used to perform a second BLAST search and the results of each "iteration" used to refine the profile. This iterative searching strategy results in increased sensitivity.

For the purposes of further describing the structure of PBP1b and PBP1b-related proteins, from the data obtained from the PBP1b crystals of the present invention, the definition of the following terms is provided:

The term "β sheet" refers to two or more polypeptide chains (or β strands) that run alongside each other and are linked in a regular manner by hydrogen bonds between the main chain C═O and N—H groups. Therefore all hydrogen bonds in a β-sheet are between different segments of polypeptide. Most β-sheets in proteins are all-parallel (protein interiors) or all-antiparallel (one side facing solvent, the other facing the hydrophobic core), Hydrogen bonds in antiparallel sheets are perpendicular to the chain direction and spaced evenly as pairs between strands. Hydrogen bonds in parallel sheets are slanted with respect to the chain direction and spaced evenly between strands.

The term "α helix" refers to the most abundant helical conformation found in globular proteins. The average length of an α helix is 10 residues. In an α helix, all amide protons point toward the N-terminus and all carbonyl oxygens point toward the C-terminus. The repeating nature of the phi, psi pairs ensure this orientation. Hydrogen bonds within an α helix also display a repeating pattern in which the backbone C═O of residue X (wherein X refers to any amino acid) hydrogen bonds to the backbone HN of residue X+4. The α helix is a coiled structure characterized by 3.6 residues per turn, and translating along its axis 1.5 Å per amino acid. Thus the pitch is 3.6.times.1.5 or 5.4 Å. The screw sense of a helices is always right-handed.

The term "loop" refers to any other conformation of amino acids (i.e. not a helix, strand or sheet). Additionally, a loop may contain bond interactions between amino acid side chains, but not in a repetitive, regular fashion.

Amino acid residues in peptides shall herein after be abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W. H. Freeman & Co., New York 1983.

The term "positively charged amino acid" refers to any amino acid having a positively charged side chain under normal physiological conditions. Examples of positively charged amino acids are Arg, Lys and His. The term "negatively charged amino acid" refers to any amino acid having a negatively charged side chain under normal physiological conditions. Examples of negatively charged amino acids are Asp and Glu. The term "hydrophobic amino acid" refers to any amino acid having an uncharged, nonpolar side chain that is relatively insoluble in water. Examples of hydrophobic amino acids are Ala, Leu, Ile, Gly, Val, Pro, Phe, Trp and Met. The term "hydrophilic amino acid" refers to any amino acid having an uncharged, polar side chain that is relatively soluble in water. Examples of hydrophilic amino acids are Ser, Thr, Tyr, Asp, Gln, and Cys. The term "aromatic amino acid" refers to any amino acid comprising a ring structure. Examples of aromatic amino acids are His, S Phe, Trp and Tyr.

The term "charge relay system" refers to a His-Asp arrangement as described by Fersht & Sperling, 1973, J. Mol. Biol. 74:137 149; Blow et al., 1969, Nature 221:337 340.

The term "active site" comprises any or all of the following sites in PBP1b, the substrate binding site, the catalytic transglycosylation site, or the site where an inhibitor of PBP1b binds. The active site, as referred to herein, comprises one or more of E114, E171, E233, E290, S398, and S510 (FIGS. 3A-3B).

Figure 4A:
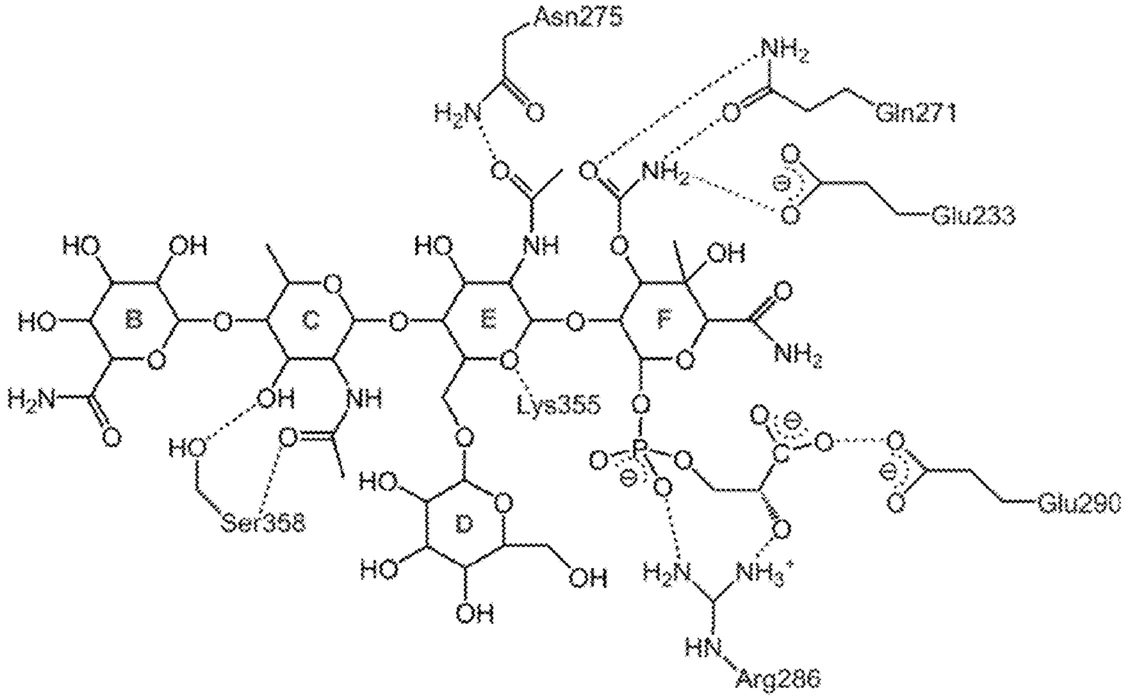
Figure 4B:
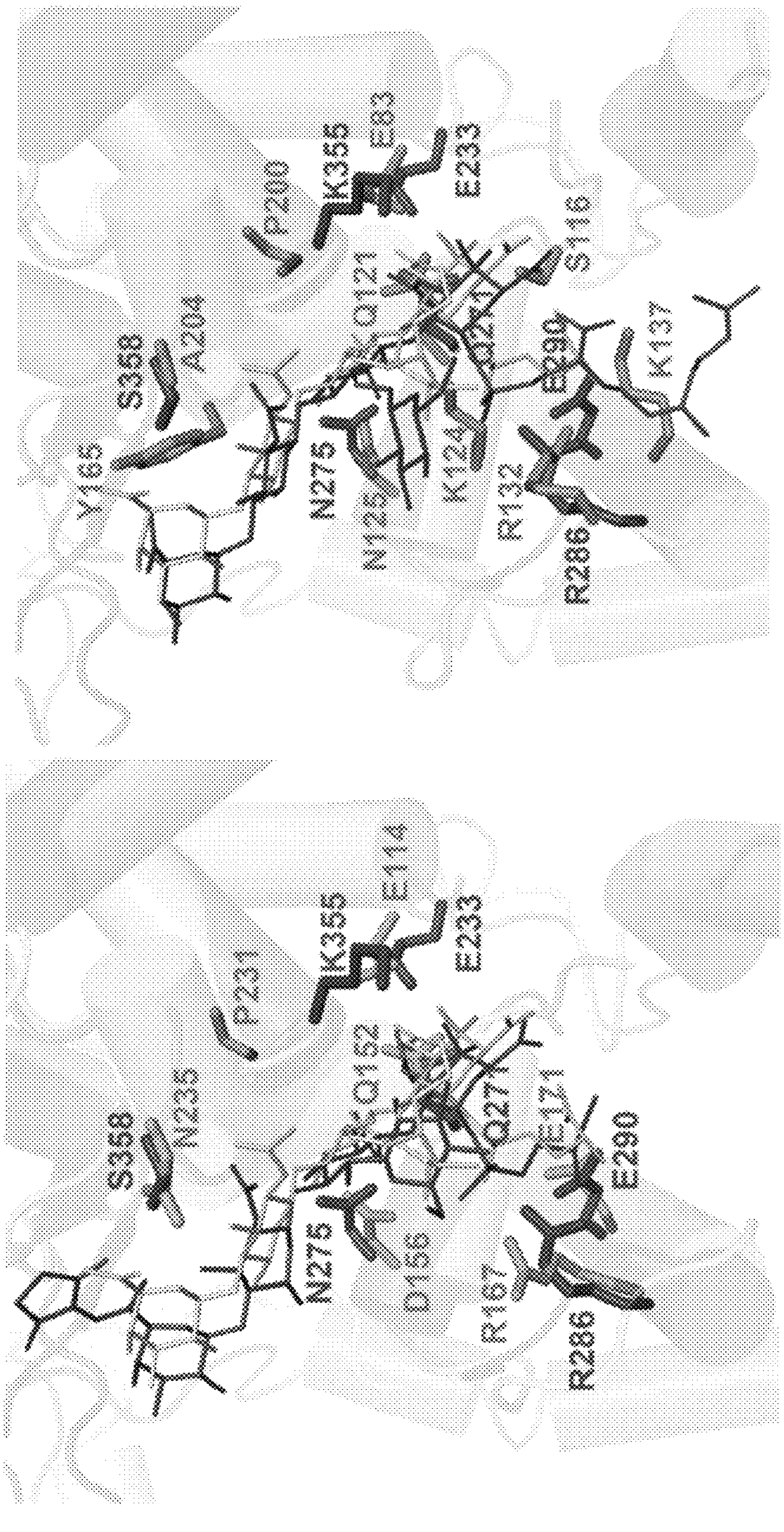

In some embodiments, the active site is defined by the Moenomycin binding site and residues involved in hydrophobic contact with moenomycin. The active site comprises one or more of Thr269, Val273, Phe277, Tyr315, Gln318, Lys355, Gly356, and Ser 358 (FIGS. 4A-4C). The active site may also involve Glu233, Arg286, Ser358 and Ile359 of *E. Coli* PBP1b.

Overall Structure of PBP1b-Moenomycin Complex

The crystal structures of two bacterial transglycosylases, a bifunctional transglycosylase from *S. aureus* (referred to as SaPBP2) and a transglycosylase domain from *Aquifex aeolicus* (referred to as AaPGT), have been determined recently with their TM domain or TM and TP domains removed, respectively (Lovering A L, de Castro L H, Lim D, Strynadka N C (2007) Science 315:1402-1405; Yuan Y, et al. (2007) Proc Natl Acad Sci USA 104:5348-5353; Yuan Y, et al. (2008) ACS Chem Biol 3:429-436). These structures revealed critical interactions between protein and moenomycin and served as good platforms for antibiotic development.

PBP1b from *E. coli* is a bifunctional enzyme containing both glycosyltransferase and transpeptidase activity (class A penicillin-binding protein). (Goffin, C. & Ghuysen, J. M. (1998). Microbiol Mol Biol Rev 62, 1079-93.) The sequence of PBP1b is composed of an N-terminal single-spanning transmembrane (TM) helix and a hitherto functionally-unknown insertion followed by the glycosyltransferase (TG) domain and the C-terminal transpeptidase (TP) domain. (Barrett, D. S., Chen, L., Litterman, N. K. & Walker, S. (2004). Biochemistry 43, 12375-81). The TM helix domain has been shown to be important for the binding between *E. coli* PBP1b and moenomycin (Cheng, T. J., et al., (2008). Proc Natl Acad Sci USA 105, 431-6). In addition, the full-length PBP1b has been found to show a substantially higher TG enzymatic activity than a TM truncated counterpart. (Id.)

Therefore, in this study, a purified full-length PBP1b possessing a similar level of enzymatic activity ($k_{cat}$ is $3.14\pm0.236\ s^{-1}$, Km is $18.3\pm4.05\ \mu M$ and kcat/Km is $(1.74\pm0.3)\times10^5\ M^{-1}s^{-1}$) to previous studies (Schwartz B, Markwalder J A, Seitz S P, Wang Y, Stein R L (2002) Biochemistry 41:12552-12561) was used for structure determination by X-ray crystallography.

The amino acid sequence of *E. coli* PBP1b is shown in FIG. 7. (Swiss-Prot Database accession number P02919). The domains of PBP1b are defined as: transmembrane (TM, residues 64-87), transglycosylase (TG, residues 195-409) and transpeptidase (TP, residues 444-736).

*E. coli* PBP1b[aa58-aa804] was cloned, expressed, purified and co-crystallized with Moenomycin. Moenomycin A (1) is a potent antibiotic that inhibits bacterial cell wall synthesis by binding to the transglycosylases that catalyze formation of the carbohydrate chains of peptidoglycan. (van Heijenoort J. Glycobiology 2001; 11:25R-36R) Moenomycin is the only natural product inhibitor known to directly bind to these enzymes. Its distinctive mechanism of action is matched by its unusual structure. Moenomycin A consists of a highly functionalized pentasaccharide attached via a unique phosphoglycerate linkage to a polyprenyl chain.

(1)

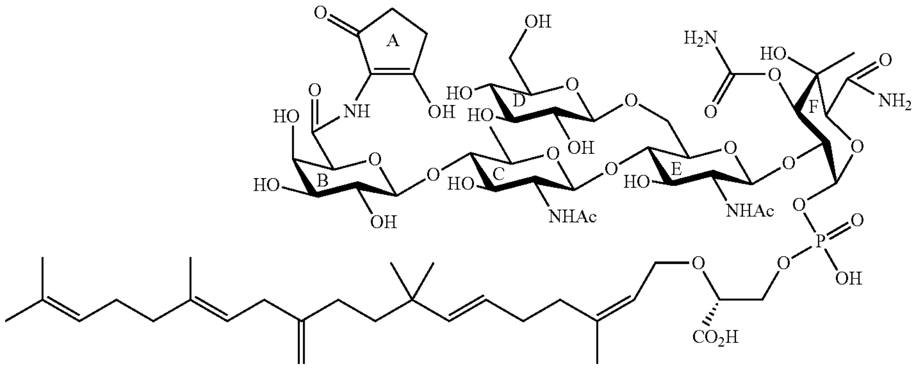

Moenomycin A

The crystal structure of *E. coli* PBP1b in complex with moenomycin was solved at 3.6 Å resolution and at 2.16 Å resolution (FIG. 2A). The atomic coordinates and structure factors have been deposited in the Protein Data Bank, pdb.org, with PDB ID codes 3FWL and 3FWM respectively. (See FIGS. 8-1 through 8-82). The protein construct includes amino acid residues 58-804, containing TM, an unknown domain, TG, and TP domains. In the process to obtain protein crystals with good X-ray diffracting quality, the solubilization, purification, and crystallization steps for the manufacture of PBP1b required the use of multiple detergents, including N-dodecyl-β-D-maltopyranoside, N-decyl-β-D-maltopyranoside, and N-dodecyl-N,N-dimethylamine-N-oxide.

By using a multi wavelength anomalous dispersion (MAD) approach with crystals from seleno-methionine labeled proteins, the phase information was obtained to generate a protein electron density map. The structure was built from residues 66-800, except two loop regions with absent electron density (residues 249-267 and 399-406), and was refined to good quality with $R_{work}$ and $R_{free}$ values of 20.6% and 25.1%, respectively. The statistics of data collection and structure determination are shown in FIG. 1.

At the amino terminus, the TM domain consists of a single long helix, encompassing residues 66-96. The residues 83-88 in the TM helix are in close vicinity to residues 292-296 in the TG domain (FIG. 3A).

Comparison with *S. aureus* PBP2 and *A. aeolicus* AaPGT Structure.

Further examination of the corresponding residues in the TM helix and TG domains among homologous transglycosylases PBP1b, PBP2 and AaPGT from *E. coli, S. aureus*, and *A. aeolicus*, respectively reveal a moderate conservation of hydrophobic amino acid residues, suggesting that similar interactions between the TM and TG domains in other transglycosylases may occur (FIG. 3B).

The overall fold of the TG domain in the PBP1b structure, in complex with moenomycin, is highly similar to the transglycosylase structures from SaPBP2 and AaPGT. The RMSD is 1.53 Å for 145 Cα atoms between TG domains from *E. coli* PBP1b and SaPBP2, and 1.46 Å for 143 Cα atoms between *E. coli* PBP1b and AaPGT. However, the residues involved in potential interactions with moenomycin (defined with distance cutoff at 3.2 Å) showed similarities and differences in these transglycosylase structures (FIGS. 4B and 4C). The resemblance between the PBP1b structure and SaPBP2 may explain the observation that transglycosylases from *E. coli* and *S. aureus* share comparable binding affinity to moenomycin (Cheng T J, et al. (2008) Proc Natl Acad Sci USA 105:431-436).

In addition, the interacting residues of the TG domain around the *E* ring, the F ring, the phosphate group, and the carboxylate group of moenomycin are more conserved than the interacting residues with the remaining parts (FIG. 3A). The conserved interacting residues in the binding pocket of transglycosylases can be considered as the most critical region to be studied in the process of antibiotic design. The result is in agreement with the previous findings to define the minimal pharmacophore in moenomycin, in which the EF-ring phosphoglycerate portion together with either the C or the D ring forms critical interactions with proteins (Yuan Y, et al. (2008) ACS Chem Biol 3:429-436).

Although *A. aeolicus* (Berezovsky I N, Shakhnovich E I (2005) Proc Natl Acad Sci USA 102:12742-12747), like *E. coli*, was classified as Gram-negative bacterium, the interaction pattern with moenomycin in AaPGT showed differences from the PBP1b structure and SaPBP2 (FIGS. 4B and

4C). It is noted that a positively charged Lys-137 residue in AaPGT can form an interaction with the carboxylate group of the phosphoglycerate in moenomycin, however, the corresponding interacting residue is a negatively charged residue glutamic acid in both the PBP1b structure and that of SaPBP2. The mutagenesis study also confirmed that the activity of AaPGT was nearly abolished after mutating Lys-137 to alanine (Yuan Y, et al. (2008) ACS Chem Biol 3:429-436). However, Lys-287 of *E. coli* PBP1b (corresponding to Lys-137 in AaPGT) seems to be less critical for the activity of peptidoglycan synthesis in *E. coli*, because the Lys-287 to alanine mutant still possessed 63% of wild-type activity, whereas the Glu-290-to-glutamine mutant displayed only 2% of wild-type activity (Terrak M, et al. (2008) J Biol Chem 283:28464-28470). Thus corresponding lysine residues act differently in *A. aeolicus* AaPGT and *E. coli* PBP1b.

The crystal structure of *E. coli* PBP1b represents a structural platform of transglycosylase, in particular for Gram-negative bacterial pathogens, for the development of antibiotics. Together with the 2 structures of transglycosylases from Grampositive (SaPBP2) and thermophilic bacteria (AaPGT), addition of the PBP1b structure completes the structural scope of transglycosylases across the bacterial spectrum.

Several compounds with molecular weights smaller than moenomycin have been reported to compete with the moenomycin and bind directly to the transglycosylase domain (9, 13). Although the inhibition efficiencies of these compounds to bacteria are lower than that of moenomycin, the structural information between these compounds and transglycosylase can be studied via molecular modeling or by X-ray crystallography using current *E. coli* PBP1b structure as a template for structure based drug design.

Structure and Function of UvrB Domain 2 Homolog (UB2H)

In addition to the TM, TG, and TP domains that are commonly found in bifunctional transglycosylases, an unexpected domain was observed in the PBP1b crystal structure (FIG. 2A). This domain, comprising residues 109-200, folds with a five antiparallel-stranded β-sheets (β2-β6) and one α-helix (α1) and forms more interactions with the TP domain (with buried surface area of 630.17 $Å^2$) and less interactions with the TG domain (313.01 $Å^2$). In comparison with the structure of SaPBP2, which shows no direct interactions between the TG and TP domain, addition of this extra domain makes *E. coli* PBP1b a more compact structure. By using Dali search (Holm L, et al. (2008) Bioinformatics 24:2780-2781), this domain was found to be structurally homologous to domains in UvrB (RMSD is 1.8 Å for 82 Cα atoms, with 24% sequence identity) and TRCF (transcription-coupled repair factor) (RMSD is 1.6 Å for 82 Cα atoms, with 14% sequence identity) (FIG. 3A). UvrB and TRCF are critical components of nucleotide excision repair (NER) system in DNA damage repairs. (Truglio J J, et al. (2004) EMBO J 23:2498-2509; Deaconescu A M, et al. (2006) Cell 124:507-520). The corresponding homologous domains in UvrB and TRCF specifically bind to a domain in UvrA in a competitive manner to coordinate the functionality of bacterial NER system. Based on the highly similar fold, this domain is referred to as UB2H (UvrB domain 2 homolog) domain.

Function of UvrB Domain 2 Homolog (UB2H)

Figure 2B:
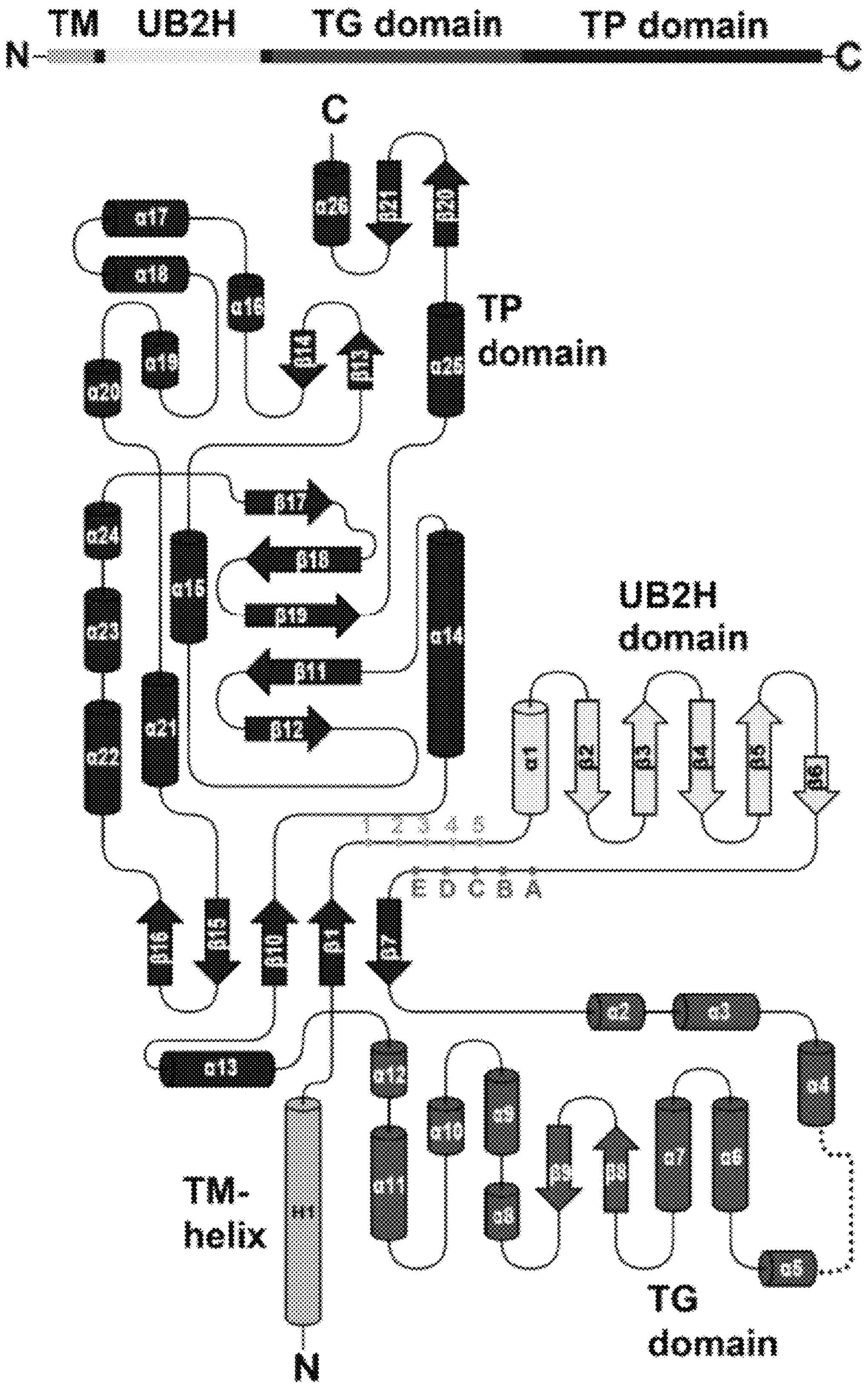
Figure 5A:
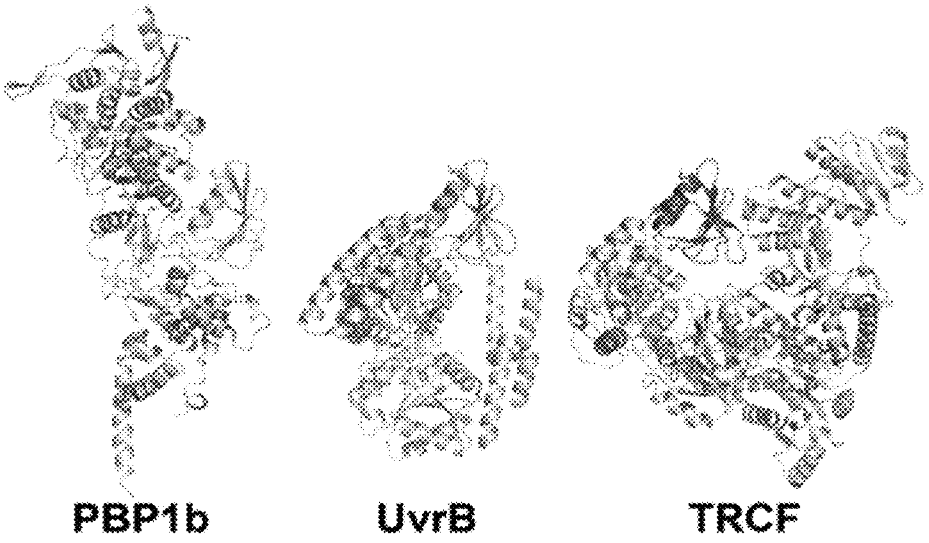
FIGS. 5A-5C show UB2H domain, its deletion phenotype and pull-down assay.
Figure 5B:
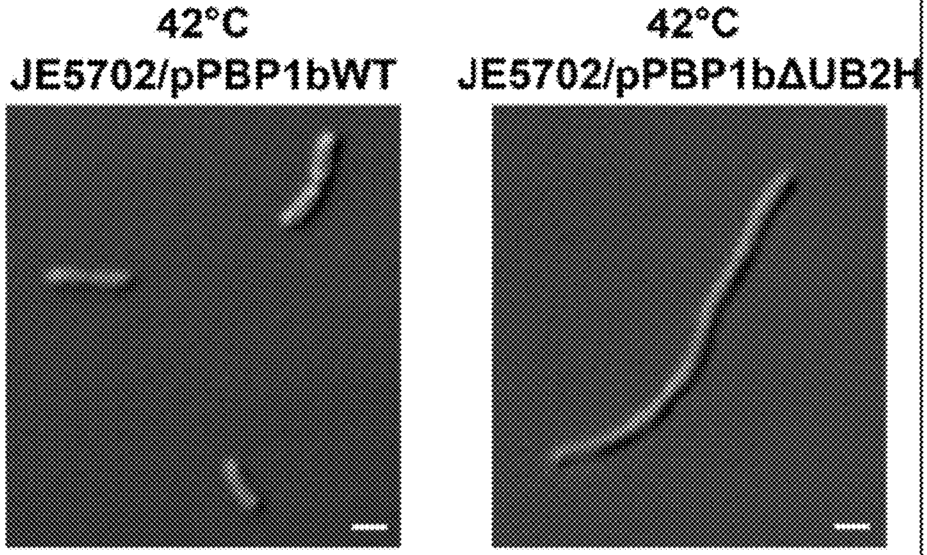

UB2H deletion mutants of PBP1b were then constructed to gain insights into their functions (FIG. 2B). The mutant PBP1bΔUB2H (Glu-114 to Gln-191 were deleted) provided on a plasmid was found to be able to rescue a PBP1b- deletion/PBP1a-temperature-sensitive *E. coli* host strain, JE5702, at 42° C. At this temperature, both PBP1b and PBP1a are not functional; thus, the survival of JE5702 indicated that PBP1b ΔUB2H can complement the enzymatic functions of TG and TP. However, it was observed that UB2H deletion caused an aberrant growth rate and an elongated cell shape containing multiple copies of DNA in JE5702 (FIG. 5B).

Figure 5C:
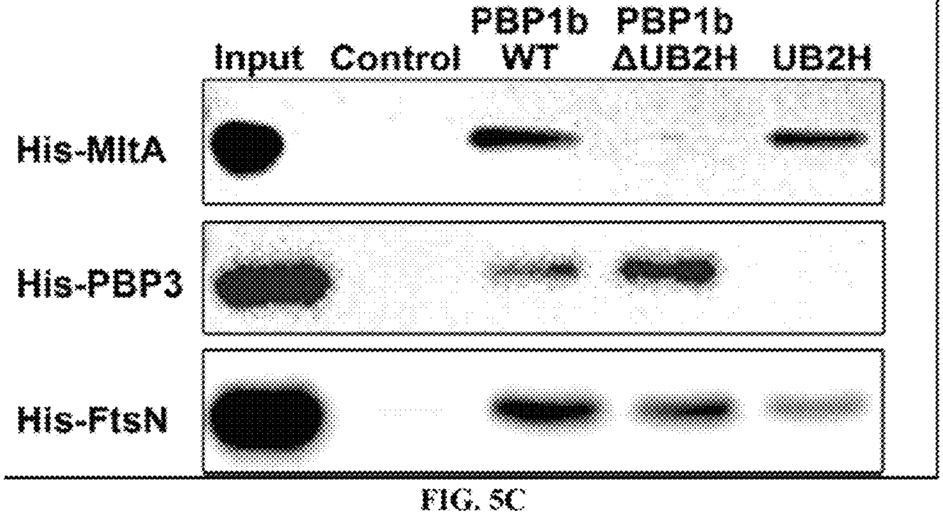

In *E. coli*, PBP1b interacts with different proteins during the course of cellular growth and division. For example, MltA, the membrane-bound lytic transglycosylase, interacts with PBP1b and participates in the peptidoglycan processing during cell elongation and cell division (Vollmer W, von Rechenberg M, Holtje J V (1999) J Biol Chem 274:6726-6734); PBP3, a transpeptidase catalyzing the formation of cross-linked peptidoglycan, interacts with PBP1b for peptidoglycan synthesis during cell division (Bertsche U, et al. (2006) Mol. Microbiol. 61:675-690); FtsN, the essential cell division protein that can interact with PBP1b, may play a role in stabilizing the divisome during cell division (Muller P, et al. (2007) J Biol. Chem. 282:36394-36402). To test whether UB2H serves as the binding domain in PBP1b for the interaction with different binding partners, pull-down assay was performed, and the result showed that PBP1bΔUB2H lost the binding ability with protein MltA, but not PBP3 or FtsN (FIG. 5C). In addition, the UB2H domain alone possessed binding ability similar to wild-type PBP1b, indicating that the UB2H domain participates in the interaction with MltA.

The UB2H domain exists only in bifunctional transglycosylases of some Gram-negative bacteria (183 of 988 bacterial genomes in the National Center for Biotechnology Information database as of November 2008). The protein-protein interaction between PBP1b and MltA established by the pull-down assay can be via a third protein MipA involved in bacterial cell-wall synthesis (Vollmer W, von Rechenberg M, Holtje J V (1999) J Biol Chem 274:6726-6734). A previous study, however, has reported that a mltA deletion did not affect the morphology of *E. coli* (Lommatzsch J, Templin M F, Kraft A R, Vollmer W, Holtje J V (1997) J Bacteriol 179:5465-5470). Thus, the aberrant morphology caused by UB2H deletion may not have a direct correlation to MltA. Other UB2H-interacting proteins can be involved in this morphological change. PBP1b, like UvrB and TRCF, can also interact with UvrA in a pull-down assay. The UB2H domain may participate in the regulation between DNA repair and/or synthesis and cell wall formation during the bacterial cell cycle.

Orientation of PBP1b in the Membrane

This PBP1b structure represents the first full-length PBP structure with the TM helix, which sheds insight on the orientation of the PBP1b molecule in the lipid bilayer. The presence of the TM helix in the PBP1b structure allows postulation of the orientation of the *E. coli* PBP1b molecule in lipid bilayers. It is commonly accepted that tryptophan and tyrosine residues have a higher frequency to be found at the lipid-water interface in membrane proteins (Yau W M, Wimley W C, Gawrisch K, White S H (1998) Biochemistry 37:14713-14718). All plausible tryptophan and tyrosine residues in the TG domain and TM helix were examined and a plane was found consisting of tryptophan and tyrosine residues that might be associated with lipids (FIG. 2A). As a result, the established membrane orientation made the bottom of the TG domain partially embedded in lipid bilayers. Also, based on this model, the C terminus of the TM helix (residues 88-96; 2 helical turns) is not embedded in the membrane.

The membrane orientation model was validated using molecular dynamics (MD) simulations (Lindahl E, Sansom M S (2008) Curr Opin Struct Biol 18:425-431). In the MD simulations, the proposed orientation of *E. coli* PBP1b in lipid bilayers was observed to be energetically stable in different MD simulations, and also suggested that the contact between TM and TG is not an artifact caused by crystal packing.

Figure 6A:
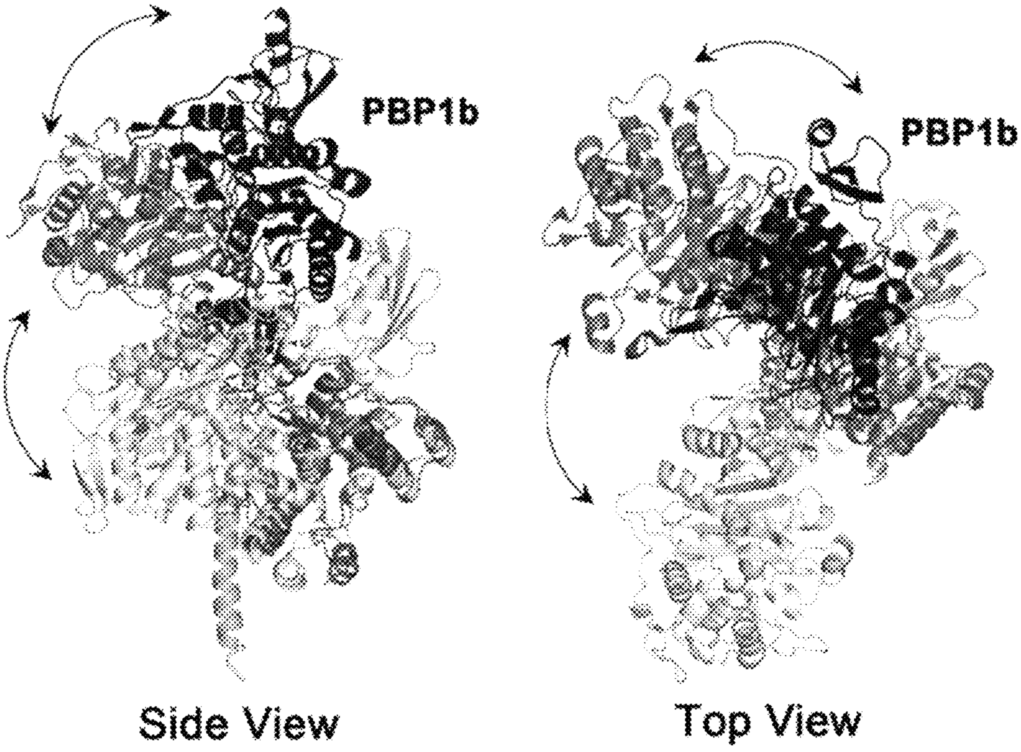
FIGS. 6A-6B show interdomain flexibility and a model for peptidoglycan synthesis.

The *E. coli* TP domain closely resembles the corresponding region in the SaPBP2 structure; however, the relative orientation between the TG and TP domains are dissimilar between our structure and SaPBP2 (FIG. 6A) (Lovering A L, de Castro L H, Lim D, Strynadka N C (2007) Science 315:1402-1405; Lovering A L, De Castro L, Strynadka N C (2008) J Mol Biol 383:167-177). Despite the discrepancy, we considered all different orientations plausible because of the possibly inherent flexibility of a hinge region (Lovering A L, De Castro L, Strynadka N C (2008) J Mol Biol 383:167-177). Different crystal structures can simply represent different structural states of the bifunctional transglycosylases. The changes in the relative orientation of SaPBP2 had been proposed to be correlated to the regulation of TG activity (Lovering A L, De Castro L, Strynadka N C (2008) J Mol Biol 383:167-177).

It has been observed that the binding affinity of moenomycin to *E. coli* PBP1b is TM domain dependent (Cheng T J, et al. (2008) Domain requirement of moenomycin binding to bifunctional transglycosylases and development of high-throughput discovery of antibiotics. Proc Natl Acad Sci USA 105:431-436.). However, no direct interaction between moenomycin and the TM helix was observed in our crystal structure. Furthermore, removal of the TM helix does not affect the structure of TG domain in the binding site, when comparing our structure and SaPBP2 in their moenomycin binding pockets (FIG. 4A). We therefore suggest that the TM helix simply stabilizes the protein-membrane interaction, and the resulting orientation limits the interaction between PBP1b and moenomycin or lipid II in the membrane in a 2D lateral diffusion fashion. Removal of TM may destabilize the protein-membrane interaction, thus affecting moenomycin or lipid II binding to TG. Indeed, stable protein-membrane interaction has been reported recently to be crucial for the normal function of some membrane proteins, and hence it has been suggested to be a target for drug discovery (Segers K, et al. (2007) Design of protein membrane interaction inhibitors by virtual ligand screening, proof of concept with the C2 domain of factor V. Proc Natl Acad Sci USA 104:12697-12702.).

A Model for Peptidoglycan Synthesis.

Figure 6B:
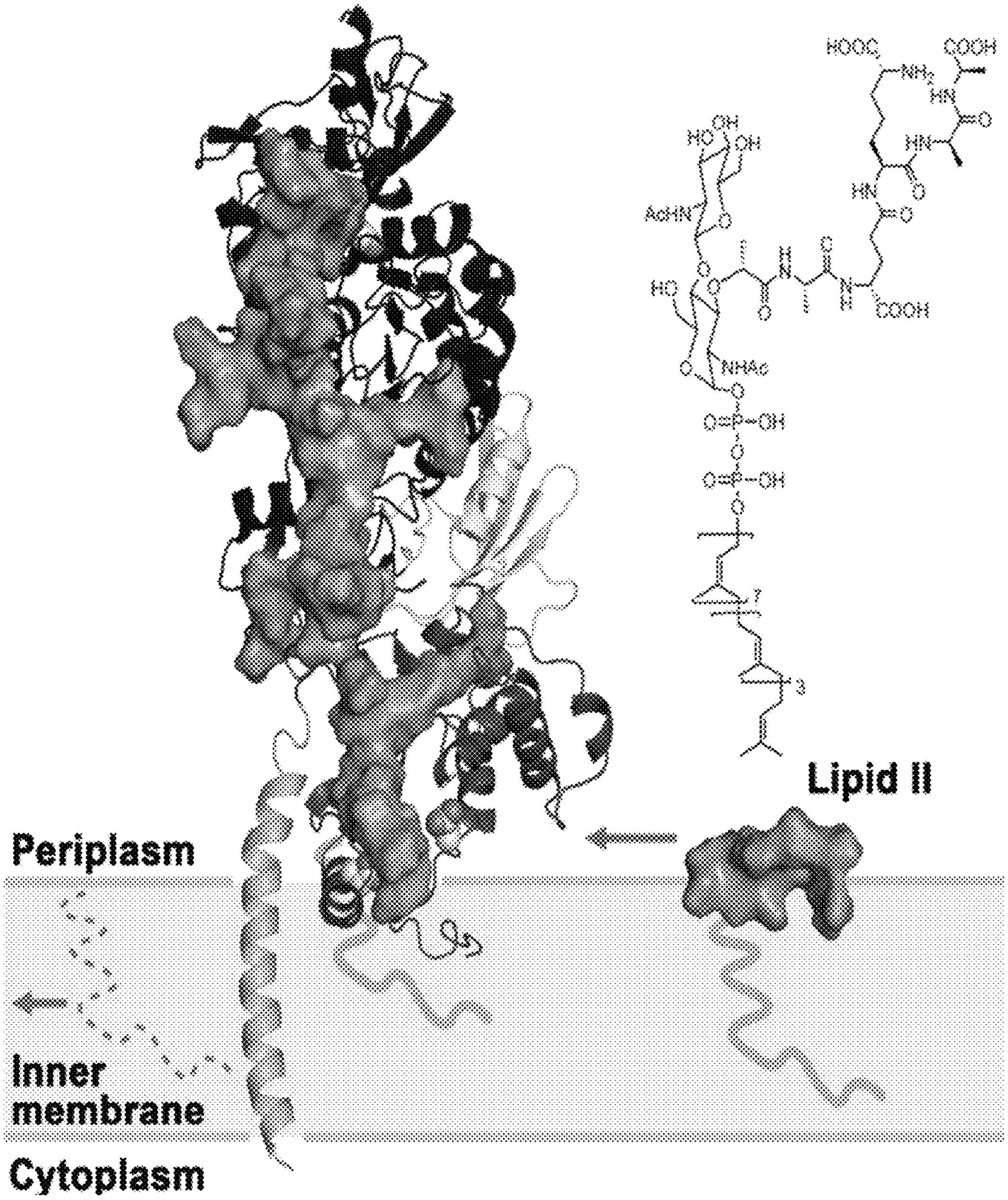

It has been proposed that the moenomycin molecule in the binding site of transglycosylase structurally mimics lipid IV, the dimerized peptidoglycan from 2 molecules of lipid II, and suggested a mechanism of peptidoglycan elongation where the growing glycan chain acts as an acceptor for the nucleophilic attack with lipid II as a donor. (Lovering A L, de Castro L H, Lim D, Strynadka N C (2007) Science 315:1402-1405; Lovering A L, De Castro L, Strynadka N C (2008) J Mol Biol 383:167-177). Recently, the architecture of peptidoglycan has been modeled based on the NMR structure of a lipid IV derivative (Meroueh S O, et al. (2006) Proc Natl Acad Sci USA 103:4404-4409). Using the proposed peptidoglycan model, a single strand of the peptidoglycan was docked onto the structure of *E. coli* PBP1b, with the lipid IV portion replacing moenomycin (FIG. 6B). It is noted that the distance (65.8 Å) between the active-site residues of the TG and TP domains in the structure corresponds well to the distance (67.1 Å) between the reaction sites on the peptidoglycan. In this model, the surface of PBP1b in contact with peptidoglycan is largely composed of loops, which are possibly flexible and capable of accommodating the polymerizing peptidoglycan. Therefore, the membrane orientation of PBP1b established by the transmembrane helix implies that its product, peptidoglycan, can be synthesized perpendicularly to the membrane surface. In contrast to the conventional views that cell wall consists of layers of cross-linked peptidoglycans with their glycan backbones lying parallel to the membrane surface, the PBP1b structure and model suggest the possibility of vertical orientation of peptidoglycans at the membrane surface, at least when they are initially synthesized. There is, however, intrinsic flexibility in both the bifunctional transglycosylases and their product peptidoglycan strands. As the peptidoglycans grow longer, the complete polymerized and cross-linked cell wall may have different appearance where the peptidoglycan strands lie parallel to the membrane surface or even form a coiled-coil cable as demonstrated by recent electron microscopic studies (Gan L, Chen S Y, Jensen G J (2008) Proc Natl Acad Sci USA 105:18953-18957; Hayhurst E J, Kailas L, Hobbs J K, Foster S J (2008) Proc Natl Acad Sci USA 105:14603-14608).

Transglycosylase Inhibitors

Any method known to the skilled artisan may be employed to design a transglycosylase inhibitor by molecular replacement. For example, the program AMORE (The CCP4 suite: Programs for computational crystallography, 1994, Acta Crystallogr. D. 50:760-763) may be employed to determine the structure of PBP1b+/−a candidate inhibitor by molecular replacement using the PBP1b-moenomycin coordinates (FIGS. 8-1 through 8-82). For the structure determination of the candidate inhibitory compound, stereochemical restraints may be used in the refinement with the program CNS (Brunger et al., 1998, Acta Crystallogr. D 54:905 921).

A library was tested for transglycosylation inhibition by using fluorescence anisotropy binding assays, followed by transglycosylation enzymatic analysis. One small molecule (Compound 009) showed inhibition activities in both fluorescence anisotropy (as discussed in co-pending U.S. patent Ser. No. 12/354,717) and lipid II polymerization assays for transglycosylation activity. The $IC_{50}$ value of transglycosyaltion inhibition of Compound 009 is 45 μM.

Structure of the transglycosylase inhibitor Compound 009 is shown below:

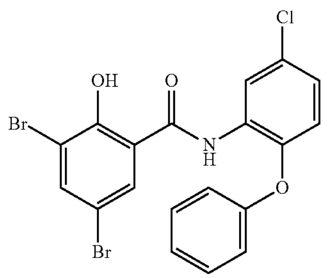 [SMILES: O=C(Nc1cc(Cl)ccc1Oc1ccccc1)c1cc(Br)cc(Br)c1O]

Anti-bacterial activities of the compound are shown in Table 1. The compounds were tested against *Staphylococcus aureus* (ATCC29213, SA), methicillin-resistant *Staphylococcus aureus* (ATCC33592, MRSA), *Mycobacterium smegmatis* (ATCC11565, MS), or *Escherichia coli* (ATCC 25922, EC).

TABLE 1

Anti-bacterial activities of Compound 009

| | MIC (μg/ml) | | | |
|---|---|---|---|---|
| | SA | MRSA | MS | EC |
| Compound 009 | 0.5 | 0.25 | 0.25 | >256 |

Several analogs were further obtained to study the structure-activity relationship (SAR) for transglycosylation inhibition activities. A general synthesis scheme is shown below with characterization of two example compounds.

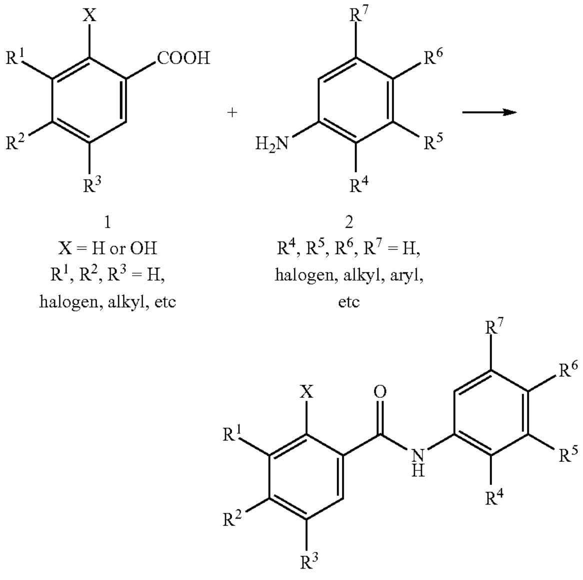

1
X = H or OH
$R^1$, $R^2$, $R^3$ = H, halogen, alkyl, etc

2
$R^4$, $R^5$, $R^6$, $R^7$ = H, halogen, alkyl, aryl, etc desired compound 3
X = H or OH
$R^1$, $R^2$, $R^3$ = H, halogen, alkyl, etc
$R^4$, $R^5$, $R^6$, $R^7$ = H, halogen, alkyl, aryl, etc Treatment of acid 1 (1 eq) and amine 2 (0.9 eq) in the presence of $PCl_3$ (1 eq) under microwave heating in toluene, followed by extraction and purification gave the desired product in a 30-75% yield range. The purified compounds were analyzed and characterized with NMR and LC-MS. For the preparation of acid 1 and amine 2, several chemical transformations are utilized such as nucleophilic aromatic substitution, alkylation, and halogenation.

Two compounds were selected:

(1) WCKTS-A1N1

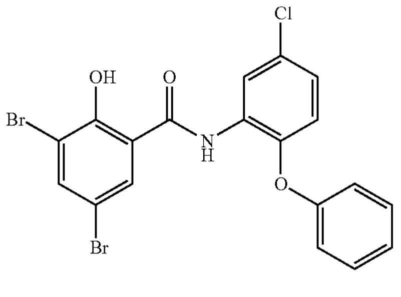 [SMILES: O=C(Nc1cc(Cl)ccc1Oc1ccccc1)c1cc(Br)cc(Br)c1O]

$^1H$ NMR ($CDCl_3$): δ 12.02 (s, 1H), 8.62 (s, 1H), 8.48 (d, 1H, J=2.4 Hz), 7.79 (d, 1H, J=2.4 Hz), 7.43-6.80 (m, 8H). HRMS calculate for $[C_{19}H_{12}Br_2ClNO_3+H]^+$ 497.89, found 497.892.

(2) WCKTS-A1N3

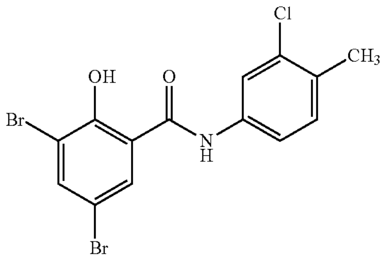 [SMILES: Cc1ccc(NC(=O)c2cc(Br)cc(Br)c2O)cc1Cl]

$^1H$ NMR (D-acetone): δ 10.17 (s, 1H), 8.21 (d, 1H, J=1.9 Hz), 7.91 (d, 1H, J=1.9 Hz), 7.86 (d, 1H, J=1.8 Hz), 7.58 (dd, 1H, J=8.2, 1.8 Hz), 7.33 (d, 1H, J=8.2 Hz), 2.33 (s, 3H). HRMS calculate for $[C_{14}H_{10}Br_2ClNO_2+H]^+$ 419.88, found 419.881.

Transglycosylase Inhibition and Antibacterial Activity of Analogs

The structure and the summarized results are shown in Tables 2-4. The hydroxyl group of ring A is critical for the activity since the methylation of the hydroxyl group abolished the transglycosylase inhibition activity. The hit and its analogues were also confirmed to be active against *Staphylococcus aureus* (SA), methicillin-resistant *Staphylococcus aureus* (MRSA), and *Mycobacterium smegmata* (MS) as shown in Tables 5-7. The inhibitory activities of all potential inhibitor compounds listed in Tables 2-7 are subsequently analyzed by computer modeling as described above to better determine their effectiveness as inhibitors.

TABLE 2

Preliminary SAR of Salicylanilides.

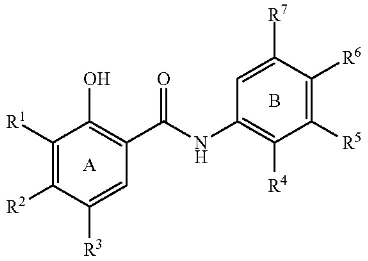

| Cmpd | $R^1$ | $R^2$ | $R^3$ | $R^4$ | $R^5$ | $R^6$ | $R^7$ | TG Activity at various concentration of cmpd 100 µM | 50 µM | 25 µM |
|---|---|---|---|---|---|---|---|---|---|---|
| 001 | Br | H | Br | H | Cl | Cl | Cl | 100% | — | — |
| 003 | Cl | H | Cl | H | Cl | Cl | H | 100% | — | — |
| 004 | Cl | H | Cl | H | Cl | Cl | Cl | 100% | — | — |
| 142 | Cl | H | Cl | H | Cl | Cl | Cl | — | — | — |
| 118 | Br | H | Br | H | H | Cl | H | 100% | 100% | — |
| 127 | Br | H | Br | Cl | H | H | Cl | 100% | 100% | — |
| 203 | Br | H | Br | H | H | H | Cl | 100% | 100% | — |
| 141 | Cl | H | Cl | Cl | H | H | Cl | — | — | — |
| 115 | Br | H | Br | Cl | 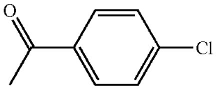 | H | Cl | 0% | 100% | — |
| 116 | Br | H | Br | Cl | 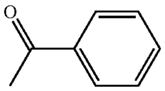 | H | Cl | 0% | 100% | — |
| 117 | Br | H | Cl | Cl | 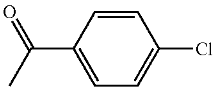 | H | Cl | 0% | 100% | — |
| 145 | Br | H | Br | Cl | 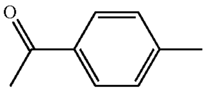 | H | Cl | 0% | 100% | — |
| 122 | Br | H | Br | H | H | 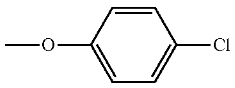 | Cl | 0% | 60% | — |

TABLE 2-continued

Preliminary SAR of Salicylanilides.

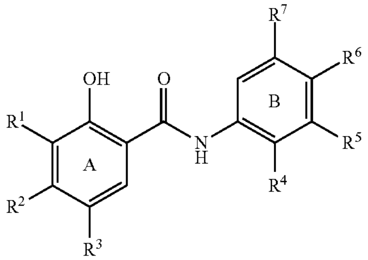

| | | | | | | | | TG Activity at various concentration of cmpd | | |
|---|---|---|---|---|---|---|---|---|---|---|
| Cmpd | $R^1$ | $R^2$ | $R^3$ | $R^4$ | $R^5$ | $R^6$ | $R^7$ | 100 μM | 50 μM | 25 μM |
| 123 | Br | H | Cl | Cl | H | Cl | 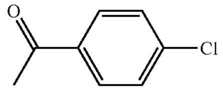 | 0% | 60% | — |
| 124 | Br | H | Br | H | H | Cl | 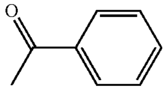 | 0% | 100% | — |
| KTS-1 | Br | H | Br | H | H | OH | H | — | 70% | — |
| KTS-3 | Br | H | Br | OH | H | H | H | — | 70% | — |
| KTS-7 | Br | H | Br | H | Cl | $CH_3$ | H | 100% | 100% | — |
| KTS-9 | Br | H | Br | H | H | Cl | H | 100% | 100% | — |
| A1N3 | Br | H | Br | H | Cl | $CH_3$ | H | — | 100% | — |
| A1N4 | Br | H | Br | H | H | Cl | H | — | 100% | — |
| A3N3 | H | H | H | H | Cl | $CH_3$ | H | 100% | 100% | — |
| A3N4 | H | H | H | H | H | Cl | H | 100% | 100% | — |
| A3N5 | H | H | H | H | H | $NO_2$ | H | 100% | 100% | — |
| A3N6 | H | H | H | H | H | $OCH_3$ | H | 100% | 100% | — |
| A5N3 | OH | OH | H | H | Cl | $CH_3$ | H | 0% | 100% | — |

TABLE 3

Preliminary SAR of Salicylanilides.

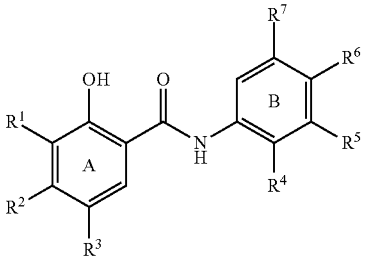

| | | | | | | | | TG Activity at various concentration of cmpd | | |
|---|---|---|---|---|---|---|---|---|---|---|
| Cmpd | $R^1$ | $R^2$ | $R^3$ | $R^4$ | $R^5$ | $R^6$ | $R^7$ | 100 μM | 50 μM | 25 μM |
| 009 | Br | H | Br | 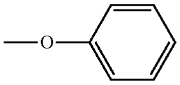 | H | H | Cl | 0% | 20% | 100% |

TABLE 3-continued
Preliminary SAR of Salicylanilides.
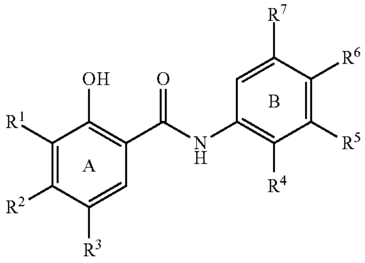
| | | | | | | | | TG Activity at various concentration of cmpd | | |
|---|---|---|---|---|---|---|---|---|---|---|
| Cmpd | $R^1$ | $R^2$ | $R^3$ | $R^4$ | $R^5$ | $R^6$ | $R^7$ | 100 μM | 50 μM | 25 μM |
| 201 | I | H | I | 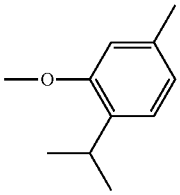 | H | H | H | — | 0% | 30% |
| 202 | Br | H | Br | 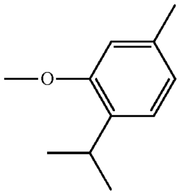 | H | Cl | H | — | 0% | 20% |
| 204 | Br | H | Br | 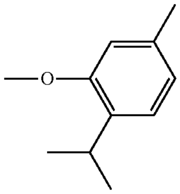 | H | H | H | — | 0% | 50% |
| 205 | H | H | Cl | 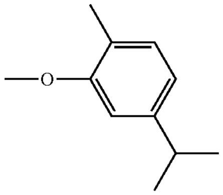 | H | H | Cl | — | 90% | — |
| 121 | Br | H | Cl | 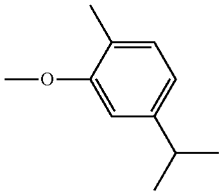 | H | H | Cl | 0% | 0% | 90% |
| 206 | Br | H | Cl | 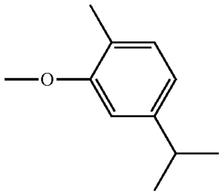 | H | H | Cl | — | 0% | 60% |

TABLE 3-continued
Preliminary SAR of Salicylanilides.
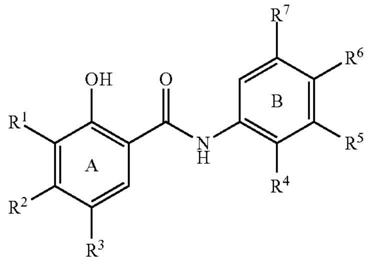
| | | | | | | | | TG Activity at various concentration of cmpd | | |
|---|---|---|---|---|---|---|---|---|---|---|
| Cmpd | $R^1$ | $R^2$ | $R^3$ | $R^4$ | $R^5$ | $R^6$ | $R^7$ | 100 μM | 50 μM | 25 μM |
| 207 | I | H | I | 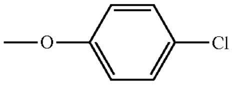 | H | H | 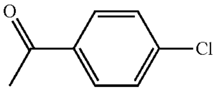 | — | 0% | 20% |
| 208 | I | H | I | 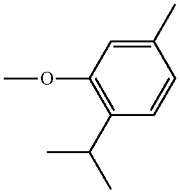 | H | H | Cl | — | 0% | 100% |
| 209 | Cl | H | Cl | 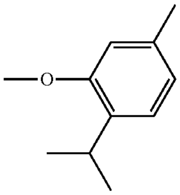 | H | H | Cl | — | 0% | 60% |
| A1N2 | Br | H | Br | 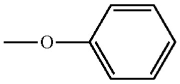 | H | H | H | 100% | 100% | — |
| A3N1 | H | H | H | 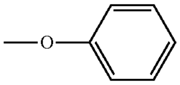 | H | H | Cl | 100% | 100% | — |
| A3N2 | H | H | H | 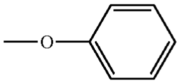 | H | H | H | 100% | 100% | — |
| A5N1 | OH | OH | H | 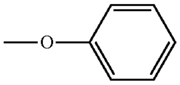 | H | H | Cl | 0% | 100% | — |

TABLE 3-continued

Preliminary SAR of Salicylanilides.

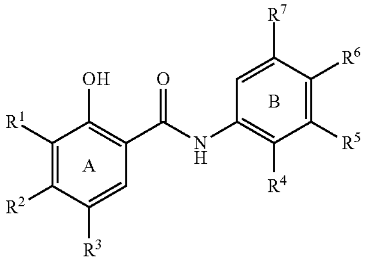

| Cmpd | $R^1$ | $R^2$ | $R^3$ | $R^4$ | $R^5$ | $R^6$ | $R^7$ | TG Activity at various concentration of cmpd 100 μM | 50 μM | 25 μM |
|---|---|---|---|---|---|---|---|---|---|---|
| A5N2 | OH | OH | H | 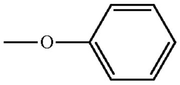 | H | H | H | 0% | 100% | — |

TABLE 4

Preliminary SAR of Salicylanilides.

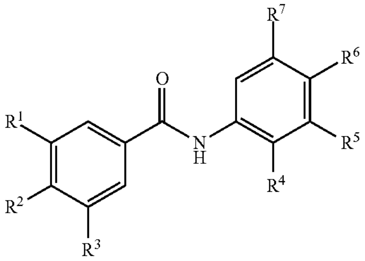

| Cmpd | $R^1$ | $R^2$ | $R^3$ | $R^4$ | $R^5$ | $R^6$ | $R^7$ | TG Activity at various concentration of cmpd 100 μM | 50 μM | 25 μM |
|---|---|---|---|---|---|---|---|---|---|---|
| 126* | H | Cl | 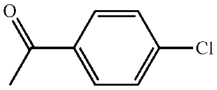 | OH | H | H | Cl | 100% | 100% | — |
| A2N1* | Br | H | Br | 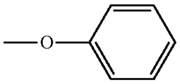 | H | H | Cl | 100% | 100% | — |
| A2N2* | Br | H | Br | 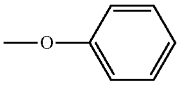 | H | H | H | 100% | 100% | — |
| A2N3* | Br | H | Br | H | Cl | $CH_3$ | H | 100% | 100% | — |
| A4N1* | H | H | H | 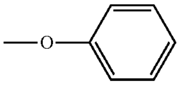 | H | H | Cl | 100% | 100% | — |
| A4N3* | H | H | H | H | Cl | $CH_3$ | H | 100% | 100% | — |
| A6N1* | H | OH | H | 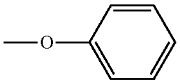 | H | H | Cl | 100% | 100% | — |

TABLE 4-continued

Preliminary SAR of Salicylanilides.

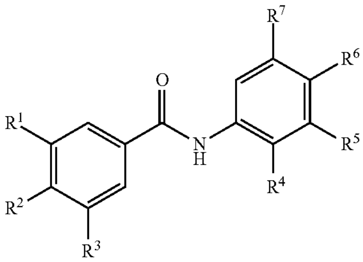

| | | | | | | | | TG Activity at various concentration of cmpd | | |
|---|---|---|---|---|---|---|---|---|---|---|
| Cmpd | $R^1$ | $R^2$ | $R^3$ | $R^4$ | $R^5$ | $R^6$ | $R^7$ | 100 μM | 50 μM | 25 μM |
| A6N2* | H | OH | H | 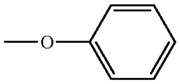 | H | H | H | 100% | 100% | — |
| A6N3* | H | OH | H | H | Cl | $CH_3$ | H | 100% | 100% | — |

The compounds were tested against *Staphylococcus aureus* (ATCC29213, SA), methicillin-resistant *Staphylococcus aureus* (ATCC33592, MRSA), *Mycobacterium smegmatis* (ATCC11565, MS), or *Escherichia coli* (ATCC 25922, EC) as shown in Table 5 below.

TABLE 5

Anti-bacterial activities of the compounds shown in Table 5.

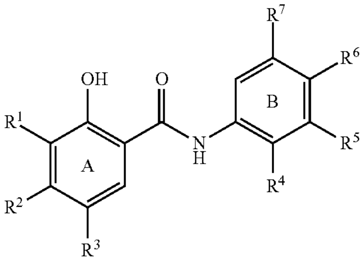

| | | | | | | | | MIC (μg/ml) | | | |
|---|---|---|---|---|---|---|---|---|---|---|---|
| Cmpd | $R^1$ | $R^2$ | $R^3$ | $R^4$ | $R^5$ | $R^6$ | $R^7$ | SA | MRSA | MS | EC |
| 001 | Br | H | Br | H | Cl | Cl | Cl | ≤0.03 | 0.06 | ≤0.03 | 16 |
| 003 | Cl | H | Cl | H | Cl | Cl | H | 0.25 | 1 | 0.06 | 32 |
| 004 | Cl | H | Cl | H | Cl | Cl | Cl | 0.125 | 0.5 | ≤0.03 | 16 |
| 142 | Cl | H | Cl | H | Cl | Cl | Cl | 0.5 | 0.5 | 0.125 | — |
| 118 | Br | H | Br | H | H | Cl | H | 1 | 4 | 1 | 128 |
| 127 | Br | H | Br | Cl | H | H | Cl | 1 | 1 | 1 | 64 |
| 203 | Br | H | Br | H | H | H | Cl | 2 | 2 | 4 | — |
| 141 | Cl | H | Cl | Cl | H | H | Cl | 1 | 0.5 | 2 | — |
| 115 | Br | H | Br | Cl | 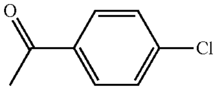 | H | Cl | 0.5 | 2 | 0.25 | >256 |

TABLE 5-continued

Anti-bacterial activities of the compounds shown in Table 5.

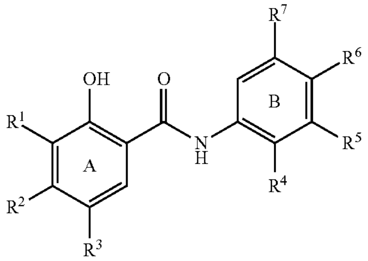

| Cmpd | $R^1$ | $R^2$ | $R^3$ | $R^4$ | $R^5$ | $R^6$ | $R^7$ | MIC (μg/ml) SA | MRSA | MS | EC |
|---|---|---|---|---|---|---|---|---|---|---|---|
| 116 | Br | H | Br | Cl | 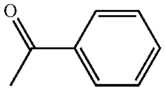 | H | Cl | 1 | 8 | 0.5 | >256 |
| 117 | Br | H | Cl | Cl | 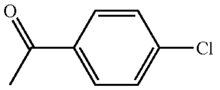 | H | Cl | 0.5 | 0.5 | 0.25 | >256 |
| 145 | Br | H | Br | Cl | 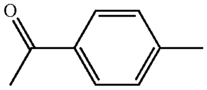 | H | Cl | >4 | >4 | >4 | — |
| 122 | Br | H | Br | H | H | 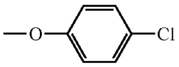 | Cl | 0.5 | 0.25 | 0.125 | >256 |
| 123 | Br | H | Cl | Cl | H | Cl | 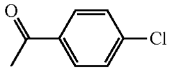 | 0.25 | 0.25 | 0.06 | >256 |
| 124 | Br | H | Br | H | H | Cl | 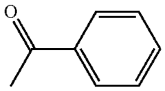 | 1 | 1 | 1 | >256 |
| KTS-1 | Br | H | Br | H | H | OH | H | 32 | >32 | 16 | — |
| KTS-3 | Br | H | Br | OH | H | H | H | 4 | 4 | 4 | — |
| KTS-7 | Br | H | Br | H | Cl | $CH_3$ | H | 1 | 1 | 1 | — |
| KTS-9 | Br | H | Br | H | H | Cl | H | 1 | 1 | 2 | — |
| A1N3 | Br | H | Br | H | Cl | $CH_3$ | H | 1 | — | — | — |
| A1N4 | Br | H | Br | H | H | Cl | H | 1 | — | — | — |
| A3N3 | H | H | H | H | Cl | $CH_3$ | H | 4 | — | — | — |
| A3N4 | H | H | H | H | H | Cl | H | 8 | — | — | — |
| A3N5 | H | H | H | H | H | $NO_2$ | H | 4 | — | — | — |
| A3N6 | H | H | H | H | H | $OCH_3$ | H | >32 | — | — | — |
| A5N3 | OH | OH | H | H | Cl | $CH_3$ | H | 4 | — | — | — |

The compounds were tested against *Staphylococcus aureus* (ATCC29213, SA), methicillin-resistant *Staphylococcus aureus* (ATCC33592, MRSA), *Mycobacterium smegmatis* (ATCC11565, MS), or *Escherichia coli* (ATCC 25922, EC) as shown in Table 6 below.

TABLE 6
Anti-bacterial activities of the compounds shown in Table 6.
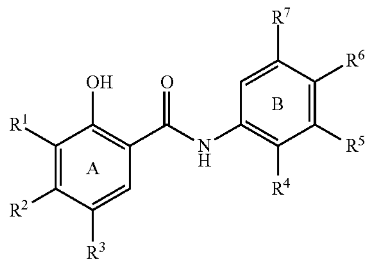
| Cmpd | $R^1$ | $R^2$ | $R^3$ | $R^4$ | $R^5$ | $R^6$ | $R^7$ | MIC (μg/ml) SA | MRSA | MS | EC |
|---|---|---|---|---|---|---|---|---|---|---|---|
| 009 | Br | H | Br | 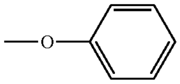 | H | H | Cl | 0.5 | 0.25 | 0.25 | >256 |
| 201 | I | H | I | 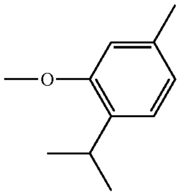 | H | H | H | 4 | 2 | 8 | — |
| 202 | Br | H | Br | 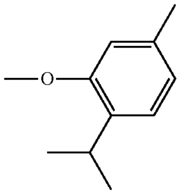 | H | Cl | H | 1 | 1 | 1 | — |
| 204 | Br | H | Br | 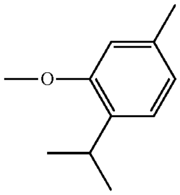 | H | H | H | 1 | 4 | 8 | — |
| 205 | H | H | Cl | 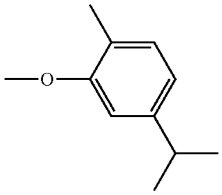 | H | H | Cl | 0.5 | 0.5 | 1 | — |
| 121 | Br | H | Cl | 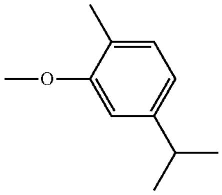 | H | H | Cl | 0.25 | 0.125 | 0.25 | >256 |

TABLE 6-continued
Anti-bacterial activities of the compounds shown in Table 6.
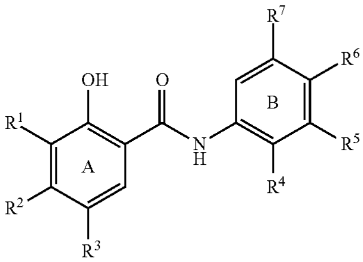
| Cmpd | $R^1$ | $R^2$ | $R^3$ | $R^4$ | $R^5$ | $R^6$ | $R^7$ | MIC (μg/ml) | | | |
|---|---|---|---|---|---|---|---|---|---|---|---|
| | | | | | | | | SA | MRSA | MS | EC |
| 206 | Br | H | Cl | 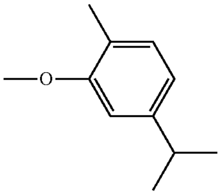 | H | H | Cl | 1 | 0.5 | 1 | — |
| 207 | I | H | I | 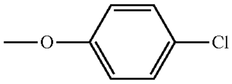 | H | H | 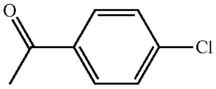 | 8 | 4 | 32 | — |
| 208 | I | H | I | 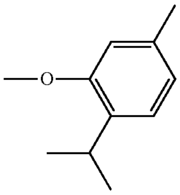 | H | H | Cl | 4 | 0.5 | 2 | — |
| 209 | Cl | H | Cl | 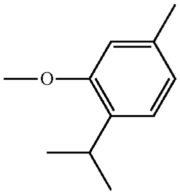 | H | H | Cl | 1 | 0.25 | 0.5 | — |
| A1N2 | Br | H | Br | 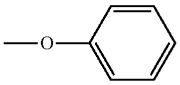 | H | H | H | >32 | — | — | — |
| A3N1 | H | H | H | 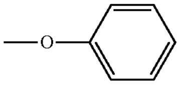 | H | H | Cl | 1 | — | — | — |
| A3N2 | H | H | H | 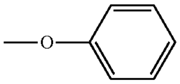 | H | H | H | 8 | — | — | — |
| A5N1 | OH | OH | H | 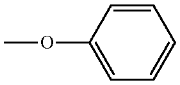 | H | H | Cl | 8 | — | — | — |
| A5N2 | OH | OH | H | 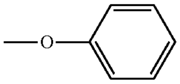 | H | H | H | 8 | — | — | — |

The compounds were tested against *Staphylococcus aureus* (ATCC29213, SA), methicillin-resistant *Staphylococcus aureus* (ATCC33592, MRSA), *Mycobacterium smegmatis* (ATCC11565, MS), or *Escherichia coli* (ATCC 25922, EC) as shown in Table 7 below.

In addition to active compound, the pharmaceutical compositions preferably comprise at least one pharmaceutically acceptable carrier. As used herein the language "pharmaceutically acceptable carrier" includes solvents, dispersion media, coatings, antibacterial and antifungal agents, isotonic

TABLE 7

Anti-bacterial activities of the compounds shown in Table 7.

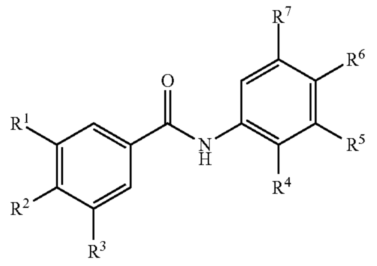

| Cmpd | $R^1$ | $R^2$ | $R^3$ | $R^4$ | $R^5$ | $R^6$ | $R^7$ | MIC (μg/ml) SA | MRSA | MS | EC |
|---|---|---|---|---|---|---|---|---|---|---|---|
| 126 | H | Cl | 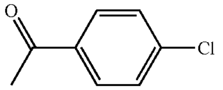 | OH | H | H | Cl | 1 | 0.125 | 0.06 | >256 |
| A2N1 | Br | H | Br | 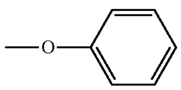 | H | H | Cl | >32 | — | — | — |
| A2N2 | Br | H | Br | 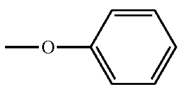 | H | H | H | >32 | — | — | — |
| A2N3 | Br | H | Br | H | Cl | $CH_3$ | H | >32 | — | — | — |
| A4N1 | H | H | H | 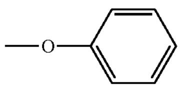 | H | H | Cl | >32 | — | — | — |
| A4N3 | H | H | H | H | Cl | $CH_3$ | H | >32 | — | — | — |
| A6N1 | H | OH | H | 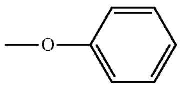 | H | H | Cl | 16 | — | — | — |
| A6N2 | H | OH | H | 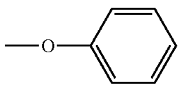 | H | H | H | >32 | — | — | — |
| A6N3 | H | OH | H | H | Cl | $CH_3$ | H | 32 | — | — | — |

Pharmaceutical Compositions

The instant disclosure also provides pharmaceutical compositions. In some implementations, the pharmaceutical compositions comprise agents, namely moenomycin analogs and small molecules (TG Inhibitors) shown to have antibiotic activity via inhibition of TG binding. In such pharmaceutical compositions, the TG Inhibitors form the "active compound" or "agent." According to implementations, the pharmaceutical compositions are administered to a subject to in need of anti-bacterial therapy, including gram-negative bacteria. According to other implementations, the pharmaceutical compositions are administered to a subject having a bacterial infection to inhibit the transglycosylation process during the synthesis of bacterial cell wall.

and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Subject as used herein refers to humans and non-human primates (e.g., guerilla, macaque, marmoset), livestock animals (e.g., sheep, cow, horse, donkey, pig), companion animals (e.g., dog, cat), laboratory test animals (e.g., mouse, rabbit, rat, guinea pig, hamster), captive wild animals (e.g., fox, deer) and any other organisms who can benefit from the agents of the present disclosure. There is no limitation on the type of animal that could benefit from the presently described agents. Human subjects are expressly contemplated. A subject regardless of whether it is a human or nonhuman organism may be referred to as a patient, individual, animal, host, or recipient.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a container or dispenser which contains a suitable propellant, e.g., a gas such as carbon dioxide, or a nebulizer. Other delivery methods and devices common in the art, including mechanically actuated atomizing-like devices are expressly contemplated.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For epidermal, dermal, or transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one implementation, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811, incorporated by reference herein.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in subjects. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in subjects. Levels in plasma can be measured, for example, by high performance liquid chromatography.

As defined herein, a therapeutically effective amount of an active compound of the disclosure may range, for examples, from about 0.001 to 30 mg/kg body weight, about 0.01 to 25 mg/kg body weight, about 0.1 to 20 mg/kg body weight, or about 1 to 10 mg/kg, 2 to 9 mg/kg, 3 to 8 mg/kg, 4 to 7 mg/kg, or 5 to 6 mg/kg body weight. Without limitation, the active compound can be administered between one time per week and three or more times per day, for between about 1 to 10 weeks, for example between 2 to 8 weeks, between about 3 to 7 weeks, or for about 4, 5, or 6 weeks. The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a pharmaceutical composition of the disclosure can include a single treatment or, preferably, can include a series of treatments.

For those agents determined to be transglycosylation inhibitors or antibiotics, further testing may then be performed for the candidate agent to determine agents that are both good transglycosylation inhibitors and also having reasonably bioavailability.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Cloning, Expression and Purification of PBP1b

Purified PBP1b gamma degraded readily into a slightly smaller protein. After N-terminal sequencing accompanying with molecular weight measurement by MALTI-TOF Mass spectrometry, we identified the stable region containing amino acid 58 to 804.

PBP1b[58-804] was amplified from *E. coli* genomic DNA and cloned into the expression vector pET15b (NovagEN; EMD Sciences, San Diego, Calif.)) at the NdeI and BamHI restriction sites. BL21(DE3) *E. coli* host cells were grown at 37° C. until $OD_{600}$ reached 0.6, and protein expression was induced with 1 mM IPTG for 3 hr. Cell pellets were resuspended in 20 mM Tris at pH 8.0, 300 mM NaCl and broken by Microfluidizer™ (Microfluidics, Newton, Mass.). Recombinant protein with an N-terminal $(His)_6$ tag was solubilized with 20 mM n-Dodecyl-β-D-maltoside (DDM; Anatrace, Maumee, Ohio, USA)) and purified by nickel chelation chromatography, in accordance with the manufacturer's instructions, in the presence of 1 mM DDM. An N-terminal $(His)_6$ tag was cleaved by thrombin (Sigma) at room temperature for overnight. Digested PBP1b was further purified using a Superdex 200™ size-exclusion column (GE Biosciences) in 20 mM Tris at pH 8.0, 300 mM NaCl, 4.5 mM DM. Peak fractions were concentrated and the detergent was exchanged to 0.28 mM LDAO using Amicon™ Ultra filter units (Millipore, Billerica, Mass.). The selenomethionine (SeMet) derivative was expressed in BL21(DE3) using minimal medium supplemented with selenomethionine and purified as described above.

Example 2: Crystallization, Data Collection and Structure Determination

Crystals of PBP1b[58-804]-Moenomycin complex were co-crystallized in sitting drop at 16° C. Crystals were obtained by mixing 12 mg/ml protein containing additional 1.4 mM moenomycin with the same volume of reservoir solution containing 1.2 M sodium formate. For cryoprotection, crystals were transferred into 3 M sodium formate and flash-frozen in liquid nitrogen.

Native dataset was collected at Beamline 44XU™ of Japan Synchrotron Radiation Research Institute (Hyogo, JP) and SeMet datasets were collected at Beamline 13B1™ of National Synchrotron Radiation Research Center (Hsinchu, T W). All data were indexed, integrated and scaled with HKL2000. (Leslie, A. G., Powell, H. R., Winter, G., Svensson, O., Spruce, D., McSweeney, S., Love, D., Kinder, S., Duke, E. & Nave, C. (2002). Automation of the collection and processing of X-ray diffraction data—a generic approach. Acta Crystallogr D Biol Crystallogr 58, 1924-8.) MAD method was used to collect anomalous datasets from SeMet derivative. The selenium sites (22 out of 24) and structure phase were obtained by SOLVE. (Terwilliger, T. C. & Berendzen, J. (1999). Automated MAD and MIR structure solution. Acta Crystallogr D Biol Crystallogr 55, 849-61.) Density modification by solvent flattening was carried out by RESOLVE (Terwilliger, T. C. & Berendzen, J. (1999). Acta Crystallogr D Biol Crystallogr 55, 849-61) to generate an interpretable 3.3 Å electron density map. The model was manual built using COOT. (Emsley, P. & Cowtan, K. (2004). Coot: model-building tools for molecular graphics. Acta Crystallogr D Biol Crystallogr 60, 2126-32) This model was subsequently refined to 2.16 Å resolution by using a native dataset. PHENIX was used at the initial refinement process, with the group atomic displacement parameter, and TLS options turned on. (Adams, P. D., Grosse-Kunstleve, R. W., Hung, L. W., Ioerger, T. R., McCoy, A. J., Moriarty, N. W., Read, R. J., Sacchettini, J. C., Sauter, N. K. & Terwilliger, T. C. (2002). PHENIX: building new software for automated crystallographic structure determination. Acta Crystallogr D Biol Crystallogr 58, 1948-54.) A final run of refinement was achieved with REFMAC5. (Murshudov, G. N., Vagin, A. A. & Dodson, E. J. (1997). Refinement of macromolecular structures by the maximum-likelihood method. Acta Crystallogr D Biol Crystallogr 53, 240-55.) TLS groups were determined by TLSMD server. (Painter, J. & Merritt, E. A. (2006). Optimal description of a protein structure in terms of multiple groups undergoing TLS motion. Acta Crystallogr D Biol Crystallogr 62, 439-50.)

Example 3: Molecular Dynamics Simulation

GROMACS (Van Der Spoel, D., Lindahl, E., Hess, B., Groenhof, G., Mark, A. E. & Berendsen, H. J. (2005). GROMACS: fast, flexible, and free. J Comput Chem 26, 1701-18) was used as the molecular dynamics simulation engine. MARTINI force field (Marrink, S. J. & Mark, A. E. (2004). Molecular view of hexagonal phase formation in phospholipid membranes. Biophys J 87, 3894-900) was used to model the coarse-grained PBP1b structure. After converting the atomic model into coarse-grained model, the structure was subjected to a brief steepest-descent energy minimization. It was then manually inserted into a water box containing pre-equilibrated lipid bilayer. A initial orientation of PBP1b were chosen subjectively to see if the final orientations would equilibrate to a specific position. Seven chloride ions were added into the box in order to maintain electrostatic neutrality. A steepest-descent energy minimization was carried out to relax any steric conflict between protein, lipid molecules, ions and solvent before the MD run. During the MD simulation, the secondary structure and the overall fold of PBP1b was restrained by using elastic network model. (Atilgan, A. R., Durell, S. R., Jernigan, R. L., Demirel, M. C., Keskin, O. & Bahar, I. (2001). Anisotropy of fluctuation dynamics of proteins with an elastic network model. Biophys J 80, 505-15)

In the production run, the time step for integration was set to 20 fs. The non-bonded neighbor list was updated every 10 steps. The simulations were performed at constant temperature, pressure and number of particles (NPT ensemble). The temperature of protein, lipid molecules, ions and solvent were coupled separately at 320 K using Berendsen algorithm (Berendsen, H. J. C., Postma, J. P. M., Vangunsteren, W. F., Dinola, A. & Haak, J. R. (1984). Molecular-Dynamics with Coupling to an External Bath. Journal of Chemical Physics 81, 3684-3690) with a coupling constant $\tau_t$=40 ps. The system pressure was semi-isotropically coupled to using Berendsen algorithm at 1 bar with a coupling constant $\tau_p$=40 ps and a compressibility of $1\times10^{-5}$ bar.

Example 4: Fluorescence Anisotropy Measurements

Fluorescence anisotropy measurements were carried out in triplicates in the wells of 384-well or 1536-well plates using a fluorescence detector that is capable to measure fluorescence anisotropy or fluorescencepolarization. For examples, a laser fluorimetry equipped with a 488 nm laser (IsoCyte) from Blueshift Biotech, Inc., (Sunnyvale, Calif., USA) of aViewlux from Perkin Elmer has been used for the application. Various buffers, salts, pH values, and divalent cations ($Ca^{++}$, $Mg^{++}$, $Co^{++}$) were optimized for fluorescence anisotropy measurements. $K_D$ and $K_I$ determinations were carried out in 100 mM NaCl, 10 mM Tris, pH 8.0. Fluorescence anisotropy values (A) were calculated using the equation: $A=(I\|-G*I^{\perp})/(I\|+2G*I^{\perp})$, where I|| is the fluorescence intensity of emitted light parallel to excitation, $I^{\perp}$ is the fluorescence intensity of emitted light perpendicular to excitation, and G is the gating factor that corrects for instrument bias. The G factor is experimentally determined for each run using the probe-only well as the basal anisotropy.

Candidate compounds to be tested were labeled with fluorescein (6-carboxyfluoresein N-hydroxysuccinimide ester) under basic conditions to prepare the fluorescent probe. One major concern about the fluorescent probe used in the FA assay is the probe itself; either the fluorophore or the structure modification, may interfere with the binding between the targeted protein and the small molecule. Therefore, the PBP binding affinities of Moe A and the fluorescent probe are compared using SPR. The determined steady-state affinity ($K_D$) values are similar for Moe A and F-Moe ($4.4\times10^{-7}$ vs. $5.2\times10^{-7}$M).

A high-throughput FA assay for transglycosylase was performed as disclosed in co-pending U.S. application Ser. No. 12/354,717. Concentration-dependent changes in fluorescence anisotropy was observed when *E. coli* PBP1b bound to F-Moe. The maximum anisotropy value was 0.2. The displacement of the PBP1b bound F-Moe complex by unlabeled candidate agents at various concentrations is measured by changes in fluorescence anisotropy is defined as $[(A_{obs}-A_{min})/(A_{max}-A_{min})\times100\%]$. The anisotropy of F-Moe increased significantly by incubation with *E. coli* PBP1b, supposedly due to the formation of F-Moe-PBP1b complex. In contrast, the anisotropy of F-Moe is unchanged when incubated with bovine serum albumin, up to 100 μM.

For the development of an assay for inhibitor screening, F-Moe was preincubated with *E. coli* PBP1b and then competed with unlabeled Moe A at various concentrations. A decrease in anisotropy was used to validate the FA assay to screen for inhibitors that displace the probe competitively from the moenomycin binding pocket of PBP1b.

$K_I$ and $IC_{50}$ values were determined from competitive displacement assay. For displacement assay, the initial condition contained 40 μl of 100 nM F-Moe, 10 μg/ml *E. coli* PBP1b in 10 mM Tris, pH 8.0, 100 mM NaCl for 384-well assays, or 10 μl of 100 nM F-Moe, 50-100 μg/ml *E. coli* PBP1b in 10 mM Tris, pH 8.0, 100 mM NaCl for 1536-well plates. Aliquots of compound stock solution were added and the anisotropy was monitored after 5 minutes of equilibration. The data from the displacement assay was used to calculate the inhibition constant ($K_I$) and $IC_{50}$ value of an inhibitor using the complete competitive binding model.

Example 5: High-Throughput Screening for Transglycosylase Inhibitors

The FA assay was used to screen against 50,000 purchased small molecules (ChemBridge Inc., San Diego, Calif., USA) and 7,000 from proprietary collections. The compounds were transferred to 96-well plates (Freedom Evo, Tecan Schweiz A G, Männedorf, Switzerland) and then to 384-well plates using a multi-dispenser (Labcyte, Sunnyvale, Calif., USA) to prepare the compound plates for screening. The *E. coli* PBP1b (10 μg/ml) in 100 nM F-Moe, 10 mM Tris, 100 mM NaCl, pH 8.0 at a final volume of 40 μl was added to 384-well plates (Freedom Evo 150, Tecan). One μl of 2 mM compound stocks were added to wells using a multi-dispenser (Labcyte). The last two columns of every plate were controls with 10 μM moenomycin and 2.5% DMSO, respectively. After a 30-minute incubation, changes in fluorescence anisotropy were determined with Isocyte (Blueshift Biotech Inc). Hits that showed greater than 75% reduction compared to the control anisotropy values were selected for further confirmation.

Example 6: Determination of Minimal Inhibitory Concentration (MIC)

The minimal inhibitory concentration (MIC) of tested compounds was determined following the NCCLS standard. The experiments were conducted in 96-well microtiter plates using two-fold dilutions in Muller-Hilton broth with (*Streptococcus pneumonia*) or without blood (*Bacillus subtilis, Enterococcus faecalis, Staphylococcus aureus, Escherichia coli*, MRSA, *Actinetobacter baumannii, Pseudomonas aeruginosa, Stenotrophomonas maltophilia*, and *Mycobacterium smegmatis*). Exponentially growing cells at $5\times10^5$ cells/ml were incubated with test compounds at various concentrations. After an 18 h to 24 h incubation at 37° C., MIC was determined as the minimal concentration of the compound that prevents bacterial growth.

Example 7: Lipid II Polymerization Assay

Lipid II polymerization assays were carried out by incubating 100 μM fluorophore-labeled lipid II and penicillin-binding protein 1b from *E. coli* in tubes containing 10 ng/μL N-acetyl muramidase in 50 mM Tris.HCl (pH 8.0), 10 mM $MgCl_2$, 0.1% Triton X-100, 10% DMSO, and 15% MeOH for 30 minutes (Van Nieuwenhze et al. *J Am Chem Soc* 2002, 124, 3656.). The fluorophore can be dansyl chloride, NBD, BODIPY, fluorescein. Reaction supernatants were then injected onto an anion-exchange HPLC column (SAX1, Supelco Co.) and eluted with a linear gradient of ammonium acetate (20 mM to 0.5 M) in methanol. The eluant was monitored for fluorescence with $\lambda_{ex}$=466 nm and $\lambda_{em}$=535 nm.

*Micrococcus flavus* vesicles (6.4 mg) were incubated with 100 mM UDP-MurNAc, 200 mM UDP-GlcNAc, 10 mg undecaprenyl monophosphate in buffer (50 mM Tris-HCl, pH 8, 10 mM $MgCl_2$, and 1% (w/v) Triton X-100) with a final volume of 100 μL (Breukink et al. *J Biol Chem* 2003, 278, 19898.). The suspension was sonicated at 30° C. for 20 min and evaporated to dryness. The crude mixture was purified by normal phase chromatography, followed by reverse phase HPLC on a Zorbax RX-C8 column (9.4 mm×250 mm, 5μ) using a gradient elution of 85:15 v/v (methanol: ammonium bicarbonate) to 100% methanol over 60 min at a flow rate of 1 mL/min. The retention time of the desired product was 27 min (detection at UV 220 nm). Lyophilization of the pure fractions gave lipid II (1.1 mg, 6.1% yield from UDP-MurNAc). HRMS (ESI) calcd for $[C_{94}H_{156}N_8O_{26}P_2\text{-}2H]^{2-}$ 936.5349, found 936.5343.

A transglycosylase assay was performed in situ as follows. Fifty μl aliquots of the lipid II reaction (above) were used as a source of preformed lipid II and transglycosylase enzymes. Either 7.5 μl of DMSO or 7.5 μl of inhibitor in DMSO was added and preincubated for 10 min. Triton X-100 was removed by addition of 35 μl of a suspension of detergent binding resin (Detergent-Out resin, Geno Technology, St. Louis, Mo., USA), followed by incubation for an additional 2 h at room temperature. The total aqueous volume in the reaction was approximately 75 μl. After the 2-h incubation, 100 μl of 10 mM Tris-HCl, pH 8.0, 150 mM NaCl, 0.2% Triton X-100 was added to each reaction. Thirty-five μl of the reactions were spotted onto Whatman 3MM paper for chromatography.

The amount of lipid II formed as a precursor and the amount of peptidoglycan generated as a result of the in situ transglycosylase reaction were determined by paper chromatography according to standard methods. (Branstrom, A. A., Midha, S., Longley, C. B., Han, K., Baizman, E. R., Axelrod, H. R. (2000) Assay for identification of inhibitors for bacterial MraY translocase or MurG transferase. Anal. Biochem. 280, 315-319.)

Example 8: Transglycosylase (TG) Activity Assay

Purified protein was concentrated in 20 mM Tris-HCl (pH 8.0), 300 mM NaCl, and 1 mM DDM. Instead of using Dansyl lipid II, 6-(N-(7-nitrobenz-2-oxa-1,3-diazol-4-yl) amino) hexanoyl (NBD)-labeled Lipid II was prepared as described (Taubes G (2008) Science 321:356-361; Payne D J (2008) Science 321:1644-1645) and used as a substrate to measure TG enzymatic activity, with approach similar to what has been described previously (Holtje J V (1998) Microbiol Mol Biol Rev 62:181-203). Assays were carried out by using the following condition: NBD-Lipid II, 20 nM protein, 50 mM Tris HCl (pH 8.0), 10 mMCaCl2, 0.085% decyl PEG (Anatrace), and 15% MeOH at 37° C. for 0, 1, 3, 5, 7, 9, 20, and 30 min. The concentration of NBD-Lipid II was varied from 1 to 100 μM to determine the rate of the TG activity. After the reaction, 200 μM moenomycin was added to stop the reaction, and 13 μM muramidase (Sigma-Aldrich) was added to digest the TG products to result in NBD-Lipid II without lipid tails. The fluorescent signal decrease of substrate and increase of NBD-Lipid II without lipid tails were detected by anion-exchange column SAX1 (Supelco) on HPLC (Hitachi). The elution procedures was a linear gradient of ammonium acetate (20 mM to 1 M) in MeOH monitored at $\lambda_{excitation}$=466 nm and $\lambda_{emission}$=535 nm. The kinetic parameter was estimated by following the Michaelis-Menten equation. To investigate the importance of transmembrane (TM) helix, PBP1b and PBP1bΔTM (residues Met-1 to Leu-87 were removed) were extracted with the buffer containing 20 mM Tris-HCl (pH 8.0), 300 mM NaCl, and 13 mM FOS-CHOLINE-14 (Anatrace). The protein was purified by nickel chelation chromatography in the presence of 1 mM DDM. The activity assay was carried out by using the following condition: 12 μM NBD-Lipid II, 20 nM protein, 50 mM Tris-HCl (pH 8.0), 10 mM $CaCl_2$, 0.085% decyl PEG, and 15% MeOH at 37° C. for time 0, 1, 3, 5, 7, 9, 20, and 30 min. The initial velocity was used to compare the activity of full-length PBP1b and PBP1bΔTM.

Example 9: Pull-Down Assay

Purified PBP1b variants (including full-length PBP1b, PBP1bΔUB2H, and UB2H only) and UvrB were coupled with CNBr-activated Sepharose (GE LifeSciences). A control Sepharose without proteins was treated in the same procedure. His tagged MltA, PBP3, FtsN, and UvrA were overexpressed in BL21(DE3) cells at 37° C. for 3 h. Overexpressed cells were extracted in lysis buffer [10 mM Tris (pH 6.8), 10 mM sodium maleate (Sigma-Aldrich), 10 mM MgCl2, and 2% Triton X-100] at 4° C. overnight and then centrifuged at 20,000×g for 30 min at 4° C. The resulting supernatant, the detergent-solubilized membrane fractions, was incubated with PBP1b variants-coupled Sepharose beads at 4° C. overnight. Beads were washed with lysis buffer 30 times column volume (CV) and further washed with 5 CV lysis buffer supplemented with 150 mM NaCl. The interacting protein was eluted with lysis buffer containing 1.0 M NaCl. The eluate was analyzed by Western blotting with anti-His antibody.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An anti-bacterial compound having the formula:

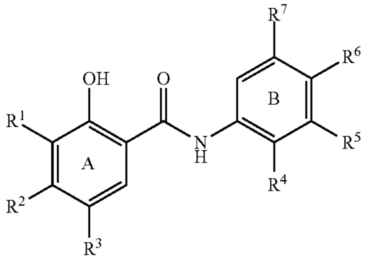

wherein $R^1$=Br, Cl, I, H or OH;

$R^2$=H, OH or Cl;

$R^3$=Br, Cl, I, H, or

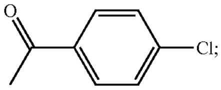

;

$R^4$=

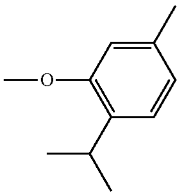

, or

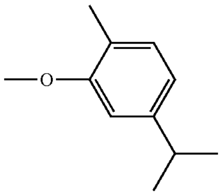

, $R^5$=Cl,

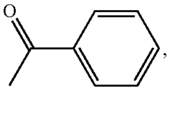

,

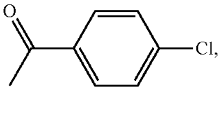

, or

-continued

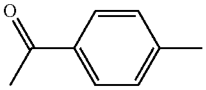

;

$R^6$=H, $CH_3$, OH, $OCH_3$, Cl, $NO_2$, or

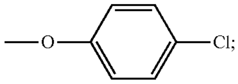

; and $R^7$=H, Cl,

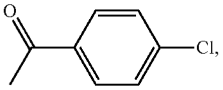

, or

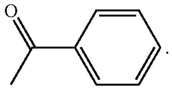

.

2. The anti-bacterial compound of claim 1, wherein, in a co-crystal of the compound with a bifunctional transglycosylase penicillin-binding protein 1b (PBP1b), the compound contacts the moenomycin-binding site of PBP1b as defined by atomic coordinates according to FIGS. 8-1 through 8-82.

3. The compound of claim 1, wherein the compound inhibits a peptidoglycan glucosyltransferase.

4. The compound of claim 3, wherein the peptidoglycan glucosyltransferase is bifunctional transglycosylase penicillin-binding protein 1b (PBP1b), bifunctional transglycosylase penicillin-binding protein 2 from *Staphylococcus aureus* (SaPBP2) or peptidoglycan glycosyltransferase domain from *Aquifex aeolicus* (AaPGT).

5. A pharmaceutical composition comprising the compound of claim 1 and a pharmaceutically acceptable carrier.

6. The anti-bacterial compound of claim 1, wherein the compound (a) binds bifunctional transglycosylase penicillin-binding protein 1b (PBP1b), and (b) inhibits the transglycosylase activity of PBP1b.

7. The compound of claim 6, wherein the PBP1b binding is determined by an anisotropic assay.

8. The compound of claim 7, wherein the anisotropic assay is a fluorescent anisotropic assay.

9. The compound of claim 6, wherein (b) is determined by a fluorescence assay using lipid II, or a derivative thereof.

10. The compound of claim 6, wherein the binding of the compound to *E. coli* PBP1b comprises binding to at least one portion of the transmembrane (TM) domain of PBP1b.

11. The compound of claim 6, wherein the binding of the compound to *E. coli* PBP1b comprises binding to at least one portion of the UvrB domain 2 homolog (UB2H) domain of PBP1b.

12. The compound of claim 11, wherein the UB2H binding further inhibits cell wall synthesis.

13. The compound of claim 11, wherein the UB2H binding further inhibits DNA repair.

14. The compound of claim 6, wherein the compound prevents peptidoglycan elongation by structurally mimicking lipid IV at the binding site of PBP1b.

* * * * *

SEQUENCE LISTING

<160> NUMBER OF SEQ ID NOS: 8

<210> SEQ ID NO 1
<211> LENGTH: 844
<212> TYPE: PRT
<213> ORGANISM: Escherichia coli

<400> SEQUENCE: 1

Met Ala Gly Asn Asp Arg Glu Pro Ile Gly Arg Lys Gly Lys Pro Thr
1 5 10 15

Arg Pro Val Lys Gln Lys Val Ser Arg Arg Arg Tyr Glu Asp Asp Asp
20 25 30

Asp Tyr Asp Asp Tyr Asp Asp Tyr Glu Asp Glu Glu Pro Met Pro Arg
35 40 45

Lys Gly Lys Gly Lys Gly Lys Gly Arg Lys Pro Arg Gly Lys Arg Gly
50 55 60

Trp Leu Trp Leu Leu Leu Lys Leu Ala Ile Val Phe Ala Val Leu Ile
65 70 75 80

Ala Ile Tyr Gly Val Tyr Leu Asp Gln Lys Ile Arg Ser Arg Ile Asp
85 90 95

Gly Lys Val Trp Gln Leu Pro Ala Ala Val Tyr Gly Arg Met Val Asn
100 105 110

Leu Glu Pro Asp Met Thr Ile Ser Lys Asn Glu Met Val Lys Leu Leu
115 120 125

Glu Ala Thr Gln Tyr Arg Gln Val Ser Lys Met Thr Arg Pro Gly Glu
130 135 140

Phe Thr Val Gln Ala Asn Ser Ile Glu Met Ile Arg Arg Pro Phe Asp
145 150 155 160

Phe Pro Asp Ser Lys Glu Gly Gln Val Arg Ala Arg Leu Thr Phe Asp
165 170 175

Gly Asp His Leu Ala Thr Ile Val Asn Met Glu Asn Asn Arg Gln Phe
180 185 190

Gly Phe Phe Arg Leu Asp Pro Arg Leu Ile Thr Met Ile Ser Ser Pro
195 200 205

Asn Gly Glu Gln Arg Leu Phe Val Pro Arg Ser Gly Phe Pro Asp Leu
210 215 220

Leu Val Asp Thr Leu Leu Ala Thr Glu Asp Arg His Phe Tyr Glu His
225 230 235 240

Asp Gly Ile Ser Leu Tyr Ser Ile Gly Arg Ala Val Leu Ala Asn Leu
245 250 255

Thr Ala Gly Arg Thr Val Gln Gly Ala Ser Thr Leu Thr Gln Gln Leu
260 265 270

Val Lys Asn Leu Phe Leu Ser Ser Glu Arg Ser Tyr Trp Arg Lys Ala
275 280 285

Asn Glu Ala Tyr Met Ala Leu Ile Met Asp Ala Arg Tyr Ser Lys Asp
290 295 300

Arg Ile Leu Glu Leu Tyr Met Asn Glu Val Tyr Leu Gly Gln Ser Gly
305 310 315 320

Asp Asn Glu Ile Arg Gly Phe Pro Leu Ala Ser Leu Tyr Tyr Phe Gly
325 330 335

Arg Pro Val Glu Glu Leu Ser Leu Asp Gln Gln Ala Leu Leu Val Gly
340 345 350

Met Val Lys Gly Ala Ser Ile Tyr Asn Pro Trp Arg Asn Pro Lys Leu
355 360 365

-continued

```
Ala Leu Glu Arg Arg Asn Leu Val Leu Arg Leu Leu Gln Gln Gln Gln
    370                 375                 380

Ile Ile Asp Gln Glu Leu Tyr Asp Met Leu Ser Ala Arg Pro Leu Gly
385                 390                 395                 400

Val Gln Pro Arg Gly Gly Val Ile Ser Pro Gln Pro Ala Phe Met Gln
                405                 410                 415

Leu Val Arg Gln Glu Leu Gln Ala Lys Leu Gly Asp Lys Val Lys Asp
            420                 425                 430

Leu Ser Gly Val Lys Ile Phe Thr Thr Phe Asp Ser Val Ala Gln Asp
        435                 440                 445

Ala Ala Glu Lys Ala Ala Val Glu Gly Ile Pro Ala Leu Lys Lys Gln
    450                 455                 460

Arg Lys Leu Ser Asp Leu Glu Thr Ala Ile Val Val Val Asp Arg Phe
465                 470                 475                 480

Ser Gly Glu Val Arg Ala Met Val Gly Gly Ser Glu Pro Gln Phe Ala
                485                 490                 495

Gly Tyr Asn Arg Ala Met Gln Ala Arg Arg Ser Ile Gly Ser Leu Ala
            500                 505                 510

Lys Pro Ala Thr Tyr Leu Thr Ala Leu Ser Gln Pro Lys Ile Tyr Arg
        515                 520                 525

Leu Asn Thr Trp Ile Ala Asp Ala Pro Ile Ala Leu Arg Gln Pro Asn
    530                 535                 540

Gly Gln Val Trp Ser Pro Gln Asn Asp Asp Arg Arg Tyr Ser Glu Ser
545                 550                 555                 560

Gly Arg Val Met Leu Val Asp Ala Leu Thr Arg Ser Met Asn Val Pro
                565                 570                 575

Thr Val Asn Leu Gly Met Ala Leu Gly Leu Pro Ala Val Thr Glu Thr
            580                 585                 590

Trp Ile Lys Leu Gly Val Pro Lys Asp Gln Leu His Pro Val Pro Ala
        595                 600                 605

Met Leu Leu Gly Ala Leu Asn Leu Thr Pro Ile Glu Val Ala Gln Ala
    610                 615                 620

Phe Gln Thr Ile Ala Ser Gly Gly Asn Arg Ala Pro Leu Ser Ala Leu
625                 630                 635                 640

Arg Ser Val Ile Ala Glu Asp Gly Lys Val Leu Tyr Gln Ser Phe Pro
                645                 650                 655

Gln Ala Glu Arg Ala Val Pro Ala Gln Ala Ala Tyr Leu Thr Leu Trp
            660                 665                 670

Thr Met Gln Gln Val Val Gln Arg Gly Thr Gly Arg Gln Leu Gly Ala
        675                 680                 685

Lys Tyr Pro Asn Leu His Leu Ala Gly Lys Thr Gly Thr Thr Asn Asn
    690                 695                 700

Asn Val Asp Thr Trp Phe Ala Gly Ile Asp Gly Ser Thr Val Thr Ile
705                 710                 715                 720

Thr Trp Val Gly Arg Asp Asn Asn Gln Pro Thr Lys Leu Tyr Gly Ala
                725                 730                 735

Ser Gly Ala Met Ser Ile Tyr Gln Arg Tyr Leu Ala Asn Gln Thr Pro
            740                 745                 750

Thr Pro Leu Asn Leu Val Pro Pro Glu Asp Ile Ala Asp Met Gly Val
        755                 760                 765

Asp Tyr Asp Gly Asn Phe Val Cys Ser Gly Gly Met Arg Ile Leu Pro
    770                 775                 780

Val Trp Thr Ser Asp Pro Gln Ser Leu Cys Gln Gln Ser Glu Met Gln
```

-continued

```
785                 790                 795                 800

Gln Gln Pro Ser Gly Asn Pro Phe Asp Gln Ser Ser Gln Pro Gln Gln
                805                 810                 815

Gln Pro Gln Gln Gln Pro Ala Gln Gln Glu Gln Lys Asp Ser Asp Gly
            820                 825                 830

Val Ala Gly Trp Ile Lys Asp Met Phe Gly Ser Asn
        835                 840


<210> SEQ ID NO 2
<211> LENGTH: 270
<212> TYPE: PRT
<213> ORGANISM: Escherichia coli

<400> SEQUENCE: 2

Lys Gly Arg Lys Pro Arg Gly Lys Arg Gly Trp Leu Trp Leu Leu Leu
1               5                   10                  15

Lys Leu Ala Ile Val Phe Ala Val Leu Ile Ala Ile Tyr Gly Val Tyr
            20                  25                  30

Leu Asp Gln Lys Ile Arg Ser Arg Ile Asp Gly Lys Val Trp Gln Leu
        35                  40                  45

Pro Ala Ala Val Tyr Gly Arg Met Val Asn Leu Glu Pro Asp Met Thr
    50                  55                  60

Ile Ser Lys Asn Glu Met Val Lys Leu Leu Glu Ala Thr Gln Tyr Arg
65                  70                  75                  80

Gln Val Ser Lys Met Thr Arg Pro Gly Glu Phe Thr Val Gln Ala Asn
                85                  90                  95

Ser Ile Glu Met Ile Arg Arg Pro Phe Asp Phe Pro Asp Ser Lys Glu
            100                 105                 110

Gly Gln Val Arg Ala Arg Leu Thr Phe Asp Gly Asp His Leu Ala Thr
        115                 120                 125

Ile Val Asn Met Glu Asn Asn Arg Gln Phe Gly Phe Phe Arg Leu Asp
    130                 135                 140

Pro Arg Leu Ile Thr Met Ile Ser Ser Pro Asn Gly Glu Gln Arg Leu
145                 150                 155                 160

Phe Val Pro Arg Ser Gly Phe Pro Asp Leu Leu Val Asp Thr Leu Leu
                165                 170                 175

Ala Thr Glu Asp Arg His Phe Tyr Glu His Asp Gly Ile Ser Leu Tyr
            180                 185                 190

Ser Ile Gly Arg Ala Val Leu Ala Asn Leu Thr Ala Gly Arg Thr Val
        195                 200                 205

Gln Gly Ala Ser Thr Leu Thr Gln Gln Leu Val Lys Asn Leu Phe Leu
    210                 215                 220

Ser Ser Glu Arg Ser Tyr Trp Arg Lys Ala Asn Glu Ala Tyr Met Ala
225                 230                 235                 240

Leu Ile Met Asp Ala Arg Tyr Ser Lys Asp Arg Ile Leu Glu Leu Tyr
                245                 250                 255

Met Asn Glu Val Tyr Leu Gly Gln Ser Gly Asp Asn Glu Ile
            260                 265                 270


<210> SEQ ID NO 3
<211> LENGTH: 181
<212> TYPE: PRT
<213> ORGANISM: Staphylococcus aureus

<400> SEQUENCE: 3

Asn Ser Lys Lys Asn Arg Asn Val Lys Arg Thr Ile Ile Lys Ile Ile
```

-continued

```
1               5                   10                  15

Gly Phe Met Ile Ile Ala Phe Phe Val Val Leu Leu Leu Gly Ile Leu
            20                  25                  30

Leu Phe Ala Tyr Tyr Ala Trp Lys Ala Pro Ala Phe Thr Glu Ala Lys
        35                  40                  45

Leu Gln Asp Pro Ile Pro Ala Lys Ile Tyr Asp Lys Asn Gly Glu Leu
    50                  55                  60

Val Lys Thr Leu Asp Asn Gly Gln Arg His Glu His Val Asn Leu Lys
65                  70                  75                  80

Asp Val Pro Lys Ser Met Lys Asp Ala Val Leu Ala Thr Glu Asp Asn
                85                  90                  95

Arg Phe Tyr Glu His Gly Ala Leu Asp Tyr Lys Arg Leu Phe Gly Ala
            100                 105                 110

Ile Gly Lys Asn Leu Thr Gly Gly Phe Gly Ser Glu Gly Ala Ser Thr
        115                 120                 125

Leu Thr Gln Gln Val Val Lys Asp Ala Phe Leu Ser Gln His Lys Ser
    130                 135                 140

Ile Gly Arg Lys Ala Gln Glu Ala Tyr Leu Ser Tyr Arg Leu Glu Gln
145                 150                 155                 160

Glu Tyr Ser Lys Asp Asp Ile Phe Gln Val Tyr Leu Asn Lys Ile Tyr
                165                 170                 175

Tyr Ser Asp Gly Val
            180
```

<210> SEQ ID NO 4
<211> LENGTH: 170
<212> TYPE: PRT
<213> ORGANISM: Aquifex aeolicus

<400> SEQUENCE: 4

```
Met Lys Lys Leu Val Ile Gly Ile Leu Gly Ile Val Ile Ala Leu Phe
1               5                   10                  15

Val Gly Leu Leu Val Phe Leu Ile Pro Ile Tyr Lys Asn Leu Pro Asp
            20                  25                  30

Pro Lys Leu Leu Glu Ser Trp Thr Pro Pro Gln Ala Ser Glu Val Tyr
        35                  40                  45

Asp Ala Lys Gly Arg Leu Tyr Gly Thr Ile Gly Ile Gln Lys Arg Phe
    50                  55                  60

Tyr Val Ser Ile Asp Lys Ile Pro Glu His Val Ile Asn Ala Phe Val
65                  70                  75                  80

Ala Thr Glu Asp Arg Asn Phe Trp His His Phe Gly Ile Asp Pro Val
                85                  90                  95

Ala Ile Val Arg Ala Ala Ile Val Asn Tyr Arg Ala Gly Arg Ile Val
            100                 105                 110

Gln Gly Gly Ser Thr Ile Thr Gln Gln Leu Ala Lys Asn Leu Phe Leu
        115                 120                 125

Thr Arg Glu Arg Thr Leu Glu Arg Lys Ile Lys Glu Ala Leu Leu Ala
    130                 135                 140

Ile Lys Ile Glu Arg Thr Phe Asp Lys Lys Lys Ile Met Glu Leu Tyr
145                 150                 155                 160

Leu Asn Gln Ile Tyr Leu Gly Ser Gly Ala
                165                 170
```

<210> SEQ ID NO 5
<211> LENGTH: 162

<212> TYPE: PRT
<213> ORGANISM: Escherichia coli

<400> SEQUENCE: 5

```
Pro Arg Ser Gly Phe Pro Asp Leu Leu Val Asp Thr Leu Leu Ala Thr
1               5                   10                  15

Glu Asp Arg His Phe Tyr Glu His Asp Gly Ile Ser Leu Tyr Ser Ile
            20                  25                  30

Gly Arg Ala Val Leu Ala Asn Leu Thr Ala Gly Arg Thr Val Gln Gly
        35                  40                  45

Ala Ser Thr Leu Thr Gln Gln Leu Val Lys Asn Leu Phe Leu Ser Ser
    50                  55                  60

Glu Arg Ser Tyr Trp Arg Lys Ala Asn Glu Ala Tyr Met Ala Leu Ile
65                  70                  75                  80

Met Asp Ala Arg Tyr Ser Lys Asp Arg Ile Leu Glu Leu Tyr Met Asn
                85                  90                  95

Glu Val Tyr Leu Gly Gln Ser Gly Asp Asn Glu Ile Arg Gly Phe Pro
            100                 105                 110

Leu Ala Ser Leu Tyr Tyr Phe Gly Arg Pro Val Glu Glu Leu Ser Leu
        115                 120                 125

Asp Gln Gln Ala Leu Leu Val Gly Met Val Lys Gly Ala Ser Ile Tyr
    130                 135                 140

Asn Pro Trp Arg Asn Pro Lys Leu Ala Leu Glu Arg Arg Asn Leu Val
145                 150                 155                 160

Leu Arg
```

<210> SEQ ID NO 6
<211> LENGTH: 158
<212> TYPE: PRT
<213> ORGANISM: Staphylococcus aureus

<400> SEQUENCE: 6

```
Asn Leu Lys Asp Val Pro Lys Ser Met Lys Asp Ala Val Leu Ala Thr
1               5                   10                  15

Glu Asp Asn Arg Phe Tyr Glu His Gly Ala Leu Asp Tyr Lys Arg Leu
            20                  25                  30

Phe Gly Ala Ile Gly Lys Asn Leu Thr Gly Gly Phe Gly Ser Glu Gly
        35                  40                  45

Ala Ser Thr Leu Thr Gln Gln Val Val Lys Asp Ala Phe Leu Ser Gln
    50                  55                  60

His Lys Ser Ile Gly Arg Lys Ala Gln Glu Ala Tyr Leu Ser Tyr Arg
65                  70                  75                  80

Leu Glu Gln Glu Tyr Ser Lys Asp Asp Ile Phe Gln Val Tyr Leu Asn
                85                  90                  95

Lys Ile Tyr Tyr Ser Asp Gly Val Thr Gly Ile Lys Ala Ala Ala Lys
            100                 105                 110

Tyr Tyr Phe Asn Lys Asp Leu Lys Asp Leu Asn Leu Ala Glu Glu Ala
        115                 120                 125

Tyr Leu Ala Gly Leu Pro Gln Val Pro Asn Asn Tyr Asn Ile Tyr Asp
    130                 135                 140

His Pro Lys Ala Ala Glu Asp Arg Lys Asn Thr Val Leu Tyr
145                 150                 155
```

<210> SEQ ID NO 7
<211> LENGTH: 158
<212> TYPE: PRT

<213> ORGANISM: Aquifex aeolicus

<400> SEQUENCE: 7

```
Ser Ile Asp Lys Ile Pro Glu His Val Ile Asn Ala Phe Val Ala Thr
1               5                   10                  15

Glu Asp Arg Asn Phe Trp His His Phe Gly Ile Asp Pro Val Ala Ile
            20                  25                  30

Val Arg Ala Ala Ile Val Asn Tyr Arg Ala Gly Arg Ile Val Gln Gly
        35                  40                  45

Gly Ser Thr Ile Thr Gln Gln Leu Ala Lys Asn Leu Phe Leu Thr Arg
    50                  55                  60

Glu Arg Thr Leu Glu Arg Lys Ile Lys Glu Ala Leu Leu Ala Ile Lys
65                  70                  75                  80

Ile Glu Arg Thr Phe Asp Lys Lys Lys Ile Met Glu Leu Tyr Leu Asn
                85                  90                  95

Gln Ile Tyr Leu Gly Ser Gly Ala Tyr Gly Val Glu Ala Ala Ala Gln
            100                 105                 110

Val Tyr Phe Gly Lys His Val Trp Glu Leu Ser Leu Asp Glu Ala Ala
        115                 120                 125

Leu Leu Ala Ala Leu Pro Lys Ala Pro Ala Lys Tyr Asn Pro Phe Tyr
    130                 135                 140

His Pro Glu Arg Ala Leu Gln Arg Arg Asn Leu Val Leu Lys
145                 150                 155
```

<210> SEQ ID NO 8
<211> LENGTH: 751
<212> TYPE: PRT
<213> ORGANISM: Escherichia coli

<400> SEQUENCE: 8

```
Gly Ser His Met Lys Pro Arg Gly Lys Arg Gly Trp Leu Trp Leu Leu
1               5                   10                  15

Leu Lys Leu Ala Ile Val Phe Ala Val Leu Ile Ala Ile Tyr Gly Val
            20                  25                  30

Tyr Leu Asp Gln Lys Ile Arg Ser Arg Ile Asp Gly Lys Val Trp Gln
        35                  40                  45

Leu Pro Ala Ala Val Tyr Gly Arg Met Val Asn Leu Glu Pro Asp Met
    50                  55                  60

Thr Ile Ser Lys Asn Glu Met Val Lys Leu Leu Glu Ala Thr Gln Tyr
65                  70                  75                  80

Arg Gln Val Ser Lys Met Thr Arg Pro Gly Glu Phe Thr Val Gln Ala
                85                  90                  95

Asn Ser Ile Glu Met Ile Arg Arg Pro Phe Asp Phe Pro Asp Ser Lys
            100                 105                 110

Glu Gly Gln Val Arg Ala Arg Leu Thr Phe Asp Gly Asp His Leu Ala
        115                 120                 125

Thr Ile Val Asn Met Glu Asn Asn Arg Gln Phe Gly Phe Phe Arg Leu
    130                 135                 140

Asp Pro Arg Leu Ile Thr Met Ile Ser Ser Pro Asn Gly Glu Gln Arg
145                 150                 155                 160

Leu Phe Val Pro Arg Ser Gly Phe Pro Asp Leu Leu Val Asp Thr Leu
                165                 170                 175

Leu Ala Thr Glu Asp Arg His Phe Tyr Glu His Asp Gly Ile Ser Leu
            180                 185                 190

Tyr Ser Ile Gly Arg Ala Val Leu Ala Asn Leu Thr Ala Gly Arg Thr
```

-continued

```
        195                 200                 205

Val Gln Gly Ala Ser Thr Leu Thr Gln Gln Leu Val Lys Asn Leu Phe
    210                 215                 220

Leu Ser Ser Glu Arg Ser Tyr Trp Arg Lys Ala Asn Glu Ala Tyr Met
225                 230                 235                 240

Ala Leu Ile Met Asp Ala Arg Tyr Ser Lys Asp Arg Ile Leu Glu Leu
                245                 250                 255

Tyr Met Asn Glu Val Tyr Leu Gly Gln Ser Gly Asp Asn Glu Ile Arg
            260                 265                 270

Gly Phe Pro Leu Ala Ser Leu Tyr Tyr Phe Gly Arg Pro Val Glu Glu
        275                 280                 285

Leu Ser Leu Asp Gln Gln Ala Leu Leu Val Gly Met Val Lys Gly Ala
    290                 295                 300

Ser Ile Tyr Asn Pro Trp Arg Asn Pro Lys Leu Ala Leu Glu Arg Arg
305                 310                 315                 320

Asn Leu Val Leu Arg Leu Leu Gln Gln Gln Gln Ile Ile Asp Gln Glu
                325                 330                 335

Leu Tyr Asp Met Leu Ser Ala Arg Pro Leu Gly Val Gln Pro Arg Gly
            340                 345                 350

Gly Val Ile Ser Pro Gln Pro Ala Phe Met Gln Leu Val Arg Gln Glu
        355                 360                 365

Leu Gln Ala Lys Leu Gly Asp Lys Val Lys Asp Leu Ser Gly Val Lys
    370                 375                 380

Ile Phe Thr Thr Phe Asp Ser Val Ala Gln Asp Ala Ala Glu Lys Ala
385                 390                 395                 400

Ala Val Glu Gly Ile Pro Ala Leu Lys Lys Gln Arg Lys Leu Ser Asp
                405                 410                 415

Leu Glu Thr Ala Ile Val Val Val Asp Arg Phe Ser Gly Glu Val Arg
            420                 425                 430

Ala Met Val Gly Gly Ser Glu Pro Gln Phe Ala Gly Tyr Asn Arg Ala
        435                 440                 445

Met Gln Ala Arg Arg Ser Ile Gly Ser Leu Ala Lys Pro Ala Thr Tyr
    450                 455                 460

Leu Thr Ala Leu Ser Gln Pro Lys Ile Tyr Arg Leu Asn Thr Trp Ile
465                 470                 475                 480

Ala Asp Ala Pro Ile Ala Leu Arg Gln Pro Asn Gly Gln Val Trp Ser
                485                 490                 495

Pro Gln Asn Asp Asp Arg Arg Tyr Ser Glu Ser Gly Arg Val Met Leu
            500                 505                 510

Val Asp Ala Leu Thr Arg Ser Met Asn Val Pro Thr Val Asn Leu Gly
        515                 520                 525

Met Ala Leu Gly Leu Pro Ala Val Thr Glu Thr Trp Ile Lys Leu Gly
    530                 535                 540

Val Pro Lys Asp Gln Leu His Pro Val Pro Ala Met Leu Leu Gly Ala
545                 550                 555                 560

Leu Asn Leu Thr Pro Ile Glu Val Ala Gln Ala Phe Gln Thr Ile Ala
                565                 570                 575

Ser Gly Gly Asn Arg Ala Pro Leu Ser Ala Leu Arg Ser Val Ile Ala
            580                 585                 590

Glu Asp Gly Lys Val Leu Tyr Gln Ser Phe Pro Gln Ala Glu Arg Ala
        595                 600                 605

Val Pro Ala Gln Ala Ala Tyr Leu Thr Leu Trp Thr Met Gln Gln Val
    610                 615                 620
```

-continued

```
Val Gln Arg Gly Thr Gly Arg Gln Leu Gly Ala Lys Tyr Pro Asn Leu
625                 630                 635                 640

His Leu Ala Gly Lys Thr Gly Thr Thr Asn Asn Asn Val Asp Thr Trp
                645                 650                 655

Phe Ala Gly Ile Asp Gly Ser Thr Val Thr Ile Thr Trp Val Gly Arg
            660                 665                 670

Asp Asn Asn Gln Pro Thr Lys Leu Tyr Gly Ala Ser Gly Ala Met Ser
        675                 680                 685

Ile Tyr Gln Arg Tyr Leu Ala Asn Gln Thr Pro Thr Pro Leu Asn Leu
    690                 695                 700

Val Pro Pro Glu Asp Ile Ala Asp Met Gly Val Asp Tyr Asp Gly Asn
705                 710                 715                 720

Phe Val Cys Ser Gly Gly Met Arg Ile Leu Pro Val Trp Thr Ser Asp
                725                 730                 735

Pro Gln Ser Leu Cys Gln Gln Ser Glu Met Gln Gln Gln Pro Ser
            740                 745                 750
```